US012674168B2

(12) United States Patent
Byrne et al.

(10) Patent No.: US 12,674,168 B2
(45) Date of Patent: Jul. 7, 2026

(54) OLIGONUCLEOTIDE COMPOSITIONS AND METHODS OF USE THEREOF

(71) Applicant: WAVE LIFE SCIENCES LTD., Singapore (SG)

(72) Inventors: Michael John Byrne, Natick, MA (US); Vinod Vathipadiekal, Stoneham, MA (US); Naoki Iwamoto, Boston, MA (US); Chandra Vargeese, Schwenksville, PA (US); Lankai Guo, Winchester, MA (US); Andrew Guzior Hoss, Cambridge, MA (US)

(73) Assignee: WAVE LIFE SCIENCES LTD., Singapore (SG)

( * ) Notice: Subject to any disclaimer, the term of this patent is extended or adjusted under 35 U.S.C. 154(b) by 1129 days.

(21) Appl. No.: 17/605,997

(22) PCT Filed: Apr. 24, 2020

(86) PCT No.: PCT/US2020/029959
§ 371 (c)(1),
(2) Date: Oct. 22, 2021

(87) PCT Pub. No.: WO2020/219983
PCT Pub. Date: Oct. 29, 2020

(65) Prior Publication Data

US 2023/0145795 A1 May 11, 2023

Related U.S. Application Data

(60) Provisional application No. 62/838,763, filed on Apr. 25, 2019.

(51) Int. Cl.
*C12N 15/113* (2010.01)
*A61P 27/00* (2006.01)
*C12Q 1/68* (2018.01)

(52) U.S. Cl.
CPC .......... *C12N 15/1138* (2013.01); *A61P 27/00* (2018.01); *C12N 2310/315* (2013.01); *C12N 2310/351* (2013.01)

(58) Field of Classification Search
None
See application file for complete search history.

(56) References Cited

U.S. PATENT DOCUMENTS

| | | | |
|---|---|---|---|
| 8,470,987 | B2 | 6/2013 | Wada et al. |
| 8,822,671 | B2 | 9/2014 | Shimizu et al. |
| 8,859,755 | B2 | 10/2014 | Wada et al. |
| 9,394,333 | B2 | 7/2016 | Wada et al. |
| 9,598,458 | B2 | 3/2017 | Shimizu et al. |
| 9,605,019 | B2 | 3/2017 | Verdine et al. |
| 9,617,547 | B2 | 4/2017 | Gemba |
| 9,695,211 | B2 | 7/2017 | Wada et al. |
| 9,744,183 | B2 | 8/2017 | Verdine et al. |
| 9,982,257 | B2 | 5/2018 | Butler et al. |
| 10,144,933 | B2 | 12/2018 | Gemba et al. |
| 10,149,905 | B2 | 12/2018 | Gemba et al. |
| 10,160,969 | B2 | 12/2018 | Meena et al. |
| 10,167,309 | B2 | 1/2019 | Shimizu et al. |
| 10,280,192 | B2 | 5/2019 | Verdine et al. |
| 10,307,434 | B2 | 6/2019 | Verdine et al. |
| 10,322,173 | B2 | 6/2019 | Gemba et al. |
| 10,329,318 | B2 | 6/2019 | Wada et al. |
| 10,428,019 | B2 | 10/2019 | Wada et al. |
| 10,450,568 | B2 | 10/2019 | Butler et al. |
| 10,479,995 | B2 | 11/2019 | Vargeese et al. |
| 10,590,413 | B2 | 3/2020 | Butler et al. |
| 10,696,711 | B2 | 6/2020 | Shimizu et al. |
| 10,724,035 | B2 | 7/2020 | Vargeese et al. |
| 10,815,482 | B2 | 10/2020 | Meena et al. |
| 11,013,757 | B2 | 5/2021 | Zhang et al. |
| 11,136,346 | B2 | 10/2021 | Shimizu et al. |
| 11,407,775 | B2 | 8/2022 | Butler et al. |
| 11,596,646 | B2 | 3/2023 | Zhang et al. |
| 11,597,927 | B2 | 3/2023 | Vargeese et al. |

(Continued)

FOREIGN PATENT DOCUMENTS

| | | |
|---|---|---|
| JP | 2003-238586 A | 8/2003 |
| JP | 2011-184318 A | 9/2011 |

(Continued)

OTHER PUBLICATIONS

Murray et al., Investigative Opthalmology & Visual Science vol. 56(11):6362-6375, 2015.*
Kupryushkin, M. S. Phosphoryl Guanidines: A New Type of Nucleic Acid Analogues, Acta Naturae, 6(4): 116-118 (2014).
Pavlova, A. S. et al., SDS-PAGE procedure: Application for characterization of new entirely uncharged nucleic acids analogs, Electrophor., 39:670-674 (2018).
U.S. Appl. No. 16/624,896, filed Dec. 19, 2019, Butler et al.
U.S. Appl. No. 17/046,752, filed Oct. 9, 2020, Zhang et al.
U.S. Appl. No. 17/177,111, filed Feb. 16, 2021, Zhang et al.
U.S. Appl. No. 17/439,755, filed Sep. 15, 2021, Kandasamy et al.

(Continued)

*Primary Examiner* — Sean McGarry
(74) *Attorney, Agent, or Firm* — Choate, Hall & Stewart LLP; Xiaodong Li

(57) ABSTRACT

Among other things, the present disclosure provides RHO oligonucleotides, compositions, and methods. In some embodiments, provided oligonucleotides comprise nucleobase modifications, sugar modifications, internucleotidic linkage modifications and/or patterns thereof, and have improved properties, activities and/or selectivities. In some embodiments, the present disclosure provides RHO oligonucleotides, compositions and methods for preventing and/or treating RHO-related conditions, disorders or diseases, such as retinopathy (e.g, retinal degeneration, retinal degenerative disease, retinal degenerative disorder, inherited retinal degenerative disorder, retinitis pigmentosa, autosomal dominant retinitis pigmentosa, etc.).

20 Claims, No Drawings

Specification includes a Sequence Listing.

(56) References Cited

U.S. PATENT DOCUMENTS

| | | | |
|---|---|---|---|
| 11,603,532 | B2 | 3/2023 | Vargeese et al. |
| 11,608,355 | B2 | 3/2023 | Bowman et al. |
| 11,634,710 | B2 | 4/2023 | Frank-Kamenetsky et al. |
| 11,643,657 | B2 | 5/2023 | Butler et al. |
| 11,718,638 | B2 | 8/2023 | Butler et al. |
| 11,739,325 | B2 | 8/2023 | Vargeese et al. |
| 11,873,316 | B2 | 1/2024 | Butler et al. |
| 12,391,942 | B2 | 8/2025 | Zhang et al. |
| 12,428,442 | B2 | 9/2025 | Butler et al. |
| 12,435,105 | B2 | 10/2025 | Bowman et al. |
| 12,473,321 | B2 | 11/2025 | Butler et al. |
| 12,486,505 | B2 | 12/2025 | Frank-Kamenetsky et al. |
| 2013/0178612 | A1 | 7/2013 | Wada et al. |
| 2016/0331835 | A1 | 11/2016 | Gemba et al. |
| 2016/0331836 | A1 | 11/2016 | Gemba et al. |
| 2016/0333349 | A1 | 11/2016 | Gemba et al. |
| 2017/0130224 | A1 | 5/2017 | Oestergaard et al. |
| 2018/0169131 | A1 | 6/2018 | Murray et al. |
| 2018/0216107 | A1 | 8/2018 | Frank-Kamenetsky et al. |
| 2019/0077817 | A1 | 3/2019 | Butler et al. |
| 2019/0127733 | A1 | 5/2019 | Butler et al. |
| 2019/0249173 | A1 | 8/2019 | Vargeese et al. |
| 2019/0264267 | A1 | 8/2019 | Yang et al. |
| 2019/0375774 | A1 | 12/2019 | Butler et al. |
| 2020/0157545 | A1 | 5/2020 | Vargeese et al. |
| 2020/0190515 | A1 | 6/2020 | Vargeese et al. |
| 2020/0231620 | A1 | 7/2020 | Bowman et al. |
| 2020/0299692 | A1 | 9/2020 | Frank-Kamenetsky et al. |
| 2020/0362337 | A1 | 11/2020 | Dodart et al. |
| 2021/0032620 | A1 | 2/2021 | Vargeese et al. |
| 2021/0115444 | A1 | 4/2021 | Meena et al. |
| 2021/0130821 | A1 | 5/2021 | Butler et al. |
| 2021/0198305 | A1 | 7/2021 | Vargeese et al. |
| 2021/0228615 | A1 | 7/2021 | Zhang et al. |
| 2021/0254062 | A1 | 8/2021 | Zhang et al. |
| 2022/0098585 | A1 | 3/2022 | Brown et al. |
| 2022/0127301 | A1 | 4/2022 | Shimizu et al. |
| 2022/0145300 | A1 | 5/2022 | Liu et al. |
| 2022/0162598 | A1 | 5/2022 | Vargeese et al. |
| 2022/0186217 | A1 | 6/2022 | Zhang et al. |
| 2022/0195429 | A1 | 6/2022 | Vargeese et al. |
| 2022/0306573 | A1 | 9/2022 | Zhang et al. |
| 2022/0307019 | A1 | 9/2022 | Yokota et al. |
| 2022/0401467 | A1 | 12/2022 | Zhang et al. |
| 2023/0089442 | A1 | 3/2023 | Kandasamy et al. |
| 2023/0136645 | A1 | 5/2023 | Butler et al. |
| 2023/0203087 | A1 | 6/2023 | Kandasamy et al. |
| 2023/0220384 | A1 | 7/2023 | Monian et al. |
| 2023/0295617 | A1 | 9/2023 | Vargeese et al. |
| 2023/0295619 | A1 | 9/2023 | Maguire et al. |
| 2023/0329201 | A1 | 10/2023 | Yang et al. |
| 2023/0348524 | A1 | 11/2023 | Bowman et al. |
| 2023/0392137 | A1 | 12/2023 | Monian et al. |
| 2024/0026358 | A1 | 1/2024 | Monian et al. |
| 2024/0109931 | A1 | 4/2024 | Vargeese et al. |
| 2024/0117347 | A1 | 4/2024 | Butler et al. |
| 2024/0132894 | A1 | 4/2024 | Vargeese et al. |
| 2024/0150756 | A1 | 5/2024 | Frank-Kamenetsky et al. |
| 2024/0174710 | A1 | 5/2024 | Butler et al. |
| 2024/0175016 | A1 | 5/2024 | Liu et al. |
| 2024/0175018 | A1 | 5/2024 | Vargeese et al. |
| 2024/0229026 | A1 | 7/2024 | Butler et al. |
| 2024/0368207 | A1 | 11/2024 | Butler et al. |
| 2025/0051778 | A1 | 2/2025 | Byrne et al. |
| 2025/0066775 | A1 | 2/2025 | Vargeese et al. |
| 2025/0135036 | A1 | 5/2025 | Acker et al. |
| 2025/0154190 | A1 | 5/2025 | Kandasamy et al. |
| 2025/0197857 | A1 | 6/2025 | Hu et al. |
| 2025/0262235 | A1 | 8/2025 | Lu et al. |
| 2025/0270628 | A1 | 8/2025 | Yang et al. |
| 2025/0302995 | A1 | 10/2025 | Shivalila et al. |
| 2025/0313836 | A1 | 10/2025 | Meena et al. |
| 2025/0333740 | A1 | 10/2025 | Monian et al. |
| 2026/0008806 | A1 | 1/2026 | Bowman et al. |

FOREIGN PATENT DOCUMENTS

| | | | |
|---|---|---|---|
| WO | WO-2005/014609 | A2 | 2/2005 |
| WO | WO-2005/023828 | A1 | 3/2005 |
| WO | WO-2005/028494 | A1 | 3/2005 |
| WO | WO-2005/070859 | A1 | 8/2005 |
| WO | WO-2005/085272 | A1 | 9/2005 |
| WO | WO-2005/092909 | A1 | 10/2005 |
| WO | WO-2010/064146 | A2 | 6/2010 |
| WO | WO-2011/005761 | A1 | 1/2011 |
| WO | WO-2011/034072 | A1 | 3/2011 |
| WO | WO-2011/108682 | A1 | 9/2011 |
| WO | WO-2012/039448 | A1 | 3/2012 |
| WO | WO-2012/073857 | A1 | 6/2012 |
| WO | WO-2013/012758 | A1 | 1/2013 |
| WO | WO-2014/010250 | A1 | 1/2014 |
| WO | WO-2014/010718 | A1 | 1/2014 |
| WO | WO-2014/012081 | A2 | 1/2014 |
| WO | WO-2015/107425 | A2 | 7/2015 |
| WO | WO-2015/108046 | A1 | 7/2015 |
| WO | WO-2015/108047 | A1 | 7/2015 |
| WO | WO-2015/108048 | A1 | 7/2015 |
| WO | WO-2016/028187 | A1 | 2/2016 |
| WO | WO-2016/138353 | A1 | 9/2016 |
| WO | WO-2017/015555 | A1 | 1/2017 |
| WO | WO-2017/015575 | A1 | 1/2017 |
| WO | WO-2017/062862 | A2 | 4/2017 |
| WO | WO-2017/160741 | A1 | 9/2017 |
| WO | WO-2017/192664 | A1 | 11/2017 |
| WO | WO-2017/192679 | A1 | 11/2017 |
| WO | WO-2017/210647 | A1 | 12/2017 |
| WO | WO-2018/022473 | A1 | 2/2018 |
| WO | WO-2018/067973 | A1 | 4/2018 |
| WO | WO-2018/098264 | A1 | 5/2018 |
| WO | WO-2018/223056 | A1 | 12/2018 |
| WO | WO-2018/223073 | A1 | 12/2018 |
| WO | WO-2018/223081 | A1 | 12/2018 |
| WO | WO-2018/237194 | A1 | 12/2018 |
| WO | WO-2019/032607 | A1 | 2/2019 |
| WO | WO-2019/032612 | A1 | 2/2019 |
| WO | WO-2019/055951 | A1 | 3/2019 |
| WO | WO-2019/075357 | A1 | 4/2019 |
| WO | WO-2019/157531 | A1 | 8/2019 |
| WO | WO-2019/200185 | A1 | 10/2019 |
| WO | WO-2019/217784 | A1 | 11/2019 |
| WO | WO-2020/118246 | A1 | 6/2020 |
| WO | WO-2020/160336 | A1 | 8/2020 |
| WO | WO-2020/191252 | A1 | 9/2020 |
| WO | WO-2020/196662 | A1 | 10/2020 |
| WO | WO-2020/219981 | A2 | 10/2020 |
| WO | WO-2020/219983 | A2 | 10/2020 |
| WO | WO-2020/227691 | A2 | 11/2020 |
| WO | WO-2021/071788 | A2 | 4/2021 |
| WO | WO-2021/071858 | A1 | 4/2021 |
| WO | WO-2021/178237 | A2 | 9/2021 |
| WO | WO-2021/234459 | A2 | 11/2021 |
| WO | WO-2021/237223 | A1 | 11/2021 |
| WO | WO-2022/046667 | A1 | 3/2022 |
| WO | WO-2022/046723 | A1 | 3/2022 |
| WO | WO-2022/099159 | A1 | 5/2022 |
| WO | WO-2023/049475 | A1 | 3/2023 |
| WO | WO-2023/049477 | A2 | 3/2023 |
| WO | WO-2023/075766 | A1 | 5/2023 |
| WO | WO-2023/076352 | A2 | 5/2023 |
| WO | WO-2023/154528 | A1 | 8/2023 |
| WO | WO-2023/168014 | A2 | 9/2023 |
| WO | WO-2023/201095 | A2 | 10/2023 |
| WO | WO-2023/220440 | A1 | 11/2023 |
| WO | WO-2024/035946 | A1 | 2/2024 |
| WO | WO-2025/030155 | A1 | 2/2025 |
| WO | WO-2025/072685 | A1 | 4/2025 |
| WO | WO-2025/072862 | A1 | 4/2025 |
| WO | WO-2025/072879 | A1 | 4/2025 |
| WO | WO-2025/072881 | A2 | 4/2025 |
| WO | WO-2025/072883 | A2 | 4/2025 |
| WO | WO-2025/072886 | A1 | 4/2025 |
| WO | WO-2025/151895 | A1 | 7/2025 |
| WO | WO-2025/160090 | A1 | 7/2025 |
| WO | WO-2025/212958 | A1 | 10/2025 |

(56) References Cited

FOREIGN PATENT DOCUMENTS

| | | | |
|---|---|---|---|
| WO | WO-2025/213136 | A1 | 10/2025 |
| WO | WO-2025/213142 | A2 | 10/2025 |
| WO | WO-2026/006477 | A1 | 1/2026 |

OTHER PUBLICATIONS

U.S. Appl. No. 17/442,663, filed Sep. 24, 2021, Yokota et al.
U.S. Appl. No. 17/605,998, filed Oct. 22, 2021, Byrne et al.
U.S. Appl. No. 17/766,677, filed Apr. 5, 2022, Monlan et al.
U.S. Appl. No. 17/766,680, filed Apr. 5, 2022, Liu et al.
Byrne, M. et al., Allele-selective Reduction Of Rho P23H-mutant Rhodopsin Rescues Phenotype Associated With Retinitis Pigmentosa In Preclinical Models, Wave Life Sciences, presented at the 17th Annual Oligonucleotide Therapeutics Society Meeting on Sep. 26-29, 2021.
Byrne, M. Stereopure oligonucleotides produce potent and durable activity in the eye supporting their development for inherited retinal diseases, Wave Life Sciences, presented at TIDES: Oligonucleotides and Peptide Therapeutics, on Sep. 18, 2020.
International Search Report for PCT/US2020/029959, 5 pages (mailed Oct. 9, 2020).
Invitation to Pay Additional Fees for PCT/US2020/029959, 2 pages (mailed Aug. 4, 2020).
Meng, M. and Ducho, C., Oligonucleotide analogues with cationic backbone linkages, Beilstein J. Org. Chem., 14:1293-1308 (2018).
Written Opinion for PCT/US2020/029959, 12 pages (mailed Oct. 9, 2020).
U.S. Appl. No. 17/956,741, filed Sep. 29, 2022, Vargeese et al.
U.S. Appl. No. 17/960,090, filed Oct. 4, 2022, Vargeese et al.
U.S. Appl. No. 18/062,422, filed Dec. 6, 2022, Butler et al.
U.S. Appl. No. 18/178,470, filed Mar. 3, 2023, Vargeese et al.
U.S. Appl. No. 18/204,895, filed Jun. 1, 2023, Vargeese et al.
U.S. Appl. No. 18/305,195, filed Apr. 21, 2023, Frank-Kamenetsky et al.
U.S. Appl. No. 18/316,932, filed May 12, 2023, Butler et al.
U.S. Appl. No. 18/522,146, filed Nov. 28, 2023, Butler et al.
Iwamoto, N. et al., Control of phosphorothioate stereochemistry substantially increases the efficacy of antisense oligonucleotides, with Supplementary Information, Nat. Biotech., 35(9):845-851 (2017).
U.S. Appl. No. 19/217,825, filed May 23, 2025, Vargeese et al.
U.S. Appl. No. 19/241,178, filed Jun. 17, 2025, Zhang et al.
U.S. Appl. No. 19/271,472, filed Jul. 16, 2025, Zhang et al.
U.S. Appl. No. 19/276,854, filed Jul. 22, 2025, Zhang et al.
U.S. Appl. No. 19/281,441, filed Jul. 25, 2025, Butler et al.
U.S. Appl. No. 19/281,453, filed Jul. 25, 2025, Liu et al.
U.S. Appl. No. 19/284,561, filed Jul. 29, 2025, Butler et al.
U.S. Appl. No. 19/297,725, filed Aug. 12, 2025, Stetsenko et al.
U.S. Appl. No. 19/367,099, filed Oct. 23, 2025, Frank-Kamenetsky et al.
U.S. Appl. No. 19/434,730, filed Dec. 29, 2025, Zhang et al.
U.S. Appl. No. 19/458,525, filed Jan. 23, 2026, Shimizu et al.
U.S. Appl. No. 19/462,715, filed Jan. 28, 2026, Kandasamy et al.
U.S. Appl. No. 19/508,309, filed Feb. 3, 2026, Lake et al.
Byrne, M. et al., Allele-selective reduction of P23H-mutant rhodopsin with stereopure oligonucleotides rescues phenotype associated with retinitis pigmentosa in preclinical models, ARVO Meeting, Abstract, published Jun. 2021.
Meng, D. et al., Therapy in Rhodopsin-Mediated Autosomal Dominant Retinitis Pigmentosa, Mol. Ther., 28(10):2139-2149 (2020).
Murray, S. F. et al., Prevention of photoreceptor cell degeneration in P23H rats after allele-specific knockdown of mutant Rhodopsin RNA expression using antisense oligonucleotide (ASO) treatment, ARVO Meeting, Abstract, published Apr. 2014.
Vathipadiekal, V. et al., Stereopure oligonucleotides achieve allele-selective reduction of P23H mutant rhodopsin, ARVO Meeting, Abstract, published Jun. 2020.
U.S. Appl. No. 18/695,346, filed Mar. 25, 2024, Monian et al.
U.S. Appl. No. 18/704,629, filed Apr. 25, 2024, Byrne et al.
U.S. Appl. No. 18/836,993, filed Aug. 8, 2024, Kandasamy et al.
U.S. Appl. No. 18/843,171, filed Aug. 30, 2024, Hu et al.
U.S. Appl. No. 18/856,553, filed Oct. 11, 2024, Lu et al.
U.S. Appl. No. 18/864,860, filed Nov. 11, 2024, Shivalila et al.
U.S. Appl. No. 18/864,863, filed Nov. 11, 2024, Liu et al.
U.S. Appl. No. 18/942,334, filed Nov. 8, 2024, Yang et al.
U.S. Appl. No. 18/953,020, filed Nov. 19, 2024, Meena et al.
U.S. Appl. No. 19/008,522, filed Jan. 2, 2025, Vargeese et al.
U.S. Appl. No. 19/085,460, filed Mar. 20, 2025, Bowman et al.
U.S. Appl. No. 19/102,669, filed Feb. 10, 2025, Lake et al.
International Search Report for PCT/US2022/047846, 6 pages (mailed Jul. 18, 2023).
Invitation to Pay Additional Fees for PCT/US2022/047846, 3 pages (mailed May 11, 2023).
Written Opinion for PCT/US2022/047846. 9 pages (Jul. 18, 2023).

* cited by examiner

OLIGONUCLEOTIDE COMPOSITIONS AND METHODS OF USE THEREOF

CROSS-REFERENCE TO RELATED APPLICATIONS

This application is a National Stage Entry of PCT Application No. PCT/US2020/029959, filed Apr. 24, 2020 and published Oct. 29, 2020 as WO 2020/219983, which claims priority to U.S. Provisional Application No. 62/838,763, filed Apr. 25, 2019, the entirety of which is incorporated herein by reference.

SEQUENCE LISTING

The instant application contains a Sequence Listing which has been submitted electronically in ASCII format and is hereby incorporated by reference in its entirety. Said ASCII copy, created on Jun. 1, 2020, is named Sequence_Listing.txt and is 71,733 bytes in size.

BACKGROUND

Oligonucleotides are useful in various applications, e.g., therapeutic, diagnostic, and/or research applications. For example, oligonucleotides targeting various genes can be useful for treatment of conditions, disorders or diseases related to such target genes.

SUMMARY

Among other things, the present disclosure provides technologies for designing, manufacturing and utilizing oligonucleotides and compositions. Particularly, in some embodiments, the present disclosure provides useful patterns of internucleotidic linkages [e.g., types, modifications, and/or configuration (Rp or Sp) of chiral linkage phosphorus, etc.] which, when combined with one or more other structural elements described herein, e.g., nucleobase modifications (and patterns thereof), sugar modifications (and patterns thereof), additional chemical moieties (and patterns thereof), etc., can provide oligonucleotides and compositions with high activities and/or various desired properties, e.g., high selectivity, low toxicity, etc.

In some embodiments, the present disclosure provides technologies (e.g., oligonucleotides, compositions, methods, etc.) for modulating levels of RHO (Rhodopsin) gene products (e.g., transcripts, proteins, etc.). Among other things, provided technologies can provide various advantages, such as high selectivity (e.g., less off-target effects), high allele-specificity (e.g., selectively reducing transcripts containing disease-associated mutation(s) and/or products encoded thereby over transcripts containing no or fewer disease-associated mutation(s) and/or products encoded thereby) and/or high activities (e.g., effectively reducing levels and/or activities of target gene products at low concentrations).

In some embodiments, the present disclosure provides technologies that have high selectivity for a target nucleic acid over a reference nucleic acid. In some embodiments, a target nucleic acid is a transcript of one allele of a gene and a reference nucleic acid is a transcript of a different allele of the same gene. In some embodiments, a target nucleic acid is a transcript of a wild-type nucleic acid sequence (e.g., a wild-type RHO gene), and a reference nucleic acid is a transcript of a mutant nucleic acid sequence (e.g., a mutant RHO gene (e.g., comprising a P23H mutation). In some embodiments, a target nucleic acid is associated with a condition, disorder or disease, and a reference nucleic acid is less or is not associated with the condition, disorder or disease. In some embodiments, provided technologies selectively reduce levels, expression, and/or activities of target nucleic acids and/or products encoded thereby over those of reference nucleic acids and/or products encoded thereby. In some embodiments, when aligned with sequences of oligonucleotides of the present disclosure (or a portion thereof, e.g., a core region), sequences of reference nucleic acids contain one or more mismatches than those of target nucleic acids. In some embodiments, a target nucleic acid is fully complementary to the base sequence of an oligonucleotide (or a portion thereof, e.g., a core region) while a reference nucleic acid comprises one ore more mismatches. In some embodiments, a target nucleic acid sequence and a reference nucleic acid sequence differs at one or more sites, e.g., a mutation site, a single-nucleotide polymorphism (SNP) site, etc. In some embodiments, a target nucleic acid sequence and a reference nucleic acid sequence comprise a difference at a SNP site. In some embodiments, a site in a target nucleic acid is fully complementary to a site in an oligonucleotide of the present disclosure while the corresponding site in a reference nucleic acid is not. In some embodiments, a target nucleic acid sequence and a reference nucleic acid sequence comprise a difference at a point mutation site. In some embodiments, a point mutation site in a target nucleic acid is fully complementary to a site in an oligonucleotide of the present disclosure while the corresponding point mutation site in a reference nucleic acid is not. In some embodiments, a point mutation site is RHO P23H mutation ([CCC]>H [CAC]).

In some embodiments, a SNP is any SNP disclosed herein (e.g., in Table S2).

In some embodiments, a SNP is SNP rs104893768. For this SNP, in some instances there is a C at this position in the wild-type (normal or non-disease-associated or less disease associated) RHO mRNA, and/or A in the mutant (or disease-associated or more disease-associated) RHO mRNA. The presence of the mutant allele of this SNP yields the missense variant P [CCC]>H [CAC], also known as P23H or RHO P23H mutation.

The RHO P23H mutation can be a dominant negative and a toxic gain-of-function mutation. ER (endoplasmic reticulum)-retention of a Rhodopsin mutant with the P23H mutation (sometimes referenced as RHO P23H or $RHO^{P23H}$ or the like) can induce the unfolded protein response (UPR), aggregation of the misfolded mutant protein, and later apoptosis of rod and cone cells, and retinal degeneration, also known as retinitis pigmentosa.

Wild-type Rhodopsin protein reportedly forms aggregates upon cellular accumulation. Some mutations of rhodopsin such as the point mutation P23H result in greater aggregation, forming aggresomes. These aggregates reportedly cause progressive degeneration of retinal cells, leading to blindness in RP.

In some embodiments, methods and compositions described herein provide for treating or delaying the onset or progression of diseases of the eye, e.g., a disorder that affects retinal cells, e.g., photoreceptor cells, including but not limited to a retinopathy or retinitis. In some embodiments, methods and compositions discussed herein, provide for treating or delaying the onset or progression of a disease associating with RHO mutation (e.g., P23H) (e.g., a RHO-related disease, disorder or condition), e.g., by a RHO oligonucleotide. In some embodiments, provided RHO oligonucleotides are oligonucleotides targeting RHO, and can reduce levels of mutant RHO transcripts and/or one or more products encoded thereby. In some embodiments, a RHO oligonucleotide is useful for preventing, treating and delaying the onset or progression of a RHO-related condition, disorder and/or disease, including retinopathy (e.g, retinal degeneration, retinal degenerative disease, retinal degenerative disorder, inherited retinal degenerative disorder, retinitis pigmentosa, autosomal dominant retinitis pigmentosa, etc.).

In some embodiments, a target nucleic acid is a wild-type or mutant RHO transcript which comprises a SNP (e.g., a SNP listed in Table S2).

In some embodiments, the present disclosure pertains to a method of knocking down a pathogenic or disease-associated mutant (e.g., a mutant allele) of RHO in a cell or in a patient (e.g., a patient in need thereof), wherein the cell is heterozygous at a particular position (e.g., a SNP), and the method comprises the step of introducing into the cell or administering to the patient a RHO oligonucleotide which targets a particular allele of the particular position which is in phase with the pathogenic or disease-associated mutation.

As a non-limiting example, at a first position, the genome of a patient may be heterozygous wild type/mutant, wherein the mutation is deleterious; for example, a patient may be heterozygous wild type/P23H; and at a second position, the patient is also heterozygous, wherein the second position is not necessarily linked to a RHO-related disease, disorder or condition; but one allele (e.g., allele 1 of position 2) for the second position is in phase with the wild-type variant of the first position, and a second allele (e.g., allele 2 of position 2) is in phase with the deleterious mutation in position 1; and a RHO oligonucleotide can target allele 2 of position 2 and be capable of allele-specific knockdown of allele 2 of position 2, thereby also decreasing the expression, level and/or activity of a RHO gene transcript having the deleterious mutation.

Various RHO SNPs are listed in Table S2. Any variant of any SNP listed therein can be an allele 1 or 2 of position 2.

As a non-limiting example, the genome of a patient suffering from a susceptible to a RHO-related disease, disorder or condition can be heterozygous at position SNP rs104893768, wherein an A allele is associated with a deleterious mutation (P23H), but a C allele is considered wild-type (non-pathogenic). The same patient may be heterozygous at another position, e.g., SNP rs2269736, which might be G, A, or C, all of which are reportedly considered benign. If, for example, the C allele of rs2269736 is in phase with (e.g., on the same chromosome as) the mutant allele of rs104893768; and if the A allele of rs2269736 is in phase with the wild-type allele of rs104893768, then a RHO oligonucleotide which targets the C allele of rs2269736 (and also knocks down this allele), would also knock down (e.g., decrease the expression, level and/or activity of) the mutant allele.

In the same manner, in some embodiments, a RHO oligonucleotide has a base sequence which is complementary to and hybridizes with a sequence of a RHO gene target comprising a first variant of a SNP, wherein the RHO oligonucleotide is capable of mediating knock down of the allele of RHO comprising the first variant of the SNP, and wherein the first variant of the SNP is in phase with a deleterious mutation in RHO, and wherein hybridization and knockdown occur in a cell, tissue, organ or patient which is heterozygous at the SNP.

In some embodiments, a target nucleic acid is a transcript (e.g., a mutant RHO mRNA) that comprises SNP rs104893768, has an A at this SNP position, and is associated with a condition, disorder or disease [e.g., retinopathy (e.g, retinal degeneration, retinal degenerative disease, retinal degenerative disorder, inherited retinal degenerative disorder, retinitis pigmentosa, autosomal dominant retinitis pigmentosa, etc.)]. In some embodiments, a reference nucleic acid is a transcript (e.g., a wide-type RHO mRNA) that comprises SNP rs104893768, has an C at this SNP position, and is less, or is not, associated with a condition, disorder or disease [e.g., retinopathy (e.g, retinal degeneration, retinal degenerative disease, retinal degenerative disorder, inherited retinal degenerative disorder, retinitis pigmentosa, autosomal dominant retinitis pigmentosa, etc.)].

In some embodiments, a target nucleic acid is a RHO mRNA that comprises the P23H mutation. In some embodiments, a reference nucleic acid is a RHO mRNA that does not contain the P23H mutation.

In some embodiments, the base sequence of a RHO oligonucleotide which targets SNP rs104893768 (e.g., as those skilled in the art will appreciate, whose base sequence is complementary to a base sequence that comprises the SNP site and its characteristic surrounding sequences in the mRNA), or P23H mutation, is, comprises, or comprises at least 10 contiguous bases (e.g., 10-15, 10-20, 10, 11, 12, 13, 14, 15, 16, 17, 18, 19, or 20) of the sequence of: GGTACTCGAAGTGGCT (SEQ ID NO: 1), GGTACTCGAAGTGGCTG (SEQ ID NO: 2), GGTACTCGAAGTGGCTGC (SEQ ID NO: 3), GGTACTCGAAGTGGCTGCG (SEQ ID NO: 4), GGTACTCGAAGTGGCTGCGT (SEQ ID NO: 5), GTACTCGAAGTGGCTGCGT (SEQ ID NO: 6), TACTCGAAGTGGCTGCGT (SEQ ID NO: 7), ACTCGAAGTGGCTGCGT (SEQ ID NO: 8), GGTACTCGAAGTGGCUGCGU (SEQ ID NO: 9), GGTACTCGAAGTGGCUGCGU (SEQ ID NO: 10), or CTCGAAGTGGCTGCGT (SEQ ID NO: 11), wherein each T can be independently substituted with U and vice versa. In some embodiments, the base sequence of such an oligonucleotide is or comprises GGTACTCGAAGTGGCT (SEQ ID NO: 1), GGTACTCGAAGTGGCTG (SEQ ID NO: 2), GGTACTCGAAGTGGCTGC (SEQ ID NO: 3), GGTACTCGAAGTGGCTGCG (SEQ ID NO: 4), GGTACTCGAAGTGGCTGCGT (SEQ ID NO: 5), GTACTCGAAGTGGCTGCGT (SEQ ID NO: 6), TACTCGAAGTGGCTGCGT (SEQ ID NO: 7), ACTCGAAGTGGCTGCGT (SEQ ID NO: 8), GGTACTCGAAGTGGCUGCGU (SEQ ID NO: 9), GGTACTCGAAGTGGCUGCGU (SEQ ID NO: 10), or CTCGAAGTGGCTGCGT (SEQ ID NO: 11), wherein each T can be independently substituted with U and vice versa. In some embodiments, the base sequence of such an oligonucleotide is GGTACTCGAAGTGGCT (SEQ ID NO: 1), GGTACTCGAAGTGGCTG (SEQ ID NO: 2), GGTACTCGAAGTGGCTGC (SEQ ID NO: 3), GGTACTCGAAGTGGCTGCG (SEQ ID NO: 4), GGTACTCGAAGTGGCTGCGT (SEQ ID NO: 5), GTACTCGAAGTGGCTGCGT (SEQ ID NO: 6), TACTCGAAGTGGCTGCGT (SEQ ID NO: 7), ACTCGAAGTGGCTGCGT (SEQ ID NO: 8), GGTACTCGAAGTGGCUGCGU (SEQ ID NO: 9), GGTACTCGAAGTGGCUGCGU (SEQ ID NO: 10), or CTCGAAGTGGCTGCGT (SEQ ID NO: 11), wherein each T can be independently substituted with U and vice versa. In some embodiments, the base sequence of such an oligonucleotide is or comprises GGTACTCGAAGTGGCT (SEQ ID NO: 1), GGTACTCGAAGTGGCTG (SEQ ID NO: 2), GGTACTCGAAGTGGCTGC (SEQ ID NO: 3), GGTACTCGAAGTGGCTGCG (SEQ ID NO: 4), GGTACTCGAAGTGGCTGCGT (SEQ ID NO: 5), GTACTCGAAGTGGCTGCGT (SEQ ID NO: 6), TACTCGAAGTGGCTGCGT (SEQ ID NO: 7), ACTCGAAGTGGCTGCGT (SEQ ID NO: 8), GGTACTCGAAGTGGCUGCGU (SEQ ID NO: 9), GGTACTCGAAGTGGCUGCGU (SEQ ID NO: 10), or CTCGAAGTGGCTGCGT (SEQ ID NO: 11).

It has been reported that: SNP rs104893768 in *Homo sapiens*: Position: chr3:129528801 (GRCh38.p12); Alleles: C>A; Variation Type: SNV, Single Nucleotide Variation; Gene: Consequence Missense Variant. rs104893768: Allele: A (allele ID: 28052) is associated with RCV000013887.17, Retinitis pigmentosa 4, Pathogenic; and RCV000490234.1, Pathogenic.

In some embodiments, a RHO oligonucleotide which targets rs104893768 (e.g., as those skilled in the art will appreciate, whose base sequence is complementary to a base sequence that comprises the SNP site and its characteristic surrounding sequences in the mRNA) has a base sequence which comprises at least 10 contiguous bases (e.g., 10-15, 10-20, 10, 11, 12, 13, 14, 15, 16, 17, 18, 19 or 20) of the mutant or wild-type sequence of: GGTACTCGAAGTGGCT (SEQ ID NO: 1), GGTACTCGAAGTGGCTG (SEQ ID NO: 2), GGTACTCGAAGTGGCTGC (SEQ ID NO: 3), GGTACTCGAAGTGGCTGCG (SEQ ID NO: 4), GGTACTCGAAGTGGCTGCGT (SEQ ID NO: 5), GTACTCGAAGTGGCTGCGT (SEQ ID NO: 6), TACTCGAAGTGGCTGCGT (SEQ ID NO: 7), ACTCGAAGTGGCTGCGT (SEQ ID NO: 8), GGTACTCGAAGTGGCUGCGU (SEQ ID NO: 9), GGTACTCGAAGTGGCUGCGU (SEQ ID NO: 10), or CTCGAAGTGGCTGCGT (SEQ ID NO: 11), wherein the nucleobase in the oligonucleotide that is complementary to the mutant isoform of rs104893768 in the mRNA is T (illustrated herein in bold, underlined), and wherein the nucleobase complementary to the wild-type isoform of the SNP would be G, wherein the at least 10 contiguous bases comprise the position of the SNP, and wherein each T can be independently substituted with U and vice versa.

In some embodiments, a target nucleic acid sequence is a RHO mRNA which comprises SNP rs104893768 and which is A in the mutant mRNA at this SNP position (and T in the corresponding RHO oligonucleotide), and its allele is associated with retinopathy (e.g, retinal degeneration, retinal degenerative disease, retinal degenerative disorder, inherited retinal degenerative disorder, retinitis pigmentosa, or autosomal dominant retinitis pigmentosa, etc.). In some embodiments, a RHO gene, gene transcript, protein or other gene product comprises the mutant variant of SNP rs104893768 and has the mutation P23H.

In some embodiments, a mutant RHO (or a RHO variant) comprises a disease-associated mutation. In some embodiments, a disease-associated mutation is a mutation which is associated with a particular disease, disorder or condition (in the present disclosure, for example, a RHO-related disease, disorder or condition). In some embodiments, a disease-associated mutation may be found in the genome of a patient suffering from or susceptible to a particular disease, disorder or condition (in the present disclosure, for example, a RHO-related disease, disorder or condition), but is either absent or more rarely found in the genome of a patient who is not suffering from or susceptible to the disease, disorder or condition. In some embodiments, a mutant RHO comprises a mutant allele of one or more SNP (the allele on the same DNA strand or chromosome as the disease-associated mutations). In some embodiments, a mutant RHO comprises both a disease-associated mutation and a mutant allele of a particular SNP on the same chromosomal strand.

In some embodiments, a RHO oligonucleotide which targets SNP rs104893768 has a base sequence which comprises at least 10 contiguous bases of the mutant or wild-type sequence of: GGTACTCGAAGTGGCT (SEQ ID NO: 1), GGTACTCGAAGTGGCTG (SEQ ID NO: 2), GGTACTCGAAGTGGCTGC (SEQ ID NO: 3), GGTACTCGAAGTGGCTGCG (SEQ ID NO: 4), GGTACTCGAAGTGGCTGCGT (SEQ ID NO: 5), GTACTCGAAGTGGCTGCGT (SEQ ID NO: 6), TACTCGAAGTGGCTGCGT (SEQ ID NO: 7), ACTCGAAGTGGCTGCGT (SEQ ID NO: 8), GGTACTCGAAGTGGCUGCGU (SEQ ID NO: 9), GGTACTCGAAGTGGCUGCGU (SEQ ID NO: 10), or CTCGAAGTGGCTGCGT (SEQ ID NO: 11), wherein each T can be independently substituted with U and vice versa.

In some embodiments, the sequence of a provided RHO oligonucleotide is fully complementary to a target nucleic acid sequence at a particular site, e.g., a SNP site (e.g., the sequence of the RHO oligonucleotide is complementary to the mutant isoform of the SNP), a mutation site (e.g., P23H mutation), etc., and is not complementary to a reference nucleic acid sequence at the site (e.g., the sequence of the RHO oligonucleotide is not complementary to the wild-type isoform of the SNP/mutation site).

In some embodiments, a RHO oligonucleotide is allele-specific, wherein the oligonucleotide preferentially decreases the expression, level and/or activity of a mutant RHO target nucleic acid compared to a wild-type or reference RHO nucleic acid. In some embodiments, an allele-specific RHO oligonucleotide can selectively reduce the expression, level and/or activity of a mutant RHO target nucleic acid over a wild-type or reference RHO nucleic acid by at least 2, 3, 4, 5, 6, 7, 8, 9, 10, 11, 12, 13, 14, 15, 16, 17, 18, 19, 20, 25, 30, 40, 50, 60, 70, 80, 90, 100 or more fold when measured by the percentage of reduction in the presence of the oligonucleotide compared to absence of the oligonucleotide (or presence of a reference oligonucleotide) (e.g., if reduction of expression, level and/or activity of a mutant RHO target nucleic acid is 90% and that of the wild-type is 10%, the selectivity is 90%/10%=9). In some embodiments, an allele-specific RHO oligonucleotide can selectively reduce the expression, level and/or activity of a mutant RHO target nucleic acid over a wild-type or reference RHO nucleic acid by at least 2, 3, 4, 5, 6, 7, 8, 9, 10, 11, 12, 13, 14, 15, 16, 17, 18, 19, 20, 25, 30, 40, 50, 60, 70, 80, 90, 100 or more fold when measured by the remaining percentage in the presence of the oligonucleotide compared to absence of the oligonucleotide (or presence of a reference oligonucleotide) (e.g., if the remaining percentage of expression, level and/or activity of a mutant RHO target nucleic acid is 10% in the presence of the oligonucleotide (100% when absence of the oligonucleotide (or presence of a reference oligonucleotide)) and that of the wild-type is 50%, the selectivity is 50%/10%=5). In some embodiments, selectivity is assessed using IC50 under a condition (e.g., as shown in the Examples, if IC50 for a mutant transcript is about 0.5 uM and for a wild-type transcript is about 30 uM, the selectivity about 60 fold). In some embodiments, for an allele-specific oligonucleotide, selectivity is at least 3 fold. In some embodiments, for an allele-specific oligonucleotide, selectivity is at least 4 fold. In some embodiments, for an allele-specific oligonucleotide, selectivity is at least 5 fold. In some embodiments, for an allele-specific oligonucleotide, selectivity is at least 10 fold. As those skilled in the art will appreciate, various technologies may be utilized to assess oligonucleotide selectivity. In some embodiments, a useful technology is or comprises a reporter assay as described in the Examples. In some embodiments, an allele-specific RHO oligonucleotide can reduce the expression, level and/or activity of a mutant RHO target nucleic acid by at least 20%, 25%, 30%, 40%, 45%, 50%, 55%, 60%, 65%, 70%, 75%, 80%, 85%, 90%, or 95% compared to absence of the oligonucleotide (or presence of a reference oligonucleotide) at a concentration (e.g., those described in the Examples, e.g., about 0.04, 0.12, 0.37, 1.11, 3.33 or 10 uM, etc.). In some embodiments, a reduction is at least 50%, 55%, 60%, 65%, 70%, 75%, 80%, 85%, 90%, or 95%. In some embodiments, the reduction is at least 60%, 65%, 70%, 75%, 80%, 85%, 90%, or 95%. In some embodiments, an allele-specific RHO oligonucleotide reduces the expression, level and/or activity of a wild-type or reference RHO target nucleic acid by no more than 20%, 25%, 30%, 40%, 45%, 50%, 55%, 60%, 65%, 70%, 75%, 80%, 85%, 90%, or 95% compared to absence of the oligonucleotide (or presence of a reference oligonucleotide) at a concentration (e.g., those described in the Examples, e.g., about 0.04, 0.12, 0.37, 1.11, 3.33 or 10 uM, etc.). In some embodiments, the percentage is no more than 20%, 25%, 30%, 40%, 45%, or 50%. In some embodiments, the percentage is no more than about 30%.

In some embodiments, a RHO oligonucleotide targets a RHO target nucleic acid, but outside a region known to comprise a SNP or mutation. In some embodiments, such a RHO oligonucleotide can decrease the expression, level and/or activity of both the mutant and wild-type alleles of the RHO target nucleic acid. In some embodiments, such a RHO oligonucleotide is pan-specific and can effectively reduce the expression, level and/or activity of both mutant and wild-type RHO target nucleic acids. In some embodiments, selectivity of a pan-specific oligonucleotide is no more than 1.1, 1.2, 1.3, 1.4, 1.5, 1.6, 1.7, 1.8, 1.9 or 2 fold. In some embodiments, a pan-specific oligonucleotide can reduce the expression, level and/or activity of a mutant and a wild-type RHO target nucleic acid by at least 20%, 25%, 30%, 40%, 45%, 50%, 55%, 60%, 65%, 70%, 75%, 80%, 85%, 90%, or 95% compared to absence of the oligonucleotide (or presence of a reference oligonucleotide) at a concentration (e.g., those described in the Examples, e.g., about 0.04, 0.12, 0.37, 1.11, 3.33 or 10 uM, etc.). In some embodiments, a pan-specific oligonucleotide can reduce the expression, level and/or activity of a mutant and a wild-type RHO target nucleic acid by at least 40%, 45%, 50%, 55%, 60%, 65%, 70%, 75%, 80%, 85%, 90%, or 95% compared to absence of the oligonucleotide (or presence of a reference oligonucleotide).

In some embodiments, the base sequence of a RHO oligonucleotide is or comprises, or comprises a span of at least 10 contiguous bases of the sequence GGTACTCGAAGTGGCT (SEQ ID NO: 1), GGTACTCGAAGTGGCTG (SEQ ID NO: 2), GGTACTCGAAGTGGCTGC (SEQ ID NO: 3), GGTACTCGAAGTGGCTGCG (SEQ ID NO: 4), GGTACTCGAAGTGGCTGCGT (SEQ ID NO: 5), GTACTCGAAGTGGCTGCGT (SEQ ID NO: 6), TACTCGAAGTGGCTGCGT (SEQ ID NO: 7), ACTCGAAGTGGCTGCGT (SEQ ID NO: 8), or CTCGAAGTGGCTGCGT (SEQ ID NO: 11), or a span thereof (e.g., 10 contiguous bases), and which does not comprise a SNP in its base sequence, and wherein each T can be independently substituted with U and vice versa.

In some embodiments, provided oligonucleotides and compositions are useful for preventing and/or treating various conditions, disorders or diseases, particularly RHO-related conditions, disorders or diseases, including retinopathy (e.g, retinal degeneration, retinal degenerative disease, retinal degenerative disorder, inherited retinal degenerative disorder, retinitis pigmentosa, autosomal dominant retinitis pigmentosa, etc.). In some embodiments, provided oligonucleotides and compositions reduce levels of RHO transcripts (e.g., mRNA) and/or products encoded thereby. In some embodiments, provided oligonucleotides and compositions selectively reduce levels of RHO transcripts and/or products encoded thereby that are associated with retinopathy (e.g, retinal degeneration, retinal degenerative disease, retinal degenerative disorder, inherited retinal degenerative disorder, retinitis pigmentosa, autosomal dominant retinitis pigmentosa, etc.). In some embodiments, provided oligonucleotides and compositions selectively reduce levels of RHO transcripts comprising disease-associated mutation(s) (e.g., 36 or more) and/or products encoded thereby.

In some embodiments, the present disclosure provides RHO oligonucleotides (e.g., oligonucleotides that can target a RHO gene) and compositions thereof that can reduce levels of RHO transcripts (or products thereof). In some embodiments, RHO oligonucleotides comprise a sequence that is identical with or complementary to a portion (e.g., a span of 10, 11, 12, 13, 14, 15, 16, 17, 18, 19 or more contiguous bases) of a RHO gene or a product encoded thereby (e.g., a RHO mRNA). In some embodiments, RHO oligonucleotides and compositions thereof selectively reduce levels of RHO transcripts (or products thereof) that are associated with a condition, disorder or disease, e.g., retinopathy (e.g, retinal degeneration, retinal degenerative disease, retinal degenerative disorder, inherited retinal degenerative disorder, retinitis pigmentosa, autosomal dominant retinitis pigmentosa, etc.).

Among other things, the present disclosure encompasses the recognition that controlling structural elements of oligonucleotides can have a significant impact on oligonucleotide properties and/or activities, including knockdown (e.g., a decrease in the activity, expression and/or level) of a RHO target gene (or a product thereof). In some embodiments, retinopathy (e.g, retinal degeneration, retinal degenerative disease, retinal degenerative disorder, inherited retinal degenerative disorder, retinitis pigmentosa, autosomal dominant retinitis pigmentosa, etc.) is associated with the presence of mutant RHO which comprises a disease-associated mutation(s). In some embodiments, knockdown is allele-specific (wherein the mutant allele of RHO is preferentially knocked down relative to the wild-type). In some embodiments, the knockdown is pan-specific (wherein both the mutant and wild-type alleles of RHO are significantly knocked down). In some embodiments, knockdown of a RHO target gene is mediated by RNase H and/or steric hindrance affecting translation. In some embodiments, knockdown of a RHO target gene is mediated by a mechanism involving RNA interference. In some embodiments, controlled structural elements of RHO oligonucleotides include but are not limited to: base sequence, chemical modifications (e.g., modifications of a sugar, base and/or internucleotidic linkage) or patterns thereof, alterations in stereochemistry (e.g., stereochemistry of a backbone chiral internucleotidic linkage) or patterns thereof, structure of a first or second wing or core, and/or conjugation with an additional chemical moiety (e.g., a carbohydrate moiety, a targeting moiety, etc.). Particularly, in some embodiments, the present disclosure demonstrates that control of stereochemistry of backbone chiral centers (stereochemistry of linkage phosphorus), optionally with controlling other aspects of oligonucleotide design and/or incorporation of carbohydrate moieties, can greatly improve properties and/or activities of RHO oligonucleotides.

In some embodiments, the present disclosure pertains to any RHO oligonucleotide which operates through any mechanism, and which comprises any sequence, structure or format (or portion thereof) described herein, wherein the oligonucleotide comprises at least one non-naturally-occurring modification of a base, sugar or internucleotidic linkage.

In some embodiments, the present disclosure provides an oligonucleotide composition comprising a plurality of oligonucleotides, wherein the oligonucleotides comprise at least one (e.g., 1-100, 1-50, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, or more) chirally controlled internucleotidic linkage [an internucleotidic linkage whose linkage phosphorus is in or is enriched for the Rp or Sp configuration (e.g., 80-100%, 85%-100%, 90%-100%, 95%-100%, or 85%, 90%, 91%, 92%, 93%, 94%, 95%, 96%, 97%, 98%, 99% or more of all oligonucleotides of the same constitution in the composition share the same stereochemistry at the linkage phosphorus) but not a random mixture of the Rp and Sp, such an internucleotidic linkage also a "stereodefined internucleotidic linkage", and such an oligonucleotide composition also a "stereodefined oligonucleotide composition"], e.g., a phosphorothioate linkage whose linkage phosphorus is Rp or Sp. In some embodiments, the number of chirally controlled internucleotidic linkages is 1-100, 1-50, 1-40, 1-35, 1-30, 1-25, 1-20, 5-100, 5-50, 5-40, 5-35, 5-30, 5-25, 5-20, 1, 2, 3, 4, 5, 6, 7, 8, 9, 10, 11, 12, 13, 14, 15, 16, 17, 18, 19, 20, 21, 22, 23, 24, or 25. In some embodiments, at least 5%, 10%, 15%, 20%, 25%, 30%, 35%, 40%, 45%, 50%, 55%, 60%, 65%, 70%, 75%, 80%, 85%, 90%, or 95%, or 100% of all chiral internucleotidic linkages are chirally controlled internucleotidic linkages. In some embodiments, at least 5%, 10%, 15%, 20%, 25%, 30%, 35%, 40%, 45%, 50%, 55%, 60%, 65%, 70%, 75%, 80%, 85%, 90%, or 95%, or 100% of all internucleotidic linkages are chirally controlled internucleotidic linkages. In some embodiments, at least 5%, 10%, 15%, 20%, 25%, 30%, 35%, 40%, 45%, 50%, 55%, 60%, 65%, 70%, 75%, 80%, 85%, 90%, or 95%, or 100% of all chiral internucleotidic linkages are chirally controlled internucleotidic linkages and are Sp. In some embodiments, at least 5%, 10%, 15%, 20%, 25%, 30%, 35%, 40%, 45%, 50%, 55% 60%, 65%, 70%, 75%, 80%, 85%, 90%, or 95%, or 100% of all internucleotidic linkages are chirally controlled internucleotidic linkages and are Sp. In some embodiments, at least 1 internucleotidic linkage is chirally controlled internucleotidic linkage and is Rp. In some embodiments, at least 2 internucleotidic linkages are chirally controlled internucleotidic linkage and are Rp. In some embodiments, at least 3 internucleotidic linkages are chirally controlled internucleotidic linkage and are Rp. In some embodiments, at least 4 internucleotidic linkages are chirally controlled internucleotidic linkage and are Rp. In some embodiments, at least 5 internucleotidic linkages are chirally controlled internucleotidic linkage and are Rp. In some embodiments, pattern of backbone chiral centers of an oligonucleotide or a portion thereof (e.g., a core) is or comprises $Rp(Sp)_2$. In some embodiments, pattern of backbone chiral centers of an oligonucleotide or a portion thereof (e.g., a core) is or comprises $SpRp(Sp)_2$. In some embodiments, pattern of backbone chiral centers of an oligonucleotide or a portion thereof (e.g., a core) is or comprises $(Rp)_2$. In some embodiments, pattern of backbone chiral centers of an oligonucleotide or a portion thereof (e.g., a core) is or comprises $Sp(Rp)_2$. In some embodiments, pattern of backbone chiral centers of an oligonucleotide or a portion thereof (e.g., a core) is or comprises $(Sp)m(Rp)_2$. In some embodiments, pattern of backbone chiral centers of an oligonucleotide or a portion thereof (e.g., a core) is or comprises (Np)t[(Rp)n(Sp)m]y, wherein each of t, n, m, and y is independently as described herein.

In some embodiments, the present disclosure demonstrates that oligonucleotides comprising an Rp chirally controlled internucleotidic linkage at certain positions, e.g., −3, −2, −1, +1, +2, or +3 position, relative to a differentiating position (a position whose base or whose complementary base can differentiate one nucleic acid from other nucleic acid(s) (e.g., a target nucleic acid and a reference nucleic acid, one allele from the other(s)), such as a point mutation site, a SNP site, etc.) can provide high activities and/or selectivities and, in some embodiments, can be particularly useful for reducing levels of disease-associated transcripts and/or products encoded thereby. Unless otherwise specified, for Rp internucleotidic linkage positioning, "−" is counting from the nucleoside at a differentiating position toward the 5'-end of an oligonucleotide with the internucleotidic linkage at the −1 position being the internucleotidic linkage bonded to the 5'-carbon of the nucleoside at the differentiating position, and "+" is counting from the nucleoside at a differentiating position toward the 3'-end of an oligonucleotide with the internucleotidic linkage at the +1 position being the internucleotidic linkage bonded to the 3'-carbon of the nucleoside at the differentiating position. In some embodiments, Rp at −3 position provided increased activity and/or selectivity. In some embodiments, Rp at −2 position provided increased activity and/or selectivity. In some embodiments, Rp at −1 position provided increased activity and/or selectivity. In some embodiments, Rp at +1 position provided increased activity and/or selectivity. In some embodiments, Rp at +2 position provided increased activity and/or selectivity. In some embodiments, Rp at +3 position provided increased activity and/or selectivity.

In some embodiments, the present disclosure pertains to a RHO oligonucleotide composition wherein the RHO oligonucleotides comprise at least one chiral internucleotidic linkage which is not chirally controlled (e.g., the RHO oligonucleotide comprises a phosphorothioate internucleotidic linkage which is not chirally controlled).

In some embodiments, oligonucleotides comprise one or more (e.g., 1, 2, 3, 4, 5, 6, 7, 8, 9, or 10) non-negatively charged internucleotidic linkages. In some embodiments, oligonucleotides comprise one or more (1, 2, 3, 4, 5, 6, 7, 8, 9, or 10) neutral internucleotidic linkages. In some embodiments, a RHO oligonucleotide comprises a non-negatively charged or neutral internucleotidic linkage. In some embodiments, the present disclosure provides an oligonucleotide, wherein the base sequence of the oligonucleotide comprises at least 10 contiguous bases of a base sequence that is identical to or complementary to a base sequence of a RHO gene or a transcript thereof, wherein the oligonucleotide comprises at least one internucleotidic linkage comprising a stereodefined linkage phosphorus, and wherein the oligonucleotide is capable of decreasing the level, expression and/or activity of a RHO target gene or a gene product thereof.

In some embodiments, the present disclosure encompasses the recognition that various optional additional chemical moieties, such as carbohydrate moieties, targeting moieties, etc., when incorporated into RHO oligonucleotides, can improve one or more properties and/or activities.

In some embodiments, an additional chemical moiety is selected from: GalNAc, glucose, GluNAc (N-acetyl amine glucosamine) and anisamide moieties and derivatives thereof, or any additional chemical moiety described herein and/or known in the art. In some embodiments, an oligonucleotide can comprise two or more additional chemical moieties, wherein the additional chemical moieties are identical or non-identical, or are of the same category (e.g., carbohydrate moiety, sugar moiety, targeting moiety, etc.) or not of the same category. In some embodiments, certain additional chemical moieties facilitate delivery of oligonucleotides to desired cells, tissues and/or organs. In some embodiments, certain additional chemical moieties facilitate internalization of oligonucleotides. In some embodiments, certain additional chemical moieties increase oligonucleotide stability.

In some embodiments, the present disclosure provides a chirally controlled RHO oligonucleotide composition comprising a plurality of RHO oligonucleotides which share:

1) a common base sequence;

2) a common pattern of backbone linkages; and 3) a common pattern of backbone chiral centers, which composition is a substantially pure preparation of a single oligonucleotide in that a non-random or controlled level of the oligonucleotides in the composition have the common base sequence, the common pattern of backbone linkages, and the common pattern of backbone chiral centers.

In some embodiments, an oligonucleotide composition is a chirally controlled oligonucleotide composition comprising a plurality of RHO oligonucleotides of a particular oligonucleotide type, which composition is chirally controlled in that it is enriched, relative to a substantially racemic preparation of oligonucleotides having the same base sequence, for oligonucleotides of the particular oligonucleotide type.

In some embodiments, the present disclosure provides a chirally controlled oligonucleotide composition comprising a plurality of oligonucleotides capable of directing RHO knockdown, wherein oligonucleotides of the plurality are of a particular oligonucleotide type, which composition is enriched, relative to a substantially racemic preparation of oligonucleotides having the same base sequence, for oligonucleotides of the particular oligonucleotide type.

In some embodiments, the present disclosure provides a chirally controlled oligonucleotide composition comprising a plurality of oligonucleotides capable of directing RHO knockdown, wherein oligonucleotides of the plurality are of a particular oligonucleotide type, which composition is enriched, relative to a substantially racemic preparation of oligonucleotides having the same base sequence, for oligonucleotides of the particular oligonucleotide type.

In some embodiments, a provided RHO oligonucleotide comprises one or more blocks. In some embodiments, a block comprises one or more consecutive nucleosides, and/or nucleotides, and/or sugars, or bases, and/or internucleotidic linkages which share a common chemistry (e.g., at least one common modification of sugar, base or internucleotidic linkage, or combination or pattern thereof, or pattern of stereochemistry) which is not present in an adjacent block, or vice versa. In some embodiments, a RHO oligonucleotide comprises three or more blocks, wherein the blocks on either end are not identical and the oligonucleotide is thus asymmetric. In some embodiments, a block is a wing or a core.

In some embodiments, an oligonucleotide comprises at least one wing and at least one core, wherein a wing differs structurally from a core in that a wing of an oligonucleotide comprises a structure [e.g., stereochemistry, or chemical modification at a sugar, base or internucleotidic linkage (or pattern thereof), etc.] not present in the core, or vice versa. In some embodiments, the structure of an oligonucleotide comprises a wing-core-wing structure. In some embodiments, the structure of an oligonucleotide comprises a wing-core, core-wing, or wing-core-wing structure, wherein one wing differs in structure [e.g., stereochemistry, additional chemical moiety, or chemical modification at a sugar, base or internucleotidic linkage (or pattern thereof)] from the other wing and the core (for example, an asymmetrical oligonucleotide). In some embodiments, the structure of an oligonucleotide has or comprises a wing-core, core-wing, or wing-core-wing structure, and a block is a wing or core. In some embodiments, a core is also referenced to as a gap.

In some embodiments, a wing comprises a sugar modification or a pattern thereof that is absent from a core. In some embodiments, a wing comprises a sugar modification that is absent from a core. In some embodiments, one or more (e.g., 1, 2, 3, 4, 5, 6, 7, 8, 9, or 10) sugars of a wing is/are independently modified. In some embodiments, each wing sugar is independently modified. In some embodiments, each sugar in a wing is the same. In some embodiments, at least one sugar in a wing is different from another sugar in the wing. In some embodiments, one or more sugar modifications and/or patterns of sugar modifications in a first wing of an oligonucleotide (e.g., a 5'-wing) is/are different from one or more sugar modifications and/or patterns of sugar modifications in a second wing of the oligonucleotide (e.g., a 3'-wing). In some embodiments, a modification is a 2'-OR modification, wherein R is as described herein. In some embodiments, R is optionally substituted $C_{1-4}$ alkyl. In some embodiments, a modification is 2'-OMe. In some embodiments, a modification is a 2'-MOE. In some embodiments, a modified sugar is a high-affinity sugar, e.g., a bicyclic sugar (e.g., a LNA sugar), 2'-MOE, etc. In some embodiments, a sugar of a 3'-wing is a high-affinity sugar. In some embodiments, a 3'-wing comprises one or more, e.g., 1, 2, 3, 4, 5, 6, 7, 8, 9, 10 or more high-affinity sugars. In some embodiments, each sugar of a 3'-wing is independently a high-affinity sugar. In some embodiments, a high-affinity sugar is a 2'-MOE sugar. In some embodiments, each sugar of a 3'-wing independently comprises 2'-MOE. In some embodiments, a high-affinity sugar is bonded to a non-negatively charged internucleotidic linkage. In some embodiments, a high-affinity sugar is bonded to a neutral internucleotidic linkage. In some embodiments, a high-affinity sugar is bonded to two non-negatively charged internucleotidic linkages. In some embodiments, a high-affinity sugar is bonded to two neutral internucleotidic linkages. In some embodiments, a 5'-wing comprises 2-OMe modifications. In some embodiments, each 5'-wing sugar is 2'-OMe modified.

In some embodiments, a wing comprises one or more (e.g., 1, 2, 3, 4, 5, 6, 7, 8, 9, or 10) natural phosphate linkages. In some embodiments, a wing comprises one or more consecutive (e.g., 1, 2, 3, 4, 5, 6, 7, 8, 9, or 10) natural phosphate linkages. In some embodiments, in a 5'-wing each internucleotidic linkage linking two wing sugars is independently a natural phosphate linkage, except the internucleotidic linkage linking the first and second wing sugar from the 5'-end of the 5'-wing (which can be a modified internucleotidic linkage, optionally chirally controlled (e.g., a Rp phosphorothioate internucleotidic linkage, a Sp phosphorothioate internucleotidic linkage, etc.)). In some embodiments, in a 3'-wing each internucleotidic linkage linking two wing sugars is independently a natural phosphate linkage, except the internucleotidic linkage linking the first and second wing sugar from the 3'-end of the 3'-wing (which can be a modified internucleotidic linkage, optionally chirally controlled (e.g., a Rp phosphorothioate internucleotidic linkage, a Sp phosphorothioate internucleotidic linkage, etc.)). In some embodiments, in a wing each wing sugar linked by a natural phosphate linkage independently comprises a 2'-OR modification. In some embodiments, R is optionally substituted methyl. In some embodiments, R is substituted methyl. In some embodiments, 2'-OR is 2'-MOE. In some embodiments, in a wing each internucleotidic linkage linking two wing sugars is independently a modified internucleotidic linkage, optionally chirally controlled. In some embodiments, in a wing each internucleotidic linkage linking two wing sugars is independently chirally controlled phosphorothioate internucleotidic linkage. In some embodiments, in a wing each internucleotidic linkage linking two wing sugars is independently chirally controlled Sp phosphorothioate internucleotidic linkage. In some embodiments, in a wing each sugar linked by a modified internucleotidic linkage to another wing sugar is 2'-OMe modified.

In some embodiments, a wing comprises one or more (e.g., 1, 2, 3, 4, 5, 6, 7, 8, 9, or 10) non-negatively charged internucleotidic linkages. In some embodiments, a 5'-wing comprises one or more (e.g., 1, 2, 3, 4, 5, 6, 7, 8, 9, or 10) consecutive non-negatively charged internucleotidic linkages. In some embodiments, a 5'-wing comprises one or more (e.g., 1, 2, 3, 4, 5, 6, 7, 8, 9, or 10) non-negatively charged internucleotidic linkages. In some embodiments, a 3'-wing comprises one or more (e.g., 1, 2, 3, 4, 5, 6, 7, 8, 9, or 10) consecutive non-negatively charged internucleotidic linkages. In some embodiments, a 3'-wing comprises one or more (e.g., 1, 2, 3, 4, 5, 6, 7, 8, 9, or 10) non-negatively charged internucleotidic linkages. In some embodiments, a wing comprises one or more (e.g., 1, 2, 3, 4, 5, 6, 7, 8, 9, or 10) consecutive non-negatively charged internucleotidic linkages. In some embodiments, each internucleotidic linkage of a wing is independently a non-negatively charged internucleotidic linkage except the last internucleotidic linkage if the wing is a 3'-wing, or the first internucleotidic linkage if the wing is a 5'-wing. In some embodiments, a non-negatively charged internucleotidic linkage is a neutral internucleotidic linkage. In some embodiments, each non-negatively charged internucleotidic linkage is independently a neutral internucleotidic linkage. In some embodiments, as demonstrated herein, oligonucleotides that comprise wings comprising non-negatively charged internucleotidic linkages can deliver high activities and/or selectivities. In some embodiments, for description of internucleotidic linkages and patterns thereof (including stereochemical patterns), internucleotidic linkages linking a wing nucleoside and a core nucleoside is considered part of the core. In some embodiments, an internucleotidic linkage connecting a 5'-wing nucleoside and a core nucleoside is chirally controlled and is Rp. In some embodiments, an internucleotidic linkage connecting a 5'-wing nucleoside and a core nucleoside is chirally controlled and is Sp. In some embodiments, an internucleotidic linkage connecting a 3'-wing nucleoside and a core nucleoside is chirally controlled and is Rp. In some embodiments, an internucleotidic linkage connecting a 3'-wing nucleoside and a core nucleoside is chirally controlled and is Sp.

In some embodiments, a core sugar is a natural DNA sugar which comprises no substitution at the 2' position (two —H at 2'-carbon). In some embodiments, each core sugar is a natural DNA sugar which comprises no substitution at the 2' position (two —H at 2'-carbon).

A differentiating position may be located at various locations of an oligonucleotide as demonstrated herein to provide activity and/or selectivity. In some embodiments, a differentiating position of a provided oligonucleotide is complementary to a characteristic sequence element (e.g., SNP, mutation, etc.) which differentiates a target nucleic acid sequence from other sequences (e.g., reference nucleic acid sequences, other allele(s) of a target nucleic acid sequence, etc.) (such differentiating position may be referred to as a SNP or mutation location/site of a provided oligonucleotide). In some embodiments, a SNP is any RHO SNP listed in Table S2. In some embodiments, a differentiating position (e.g., a SNP location or mutation which differentiates a wild-type target sequence from a disease-associated or mutant sequence) is position 4, 5, 6, 7, 8, 9, etc., from the 5'-end of a core region. In some embodiments, the $4^{th}$, $5^{th}$, $6^{th}$, $7^{th}$, or $8^{th}$ nucleobase of a core region (from the 5' end of a core) is characteristic of a sequence and differentiates a sequence from another sequence (e.g., a SNP, a mutation, etc.). In some embodiments, a differentiating position is position 4 from the 5'-end of a core region. In some embodiments, a differentiating position is position 5 from the 5'-end of a core region. In some embodiments, a differentiating position is position 6 from the 5'-end of a core region. In some embodiments, a differentiating position is position 7 from the 5'-end of a core region. In some embodiments, a differentiating position is position 8 from the 5'-end of a core region. In some embodiments, a differentiating position is position 9, 10, 11, 12, etc. from the 5'-end of an oligonucleotide. In some embodiments, a differentiating position is position 9 from the 5'-end of an oligonucleotide. In some embodiments, a differentiating position is position 10 from the 5'-end of an oligonucleotide. In some embodiments, a differentiating position is position 11 from the 5'-end of an oligonucleotide. In some embodiments, a differentiating position is position 12 from the 5'-end of an oligonucleotide.

In some embodiments, an oligonucleotide or oligonucleotide composition is useful for preventing or treating a condition, disorder or disease. In some embodiments, a RHO oligonucleotide or RHO oligonucleotide composition is useful for a method of treatment of a RHO-related condition, disorder or disease, such as retinopathy (e.g, retinal degeneration, retinal degenerative disease, retinal degenerative disorder, inherited retinal degenerative disorder, retinitis pigmentosa, autosomal dominant retinitis pigmentosa, etc.), in a subject in need thereof.

In some embodiments, an oligonucleotide or oligonucleotide composition is useful for the manufacture of a medicament for treatment of a condition, disorder or disease, such as retinopathy (e.g, retinal degeneration, retinal degenerative disease, retinal degenerative disorder, inherited retinal degenerative disorder, retinitis pigmentosa, autosomal dominant retinitis pigmentosa, etc.), in a subject in need thereof. In some embodiments, a RHO oligonucleotide or RHO oligonucleotide composition is useful for the manufacture of a medicament for treatment of a RHO-related condition, disorder or disease, such as retinopathy (e.g, retinal degeneration, retinal degenerative disease, retinal degenerative disorder, inherited retinal degenerative disorder, retinitis pigmentosa, autosomal dominant retinitis pigmentosa, etc.), in a subject in need thereof.

In some embodiments, the present disclosure provides a pharmaceutical composition comprising a therapeutically effective amount of a provided oligonucleotide, which is optionally in a salt form. In some embodiments, an oligonucleotide is provided as its sodium salt form. In some embodiments, a pharmaceutical composition further comprises a pharmaceutically acceptable carrier.

In some embodiments, the present disclosure provides methods for preventing, delaying the onset and/or development of, and/or treating a condition, disorder or disease, comprising administering to a subject susceptible thereto or suffering therefrom an effective amount of a provided oligonucleotide or a composition thereof. In some embodiments, a condition, disorder or disease is associated with a RHO mutation. In some embodiments, a condition, disorder or disease is associated with a RHO P23H mutation. In some embodiments, a condition, disorder or disease is retinopathy (e.g, retinal degeneration, retinal degenerative disease, retinal degenerative disorder, inherited retinal degenerative disorder, retinitis pigmentosa, autosomal dominant retinitis pigmentosa, etc.). In some embodiments, an administered oligonucleotide can provide reduction of levels of RHO transcripts and/or products encoded thereby (e.g., proteins). In some embodiments, a subject has a RHO mutation (e.g., P23H; can be homozygous or heterozygous). In some embodiments, an administered oligonucleotide can provide selective reduction of levels of RHO transcripts and/or products encoded thereby (e.g., proteins) that are associated with the condition, disorder or disease (e.g., those containing P23H) over those that are less associated or not associated with the condition, disorder or disease.

DETAILED DESCRIPTION OF CERTAIN EMBODIMENTS

Technologies of the present disclosure may be understood more readily by reference to the following detailed description of certain embodiments.

Definitions

As used herein, the following definitions shall apply unless otherwise indicated. For purposes of this disclosure, the chemical elements are identified in accordance with the Periodic Table of the Elements, CAS version, Handbook of Chemistry and Physics, 75th Ed. Additionally, general principles of organic chemistry are described in "Organic Chemistry", Thomas Sorrell, University Science Books, Sausalito: 1999, and "March's Advanced Organic Chemistry", 5th Ed., Ed.: Smith, M. B. and March, J., John Wiley & Sons, New York: 2001.

As used herein in the present disclosure, unless otherwise clear from context, (i) the term "a" or "an" may be understood to mean "at least one"; (ii) the term "or" may be understood to mean "and/or"; (iii) the terms "comprising", "comprise", "including" (whether used with "not limited to" or not), and "include" (whether used with "not limited to" or not) may be understood to encompass itemized components or steps whether presented by themselves or together with one or more additional components or steps; (iv) the term "another" may be understood to mean at least an additional/second one or more; (v) the terms "about" and "approximately" may be understood to permit standard variation as would be understood by those of ordinary skill in the art; and (vi) where ranges are provided, endpoints are included.

Unless otherwise specified, description of oligonucleotides and elements thereof (e.g., base sequence, sugar modifications, internucleotidic linkages, linkage phosphorus stereochemistry, etc.) is from 5' to 3'. Unless otherwise specified, oligonucleotides described herein may be provided and/or utilized in a salt form, particularly a pharmaceutically acceptable salt form. As those skilled in the art will appreciate, oligonucleotides may be in various forms, e.g., acid, base or salt forms. In some embodiments, individual oligonucleotides within a composition may be considered to be of the same constitution and/or structure even though, within such composition (e.g., a liquid composition), particular such oligonucleotides might be in different salt form(s) (and may be dissolved and the oligonucleotide chain may exist as an anion form when, e.g., in a liquid composition) at a particular moment in time. For example, those skilled in the art will appreciate that, at a given pH, individual internucleotidic linkages along an oligonucleotide chain may be in an acid (H) form, or in one of a plurality of possible salt forms (e.g., a sodium salt, or a salt of a different cation, depending on which ions might be present in the preparation or composition), and will understand that, so long as their acid forms (e.g., replacing all cations, if any, with H+) are of the same constitution and/or structure, such individual oligonucleotides may properly be considered to be of the same constitution and/or structure.

Aliphatic: As used herein, "aliphatic" means a straight-chain (i.e., unbranched) or branched, substituted or unsubstituted hydrocarbon chain that is completely saturated or that contains one or more units of unsaturation, or a substituted or unsubstituted monocyclic, bicyclic, or polycyclic hydrocarbon ring that is completely saturated or that contains one or more units of unsaturation (but not aromatic), or combinations thereof. In some embodiments, aliphatic groups contain 1-50 aliphatic carbon atoms. In some embodiments, aliphatic groups contain 1-20 aliphatic carbon atoms. In other embodiments, aliphatic groups contain 1-10 aliphatic carbon atoms. In other embodiments, aliphatic groups contain 1-9 aliphatic carbon atoms. In other embodiments, aliphatic groups contain 1-8 aliphatic carbon atoms. In other embodiments, aliphatic groups contain 1-7 aliphatic carbon atoms. In other embodiments, aliphatic groups contain 1-6 aliphatic carbon atoms. In still other embodiments, aliphatic groups contain 1-5 aliphatic carbon atoms, and in yet other embodiments, aliphatic groups contain 1, 2, 3, or 4 aliphatic carbon atoms. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl.

Alkenyl: As used herein, the term "alkenyl" refers to an aliphatic group, as defined herein, having one or more double bonds.

Alkyl: As used herein, the term "alkyl" is given its ordinary meaning in the art and may include saturated aliphatic groups, including straight-chain alkyl groups, branched-chain alkyl groups, cycloalkyl (alicyclic) groups, alkyl substituted cycloalkyl groups, and cycloalkyl substituted alkyl groups. In some embodiments, alkyl has 1-100 carbon atoms. In certain embodiments, a straight chain or branched chain alkyl has about 1-20 carbon atoms in its backbone (e.g., $C_1$-$C_{20}$ for straight chain, $C_2$-$C_{20}$ for branched chain), and alternatively, about 1-10. In some embodiments, cycloalkyl rings have from about 3-10 carbon atoms in their ring structure where such rings are monocyclic, bicyclic, or polycyclic, and alternatively about 5, 6 or 7 carbons in the ring structure. In some embodiments, an alkyl group may be a lower alkyl group, wherein a lower alkyl group comprises 1-4 carbon atoms (e.g., $C_1$-$C_4$ for straight chain lower alkyls).

Alkynyl: As used herein, the term "alkynyl" refers to an aliphatic group, as defined herein, having one or more triple bonds.

Analog: The term "analog" includes any chemical moiety which differs structurally from a reference chemical moiety or class of moieties, but which is capable of performing at least one function of such a reference chemical moiety or class of moieties. As non-limiting examples, a nucleotide analog differs structurally from a nucleotide but performs at least one function of a nucleotide; a nucleobase analog differs structurally from a nucleobase but performs at least one function of a nucleobase; etc.

Animal: As used herein, the term "animal" refers to any member of the animal kingdom. In some embodiments, "animal" refers to humans, at any stage of development. In some embodiments, "animal" refers to non-human animals, at any stage of development. In certain embodiments, the non-human animal is a mammal (e.g., a rodent, a mouse, a rat, a rabbit, a monkey, a dog, a cat, a sheep, cattle, a primate and/or a pig). In some embodiments, animals include, but are not limited to, mammals, birds, reptiles, amphibians, fish and/or worms. In some embodiments, an animal may be a transgenic animal, a genetically-engineered animal and/or a clone.

Antisense: The term "antisense", as used herein, refers to a characteristic of an oligonucleotide or other nucleic acid having a base sequence complementary or substantially complementary to a target nucleic acid to which it is capable of hybridizing. In some embodiments, a target nucleic acid is a target gene mRNA. In some embodiments, hybridization is required for or results in at one activity, e.g., a decrease in the level, expression or activity of the target nucleic acid or a gene product thereof. The term "antisense oligonucleotide", as used herein, refers to an oligonucleotide complementary to a target nucleic acid. In some embodiments, an antisense oligonucleotide is capable of directing a decrease in the level, expression or activity of a target nucleic acid or a product thereof. In some embodiments, an antisense oligonucleotide is capable of directing a decrease in the level, expression or activity of the target nucleic acid or a product thereof, via a mechanism that involves RNaseH, steric hindrance and/or RNA interference.

Aryl: The term "aryl", as used herein, used alone or as part of a larger moiety as in "aralkyl," "aralkoxy," or "aryloxyalkyl," refers to monocyclic, bicyclic or polycyclic ring systems having a total of five to thirty ring members, wherein at least one ring in the system is aromatic. In some embodiments, an aryl group is a monocyclic, bicyclic or polycyclic ring system having a total of five to fourteen ring members, wherein at least one ring in the system is aromatic, and wherein each ring in the system contains 3 to 7 ring members. In some embodiments, an aryl group is a biaryl group. The term "aryl" may be used interchangeably with the term "aryl ring." In certain embodiments of the present disclosure, "aryl" refers to an aromatic ring system which includes, but is not limited to, phenyl, biphenyl, naphthyl, binaphthyl, anthracyl and the like, which may bear one or more substituents. Also included within the scope of the term "aryl," as it is used herein, is a group in which an aromatic ring is fused to one or more non-aromatic rings, such as indanyl, phthalimidyl, naphthimidyl, phenanthridinyl, or tetrahydronaphthyl, and the like.

Chiral control: As used herein, "chiral control" refers to control of the stereochemical designation of the chiral linkage phosphorus in a chiral internucleotidic linkage within an oligonucleotide. As used herein, a chiral internucleotidic linkage is an internucleotidic linkage whose linkage phosphorus is chiral. In some embodiments, a control is achieved through a chiral element that is absent from the sugar and base moieties of an oligonucleotide, for example, in some embodiments, a control is achieved through use of one or more chiral auxiliaries during oligonucleotide preparation as described in the present disclosure, which chiral auxiliaries often are part of chiral phosphoramidites used during oligonucleotide preparation. In contrast to chiral control, a person having ordinary skill in the art appreciates that conventional oligonucleotide synthesis which does not use chiral auxiliaries cannot control stereochemistry at a chiral internucleotidic linkage if such conventional oligonucleotide synthesis is used to form the chiral internucleotidic linkage. In some embodiments, the stereochemical designation of each chiral linkage phosphorus in each chiral internucleotidic linkage within an oligonucleotide is controlled.

Chirally controlled oligonucleotide composition: The terms "chirally controlled oligonucleotide composition", "chirally controlled nucleic acid composition", and the like, as used herein, refers to a composition that comprises a plurality of oligonucleotides (or nucleic acids) which share 1) a common base sequence, 2) a common pattern of backbone linkages, and 3) a common pattern of backbone phosphorus modifications, wherein the plurality of oligonucleotides (or nucleic acids) share the same linkage phosphorus stereochemistry at one or more chiral internucleotidic linkages (chirally controlled or stereodefined internucleotidic linkages, whose chiral linkage phosphorus is Rp or Sp in the composition ("stereodefined"), not a random Rp and Sp mixture as non-chirally controlled internucleotidic linkages). Level of the plurality of oligonucleotides (or nucleic acids) in a chirally controlled oligonucleotide composition is pre-determined/controlled (e.g., through chirally controlled oligonucleotide preparation to stereoselectively form one or more chiral internucleotidic linkages). In some embodiments, about 1%-100%, (e.g., about 5%-100%, 10%-100%, 20%-100%, 30%-100%, 40%-100%, 50%-100%, 60%-100%, 70%-100%, 80-100%, 90-100%, 95-100%, 50%-90%, or about 5%, 10%, 20%, 30%, 40%, 50%, 60%, 70%, 80%, 85%, 90%, 91%, 92%, 93%, 94%, 95%, 96%, 97%, 98%, 99%, or 100%, or at least 5%, 10%, 20%, 30%, 40%, 50%, 60%, 70%, 80%, 85%, 90%, 91%, 92%, 93%, 94%, 95%, 96%, 97%, 98%, or 99%) of all oligonucleotides in a chirally controlled oligonucleotide composition are oligonucleotides of the plurality. In some embodiments, about 1%-100%, (e.g., about 5%-100%, 10%-100%, 20%-100%, 30%-100%, 40%-100%, 50%-100%, 60%-100%, 70%-100%, 80-100%, 90-100%, 95-100%, 50%-90%, or about 5%, 10%, 20%, 30%, 40%, 50%, 60%, 70%, 80%, 85%, 90%, 91%, 92%, 93%, 94%, 95%, 96%, 97%, 98%, 99%, or 100%, or at least 5%, 10%, 20%, 30%, 40%, 50%, 60%, 70%, 80%, 85%, 90%, 91%, 92%, 93%, 94%, 95%, 96%, 97%, 98%, or 99%) of all oligonucleotides in a chirally controlled oligonucleotide composition that share the common base sequence, the common pattern of backbone linkages, and the common pattern of backbone phosphorus modifications are oligonucleotides of the plurality. In some embodiments, a level is about 1%-100%, (e.g., about 5%-100%, 10%-100%, 20%-100%, 30%-100%, 40%-100%, 50%-100%, 60%-100%, 70%-100%, 80-100%, 90-100%, 95-100%, 50%-90%, or about 5%, 10%, 20%, 30%, 40%, 50%, 60%, 70%, 80%, 85%, 90%, 91%, 92%, 93%, 94%, 95%, 96%, 97%, 98%, 99%, or 100%, or at least 5%, 10%, 20%, 30%, 40%, 50%, 60%, 70%, 80%, 85%, 90%, 91%, 92%, 93%, 94%, 95%, 96%, 97%, 98%, or 99%) of all oligonucleotides in a composition, or of all oligonucleotides in a composition that share a common base sequence (e.g., of a plurality of oligonucleotide or an oligonucleotide type), or of all oligonucleotides in a composition that share a common base sequence, a common pattern of backbone linkages, and a common pattern of backbone phosphorus modifications, or of all oligonucleotides in a composition that share a common base sequence, a common patter of base modifications, a common pattern of sugar modifications, a common pattern of internucleotidic linkage types, and/or a common pattern of internucleotidic linkage modifications. In some embodiments, the plurality of oligonucleotides share the same stereochemistry at about 1-50 (e.g., about 1-10, 1-20, 5-10, 5-20, 10-15, 10-20, 10-25, 10-30, or about 1, 2, 3, 4, 5, 6, 7, 8, 9, 10, 11, 12, 13, 14, 15, 16, 17, 18, 19, or 20, or at least 1, 2, 3, 4, 5, 6, 7, 8, 9, 10, 11, 12, 13, 14, 15, 16, 17, 18, 19, or 20) chiral internucleotidic linkages. In some embodiments, the plurality of oligonucleotides share the same stereochemistry at about 1%-100% (e.g., about 5%-100%, 10%-100%, 20%-100%, 30%-100%, 40%-100%, 50%-100%, 60%-100%, 70%-100%, 80-100%, 90-100%, 95-100%, 50%-90%, about 5%, 10%, 15%, 20%, 25%, 30%, 35%, 40%, 45%, 50%, 55%, 60%, 65%, 70%, 75%, 80%, 85%, 90%, 95%, or 100%, or at least 5%, 10%, 15%, 20%, 25%, 30%, 35%, 40%, 45%, 50%, 55%, 60%, 65%, 70%, 75%, 80%, 85%, 90%, 95%, or 99%) of chiral internucleotidic linkages. In some embodiments, oligonucleotides (or nucleic acids) of a plurality are of the same constitution. In some embodiments, level of the oligonucleotides (or nucleic acids) of the plurality is about 1%-100%, (e.g., about 5%-100%, 10%-100%, 20%-100%, 30%-100%, 40%-100%, 50%-100%, 60%-100%, 70%-100%, 80-100%, 90-100%, 95-100%, 50%-90%, or about 5%, 10%, 20%, 30%, 40%, 50%, 60%, 70%, 80%, 85%, 90%, 91%, 92%, 93%, 94%, 95%, 96%, 97%, 98%, 99%, or 100%, or at least 5%, 10%, 20%, 30%, 40%, 50%, 60%, 70%, 80%, 85%, 90%, 91%, 92%, 93%, 94%, 95%, 96%, 97%, 98%, or 99%) of all oligonucleotides (or nucleic acids) in a composition that share the same constitution as the oligonucleotides (or nucleic acids) of the plurality. In some embodiments, each chiral internucleotidic linkage is a chiral controlled internucleotidic linkage, and the composition is a completely chirally controlled oligonucleotide composition. In some embodiments, oligonucleotides (or nucleic acids) of a plurality are structurally identical. In some embodiments, a chirally controlled internucleotidic linkage has a diastereopurity of at least 80%, 85%, 90%, 91%, 92%, 93%, 94%, 95%, 96%, 97%, 98%, 99% or 99.5%, typically at least 90%, 91%, 92%, 93%, 94%, 95%, 96%, 97%, 98%, 99% or 99.5%. In some embodiments, a chirally controlled internucleotidic linkage has a diastereopurity of at least 95%. In some embodiments, a chirally controlled internucleotidic linkage has a diastereopurity of at least 96%. In some embodiments, a chirally controlled internucleotidic linkage has a diastereopurity of at least 97%. In some embodiments, a chirally controlled internucleotidic linkage has a diastereopurity of at least 98%. In some embodiments, a chirally controlled internucleotidic linkage has a diastereopurity of at least 99%. In some embodiments, a percentage of a level is or is at least $(DS)^{nc}$, wherein DS is a diastereopurity as described in the present disclosure (e.g., 90%, 91%, 92%, 93%, 94%, 95%, 96%, 97%, 98%, 99% or 99.5% or more) and nc is the number of chirally controlled internucleotidic linkages as described in the present disclosure (e.g., 1-50, 1-40, 1-30, 1-25, 1-20, 5-50, 5-40, 5-30, 5-25, 5-20, 1, 2, 3, 4, 5, 6, 7, 8, 9, 10, 11, 12, 13, 14, 15, 16, 17, 18, 19, 20, 21, 22, 23, 24, 25 or more). In some embodiments, a percentage of a level is or is at least $(DS)^{nc}$, wherein DS is 95%-100%. For example, when DS is 99% and nc is 10, the percentage is or is at least 90% ($(99\%)^{10} \approx 0.90=90\%$). In some embodiments, level of a plurality of oligonucleotides in a composition is represented as the product of the diastereopurity of each chirally controlled internucleotidic linkage in the oligonucleotides. In some embodiments, diastereopurity of an internucleotidic linkage connecting two nucleosides in an oligonucleotide (or nucleic acid) is represented by the diastereopurity of an internucleotidic linkage of a dimer connecting the same two nucleosides, wherein the dimer is prepared using comparable conditions, in some instances, identical synthetic cycle conditions (e.g., for the linkage between Nx and Ny in an oligonucleotide . . . NxNy . . . , the dimer is NxNy). In some embodiments, not all chiral internucleotidic linkages are chiral controlled internucleotidic linkages, and the composition is a partially chirally controlled oligonucleotide composition. In some embodiments, a non-chirally controlled internucleotidic linkage has a diastereopurity of less than about 80%, 75%, 70%, 65%, 60%, 55%, or of about 50%, as typically observed in stereorandom oligonucleotide compositions (e.g., as appreciated by those skilled in the art, from traditional oligonucleotide synthesis, e.g., the phosphoramidite method). In some embodiments, oligonucleotides (or nucleic acids) of a plurality are of the same type. In some embodiments, a chirally controlled oligonucleotide composition comprises non-random or controlled levels of individual oligonucleotide or nucleic acids types. For instance, in some embodiments a chirally controlled oligonucleotide composition comprises one and no more than one oligonucleotide type. In some embodiments, a chirally controlled oligonucleotide composition comprises more than one oligonucleotide type. In some embodiments, a chirally controlled oligonucleotide composition comprises multiple oligonucleotide types. In some embodiments, a chirally controlled oligonucleotide composition is a composition of oligonucleotides of an oligonucleotide type, which composition comprises a non-random or controlled level of a plurality of oligonucleotides of the oligonucleotide type.

Comparable: The term "comparable" is used herein to describe two (or more) sets of conditions or circumstances that are sufficiently similar to one another to permit comparison of results obtained or phenomena observed. In some embodiments, comparable sets of conditions or circumstances are characterized by a plurality of substantially identical features and one or a small number of varied features. Those of ordinary skill in the art will appreciate that sets of conditions are comparable to one another when characterized by a sufficient number and type of substantially identical features to warrant a reasonable conclusion that differences in results obtained or phenomena observed under the different sets of conditions or circumstances are caused by or indicative of the variation in those features that are varied.

Cycloaliphatic: The term "cycloaliphatic," "carbocycle," "carbocyclyl," "carbocyclic radical," and "carbocyclic ring," are used interchangeably, and as used herein, refer to saturated or partially unsaturated, but non-aromatic, cyclic aliphatic monocyclic, bicyclic, or polycyclic ring systems, as described herein, having, unless otherwise specified, from 3 to 30 ring members. Cycloaliphatic groups include, without limitation, cyclopropyl, cyclobutyl, cyclopentyl, cyclopentenyl, cyclohexyl, cyclohexenyl, cycloheptyl, cycloheptenyl, cyclooctyl, cyclooctenyl, norbornyl, adamantyl, and cyclooctadienyl. In some embodiments, a cycloaliphatic group has 3-6 carbons. In some embodiments, a cycloaliphatic group is saturated and is cycloalkyl. The term "cycloaliphatic" may also include aliphatic rings that are fused to one or more aromatic or nonaromatic rings, such as decahydronaphthyl or tetrahydronaphthyl. In some embodiments, a cycloaliphatic group is bicyclic. In some embodiments, a cycloaliphatic group is tricyclic. In some embodiments, a cycloaliphatic group is polycyclic. In some embodiments, "cycloaliphatic" refers to $C_3$-$C_6$ monocyclic hydrocarbon, or $C_8$-$C_{10}$ bicyclic or polycyclic hydrocarbon, that is completely saturated or that contains one or more units of unsaturation, but which is not aromatic, that has a single point of attachment to the rest of the molecule, or a $C_9$-$C_{16}$ polycyclic hydrocarbon that is completely saturated or that contains one or more units of unsaturation, but which is not aromatic, that has a single point of attachment to the rest of the molecule.

Dosing regimen: As used herein, a "dosing regimen" or "therapeutic regimen" refers to a set of unit doses (typically more than one) that are administered individually to a subject, typically separated by periods of time. In some embodiments, a given therapeutic agent has a recommended dosing regimen, which may involve one or more doses. In some embodiments, a dosing regimen comprises a plurality of doses each of which are separated from one another by a time period of the same length; in some embodiments, a dosing regimen comprises a plurality of doses and at least two different time periods separating individual doses. In some embodiments, all doses within a dosing regimen are of the same unit dose amount. In some embodiments, different doses within a dosing regimen are of different amounts. In some embodiments, a dosing regimen comprises a first dose in a first dose amount, followed by one or more additional doses in a second dose amount different from the first dose amount. In some embodiments, a dosing regimen comprises a first dose in a first dose amount, followed by one or more additional doses in a second dose amount same as the first dose amount.

Gapmer: as used herein, the term "gapmer" refers to an oligonucleotide characterized in that it comprises a core flanked by a 5' and a 3' wing. In some embodiments, in a gapmer, at least one internucleotidic phosphorus linkage of the oligonucleotide is a natural phosphate linkage. In some embodiments, more than one internucleotidic phosphorus linkage of the oligonucleotide strand is a natural phosphate linkage. In some embodiments, a gapmer is a sugar modification gapmer, wherein each wing sugar independently comprises a sugar modification, and no core sugar comprises a sugar modification found in a wing sugar. In some embodiments, each core sugar comprises no modification and are 2'-unsubstituted (as in natural DNA). In some embodiments, each wing sugar is independently a 2'-modified sugar. In some embodiments, at least one wing sugar is a bicyclic sugar. In some embodiments, sugar units in each wing have the same sugar modification (e.g., 2'-OMe (a 2'-OMe wing), 2'-MOE (a 2'-MOE wing), etc.). In some embodiments, each wing sugar has the same modification. Core and wing can have various lengths. In some embodiments, a wing is 2, 3, 4, 5, 6, 7, 8, 9, 10 or more nucleosides (in many embodiments, 3, 4, 5, or 6 or more) in length, and a core is 2, 3, 4, 5, 6, 7, 8, 9, 10, 11, 12, 13, 14, 15, 16, 17, 18, 19, 20 or more nucleosides (in many embodiments, 8, 9, 10, 11, 12, or more) in length. In some embodiments, an oligonucleotide comprises or consists of a wing-core-wing structure of 2-9-6, 3-9-3, 3-9-4, 3-9-5, 4-7-4, 4-9-4, 4-9-5, 4-10-5, 4-11-4, 4-11-5, 5-7-5, 5-8-6, 5-9-3, 5-9-5, 5-10-4, 5-10-5, 6-7-6, 6-8-5, or 6-9-2. In some embodiments, an oligonucleotide is a gapmer.

Heteroaliphatic: The term "heteroaliphatic", as used herein, is given its ordinary meaning in the art and refers to aliphatic groups as described herein in which one or more carbon atoms are independently replaced with one or more heteroatoms (e.g., oxygen, nitrogen, sulfur, silicon, phosphorus, and the like). In some embodiments, one or more units selected from C, CH, $CH_2$, and $CH_3$ are independently replaced by one or more heteroatoms (including oxidized and/or substituted forms thereof). In some embodiments, a heteroaliphatic group is heteroalkyl. In some embodiments, a heteroaliphatic group is heteroalkenyl.

Heteroalkyl: The term "heteroalkyl", as used herein, is given its ordinary meaning in the art and refers to alkyl groups as described herein in which one or more carbon atoms are independently replaced with one or more heteroatoms (e.g., oxygen, nitrogen, sulfur, silicon, phosphorus, and the like). Examples of heteroalkyl groups include, but are not limited to, alkoxy, poly(ethylene glycol)-, alkyl-substituted amino, tetrahydrofuranyl, piperidinyl, morpholinyl, etc.

Heteroaryl: The terms "heteroaryl" and "heteroar-", as used herein, used alone or as part of a larger moiety, e.g., "heteroaralkyl," or "heteroaralkoxy," refer to monocyclic, bicyclic or polycyclic ring systems having a total of five to thirty ring members, wherein at least one ring in the system is aromatic and at least one aromatic ring atom is a heteroatom. In some embodiments, a heteroaryl group is a group having 5 to 10 ring atoms (i.e., monocyclic, bicyclic orpolycyclic), in some embodiments 5, 6, 9, or 10 ring atoms. In some embodiments, a heteroaryl group has 6, 10, or 14 $\pi$ electrons shared in a cyclic array; and having, in addition to carbon atoms, from one to five heteroatoms. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. In some embodiments, a heteroaryl is a heterobiaryl group, such as bipyridyl and the like. The terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Non-limiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group may be monocyclic, bicyclic or polycyclic. The term "heteroaryl" may be used interchangeably with the terms "heteroaryl ring," "heteroaryl group," or "heteroaromatic," any of which terms include rings that are optionally substituted. The term "heteroaralkyl" refers to an alkyl group substituted by a heteroaryl group, wherein the alkyl and heteroaryl portions independently are optionally substituted.

Heteroatom: The term "heteroatom", as used herein, means an atom that is not carbon or hydrogen. In some embodiments, a heteroatom is boron, oxygen, sulfur, nitrogen, phosphorus, or silicon (including oxidized forms of nitrogen, sulfur, phosphorus, or silicon; charged forms of nitrogen (e.g., quaternized forms, forms as in iminium groups, etc.), phosphorus, sulfur, oxygen; etc.). In some embodiments, a heteroatom is oxygen, sulfur or nitrogen.

Heterocycle: As used herein, the terms "heterocycle," "heterocyclyl," "heterocyclic radical," and "heterocyclic ring", as used herein, are used interchangeably and refer to a monocyclic, bicyclic or polycyclic ring moiety (e.g., 3-30 membered) that is saturated or partially unsaturated and has one or more heteroatom ring atoms. In some embodiments, a heterocyclyl group is a stable 5- to 7-membered monocyclic or 7- to 10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes substituted nitrogen. As an example, in a saturated or partially unsaturated ring having 0-3 heteroatoms selected from oxygen, sulfur and nitrogen, the nitrogen may be N (as in 3,4-dihydro-2H-pyrrolyl), NH (as in pyrrolidinyl), or $^{+}$NR (as in N-substituted pyrrolidinyl). A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothienyl, pyrrolidinyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle," "heterocyclyl," "heterocyclyl ring," "heterocyclic group," "heterocyclic moiety," and "heterocyclic radical," are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl. A heterocyclyl group may be monocyclic, bicyclic or polycyclic. The term "heterocyclylalkyl" refers to an alkyl group substituted by a heterocyclyl, wherein the alkyl and heterocyclyl portions independently are optionally substituted.

Homology: "Homology" or "identity" or "similarity" refers to sequence similarity between two nucleic acid molecules. Homology and identity can each be determined by comparing a position in each sequence which can be aligned for purposes of comparison. When an equivalent position in the compared sequences is occupied by the same base, then the molecules are identical at that position; when the equivalent site occupied by the same or a similar nucleic acid residue (e.g., similar in steric and/or electronic nature), then the molecules can be referred to as homologous (similar) at that position. Expression as a percentage of homology/similarity or identity refers to a function of the number of identical or similar nucleic acids at positions shared by the compared sequences. In some embodiments, a sequence which is "unrelated" or "non-homologous" shares less than 40% identity, less than 35% identity, less than 30% identity, or less than 25% identity with a sequence described herein. In comparing two sequences, the absence of residues (amino acids or nucleic acids) or presence of extra residues also decreases the identity and homology/similarity. In some embodiments, polymeric molecules (e.g., oligonucleotides, nucleic acids, proteins, etc.) are considered to be "homologous" to one another if their sequences are at least 25%, 30%, 35%, 40%, 45%, 50%, 55%, 60%, 65%, 70%, 75%, 80%, 85%, 90%, 95%, or 99% identical. In some embodiments, polymeric molecules are considered to be "homologous" to one another if their sequences are at least 25%, 30%, 35%, 40%, 45%, 50%, 55%, 60%, 65%, 70%, 75%, 80%, 85%, 90%, 95%, or 99% similar.

In some embodiments, the term "homology" describes a mathematically based comparison of sequence similarities which is used to identify genes with similar functions or motifs. The nucleic acid sequences described herein can be used as a "query sequence" to perform a search against public databases, for example, to identify other family members, related sequences or homologs. In some embodiments, such searches can be performed using the NBLAST and XBLAST programs (version 2.0) of Altschul, et al. (1990) J. Mol. Biol. 215:403-10. In some embodiments, BLAST nucleotide searches can be performed with the NBLAST program, score=100, wordlength=12 to obtain nucleotide sequences homologous to nucleic acid molecules of the disclosure. In some embodiments, to obtain gapped alignments for comparison purposes, Gapped BLAST can be utilized as described in Altschul et al., (1997) Nucleic Acids Res. 25(17):3389-3402. When utilizing BLAST and Gapped BLAST programs, the default parameters of the respective programs (e.g., XBLAST and BLAST) can be used (See www.ncbi.nlm.nih.gov).

Identity: As used herein, the term "identity" refers to the overall relatedness between polymeric molecules, e.g., between nucleic acid molecules (e.g., oligonucleotides, DNA, RNA, etc.) and/or between polypeptide molecules. In some embodiments, polymeric molecules are considered to be "substantially identical" to one another if their sequences are at least 25%, 30%, 35%, 40%, 45%, 50%, 55%, 60%, 65%, 70%, 75%, 80%, 85%, 90%, 95%, or 99% identical. Calculation of the percent identity of two nucleic acid or polypeptide sequences, for example, can be performed by aligning the two sequences for optimal comparison purposes (e.g., gaps can be introduced in one or both of a first and a second sequences for optimal alignment and non-identical sequences can be disregarded for comparison purposes). In certain embodiments, the length of a sequence aligned for comparison purposes is at least 30%, at least 40%, at least 50%, at least 60%, at least 70%, at least 80%, at least 90%, at least 95%, or substantially 100% of the length of a reference sequence. The nucleotides at corresponding positions are then compared. When a position in the first sequence is occupied by the same residue (e.g., nucleotide or amino acid) as the corresponding position in the second sequence, then the molecules are identical at that position. The percent identity between the two sequences is a function of the number of identical positions shared by the sequences, taking into account the number of gaps, and the length of each gap, which needs to be introduced for optimal alignment of the two sequences. The comparison of sequences and determination of percent identity between two sequences can be accomplished using a mathematical algorithm. For example, the percent identity between two nucleotide sequences can be determined using the algorithm of Meyers and Miller (CABIOS, 1989, 4: 11-17), which has been incorporated into the ALIGN program (version 2.0). In some exemplary embodiments, nucleic acid sequence comparisons made with the ALIGN program use a PAM120 weight residue table, a gap length penalty of 12 and a gap penalty of 4. The percent identity between two nucleotide sequences can, alternatively, be determined using the GAP program in the GCG software package using an NWSgapdna.CMP matrix.

Internucleotidic linkage: As used herein, the phrase "internucleotidic linkage" refers generally to a linkage linking nucleoside units of an oligonucleotide or a nucleic acid. In some embodiments, an internucleotidic linkage is a phosphodiester linkage, as extensively found in naturally occurring DNA and RNA molecules (natural phosphate linkage (—OP(=O)(OH)O—), which as appreciated by those skilled in the art may exist as a salt form). In some embodiments, an internucleotidic linkage is a modified internucleotidic linkage (not a natural phosphate linkage). In some embodiments, an internucleotidic linkage is a "modified internucleotidic linkage" wherein at least one oxygen atom or —OH of a phosphodiester linkage is replaced by a different organic or inorganic moiety. In some embodiments, such an organic or inorganic moiety is selected from =S, =Se, =NR', —SR', —SeR', —$N(R')_2$, $B(R')_3$, —S—, —Se—, and —N(R')—, wherein each R' is independently as defined and described in the present disclosure. In some embodiments, an internucleotidic linkage is a phosphotriester linkage, phosphorothioate linkage (or phosphorothioate diester linkage, —OP(═O)(SH)O—, which as appreciated by those skilled in the art may exist as a salt form), or phosphorothioate triester linkage. In some embodiments, a modified internucleotidic linkage is a phosphorothioate linkage. In some embodiments, an internucleotidic linkage is one of, e.g., PNA (peptide nucleic acid) or PMO (phosphorodiamidate Morpholino oligomer) linkage. In some embodiments, a modified internucleotidic linkage is a non-negatively charged internucleotidic linkage. In some embodiments, a modified internucleotidic linkage is a neutral internucleotidic linkage (e.g., n001 in certain provided oligonucleotides). It is understood by a person of ordinary skill in the art that an internucleotidic linkage may exist as an anion or cation at a given pH due to the existence of acid or base moieties in the linkage. In some embodiments, a modified internucleotidic linkages is a modified internucleotidic linkages designated as s, s1, s2, s3, s4, s5, s6, s7, s8, s9, s10, s11, s12, s13, s14, s15, s16, s17 and s18 as described in WO 2017/210647.

In vitro: As used herein, the term "in vitro" refers to events that occur in an artificial environment, e.g., in a test tube or reaction vessel, in cell culture, etc., rather than within an organism (e.g., animal, plant and/or microbe).

In vivo: As used herein, the term "in vivo" refers to events that occur within an organism (e.g., animal, plant and/or microbe).

Linkage phosphorus: as defined herein, the phrase "linkage phosphorus" is used to indicate that the particular phosphorus atom being referred to is the phosphorus atom present in the internucleotidic linkage, which phosphorus atom corresponds to the phosphorus atom of a phosphodiester internucleotidic linkage as occurs in naturally occurring DNA and RNA. In some embodiments, a linkage phosphorus atom is in a modified internucleotidic linkage, wherein each oxygen atom of a phosphodiester linkage is optionally and independently replaced by an organic or inorganic moiety. In some embodiments, a linkage phosphorus atom is the P of Formula I as defined herein. In some embodiments, a linkage phosphorus atom is chiral. In some embodiments, a linkage phosphorus atom is achiral (e.g., as in natural phosphate linkages).

Linker: The terms "linker", "linking moiety" and the like refer to any chemical moiety which connects one chemical moiety to another. As appreciated by those skilled in the art, a linker can be bivalent or trivalent or more, depending on the number of chemical moieties the linker connects. In some embodiments, a linker is a moiety which connects one oligonucleotide to another oligonucleotide in a multimer. In some embodiments, a linker is a moiety optionally positioned between the terminal nucleoside and the solid support or between the terminal nucleoside and another nucleoside, nucleotide, or nucleic acid. In some embodiments, in an oligonucleotide a linker connects a chemical moiety (e.g., a targeting moiety, a lipid moiety, a carbohydrate moiety, etc.) with an oligonucleotide chain (e.g., through its 5'-end, 3'-end, nucleobase, sugar, internucleotidic linkage, etc.)

Lower alkyl: The term "lower alkyl" refers to a $C_{1-4}$ straight or branched alkyl group. Example lower alkyl groups are methyl, ethyl, propyl, isopropyl, butyl, isobutyl, and tert-butyl.

Lower haloalkyl: The term "lower haloalkyl" refers to a $C_{1-4}$ straight or branched alkyl group that is substituted with one or more halogen atoms.

Modified nucleobase: The terms "modified nucleobase", "modified base" and the like refer to a chemical moiety which is chemically distinct from a nucleobase, but which is capable of performing at least one function of a nucleobase. In some embodiments, a modified nucleobase is a nucleobase which comprises a modification. In some embodiments, a modified nucleobase is capable of at least one function of a nucleobase, e.g., forming a moiety in a polymer capable of base-pairing to a nucleic acid comprising an at least complementary sequence of bases. In some embodiments, a modified nucleobase is substituted A, T, C, G, or U, or a substituted tautomer of A, T, C, G, or U. In some embodiments, a modified nucleobase in the context of oligonucleotides refer to a nucleobase that is not A, T, C, G or U.

Modified nucleoside: The term "modified nucleoside" refers to a moiety derived from or chemically similar to a natural nucleoside, but which comprises a chemical modification which differentiates it from a natural nucleoside. Non-limiting examples of modified nucleosides include those which comprise a modification at the base and/or the sugar. Non-limiting examples of modified nucleosides include those with a 2' modification at a sugar. Non-limiting examples of modified nucleosides also include abasic nucleosides (which lack a nucleobase). In some embodiments, a modified nucleoside is capable of at least one function of a nucleoside, e.g., forming a moiety in a polymer capable of base-pairing to a nucleic acid comprising an at least complementary sequence of bases.

Modified nucleotide: The term "modified nucleotide" includes any chemical moiety which differs structurally from a natural nucleotide but is capable of performing at least one function of a natural nucleotide. In some embodiments, a modified nucleotide comprises a modification at a sugar, base and/or internucleotidic linkage. In some embodiments, a modified nucleotide comprises a modified sugar, modified nucleobase and/or modified internucleotidic linkage. In some embodiments, a modified nucleotide is capable of at least one function of a nucleotide, e.g., forming a subunit in a polymer capable of base-pairing to a nucleic acid comprising an at least complementary sequence of bases.

Modified sugar: The term "modified sugar" refers to a moiety that can replace a sugar. A modified sugar mimics the spatial arrangement, electronic properties, or some other physicochemical property of a sugar. In some embodiments, as described in the present disclosure, a modified sugar is substituted ribose or deoxyribose. In some embodiments, a modified sugar comprises a 2'-modification. Examples of useful 2'-modification are widely utilized in the art and described herein. In some embodiments, a 2'-modification is 2'-OR, wherein R is optionally substituted $C_{1-10}$ aliphatic. In some embodiments, a 2'-modification is 2'-OMe. In some embodiments, a 2'-modification is 2'-MOE. In some embodiments, a modified sugar is a bicyclic sugar (e.g., a sugar used in LNA, BNA, etc.). In some embodiments, in the context of oligonucleotides, a modified sugar is a sugar that is not ribose or deoxyribose as typically found in natural RNA or DNA.

Nucleic acid: The term "nucleic acid", as used herein, includes any nucleotides and polymers thereof. The term "polynucleotide", as used herein, refers to a polymeric form of nucleotides of any length, either ribonucleotides (RNA) or deoxyribonucleotides (DNA) or a combination thereof. These terms refer to the primary structure of the molecules and, thus, include double- and single-stranded DNA, and double- and single-stranded RNA. These terms include, as equivalents, analogs of either RNA or DNA comprising modified nucleotides and/or modified polynucleotides, such as, though not limited to, methylated, protected and/or capped nucleotides or polynucleotides. The terms encompass poly- or oligo-ribonucleotides (RNA) and poly- or oligo-deoxyribonucleotides (DNA); RNA or DNA derived from N-glycosides or C-glycosides of nucleobases and/or modified nucleobases; nucleic acids derived from sugars and/or modified sugars; and nucleic acids derived from phosphate bridges and/or modified internucleotidic linkages. The term encompasses nucleic acids containing any combinations of nucleobases, modified nucleobases, sugars, modified sugars, phosphate bridges or modified internucleotidic linkages. Examples include, and are not limited to, nucleic acids containing ribose moieties, nucleic acids containing deoxyribose moieties, nucleic acids containing both ribose and deoxyribose moieties, nucleic acids containing ribose and modified ribose moieties. Unless otherwise specified, the prefix poly- refers to a nucleic acid containing 2 to about 10,000 nucleotide monomer units and wherein the prefix oligo- refers to a nucleic acid containing 2 to about 200 nucleotide monomer units.

Nucleobase: The term "nucleobase" refers to the parts of nucleic acids that are involved in the hydrogen-bonding that binds one nucleic acid strand to another complementary strand in a sequence specific manner. The most common naturally-occurring nucleobases are adenine (A), guanine (G), uracil (U), cytosine (C), and thymine (T). In some embodiments, a naturally-occurring nucleobases are modified adenine, guanine, uracil, cytosine, or thymine. In some embodiments, a naturally-occurring nucleobases are methylated adenine, guanine, uracil, cytosine, or thymine. In some embodiments, a nucleobase comprises a heteroaryl ring wherein a ring atom is nitrogen, and when in a nucleoside, the nitrogen is bonded to a sugar moiety. In some embodiments, a nucleobase comprises a heterocyclic ring wherein a ring atom is nitrogen, and when in a nucleoside, the nitrogen is bonded to a sugar moiety. In some embodiments, a nucleobase is a "modified nucleobase," a nucleobase other than adenine (A), guanine (G), uracil (U), cytosine (C), and thymine (T). In some embodiments, a modified nucleobase is substituted A, T, C, G or U. In some embodiments, a modified nucleobase is a substituted tautomer of A, T, C, G, or U. In some embodiments, a modified nucleobases is methylated adenine, guanine, uracil, cytosine, or thymine. In some embodiments, a modified nucleobase mimics the spatial arrangement, electronic properties, or some other physicochemical property of the nucleobase and retains the property of hydrogen-bonding that binds one nucleic acid strand to another in a sequence specific manner. In some embodiments, a modified nucleobase can pair with all of the five naturally occurring bases (uracil, thymine, adenine, cytosine, or guanine) without substantially affecting the melting behavior, recognition by intracellular enzymes or activity of the oligonucleotide duplex. As used herein, the term "nucleobase" also encompasses structural analogs used in lieu of natural or naturally-occurring nucleotides, such as modified nucleobases and nucleobase analogs. In some embodiments, a nucleobase is optionally substituted A, T, C, G, or U, or an optionally substituted tautomer of A, T, C, G, or U. In some embodiments, a "nucleobase" refers to a nucleobase unit in an oligonucleotide or a nucleic acid (e.g., A, T, C, G or U as in an oligonucleotide or a nucleic acid).

Nucleoside: The term "nucleoside" refers to a moiety wherein a nucleobase or a modified nucleobase is covalently bound to a sugar or a modified sugar. In some embodiments, a nucleoside is a natural nucleoside, e.g., adenosine, deoxyadenosine, guanosine, deoxyguanosine, thymidine, uridine, cytidine, or deoxycytidine. In some embodiments, a nucleoside is a modified nucleoside, e.g., a substituted natural nucleoside selected from adenosine, deoxyadenosine, guanosine, deoxyguanosine, thymidine, uridine, cytidine, and deoxycytidine. In some embodiments, a nucleoside is a modified nucleoside, e.g., a substituted tautomer of a natural nucleoside selected from adenosine, deoxyadenosine, guanosine, deoxyguanosine, thymidine, uridine, cytidine, and deoxycytidine. In some embodiments, a "nucleoside" refers to a nucleoside unit in an oligonucleotide or a nucleic acid.

Nucleoside analog: The term "nucleoside analog" refers to a chemical moiety which is chemically distinct from a natural nucleoside, but which is capable of performing at least one function of a nucleoside. In some embodiments, a nucleoside analog comprises an analog of a sugar and/or an analog of a nucleobase. In some embodiments, a modified nucleoside is capable of at least one function of a nucleoside, e.g., forming a moiety in a polymer capable of base-pairing to a nucleic acid comprising a complementary sequence of bases.

Nucleotide: The term "nucleotide" as used herein refers to a monomeric unit of a polynucleotide that consists of a nucleobase, a sugar, and one or more internucleotidic linkages (e.g., phosphate linkages in natural DNA and RNA). The naturally occurring bases [guanine, (G), adenine, (A), cytosine, (C), thymine, (T), and uracil (U)] are derivatives of purine or pyrimidine, though it should be understood that naturally and non-naturally occurring base analogs are also included. The naturally occurring sugar is the pentose (five-carbon sugar) deoxyribose (which forms DNA) or ribose (which forms RNA), though it should be understood that naturally and non-naturally occurring sugar analogs are also included. Nucleotides are linked via internucleotidic linkages to form nucleic acids, or polynucleotides. Many internucleotidic linkages are known in the art (such as, though not limited to, phosphate, phosphorothioates, boranophosphates and the like). Artificial nucleic acids include PNAs (peptide nucleic acids), phosphotriesters, phosphorothionates, H-phosphonates, phosphoramidates, boranophosphates, methylphosphonates, phosphonoacetates, thiophosphonoacetates and other variants of the phosphate backbone of native nucleic acids, such as those described herein. In some embodiments, a natural nucleotide comprises a naturally occurring base, sugar and internucleotidic linkage. As used herein, the term "nucleotide" also encompasses structural analogs used in lieu of natural or naturally-occurring nucleotides, such as modified nucleotides and nucleotide analogs. In some embodiments, a "nucleotide" refers to a nucleotide unit in an oligonucleotide or a nucleic acid.

Oligonucleotide: The term "oligonucleotide" refers to a polymer or oligomer of nucleotides, and may contain any combination of natural and non-natural nucleobases, sugars, and internucleotidic linkages.

Oligonucleotides can be single-stranded or double-stranded. A single-stranded oligonucleotide can have double-stranded regions (formed by two portions of the single-stranded oligonucleotide) and a double-stranded oligonucleotide, which comprises two oligonucleotide chains, can have single-stranded regions for example, at regions where the two oligonucleotide chains are not complementary to each other. Example oligonucleotides include, but are not limited to structural genes, genes including control and termination regions, self-replicating systems such as viral or plasmid DNA, single-stranded and double-stranded RNAi agents and other RNA interference reagents (RNAi agents or iRNA agents), shRNA, antisense oligonucleotides, ribozymes, microRNAs, microRNA mimics, supermirs, aptamers, antimirs, antagomirs, Ul adaptors, triplex-forming oligonucleotides, G-quadruplex oligonucleotides, RNA activators, immuno-stimulatory oligonucleotides, and decoy oligonucleotides.

Oligonucleotides of the present disclosure can be of various lengths. In particular embodiments, oligonucleotides can range from about 2 to about 200 nucleosides in length. In various related embodiments, oligonucleotides, single-stranded, double-stranded, or triple-stranded, can range in length from about 4 to about 10 nucleosides, from about 10 to about 50 nucleosides, from about 20 to about 50 nucleosides, from about 15 to about 30 nucleosides, from about 20 to about 30 nucleosides in length. In some embodiments, the oligonucleotide is from about 9 to about 39 nucleosides in length. In some embodiments, the oligonucleotide is at least 4, 5, 6, 7, 8, 9, 10, 11, 12, 13, 14, 15, 16, 17, 18, 19, 20, 21, 22, 23, 24, or 25 nucleosides in length. In some embodiments, the oligonucleotide is at least 4 nucleosides in length. In some embodiments, the oligonucleotide is at least 5 nucleosides in length. In some embodiments, the oligonucleotide is at least 6 nucleosides in length. In some embodiments, the oligonucleotide is at least 7 nucleosides in length. In some embodiments, the oligonucleotide is at least 8 nucleosides in length. In some embodiments, the oligonucleotide is at least 9 nucleosides in length. In some embodiments, the oligonucleotide is at least 10 nucleosides in length. In some embodiments, the oligonucleotide is at least 11 nucleosides in length. In some embodiments, the oligonucleotide is at least 12 nucleosides in length. In some embodiments, the oligonucleotide is at least 15 nucleosides in length. In some embodiments, the oligonucleotide is at least 15 nucleosides in length. In some embodiments, the oligonucleotide is at least 16 nucleosides in length. In some embodiments, the oligonucleotide is at least 17 nucleosides in length. In some embodiments, the oligonucleotide is at least 18 nucleosides in length. In some embodiments, the oligonucleotide is at least 19 nucleosides in length. In some embodiments, the oligonucleotide is at least 20 nucleosides in length. In some embodiments, the oligonucleotide is at least 25 nucleosides in length. In some embodiments, the oligonucleotide is at least 30 nucleosides in length. In some embodiments, the oligonucleotide is a duplex of complementary strands of at least 18 nucleosides in length. In some embodiments, the oligonucleotide is a duplex of complementary strands of at least 21 nucleosides in length. In some embodiments, each nucleoside counted in an oligonucleotide length independently comprises A, T, C, G, or U, or optionally substituted A, T, C, G, or U, or an optionally substituted tautomer of A, T, C, G or U.

Oligonucleotide type: As used herein, the phrase "oligonucleotide type" is used to define an oligonucleotide that has a particular base sequence, pattern of backbone linkages (i.e., pattern of internucleotidic linkage types, for example, phosphate, phosphorothioate, phosphorothioate triester, etc.), pattern of backbone chiral centers [i.e., pattern of linkage phosphorus stereochemistry (Rp/Sp)], and pattern of backbone phosphorus modifications (e.g., pattern of "$-XLR^1$" groups in Formula I as defined herein). In some embodiments, oligonucleotides of a common designated "type" are structurally identical to one another.

One of skill in the art will appreciate that synthetic methods of the present disclosure provide for a degree of control during the synthesis of an oligonucleotide strand such that each nucleotide unit of the oligonucleotide strand can be designed and/or selected in advance to have a particular stereochemistry at the linkage phosphorus and/or a particular modification at the linkage phosphorus, and/or a particular base, and/or a particular sugar. In some embodiments, an oligonucleotide strand is designed and/or selected in advance to have a particular combination of stereocenters at the linkage phosphorus. In some embodiments, an oligonucleotide strand is designed and/or determined to have a particular combination of modifications at the linkage phosphorus. In some embodiments, an oligonucleotide strand is designed and/or selected to have a particular combination of bases. In some embodiments, an oligonucleotide strand is designed and/or selected to have a particular combination of one or more of the above structural characteristics. In some embodiments, the present disclosure provides compositions comprising or consisting of a plurality of oligonucleotide molecules (e.g., chirally controlled oligonucleotide compositions). In some embodiments, all such molecules are of the same type (i.e., are structurally identical to one another). In some embodiments, however, provided compositions comprise a plurality of oligonucleotides of different types, typically in pre-determined relative amounts.

Optionally Substituted: As described herein, compounds, e.g., oligonucleotides, of the disclosure may contain optionally substituted and/or substituted moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. In some embodiments, an optionally substituted group is unsubstituted. Combinations of substituents envisioned by this disclosure are preferably those that result in the formation of stable or chemically feasible compounds. The term "stable," as used herein, refers to compounds that are not substantially altered when subjected to conditions to allow for their production, detection, and, in certain embodiments, their recovery, purification, and use for one or more of the purposes disclosed herein. Certain substituents are described below.

Suitable monovalent substituents on a substitutable atom, e.g., a suitable carbon atom, are independently halogen; $-(CH_2)_{0-4}R^\circ$; $-(CH_2)_{0-4}R^\circ$; $-O(CH_2)_{0-4}R^\circ$, $-O-(CH_2)_{0-4}C(O)OR^\circ$; $-(CH_2)_{0-4}CH(OR^\circ)_2$; $-(CH_2)_{0-4}Ph$, which may be substituted with $R^\circ$; $-(CH_2)_{0-4}O(CH_2)_{0-1}Ph$ which may be substituted with $R^\circ$; $-CH{=}CHPh$, which may be substituted with $R^\circ$; $-(CH_2)_{0-4}O(CH_2)_{0-1}$-pyridyl which may be substituted with $R^\circ$; $-NO_2$; $-CN$; $-N_3$; $-(CH_2)_{0-4}N(R^\circ)_2$; $-(CH_2)_{0-4}N(R^\circ)C(O)R^\circ$; $-N(R^\circ)C(S)R^\circ$; $-(CH_2)_{0-4}N(R^\circ)C(O)NR^\circ_2$; $-N(R^\circ)C(S)NR^\circ_2$; $-(CH_2)_{0-4}N(R^\circ)C(O)OR^\circ$; $-N(R^\circ)N(R^\circ)C(O)R^\circ$; $-N(R^\circ)N(R^\circ)C(O)NR^\circ_2$; $-N(R^\circ)N(R^\circ)C(O)OR^\circ$; $-(CH_2)_{0-4}C(O)R^\circ$; $-C(S)R^\circ$; $-(CH_2)_{0-4}C(O)OR^\circ$; $-(CH_2)_{0-4}C(O)SR^\circ$; $-(CH_2)_{0-4}C(O)OSiR^\circ_3$; $-(CH_2)_{0-4}C(O)R^\circ$; $-OC(O)(CH_2)_{0-4}SR^\circ$, $-SC(S)SR^\circ$; $-(CH_2)_{0-4}SC(O)R^\circ$; $-(CH_2)_{0-4}C(O)NR^\circ_2$; $-C(S)NR^\circ_2$; $-C(S)SR^\circ$; $-(CH_2)_{0-4}C(O)NR^\circ_2$; $-C(O)N(OR^\circ)R^\circ$; $-C(O)C(O)R^\circ$; $-C(O)CH_2C(O)R^\circ$; $-C(NOR^\circ)R^\circ$; $-(CH_2)_{0-4}SSR^\circ$; $-(CH_2)_{0-4}S(O)_2R^\circ$; $-(CH_2)_{0-4}S(O)_2OR^\circ$; $-(CH_2)_{0-4}S(O)_2 R^\circ$; $-S(O)_2NR^\circ_2$; $-(CH_2)_{0-4}S(O)R^\circ$; $-N(R^\circ)S(O)_2NR^\circ_2$; $-N(R^\circ)S(O)_2R^\circ$; $-N(OR^\circ)R^\circ$; $-C(NH)NR^\circ_2$;

—$Si(R^\circ)_3$; —$OSi(R^\circ)_3$; —$B(R^\circ)_2$; —$OB(R^\circ)_2$; —$OB(OR^\circ)_2$; —$P(R^\circ)_2$; —$P(OR^\circ)_2$; —$P(R^\circ)(OR^\circ)$; —$OP(R^\circ)_2$; —$OP(OR^\circ)_2$; —$OP(R^\circ)(OR^\circ)$; —$P(O)(R^\circ)_2$; —$P(O)(OR^\circ)_2$; —$OP(O)(R^\circ)_2$; —$OP(O)(OR^\circ)_2$; —$OP(O)(OR^\circ)(SR^\circ)$; —$SP(O)(R^\circ)_2$; —$SP(O)(OR^\circ)_2$; —$N(R^\circ)P(O)(R^\circ)_2$; —$N(R^\circ)P(O)(OR^\circ)_2$; —$P(R^\circ)_2[B(R^\circ)_3]$; —$P(OR^\circ)_2[B(R^\circ)_3]$; —$OP(R^\circ)_2[B(R^\circ)_3]$; —$OP(OR^\circ)_2[B(R^\circ)_3]$; —($C_{1-4}$ straight or branched alkylene)O—$N(R^\circ)_2$; or —($C_{1-4}$ straight or branched alkylene)C(O)O—$N(R^\circ)_2$, wherein each $R^\circ$ may be substituted as defined herein and is independently hydrogen, $C_{1-20}$ aliphatic, $C_{1-20}$ heteroaliphatic having 1-5 heteroatoms independently selected from nitrogen, oxygen, sulfur, silicon and phosphorus, —$CH_2$—($C_{6-14}$ aryl), —$O(CH_2)_{0-1}$($C_{6-14}$ aryl), —$CH_2$-(5-14 membered heteroaryl ring), a 5-20 membered, monocyclic, bicyclic, or polycyclic, saturated, partially unsaturated or aryl ring having 0-5 heteroatoms independently selected from nitrogen, oxygen, sulfur, silicon and phosphorus, or, notwithstanding the definition above, two independent occurrences of $R^\circ$, taken together with their intervening atom(s), form a 5-20 membered, monocyclic, bicyclic, or polycyclic, saturated, partially unsaturated or aryl ring having 0-5 heteroatoms independently selected from nitrogen, oxygen, sulfur, silicon and phosphorus, which may be substituted as defined below.

Suitable monovalent substituents on $R^\circ$ (or the ring formed by taking two independent occurrences of $R^\circ$ together with their intervening atoms), are independently halogen, —$(CH_2)_{0-2}R^\bullet$, -(halo$R^\bullet$), —$(CH_2)_{0-2}OH$, —$(CH_2)_{0-2}OR^\bullet$, —$(CH_2)_{0-2}CH(OR^\bullet)_2$; —O(halo$R^\bullet$), —CN, —$N_3$, —$(CH_2)_{0-2}C(O)R^\bullet$, —$(CH_2)_{0-2}C(O)OH$, —$(CH_2)_{0-2}C(O)OR^\bullet$, —$(CH_2)_{0-2}SR^\bullet$, —$(CH_2)_{0-2}SH$, —$(CH_2)_{0-2}NH_2$, —$(CH_2)_{0-2}NHR^\bullet$, —$(CH_2)_{0-2}NR^\bullet_2$, —$NO_2$, —$SiR^\bullet_3$, —$OSiR^\bullet_3$, —$C(O)SR^\bullet$, —($C_{1-4}$ straight or branched alkylene)$C(O)OR^\bullet$, or —$SSR^\bullet$ wherein each $R^\bullet$ is unsubstituted or where preceded by "halo" is substituted only with one or more halogens, and is independently selected from $C_{1-4}$ aliphatic, —$CH_2Ph$, —$O(CH_2)_{0-1}Ph$, and a 5-6-membered saturated, partially unsaturated, or aryl ring having 0-4 heteroatoms independently selected from nitrogen, oxygen, and sulfur. Suitable divalent substituents on a saturated carbon atom of $R^\circ$ include ═O and ═S.

Suitable divalent substituents, e.g., on a suitable carbon atom, are independently the following: ═O, ═S, ═$NNR^*_2$, ═$NNHC(O)R^*$, ═$NNHC(O)OR^*$, ═$NNHS(O)_2R^*$, ═$NR^*$, ═$NOR^*$, —$O(C(R^*_2))_{2-3}$ O—, or —$S(C(R^*_2))_{2-3}S$—, wherein each independent occurrence of $R^*$ is selected from hydrogen, $C_{1-6}$ aliphatic which may be substituted as defined below, and an unsubstituted 5-6-membered saturated, partially unsaturated, or aryl ring having 0-4 heteroatoms independently selected from nitrogen, oxygen, and sulfur. Suitable divalent substituents that are bound to vicinal substitutable carbons of an "optionally substituted" group include: —$O(CR^*_2)_{2-3}O$—, wherein each independent occurrence of $R^*$ is selected from hydrogen, $C_{1-6}$ aliphatic which may be substituted as defined below, and an unsubstituted 5-6-membered saturated, partially unsaturated, and aryl ring having 0-4 heteroatoms independently selected from nitrogen, oxygen, and sulfur.

Suitable substituents on the aliphatic group of $R^*$ are independently halogen, —$R^\bullet$, -(halo$R^\bullet$), —OH, —$OR^\bullet$, —O(halo$R^\bullet$), —CN, —C(O)OH, —$C(O)OR^\bullet$, —$NH_2$, —$NHR^\bullet$, —$NR^\bullet$2, or —$NO_2$, wherein each $R^\bullet$ is unsubstituted or where preceded by "halo" is substituted only with one or more halogens, and is independently $C_{1-4}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, and sulfur.

In some embodiments, suitable substituents on a substitutable nitrogen are independently —$R^\dagger$, —$NR^\dagger_2$, —$C(O)R^\dagger$, —$C(O)OR^\dagger$, —$C(O)C(O)R^\dagger$, —$C(O)CH_2C(O)R^\dagger$, —$S(O)_2R^\dagger$, —$S(O)_2NR^\dagger_2$, —$C(S)NR^\dagger_2$, —$C(NH)NR^\dagger_2$, or —$N(R^\dagger)S(O)_2R^\dagger$; wherein each $R^\dagger$is independently hydrogen, $C_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, and sulfur, or, notwithstanding the definition above, two independent occurrences of RT, taken together with their intervening atom(s) form an unsubstituted 3-12-membered saturated, partially unsaturated, or aryl mono- or bicyclic ring having 0-4 heteroatoms independently selected from nitrogen, oxygen, and sulfur.

Suitable substituents on the aliphatic group of $R^\dagger$ are independently halogen, —$R^\bullet$, -(halo$R^\bullet$), —OH, —$OR^\bullet$, —O(halo$R^\bullet$), —CN, —C(O)OH, —$C(O)OR^\bullet$, —$NH_2$, —$NHR^\bullet$, —$NR^\bullet_2$, or —$NO_2$, wherein each $R^\bullet$ is unsubstituted or where preceded by "halo" is substituted only with one or more halogens, and is independently $C_{1-4}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, and sulfur.

Oral: The phrases "oral administration" and "administered orally" as used herein have their art-understood meaning referring to administration by mouth of a compound or composition.

P-modification: as used herein, the term "P-modification" refers to any modification at the linkage phosphorus other than a stereochemical modification. In some embodiments, a P-modification comprises addition, substitution, or removal of a pendant moiety covalently attached to a linkage phosphorus.

Parenteral: The phrases "parenteral administration" and "administered parenterally" as used herein have their art-understood meaning referring to modes of administration other than enteral and topical administration, usually by injection, and include, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal, and intrasternal injection and infusion.

Partially unsaturated: As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

Pharmaceutical composition: As used herein, the term "pharmaceutical composition" refers to an active agent, formulated together with one or more pharmaceutically acceptable carriers. In some embodiments, an active agent is present in unit dose amount appropriate for administration in a therapeutic regimen that shows a statistically significant probability of achieving a predetermined therapeutic effect when administered to a relevant population. In some embodiments, pharmaceutical compositions may be specially formulated for administration in solid or liquid form, including those adapted for the following: oral administration, for example, drenches (aqueous or non-aqueous solutions or suspensions), tablets, e.g., those targeted for buccal, sublingual, and systemic absorption, boluses, powders, granules, pastes for application to the tongue; parenteral administration, for example, by subcutaneous, intramuscular, intravenous or epidural injection as, for example, a sterile solution or suspension, or sustained-release formulation; topical application, for example, as a cream, ointment, or a controlled-release patch or spray applied to the skin, lungs, or oral cavity; intravaginally or intrarectally, for example, as a pessary, cream, or foam; sublingually; ocularly; transdermally; or nasally, pulmonary, and to other mucosal surfaces.

Pharmaceutically acceptable: As used herein, the phrase “pharmaceutically acceptable” refers to those compounds, materials, compositions and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

Pharmaceutically acceptable carrier: As used herein, the term “pharmaceutically acceptable carrier” means a pharmaceutically-acceptable material, composition or vehicle, such as a liquid or solid filler, diluent, excipient, or solvent encapsulating material, involved in carrying or transporting the subject compound from one organ, or portion of the body, to another organ, or portion of the body. Each carrier must be “acceptable” in the sense of being compatible with the other ingredients of the formulation and not injurious to the patient. Some examples of materials which can serve as pharmaceutically-acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer’s solution; ethyl alcohol; pH buffered solutions; polyesters, polycarbonates and/or polyanhydrides; and other non-toxic compatible substances employed in pharmaceutical formulations.

Pharmaceutically acceptable salt: The term “pharmaceutically acceptable salt”, as used herein, refers to salts of such compounds that are appropriate for use in pharmaceutical contexts, i.e., salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describes pharmaceutically acceptable salts in detail in J. Pharmaceutical Sciences, 66: 1-19 (1977). In some embodiments, pharmaceutically acceptable salt include, but are not limited to, nontoxic acid addition salts, which are salts of an amino group formed with inorganic acids such as hydrochloric acid, hydrobromic acid, phosphoric acid, sulfuric acid and perchloric acid or with organic acids such as acetic acid, maleic acid, tartaric acid, citric acid, succinic acid or malonic acid or by using other methods used in the art such as ion exchange. In some embodiments, pharmaceutically acceptable salts include, but are not limited to, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. In some embodiments, a provided compound comprises one or more acidic groups, e.g., an oligonucleotide, and a pharmaceutically acceptable salt is an alkali, alkaline earth metal, or ammonium (e.g., an ammonium salt of $N(R)_3$, wherein each R is independently defined and described in the present disclosure) salt. Representative alkali or alkaline earth metal salts include sodium, lithium, potassium, calcium, magnesium, and the like. In some embodiments, a pharmaceutically acceptable salt is a sodium salt. In some embodiments, a pharmaceutically acceptable salt is a potassium salt. In some embodiments, a pharmaceutically acceptable salt is a calcium salt. In some embodiments, pharmaceutically acceptable salts include, when appropriate, nontoxic ammonium, quaternary ammonium, and amine cations formed using counterions such as halide, hydroxide, carboxylate, sulfate, phosphate, nitrate, alkyl having from 1 to 6 carbon atoms, sulfonate and aryl sulfonate. In some embodiments, a provided compound comprises more than one acid groups, for example, an oligonucleotide may comprise two or more acidic groups (e.g., in natural phosphate linkages and/or modified internucleotidic linkages). In some embodiments, a pharmaceutically acceptable salt, or generally a salt, of such a compound comprises two or more cations, which can be the same or different. In some embodiments, in a pharmaceutically acceptable salt (or generally, a salt), all ionizable hydrogen (e.g., in an aqueous solution with a pKa no more than about 11, 10, 9, 8, 7, 6, 5, 4, 3, or 2; in some embodiments, no more than about 7; in some embodiments, no more than about 6; in some embodiments, no more than about 5; in some embodiments, no more than about 4; in some embodiments, no more than about 3) in the acidic groups are replaced with cations. In some embodiments, each phosphorothioate and phosphate group independently exists in its salt form (e.g., if sodium salt, —O—P(O)(SNa)—O— and —O—P(O)(ONa)—O—, respectively). In some embodiments, each phosphorothioate and phosphate internucleotidic linkage independently exists in its salt form (e.g., if sodium salt, —O—P(O)(SNa)—O— and —O—P(O)(ONa)—O—, respectively). In some embodiments, a pharmaceutically acceptable salt is a sodium salt of an oligonucleotide. In some embodiments, a pharmaceutically acceptable salt is a sodium salt of an oligonucleotide, wherein each acidic phosphate and modified phosphate group (e.g., phosphorothioate, phosphate, etc.), if any, exists as a salt form (all sodium salt).

Protecting group: The term “protecting group,” as used herein, is well known in the art and includes those described in detail in Protecting Groups in Organic Synthesis, T. W. Greene and P. G. M. Wuts, 3rd edition, John Wiley & Sons, 1999, the entirety of which is incorporated herein by reference. Also included are those protecting groups specially adapted for nucleoside and nucleotide chemistry described in Current Protocols in Nucleic Acid Chemistry, edited by Serge L. Beaucage et al. June 2012, the entirety of Chapter 2 is incorporated herein by reference. Suitable amino-protecting groups include methyl carbamate, ethyl carbamante, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, phenothiazinyl-(10)-carbonyl derivative, N'-p-toluenesulfonylaminocarbonyl derivative, N'-phenylaminothiocarbonyl derivative, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxycarbonylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isoborynl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium)benzyl carbamate, 2,4,6-trimethylbenzyl carbamate, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitophenylacetamide, o-nitrophenoxyacetamide, acetoacetamide, (N'-dithiobenzyloxycarbonylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide, o-(benzoyloxymethyl)benzamide, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene)amine, N,N'-isopropylidenediamine, N-p-nitrobenzylideneamine, N-salicylideneamine, N-5-chlorosalicylideneamine, N-(5-chloro-2-hydroxyphenyl)phenylmethyleneamine, N-cyclohexylideneamine, N-(5,5-dimethyl-3-oxo-1-cyclohexenyl)amine, N-borane derivative, N-diphenylborinic acid derivative, N-[phenyl(pentacarbonylchromium- or tungsten)carbonyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, 3-nitropyridinesulfenamide (Npys), p-toluenesulfonamide (Ts), benzenesulfonamide, 2,3,6-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Suitably protected carboxylic acids further include, but are not limited to, silyl-, alkyl-, alkenyl-, aryl-, and arylalkyl-protected carboxylic acids. Examples of suitable silyl groups include trimethylsilyl, triethylsilyl, t-butyldimethylsilyl, t-butyldiphenylsilyl, triisopropylsilyl, and the like. Examples of suitable alkyl groups include methyl, benzyl, p-methoxybenzyl, 3,4-dimethoxybenzyl, trityl, t-butyl, tetrahydropyran-2-yl. Examples of suitable alkenyl groups include allyl. Examples of suitable aryl groups include optionally substituted phenyl, biphenyl, or naphthyl. Examples of suitable arylalkyl groups include optionally substituted benzyl (e.g., p-methoxybenzyl (MPM), 3,4-dimethoxybenzyl, O-nitrobenzyl, p-nitrobenzyl, p-halobenzyl, 2,6-dichlorobenzyl, p-cyanobenzyl), and 2- and 4-picolyl.

Suitable hydroxyl protecting groups include methyl, methoxylmethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl, p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4"-tris(4,5-dichlorophthalimidophenyl)methyl, 4,4',4"-tris(levulinoyloxyphenyl)methyl, 4,4',4"-tris(benzoyloxyphenyl)methyl, 3-(imidazol-1-yl)bis(4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), alkyl methyl carbonate, 9-fluorenylmethyl carbonate (Fmoc), alkyl ethyl carbonate, alkyl 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), alkyl isobutyl carbonate, alkyl vinyl carbonate alkyl allyl carbonate, alkyl p-nitrophenyl carbonate, alkyl benzyl carbonate, alkyl p-methoxybenzyl carbonate, alkyl 3,4-dimethoxybenzyl carbonate, alkyl o-nitrobenzyl carbonate, alkyl p-nitrobenzyl carbonate, alkyl S-benzyl thiocarbonate, 4-ethoxy-1-napththyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxycarbonyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts). For protecting 1,2- or 1,3-diols, the protecting groups include methylene acetal, ethylidene acetal, 1-t-butylethylidene ketal, 1-phenylethylidene ketal, (4-methoxyphenyl)ethylidene acetal, 2,2,2-trichloroethylidene acetal, acetonide, cyclopentylidene ketal, cyclohexylidene ketal, cycloheptylidene ketal, benzylidene acetal, p-methoxybenzylidene acetal, 2,4-dimethoxybenzylidene ketal, 3,4-dimethoxybenzylidene acetal, 2-nitrobenzylidene acetal, methoxymethylene acetal, ethoxymethylene acetal, dimethoxymethylene ortho ester, 1-methoxyethylidene ortho ester, 1-ethoxyethylidine ortho ester, 1,2-dimethoxyethylidene ortho ester, α-methoxybenzylidene ortho ester, 1-(N,N-dimethylamino)ethylidene derivative, α-(N,N'-dimethylamino)benzylidene derivative, 2-oxacyclopentylidene ortho ester, di-t-butylsilylene group (DTBS), 1,3-(1,1,3,3-tetraisopropyldisiloxanylidene) derivative (TIPDS), tetra-t-butoxydisiloxane-1,3-diylidene derivative (TBDS), cyclic carbonates, cyclic boronates, ethyl boronate, and phenyl boronate.

In some embodiments, a hydroxyl protecting group is acetyl, t-butyl, tbutoxymethyl, methoxymethyl, tetrahydropyranyl, 1-ethoxyethyl, 1-(2-chloroethoxy)ethyl, 2-trimethylsilylethyl, p-chlorophenyl, 2,4-dinitrophenyl, benzyl, benzoyl, p-phenylbenzoyl, 2,6-dichlorobenzyl, diphenylmethyl, p-nitrobenzyl, triphenylmethyl (trityl), 4,4'-dimethoxytrityl, trimethylsilyl, triethylsilyl, t-butyldimethylsilyl, t-butyldiphenylsilyl, triphenylsilyl, triisopropylsilyl, benzoylformate, chloroacetyl, trichloroacetyl, trifiuoroacetyl, pivaloyl, 9-fluorenylmethyl carbonate, mesylate, tosylate, triflate, trityl, monomethoxytrityl (MMTr), 4,4'-dimethoxytrityl, (DMTr) and 4,4',4"-trimethoxytrityl (TMTr), 2-cyanoethyl (CE or Cne), 2-(trimethylsilyl)ethyl (TSE), 2-(2-nitrophenyl)ethyl, 2-(4-cyanophenyl)ethyl 2-(4-nitrophenyl)ethyl (NPE), 2-(4-nitrophenylsulfonyl)ethyl, 3,5-dichlorophenyl, 2,4-dimethylphenyl, 2-nitrophenyl, 4-nitrophenyl, 2,4,6-trimethylphenyl, 2-(2-nitrophenyl)ethyl, butylthiocarbonyl, 4,4',4"-tris(benzoyloxy)trityl, diphenylcarbamoyl, levulinyl, 2-(dibromomethyl)benzoyl (Dbmb), 2-(isopropylthiomethoxymethyl)benzoyl (Ptmt), 9-phenylxanthen-9-yl (pixyl) or 9-(p-methoxyphenyl)xanthine-9-yl (MOX). In some embodiments, each of the hydroxyl protecting groups is, independently selected from acetyl, benzyl, t-butyldimethylsilyl, t-butyldiphenylsilyl and 4,4'-dimethoxytrityl. In some embodiments, the hydroxyl protecting group is selected from the group consisting of trityl, monomethoxytrityl and 4,4'-dimethoxytrityl group. In some embodiments, a phosphorous linkage protecting group is a group attached to the phosphorous linkage (e.g., an internucleotidic linkage) throughout oligonucleotide synthesis. In some embodiments, a protecting group is attached to a sulfur atom of an phosphorothioate group. In some embodiments, a protecting group is attached to an oxygen atom of an internucleotide phosphorothioate linkage. In some embodiments, a protecting group is attached to an oxygen atom of the internucleotide phosphate linkage. In some embodiments a protecting group is 2-cyanoethyl (CE or Cne), 2-trimethylsilylethyl, 2-nitroethyl, 2-sulfonylethyl, methyl, benzyl, o-nitrobenzyl, 2-(p-nitrophenyl)ethyl (NPE or Npe), 2-phenylethyl, 3-(N-tert-butylcarboxamido)-1-propyl, 4-oxopentyl, 4-methylthio-1-butyl, 2-cyano-1,1-dimethylethyl, 4-N-methylaminobutyl, 3-(2-pyridyl)-1-propyl, 2-[N-methyl-N-(2-pyridyl)]aminoethyl, 2-(N-formyl,N-methyl)aminoethyl, or 4-[N-methyl-N-(2,2,2-trifluoroacetyl)amino]butyl.

Subject: As used herein, the term "subject" or "test subject" refers to any organism to which a provided compound (e.g., a provided oligonucleotide) or composition is administered in accordance with the present disclosure e.g., for experimental, diagnostic, prophylactic and/or therapeutic purposes. Typical subjects include animals (e.g., mammals such as mice, rats, rabbits, non-human primates, and humans; insects; worms; etc.) and plants. In some embodiments, a subject is a human. In some embodiments, a subject may be suffering from and/or susceptible to a disease, disorder and/or condition.

Substantially: As used herein, the term "substantially" refers to the qualitative condition of exhibiting total or near-total extent or degree of a characteristic or property of interest. A base sequence which is substantially complementary to a second sequence is not identical to the second sequence, but is mostly or nearly identical to the second sequence. In addition, one of ordinary skill in the biological and/or chemical arts will understand that biological and chemical phenomena rarely, if ever, go to completion and/or proceed to completeness or achieve or avoid an absolute result. The term "substantially" is therefore used herein to capture the potential lack of completeness inherent in many biological and/or chemical phenomena.

Sugar: The term "sugar" refers to a monosaccharide or polysaccharide in closed and/or open form. In some embodiments, sugars are monosaccharides. In some embodiments, sugars are polysaccharides. Sugars include, but are not limited to, ribose, deoxyribose, pentofuranose, pentopyranose, and hexopyranose moieties. As used herein, the term "sugar" also encompasses structural analogs used in lieu of conventional sugar molecules, such as glycol, polymer of which forms the backbone of the nucleic acid analog, glycol nucleic acid ("GNA"), etc. As used herein, the term "sugar" also encompasses structural analogs used in lieu of natural or naturally-occurring nucleotides, such as modified sugars and nucleotide sugars. In some embodiments, a sugar is a RNA or DNA sugar (ribose or deoxyribose). In some embodiments, a sugar is a modified ribose or deoxyribose sugar, e.g., 2'-modified, 5'-modified, etc. As described herein, in some embodiments, when used in oligonucleotides and/or nucleic acids, modified sugars may provide one or more desired properties, activities, etc. In some embodiments, a sugar is optionally substituted ribose or deoxyribose. In some embodiments, a "sugar" refers to a sugar unit in an oligonucleotide or a nucleic acid.

Susceptible to: An individual who is "susceptible to" a disease, disorder and/or condition is one who has a higher risk of developing the disease, disorder and/or condition than does a member of the general public. In some embodiments, an individual who is susceptible to a disease, disorder and/or condition is predisposed to have that disease, disorder and/or condition. In some embodiments, an individual who is susceptible to a disease, disorder and/or condition may not have been diagnosed with the disease, disorder and/or condition. In some embodiments, an individual who is susceptible to a disease, disorder and/or condition may exhibit symptoms of the disease, disorder and/or condition. In some embodiments, an individual who is susceptible to a disease, disorder and/or condition may not exhibit symptoms of the disease, disorder and/or condition. In some embodiments, an individual who is susceptible to a disease, disorder, and/or condition will develop the disease, disorder, and/or condition. In some embodiments, an individual who is susceptible to a disease, disorder, and/or condition will not develop the disease, disorder, and/or condition.

Therapeutic agent: As used herein, the term "therapeutic agent" in general refers to any agent that elicits a desired effect (e.g., a desired biological, clinical, or pharmacological effect) when administered to a subject. In some embodiments, an agent is considered to be a therapeutic agent if it demonstrates a statistically significant effect across an appropriate population. In some embodiments, an appropriate population is a population of subjects suffering from and/or susceptible to a disease, disorder or condition. In some embodiments, an appropriate population is a population of model organisms. In some embodiments, an appropriate population may be defined by one or more criterion such as age group, gender, genetic background, preexisting clinical conditions, prior exposure to therapy. In some embodiments, a therapeutic agent is a substance that alleviates, ameliorates, relieves, inhibits, prevents, delays onset of, reduces severity of, and/or reduces incidence of one or more symptoms or features of a disease, disorder, and/or condition in a subject when administered to the subject in an effective amount. In some embodiments, a "therapeutic agent" is an agent that has been or is required to be approved by a government agency before it can be marketed for administration to humans. In some embodiments, a "therapeutic agent" is an agent for which a medical prescription is required for administration to humans. In some embodiments, a therapeutic agent is a provided compound, e.g., a provided oligonucleotide.

Therapeutically effective amount: As used herein, the term "therapeutically effective amount" means an amount of a substance (e.g., a therapeutic agent, composition, and/or formulation) that elicits a desired biological response when administered as part of a therapeutic regimen. In some embodiments, a therapeutically effective amount of a substance is an amount that is sufficient, when administered to a subject suffering from or susceptible to a disease, disorder, and/or condition, to treat, diagnose, prevent, and/or delay the onset of the disease, disorder, and/or condition. As will be appreciated by those of ordinary skill in this art, the effective amount of a substance may vary depending on such factors as the desired biological endpoint, the substance to be delivered, the target cell or tissue, etc. For example, the effective amount of compound in a formulation to treat a disease, disorder, and/or condition is the amount that alleviates, ameliorates, relieves, inhibits, prevents, delays onset of, reduces severity of and/or reduces incidence of one or more symptoms or features of the disease, disorder, and/or condition. In some embodiments, a therapeutically effective amount is administered in a single dose; in some embodiments, multiple unit doses are required to deliver a therapeutically effective amount.

Treat: As used herein, the term "treat," "treatment," or "treating" refers to any method used to partially or completely alleviate, ameliorate, relieve, inhibit, prevent, delay onset of, reduce severity of, and/or reduce incidence of one or more symptoms or features of a disease, disorder, and/or condition. Treatment may be administered to a subject who does not exhibit signs of a disease, disorder, and/or condition. In some embodiments, treatment may be administered to a subject who exhibits only early signs of the disease, disorder, and/or condition, for example for the purpose of decreasing the risk of developing pathology associated with the disease, disorder, and/or condition.

Unit dose: The expression "unit dose" as used herein refers to an amount administered as a single dose and/or in a physically discrete unit of a pharmaceutical composition. In many embodiments, a unit dose contains a predetermined quantity of an active agent. In some embodiments, a unit dose contains an entire single dose of the agent. In some embodiments, more than one unit dose is administered to achieve a total single dose. In some embodiments, administration of multiple unit doses is required, or expected to be required, in order to achieve an intended effect. A unit dose may be, for example, a volume of liquid (e.g., an acceptable carrier) containing a predetermined quantity of one or more therapeutic agents, a predetermined amount of one or more therapeutic agents in solid form, a sustained release formulation or drug delivery device containing a predetermined amount of one or more therapeutic agents, etc. It will be appreciated that a unit dose may be present in a formulation that includes any of a variety of components in addition to the therapeutic agent(s). For example, acceptable carriers (e.g., pharmaceutically acceptable carriers), diluents, stabilizers, buffers, preservatives, etc., may be included as described infra. It will be appreciated by those skilled in the art, in many embodiments, a total appropriate daily dosage of a particular therapeutic agent may comprise a portion, or a plurality, of unit doses, and may be decided, for example, by the attending physician within the scope of sound medical judgment. In some embodiments, the specific effective dose level for any particular subject or organism may depend upon a variety of factors including the disorder being treated and the severity of the disorder; activity of specific active compound employed; specific composition employed; age, body weight, general health, sex and diet of the subject; time of administration, and rate of excretion of the specific active compound employed; duration of the treatment; drugs and/or additional therapies used in combination or coincidental with specific compound(s) employed, and like factors well known in the medical arts.

Unsaturated: The term “unsaturated,” as used herein, means that a moiety has one or more units of unsaturation.

Wild-type: As used herein, the term “wild-type” has its art-understood meaning that refers to an entity having a structure and/or activity as found in nature in a “normal” (as contrasted with mutant, diseased, altered, etc.) state or context. Those of ordinary skill in the art will appreciate that wild type genes and polypeptides often exist in multiple different forms (e.g., alleles).

As those skilled in the art will appreciate, methods and compositions described herein relating to provided compounds (e.g., oligonucleotides) generally also apply to pharmaceutically acceptable salts of such compounds.

DESCRIPTION OF CERTAIN EMBODIMENTS

Oligonucleotides are useful tools for a wide variety of applications. For example, RHO oligonucleotides are useful in therapeutic, diagnostic, and research applications, including the treatment of a variety of RHO-related conditions, disorders, and diseases, including retinopathy (e.g, retinal degeneration, retinal degenerative disease, retinal degenerative disorder, inherited retinal degenerative disorder, retinitis pigmentosa, autosomal dominant retinitis pigmentosa, etc.). The use of naturally occurring nucleic acids (e.g., unmodified DNA or RNA) is limited, for example, by their susceptibility to endo- and exo-nucleases. As such, various synthetic counterparts have been developed to circumvent these shortcomings and/or to further improve various properties and activities. These include synthetic oligonucleotides that contain chemical modifications, e.g., base modifications, sugar modifications, backbone modifications, etc., which, among other things, render these molecules less susceptible to degradation and improve other properties and/or activities. From a structural point of view, modifications to internucleotidic linkages can introduce chirality, and certain properties may be affected by configurations of linkage phosphorus atoms of oligonucleotides. For example, binding affinity, sequence specific binding to complementary RNA, stability to nucleases, cleavage of target nucleic acids, delivery, pharmacokinetics, etc. can be affected by, inter alia, chirality of backbone linkage phosphorus atoms. Among other things, the present disclosure provides technologies for controlling and/or utilizing various structural elements, e.g., sugar modifications and patterns thereof, nucleobase modifications and patterns thereof, modified internucleotidic linkages and patterns thereof, linkage phosphorus stereochemistry and patterns thereof, additional chemical moieties (moieties that are not typically in an oligonucleotide chain) and patterns thereof, etc., and various combinations of one or more or all of such structural elements, in oligonucleotides. With the capability to fully control structural elements of oligonucleotides, the present disclosure provides oligonucleotides comprising various structural features for assessing, optimizing, and/or improving properties and/or activities of oligonucleotides for various applications, e.g., as therapeutic agents, probes, etc. For example, as demonstrated herein, provided oligonucleotides and compositions thereof are particularly powerful for reducing levels of transcripts (and products (e.g., proteins) encoded thereby) associated with various conditions, disorders or diseases.

In some embodiments, provided oligonucleotides are oligonucleotides targeting RHO, and can reduce levels of RHO transcripts and/or one or more products encoded thereby. Such oligonucleotides are particularly useful for preventing and/or treating RHO-related conditions, disorders and/or diseases, including retinopathy (e.g, retinal degeneration, retinal degenerative disease, retinal degenerative disorder, inherited retinal degenerative disorder, retinitis pigmentosa, autosomal dominant retinitis pigmentosa, etc.).

In some embodiments, base sequences of RHO oligonucleotides are identical or complementary to bases sequences of RHO nucleic acids (e.g., RHO genes or transcripts (e.g., mRNA (e.g., pre-mRNA or spliced RNA)) thereof. In some embodiments, identity or complementarity is at least 85%, 90%, or 95%, and in many instances, 100% (when aligned for maximum homology/complementarity, there are no differences/mismatches between base sequences of RHO oligonucleotides and corresponding same-length portions of RHO nucleic acids (e.g., RHO genes, transcripts thereof, etc.)). In some embodiments, a RHO oligonucleotide comprises a sequence that is identical to or is completely or substantially complementary to 10, 11, 12, 13, 14, 15, 16, 17, 18, 19, 20, 21, 22, 23, 24, 25, typically 15, 16, 17, 18, 19, 20, 21, 22, 23, 24, 25 or more, contiguous bases of a RHO genomic sequence or a transcript therefrom (e.g., pre-mRNA, mRNA, etc.). In some embodiments, a RHO oligonucleotide comprises a sequence that is completely complementary to 10, 11, 12, 13, 14, 15, 16, 17, 18, 19, 20, 21, 22, 23, 24, 25 or more, typically 15, 16, 17, 18, 19, 20, 21, 22, 23, 24, 25 or more, contiguous bases of a RHO transcript. In some embodiments, an oligonucleotide that targets RHO can hybridize with a RHO transcript (e.g., pre-mRNA, RNA, etc.) and can reduce the level of the RHO transcript and/or a protein encoded by the RHO transcript. Those skilled in the art will appreciate that a “RHO oligonucleotide” may have a nucleotide sequence that is identical (or substantially identical) or complementary (or substantially complementary) to a RHO base sequence (e.g., a genomic sequence, a transcript sequence, a mRNA sequence, etc.) or a portion thereof. In some embodiments, a RHO oligonucleotide comprises a sequence that is identical to or is completely complementary to 10, 11, 12, 13, 14, 15, 16, 17, 18, 19, 20, 21, 22, 23, 24, 25, typically 15, 16, 17, 18, 19, 20, 21, 22, 23, 24, 25 or more, contiguous bases of a RHO genomic sequence or a transcript therefrom. In some embodiments, a RHO oligonucleotide comprises a sequence that is completely complementary to 10, 11, 12, 13, 14, 15, 16, 17, 18, 19, 20, 21, 22, 23, 24, 25 or more, typically 15, 16, 17, 18, 19, 20, 21, 22, 23, 24, 25 or more, contiguous bases of a RHO transcript. In some embodiments, matches are Watson-Crick base pairs.

In some embodiments, the present disclosure provides an oligonucleotide, e.g., a RHO oligonucleotide, wherein the oligonucleotide has a base sequence which is or comprises at least 10 contiguous bases of a RHO sequence (e.g., a sequence of a RHO gene, transcript, etc.) disclosed herein, or of a sequence that is complementary to a RHO sequence disclosed herein, and wherein each T can be independently substituted with U and vice versa. In some embodiments, the present disclosure provides a RHO oligonucleotide as disclosed herein, e.g., in a Table. In some embodiments, the present disclosure provides a RHO oligonucleotide having a base sequence disclosed herein, e.g., in a Table, or a portion thereof comprising at least 10 contiguous bases, wherein the RHO oligonucleotide is stereorandom or not chirally controlled, and wherein each T can be independently substituted with U and vice versa.

In some embodiments, internucleotidic linkages of an oligonucleotide comprise or consist of 1-5, 1-10, 1-15, 1-20, 1-25, 1-30, 1-40, 1-50, or 1, 2, 3, 4, 5, 6, 7, 8, 9, 10, 11, 12, 13, 14, 15, 16, 17, 18, 19, 20 or more chirally controlled internucleotidic linkages. In some embodiments, two or more chirally controlled internucleotidic linkages (e.g., 2-5, 2-10, 2-15, 2-20, 2-25, 2-30, 2-40, 2-50, or 2, 3, 4, 5, 6, 7, 8, 9, 10, 11, 12, 13, 14, 15, 16, 17, 18, 19, or 20 more) are consecutive. In some embodiments, an oligonucleotide composition of the present disclosure comprises oligonucleotides of the same constitution, wherein one or more (e.g., 1-5, 1-10, 1-15, 1-20, 1-25, 1-30, 1-40, 1-50, or 1, 2, 3, 4, 5, 6, 7, 8, 9, 10, 11, 12, 13, 14, 15, 16, 17, 18, 19, 20 or more) internucleotidic linkages are chirally controlled and one or more (e.g., 1-5, 1-10, 1-15, 1-20, 1-25, 1-30, 1-40, 1-50, or 1, 2, 3, 4, 5, 6, 7, 8, 9, 10, 11, 12, 13, 14, 15, 16, 17, 18, 19, 20 or more) internucleotidic linkages are stereorandom (not chirally controlled). In some embodiments, the present disclosure provides a RHO oligonucleotide composition wherein the RHO oligonucleotides comprise at least one chirally controlled internucleotidic linkage. In some embodiments, the present disclosure provides a RHO oligonucleotide composition wherein the RHO oligonucleotides are stereorandom or not chirally controlled. In some embodiments, in a plurality of RHO oligonucleotide, at least one internucleotidic linkage is stereorandom and at least one internucleotidic linkage is chirally controlled.

In some embodiments, internucleotidic linkages of an oligonucleotide comprise or consist of one or more (e.g., 1-5, 1-10, 1-15, 1-20, 1-25, 1-30, 1-40, 1-50, or 1, 2, 3, 4, 5, 6, 7, 8, 9, 10, 11, 12, 13, 14, 15, 16, 17, 18, 19, 20 or more) negatively charged internucleotidic linkages (e.g., phosphorothioate internucleotidic linkages, natural phosphate linkages, etc.). In some embodiments, internucleotidic linkages of an oligonucleotide comprise or consist of one or more (e.g., 1-5, 1-10, 1-15, 1-20, 1-25, 1-30, 1-40, 1-50, or 1, 2, 3, 4, 5, 6, 7, 8, 9, 10, 11, 12, 13, 14, 15, 16, 17, 18, 19, 20 or more) negatively charged chiral internucleotidic linkages (e.g., phosphorothioate internucleotidic linkages). In some embodiments, internucleotidic linkages of an oligonucleotide comprise or consist of one or more (e.g., 1-5, 1-10, 1-15, 1-20, 1-25, 1-30, 1-40, 1-50, or 1, 2, 3, 4, 5, 6, 7, 8, 9, 10, 11, 12, 13, 14, 15, 16, 17, 18, 19, 20 or more) non-negatively charged internucleotidic linkages. In some embodiments, internucleotidic linkages of an oligonucleotide comprise or consist of one or more (e.g., 1-5, 1-10, 1-15, 1-20, 1-25, 1-30, 1-40, 1-50, or 1, 2, 3, 4, 5, 6, 7, 8, 9, 10, 11, 12, 13, 14, 15, 16, 17, 18, 19, 20 or more) neutral chiral internucleotidic linkages. In some embodiments, the present disclosure pertains to a RHO oligonucleotide which comprises at least one neutral or non-negatively charged internucleotidic linkage as described in the present disclosure. In some embodiments, provided oligonucleotides comprise one or more natural phosphate linkages, one or more modified negatively charged internucleotidic linkages (e.g., phosphorothioate internucleotidic linkages), and one or more non-negatively charged internucleotidic linkages (e.g., neutral internucleotidic linkages such as n001). In some embodiments, provided oligonucleotides comprises one or more natural phosphate linkages, one or more phosphorothioate internucleotidic linkages and one or more non-negatively charged internucleotidic linkages (e.g., neutral internucleotidic linkages such as n001). In some embodiments, each internucleotidic linkage of an oligonucleotide is independently a natural phosphate linkage, a phosphorothioate internucleotidic linkage, and a non-negatively charged internucleotidic linkage. In some embodiments, each internucleotidic linkage of an oligonucleotide is independently a natural phosphate linkage, a phosphorothioate internucleotidic linkage, and n001. In some embodiments, each phosphorothioate internucleotidic linkage is independently chirally controlled. In some embodiments, one or more non-negatively charged internucleotidic linkages, e.g., n001, are not chirally controlled. In some embodiments, each chiral internucleotidic linkage is independently chirally controlled.

RHO (Rhodopsin)

In some embodiments, RHO refers to a gene or a gene product thereof (including but not limited to, a nucleic acid, including but not limited to a DNA or RNA, or a wild-type or mutant protein encoded thereby), from any species, and which may be known as: Rho or Rhodopsin or visual purple. Various RHO sequences, including variants thereof, from human, mouse, rat, monkey, etc., are readily available to those of skill in the art. In some embodiments, RHO is a human or mouse RHO, which is wild-type or mutant.

Without wishing to be bound by any particular theory, the present disclosure notes that a mutation (e.g., a disease-associated mutation(s)) in RHO is reportedly a key factor in RHO-related diseases and disorders such as retinopathy (e.g, retinal degeneration, retinal degenerative disease, retinal degenerative disorder, inherited retinal degenerative disorder, retinitis pigmentosa, autosomal dominant retinitis pigmentosa, etc.).

In some embodiments, RHO is also referenced, known or identified as: Rhodopsin, RHO, Rho, rho, CSNBAD1, OPN2, RP4, visual purple; External IDs: OMIM: 180380; MGI: 97914; HomoloGene: 68068; GeneCards: RHO; Orthologs: Species: Human: Entrez 6010; Ensembl ENSG00000163914; UniProt P08100; RefSeq (mRNA) NM_000539; RefSeq (protein) NP_000530; Location (UCSC) Chr 3: 129.53-129.54 Mb; Species: Mouse: Entrez 212541; Ensembl ENSMUSG00000030324; UniProt P15409; RefSeq (mRNA) NM_145383; RefSeq (protein) NP_663358; Location (UCSC) Chr 6: 115.93-115.94 Mb. In some embodiments, Rhodopsin is described as an opsin.

RHO (also known as visual purple) is reportedly a light-sensitive receptor protein involved in visual phototransduction. RHO is reportedly a biological pigment found in the rods of the retina and is a G-protein-coupled receptor (GPCR). It reportedly belongs to opsins. RHO is reportedly extremely sensitive to light, and thus enables vision in low-light conditions. When rhodopsin is exposed to light, it reportedly immediately photobleaches. In humans, it is reportedly regenerated fully in about 30 minutes, after which rods are more sensitive.

RHO reportedly can comprise two components, a protein molecule also called scotopsin and a covalently-bound cofactor called retinal. Scotopsin is reportedly an opsin, a light-sensitive G protein coupled receptor that embeds in the lipid bilayer of cell membranes using seven protein trans-membrane domains. These domains reportedly form a pocket where the photoreactive chromophore, retinal, lies horizontally to the cell membrane, linked to a lysine residue in the seventh transmembrane domain of the protein. Thousands of rhodopsin molecules are reportedly found in each outer segment disc of the host rod cell. Retinal is reportedly produced in the retina from vitamin A, from dietary beta-carotene. Isomerization of 11-cis-retinal into all-trans-retinal by light sets off a series of conformational changes ('bleaching') in the opsin, eventually leading it to a form called metarhodopsin II (Meta II), which activates an associated G protein, transducin, to trigger a cyclic guanosine monophosphate (cGMP) second messenger cascade.

RHO of the rods reportedly most strongly absorbs green-blue light and, therefore, appears reddish-purple; it is also called "visual purple". It is responsible for monochromatic vision in the dark.

Several closely related opsins reportedly differ only in a few amino acids and in the wavelengths of light that they absorb most strongly. Humans reportedly have eight other opsins besides rhodopsin, as well as cryptochrome (light-sensitive, but not an opsin).

The photopsins are reportedly found in the cone cells of the retina and are the basis of color vision. They have absorption maxima for yellowish-green (photopsin I), green (photopsin II), and bluish-violet (photopsin III) light. The remaining opsin, melanopsin, is reportedly found in photo-sensitive ganglion cells and absorbs blue light most strongly.

In rhodopsin, the aldehyde group of retinal is reportedly covalently linked to the amino group of a lysine residue on the protein in a protonated Schiff base. When rhodopsin absorbs light, its retinal cofactor reportedly isomerizes from the 11-cis to the all-trans configuration, and the protein subsequently undergoes a series of relaxations to accommodate the altered shape of the isomerized cofactor. The intermediates formed during this process were reportedly first investigated in the laboratory of George Wald, who received the Nobel prize for this research in 1967. The photoisomerization dynamics has reportedly been subsequently investigated with time-resolved IR spectroscopy and UV/Vis spectroscopy. A first photoproduct called photorhodopsin reportedly forms within 200 femtoseconds after irradiation, followed within picoseconds by a second one called bathorhodopsin with distorted all-trans bonds. This intermediate can be trapped and studied at cryogenic temperatures, and was initially referred to as prelumirhodopsin. In subsequent intermediates lumirhodopsin and metarhodopsin I, the Schiffs base linkage to all-trans retinal reportedly remains protonated, and the protein retains its reddish color. The critical change that initiates the neuronal excitation reportedly involves the conversion of metarhodopsin I to metarhodopsin II, which is associated with deprotonation of the Schiffs base and change in color from red to yellow. The structure of rhodopsin has reportedly been studied in detail via x-ray crystallography on rhodopsin crystals. Several models (e.g., the bicycle-pedal mechanism, hula-twist mechanism) reportedly attempt to explain how the retinal group can change its conformation without clashing with the enveloping rhodopsin protein pocket.

Mutation of the rhodopsin gene is reportedly a major contributor to various retinopathies such as retinitis pigmentosa. In general, the disease-causing protein reportedly aggregates with ubiquitin in inclusion bodies, disrupts the intermediate filament network, and impairs the ability of the cell to degrade non-functioning proteins, which leads to photoreceptor apoptosis. Other mutations on rhodopsin reportedly lead to X-linked congenital stationary night blindness, mainly due to constitutive activation, when the mutations occur around the chromophore binding pocket of rhodopsin. Several other pathological states reportedly relating to rhodopsin have been discovered including poor post-Golgi trafficking, dysregulative activation, rod outer segment instability and arrestin binding.

RHO proteins and homologs and isoforms thereof in various species include: RHO, RHO isoforms, including but not limited to variably or multiply-phosphorylated isoforms, including two forms of monophosphorylated and two diphosphorylated species of rhodopsin, and other species, containing up to five phosphates. Alternatively, spliced RHO transcript variants encoding different isoforms have been reported for this gene; in some embodiments, the present disclosure pertains to the use of a RHO oligonucleotide in decreasing the expression, level and/or activity of any isoform or alternatively spliced transcript or variant of a RHO gene or a gene product thereof.

In some embodiments, a mutant RHO is designated mRho, muRho, m RHO, mu RHO, MU RHO, or the like, wherein m or mu indicate mutant. In some embodiments, a wild type RHO is designated wild-type RHO, wtRho, wt RHO, WT RHO, WTRho, or the like, wherein wt indicates wild-type. In some embodiments, a mutant RHO comprises a deleterious or pathogenic mutation. In some embodiments, a mutant RHO comprises a P23H mutation.

In some embodiments, a human RHO is designated hRho or hRHO or hrho. In some embodiments, a mutant human RHO is designated mRho or mRho or mRHO or mRho or mrho. In some embodiments, when a mouse is utilized, a mouse RHO may be referred to as mRho or muRho or mRHO or muRHO or murho, as those skilled in the art will appreciate in view of the context.

In some embodiments, a RHO oligonucleotide is complementary to a portion of a RHO nucleic acid sequence, e.g., a RHO gene sequence, a RHO transcript, a RHO mRNA sequence, etc. In some embodiments, when a base sequence is aligned with a base sequence of a same-length portion of a RHO nucleic acid sequence, there are no more than 1, 2, 3, 4, or 5 mismatches, and in many instances, no more than one or two mismatches (as demonstrated herein, in many instances, no mismatches). In some embodiments, a portion is or comprises 10, 11, 12, 13, 14, 15, 16, 17, 18, 19, 20, 21, 22, 23, 24, 25, typically 15, 16, 17, 18, 19, 20, 21, 22, 23, 24, 25 or more contiguous nucleobases. In some embodiments, a portion is or comprises at least 15 contiguous nucleobases. In some embodiments, a portion is or comprises at least 16 contiguous nucleobases. In some embodiments, a portion is or comprises at least 17 contiguous nucleobases. In some embodiments, a portion is or comprises at least 18 contiguous nucleobases. In some embodiments, a portion is or comprises at least 19 contiguous nucleobases. In some embodiments, a portion is or comprises at least 20 contiguous nucleobases. In some embodiments, the base sequence of such a portion is characteristic of RHO in that no other genomic or transcript sequences have the same sequence as the portion. In some embodiments, a portion of a nucleic acid, e.g., a gene, a transcript, an RNA (pre-mRNA, spliced mRNA, etc.), that is complimentary to an oligonucleotide is referred to as the target sequence of the oligonucleotide.

In some embodiments, a RHO gene sequence (or a portion thereof, e.g., complementary to a RHO oligonucleotide) is a RHO gene sequence (or a portion thereof) known in the art or reported in the literature. Certain nucleotide and amino acid sequences of a human RHO can be found in public sources, for example, one or more publicly available databases, e.g., GenBank, UniProt, OMEVI, etc. Those skilled in the art will appreciate that, for example, where a described nucleic acid sequence may be or include a genomic sequence, transcripts, splicing products, and/or encoded proteins, etc., may readily be appreciated from such genomic sequence.

In some embodiments, a RHO gene, mRNA or protein variant or isoform comprises a mutation. In some embodiments, a RHO gene, mRNA or protein is or a transcription or translation product of an alternatively spliced variant or isoform. Alternatively spliced transcript variants encoding different isoforms have been reported for the RHO gene. In some embodiments, a RHO splicing variant is generated by an alternative splicing event not normally performed by a wild-type cell on a wild-type RHO gene. In some embodiments, a RHO variant or isoform comprises one or more fewer or extra or different exons compared to a wild-type RHO. In some embodiments, a RHO variant or isoform comprises a frameshift mutation, leading to a premature stop codon.

In some embodiments, a variant or isoform of RHO is incapable of performing at least one function, or has a decreased ability to perform at least one function, compared to a wild-type RHO.

In some embodiments, a variant or isoform of RHO is incapable of performing at least one function, or has a decreased ability to perform at least one function, compared to a wild-type RHO, wherein the function is any of: photoreceptor activity, signal transducer activity, metal ion binding, protein binding, G-protein coupled receptor activity, 11-cis retinal binding activity, or G-protein coupled photoreceptor activity, or a role in retina development in camera-type eye, sensory perception of light stimulus, signal transduction, response to stimulus, detection of light stimulus, absorption of visible light, cellular response to light stimulus, protein phosphorylation, response to light stimulus, regulation of rhodopsin mediated signaling pathway, retinoid metabolic process, phototransduction, phototransduction of visible light, phtoreceptor cell maintenance, visual perception, protein-chromophore linkage, G-protein coupled receptor signaling pathway, or rhodopsin-mediated signaling pathway, a component in double membrane discs in the out segments of rod photoceptor cells (ROS), preventing retinal degeneration, or another other function of RHO described herein or known in the art.

In some embodiments, a RHO gene (or a portion thereof with a sequence complementary to a RHO oligonucleotide) includes a single nucleotide polymorphism or SNP. RHO SNPs have been reported and may be found at, for example, NCBI dbSNP (see, e.g., www.ncbi.nlm.nih.gov/snp). Non-limiting examples of SNPs within the RHO gene may be found at, NCBI dbSNP Accession, and include, for example, those described herein. In some embodiments, a RHO oligonucleotide targets a SNP allele which is on the same chromosome as the disease-associated mutation(s) and not present on the wild-type allele (which does not comprise the disease-associated mutation(s)).

Various RHO SNPs include:

TABLE S2

RHO SNPs.

| rsID (SNP number) | Position | Alleles | rsID | Position | Alleles |
|---|---|---|---|---|---|
| rs1407074082 | 129531681 | C/G | rs1168144126 | 129531662 | C/A |
| rs1007788678 | 129528679 | C/G/T | rs1369128697 | 129531665 | A/G |
| rs559421777 | 129528682 | C/T | rs900199087 | 129531680 | G/A |
| rs2269736 | 129528683 | G/A/C | rs1407074082 | 129531681 | C/G |
| rs1354043935 | 129528684 | C/T | rs1304294353 | 129531682 | C/T |
| rs1245135960 | 129528685 | A/T | rs562374398 | 129531684 | A/G |
| rs753353276 | 129528698 | G/A | rs1364847643 | 129531701 | G/A |
| rs754584217 | 129528699 | G/A | rs1027573459 | 129531708 | C/T |
| rs1289056583 | 129528707 | C/T | rs1417383023 | 129531709 | G/A |
| rs7984 | 129528708 | A/G | rs532949412 | 129531715 | C/T |
| rs747620121 | 129528709 | C/T | rs139435571 | 129531716 | G/A |
| rs771188148 | 129528710 | G/A/T | rs566186118 | 129531721 | G/A |
| rs746247806 | 129528716 | G/C | rs80263713 | 129531723 | G/A |
| rs1184141164 | 129528718 | C/T | rs1207824529 | 129531727 | C/T |
| rs1364447526 | 129528722 | A/G | rs1352623901 | 129531728 | C/T |
| rs1444009632 | 129528723 | G/A | rs757524357 | 129531736 | C/T |
| rs769954281 | 129528724 | G/T | rs1035021501 | 129531748 | C/T |

TABLE S2-continued

| RHO SNPs. | | | | | |
|---|---|---|---|---|---|
| rsID (SNP number) | Position | Alleles | rsID | Position | Alleles |
| rs143193489 | 129528728 | -/C | rs370746434 | 129531751 | A/G |
| rs1367626681 | 129528730 | A/G | rs1000193322 | 129531753 | A/G |
| rs962827025 | 129528732 | C/G | rs991048116 | 129531758 | G/C |
| rs1426348071 | 129528734 | A/G | rs1369759641 | 129531761 | C/A |
| rs1293863853 | 129528736 | G/A | rs1223028434 | 129531766 | G/T |
| rs972605266 | 129528741 | G/A | rs1031674551 | 129531770 | C/T |
| rs1389590526 | 129528745 | A/T | rs764956905 | 129531771 | G/A |
| rs144270441 | 129528747 | A/G | rs1158435325 | 129531774 | C/T |
| rs145024369 | 129528749 | G/A | rs1452264662 | 129531778 | T/G |
| rs919315991 | 129528750 | G/A | rs946860061 | 129531781 | C/T |
| rs768787274 | 129528751 | C/T | rs978249998 | 129531782 | G/A |
| rs1312492810 | 129528753 | C/T | rs548932276 | 129531785 | C/T |
| rs1361105199 | 129528760 | C/A | rs775382640 | 129531786 | G/A |
| rs138142023 | 129528763 | C/G/T | rs1388489669 | 129531787 | C/T |
| rs1251088622 | 129528764 | G/A | rs1040564520 | 129531790 | G/A |
| rs767363145 | 129528766 | G/C | rs979934723 | 129531801 | T/C |
| rs773022490 | 129528767 | C/A | rs900123746 | 129531813 | G/C |
| rs1172673857 | 129528767 | C/- | rs1027522033 | 129531816 | C/A |
| rs1198077854 | 129528768 | C/T | rs145310205 | 129531821 | A/G |
| rs1239256015 | 129528769 | C/T | rs750220975 | 129531833 | C/T |
| rs1456787939 | 129528775 | C/T | rs1048978598 | 129531845 | A/C |
| rs104893786 | 129528777 | A/G | rs1351446086 | 129531847 | C/T |
| rs201340914 | 129528780 | C/T | rs887712134 | 129531852 | G/C |
| rs766112074 | 129528781 | G/A/T | rs1234342586 | 129531857 | G/T |
| rs1387357649 | 129528782 | A/G | rs1369693779 | 129531868 | C/T |
| rs104893769 | 129528783 | C/T | rs1456881458 | 129531870 | C/G |
| rs753585848 | 129528784 | G/A/C | rs1432472012 | 129531872 | C/A |
| rs200946638 | 129528786 | G/A/C | rs1327321121 | 129531877 | G/T |
| rs1372284722 | 129528788 | G/A | rs952004771 | 129531878 | C/G |
| rs757740913 | 129528790 | G/A | rs1291091183 | 129531885 | G/A |
| rs370401948 | 129528791 | G/A | rs1380979002 | 129531889 | T/C |
| rs746210043 | 129528792 | T/C | rs543124635 | 129531890 | C/T |
| rs1451320951 | 129528794 | C/T | rs1014751301 | 129531891 | G/A |
| rs552455660 | 129528795 | G/A | rs147640435 | 129531892 | G/A |
| rs376111618 | 129528798 | G/A | rs1294754691 | 129531896 | G/A |
| rs749567084 | 129528799 | C/T | rs1169815207 | 129531897 | T/C |
| rs104893797 | 129528800 | C/G | rs1384632793 | 129531900 | A/- |
| rs104893768 | 129528801 | C/A | rs1246224503 | 129531901 | A/G |

TABLE S2-continued

| RHO SNPs. | | | | | |
|---|---|---|---|---|---|
| rsID (SNP number) | Position | Alleles | rsID | Position | Alleles |
| rs768877243 | 129528805 | C/G/T | rs1242434982 | 129531905 | T/G |
| rs774425557 | 129528806 | G/A/C | rs1192172974 | 129531914 | G/A |
| rs748211662 | 129528808 | G/A/T | rs1487208664 | 129531923 | G/A |
| rs1309373132 | 129528810 | A/G | rs538560123 | 129531927 | G/A |
| rs966749682 | 129528811 | C/A | rs1259524394 | 129531928 | C/G |
| rs560600890 | 129528812 | C/A | rs907065802 | 129531932 | C/T |
| rs1553780837 | 129528816 | NA | rs1211576750 | 129531937 | CCT/- |
| rs1323411269 | 129528818 | T/C | rs755921724 | 129531949 | C/- |
| rs149084537 | 129528820 | C/T | rs1319651025 | 129531949 | C/T |
| rs1245030121 | 129528823 | C/T | rs56120415 | 129531950 | C/A/G/T |
| rs773077062 | 129528824 | C/G/T | rs975836054 | 129531951 | C/G |
| rs1232548343 | 129528832 | G/C | rs1217154881 | 129531955 | G/A |
| rs1186151173 | 129528835 | A/G | rs1035517938 | 129531956 | C/T |
| rs1259844494 | 129528836 | T/C | rs921704392 | 129531957 | G/A |
| rs771123958 | 129528838 | G/A | rs1261172385 | 129531960 | G/A |
| rs760515764 | 129528839 | C/A | rs1414727538 | 129531965 | G/T |
| rs755171690 | 129528840 | A/G | rs1373641913 | 129531972 | C/A |
| rs766344345 | 129528841 | G/C | rs1331014044 | 129531976 | A/G |
| rs776411064 | 129528848 | A/C | rs1410650567 | 129531977 | GCGGG CAGTG GATGC TGGGG CTGG /- |
| rs759209103 | 129528851 | C/T | rs1419035138 | 129531978 | C/T |
| rs927794488 | 129528854 | G/A | rs571916150 | 129531979 | G/A |
| rs781550757 | 129528856 | C/T | rs932797144 | 129531993 | G/- |
| rs538820015 | 129528857 | G/A | rs1049959434 | 129531994 | G/A |
| rs748429090 | 129528861 | A/G | rs1188071105 | 129532000 | G/A |
| rs1287941897 | 129528863 | A/C | rs199573532 | 129532002 | C/T |
| rs774336493 | 129528864 | T/C | rs370441842 | 129532007 | A/G |
| rs1289938976 | 129528865 | G/T | rs1485320710 | 129532014 | G/A |
| rs104893770 | 129528866 | T/C | rs1022482420 | 129532020 | G/A |
| rs1257389194 | 129528872 | C/T | rs996435947 | 129532021 | T/G |
| rs756454203 | 129528877 | C/T | rs1413549934 | 129532024 | T/G |
| rs534819675 | 129528878 | G/A | rs1422389197 | 129532032 | G/C |
| rs1264758702 | 129528883 | G/A | rs554315811 | 129532036 | A/C |
| rs104893792 | 129528884 | G/C | rs978344646 | 129532037 | C/T |
| rs149079952 | 129528885 | G/C | rs891812778 | 129532038 | G/A |
| rs926235922 | 129528887 | T/C | rs140851495 | 129532039 | C/A |

TABLE S2-continued

| RHO SNPs. | | | | | |
|---|---|---|---|---|---|
| rsID (SNP number) | Position | Alleles | rsID | Position | Alleles |
| rs28933395 | 129528891 | C/G | rs966612186 | 129532042 | C/G |
| rs755190538 | 129528893 | A/G | rs1337333486 | 129532047 | A/C |
| rs1312862210 | 129528898 | C/T | rs1294300374 | 129532051 | A/C |
| rs779029199 | 129528904 | C/T | rs1407628323 | 129532058 | C/T |
| rs28933394 | 129528906 | C/G/T | rs1452945428 | 129532059 | G/A |
| rs112640710 | 129528907 | G/A | rs1281818340 | 129532065 | G/T |
| rs777849735 | 129528908 | C/A/T | rs1443011054 | 129532070 | C/T |
| rs747002188 | 129528910 | C/G | rs751561815 | 129532076 | G/A |
| rs771007146 | 129528911 | T/C | rs975821631 | 129532078 | G/T |
| rs527236101 | 129528913 | C/A | rs1354066220 | 129532080 | A/T |
| rs776504351 | 129528914 | G/A | rs1329490519 | 129532081 | T/G |
| rs1427114435 | 129528915 | T/C | rs1024381325 | 129532086 | A/C |
| rs759425622 | 129528917 | A/G | rs111871140 | 129532087 | T/C |
| rs769464362 | 129528918 | C/A | rs1396357078 | 129532090 | C/G |
| rs367909246 | 129528919 | C/G/T | rs549470128 | 129532097 | A/C |
| rs146936681 | 129528920 | G/A | rs181387582 | 129532098 | T/A |
| rs1323752581 | 129528933 | A/G | rs1411495217 | 129532101 | A/G |
| rs763566456 | 129528934 | G/A/T | rs1178949302 | 129532102 | T/- |
| rs137883686 | 129528936 | T/G | rs749280021 | 129532105 | CATCCTGT/- |
| rs761101263 | 129528938 | C/T | rs1225199401 | 129532109 | CTGT/- |
| rs118173887 | 129528939 | G/A | rs1231831284 | 129532114 | A/T |
| rs143559914 | 129528942 | C/T | rs780785077 | 129532122 | A/G |
| rs755350955 | 129528943 | G/A | rs1027448730 | 129532128 | A/G |
| rs1305158106 | 129528944 | C/T | rs150129519 | 129532129 | C/T |
| rs398122525 | 129528950 | AAC/- | rs145248729 | 129532130 | G/A |
| rs779169631 | 129528951 | A/G | rs983404024 | 129532135 | T/C |
| rs374902462 | 129528952 | C/A | rs1286935244 | 129532140 | C/T |
| rs758491851 | 129528953 | T/C | rs55851525 | 129532152 | G/A |
| rs777943803 | 129528955 | C/T | rs1372614675 | 129532154 | G/A |
| rs367633279 | 129528956 | A/G | rs1266369222 | 129532160 | G/T |
| rs1470359420 | 129528961 | G/A | rs965725615 | 129532161 | T/C |
| rs1405507439 | 129528962 | C/T | rs1443314566 | 129532169 | C/T |
| rs1248203737 | 129528965 | A/C | rs976185389 | 129532177 | G/A |
| rs1478248064 | 129528967 | C/- | rs921675840 | 129532181 | GCGCTCG/- |
| rs1463779730 | 129528968 | C/T | rs532967085 | 129532182 | C/T |
| rs1176212506 | 129528971 | G/T | rs985591614 | 129532183 | G/A/T |
| rs770941561 | 129528973 | C/G/T | rs1003128409 | 129532186 | C/T |
| rs781325869 | 129528974 | G/A | rs1056526280 | 129532187 | G/A |

TABLE S2-continued

RHO SNPs.

| rsID (SNP number) | Position | Alleles | rsID | Position | Alleles |
|---|---|---|---|---|---|
| rs745643650 | 129528975 | T/C | rs1176266890 | 129532205 | T/G |
| rs1017235221 | 129528978 | C/T | rs368819173 | 129532206 | C/T |
| rs769544430 | 129528979 | T/C | rs1400567436 | 129532207 | C/T |
| rs1423255875 | 129528980 | G/T | rs1469020356 | 129532210 | A/G |
| rs1326147175 | 129528981 | A/G | rs1300540322 | 129532211 | G/A |
| rs1284225815 | 129528982 | C/T | rs758844049 | 129532215 | C/T |
| rs775191474 | 129528983 | C/G | rs376708009 | 129532219 | C/A/T |
| rs1246150736 | 129528985 | C/T | rs766027021 | 129532223 | C/G |
| rs1184850844 | 129528991 | G/A | rs747369599 | 129532225 | G/A |
| rs104893771 | 129528993 | T/A | rs1338821704 | 129532226 | G/A |
| rs1350780957 | 129528995 | C/T | rs1220849092 | 129532227 | G/T |
| rs1057521112 | 129528996 | T/C | rs1259177526 | 129532229 | C/G |
| rs104893772 | 129528999 | G/A/C | rs544766619 | 129532231 | C/G |
| rs762451457 | 129529000 | T/C | rs776890381 | 129532236 | C/A/T |
| rs104893790 | 129529002 | G/A | rs745920387 | 129532239 | G/A |
| rs768298431 | 129529007 | A/G | rs1483633045 | 129532240 | C/T |
| rs773808406 | 129529012 | C/T | rs104893776 | 129532253 | A/G |
| rs104893796 | 129529014 | C/T | rs1271669044 | 129532257 | C/- |
| rs761338278 | 129529021 | C/T | rs189018030 | 129532260 | C/T |
| rs1341056779 | 129529023 | C/A | rs775557680 | 129532261 | G/A/C |
| rs766852589 | 129529026 | C/G | rs104893780 | 129532264 | G/A |
| rs1252183229 | 129529028 | C/T | rs-1 | 129532269 | NA |
| rs1357414784 | 129529031 | C/A | rs1402468701 | 129532271 | A/G |
| rs143735182 | 129529032 | A/G | rs1236550448 | 129532273 | T/C |
| rs1291957024 | 129529034 | G/A | rs371288618 | 129532277 | C/T |
| rs759945007 | 129529035 | G/A | rs145549270 | 129532278 | G/A/T |
| rs1011170952 | 129529040 | T/G | rs527236100 | 129532282 | G/A |
| rs149615742 | 129529042 | C/T | rs1424131846 | 129532283 | G/A |
| rs144317206 | 129529043 | G/A | rs761562089 | 129532287 | C/T |
| rs758484916 | 129529045 | C/T | rs104893779 | 129532288 | G/A/T |
| rs778173978 | 129529048 | C/T | rs104893777 | 129532289 | A/G |
| rs104893773 | 129529049 | G/A/T | rs1022242191 | 129532296 | C/T |
| rs1488067054 | 129529051 | G/A | rs373974298 | 129532298 | C/A/T |
| rs1442262560 | 129529052 | C/T | rs755674549 | 129532299 | G/A/C |
| rs757449302 | 129529053 | C/A | rs1359176166 | 129532302 | C/G |
| rs781266982 | 129529054 | C/A/T | rs1402455011 | 129532305 | G/A |
| rs751153075 | 129529054 | -/A | rs765931092 | 129532306 | C/A/T |

TABLE S2-continued

RHO SNPs.

| rsID (SNP number) | Position | Alleles | rsID | Position | Alleles |
|---|---|---|---|---|---|
| rs1209988233 | 129529055 | A/C/G | rs141468335 | 129532307 | C/T |
| rs1415160298 | 129529058 | G/A/T | rs758901694 | 129532308 | G/A/C |
| rs104893787 | 129529062 | G/A | rs1374343616 | 129532313 | T/C |
| rs745851408 | 129529065 | A/G | rs778170529 | 129532314 | C/G |
| rs371461422 | 129529068 | T/C | rs756162630 | 129532314 | CAA/- |
| rs104893788 | 129529074 | G/A/C | rs368157839 | 129532317 | C/G |
| rs1447750550 | 129529075 | C/T | rs777637179 | 129532318 | A/G |
| rs1336351157 | 129529078 | C/T | rs147005807 | 129532320 | C/T |
| rs148801522 | 129529080 | T/A | rs781375897 | 129532321 | G/T |
| rs1454654794 | 129529084 | C/T | rs966207295 | 129532326 | T/C |
| rs749137786 | 129529088 | C/T | rs1001583714 | 129532333 | A/G |
| rs1476531540 | 129529090 | G/A | rs886057967 | 129532334 | T/G |
| rs1356947962 | 129529091 | G/T | rs746029882 | 129532339 | A/G |
| rs768251138 | 129529092 | G/A/C | rs104893782 | 129532340 | T/G |
| rs1057518210 | 129529092 | G/- | rs113751838 | 129532344 | C/G/T |
| rs79765751 | 129529093 | C/A/T | rs567288669 | 129532345 | G/A |
| rs771637224 | 129529094 | G/A | rs1488045716 | 129532347 | G/T |
| rs1198830014 | 129529102 | C/T | rs768616082 | 129532348 | G/A/T |
| rs541163949 | 129529103 | C/T | rs371192803 | 129532350 | C/T |
| rs372128112 | 129529104 | G/A | rs28933993 | 129532352 | A/C |
| rs1423460306 | 129529104 | G/- | rs374685958 | 129532353 | C/T |
| rs1459534591 | 129529105 | G/T | rs1435773040 | 129532358 | C/A |
| rs376995477 | 129529106 | G/- | rs887633046 | 129532359 | C/G |
| rs1189010269 | 129529107 | T/C | rs1005150205 | 129532360 | A/G |
| rs765781218 | 129529108 | G/A | rs368534414 | 129532362 | C/A/T |
| rs375391319 | 129529116 | G/C | rs777851867 | 129532366 | A/- |
| rs763422574 | 129529119 | G/A | rs1422016730 | 129532366 | A/T |
| rs369851208 | 129529121 | G/T | rs984572250 | 129532367 | T/G |
| rs1359364310 | 129529123 | A/G | rs1299366616 | 129532369 | A/G |
| rs751894032 | 129529125 | G/A | rs1365280636 | 129532370 | T/G |
| rs757395830 | 129529127 | G/A | rs766161322 | 129532379 | T/G |
| rs767646428 | 129529128 | C/G/T | rs141956356 | 129532380 | T/G |
| rs750519691 | 129529129 | C/T | rs759021503 | 129532390 | G/A/C |
| rs372349714 | 129529130 | C/T | rs764633076 | 129532391 | G/A |
| rs780060597 | 129529131 | G/A | rs752076372 | 129532393 | C/T |
| rs1408274470 | 129529133 | G/A | rs1323701516 | 129532395 | G/C |
| rs1325971237 | 129529135 | G/A | rs746223530 | 129532398 | C/T |
| rs1429888921 | 129529141 | A/C | rs781465927 | 129532399 | G/A/T |

TABLE S2-continued

RHO SNPs.

| rsID (SNP number) | Position | Alleles | rsID | Position | Alleles |
|---|---|---|---|---|---|
| rs749016955 | 129529142 | G/A/T | rs1286665566 | 129532400 | T/G |
| rs1053329735 | 129529150 | G/A | rs1301777085 | 129532403 | T/C |
| rs1425151130 | 129529151 | G/A | rs143003934 | 129532407 | C/A/T |
| rs192412661 | 129529159 | C/T | rs780188527 | 129532408 | G/A |
| rs185011073 | 129529160 | G/A | rs1248295015 | 129532413 | G/A |
| rs564018441 | 129529166 | G/A | rs749356883 | 129532417 | G/C |
| rs531077633 | 129529168 | C/T | rs56340615 | 129532420 | C/G/T |
| rs889556515 | 129529169 | G/A | rs376802160 | 129532421 | G/A/C |
| rs1006944068 | 129529172 | G/A | rs1441016547 | 129532422 | G/A |
| rs1038019804 | 129529185 | C/A | rs1256841395 | 129532423 | G/A |
| rs1011138447 | 129529185 | CCTTCTC/- | rs368352202 | 129532425 | C/A/G/T |
| rs1451948818 | 129529196 | C/T | rs372570611 | 129532426 | G/A/C/T |
| rs775095233 | 129529201 | G/A | rs749155432 | 129532426 | G/- |
| rs546065873 | 129529207 | T/C | rs55915536 | 129532428 | G/A/C/T |
| rs148110888 | 129529210 | A/G/T | rs376727697 | 129532429 | G/A |
| rs1003947341 | 129529217 | C/T | rs764590515 | 129532430 | G/T |
| rs1240025893 | 129529218 | C/G | rs1350872553 | 129532431 | G/A |
| rs1025604117 | 129529228 | A/G | rs913483379 | 129532433 | G/A |
| rs1351451259 | 129529229 | T/C | rs369198420 | 129532435 | G/A |
| rs896282715 | 129529235 | C/A | rs373118114 | 129532436 | C/T |
| rs115345357 | 129529242 | C/T | rs768030547 | 129532437 | G/A |
| rs959682812 | 129529248 | C/T | rs1314532127 | 129532439 | C/T |
| rs1012342900 | 129529260 | A/G | rs1378322146 | 129532440 | C/G |
| rs1024369421 | 129529264 | C/T | rs750763646 | 129532444 | C/T |
| rs970189152 | 129529265 | C/T | rs756509737 | 129532445 | G/A |
| rs1349141081 | 129529266 | G/C | rs376626260 | 129532448 | T/A |
| rs75456752 | 129529267 | G/C | rs754064314 | 129532454 | G/A/C/T |
| rs76257822 | 129529268 | G/C | rs1368372506 | 129532455 | G/A |
| rs1321477975 | 129529278 | G/T | rs376271158 | 129532456 | T/A |
| rs980618653 | 129529281 | C/T | rs778794165 | 129532457 | C/T |
| rs141844397 | 129529293 | T/G | rs1458865163 | 129532461 | C/- |
| rs765586234 | 129529296 | A/G | rs1178698486 | 129532462 | C/T |
| rs373450899 | 129529303 | C/G/T | rs1420894712 | 129532463 | C/T |
| rs988982108 | 129529309 | C/T | rs1236436231 | 129532464 | C/T |
| rs972565823 | 129529315 | T/C | rs1178213438 | 129532469 | A/T |
| rs1200531083 | 129529322 | A/G | rs1456628166 | 129532471 | G/A |
| rs913494008 | 129529324 | A/G/T | rs370370574 | 129532478 | C/T |

TABLE S2-continued

RHO SNPs.

| rsID (SNP number) | Position | Alleles | rsID | Position | Alleles |
|---|---|---|---|---|---|
| rs1245384573 | 129529325 | T/A | rs927312739 | 129532479 | G/A |
| rs879100706 | 129529327 | C/T | rs1472077837 | 129532484 | C/T |
| rs934131532 | 129529329 | C/T | rs748269752 | 129532485 | T/C |
| rs1267513138 | 129529331 | T/C | rs1414909936 | 129532496 | G/A |
| rs1467341001 | 129529333 | T/A | rs539249995 | 129532497 | G/A |
| rs763447187 | 129529342 | A/G | rs772086479 | 129532503 | T/C/G |
| rs986948449 | 129529343 | C/T | rs1335310386 | 129532505 | G/T |
| rs1405194008 | 129529344 | A/G | rs997805225 | 129532509 | G/A |
| rs1263966091 | 129529355 | TG/- | rs1264782419 | 129532512 | C/T |
| rs955355818 | 129529356 | G/A | rs373369517 | 129532514 | C/G/T |
| rs986830009 | 129529364 | G/C | rs746773592 | 129532515 | G/A |
| rs1334877177 | 129529366 | T/G | rs1464857862 | 129532518 | T/A |
| rs529295739 | 129529369 | A/G | rs770701400 | 129532521 | C/T |
| rs911401021 | 129529371 | G/A | rs367631575 | 129532522 | G/A |
| rs1375588335 | 129529380 | C/T | rs1016029927 | 129532527 | C/T |
| rs1319249372 | 129529381 | G/A | rs1338813260 | 129532535 | C/G/T |
| rs1432285653 | 129529383 | C/T | rs547981493 | 129532536 | G/A/T |
| rs1407721146 | 129529388 | -/G | rs1390478420 | 129532540 | C/A |
| rs942450807 | 129529391 | G/A | rs774809893 | 129532546 | A/T |
| rs1038560594 | 129529393 | C/T | rs374550929 | 129532547 | G/A/T |
| rs560370759 | 129529394 | G/A/T | rs1217784259 | 129532550 | G/T |
| rs144939863 | 129529401 | A/G | rs1364403778 | 129532552 | A/G |
| rs1476005736 | 129529403 | G/A | rs767979610 | 129532561 | C/G |
| rs929633130 | 129529404 | G/T | rs1273934052 | 129532566 | C/T |
| rs569952875 | 129529405 | A/C | rs148222991 | 129532568 | G/A |
| rs896419629 | 129529406 | C/T | rs761013258 | 129532569 | A/G |
| rs1013403650 | 129529411 | G/A | rs1437946997 | 129532575 | G/A |
| rs766787635 | 129529416 | G/A | rs141185480 | 129532580 | G/A/T |
| rs536977497 | 129529419 | G/A | rs104893783 | 129532581 | G/A/T |
| rs529438885 | 129529422 | T/C | rs765519035 | 129532585 | T/C/G |
| rs946853189 | 129529430 | C/G | rs1224848814 | 129532588 | C/T |
| rs1202323610 | 129529431 | C/T | rs752805805 | 129532590 | C/T |
| rs1252596172 | 129529433 | C/T | rs765438313 | 129532591 | G/A/C |
| rs1276157724 | 129529436 | C/T | rs1207948458 | 129532593 | A/G |
| rs1216139012 | 129529438 | A/G | rs1191932068 | 129532594 | T/C |
| rs558877754 | 129529441 | T/A | rs756658659 | 129532595 | G/T |
| rs73204245 | 129529442 | C/T | rs-1 | 129532595 | NA |
| rs755085836 | 129529443 | G/A | rs1286718279 | 129532601 | C/T |

TABLE S2-continued

| RHO SNPs. | | | | | |
|---|---|---|---|---|---|
| rsID (SNP number) | Position | Alleles | rsID | Position | Alleles |
| rs1384358972 | 129529446 | C/A | rs757219458 | 129532602 | A/G |
| rs781460558 | 129529449 | T/A/C | rs1238756481 | 129532605 | A/G |
| rs1056834120 | 129529460 | CCAAG/- | rs1478250192 | 129532608 | G/A |
| rs1331239499 | 129529465 | C/A | rs371853220 | 129532613 | C/T |
| rs1389991043 | 129529466 | C/T | rs150250946 | 129532614 | G/A |
| rs1199960057 | 129529466 | CT/- | rs199583468 | 129532619 | C/A |
| rs895163307 | 129529469 | T/C | rs1335011235 | 129532620 | C/T |
| rs957332793 | 129529471 | T/A | rs121918590 | 129532626 | TGC/- |
| rs534810430 | 129529476 | C/G/T | rs1375981120 | 129532633 | T/G |
| rs1385882841 | 129529478 | T/G | rs1399379654 | 129532634 | G/A |
| rs988784553 | 129529486 | C/A | rs104893781 | 129532636 | C/T |
| rs1020469708 | 129529492 | T/G | rs200826498 | 129532640 | C/T |
| rs898615712 | 129529497 | CAGACC/- | rs200894277 | 129532641 | G/A |
| rs1234834039 | 129529498 | A/G | rs768210562 | 129532646 | C/T |
| rs1205546729 | 129529505 | -/GCT GGGCA CTGAG GGAGA | rs201008735 | 129532647 | G/A |
| rs553108022 | 129529506 | G/A | rs1417922380 | 129532649 | G/C |
| rs987040087 | 129529510 | G/C | rs1396983168 | 129532658 | C/T |
| rs1172707327 | 129529525 | C/G | rs761022507 | 129532659 | A/G |
| rs201411679 | 129529527 | G/A | rs766943400 | 129532662 | T/G |
| rs78872255 | 129529528 | G/A/T | rs776812466 | 129532664 | C/T |
| rs541825239 | 129529534 | C/G | rs947228214 | 129532667 | C/A |
| rs986746861 | 129529535 | C/T | rs377120794 | 129532685 | C/T |
| rs569445278 | 129529539 | C/T | rs765350593 | 129532686 | G/A/T |
| rs1394528411 | 129529540 | C/A/T | rs761500453 | 129532689 | C/G |
| rs1427035391 | 129529550 | T/C | rs1488831597 | 129532693 | T/C |
| rs1366765139 | 129529555 | G/A | rs753036982 | 129532701 | A/T |
| rs1164108567 | 129529559 | A/- | rs1376126715 | 129532703 | C/T |
| rs756306377 | 129529568 | G/T | rs758543619 | 129532705 | T/A/C |
| rs1364687022 | 129529570 | G/C | rs554753426 | 129532706 | C/T |
| rs1244509367 | 129529571 | G/T | rs104893789 | 129532711 | C/A |
| rs1406981060 | 129529572 | G/T | rs145004306 | 129532712 | G/A |
| rs1472419291 | 129529574 | A/C | rs29001653 | 129532722 | A/G |
| rs1284402553 | 129529577 | G/C | rs142285818 | 129532727 | C/T |
| rs919680291 | 129529585 | C/T | rs781237162 | 129532728 | G/A/T |
| rs1250724706 | 129529593 | A/G | rs745616372 | 129532730 | C/G/T |
| rs929602050 | 129529614 | C/T | rs779665096 | 129532731 | G/A/T |

TABLE S2-continued

| RHO SNPs. | | | | | |
|---|---|---|---|---|---|
| rsID (SNP number) | Position | Alleles | rsID | Position | Alleles |
| rs1490806446 | 129529618 | G/A | rs768300463 | 129532734 | A/T |
| rs1046784691 | 129529624 | G/C | rs778356027 | 129532743 | C/T |
| rs989842922 | 129529627 | T/C | rs199701338 | 129532749 | A/C/G |
| rs1222273563 | 129529628 | C/T | rs1303453819 | 129532754 | T/C |
| rs917615940 | 129529629 | G/A | rs771322615 | 129532755 | A/T |
| rs1228564325 | 129529632 | C/A | rs1238542520 | 129532757 | C/G |
| rs556655422 | 129529633 | C/T | rs146391463 | 129532761 | A/T |
| rs575161157 | 129529634 | C/T | rs759818475 | 129532762 | T/A/C |
| rs546127355 | 129529637 | C/T | rs1553781406 | 129532765 | NA |
| rs777559042 | 129529639 | G/T | rs998172502 | 129532766 | C/T |
| rs1203121815 | 129529652 | T/C | rs139566602 | 129532769 | G/A |
| rs1249104278 | 129529654 | C/T | rs1327446595 | 129532772 | G/A |
| rs1368803877 | 129529655 | C/G | rs776014770 | 129532773 | G/T |
| rs1490758813 | 129529656 | C/T | rs1475042732 | 129532776 | C/- |
| rs1456900243 | 129529659 | T/- | rs763223221 | 129532778 | T/C |
| rs945820133 | 129529663 | C/- | rs762711356 | 129532783 | C/A/T |
| rs1160019893 | 129529663 | C/T | rs770703927 | 129532784 | G/- |
| rs186719544 | 129529664 | C/T | rs1199889529 | 129532784 | G/A |
| rs924141038 | 129529670 | C/T | rs200076128 | 129532789 | G/T |
| rs1201927865 | 129529679 | C/T | rs1400301625 | 129532796 | C/A |
| rs1045421768 | 129529681 | C/T | rs761990733 | 129532798 | C/A/T |
| rs1267882076 | 129529687 | G/A | rs75783569 | 129532799 | A/G |
| rs1190541236 | 129529687 | -/CCT | rs750430777 | 129532802 | G/A |
| rs905024147 | 129529691 | C/G | rs1454297160 | 129532806 | C/T |
| rs544170990 | 129529696 | C/- | rs372010849 | 129532816 | G/A/T |
| rs1489774710 | 129529696 | C/T | rs753665727 | 129532817 | C/T |
| rs528662813 | 129529697 | C/T | rs560324786 | 129532818 | G/A |
| rs540386305 | 129529698 | G/A | rs1192799558 | 129532827 | C/T |
| rs139028150 | 129529699 | C/T | rs777625206 | 129532830 | G/A/C |
| rs529338772 | 129529700 | G/T | rs937332103 | 129532831 | G/A |
| rs551028346 | 129529701 | T/G | rs1437298068 | 129532836 | G/A |
| rs1313142209 | 129529702 | T/G | rs369233304 | 129532864 | C/G |
| rs1301083495 | 129529705 | A/G | rs181047668 | 129532865 | C/A |
| rs1010299725 | 129529712 | C/T | rs909258142 | 129532867 | T/G |
| rs569194631 | 129529714 | G/A | rs991779602 | 129532868 | C/T |
| rs1426832307 | 129529721 | A/G | rs915839107 | 129532871 | G/A |
| rs1303960511 | 129529724 | A/G | rs1197194560 | 129532873 | T/A |
| rs1434435452 | 129529725 | C/A | rs1364815089 | 129532880 | C/T |

TABLE S2-continued

| RHO SNPs. | | | | | |
|---|---|---|---|---|---|
| rsID (SNP number) | Position | Alleles | rsID | Position | Alleles |
| rs1020226107 | 129529726 | C/T | rs940777503 | 129532888 | T/G |
| rs1178849428 | 129529727 | G/A | rs947197037 | 129532903 | C/A/T |
| rs529422419 | 129529731 | G/A | rs1357893715 | 129532928 | G/C |
| rs955406718 | 129529736 | C/T | rs1285346882 | 129532937 | C/T |
| rs778804021 | 129529737 | G/A | rs1294460125 | 129532942 | C/T |
| rs1018943119 | 129529782 | A/T | rs542748394 | 129532948 | A/G |
| rs1175100948 | 129529784 | C/T | rs1331072853 | 129532953 | T/G |
| rs964211475 | 129529785 | A/G | rs186091794 | 129532963 | G/C |
| rs745849174 | 129529794 | G/T | rs924475172 | 129532964 | G/A |
| rs533358632 | 129529799 | G/A | rs933191288 | 129532970 | C/T |
| rs1431334232 | 129529804 | T/C | rs1169663614 | 129532971 | C/T |
| rs890979889 | 129529805 | G/T | rs1288268641 | 129532974 | G/A |
| rs74578881 | 129529809 | G/T | rs1050320955 | 129533001 | C/T |
| rs1464022886 | 129529824 | C/T | rs1182433925 | 129533003 | G/T |
| rs775005384 | 129529828 | A/G | rs1472143913 | 129533007 | G/C |
| rs1205158566 | 129529844 | A/T | rs754963794 | 129533021 | T/G |
| rs1483379450 | 129529845 | G/A | rs1183487265 | 129533022 | CAGGT GGGAGAAGC TC/- |
| rs570714427 | 129529847 | C/G | rs889070870 | 129533027 | G/A |
| rs1255704741 | 129529850 | G/A | rs1052570874 | 129533028 | G/A |
| rs1360952243 | 129529861 | G/T | rs1197107837 | 129533029 | G/C |
| rs1018176602 | 129529867 | C/A | rs1000532131 | 129533034 | G/A |
| rs1246288861 | 129529874 | G/A | rs901802259 | 129533035 | C/A |
| rs951094548 | 129529875 | G/C | rs1228269550 | 129533042 | C/G |
| rs964339101 | 129529876 | A/T | rs1208869736 | 129533047 | A/C/G |
| rs1228399737 | 129529881 | G/A | rs531346738 | 129533054 | G/A |
| rs1290534863 | 129529882 | C/T | rs1281367465 | 129533060 | C/T |
| rs1011244966 | 129529895 | A/G | rs1447671364 | 129533069 | AGTC/- |
| rs1338799697 | 129529896 | G/C | rs1376394230 | 129533071 | T/A |
| rs1396756083 | 129529902 | A/G | rs1329636114 | 129533072 | C/G |
| rs1401810723 | 129529906 | C/T | rs933344851 | 129533077 | G/A |
| rs1301998520 | 129529912 | G/A | rs2855557 | 129533079 | A/G/T |
| rs1357015222 | 129529914 | T/A | rs889390884 | 129533080 | C/T |
| rs1464333732 | 129529919 | T/A | rs1185001327 | 129533082 | C/T |
| rs551679853 | 129529929 | T/A | rs1368866095 | 129533085 | G/T |
| rs1242472306 | 129529933 | T/- | rs1159773161 | 129533086 | T/C |
| rs967085224 | 129529939 | G/A | rs1006504273 | 129533087 | C/T |
| rs1448847236 | 129529943 | C/G | rs1037862444 | 129533088 | G/A |

TABLE S2-continued

| RHO SNPs. | | | | | |
|---|---|---|---|---|---|
| rsID (SNP number) | Position | Alleles | rsID | Position | Alleles |
| rs1387723724 | 129529952 | A/G | rs1176459492 | 129533098 | T/C |
| rs917581758 | 129529953 | C/T | rs958988786 | 129533102 | C/T |
| rs1184673598 | 129529954 | G/A | rs565597965 | 129533105 | G/A |
| rs1255073902 | 129529965 | C/A | rs1247665295 | 129533108 | T/A |
| rs949072687 | 129529966 | C/T | rs1387127393 | 129533111 | A/G |
| rs750219764 | 129529979 | G/C | rs1457701979 | 129533113 | A/G |
| rs924083862 | 129529982 | G/C | rs984749754 | 129533115 | A/G |
| rs768195502 | 129529984 | C/G/T | rs1240955090 | 129533125 | G/A |
| rs1164482260 | 129529985 | G/A | rs1353148402 | 129533127 | A/C |
| rs1275873599 | 129529990 | G/T | rs191009602 | 129533131 | A/T |
| rs992766298 | 129529992 | G/C | rs1307277111 | 129533131 | A/- |
| rs992480823 | 129529996 | A/C | rs1387966572 | 129533133 | A/G |
| rs571636757 | 129529998 | C/T | rs909234511 | 129533134 | A/C |
| rs916832235 | 129529999 | G/C | rs1236776120 | 129533136 | G/T |
| rs534820968 | 129530003 | G/A | rs898032106 | 129533144 | C/T |
| rs1340002495 | 129530004 | CCA/- | rs993652617 | 129533158 | G/A |
| rs1310803766 | 129530007 | C/A | rs1035450700 | 129533165 | G/A |
| rs936492822 | 129530008 | A/G | rs548091071 | 129533172 | C/T |
| rs1054009367 | 129530010 | G/A | rs566301956 | 129533173 | G/A |
| rs192461600 | 129530011 | C/A/T | rs1348020029 | 129533174 | G/A |
| rs1368664660 | 129530012 | G/A | rs1300033375 | 129533179 | G/T |
| rs1164441983 | 129530018 | -/T | rs1341450163 | 129533183 | C/T |
| rs568169643 | 129530025 | C/A | rs1379174415 | 129533186 | C/T |
| rs1472823133 | 129530031 | C/T | rs1012602093 | 129533187 | G/A |
| rs1367455258 | 129530039 | C/T | rs1282771985 | 129533191 | G/A |
| rs1184946002 | 129530041 | C/T | rs1331895333 | 129533197 | C/T |
| rs1473377384 | 129530044 | T/C | rs752248867 | 129533198 | A/T |
| rs1360638002 | 129530049 | A/G | rs1190941811 | 129533206 | A/G |
| rs535230697 | 129530055 | C/T | rs182735834 | 129533210 | A/C |
| rs1181951167 | 129530057 | G/C | rs187430296 | 129533225 | C/T |
| rs1482334501 | 129530059 | C/T | rs978681828 | 129533229 | G/T |
| rs1292625061 | 129530060 | T/G | rs1463131161 | 129533230 | C/T |
| rs1041822252 | 129530062 | G/A | rs1205184873 | 129533232 | A/G |
| rs1287584881 | 129530066 | C/T | rs1438208750 | 129533250 | C/T |
| rs1263815511 | 129530069 | T/G | rs1256356401 | 129533252 | T/C |
| rs1241377560 | 129530076 | G/A | rs1050253507 | 129533256 | C/A |
| rs2855552 | 129530082 | T/G | rs1185233895 | 129533259 | G/T |

TABLE S2-continued

| RHO SNPs. | | | | | |
|---|---|---|---|---|---|
| rsID (SNP number) | Position | Alleles | rsID | Position | Alleles |
| rs1288703258 | 129530083 | C/G/T | rs1284011618 | 129533265 | T/A |
| rs1348452172 | 129530084 | T/G | rs1365291770 | 129533266 | T/C |
| rs575196456 | 129530087 | C/T | rs1236711758 | 129533271 | C/T |
| rs1452647950 | 129530094 | T/C | rs1312974008 | 129533273 | C/T |
| rs1018501151 | 129530101 | T/C | rs538825293 | 129533281 | T/C |
| rs1047117281 | 129530105 | T/C | rs74435833 | 129533283 | G/A/T |
| rs1160956574 | 129530106 | G/A | rs1279954881 | 129533291 | A/G |
| rs538999065 | 129530113 | A/G | rs1400546315 | 129533297 | A/G |
| rs558037874 | 129530127 | C/T | rs1359309784 | 129533300 | A/G |
| rs1008053580 | 129530147 | G/- | rs537065273 | 129533303 | G/T |
| rs1039984223 | 129530161 | C/T | rs1467166302 | 129533306 | G/A |
| rs1027145519 | 129530162 | G/A | rs1359374123 | 129533310 | G/A |
| rs1200179703 | 129530167 | GTT/- | rs988597337 | 129533311 | G/A |
| rs1213585726 | 129530168 | T/C | rs1411362216 | 129533320 | C/T |
| rs573163746 | 129530169 | T/G | rs1431743805 | 129533323 | A/G |
| rs982527490 | 129530173 | C/T | rs923393987 | 129533325 | C/G/T |
| rs1210704588 | 129530174 | T/C | rs933295383 | 129533329 | T/A |
| rs146389280 | 129530178 | C/T | rs1455647531 | 129533332 | A/G |
| rs73863103 | 129530180 | G/A/C | rs1009251610 | 129533335 | A/G |
| rs1226864693 | 129530183 | T/C | rs558503555 | 129533336 | C/T |
| rs1326800808 | 129530201 | T/C | rs1261718625 | 129533342 | A/T |
| rs1242592588 | 129530216 | T/C | rs1213072953 | 129533356 | A/C |
| rs1276412304 | 129530231 | A/G | rs1483659732 | 129533358 | C/T |
| rs1437027442 | 129530235 | T/G | rs1050400032 | 129533359 | C/G |
| rs1330485529 | 129530236 | G/A | rs910586928 | 129533374 | G/A |
| rs1471957665 | 129530238 | TTGA/- | rs906286941 | 129533380 | T/G |
| rs1021271948 | 129530242 | T/A | rs1304820785 | 129533388 | C/G/T |
| rs1409206433 | 129530254 | C/G | rs116351742 | 129533390 | C/A/G/T |
| rs1400451879 | 129530260 | T/G | rs1397252875 | 129533391 | G/A |
| rs980862798 | 129530262 | C/T | rs867577959 | 129533405 | C/T |
| rs1157595571 | 129530265 | A/G | rs1301829625 | 129533409 | G/A |
| rs2855553 | 129530268 | G/A | rs1254209060 | 129533416 | G/A |
| rs1455365585 | 129530276 | T/C | rs748989122 | 129533423 | G/A |
| rs1427627078 | 129530277 | G/T | rs1395665289 | 129533428 | T/C |
| rs926330760 | 129530278 | G/A | rs772528490 | 129533429 | C/G |
| rs936569686 | 129530283 | G/A/T | rs993692054 | 129533430 | T/A |
| rs574163826 | 129530290 | G/A | rs1352666271 | 129533440 | G/A |
| rs1376454149 | 129530293 | C/T | rs1465469785 | 129533442 | G/A |

TABLE S2-continued

RHO SNPs.

| rsID (SNP number) | Position | Alleles | rsID | Position | Alleles |
|---|---|---|---|---|---|
| rs139374423 | 129530294 | A/G | rs1229581864 | 129533443 | C/G |
| rs913734629 | 129530296 | A/G | rs1422105627 | 129533444 | G/A |
| rs1247554748 | 129530298 | G/A | rs2625964 | 129533463 | T/A |
| rs945214053 | 129530301 | T/C | rs1057258150 | 129533466 | A/G |
| rs544423048 | 129530309 | A/G | rs962326560 | 129533491 | G/A |
| rs1206997948 | 129530311 | C/A | rs895547273 | 129533492 | C/T |
| rs1444350185 | 129530317 | CTT/- | rs538581410 | 129533493 | G/A |
| rs1280428587 | 129530318 | T/C | rs1180299189 | 129533497 | G/A |
| rs1219612108 | 129530319 | T/C | rs1481757170 | 129533498 | A/G |
| rs1379898909 | 129530326 | C/T | rs1022578791 | 129533501 | C/T |
| rs1344102691 | 129530327 | C/T | rs780494657 | 129533502 | G/A/T |
| rs562999077 | 129530343 | G/A | rs746121931 | 129533504 | G/C |
| rs1443986428 | 129530351 | C/G | rs553775083 | 129533513 | A/G |
| rs1230611312 | 129530356 | T/C | rs572252938 | 129533521 | A/G |
| rs1365270538 | 129530359 | C/T | rs1256072074 | 129533526 | G/A |
| rs1319315167 | 129530360 | T/C | rs1000029963 | 129533528 | C/T |
| rs1432353191 | 129530361 | C/G | rs569161209 | 129533533 | C/T |
| rs891224636 | 129530365 | G/A | rs561052129 | 129533534 | G/A |
| rs992298293 | 129530368 | G/A | rs1252428841 | 129533546 | C/T |
| rs533370883 | 129530371 | G/A | rs747418983 | 129533547 | G/A/C |
| rs551759609 | 129530375 | C/G | rs1054086365 | 129533552 | A/G |
| rs1171019870 | 129530376 | C/A | rs778587340 | 129533558 | A/C |
| rs944030796 | 129530380 | T/C | rs775579127 | 129533559 | AGCAC ACTGT GGGC /- |
| rs969581772 | 129530384 | C/G/T | rs747582133 | 129533563 | C/T |
| rs1186791085 | 129530385 | G/A | rs1443931644 | 129533565 | C/T |
| rs980808987 | 129530387 | GTTATTTCAT TTC CC/- | rs771682972 | 129533567 | G/A |
| rs1221785801 | 129530390 | A/G | rs781539793 | 129533568 | T/C |
| rs1285128834 | 129530395 | A/G | rs746332355 | 129533570 | G/A |
| rs1040092068 | 129530401 | C/T | rs1264004508 | 129533575 | C/G |
| rs1209735595 | 129530402 | G/A | rs954807098 | 129533577 | C/T |
| rs1441632815 | 129530404 | G/A | rs1358934207 | 129533578 | T/C/G |
| rs564388429 | 129530409 | G/C | rs770432635 | 129533580 | G/C |
| rs774967666 | 129530419 | A/G | rs755540170 | 129533581 | C/T |
| rs912645736 | 129530423 | A/G | rs775945120 | 129533582 | C/A |
| rs1202926964 | 129530427 | C/A | rs763455152 | 129533583 | C/G |
| rs779747890 | 129530437 | G/A | rs2071092 | 129533585 | G/A |

TABLE S2-continued

| RHO SNPs. | | | | | |
|---|---|---|---|---|---|
| rsID (SNP number) | Position | Alleles | rsID | Position | Alleles |
| rs996155575 | 129530443 | A/G | rs774698907 | 129533587 | C/T |
| rs1212313979 | 129530457 | C/T | rs761784827 | 129533593 | C/G |
| rs1262644778 | 129530464 | A/G | rs767573351 | 129533594 | C/T |
| rs1380772693 | 129530471 | A/C | rs750473517 | 129533598 | T/C |
| rs1440728660 | 129530474 | T/C | rs374334512 | 129533599 | G/C |
| rs1284392006 | 129530478 | C/T | rs543521798 | 129533602 | T/C |
| rs200054443 | 129530483 | CATTAGGATG /- | rs1399079770 | 129533604 | C/T |
| rs1027281365 | 129530488 | G/A | rs766326902 | 129533611 | C/T |
| rs1373966487 | 129530505 | A/C | rs753609310 | 129533612 | G/A/T |
| rs944123514 | 129530506 | AACAC ACACAC ACACA CACAC ACACA C/- | rs1064793749 | 129533617 | T/- |
| rs1310245123 | 129530506 | -/AC/ACAC/ ACACAC/ACACA CAC | rs1396630102 | 129533618 | G/A |
| rs146327704 | 129530507 | AC/- | rs754809715 | 129533619 | C/G/T |
| rs762150760 | 129530507 | ACAC/- | rs778536018 | 129533621 | T/A |
| rs1181480449 | 129530507 | ACACAC/- | rs752455127 | 129533623 | C/G |
| rs1471943001 | 129530507 | ACACA CACAC AC /- | rs1239004607 | 129533625 | C/T |
| rs1255058178 | 129530508 | C/A | rs138831590 | 129533630 | C/A/T |
| rs1039506093 | 129530509 | A/C | rs777274073 | 129533632 | A/C/G |
| rs761682198 | 129530509 | AC/- | rs1316267671 | 129533633 | T/A |
| rs1469959658 | 129530511 | ACACA CACAC ACACA CACAC ACA/- | rs1200800092 | 129533636 | G/A |
| rs1273801833 | 129530516 | -/A | rs1251916916 | 129533639 | G/A |
| rs1202404945 | 129530522 | C/- | rs142771862 | 129533640 | C/T |
| rs1322995057 | 129530522 | -/ACA CACACA | rs756663175 | 129533641 | G/A |
| rs1289987340 | 129530523 | ACACA CACACA/- | rs780743370 | 129533642 | G/C |
| rs1180546861 | 129530523 | -/CC | rs1264835715 | 129533648 | A/G |
| rs1227317514 | 129530524 | C/- | rs527236102 | 129533648 | ACCC/- |
| rs1431900174 | 129530524 | -/A/AC ACACA | rs749663446 | 129533650 | C/G |
| rs1481072835 | 129530526 | C/- | rs1476179838 | 129533652 | A/C/T |
| rs1176304531 | 129530526 | -/A/ACA/ACA CA | rs368995053 | 129533654 | T/C |
| rs1182924383 | 129530528 | C/- | rs1422707451 | 129533655 | G/C |
| rs1350488300 | 129530528 | CAC/- | rs548113513 | 129533661 | C/T |
| rs899681814 | 129530528 | CACAC AAC/- | rs200095648 | 129533662 | G/A/C |
| rs1403779259 | 129530528 | CACAC AACAC/- | rs1373092759 | 129533663 | A/G |
| rs1399464043 | 129530528 | -/A/ACA | rs773295145 | 129533666 | A/T |

TABLE S2-continued

RHO SNPs.

| rsID (SNP number) | Position | Alleles | rsID | Position | Alleles |
|---|---|---|---|---|---|
| rs1411113214 | 129530530 | C/- | rs1300633110 | 129533668 | G/A |
| rs1250888081 | 129530530 | -/A | rs760792843 | 129533669 | C/T |
| rs1175399101 | 129530531 | ACA/- | rs766275471 | 129533679 | C/T |
| rs60744548 | 129530531 | -/A | rs201989308 | 129533680 | G/A/C |
| rs370601606 | 129530532 | C/A | rs759316820 | 129533681 | T/C |
| rs773127460 | 129530532 | CAAC/- | rs144211117 | 129533685 | C/A/T |
| rs1246741626 | 129530532 | CAAC AC/- | rs148748781 | 129533690 | C/T |
| rs750974086 | 129530532 | CAACA CAC/- | rs559747229 | 129533691 | G/A/C |
| rs1220213959 | 129530532 | CAACA CACAC/- | rs142322202 | 129533692 | G/A |
| rs1332092021 | 129530532 | CAACA CACAC ACAC/- | rs183318466 | 129533696 | C/A/T |
| rs1228696723 | 129530532 | -/AA | rs1200695176 | 129533697 | G/A |
| rs138115019 | 129530533 | A/C | rs1486594657 | 129533700 | C/G |
| rs766932095 | 129530533 | A/- | rs104893778 | 129533701 | C/T |
| rs1305320311 | 129530533 | AACA/- | rs749753555 | 129533703 | G/A/C |
| rs60120581 | 129530533 | -/AC/ACAC/A CACAC/ACACACAC/ ACACACACAC/ ACACACACACAC/A CACACACACACAC/ ACACACACACACA CAC/ACACACACAC ACACACAC/ACACA CACACACACA CACAC/ACACA CACACACACACACA CAC/ACACACACAC ACACACACACACAC/ C/CAAAAC/CAAC/ CAACAC/CAACACAC /CAACACACAC/ CAACACACACAC/ CAACACACACACAC/ CAC/CACAAC/ CACAA | rs104893795 | 129533704 | G/A/c |
| rs867450441 | 129530534 | A/C | rs29001637 | 129533710 | C/T |
| rs1259209102 | 129530534 | AC/- | rs29001566 | 129533711 | C/A/G/ T |
| rs1446254145 | 129530534 | ACAC/- | rs779296525 | 129533712 | G/A |
| rs1483781822 | 129530534 | ACACAC/- | rs1187838977 | 129533714 | C/A |
| rs1255832125 | 129530534 | ACACA CAC/- | rs867005068 | 129533722 | C/T |
| rs1209285268 | 129530534 | ACACA CACAC/- | rs748483575 | 129533724 | G/A |
| rs1344976756 | 129530534 | ACACA CACAC AC/ - | rs1286150902 | 129533725 | C/T |
| rs1298358258 | 129530534 | ACACA CACACA CACAC/- | rs1215381293 | 129533731 | A/T |
| rs1004394301 | 129530535 | C/A | rs1432291926 | 129533733 | T/C/G |
| rs1011477724 | 129530535 | C/- | rs747215789 | 129533735 | TG/- |
| rs1396884956 | 129530535 | -/A | rs1234400824 | 129533739 | G/A |

TABLE S2-continued

| RHO SNPs. | | | | | |
|---|---|---|---|---|---|
| rsID (SNP number) | Position | Alleles | rsID | Position | Alleles |
| rs1329123541 | 129530537 | C/- | rs772316842 | 129533741 | C/T |
| rs1353498371 | 129530544 | A/C | rs1435838714 | 129533742 | G/A |
| rs1439550769 | 129530545 | -/AA | rs773347364 | 129533744 | C/T |
| rs1379548548 | 129530548 | -/CACACA CACAACC | rs1402429783 | 129533745 | T/G |
| rs1024704718 | 129530549 | C/A | rs962322955 | 129533746 | A/G |
| rs570795323 | 129530549 | -/AA/ACAA/ ACACAA/ACACA CACACA CACACAA | rs1297633277 | 129533747 | T/G |
| rs1169200718 | 129530552 | A/G | rs548460589 | 129533750 | G/A/C |
| rs1461018190 | 129530555 | C/A | rs113310993 | 129533751 | C/T |
| rs1370910820 | 129530559 | C/T | rs759406692 | 129533752 | G/A |
| rs1189174445 | 129530565 | C/A | rs1426158544 | 129533754 | C/T |
| rs970863466 | 129530567 | C/A | rs1367145272 | 129533756 | C/G |
| rs1257173881 | 129530567 | -/ACAA | rs886057968 | 129533758 | C/T |
| rs866387343 | 129530569 | A/C | rs375306799 | 129533759 | A/C/G |
| rs1222852881 | 129530570 | A/C | rs2071093 | 129533761 | C/A/T |
| rs1033753020 | 129530580 | C/T | rs1348719352 | 129533767 | C/T |
| rs957767431 | 129530581 | G/A | rs763794994 | 129533768 | A/C |
| rs903131767 | 129530583 | G/A | rs751311620 | 129533769 | C/A |
| rs1216344354 | 129530586 | C/T | rs1355119221 | 129533772 | T/C/G |
| rs1205155690 | 129530590 | G/- | rs986177595 | 129533776 | C/G |
| rs998517009 | 129530593 | C/A | rs552237368 | 129533786 | C/T |
| rs1267314379 | 129530600 | G/C | rs369102407 | 129533804 | C/T |
| rs989317594 | 129530602 | C/T | rs1310287805 | 129533805 | G/A |
| rs1245706191 | 129530603 | C/G | rs1191655979 | 129533806 | C/T |
| rs1321379369 | 129530606 | C/T | rs1268188022 | 129533807 | C/A |
| rs1273792671 | 129530607 | T/- | rs963347381 | 129533810 | T/C |
| rs377157554 | 129530612 | T/C | rs973381824 | 129533815 | A/C |
| rs77154523 | 129530616 | T/C | rs76288565 | 129533821 | C/A/G/T |
| rs1203244525 | 129530617 | C/T | rs534695614 | 129533822 | G/A/C |
| rs1271560435 | 129530623 | C/T | rs376184299 | 129533828 | A/G |
| rs1308560636 | 129530627 | A/G | rs989333591 | 129533829 | C/T |
| rs1390809098 | 129530628 | T/C | rs913808639 | 129533830 | A/G/T |
| rs1393623254 | 129530636 | G/A | rs886057969 | 129533833 | G/A |
| rs767654426 | 129530639 | C/T | rs1278192906 | 129533833 | G/- |
| rs1490601539 | 129530640 | G/A | rs1342358879 | 129533834 | G/A |
| rs1416686900 | 129530649 | A/G | rs917384196 | 129533836 | T/G |
| rs752830466 | 129530654 | T/C | rs1168397592 | 129533841 | A/- |

TABLE S2-continued

| RHO SNPs. | | | | | |
|---|---|---|---|---|---|
| rsID (SNP number) | Position | Alleles | rsID | Position | Alleles |
| rs1199366735 | 129530659 | C/T | rs948896484 | 129533842 | A/T |
| rs546852513 | 129530666 | C/G | rs927658993 | 129533842 | AT/- |
| rs1473773483 | 129530681 | C/G | rs1491118185 | 129533842 | -/T |
| rs1253057494 | 129530686 | -/CTCC | rs1402264965 | 129533843 | T/- |
| rs1181644601 | 129530694 | G/T | rs1363313275 | 129533843 | TT/- |
| rs1013090672 | 129530695 | C/G/T | rs1192866487 | 129533843 | TTT/- |
| rs969508648 | 129530696 | G/A | rs1474100936 | 129533856 | T/C |
| rs1168047248 | 129530697 | T/A | rs796247959 | 129533857 | TT/- |
| rs867279546 | 129530698 | G/T | rs796098464 | 129533858 | T/- |
| rs1271477680 | 129530703 | C/T | rs1238730903 | 129533858 | T/A |
| rs1230542126 | 129530705 | C/T | rs1187750228 | 129533859 | A/- |
| rs974240725 | 129530709 | -/C | rs1369075898 | 129533859 | A/T |
| rs1418157003 | 129530710 | C/T | rs62267563 | 129533861 | G/T |
| rs1238160463 | 129530712 | C/T | rs1240931894 | 129533879 | C/T |
| rs911753205 | 129530716 | C/T | rs554039303 | 129533884 | C/T |
| rs1027184412 | 129530718 | C/G | rs1200908059 | 129533893 | G/C |
| rs751084368 | 129530721 | T/C | rs1294586919 | 129533897 | G/T |
| rs1386815018 | 129530722 | C/T | rs1389388209 | 129533902 | A/C |
| rs944108470 | 129530724 | T/A | rs112963101 | 129533914 | C/T |
| rs1039824365 | 129530725 | C/G | rs1044096166 | 129533916 | C/G |
| rs899831224 | 129530727 | C/G/T | rs1384504293 | 129533921 | ACCT/- |
| rs1413069583 | 129530743 | C/T | rs202215179 | 129533923 | C/T |
| rs1158379876 | 129530748 | C/T | rs386665775 | 129533923 | CTACT/TG |
| rs1365999819 | 129530754 | G/A | rs935776976 | 129533927 | T/C |
| rs1469007434 | 129530766 | C/A | rs1365555627 | 129533927 | -/G |
| rs568202024 | 129530769 | T/C | rs536467893 | 129533931 | C/T |
| rs1321522954 | 129530773 | C/A | rs1227169787 | 129533932 | T/C |
| rs1200252369 | 129530777 | T/G | rs886057970 | 129533942 | C/T |
| rs1328189703 | 129530793 | A/G | rs773291833 | 129533943 | G/A |
| rs1048645997 | 129530795 | C/A | rs891491842 | 129533946 | C/G |
| rs1251285870 | 129530798 | C/T | rs2410 | 129533950 | A/G |
| rs1210762726 | 129530799 | C/T | rs766225946 | 129533958 | C/T |
| rs756285704 | 129530802 | C/T | rs1029997992 | 129533959 | G/A |
| rs1004490446 | 129530807 | T/C | rs1400759640 | 129533960 | G/A |
| rs1284647593 | 129530809 | T/C | rs562985533 | 129533970 | C/A |
| rs1025132463 | 129530811 | T/A | rs1169819656 | 129533975 | C/T |
| rs912562061 | 129530812 | -/G | rs759322778 | 129533994 | C/A/T |

TABLE S2-continued

| RHO SNPs. | | | | | |
|---|---|---|---|---|---|
| rsID (SNP number) | Position | Alleles | rsID | Position | Alleles |
| rs1204307378 | 129530813 | G/- | rs1006762563 | 129534002 | C/T |
| rs764208456 | 129530814 | G/C/T | rs1487459358 | 129534003 | G/A |
| rs535635302 | 129530815 | G/T | rs1037912093 | 129534006 | G/T |
| rs921374781 | 129530818 | G/A/T | rs1006744824 | 129534018 | C/T |
| rs947191845 | 129530821 | T/G | rs1211979809 | 129534020 | G/C |
| rs1400408135 | 129530822 | G/T | rs1382991179 | 129534026 | G/A |
| rs1342079756 | 129530829 | C/- | rs55941599 | 129534031 | C/T |
| rs375593312 | 129530840 | G/A | rs1458449459 | 129534037 | T/C |
| rs553392884 | 129530841 | G/T | rs963441852 | 129534041 | G/A |
| rs1297666027 | 129530842 | G/A | rs1237976705 | 129534046 | G/A |
| rs1262343887 | 129530843 | G/T | rs973516304 | 129534056 | C/T |
| rs113823926 | 129530844 | T/C | rs1202986126 | 129534063 | G/A |
| rs780707497 | 129530848 | T/- | rs1450380650 | 129534065 | G/T |
| rs778533886 | 129530851 | T/C | rs1291281286 | 129534075 | G/C |
| rs747855401 | 129530853 | A/T | rs1227793264 | 129534076 | G/A |
| rs369893168 | 129530855 | C/T | rs1357452660 | 129534083 | A/G |
| rs772533932 | 129530857 | C/G/T | rs545193682 | 129534085 | A/C |
| rs746563423 | 129530859 | T/G | rs1026310752 | 129534090 | C/G |
| rs1454233776 | 129530864 | A/C | rs1311669495 | 129534108 | G/T |
| rs957907715 | 129530865 | C/T | rs1241182098 | 129534123 | T/C |
| rs568571580 | 129530866 | T/C | rs1377314852 | 129534133 | G/C |
| rs776101913 | 129530867 | G/A | rs188052820 | 129534143 | A/G |
| rs763402049 | 129530868 | C/A | rs993793446 | 129534154 | C/A |
| rs764607760 | 129530873 | C/T | rs886057971 | 129534158 | C/G/T |
| rs774865494 | 129530878 | G/A | rs145921862 | 129534159 | G/A |
| rs762059468 | 129530879 | A/G | rs1166122252 | 129534169 | C/T |
| rs895489077 | 129530885 | C/T | rs1404175084 | 129534171 | A/G |
| rs1384283117 | 129530886 | C/T | rs1382867094 | 129534172 | C/T |
| rs1399039412 | 129530888 | T/C | rs148165044 | 129534185 | A/G |
| rs146311684 | 129530895 | C/G/T | rs1439951941 | 129534187 | T/C |
| rs747643955 | 129530895 | CT/- | rs1269556656 | 129534187 | TGATAT GGAGCAGT /- |
| rs1246476415 | 129530904 | C/T | rs954668655 | 129534191 | A/G |
| rs1553781140 | 129530906 | NA | rs948866852 | 129534192 | T/C |
| rs1022655604 | 129530910 | C/A | rs1456836682 | 129534193 | G/A |
| rs372812523 | 129530913 | C/A/T | rs540632143 | 129534195 | A/T |
| rs766196737 | 129530914 | G/A | rs1017665289 | 129534202 | G/A |
| rs104893775 | 129530917 | C/T | rs78163008 | 129534206 | T/C |

TABLE S2-continued

| RHO SNPs. | | | | | |
|---|---|---|---|---|---|
| rsID (SNP number) | Position | Alleles | rsID | Position | Alleles |
| rs104893774 | 129530918 | G/A/T | rs1433947193 | 129534214 | C/A |
| rs886041233 | 129530918 | GG/TT | rs1318045824 | 129534218 | G/A |
| rs1057522760 | 129530919 | G/A/T | rs989713390 | 129534220 | C/T |
| rs200248198 | 129530922 | C/A/T | rs1020816340 | 129534227 | T/C |
| rs778626065 | 129530923 | G/A | rs1489867195 | 129534231 | CTC/- |
| rs1213823882 | 129530928 | G/C | rs1288292362 | 129534241 | A/G |
| rs752496804 | 129530942 | T/A/G | rs935745844 | 129534258 | C/G |
| rs1488892105 | 129530946 | C/T | rs369408405 | 129534260 | G/T |
| rs1222453447 | 129530950 | T/A | rs912859855 | 129534264 | C/T |
| rs1269229442 | 129530952 | C/A | rs1353232788 | 129534268 | C/T |
| rs200165530 | 129530953 | C/T | rs933661466 | 129534269 | G/A |
| rs746468201 | 129530954 | G/A | rs1311742715 | 129534270 | A/G |
| rs1342580020 | 129530955 | C/T | rs1369471699 | 129534273 | C/T |
| rs139502149 | 129530958 | C/T | rs1275311432 | 129534274 | G/A |
| rs780408367 | 129530959 | G/A | rs1404280839 | 129534277 | G/A |
| rs931275670 | 129530960 | G/A | rs1363120335 | 129534278 | C/A |
| rs1297879534 | 129530961 | G/A | rs1299462326 | 129534280 | A/C |
| rs104893791 | 129530962 | G/A/C | rs1050996886 | 129534285 | G/A |
| rs1171093745 | 129530964 | G/C | rs1344221731 | 129534290 | C/T |
| rs1381050525 | 129530966 | A/G | rs1156571156 | 129534292 | A/G |
| rs1420195862 | 129530968 | C/T | rs927899533 | 129534296 | G/A |
| rs1433023778 | 129530971 | G/A | rs889686368 | 129534297 | A/G |
| rs1418964117 | 129530972 | C/T | rs1230131282 | 129534298 | -/GT |
| rs1302502291 | 129530973 | C/G | rs1006838285 | 129534303 | G/T |
| rs774816413 | 129530977 | A/G | rs1479726854 | 129534313 | A/G |
| rs762290223 | 129530978 | T/C | rs990449127 | 129534314 | TG/- |
| rs557301477 | 129530981 | G/A/C/T | rs755654296 | 129534315 | G/C |
| rs760667657 | 129530982 | C/T | rs558624347 | 129534329 | A/- |
| rs200207070 | 129530983 | G/A | rs1038200438 | 129534334 | G/C |
| rs144339478 | 129530993 | C/T | rs898370434 | 129534344 | A/G |
| rs151063543 | 129530994 | C/A | rs1259117244 | 129534348 | G/A |
| rs869320618 | 129530996 | G/A | rs886057972 | 129534351 | G/A |
| rs759406789 | 129530997 | G/C | rs1313687544 | 129534353 | A/T |
| rs745759264 | 129530998 | G/C | rs1279103243 | 129534354 | C/G |
| rs765193154 | 129531000 | C/G/T | rs1465369340 | 129534356 | G/A |
| rs556019320 | 129531003 | G/A | rs909632533 | 129534358 | T/C |
| rs104893793 | 129531005 | C/A/T | rs886057973 | 129534363 | G/C |

TABLE S2-continued

RHO SNPs.

| rsID (SNP number) | Position | Alleles | rsID | Position | Alleles |
|---|---|---|---|---|---|
| rs1046717534 | 129531006 | G/A | rs1280078792 | 129534366 | A/G |
| rs1351316742 | 129531008 | T/C | rs1400072056 | 129534367 | A/G |
| rs777283396 | 129531009 | G/T | rs1360660046 | 129534369 | G/A |
| rs1255285319 | 129531014 | GCGCC/- | rs763728621 | 129534376 | A/G |
| rs751280060 | 129531015 | C/T | rs1286711401 | 129534383 | C/T |
| rs574202023 | 129531016 | G/A | rs1449821629 | 129534387 | T/A |
| rs780682812 | 129531018 | C/T | rs1359424642 | 129534397 | A/G |
| rs377687329 | 129531019 | G/A | rs747159750 | 129534405 | A/- |
| rs1553781176 | 129531023 | NA | rs1208347093 | 129534408 | A/G |
| rs104893794 | 129531025 | C/T | rs1240512478 | 129534411 | A/T |
| rs769236224 | 129531028 | C/T | rs1468624776 | 129534420 | T/A |
| rs779609930 | 129531030 | C/T | rs941152137 | 129534426 | T/C |
| rs139731264 | 129531031 | G/A | rs531691276 | 129534433 | C/T |
| rs1461270517 | 129531032 | C/A | rs1182873038 | 129534439 | G/C |
| rs149722668 | 129531033 | C/T | rs1427934792 | 129534440 | A/C |
| rs527236103 | 129531034 | G/A | rs868784437 | 129534443 | T/C |
| rs760894205 | 129531038 | G/T | rs1026823657 | 129534453 | A/G |
| rs562853201 | 129531042 | C/T | rs898016351 | 129534455 | A/- |
| rs776654836 | 129531044 | G/A | rs753496233 | 129534459 | T/C |
| rs1354028828 | 129531048 | A/C | rs1014689707 | 129534463 | G/A/T |
| rs759637818 | 129531049 | T/C | rs1202779984 | 129534469 | C/T |
| rs765139791 | 129531053 | A/C | rs1474540077 | 129534477 | T/C |
| rs1310373565 | 129531054 | C/T | rs1321237779 | 129534478 | G/T |
| rs1324015340 | 129531058 | G/A | rs1259833253 | 129534479 | G/A |
| rs752695098 | 129531061 | G/A | rs1024333938 | 129534482 | C/A |
| rs375044079 | 129531064 | G/A | rs1219183346 | 129534497 | T/A |
| rs1316474875 | 129531066 | G/A | rs1306377685 | 129534500 | C/G |
| rs763887860 | 129531069 | G/A | rs1292787618 | 129534501 | T/A |
| rs1407241381 | 129531070 | A/G | rs1161955182 | 129534506 | A/T |
| rs374788784 | 129531072 | G/A | rs1397321795 | 129534512 | G/C |
| rs556049666 | 129531073 | C/T | rs1412073721 | 129534515 | A/C |
| rs751312906 | 129531074 | T/C | rs1456194676 | 129534521 | G/- |
| rs895760966 | 129531075 | C/T | rs1379431095 | 129534524 | C/T |
| rs545440059 | 129531076 | C/G/T | rs1156301240 | 129534525 | T/C |
| rs749929388 | 129531077 | G/A/C | rs1051986521 | 129534527 | G/A |
| rs779560689 | 129531078 | G/C | rs970272260 | 129534538 | G/A |
| rs1372241746 | 129531081 | G/A | rs1360610364 | 129534543 | C/T |
| rs748723598 | 129531082 | C/T | rs890717725 | 129534548 | A/G |

TABLE S2-continued

RHO SNPs.

| rsID (SNP number) | Position | Alleles | rsID | Position | Alleles |
|---|---|---|---|---|---|
| rs1463878766 | 129531084 | C/G | rs886057974 | 129534556 | A/T |
| rs964869603 | 129531088 | G/A | rs1371889254 | 129534557 | G/A |
| rs1480922923 | 129531110 | -/A | rs1007523809 | 129534558 | G/A |
| rs974618733 | 129531115 | C/A | rs1424527733 | 129534564 | A/G |
| rs1044079158 | 129531117 | A/G | rs2625969 | 129534566 | A/G |
| rs776124711 | 129531118 | G/A | rs1384837365 | 129534568 | T/A |
| rs781681710 | 129531121 | G/T | rs1017653970 | 129534572 | G/A |
| rs560500100 | 129531123 | G/A | rs1459764142 | 129534580 | A/G |
| rs921326502 | 129531125 | C/A | rs1239814998 | 129534582 | C/A |
| rs1273393381 | 129531126 | T/C | rs893871699 | 129534584 | G/A |
| rs1232361259 | 129531139 | T/C | rs1011016953 | 129534585 | A/G/T |
| rs1333073685 | 129531148 | A/G | rs1021477770 | 129534598 | G/- |
| rs751167062 | 129531159 | C/- | rs1321799497 | 129534600 | G/A |
| rs1290603751 | 129531159 | C/A | rs980356319 | 129534601 | G/A/T |
| rs1224783217 | 129531160 | C/T | rs1379524731 | 129534603 | A/C |
| rs184850373 | 129531165 | T/A | rs886057975 | 129534605 | G/C |
| rs1337907729 | 129531166 | G/A | rs1310410853 | 129534606 | G/A |
| rs984237144 | 129531176 | G/C | rs1376639826 | 129534608 | G/A |
| rs994553550 | 129531179 | A/G/T | rs926123122 | 129534610 | C/T |
| rs1288103396 | 129531181 | G/A | rs1288827122 | 129534611 | G/A/C |
| rs908539146 | 129531183 | G/T | rs1458412420 | 129534612 | G/T |
| rs940006295 | 129531191 | C/T | rs981919115 | 129534614 | G/A |
| rs35822883 | 129531192 | A/G | rs756986191 | 129534618 | G/A |
| rs1460444620 | 129531203 | C/G | rs1329945487 | 129534629 | A/C |
| rs1419551493 | 129531207 | C/T | rs2855558 | 129534630 | A/G |
| rs1407137682 | 129531220 | A/C | rs959322448 | 129534631 | T/A/C |
| rs189786911 | 129531224 | G/A | rs1182244003 | 129534636 | G/T |
| rs1020274333 | 129531229 | G/A | rs548089979 | 129534641 | A/C/G |
| rs1253095866 | 129531233 | C/G | rs60645924 | 129534643 | T/C |
| rs1212604913 | 129531242 | G/T | rs933776948 | 129534659 | C/T |
| rs1466882199 | 129531244 | G/T | rs529674071 | 129534666 | T/C |
| rs1270355603 | 129531245 | C/T | rs918343259 | 129534672 | G/T |
| rs1216921404 | 129531246 | C/T | rs368910470 | 129534677 | A/G |
| rs1316735386 | 129531251 | G/T | rs929455758 | 129534679 | G/A |
| rs938152581 | 129531264 | C/T | rs1051933883 | 129534683 | C/T |
| rs1221492219 | 129531269 | C/T | rs886057976 | 129534688 | C/T |
| rs1371749392 | 129531271 | T/C | rs942590356 | 129534689 | T/C |

TABLE S2-continued

| RHO SNPs. | | | | | |
|---|---|---|---|---|---|
| rsID (SNP number) | Position | Alleles | rsID | Position | Alleles |
| rs143977825 | 129531273 | C/T | rs141951118 | 129534691 | C/T |
| rs1438934322 | 129531274 | -/A | rs1253242607 | 129534694 | T/- |
| rs1055281862 | 129531278 | C/G/T | rs943633700 | 129534696 | C/T |
| rs1454094767 | 129531284 | C/T | rs369445725 | 129534700 | A/G |
| rs1028332793 | 129531290 | C/T | rs1039036712 | 129534700 | -/T |
| rs148627764 | 129531292 | G/C | rs570565774 | 129534703 | T/C |
| rs568632402 | 129531295 | C/T | rs1156347795 | 129534704 | G/A |
| rs978856569 | 129531300 | A/G | rs1158219076 | 129534705 | G/A |
| rs866616372 | 129531301 | A/G | rs528482125 | 129534709 | A/G |
| rs1010603965 | 129531307 | A/C | rs1452714353 | 129534726 | TC/- |
| rs1042159674 | 129531308 | A/G | rs751475771 | 129534726 | TCTC/- |
| rs924712150 | 129531316 | A/G | rs1200863832 | 129534734 | C/A |
| rs539172762 | 129531319 | C/T | rs1480704342 | 129534735 | C/T |
| rs551043575 | 129531320 | G/A | rs994419734 | 129534752 | T/G |
| rs1186809728 | 129531333 | C/T | rs1047784296 | 129534753 | C/G |
| rs1485740219 | 129531335 | C/T | rs1489022460 | 129534754 | T/C |
| rs1259352458 | 129531340 | G/A | rs1414709663 | 129534759 | C/G |
| rs1212780835 | 129531342 | -/T | rs886505372 | 129534761 | C/G |
| rs1177039502 | 129531343 | T/A | rs1014370009 | 129534768 | C/G |
| rs1406966931 | 129531346 | T/C | rs748689832 | 129534771 | G/T |
| rs1279641372 | 129531351 | C/A/T | rs1348918732 | 129534775 | C/G |
| rs1232154332 | 129531351 | -/G | rs1258164184 | 129534777 | A/C |
| rs1285674805 | 129531352 | G/- | rs551828590 | 129534795 | C/A/G/T |
| rs1381874878 | 129531352 | G/A | rs970072766 | 129534799 | T/C |
| rs566173741 | 129531353 | G/A | rs1001703259 | 129534807 | A/G |
| rs1360930042 | 129531354 | G/C | rs1341225551 | 129534811 | T/C |
| rs992708114 | 129531355 | G/T | rs1003329675 | 129534812 | C/G/T |
| rs1465553433 | 129531356 | G/A | rs192710452 | 129534814 | C/T |
| rs917150600 | 129531363 | C/T | rs959269065 | 129534816 | C/T |
| rs1375966150 | 129531370 | C/T | rs3733148 | 129534817 | G/A/T |
| rs948667607 | 129531387 | A/G | rs989406033 | 129534827 | A/G |
| rs1008527089 | 129531388 | G/A | rs913426403 | 129534830 | T/A/C |
| rs1320828933 | 129531398 | CAC/- | rs1191972988 | 129534834 | A/T |
| rs1044005909 | 129531402 | T/C | rs772137360 | 129534844 | C/G |
| rs1398986167 | 129531403 | TCC/- | rs1369756734 | 129534846 | G/C |
| rs1019250947 | 129531404 | C/T | rs962375748 | 129534854 | C/T |
| rs920274594 | 129531409 | T/C | rs972816716 | 129534859 | T/- |
| rs964678553 | 129531411 | C/G | rs886057977 | 129534862 | C/T |

TABLE S2-continued

| RHO SNPs. | | | | | |
|---|---|---|---|---|---|
| rsID (SNP number) | Position | Alleles | rsID | Position | Alleles |
| rs1183990031 | 129531413 | G/T | rs918301481 | 129534863 | G/A/T |
| rs562439338 | 129531421 | T/- | rs1207825783 | 129534878 | AA/- |
| rs1257395589 | 129531432 | C/T | rs987627051 | 129534880 | A/G |
| rs6803468 | 129531436 | G/T | rs1275763569 | 129534886 | G/C |
| rs555790621 | 129531441 | G/T | rs569761830 | 129534897 | T/A/C |
| rs951896447 | 129531445 | C/A | rs1180229643 | 129534901 | C/A |
| rs73204247 | 129531451 | C/T | rs763538125 | 129534909 | C/A/T |
| rs572406990 | 129531462 | C/T | rs1453013711 | 129534912 | T/C |
| rs1311107090 | 129531463 | G/A | rs35649104 | 129534912 | -/G |
| rs556769049 | 129531465 | T/C | rs538744995 | 129534918 | T/C |
| rs1315161368 | 129531472 | C/T | rs3733149 | 129534926 | G/A/C |
| rs997111072 | 129531477 | G/A | rs1420184640 | 129534931 | C/T |
| rs6803484 | 129531483 | G/A | rs946701532 | 129534940 | -/T |
| rs1312180049 | 129531484 | A/G | rs1474181983 | 129534946 | C/T |
| rs968685580 | 129531485 | G/A/C | rs1392939922 | 129534952 | A/G |
| rs1397930176 | 129531486 | A/G | rs1042822020 | 129534953 | G/A |
| rs77530178 | 129531487 | T/A/C | rs1461112461 | 129534959 | C/- |
| rs1203954886 | 129531490 | G/A | rs1450936021 | 129534960 | C/T |
| rs2855556 | 129531493 | A/T | rs1200962380 | 129534967 | C/T |
| rs1032164151 | 129531516 | A/G | rs774496991 | 129534973 | T/C |
| rs554303709 | 129531518 | T/C | rs1272994648 | 129534974 | -/G |
| rs144222821 | 129531520 | G/A | rs1369690965 | 129534976 | C/T |
| rs542966841 | 129531522 | A/T | rs973956027 | 129534978 | A/C |
| rs917097122 | 129531524 | T/C | rs1003611523 | 129534986 | C/T |
| rs764277444 | 129531529 | A/G | rs919859410 | 129534989 | C/T |
| rs915408640 | 129531538 | C/G | rs113312341 | 129534996 | G/T |
| rs946889355 | 129531549 | C/A | rs1047324551 | 129535012 | A/G |
| rs879648140 | 129531554 | C/A | rs1245547481 | 129535021 | A/G |
| rs920536110 | 129531555 | C/T | rs1012047887 | 129535022 | C/A |
| rs147761866 | 129531556 | C/T | rs1381715030 | 129535022 | C/- |
| rs1335170531 | 129531565 | C/T | rs1016815544 | 129535032 | G/A |
| rs1431359617 | 129531575 | C/T | rs1355038365 | 129535050 | C/G |
| rs1231341641 | 129531580 | C/G | rs962948896 | 129535061 | C/G/T |
| rs902287169 | 129531582 | C/T | rs112302797 | 129535065 | C/T |
| rs529156413 | 129531587 | C/T | rs1163781599 | 129535067 | C/G/T |
| rs944350253 | 129531588 | C/T | rs1383053992 | 129535068 | T/G |
| rs772222838 | 129531594 | C/T | rs754349343 | 129535080 | G/A |

TABLE S2-continued

| RHO SNPs. | | | | | |
|---|---|---|---|---|---|
| rsID (SNP number) | Position | Alleles | rsID | Position | Alleles |
| rs1337492670 | 129531601 | G/T | rs950177366 | 129535092 | G/A |
| rs1174134742 | 129531602 | T/A | rs1025763585 | 129535109 | C/T |
| rs930299608 | 129531608 | T/C | rs1232742504 | 129535128 | C/G |
| rs1393777151 | 129531627 | C/T | rs955092673 | 129535131 | A/G |
| rs544155208 | 129531637 | T/C | rs1274334066 | 129535134 | G/T |
| rs1374834362 | 129531645 | -/C | rs1453347943 | 129535149 | C/T |
| rs1327488625 | 129531648 | C/G | rs558693495 | 129535158 | T/A |
| rs1040022905 | 129531654 | A/G | rs552362456 | 129535173 | NA |
| rs1462732242 | 129531659 | T/C | rs576980794 | 129535317 | NA |
| rs187923166 | 129535319 | NA | | | |

In some embodiments, target sequences of RHO oligonucleotides comprise a SNP. In some embodiments, base sequences of RHO oligonucleotides are identical or complementary (e.g., with no more than 1, 2, or 3 differences/mismatches, and often with no differences/mismatches when aligned) to base sequences comprising SNPs. In some embodiments, as demonstrated herein, compositions of the present disclosure can selectively reduce levels, activities, etc. of transcripts of alleles associated with various conditions, disorders or diseases (in many instances, SNP alleles on the same chromosome as elements associated with conditions, disorders or diseases (e.g., SNPs, mutations, other sequence variations, etc. associated with conditions, disorders or diseases (e.g., P23H)) and/or products encoded (e.g., proteins) thereby compared to transcripts of alleles less or not associated with various conditions, disorders or diseases (e.g., a wild-type allele) and/or products encoded thereby.

In some embodiments, provided technologies can modulate one or more of RHO functions, e.g., through modulating expression, level and/or activity of a RHO transcript or a product thereof. In some embodiments, a RHO oligonucleotide is capable of decreasing the expression, level and/or activity of a RHO transcript or a gene product thereof, wherein an activity is an ability of RHO to perform any known function, including but not limited to those described herein or known in the art.

Without wishing to be bound by any particular theory, the present disclosure notes that wild-type RHO may have at least one function which is not yet reported in the scientific literature.

In some embodiments, a RHO oligonucleotide is capable of decreasing the expression, level and/or activity of RHO, wherein an activity of RHO is a reported function of RHO.

RHO is reportedly expressed in several tissues including the retina and other tissues. In some embodiments, the present disclosure pertains to the use of a RHO oligonucleotide to decrease the expression, level and/or activity of a RHO gene or a gene product thereof in any of these tissues, or in a cell derived from any of these tissues.

RHO is reportedly distributed in various tissues, including but not limited to: Blood; Whole Blood; Monocytes; Myeloid; NK Cells; T cells; Dentritic Cells; B Cells; B lymphoblasts; Endothelial; Cerebellum Peduncles; Cerebellum; Globus Pallidus Pons; Subthalamic Nucleus; Temporal Lobe; Occipital Lobe; Cingulate Cortex; Medulla Oblongata; Parietal lobe; Caudate nucleus; Thalamus; Fetal brain; Hypothalamus; Spinal cord; Prefrontal Cortex; Amygdala; brain; Whole brain; Skeletal Muscle; Tongue; Superior Cervical Ganglion; Trigeminal Ganglion; Skin; Atrioventricular Node; Ciliary Ganglion; Dorsal Root Ganglion; Ovary; Appendix; Uterus corpus; Heart; Liver; Early Erythroid; Placenta; Lung; Prostate; Thyroid; Lymphoma Burkitt's; Leukemia promyelocytic; Lymphoma; Leukemia chronic myelogenous; Leukemia lymphoblastic; Cardiac Myocytes; Smooth Muscle; Bronchial Epithelial Cells; Colorectal adenocarcinoma; Testis; Testis Germ Cell; Testis Intersitial; Testis Leydig Cell; Testis Seminiferous Tubule; Pancreas; Pancreatic Islet; Adipocyte; Uterus; Fetal Thyroid; Fetal lung; Pituitary; Salivary gland; Trachea; Olfactory bulb; Adrenal cortex; Bone marrow; Thymus; Lymph node; Tonsil; Fetal Liver; and Kidney. In some embodiments, the present disclosure pertains to the use of a RHO oligonucleotide in decreasing the expression, level, and/or activity of a RHO gene or a gene product thereof, in any of these tissues. In some embodiments, a RHO oligonucleotide further comprises an additional chemical moiety which increases delivery to and/or entrance into a particular cell type or tissue or organ. In some embodiments, the present disclosure pertains to the use of a RHO oligonucleotide in decreasing the expression, level, and/or activity of a RHO gene or a gene product thereof, in any of these tissues in a human patient in need thereof (e.g., a human patient suffering from or susceptible to a RHO-related disease, disorder or condition). In some embodiments, the present disclosure pertains to a method of treatment or amelioration of a RHO-related disease, disorder or condition, comprising the step of decreasing the expression, level or activity of a RHO gene or a gene product thereof, in any of these tissues in a human patient in need thereof. In various embodiments described herein, a RHO gene or gene product thereof is a mutant or comprises a mutation, including but not limited to a P23H mutation.

In some embodiments, the present disclosure pertains to a method of administration of an USH2A oligonucleotide to a subject/patient suffering from or susceptible to an USH2A-related disease, disorder, or condition, wherein the disease, disorder or condition manifests (e.g., is characterized by at least one symptom in) (A) the eye; and (B) another tissue in the body that expresses USH2A. In some embodiments, the present disclosure pertains to a method of administration of an USH2A oligonucleotide to a subject/patient suffering from or susceptible to an USH2A-related disease, disorder, or condition, wherein the disease, disorder or condition manifests (e.g., is characterized by at least one symptom in) (A) the eye; and (B) another tissue in the body that expresses USH2A, wherein the USH2A oligonucleotide is administered to (A) the eye; and (B) the another tissue in the body that expresses USH2A. In some embodiments, the present disclosure pertains to a method of administration of an USH2A oligonucleotide to a subject/patient suffering from or susceptible to an USH2A-related disease, disorder, or condition, wherein the disease, disorder or condition manifests (e.g., is characterized by at least one symptom in) (A) the eye; and (B) another tissue in the body that expresses USH2A, wherein the USH2A oligonucleotide is administered to (A) the eye; and (B) the another tissue in the body that expresses USH2A, wherein a first USH2A oligonucleotide administered to (A) the eye is in a formulation and/or delivered via a method and/or comprises an additional chemical moiety suitable for administration to the eye; and a second USH2A oligonucleotide administered to (B) the another tissue in the body that expresses USH2A is in a formulation and/or delivered via a method and/or comprises an additional chemical moiety suitable for administration to the another tissue in the body that expresses USH2A.

Additional information about RHO and related retinopathies and additional information related to RHO, RHO P23H, and related tools, techniques, methods, cells, animal models, etc., are provided in the scientific literature, including but not limited to: al-Maghtheh M, Gregory C, Inglehearn C, Hardcastle A, Bhattacharya S (1993). "Rhodopsin mutations in autosomal dominant retinitis pigmentosa". Human Mutation. 2 (4): 249-55. doi:10.1002/humu.1380020403; Andréasson S, Ehinger B, Abrahamson M, Fex G (September 1992). "A six-generation family with autosomal dominant retinitis pigmentosa and a rhodopsin gene mutation (arginine-135-leucine)". Ophthalmic Paediatrics and Genetics. 13 (3): 145-53. doi:10.3109/13816819209046483; Bownds D, Wald G (January 1965). "Reaction of the rhodopsin chromophore with sodium borohydride". Nature. 205 (4968): 254-7. Bibcode:1965Natur.205 . . . 254B. doi:10.1038/205254a0; Bryant D A, Frigaard N U (November 2006). "Prokaryotic photosynthesis and phototrophy illuminated". Trends in Microbiology. 14 (11): 488-96. doi:10.1016/j.tim.2006.09.001; Chabre M, le Maire M (July 2005). "Monomeric G-protein-coupled receptor as a functional unit". Biochemistry. 44 (27): 9395-403. doi:10.1021/bi050720o; Dryja T P, Hahn L B, Cowley G S, McGee T L, Berson E L (October 1991). "Mutation spectrum of the rhodopsin gene among patients with autosomal dominant retinitis pigmentosa". Proceedings of the National Academy of Sciences of the United States of America. 88 (20): 9370-4. Bibcode:1991PNAS . . . 88.9370D. doi:10.1073/pnas.88.20.9370; Edwards S C (July 1995). "Involvement of cGMP and calcium in the photoresponse in vertebrate photoreceptor cells". The Journal of the Florida Medical Association. 82 (7): 485-8; Encyclopedia of the Neurological Sciences. Academic Press. 29 Apr. 2014. pp. 441; Farrar G J, Findlay J B, Kumar-Singh R, Kenna P, Humphries M M, Sharpe E, Humphries P (December 1992). "Autosomal dominant retinitis pigmentosa: a novel mutation in the rhodopsin gene in the original 3q linked family". Human Molecular Genetics. 1 (9): 769-71. doi:10.1093/hmg/1.9.769; Fishman G A, Stone E M, Gilbert L D, Sheffield V C (May 1992). "Ocular findings associated with a rhodopsin gene codon 106 mutation. Glycine-to-arginine change in autosomal dominant retinitis pigmentosa". Archives of Ophthalmology. 110 (5): 646-53. doi:10.1001/archopht.1992.01080170068026; Foley L E, Gegear R J, Reppert S M (June 2011). "Human cryptochrome exhibits light-dependent magnetosensitivity". Nature Communications. 2: 356. Bibcode:2011NatCo . . . 2E.356F. doi:10.1038/ncomms1364; Fujiki K, Hotta Y, Hayakawa M, Sakuma H, Shiono T, Noro M, Sakuma T, Tamai M, Hikiji K, Kawaguchi R (June 1992). "Point mutations of rhodopsin gene found in Japanese families with autosomal dominant retinitis pigmentosa (ADRP)". The Japanese Journal of Human Genetics. 37 (2): 125-32. doi:10.1007/BF01899733; Gal A, Artlich A, Ludwig M, Niemeyer G, Olek K, Schwinger E, Schinzel A (October 1991). "Pro-347-Arg mutation of the rhodopsin gene in autosomal dominant retinitis pigmentosa". Genomics. 11 (2): 468-70. doi:10.1016/0888-7543(91)90159-C; Gao S Q, Nagpal J, Schneider M W, Kozjak-Pavlovic V, Nagel G, Gottschalk A (July 2015). "Optogenetic manipulation of cGMP in cells and animals by the tightly light-regulated guanylyl-cyclase opsin CyclOp". Nature Communications. 6 (8046): 8046. Bibcode:2015NatCo . . . 6E8046G. doi:10.1038/ncomms9046; Garriga P, Manyosa J (September 2002). "The eye photoreceptor protein rhodopsin. Structural implications for retinal disease". FEBS Letters. 528 (1-3): 17-22. doi:10.1016/S0014-5793(02)03241-6; Giese A C (24 Sep. 2013). Photophysiology: General Principles; Action of Light on Plants. Elsevier. p. 9; Gulati S, Jastrzebska B, Banerjee S, Placeres Á L, Miszta P, Gao S, Gunderson K, Tochtrop G P, Filipek S, Katayama K, Kiser P D, Mogi M, Stewart P L, Palczewski K (March 2017). "Photocyclic behavior of rhodopsin induced by an atypical isomerization mechanism". Proceedings of the National Academy of Sciences. 114 (13): E2608-15. doi:10.1073/pnas.1617446114; Heck M, Schädel S A, Maretzki D, Bartl F J, Ritter E, Palczewski K, Hofmann K P (January 2003). "Signaling states of rhodopsin. Formation of the storage form, metarhodopsin III, from active metarhodopsin II". The Journal of Biological Chemistry. 278 (5): 3162-9. doi:10.1074/jbc.M209675200; Hofiann K P, Heck M (1996). "Light-induced protein-protein interactions on the rod photoreceptor disc membrane". In Lee A G (ed.). Rhodopsin and G-Protein Linked Receptors, Part A (Vol 2, 1996) (2 Vol Set). Greenwich, Conn.: JAI Press. pp. 141-198; Humphries P, Kenna P, Farrar G J (May 1992). "On the molecular genetics of retinitis pigmentosa". Science. 256 (5058): 804-8. Bibcode:1992Sci . . . 256 . . . 804H. doi:10.1126/science.1589761; Inglehearn C F, Keen T J, Bashir R, Jay M, Fitzke F, Bird A C, Crombie A, Bhattacharya S (April 1992). "A completed screen for mutations of the rhodopsin gene in a panel of patients with autosomal dominant retinitis pigmentosa". Human Molecular Genetics. 1 (1): 41-5. doi:10.1093/hmg/1.1.41; Inglehearn C F, Lester D H, Bashir R, Atif U, Keen T J, Sertedaki A, Lindsey J, Jay M, Bird A C, Farrar G J (March 1992). "Recombination between rhodopsin and locus D3S47 (C17) in rhodopsin retinitis pigmentosa families". American Journal of Human Genetics. 50 (3): 590-7; Jacobson S G, Kemp C M, Sung C H, Nathans J (September 1991). "Retinal function and rhodopsin levels in autosomal dominant retinitis pigmentosa with rhodopsin mutations". American Journal of Ophthalmology. 112 (3): 256-71. doi:10.1016/s0002-9394(14)76726-1; Keen T J, Inglehearn C F, Lester D H, Bashir R, Jay M, Bird A C, Jay B, Bhattacharya S S (September 1991). "Autosomal dominant retinitis pigmentosa: four new mutations in rhodopsin, one of them in the retinal attachment site". Genomics. 11 (1): 199-205. doi:10.1016/0888-7543 (91)90119-Y; Kolb H, Fernandez E, Nelson R, Jones B W (1 Mar. 2010). "Webvision: Photoreceptors". University of Utah. Archived from the original on 16 Aug. 2000; Litmann B J, Mitchell D C (1996). "Rhodopsin structure and function". In Lee A G (ed.). Rhodopsin and G-Protein Linked Receptors, Part A (Vol 2, 1996) (2 Vol Set). Greenwich, Conn.: JAI Press. pp. 1-32; Matthews R G, Hubbard R, Brown P K, Wald G (November 1963). "Tautomeric forms of metarhodopsin". The Journal of General Physiology. 47 (2): 215-40. doi:10.1085/jgp.47.2.215; Mendes H F, van der Spuy J, Chapple J P, Cheetham M E (April 2005). "Mechanisms of cell death in rhodopsin retinitis pigmentosa: implications for therapy". Trends in Molecular Medicine. 11 (4): 177-85. doi:10.1016/j.molmed.2005.02.007; Nakamichi H, Okada T (June 2006). "Crystallographic analysis of primary visual photochemistry". Angewandte Chemie. 45 (26): 4270-3. doi:10.1002/anie.200600595; Olsson J E, Gordon J W, Pawlyk B S, Roof D, Hayes A, Molday R S, Mukai S, Cowley G S, Berson E L, Dryja T P (November 1992). "Transgenic mice with a rhodopsin mutation (Pro23His): a mouse model of autosomal dominant retinitis pigmentosa". Neuron. 9 (5): 815-30. doi:10.1016/0896-6273(92)90236-7; Perception (2008), Guest Editorial Essay, Perception, p. 1; Robinson P R, Cohen G B, Zhukovsky E A, Oprian D D (October 1992). "Constitutively active mutants of rhodopsin". Neuron. 9 (4): 719-25. doi: 10.1016/0896-6273(92) 90034-B; Rogers K. "Rhodopsin". Encyclopædia Britannica. Britannica.com. Retrieved 30 Jan. 2016; Saliba R S, Munro P M, Luthert P J, Cheetham M E (July 2002). "The cellular fate of mutant rhodopsin: quality control, degradation and aggresome formation". Journal of Cell Science. 115 (Pt 14): 2907-18; Scheib U, Broser M, Constantin O M, Yang S, Gao S, Mukherjee S, et al. (May 2018). "Rhodopsin-cyclases for photocontrol of cGMP/cAMP and 2.3 Å structure of the adenylyl cyclase domain". Nature Communications. 9 (1): 2046. Bibcode:2018NatCo . . . 9.2046S. doi:10.1038/s41467-018-04428-w; Scheib U, Stehfest K, Gee C E, Korschen H G, Fudim R, Oertner T G, Hegemann P (August 2015). "The rhodopsin-guanylyl cyclase of the aquatic fungus *Blastocladiella emersonii* enables fast optical control of cGMP signaling". Science Signaling. 8 (389): rs8. doi:10.1126/scisignal.aab0611; Schreiber M, Sugihara M, Okada T, Buss V (June 2006). "Quantum mechanical studies on the crystallographic model of bathorhodopsin". Angewandte Chemie. 45 (26): 4274-7. doi:10.1002/anie.200600585; Sheffield V C, Fishman G A, Beck J S, Kimura A E, Stone E M (October 1991). "Identification of novel rhodopsin mutations associated with retinitis pigmentosa by G C-clamped denaturing gradient gel electrophoresis". American Journal of Human Genetics. 49 (4): 699-706; Stuart J A, Brige R R (1996). "Characterization of the primary photochemical events in bacteriorhodopsin and rhodopsin". In Lee A G (ed.). Rhodopsin and G-Protein Linked Receptors, Part A (Vol 2, 1996) (2 Vol Set). Greenwich, Conn.: JAI Press. pp. 33-140; Sung C H, Davenport C M, Hennessey J C, Maumenee I H, Jacobson S G, Heckenlively J R, Nowakowski R, Fishman G, Gouras P, Nathans J (August 1991). "Rhodopsin mutations in autosomal dominant retinitis pigmentosa". Proceedings of the National Academy of Sciences of the United States of America. 88 (15): 6481-5. Bibcode:1991PNAS . . . 88.6481S. doi: 10.1073/pnas.88.15.6481; TerakitaA (2005). "The opsins". Genome Biology. 6 (3): 213. doi:10.1186/gb-2005-6-3-213; The Nobel Foundation. "The Nobel Prize in Physiology or Medicine 1967". Nobelprize.org. Nobel Media AB 2014. Retrieved 12 Dec. 2015; Weingart O (September 2007). "The twisted C11=C12 bond of the rhodopsin chromophore—a photochemical hot spot". Journal of the American Chemical Society. 129 (35): 10618-9. doi:10.1021/ja071793t; Yoshizawa T, Wald G (March 1963). "Prelumirhodopsin and the bleaching of visual pigments". Nature. 197 (March 30): 1279-86. Bibcode: 1963Natur.197.1279Y. doi:10.1038/1971279a0; Saito et al. 2008 Clin. Ophth. 2: 821-828; Sakami et al. 2013 Hum. Mol. Genet. 23: 1723-1741; Sizova et al. 2014 Cell. Signal. 26: 665; Tam et al. 2006 Inv. Ophth. Vis. Sci. 47: 3234; Vasireddy et al. 2011 PLoS One 6, e21193; Whyte et al. 2011 Mol. Reprod. Dev. 78: 879-891; Gorbatyuk et al. 2010 Proc. Natl. Acad. Sci. US 107: 5961; Haeri et al. 2012 PLoS ONE 1, e30101; Fernandez-Sanchez et al. Invest. Ophth. Vis. Sci. 52: 4998; Baid et al. 2011 PLoS ONE 6, e24616; Orhan et al. 2015 PLoS ONE 0127319. Roof et al. 1994 Invest. Opth. Vis. Sci. 35: 12; Ozaki et al. 2013 PLoS ONE 8, e71650; Lewin et al. 2014 Additional Perspectives on Retinal Disorders, et. Pierce et al., Cold Spring Harb Perspect Med 4: a017400; Giannelli et al. Hum. Mol. Genet. 27: 760-779; Cai et al. 2014 Invest. Ophth. Vis. Sci. 55: 7417; Adekeye et al. 2014 PLoS ONE 9, e83871; Cheri et al. 2014 J. Biol. Chem. 289: 9288; WO 2016/138353, WO 2017/044649, WO 2017/186739, and WO 2018/201146; Berson E L (1990). "Ocular findings in a form of retinitis pigmentosa with RHO gene defect". Trans Am Ophthalmol Soc. 88: 355-388; Berson E L, Rosner B, Sandberg M A, Dryja T P (1991). "Ocular findings in patients with autosomal dominant retinitis pigmentosa and a RHO gene defect (Pro-23-His)". Arch Ophthalmol. 109 (1): 92-101; Berson E L, Rosner B, Sandberg M A, Weigel-DiFranco C, Dryja T P (1991). "Ocular findings in patients with autosomal dominant retinitis pigmentosa and RHO, proline-347-leucine". Am J Ophthalmol. 111 (5): 614-623; Brill, E; Malanson, K. M; Radu, R. A; Boukharov, N. V; Wang, Z; Chung, H. Y; Lloyd, M. B; Bok, D; Travis, G. H; Obin, M; Lem, J (2007). "A Novel Form of Transducin-Dependent Retinal Degeneration: Accelerated Retinal Degeneration in the Absence of Rod Transducin". Investigative Ophthalmology &Visual Science. 48 (12): 5445-5453; Brill, E; Malanson, K. M; Radu, R. A; Boukharov, N. V; Wang, Z; Chung, H. Y; Lloyd, M. B; Bok, D; Travis, G. H; Obin, M; Lem, J (2007). "A Novel Form of Transducin-Dependent Retinal Degeneration: Accelerated Retinal Degeneration in the Absence of Rod Transducin". Investigative Ophthalmology & Visual Science. 48 (12): 5445-5453; Brill, E; Malanson, K. M; Radu, R. A; Boukharov, N. V; Wang, Z; Chung, H. Y; Lloyd, M. B; Bok, D; Travis, G. H; Obin, M; Lem, J (2007). "A Novel Form of Transducin-Dependent Retinal Degeneration: Accelerated Retinal Degeneration in the Absence of Rod Transducin". Investigative Ophthalmology & Visual Science. 48 (12): 5445-5453; Chang G Q, Hao Y, Wong F (1993). "Apoptosis: final common pathway of photoreceptor death in rd, rds, and RHO mutant mice". Neuron. 11 (4): 595-605; Chen C K, Burns M E, Spencer M, et al. (1999). "Abnormal photoresponses and light-induced apoptosis in rods lacking RHO kinase". Proc Natl Acad Sci USA. 96 (7): 3718-3722; Chen J; Shi G; Concepcion F A; Xie G; Oprian D; et al. (2006). "Stable RHO/arrestin complex leads to retinal degeneration in a transgenic mouse model of autosomal dominant retinitis pigmentosa". J Neurosci. 26 (46): 11929-11937; Chinchore, Yashodhan; Mitra, Amitavo; Dolph, Patrick J. (2009). "Accumulation of RHO in Late Endosomes Triggers Photoreceptor Cell Degeneration". PLoS Genetics. 5 (2): e1000377; Chuang J Z, Vega C, Jun W, Sung C H; Vega; Jun; Sung (2004). "Structural and functional impairment of endocytic pathways by retinitis pigmentosa mutant Rhoarrestin complexes". J Clin Invest. 114 (1): 131-140; Dejneka N S, Bennett J (2001). "Gene therapy and retinitis pigmentosa: advances and future challenges". BioEssays. 23 (7): 662-668; Dryja T P (1992). "Doyne Lecture: RHO and autosomal dominant retinitis pigmentosa". Eye. 6: 1-10; Dryja T P, McGee T L, Reichel E, Hahn L B, Cowley G S, Yandell D W, Sandberg M A, Berson E L, et al. (1990). "A point mutation of the RHO gene in one form of retinitis pigmentosa". Nature. 343 (6256): 364-366; Dryja T P; Hahn L B; Cowley G S; McGee T L; Berson E L (1991). "Mutation spectrum of the RHO gene among patients with autosomal dominant retinitis pigmentosa". Proc Natl Acad Sci USA. 88 (20): 9370-9374; Dryja T P; McGee T L; Hahn L B; et al. (1990). "Mutations within the RHO gene in patients with autosomal dominant retinitis pigmentosa". N Engl J Med. 323 (19): 1302-1307; Dryja T P; McGee T L; Reichel E; Hahn L B; Cowley G S; et al. (1990). "A point mutation of the RHO gene in one form of retinitis pigmentosa". Nature. 343 (6256): 364-366; Dryja, T. P; McEvoy, J. A; McGee, T. L; Berson, E. L. (September 2000). "Novel RHO mutations Gly114Val and Gln184Pro in dominant retinitis pigmentosa". Invest Ophthalmol Vis Sci. 41 (10): 3124-7; Fishman G A, Stone E M, Gilbert L D, Kenna P, Sheffield V C; Stone; Gilbert; Kenna; Sheffield (1991). "Ocular findings associated with a RHO gene codon 58 transversion mutation in autosomal dominant retinitis pigmentosa". Arch Ophthalmol. 109 (10): 1387-1393; Fishman G A, Stone E M, Gilbert L D, Sheffield V C; Stone; Gilbert; Sheffield (1992). "Ocular findings associated with a RHO gene codon 106 mutation: glycine-to-arginine change in autosomal dominant retinitis pigmentosa". Arch Ophthalmol. 110 (5): 646-653; Fishman G A, Stone E M, Sheffield V C, Gilbert L D, Kimura A E; Stone; Sheffield; Gilbert; Kimura (1992). "Ocular findings associated with RHO gene codon 17 and codon 182 transition mutations in dominant retinitis pigmentosa". Arch Ophthalmol. 110 (1): 54-62; Fishman G A, Vandenburgh K, Stone E M, Gilbert L D, Alexander K R, Sheffield V C (1992). "Ocular findings associated with RHO gene codon 267 and 190 mutations in autosomal dominant retinitis pigmentosa". Arch Ophthalmol. 110 (11): 1582-1588; Heckenlively J R, Rodriguez J A, Daiger S P (1991). "Autosomal dominant sectoral retinitis pigmentosa: two families with transversion mutation in codon 23 of RHO". Arch Ophthalmol. 109 (1): 84-91; Horn M; Humphries P; Kunisch M; et al. (1992). "Deletions in exon 5 of the human RHO gene causing a shift in the reading frame and autosomal dominant retinitis pigmentosa". Hum Genet. 90 (3): 255-257; Jacobson S G, Kemp C M, Cideciyan A V, Macke J P, Sung C H, Nathans J (1994). "Phenotypes of stop codon and splice site RHO mutations causing retinitis pigmentosa". Invest Ophthalmol Vis Sci. 35 (5): 2521-2534; Lee, E. S; Flannery, J. G. (2007). "Transport of Truncated RHO and Its Effects on Rod Function and Degeneration". Investigative Ophthalmology & Visual Science. 48 (6): 2868-2876; Lee, E. S; Flannery, J. G. (2007). "Transport of Truncated RHO and Its Effects on Rod Function and Degeneration". Investigative Ophthalmology & Visual Science. 48 (6): 2868-2876; Lem J, Fain G L (2004). "Constitutive opsin signaling: night blindness or retinal degeneration?". Trends Mol Med. 10 (4): 150-157; Menon, S. T., Han, M. & Sakmar, T. P. (2001) Physiol. Rev. 81, 1659-1688; Orem N R, Dolph P J; Dolph (2002). "Epitope masking of rhabdomeric RHO during endocytosis-induced retinal degeneration". Mol Vis. 8: 455-461; Pannarale M R; Grammatico B; Iannaccone A; et al. (1996). "Autosomal dominant retinitis pigmentosa associated with an Arg-135-Trp point mutation of the RHO gene: clinical features and longitudinal observations". Ophthalmology. 103 (9): 1443-1452; Rivolta, C., Sharon, D., DeAngelis, M. M. & Dryja, T. P. (2002) Hum. Mol. Genet. 11, 1219-1227; Sandberg M A, Weigel-DiFranco C, Dryja T P, Berson E L (1995). "Clinical expression correlates with location of RHO mutation in dominant retinitis pigmentosa". Invest Ophthalmol Vis Sci. 36 (9): 1934-1942; Satoh A K, Ready D F; Ready (2005). "Arrestin1 mediates light-dependent RHO endocytosis and cell survival". Curr Biol. 15 (19): 1722-1733; Sohocki, M. M; Daiger, S. P; Bowne, S. J; Rodriquez, J. A; Northrup, H; Heckenlively, J. R; Birch, D. G; Mintz-Hittner, H; Ruiz, R. S; Lewis, R. A; Saperstein, D. A; Sullivan, L. S. (2001). "Prevalence of Mutations Causing Retinitis Pigmentosa and Other Inherited Retinopathies". Human Mutation. 17 (1): 42-51; Sohocki, M. M; Daiger, S. P; Bowne, S. J; Rodriquez, J. A; Northrup, H; Heckenlively, J. R; Birch, D. G; Mintz-Hittner, H; Ruiz, R. S; Lewis, R. A; Saperstein, D. A; Sullivan, L. S. (2001). "Prevalence of Mutations Causing Retinitis Pigmentosa and Other Inherited Retinopathies". Human Mutation. 17 (1): 42-51; Sullivan L S, Daiger S P; Daiger (1996). "Inherited retinal degeneration: exceptional genetic and clinical heterogeneity". Mol Med Today. 2 (9): 380-386; Sung C-H, Schneider B G, Agarwal N, Papermaster D S, Nathans J. Functional heterogeneity of mutant Rhos responsible for autosomal dominant retinitis pigmentosa" Proc Natl Acad Sci USA 1991; 88:8840-8844; Sung C-H; Davenport C M; Hennessey J C; et al. (1991). "RHO mutations in autosomal dominant retinitis pigmentosa". Proc Natl Acad Sci USA. 88 (15): 6481-6485; Sung C H; Schneider B G; Agarwal N; et al. (1991). "Functional heterogeneity of mutant Rhos responsible for autosomal dominant retinitis pigmentosa". Proc Natl Acad Sci USA. 88 (19): 8840-8844; Taylor J P, Hardy J, Fischbeck K H; Hardy; Fischbeck (2002). "Toxic proteins in neurodegenerative disease". Science. 296 (5575): 1991-1995; Weleber R G, Murphey W H, Rodriguez J A, Lovrien E W, Litt M, Daiger S P (1991). "Phenotypic expression of Pro-23-His mutation of RHO in a large family with autosomal dominant retinitis pigmentosa [abstract]". Invest Ophthalmol Vis Sci. 32: 913; Xu J, Dodd R L, Makino C L, Simon M I, Baylor D A, Chen J (1997). "Prolonged photoresponses in transgenic mouse rods lacking arrestin". Nature. 389 (6650): 505-509; and Yuan, L; Kawada, M; Havlioglu, N; Tang, H; Wu, J. Y. (2005). "Mutations in PRPF31 Inhibit Pre-mRNA Splicing of RHO Gene and Cause Apoptosis of Retinal Cells". Journal of Neuroscience. 25 (3): 748-757. In some embodiments, an additional therapeutic agent or method includes but is not limited to any treatment described in any of these documents; and a tool, technique, a cell or animal model useful for the evaluation of an oligonucleotide can include but is not limited to a tool, technique, cell or animal model described in any of these documents.

RHO and RHO-Related Conditions, Disorders or Diseases

A RHO-related disease, disorder or condition is any of various conditions, disorders or diseases are associated with a mutation(s) in RHO; or, any disease, disorder or condition wherein at least one symptom is ameliorated by or the delayed in onset by a decrease in the expression, level and/or activity of a mutant HO gene or a gene product thereof, such a disease, disorder or condition includes retinopathy. Among other things, provided technologies are useful for treating or preventing a RHO-related-disorder or -disease, including but not limited to, a retinopathy or retinitis pigmentosa. As appreciated by those skilled in the art, two events or entities are "associated" with one another if the presence, level and/or form of one (e.g., a RHO mutation) is correlated with that of the other (e.g., a condition, disorder or disease). For example, a particular entity (e.g., polypeptide, genetic signature, metabolite, microbe, etc) is considered to be associated with a particular disease, disorder, or condition, if its presence, level and/or form correlates with incidence of and/or susceptibility to the disease, disorder, or condition (e.g., across a relevant population).

In some embodiments, a retinopathy is retinal degeneration, retinal degenerative disease, retinal degenerative disorder, inherited retinal degenerative disorder, retinitis pigmentosa (RP), or autosomal dominant retinitis pigmentosa (adRP). In some embodiments, adRP is also referenced as Retinitis pigmentosa 4 (RP4) or Retinitis pigmentosa, RHO-related. Retinal degeneration is a retinopathy which reportedly relates to the deterioration of the retina caused by the progressive death of its cells. There are reportedly several reasons for and/or symptoms of retinal degeneration or retinitis pigmentosa, including artery or vein occlusion, diabetic retinopathy, R.L.F./R.O.P. (retrolental fibroplasia/retinopathy of prematurity), or disease (usually hereditary). Reportedly, these may present in many different ways such as impaired vision, night blindness, retinal detachment, light sensitivity, tunnel vision, and loss of peripheral vision to total loss of vision. retinitis pigmentosa (RP) is an important example of a retinal degenerative disease.

Retinitis pigmentosa (RP) reportedly comprises a heterogeneous group of inherited neurodegenerative retinal disorders characterized by progressive peripheral vision loss and night vision difficulties, subsequently leading to central vision impairment. More than 100 different mutations in the rhodopsin-encoding gene (RHO) are reportedly associated with RP, together accounting for 30% to 40% of autosomal dominant cases. The P23H mutation in this gene is reportedly one of the most prevalent causes of RP. Most RP-causing mutations in the RHO gene, including P23H (RHO P23H), reportedly can cause misfolding and retention of rhodopsin in the endoplasmic reticulum of transfected cultured cells. These studies also reportedly suggest that the mechanism of RP involves a cellular stress response, the final common pathway of which is programmed photoreceptor cell death, or apoptosis.

Inherited retinal degenerative disorders in humans reportedly exhibit genetic and phenotypic heterogeneity in their underlying causes and clinical outcomes. Reportedly, a wide variety of causes have been attributed to retinal degeneration, such as disruption of genes that are involved in phototransduction, biosynthesis and folding of the RHO molecule, and the structural support of the retina. Mutations in the RHO gene reportedly account for a significant minority of all cases of autosomal dominant retinitis pigmentosa (adRP) in North America.

Mutations in the RHO that affect its folding, trafficking and/or activity are among the most commonly reported causes of retinal degeneration in afflicted patients. A single base-substitution at the codon position 23 in the human opsin gene (P23H) is reportedly the most common cause of ADRP in American patients. ADRP due to RHO mutations reportedly has a wide range of clinical presentation and severity. Before 1991, phenotypic evidence pointed to different subsets of ADRP with varying prognoses. Molecular classification of ADRP and further sub-classification based on the region of the mutation in the RHO gene reportedly allowed better prediction of a particular disease course. But even within these specific subsets, the prognosis is reportedly influenced by the specific mutation itself.

There are many mechanisms of retinal degeneration reportedly attributed to RHO mutations or mutations that involve or affect the function of RHO. One mechanism of retinal degeneration is reportedly RHO overexpression. Another reported mechanism, whereby a mutation causes a truncated RHO, was found to affect rod function and increased the rate of photoreceptor degeneration.

Photoreceptor cell death is reportedly the eventual outcome of retinal degeneration. Without proper function of the photoreceptor cells, vision is reportedly not possible. Reportedly, irreversible loss of these cells has been attributed as a cause of blindness in many retinal degenerative disorders, including RP. The exact mechanism of photoreceptor cell death is reportedly not clearly understood. Among potential causes is reportedly the endocytosis of stable complexes formed between RHO and its regulatory protein arrestin in certain mutants.

Various studies have also reported that over-expression of RHO itself (mutations in genes involved in the termination of RHO signaling activity have been shown to cause degeneration by persistent activation of the phototransduction cascade) causes photoreceptor cell death and may induce photoreceptor cell loss in transgenic animals expressing truncated RHO. Yet another mechanism may reportedly be prolonged photoreceptor responses and also abnormal RHO deactivation may induce outer segment shortening and eventual photoreceptor death. In RP photoreceptor cell death is reported to occur by programmed cell death or apoptosis.

Retinitis pigmentosa is reportedly a progressive neurodegenerative disorder. Autosomal dominant RP reportedly accounts for approximately 15% of these cases. Autosomal dominant retinitis pigmentosa (ADRP) is a genetically heterogeneous group of inherited retinal degenerations that cause blindness in humans.

RP reportedly begins with death of rod photoreceptor cells, which are the only cells in the retina to express RHO and which express it as their most abundant protein. Eventually, loss of rod cells reportedly leads to loss of cone cells (cone photoreceptors), the mainstay of human vision.

Symptoms of RP reportedly include loss of sensitivity to dim light, abnormal visual function, and characteristic bone spicule deposits of pigment in the retina. Affected individuals reportedly progressively lose visual field and visual acuity, and photoreceptor cell death can ultimately lead to blindness. A prominent early clinical feature of retinitis pigmentosa is reportedly the loss of night vision as a result of death of rod photoreceptor cells. Proper expression of the wild-type RHO gene is reportedly essential for the development and sustained function of photoreceptor cells.

In some embodiments, administration of a RHO oligonucleotide improves, preserves, or prevents worsening of visual function; visual field; photoreceptor cell function; electroretinogram (ERG) response such as full field ERG measuring retina wide function, dark adapted ERG measuring scotopic rod function, or light adapted ERG measuring photopic cone function; visual acuity; and/or vision-related quality of life. In some embodiments, administration of a RHO oligonucleotide inhibits, prevents, or delays progression of photoreceptor cell loss and/or deterioration of the retina outer nuclear layer (ONL).

Symptoms of retinopathy that can be ameliorated, abated or delayed in onset by a RHO oligonucleotide include any symptom of retinopathy described herein or known in the art.

In some embodiments, a RHO oligonucleotide, when administered to a patient suffering from or susceptible to retinopathy, is capable of reducing at least one symptom of retinopathy and/or capable of delaying or preventing the onset, worsening, and/or reducing the rate and/or degree of worsening of at least one symptom of retinopathy.

In some embodiments, a symptom of a RHO-related disease, disorder or condition [e.g., Usher Syndrome Type IIA (2A), atypical Usher syndrome, or nonsyndromic retinitis pigmentosa] is any symptom described herein, including but not limited to: blindness, night blindness (nyctalopia), photopsia, loss of peripheral vision, progressive visual loss, retinitis pigmentosa, onset of night blindness, onset of visual field loss, decline in or loss of visual field, decline in or loss of visual acuity, abnormal eye fundus, increase in death of photoreceptors, loss of mid-peripheral visual field, anatomical abnormalities in the central retina, visual hallucinations, animated visual hallucinations, Charles Bonnet syndrome, photophobia, chromatopsia, aggregation of wild-type and/or mutant Rho protein, loss of rod cells, loss of cone cells, retinal degeneration, increase in mTor levels, accumulation of Rhodopsin in an outer nuclear layer and within the photoreceptor synaptic terminal, Rhodopsin-mediated cellular damage, and apoptosis of cells in the eye, including but not limited to, the retina.

In some embodiments, the symptoms of a patient suffering from or susceptible to a USH2A-related disease, disorder or condition can be evaluated using any method known in the art, including but not limited to: functional acuity score (FAS); functional field score (FFS); and functional vision score (FVS); Snellen visual acuity; Goldmann visual field area (V4c white test light), and 30-Hz (cone) full-field electroretinogram amplitude, electroretinogram (ERG), analysis of tissue samples, and light and/or immunofluorescence microscopy, immunofluorescence microscopy, immunohistochemistry and confocal microscopy, and terminal deoxynucleotidyl transferase-mediated dUTP nick-end labeling (TUNEL) assay, and optical coherence tomography (OCT).

In some embodiments, the present disclosure pertains to a method of administering a therapeutic amount of a RHO oligonucleotide to a patient suffering from or susceptible to retinopathy.

In some embodiments, a patient is heterozygous, comprising both a mutant and a wild-type RHO allele.

In some embodiments, a subject comprises a SNP, wherein at least one allele of the SNP is on the same copy of a chromosome, gene and/or transcript that is associated with a condition, disorder or disease (e.g., comprising a mutation such as P23H). In some embodiments, one allele of the SNP is on the same copy of a chromosome, gene and/or transcript that is less or is not associated with a condition, disorder or disease (e.g., does not contain P23H). In some embodiments, as described herein, provided technologies can selectively reduce levels of transcripts (and/or products encoded thereby such as proteins) from an allele that is associated with a condition, disorder or disease (e.g., in transcripts comprising P23H) over an allele that is not or is less associated with a condition, disorder or disease. In some embodiments, selectivity is at least 10, 20, 30, 40, 50, 60, 70, 80, 90, 100, 200, 500, 1000, 2000, 5000, or fold, e.g., as measured by IC50-1/IC50-2 using an available technology (e.g., luciferase assay, cell lines, etc. as described herein), wherein IC50-1 is an IC50 for an allele that is not or is less associated with a condition, disorder or disease (e.g., no P23H), and IC50-2 is an IC50 for an allele that is associated with a condition, disorder or disease (e.g., comprising P23H). Certain selective oligonucleotide compositions and technologies useful for assessing them are described in the Examples. In some embodiments, a SNP is SNP rs104893768. In some embodiments, an A allele of rs104893768 is associated with a condition, disorder or disease. Those skilled in the art reading the present disclosure will appreciate that many other alleles of various SNPs can also be targeted.

In some embodiments, a patient is homozygous, wherein both RHO alleles are mutant.

In some embodiments, a patient has two alleles of RHO which are both mutant but different from each other.

In some embodiments, a RHO oligonucleotide capable of decreasing the level, activity and/or expression of a RHO gene (e.g., a RHO gene comprising a disease-associated mutation) is useful in a method of preventing or treating a RHO-related condition, disorder or disease, e.g., retinopathy.

In some embodiments, the present disclosure provides methods for preventing or treating a RHO-related condition, disorder or disease, by administering to a subject suffering from or susceptible to such a condition, disorder or disease a therapeutically effective amount of a provided RHO oligonucleotide or a composition thereof. In some embodiments, an oligonucleotide is a chirally controlled oligonucleotide. In some embodiments, an oligonucleotide is a chirally pure oligonucleotide. In some embodiments, a composition is a chirally controlled oligonucleotide composition. In some embodiments, a composition is a pharmaceutical composition. In some embodiments, in a composition oligonucleotides are independently in salt forms (e.g., sodium salts).

In some embodiments, the present disclosure pertains to a method of decreasing the expression, level and/or activity of a mutant RHO gene or a gene product thereof in a body cell, tissue or organ affected by a RHO-related disorder.

In some embodiments, a body cell, tissue or organ affected by a RHO-related disorder does not exhibit normal function in an organism comprising a mutant RHO gene.

In some embodiments, the present disclosure encompasses a method of decreasing the level, expression and/or activity of a mutant RHO in a body cell, tissue or organ affected by a RHO-related disorder.

In some embodiments, the present disclosure pertains to the use of a RHO oligonucleotide in the treatment of any RHO-related disorder, disease or condition.

Oligonucleotides

Among other things, the present disclosure provides oligonucleotides of various designs, which may comprises various nucleobases and patterns thereof, sugars and patterns thereof, internucleotidic linkages and patterns thereof, and/or additional chemical moieties and patterns thereof as described in the present disclosure. In some embodiments, provided oligonucleotides are RHO oligonucleotides. In some embodiments, provided RHO oligonucleotides can direct a decrease in the expression, level and/or activity of a RHO gene and/or one or more of its products (e.g., transcripts, mRNA, proteins, etc.). In some embodiments, provided RHO oligonucleotides can direct a decrease in the expression, level and/or activity of a RHO gene and/or one or more of its products in any cell of a subject or patient. In some embodiments, a cell is a any cell that normally expresses RHO or produces RHO protein. In some embodiments, provided RHO oligonucleotides can direct a decrease in the expression, level and/or activity of a RHO target gene or a gene product and has a base sequence which consists of, comprises, or comprises a portion (e.g., a span of 10, 11, 12, 13, 14, 15, 16, 17, 18, 19 or more contiguous bases) of the base sequence of a RHO oligonucleotide disclosed herein, wherein each T can be independently substituted with U and vice versa, and the oligonucleotide comprises at least one non-naturally-occurring modification of a base, sugar and/or internucleotidic linkage.

In some embodiments, a provided oligonucleotide, e.g., a RHO oligonucleotide, comprises one or more carbohydrate moieties. In some embodiments, a provided oligonucleotide, e.g., a RHO oligonucleotide, comprises one or more lipid moieties. In some embodiments, a provided oligonucleotide, e.g., a RHO oligonucleotide, comprises one or more targeting moieties. Non-limiting examples of such additional chemical moieties which can be conjugated to an oligonucleotide chain are described herein.

In some embodiments, provided oligonucleotides can direct a decrease in the expression, level and/or activity of a target gene, e.g., a RHO target gene, or a product thereof. In some embodiments, provided oligonucleotides can direct a decrease in the expression, level and/or activity of a RHO target gene or a product thereof via RNase H-mediated knockdown. In some embodiments, provided oligonucleotides can direct a decrease in the expression, level and/or activity of a RHO target gene or a product thereof by sterically blocking translation after binding to a RHO target gene mRNA, and/or by altering or interfering with mRNA splicing. Regardless, however, the present disclosure is not limited to any particular mechanism. In some embodiments, the present disclosure provides oligonucleotides, compositions, methods, etc., capable of operating via double-stranded RNA interference, single-stranded RNA interference, RNase H-mediated knock-down, steric hindrance of translation, or a combination of two or more such mechanisms.

In some embodiments, a RHO oligonucleotide is capable of mediating a decrease in the expression, level and/or activity of a mutant RHO.

In some embodiments, a RHO oligonucleotide is allele-specific and is capable of mediating allele-specific knockdown of RHO, for example, a decrease in the expression, level and/or activity of a mutant RHO (e.g., P23H), to a greater extent than a wild-type RHO (e.g., without P23H). In some embodiments, a RHO oligonucleotide is allele-specific and is capable of mediating allele-specific knockdown of RHO, for example, a decrease in the expression, level and/or activity of P23H RHO, to a greater extent than RHO that does not contain P23H. In some embodiments, a RHO oligonucleotide is allele-specific and is capable of mediating a decrease in the expression, level and/or activity of a mutant RHO, to a greater extent than a wild-type RHO, in an in vivo assay.

In some embodiments, a RHO oligonucleotide is allele-specific and is capable of mediating a decrease in the expression, level and/or activity of a mutant RHO, to a greater extent than a wild-type RHO, at a concentration of about 10 nM in an in vivo assay.

In some embodiments, a RHO oligonucleotide is allele-specific and is capable of mediating a decrease in the expression, level and/or activity of a mutant RHO, to a greater extent than a wild-type RHO, at a concentration of at any concentration between about 1 nM and about 10 nM (inclusive) in an in vivo assay.

In some embodiments, a RHO oligonucleotide capable of allele-specific knockdown (e.g., a decrease in the expression, level, and/or activity) of RHO [e.g., a greater knockdown of a mutant allele of RHO compared to knockdown of a wild-type allele of RHO at a particular concentration (e.g., in vitro)].

In some embodiments, a RHO oligonucleotide capable of knocking down (decreasing) the expression, level and/or activity of a wild-type and/or mutant RHO has any structure (or a portion thereof) illustrated in FIG. 23 (FIG. 23A, B, C or D).

In some embodiments, a RHO oligonucleotide capable of allele-specific knockdown of RHO. Non-limiting examples of such a RHO oligonucleotide include but are not limited to: WV-20828, WV-20846, WV-20847, WV-20865, WV-21503, WV-21505, WV-23658, WV-23668, WV-20808, WV-20827, WV-20843, WV-20845, WV-23654, WV-23655, WV-23657, WV-23661, WV-23664, WV-23665, WV-23667, WV-23675, WV-23676, WV-23677, WV-23678, WV-23679, WV-23683, WV-23684, WV-23685, WV-23686, WV-23687, WV-23680, WV-23671, WV-23674, and WV-23651. In some embodiments, an oligonucleotide is WV-34284, WV-34301, WV-34305, WV-34309, WV-34318, WV-34319, or WV-34327.

In some embodiments, a RHO oligonucleotide is capable of mediating a decrease in the expression, level and/or activity of a mutant RHO via a mechanism involving mRNA degradation and/or steric hindrance of translation of a mutant RHO mRNA.

In some embodiments, provided oligonucleotides, e.g., RHO oligonucleotides, are antisense oligonucleotides (ASOs); they have a base sequence which is antisense to the target nucleic acid sequence. In some embodiments, provided oligonucleotides, e.g., RHO oligonucleotides, are double-stranded siRNAs. In some embodiments, provided oligonucleotides, e.g., RHO oligonucleotides, are single-stranded siRNAs. In some embodiments, a RHO oligonucleotide described herein or a variant thereof can be combined with (e.g., annealed to) a complementary (or at least partially complementary) oligonucleotide to create a siRNA; in some embodiments, the siRNA can comprise a double-stranded region and zero, one or two overhangs (e.g, 3' overhangs and/or 5' overhangs). Provided oligonucleotides and compositions thereof may be utilized for many purposes. For example, provided RHO oligonucleotides can be co-administered or be used as part of a treatment regimen along with one or more treatment for retinopathy or a symptom thereof, including but not limited to: aptamers, lncRNAs, lncRNA inhibitors, antibodies, peptides, small molecules, other oligonucleotides to RHO or other targets, and/or other agents capable of inhibiting the expression of a RHO transcript, reducing the level and/or activity of a RHO gene product, and/or inhibiting the expression of a gene or reducing a gene product thereof which increases the expression, activity and/or level of a RHO transcript or a RHO gene product, or a gene or gene product which is associated with a RHO-related disorder.

In some embodiments, an oligonucleotide, e.g., a RHO oligonucleotide, comprises a structural element or a portion thereof described herein, e.g., in a text, a Table or Figure, etc. In some embodiments, an oligonucleotide, e.g., a RHO oligonucleotide, comprises a base sequence (or a portion thereof) described herein, wherein each T can be independently substituted with U and vice versa, a chemical modification or a pattern of chemical modifications (or a portion thereof), and/or a format or a portion thereof described herein. In some embodiments, an oligonucleotide, e.g., a RHO oligonucleotide, has a base sequence which comprises the base sequence (or a portion thereof) wherein each T can be independently substituted with U, pattern of chemical modifications (or a portion thereof), and/or a format of an oligonucleotide disclosed herein, e.g., in a Table or in the Figures, or otherwise disclosed herein. In some embodiments, such oligonucleotides, e.g., RHO oligonucleotides reduce expression, level and/or activity of a gene, e.g., a RHO gene, or a gene product thereof.

Among other things, provided oligonucleotides may hybridize to their target nucleic acids (e.g., pre-mRNA, mature mRNA, etc.). For example, in some embodiments, a RHO oligonucleotide can hybridize to a RHO nucleic acid derived from a DNA strand (either strand of the RHO gene). In some embodiments, a RHO oligonucleotide can hybridize to a RHO transcript. In some embodiments, a RHO oligonucleotide can hybridize to a RHO nucleic acid in any stage of RNA processing, including but not limited to a pre-mRNA or a mature mRNA. In some embodiments, a RHO oligonucleotide can hybridize to any element of a RHO nucleic acid or its complement, including but not limited to: a promoter region, an enhancer region, a transcriptional stop region, a translational start signal, a translation stop signal, a coding region, a non-coding region, an exon, an intron, an intron/exon or exon/intron junction, the 5' UTR, or the 3' UTR.

In some embodiments, an oligonucleotide hybridizes to two or more variants of transcripts derived from a sense strand. In some embodiments, a RHO oligonucleotide hybridizes to two or more variants of RHO derived from the sense strand. In some embodiments, a RHO oligonucleotide hybridizes to all variants of RHO derived from the sense strand.

In some embodiments, a RHO target of a RHO oligonucleotide is a RHO RNA which is not a mRNA.

In some embodiments, provided oligonucleotides, e.g., RHO oligonucleotides, contain increased levels of one or more isotopes. In some embodiments, provided oligonucleotides are labeled, e.g., by one or more isotopes of one or more elements, e.g., hydrogen, carbon, nitrogen, etc. In some embodiments, provided oligonucleotides in provided compositions, e.g., oligonucleotides of a plurality of a composition, comprise base modifications, sugar modifications, and/or internucleotidic linkage modifications, wherein the oligonucleotides contain an enriched level of deuterium. In some embodiments, provided oligonucleotides are labeled with deuterium (replacing $-^{1}H$ with $-^{2}H$) at one or more positions. In some embodiments, one or more $^{1}H$ of an oligonucleotide chain or any moiety conjugated to the oligonucleotide chain (e.g., a targeting moiety, etc.) is substituted with $^{2}H$. Such oligonucleotides can be used in compositions and methods described herein.

In some embodiments, the present disclosure provides an oligonucleotide composition comprising a plurality of oligonucleotides which:

1) have a common base sequence complementary to a target sequence (e.g., a RHO target sequence) in a transcript; and 2) comprise one or more modified sugar moieties and/or modified internucleotidic linkages.

In some embodiments, oligonucleotides, e.g., RHO oligonucleotides, having a common base sequence may have the same pattern of nucleoside modifications, e.g., sugar modifications, base modifications, etc. In some embodiments, a pattern of nucleoside modifications may be represented by a combination of locations and modifications. In some embodiments, a pattern of backbone linkages comprises locations and types (e.g., phosphate, phosphorothioate, substituted phosphorothioate, etc.) of each internucleotidic linkage.

Oligonucleotides of the present disclosure can comprise various modified internucleotidic linkages. In some embodiments, an internucleotidic linkage has the structure of formula I, I-a, I-b, I-c, I-n-1, I-n-2, I-n-3, I-n-4, II, II-a-1, II-a-2, II-b-1, II-b-2, II-c-1, II-c-2, II-d-1, or II-d-2, or a salt form thereof, as described in U.S. Pat. Nos. 9,394,333, 9,744,183, 9,605,019, 9,598,458, 9,982,257, U.S. Ser. No. 10/160,969, U.S. Ser. No. 10/479,995, US 2020/0056173, US 2018/0216107, US 2019/0127733, U.S. Ser. No. 10/450,568, US 2019/0077817, US 2019/0249173, US 2019/0375774, WO 2018/223056, WO 2018/223073, WO 2018/223081, WO 2018/237194, WO 2019/032607, WO 2019/055951, WO 2019/075357, WO 2019/200185, WO 2019/217784, and/or WO 2019/032612 the internucleotidic linkages (e.g., those of Formula I, I-a, I-b, or I-c, I-n-1, I-n-2, I-n-3, I-n-4, II, II-a-1, II-a-2, II-b-1, II-b-2, II-c-1, II-c-2, II-d-1, II-d-2, etc.) of each of which are independently incorporated herein by reference.

In some embodiments, oligonucleotides of a plurality, e.g., in provided compositions, are of the same oligonucleotide type. In some embodiments, oligonucleotides of an oligonucleotide type have a common pattern of sugar modifications. In some embodiments, oligonucleotides of an oligonucleotide type have a common pattern of base modifications. In some embodiments, oligonucleotides of an oligonucleotide type have a common pattern of nucleoside modifications. In some embodiments, oligonucleotides of an oligonucleotide type have the same constitution. In some embodiments, oligonucleotides of an oligonucleotide type are identical. In some embodiments, oligonucleotides of a plurality are identical. In some embodiments, oligonucleotides of a plurality share the same constitution.

In some embodiments, as exemplified herein, oligonucleotides, e.g., RHO oligonucleotides, are chiral controlled, comprising one or more chirally controlled internucleotidic linkages. In some embodiments, provided oligonucleotides are stereochemically pure. In some embodiments, provided oligonucleotides are substantially separated from other stereoisomers.

In some embodiments, oligonucleotides, e.g., RHO oligonucleotides, comprise one or more modified nucleobases, one or more modified sugars, and/or one or more modified internucleotidic linkages.

In some embodiments, oligonucleotides, e.g., RHO oligonucleotides, comprise one or more modified sugars. In some embodiments, oligonucleotides of the present disclosure comprise one or more modified nucleobases. Various modifications can be introduced to a sugar and/or nucleobase in accordance with the present disclosure. For example, in some embodiments, a modification is a modification described in U.S. Pat. No. 9,006,198. In some embodiments, a modification is a modification described in U.S. Pat. Nos. 9,394,333, 9,744,183, 9,605,019, 9,982,257, US 20170037399, US 20180216108, US 20180216107, U.S. Pat. No. 9,598,458, WO 2017/062862, WO 2018/067973, WO 2017/160741, WO 2017/192679, WO 2017/210647, or WO 2018/098264, the sugar, base, and internucleotidic linkage modifications of each of which are independently incorporated herein by reference.

As used in the present disclosure, in some embodiments, "one or more" is 1-200, 1-150, 1-100, 1-90, 1-80, 1-70, 1-60, 1-50, 1-40, 1-30, or 1, 2, 3, 4, 5, 6, 7, 8, 9, 10, 11, 12, 13, 14, 15, 16, 17, 18, 19, 20, 21, 22, 23, 24, or 25. In some embodiments, "one or more" is one. In some embodiments, "one or more" is two. In some embodiments, "one or more" is three. In some embodiments, "one or more" is four. In some embodiments, "one or more" is five. In some embodiments, "one or more" is six. In some embodiments, "one or more" is seven. In some embodiments, "one or more" is eight. In some embodiments, "one or more" is nine. In some embodiments, "one or more" is ten. In some embodiments, "one or more" is at least one. In some embodiments, "one or more" is at least two. In some embodiments, "one or more" is at least three. In some embodiments, "one or more" is at least four. In some embodiments, "one or more" is at least five. In some embodiments, "one or more" is at least six. In some embodiments, "one or more" is at least seven. In some embodiments, "one or more" is at least eight. In some embodiments, "one or more" is at least nine. In some embodiments, "one or more" is at least ten.

As used in the present disclosure, in some embodiments, "at least one" is 1-200, 1-150, 1-100, 1-90, 1-80, 1-70, 1-60, 1-50, 1-40, 1-30, or 1, 2, 3, 4, 5, 6, 7, 8, 9, 10, 11, 12, 13, 14, 15, 16, 17, 18, 19, 20, 21, 22, 23, 24, or 25. In some embodiments, "at least one" is one. In some embodiments, "at least one" is two. In some embodiments, "at least one" is three. In some embodiments, "at least one" is four. In some embodiments, "at least one" is five. In some embodiments, "at least one" is six. In some embodiments, "at least one" is seven. In some embodiments, "at least one" is eight. In some embodiments, "at least one" is nine. In some embodiments, "at least one" is ten.

In some embodiments, a RHO oligonucleotide is or comprises a RHO oligonucleotide described in a Table or Figure.

As demonstrated in the present disclosure, in some embodiments, a provided oligonucleotide (e.g., a RHO oligonucleotide) is characterized in that, when it is contacted with the transcript in a knockdown system, knockdown of its target (e.g., a RHO transcript for a RHO oligonucleotide, a mutant RHO transcript comprising disease-associated mutation(s), etc.) is improved relative to that observed under reference conditions (e.g., selected from the group consisting of absence of the composition, presence of a reference composition, and combinations thereof). In some embodiments, knockdown is increased 10%, 20%, 30%, 40%, 50%, 60%, 70%, 80%, 90%, 100%, or 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 50, 60, 70, 80, 90, 100, 200, 300, 400, 500, 600, 700, 800, 900, 1000 fold or more.

In some embodiments, oligonucleotides are provided as salt forms. In some embodiments, oligonucleotides are provided as salts comprising negatively-charged internucleotidic linkages (e.g., phosphorothioate internucleotidic linkages, natural phosphate linkages, etc.) existing as their salt forms. In some embodiments, oligonucleotides are provided as pharmaceutically acceptable salts. In some embodiments, oligonucleotides are provided as metal salts. In some embodiments, oligonucleotides are provided as sodium salts. In some embodiments, oligonucleotides are provided as metal salts, e.g., sodium salts, wherein each negatively-charged internucleotidic linkage is independently in a salt form (e.g., for sodium salts, —O—P(O)(SNa)—O— for a phosphorothioate internucleotidic linkage, —O—P(O)(ONa)—O— for a natural phosphate linkage, etc.).

Base Sequences

In some embodiments, an oligonucleotide, e.g., a RHO oligonucleotide, comprises a base sequence described herein or a portion (e.g., a span of 5-50, 5-40, 5-30, 5-20, or 5, 6, 7, 8, 9, 10, 11, 12, 13, 14, 15, 16, 17, 18, 19, 20, or at least 10, at least 15, contiguous nucleobases) thereof with 0-5 (e.g., 0, 1, 2, 3, 4 or 5) mismatches, wherein each T can be independently substituted with U and vice versa. In some embodiments, an oligonucleotide, e.g., a RHO oligonucleotide, comprises a base sequence described herein, or a portion thereof, wherein a portion is a span of at least 10 contiguous nucleobases, or a span of at least 15 contiguous nucleobases with 1-5 mismatches. In some embodiments, provided oligonucleotides comprise a base sequence described herein, or a portion thereof, wherein a portion is a span of at least 10 contiguous nucleobases, or a span of at least 10 contiguous nucleobases with 1-5 mismatches, wherein each T can be independently substituted with U and vice versa. In some embodiments, base sequences of oligonucleotides comprise or consists of 10-50 (e.g., about or at least 10, 11, 12, 13, 14, 15, 16, 17, 18, 19, 20, 21, 22, 23, 24, 25, 30, 35, 40, 45; in some embodiments, at least 15; in some embodiments, at least 16; in some embodiments, at least 17; in some embodiments, at least 18; in some embodiments, at least 19; in some embodiments, at least 20; in some embodiments, at least 21; in some embodiments, at least 22; in some embodiments, at least 23; in some embodiments, at least 24; in some embodiments, at least 25) contiguous bases of a base sequence that is identical to or complementary to a base sequence of a RHO gene or a transcript (e.g., mRNA) thereof. In some embodiments, the base sequence of an oligonucleotide is or comprises a sequence that is complementary to a target sequence in a RHO gene or a transcript thereof. In some embodiments, the complementary sequence is 10. 11, 12, 13, 14, 15, 16, 17, 18, 19 or 20 or more nucleobases in length. In some embodiments, the target sequence is a characteristic sequence of a nucleic acid sequence (e.g., of a RHO gene or a transcript thereof) in that it defines the nucleic acid sequence over others in a relevant organism; for example, the characteristic sequence is not in other genomic nucleic acid sequences (e.g., genes) or transcripts thereof in a relevant organism (e.g., for human RHO, its characteristic sequence not in other human nucleic acid sequences or transcripts thereof). In some embodiments, a characteristic sequence of a transcript defines that transcript over other transcripts in a relevant organism; for example, in some embodiments, the characteristic sequence is not in transcripts that are transcribed from a different nucleic acid sequence (e.g., a different gene). In some embodiments, transcript variants from a nucleic acid sequence (e.g., mRNA variants of a gene) may share a common characteristic sequence that defines them from, e.g., transcripts of other genes. In some embodiments, a characteristic sequence in a transcript defines the transcript from other transcript(s) of the same nucleic acid sequence (e.g., a gene) and/or other alleles of the nucleic acid sequence. In some embodiments, a characteristic sequence defines a particular allele (and/or transcripts thereof) over other allele(s) (and/or transcripts thereof) as described herein. In some embodiments, as described herein, a SNP may define a disease-associated allele over another allele which is not, or is less, associated with the disease. A characteristic sequence may be of various lengths; for example, in some embodiments, it comprises 10. 11, 12, 13, 14, 15, 16, 17, 18, 19 or 20 or more nucleobases. In some embodiments, a RHO oligonucleotide comprises a sequence that is identical or complementary to a characteristic sequence of a RHO gene or a transcript thereof.

In certain embodiments, a base sequence of a RHO oligonucleotide is at least about 50%, about 60%, about 70%, about 75%, about 80%, about 85%, about 90%, about 91%, about 92%, about 93%, about 94%, about 95%, about 96%, about 97%, about 98%, or about 99%, or 100% complementary to a target nucleic acid sequence (e.g., a RNA sequence).

In some embodiments, a base sequence of a RHO oligonucleotide is complementary to an allele of a SNP (e.g., one associated with a condition, disorder or disease). In some embodiments, a base sequence of RHO oligonucleotide is complementary to one allele of a SNP (e.g., one associated with a condition, disorder or disease) and not the other alleles (e.g., those less or not associated with a condition, disorder or disease). In some embodiments, transcripts comprising a SNP allele that is associated with a condition, disorder or disease comprises a mutation associated with a condition, disorder or disease. In some embodiments, a mutation is P23H (e.g., P [CCC]>H [CAC]). In some embodiments, a SNP is rs104893768. In some embodiments, a base sequence of an oligonucleotide is complementary to an A allele (having a corresponding T in the base sequence) and not the other alleles of rs104893768 (e.g., a C allele).

In some embodiments, a base sequence is complementary to a target nucleic acid (e.g., a transcript) at a mutation site encoding a P23H mutation (H [CAC]) and is not complementary to the wild type (P [CCC]).

In some embodiments, a provided oligonucleotide comprises a mismatch (e.g., a G:U mismatch) when aligned with its target nucleic acid sequence, e.g., as described in the examples below. In some embodiments, such oligonucleotide can still effectively reduce levels of transcripts of its target nucleic acid sequence (and/or products encoded thereby), but have significantly reduced undesired reduction of levels of transcripts of non-target nucleic acid sequences (and/or products encoded thereby). In some embodiments, such a mismatch is 1, 2, 3, 4, 5, 6, 7, 8, 9, 10 or more nucleobases away from a nucleobase that is complementary to the nucleobase of a characteristic sequence element, e.g., a SNP, a point mutation, etc; in some embodiments, such a mismatch is 1 nucleobase away (next to the nucleobase that is complementary to the nucleobase of a characteristic sequence element, e.g., a SNP, a point mutation, etc.); in some embodiments, such a mismatch is at least 2 nucleobases away; in some embodiments, such a mismatch is at least 3 nucleobases away; in some embodiments, such a mismatch is at least 4 nucleobases away; in some embodiments, such a mismatch is at least 5 nucleobases away.

In some embodiments, the present disclosure pertains to an oligonucleotide that targets a first gene target and knocks down the first gene target (e.g., decreases the expression, level and/or activity of the gene target or a gene product thereof); in some embodiments, the first target is RHO.

In some embodiments, the present disclosure pertains to: an oligonucleotide capable of knocking down a first gene target, wherein the ability of the oligonucleotide to knock down a second gene target is decreased by replacing one or more bases in the oligonucleotide with a base that would participate in G:U basepairing with the second gene target.

In some embodiments, the present disclosure pertains to a method related to an oligonucleotide that targets and knocks down a first gene target, wherein the method pertains to reducing the ability of the oligonucleotide to target and knock down to a second gene target, wherein knocking down the second gene target is not desirable, and wherein reduction of the ability of the oligonucleotide to knock down the second gene target is mediated by replacement of one or more bases in the oligonucleotide with a base that would participate in G:U basepairing with a particular position in the second target.

In some embodiments, the present disclosure pertains to a method of reducing the ability of an oligonucleotide targeting a first gene target to knock down a second gene target, comprising the step of replacing one or more bases in the oligonucleotide with a base that would participate in G:U basepairing with the second target.

For example, an oligonucleotide can be designed to knock down RHO, where the oligonucleotide has zero mismatches to the target RHO sequence, but also, for example, 2 mismatches from a second gene sequence (e.g., an off-target gene sequence). For example, the oligonucleotide hybridizing to and knocking down the off-target gene sequence can be undesirable if the off-target gene is necessary or beneficial for the proper functioning of a particular cell, tissue or organ. If the oligonucleotide comprises a base which bonds via Watson-Crick basepairing to a corresponding base in the desired RHO target sequence, that base can be replaced by a base which would participate in G:U base-pairing with the desired RHO target sequence. Without wishing to be bound by any particular theory, the present disclosure notes that G:U basepairing is reportedly weaker than Watson-Crick basepairing, but the decrease in the strength of one base pair should still allow hybridization of the oligonucleotide to the target sequence, thereby mediating knockdown of the RHO target. However, the replacement of the base with a base that participates in G:U basepairing would also decrease the ability of the oligonucleotide to hybridize to the off-target gene sequence, which already (in this example) has 2 mismatches from the oligonucleotide. The combination of the two mismatches and the newly-introduced G:U may decrease the ability of the oligonucleotide to hybridize to the off-target sequence, thereby reducing the ability of the oligonucleotide to knock-down the off-target gene.

As a non-limiting example, an example mutant RHO target sequence has one mismatch (bold, underlined) from the wild-type sequence and two mismatches from the sequence of an off-target gene, IRF2BPL. Knocking down IRF2BPL in at least some cases may be undesirable.

| | Genomic sequence: | Number of mismatches |
|---|---|---|
| Mutant RHO | 5'-ACGCAGCC**A**CTTCGAGTACC-3 | 0 (SEQ ID NO: 12) |
| WT RHO | 5'-ACGCAGCC**C**CTTCGAGTACC-3 | 1 (SEQ ID NO: 13) |
| IRF2BPL | 5'-**G**CGCAGCC**G**CTTCGAGTACC-3 | 2 (SEQ ID NO: 14) |

As a non-limiting example, a RHO oligonucleotide (1) is designed with perfect complementarity (0 mismatches) to the mutant RHO sequence, 1 mismatch from the wild-type RHO sequence, and 2 mismatches from the off-target IRF2BPL sequence. In some cases, but not necessarily all, it is possible but not certain that two mismatches may not be sufficient to completely prevent the oligonucleotide from hybridizing to and knocking down IRF2BPL.

| | OLIGONUCLEOTIDE 1: | Number of mismatches |
|---|---|---|
| | 3'-TGCGTCGG**T**GAAGCTCATGG-5' | (SEQ ID NO: 15) |
| Mutant RHO | 5'-ACGCAGCC**A**CTTCGAGTACC-3 | 0 (SEQ ID NO: 12) |

-continued

| | OLIGONUCLEOTIDE 1: | Number of mismatches |
|---|---|---|
| WT RHO | 5'-ACGCAGCCCCTTCGAGTACC-3 | 1 (SEQ ID NO: 13) |
| IRF2BPL | 5'-GCGCAGCCGCTTCGAGTACC-3 | 2 (SEQ ID NO: 14) |

In some embodiments, a base in oligonucleotide 1 is replaced by a base capable of mediating G:U (wobble) basepairing with a corresponding base in the mutant RHO sequence (which is the same in the wt RHO and IRF2BPL. Introducing the G:U basepair (underlined, not bold) into the oligonucleotide decreases its ability to hybridize to the mutant RHO, the wt RHO and the off-target gene. However, in some embodiments, a single G:U basepair does not substantially decrease the ability of the oligonucleotide to hybridize to and knock down the mutant RHO gene target. In addition, the single G:U basepair will further decrease the ability of the oligonucleotide to hybridize to and knock down the wt RHO or the off-target gene, thus mitigating an off-target effect.

| | OLIGONUCLEOTIDE 2 (1 G:U): | Number of mismatches |
|---|---|---|
| | 3'-TGCGTUGGTGAAGCTCATGG-5' | (SEQ ID NO: 16) |
| Mutant RHO | 5'-ACGCAGCCACTTCGAGTACC-3 | 0 + 1 G:U (SEQ ID NO: 12) |
| WT RHO | 5'-ACGCAGCCCCTTCGAGTACC-3 | 1 + 1 G:U (SEQ ID NO: 13) |
| IRF2BPL | 5'-GCGCAGCCGCTTCGAGTACC-3 | 2 + 1 G:U (SEQ ID NO: 14) |

In some embodiments, the replacement of two bases with bases capable of mediating G:U basepairing with the mutant RHO target can also substantially decrease the ability of the oligonucleotide to hybridize to and knockdown the wt RHO and off-target gene, without preventing the oligonucleotide from knocking down the mutant RHO.

For example, two bases in oligonucleotide 1 are replaced by bases which can participate in G:U basepairing with the target sequence:

| | OLIGONUCLEOTIDE 3 (2 G:U): | Number of mismatches |
|---|---|---|
| | 3'-TGUGTCGGTGAAGUTCATGG-5' | (SEQ ID NO: 17) |
| Mutant RHO | 5'-ACGCAGCCACTTCGAGTACC-3 | 0 + 2 G:U (SEQ ID NO: 12) |
| WT RHO | 5'-ACGCAGCCCCTTCGAGTACC-3 | 1 + 2 G:U (SEQ ID NO: 13) |
| IRF2BPL | 5'-GCGCAGCCGCTTCGAGTACC-3 | 2 + 2 G:U (SEQ ID NO: 14) |

In some embodiments, a mismatch is in a core. In some embodiments, a mismatch is in a wing. In some embodiments, when an oligonucleotide is aligned with its target sequence, there is a G:U pairing.

In some embodiments, a RHO oligonucleotide capable of knocking down mutant RHO has a number of mismatches from the off-target gene CHST6.

In some embodiments, a RHO oligonucleotide has 2 mismatches from the off-target gene CHST6.

In some embodiments, a RHO oligonucleotide has 2 mismatches from the off-target gene CHST6, and one or more bases of the RHO oligonucleotide are replaced with a base capable of mediating G:U basepairing with the mutant RHO and the off-target gene.

In some embodiments, the present disclosure pertains to a RHO oligonucleotide, wherein the RHO oligonucleotide is capable of mediating an allele-specific decrease in the expression, level an/or activity of a mutant RHO gene target or a gene product thereof.

In some embodiments, the present disclosure pertains to a RHO oligonucleotide, wherein the RHO oligonucleotide is capable of mediating an allele-specific decrease in the expression, level an/or activity of a mutant RHO gene target or a gene product thereof, wherein base sequence of the oligonucleotide is, comprises, or comprises at least 15 contiguous bases of, the base sequence of any RHO oligonucleotide disclosed herein, except that at least one base in the oligonucleotide is replaced by a base capable of mediating G:U basepairing with the mutant RHO target sequence.

In some embodiments, the present disclosure pertains to a RHO oligonucleotide, wherein the RHO oligonucleotide is capable of mediating an allele-specific decrease in the expression, level an/or activity of a mutant RHO gene target or a gene product thereof, wherein base sequence of the oligonucleotide is, comprises, or comprises at least 15 contiguous bases of, the base sequence of any RHO oligonucleotide disclosed herein, except that one base in the oligonucleotide is replaced by a base capable of mediating G:U basepairing with the mutant RHO target sequence.

In some embodiments, the present disclosure pertains to a RHO oligonucleotide, wherein the RHO oligonucleotide is capable of mediating an allele-specific decrease in the expression, level an/or activity of a mutant RHO gene target or a gene product thereof, wherein base sequence of the oligonucleotide is, comprises, or comprises at least 15 contiguous bases of, the base sequence of any RHO oligonucleotide disclosed herein, except that two bases in the oligonucleotide are replaced by a base capable of mediating G:U basepairing with the mutant RHO target sequence.

In some embodiments, the present disclosure pertains to a RHO oligonucleotide, wherein the RHO oligonucleotide is capable of mediating an allele-specific decrease in the expression, level an/or activity of a mutant RHO gene target or a gene product thereof, wherein base sequence of the oligonucleotide is, comprises, or comprises at least 15 contiguous bases of, the base sequence of any RHO oligonucleotide disclosed herein, except that three bases in the oligonucleotide are replaced by a base capable of mediating G:U basepairing with the mutant RHO target sequence.

Base sequences of provided oligonucleotides, as appreciated by those skilled in the art, typically have sufficient length and complementarity to their targets, e.g., RNA transcripts (e.g., pre-mRNA, mature mRNA, etc.) to mediate target-specific knockdown. In some embodiments, the base sequence of a RHO oligonucleotide has a sufficient length and identity to a RHO transcript target to mediate target-specific knockdown. In some embodiments, a RHO oligonucleotide is complementary to a portion of a RHO transcript (an RHO transcript target sequence). In some embodiments, the base sequence of a RHO oligonucleotide has 90% or more identity with the base sequence of an oligonucleotide disclosed in a Table, wherein each T can be independently substituted with U and vice versa. In some embodiments, the base sequence of a RHO oligonucleotide has 95% or more identity with the base sequence of an oligonucleotide disclosed in a Table, wherein each T can be independently substituted with U and vice versa. In some embodiments, the base sequence of a RHO oligonucleotide comprises a continuous span of 15 or more bases of an oligonucleotide disclosed in a Table, wherein each T can be independently substituted with U and vice versa, except that one or more bases within the span are abasic (e.g., a nucleobase is absent from a nucleotide). In some embodiments, the base sequence of a RHO oligonucleotide comprises a continuous span of 19 or more bases of a RHO oligonucleotide disclosed herein, except that one or more bases within the span are abasic (e.g., a nucleobase is absent from a nucleotide). In some embodiments, the base sequence of a RHO oligonucleotide comprises a continuous span of 19 or more bases of an oligonucleotide disclosed herein, wherein each T can be independently substituted with U and vice versa, except for a difference in the 1 or 2 bases at the 5' end and/or 3' end of the base sequences.

In some embodiments, a base sequence of an oligonucleotide is, comprises, or comprises 10-20, e.g., 10, 11, 12, 13, 14, 15, 16, 17, 18, 19 or 20 contiguous bases of an oligonucleotide selected from WV-20828, WV-20846, WV-20847, WV-20865, WV-21503, WV-21505, WV-23658, WV-23668, WV-20808, WV-20827, WV-20843, WV-20845, WV-23654, WV-23655, WV-23657, WV-23661, WV-23664, WV-23665, WV-23667, WV-23675, WV-23676, WV-23677, WV-23678, WV-23679, WV-23683, WV-23684, WV-23685, WV-23686, WV-23687, WV-23680, WV-23671, WV-23674, WV-23651, WV-34284, WV-34301, WV-34305, WV-34309, WV-34318, WV-34319, and WV-34327 (some of which may share the same base sequences), wherein each T may be independently replaced with U and vice versa. In some embodiments, a base sequence of an oligonucleotide is, comprises, or comprises 10-20, e.g., 10, 11, 12, 13, 14, 15, 16, 17, 18, 19 or 20 contiguous bases of a base sequence selected from TCGAAGTGGCTGCGTACCAC (SEQ ID NO: 18), ACTCGAAGTGGCTGCGTACC (SEQ ID NO: 19), ACTCGAAGTGGCTGCGUACC (SEQ ID NO: 20), CCTTCCCTGAAGGTTCCUCC (SEQ ID NO: 21), CTCGAAGGGGCTCCGCACCA (SEQ ID NO: 22), CTCGAAGTGGCTGCGTACCA (SEQ ID NO: 23), CTCGAAGTGGCTGCGUACCA (SEQ ID NO: 24), CTGCTCGAAGGGGCTCCGCA (SEQ ID NO: 25), CTGCTCGAAGTGGCTCCGCA (SEQ ID NO: 26), GCTCGAAGGGGCTCCGCACC (SEQ ID NO: 27), GCTCGAAGTGGCTCCGCACC (SEQ ID NO: 28), GCTGCTCGAAGGGGCUCCGC (SEQ ID NO: 29), GCTGCTCGAAGGTGCUCCGC (SEQ ID NO: 30), GGTACTCGAAGTGGCT (SEQ ID NO: 31), GGTACTCGAAGTGGCT (SEQ ID NO: 32), GGTACTCGAAGTGGCTGCGT (SEQ ID NO: 33), GGTACTCGAAGTGGCUGCGU (SEQ ID NO: 34), GTACTCGAAGTGGCTGCGTA (SEQ ID NO: 35), GTACTCGAAGTGGCTGCGUA (SEQ ID NO: 36), GUGGUACGCAGCCACUUCGAGUACC (SEQ ID NO: 37), TACTCGAAGTGGCTGC (SEQ ID NO: 38), TACTCGAAGTGGCTGCGTAC (SEQ ID NO: 39), TACTCGAAGTGGCTGCGUAC (SEQ ID NO: 40), TCGAAGTGGCTGCGTACCAC (SEQ ID NO: 41), and TGCTCGAAGGGGCTCCGCAC (SEQ ID NO: 42), wherein each T may be independently replaced with U and vice versa. In some embodiments, a base sequence comprises one of these sequence. In some embodiments, a base sequence is one of these sequence.

In some embodiments, the present disclosure pertains to an oligonucleotide having a base sequence which comprises the base sequence of any oligonucleotide disclosed herein, wherein each T may be independently replaced with U and vice versa.

In some embodiments, the present disclosure pertains to an oligonucleotide having a base sequence which is the base sequence of any oligonucleotide disclosed herein, wherein each T may be independently replaced with U and vice versa.

In some embodiments, the present disclosure pertains to an oligonucleotide having a base sequence which comprises at least 15 contiguous bases of the base sequence of any oligonucleotide disclosed herein, wherein each T may be independently replaced with U and vice versa.

In some embodiments, the present disclosure pertains to an oligonucleotide having a base sequence which is at least 90% identical to the base sequence of any oligonucleotide disclosed herein, wherein each T may be independently replaced with U and vice versa.

In some embodiments, the present disclosure pertains to an oligonucleotide having a base sequence which is at least 95% identical to the base sequence of any oligonucleotide disclosed herein, wherein each T may be independently replaced with U and vice versa.

In some embodiments, a base sequence of an oligonucleotide is, comprises, or comprises 10-20, e.g., 10, 11, 12, 13, 14, 15, 16, 17, 18, 19 or 20 contiguous bases of the base sequence of any oligonucleotide describer herein, wherein each T may be independently replaced with U and vice versa.

In some embodiments, a RHO oligonucleotide is any RHO oligonucleotide provided herein.

In some embodiments, a RHO oligonucleotide is WV-20847, WV-20846, WV-20865, WV-20828, WV-21503, WV-21505, WV-23658, or WV-23668. In some embodiments, a RHO oligonucleotide is WV-34284, WV-34301, WV-34305, WV-34309, WV-34318, WV-34319, or WV-34327.

In some embodiments, the base sequence of a RHO oligonucleotide is complementary to that of a RHO transcript or a portion thereof.

In some embodiments, a RHO target gene is an allele of the RHO gene. In some embodiments, a RHO oligonucleotide is allele-specific and is designed to target a specific allele of RHO (e.g., an allele associated with a RHO-associated condition, disorder or disease).

Wild-type RHO performs many functions, some of which may not yet be identified. In some embodiments, it is preferable that a RHO oligonucleotide can mediate allele-specific knockdown, wherein the RHO oligonucleotide decreases the expression, activity and/or level of a mutant RHO gene or a gene product thereof to a greater extent as described herein relative to a wild-type RHO gene or a gene product thereof. In some embodiments, the present disclosure provides allele-specific technologies that can selectively reduce decreases the expression, activity and/or level of a mutant RHO gene or a gene product thereof relative to a wild-type RHO gene (or a RHO gene that is not, or is less, associated with a condition, disorder or disease) or a gene product thereof.

In some embodiments, the base sequence of an oligonucleotide fully complements the sequence of a RHO transcript (or a portion thereof) from an allele associated with a condition, disorder or disease and is not fully complement the sequence of a RHO transcript (or a portion thereof) less or not associated with a condition, disorder or disease. In some embodiments, a disorder-associated allele of RHO comprises a SNP, mutation or other sequence variation and the RHO oligonucleotide is designed to complement this sequence. In some embodiments, a RHO SNP is any SNP listed in Table S2. In some embodiments, base sequence of an oligonucleotide complement one allele of a SNP and not the others. In some embodiments, base sequence of an oligonucleotide complement one allele of a SNP, which allele is on the same DNA strand of disease-associated mutation(s). In some embodiments, the base sequence of an oligonucleotide is fully complementary to the sequence of a RHO transcript (or a portion thereof) from an allele comprising disease-associated mutation(s) and is not fully complementary to the sequence of a RHO transcript (or a portion thereof) from an allele comprising a corresponding wild-type (or not disease-associated) sequence. In some embodiments, a RHO oligonucleotide is pan-specific and designed to target all alleles of RHO (e.g., all or most known alleles of RHO comprise the same sequence, or a sequence complementary thereto, within the span of bases recognized by the RHO oligonucleotide). In some embodiments, an oligonucleotide reduces expressions, levels and/or activities of both wild-type RHO and mutant RHO, and/or transcripts and/or products thereof.

In some embodiments, a RHO oligonucleotide comprises a base sequence or portion (e.g., a portion comprising 10, 11, 12, 13, 14, 15, 16, 17, 18, 19, or 20 nucleobases) thereof described in the Tables, wherein each T may be independently replaced with U and vice versa, and/or a sugar, nucleobase, and/or internucleotidic linkage modification and/or a pattern thereof described in the Tables, and/or an additional chemical moiety (in addition to an oligonucleotide chain, e.g., a target moiety, a lipid moiety, a carbohydrate moiety, etc.) described in the Tables.

In some embodiments, the terms "complementary," "fully complementary" and "substantially complementary" may be used with respect to the base matching between an oligonucleotide (e.g., a RHO oligonucleotide) and a target sequence (e.g., a RHO target sequence), as will be understood by those skilled in the art from the context of their use. As a non-limiting example, if a target sequence has, for example, a base sequence of 5'-GUGCUAGUAGCCAACCCCC-3' (SEQ ID NO: 43), an oligonucleotide with a base sequence of 5'-GGGGGTTGGCTACTAGCAC-3' (SEQ ID NO: 44) is complementary (fully complementary) to such a target sequence. It is noted that substitution of T for U, or vice versa, generally does not alter the amount of complementarity. As used herein, an oligonucleotide that is "substantially complementary" to a target sequence is largely or mostly complementary but not 100% complementary. In some embodiments, a sequence (e.g., a RHO oligonucleotide) which is substantially complementary has 1, 2, 3, 4 or 5 mismatches when aligned to its target sequence. In some embodiments, a RHO oligonucleotide has a base sequence which is substantially complementary to a RHO target sequence. In some embodiments, a RHO oligonucleotide has a base sequence which is substantially complementary to the complement of the sequence of a RHO oligonucleotide disclosed herein. As appreciated by those skilled in the art, in some embodiments, sequences of oligonucleotides need not be 100% complementary to their targets for the oligonucleotides to perform their functions (e.g., knockdown of target nucleic acids. In some embodiments, homology, sequence identity or complementarity is 60%-100%, e.g., about or at least 60%, 70%, 75%, 80%, 85%, 90%, 91%, 92%, 93%, 94%, 95%, 96%, 97%, 98%, or 99%, or 100%. In some embodiments, a provided oligonucleotide has 75%-100% (e.g., about or at least 80%, 85%, 90%, 91%, 92%, 93%, 94%, 95%, 96%, 97%, 98%, or 99%, or 100%) sequence complementarity to a target region (e.g., a target sequence) within its target nucleic acid. In some embodiments, the percentage is about 80% or more. In some embodiments, the percentage is about 85% or more. In some embodiments, the percentage is about 90% or more. In some embodiments, the percentage is about 95% or more. For example, a provided oligonucleotide which is 20 nucleobases long will have 90 percent complementarity if 18 of its 20 nucleobases are complementary. Typically when determining complementarity, A and T (or U) are complementary nucleobases and C and G are complementary nucleobases.

In some embodiments, the present disclosure provides a RHO oligonucleotide comprising a sequence found in an oligonucleotide described in a Table. In some embodiments, the present disclosure provides a RHO oligonucleotide comprising a sequence found in an oligonucleotide described in a Table, wherein one or more U is independently and optionally replaced with T or vice versa. In some embodiments, a RHO oligonucleotide can comprise at least one T and/or at least one U. In some embodiments, the present disclosure provides a RHO oligonucleotide comprising a sequence found in an oligonucleotide described in a Table, wherein the said sequence has over 50% identity with the sequence of the oligonucleotide described in the Table. In some embodiments, the present disclosure provides a RHO oligonucleotide comprising a sequence found in an oligonucleotide described in a Table, wherein the said sequence has over 60% identity with the sequence of the oligonucleotide described in the Table. In some embodiments, the present disclosure provides a RHO oligonucleotide comprising a sequence found in an oligonucleotide described in a Table, wherein the said sequence has over 70% identity with the sequence of the oligonucleotide described in the Table. In some embodiments, the present disclosure provides a RHO oligonucleotide comprising a sequence found in an oligonucleotide described in a Table, wherein the said sequence has over 80% identity with the sequence of the oligonucleotide described in the Table. In some embodiments, the present disclosure provides a RHO oligonucleotide comprising a sequence found in an oligonucleotide described in a Table, wherein the said sequence has over 90% identity with the sequence of the oligonucleotide described in the Table. In some embodiments, the present disclosure provides a RHO oligonucleotide comprising a sequence found in an oligonucleotide described in a Table, wherein the said sequence has over 95% identity with the sequence of the oligonucleotide described in the Table. In some embodiments, the present disclosure provides a RHO oligonucleotide comprising the sequence of an oligonucleotide disclosed in a Table. In some embodiments, the present disclosure provides a RHO oligonucleotide whose base sequence is the sequence of an oligonucleotide disclosed in a Table, wherein each T may be independently replaced with U and vice versa. In some embodiments, the present disclosure provides a RHO oligonucleotide comprising a sequence found in an oligonucleotide in a Table, wherein the oligonucleotides have a pattern of backbone linkages, pattern of backbone chiral centers, and/or pattern of backbone phosphorus modifications of the same oligonucleotide or another oligonucleotide in a Table herein.

Among other things, the present disclosure presents, in Table A1, Table A2 and elsewhere, various oligonucleotides and/or compositions thereof, each of which has a defined base sequence. In some embodiments, the present disclosure, the present disclosure provides an oligonucleotide whose base sequence which is, comprises, or comprises a portion of the base sequence of an oligonucleotide disclosed herein, e.g., in a Table, e.g., Table A1 or A2 herein, wherein each T may be independently replaced with U and vice versa. In some embodiments, the disclosure provides an oligonucleotide having a base sequence which is, comprises, or comprises a portion of the base sequence of an oligonucleotide disclosed herein, e.g., in a Table, wherein each T may be independently replaced with U and vice versa, wherein the oligonucleotide further comprises a chemical modification, stereochemistry, format, an additional chemical moiety described herein (e.g., a targeting moiety, lipid moiety, carbohydrate moiety, etc.), and/or another structural feature.

In some embodiments, a "portion" (e.g., of a base sequence or a pattern of modifications) is at least 5, 6, 7, 8, 9, 10, 11, 12, 13, 14, 15, 16, 17, 18, 19, or 20 monomeric units long (e.g., for a base sequence, at least 5, 6, 7, 8, 9, 10, 11, 12, 13, 14, 15, 16, 17, 18, 19, or 20 bases long). In some embodiments, a "portion" of a base sequence is at least 5 bases long. In some embodiments, a "portion" of a base sequence is at least 10 bases long. In some embodiments, a "portion" of a base sequence is at least 15 bases long. In some embodiments, a "portion" of a base sequence is at least 20 bases long. In some embodiments, a portion of a base sequence is 10, 11, 12, 13, 14, 15, 16, 17, 18, 19 or more contiguous (consecutive) bases. In some embodiments, a portion of a base sequence is 15 or more contiguous (consecutive) bases.

In some embodiments, the present disclosure provides an oligonucleotide (e.g., a RHO oligonucleotide) whose base sequence is a base sequence of an oligonucleotide in a Table or a portion thereof, wherein each T may be independently replaced with U and vice versa. In some embodiments, the present disclosure provides a RHO oligonucleotide of a sequence of an oligonucleotide in a Table, wherein the oligonucleotide is capable of directing a decrease in the expression, level and/or activity of a RHO gene or a gene product thereof. As appreciated by those skilled in the art, in provided base sequence, each U may be optionally and independently replaced by T or vice versa, and a sequence can comprise a mixture of U and T. In some embodiments, C may be optionally and independently replaced with 5mC.

In some embodiments, a portion is a span of at least 15, 16, 17, 18, 19, 20, 21, 22, 23, 24, or 25 total nucleotides. In some embodiments, a portion is a span of at least 15, 16, 17, 18, 19, 20, 21, 22, 23, 24, or 25 total nucleotides with 0-3 mismatches. In some embodiments, a portion is a span of at least 15, 16, 17, 18, 19, 20, 21, 22, 23, 24, or 25 total nucleotides with 0-3 mismatches, wherein a span with 0 mismatches is complementary and a span with 1 or more mismatches is a non-limiting example of substantial complementarity. In some embodiments, a base comprises a portion characteristic of a nucleic acid (e.g., a gene) in that the portion is identical or complementary to a portion of the nucleic acid or a transcript thereof, and is not identical or complementary to a portion of any other nucleic acid (e.g., a gene) or a transcript thereof in the same genome. In some embodiments, a portion is characteristic of human RHO. In some embodiments, a portion is characteristic of human mRho.

In some embodiments, a provided oligonucleotide, e.g., a RHO oligonucleotide, has a length of no more than about 49, 45, 40, 30, 35, 25, or 23 total nucleotides as described herein. In some embodiments, wherein the sequence recited herein starts with a U or T at the 5'-end, the U can be deleted and/or replaced by another base. In some embodiments, an oligonucleotide has a base sequence which is or comprises or comprises a portion of the base sequence of an oligonucleotide in a Table, wherein each T may be independently replaced with U and vice versa, which has a format or a portion of a format disclosed herein.

In some embodiments, oligonucleotides, e.g., RHO oligonucleotides are stereorandom. In some embodiments, oligonucleotides, e.g., RHO oligonucleotides, are chirally controlled. In some embodiments, an oligonucleotide, e.g., a RHO oligonucleotide, is chirally pure (or "stereopure", "stereochemically pure"), wherein the oligonucleotide exists as a single stereoisomeric form (in many cases a single diastereoisomeric (or "diastereomeric") form as multiple chiral centers may exist in an oligonucleotide, e.g., at linkage phosphorus, sugar carbon, etc.). As appreciated by those skilled in the art, a chirally pure oligonucleotide is separated from its other stereoisomeric forms (to the extent that some impurities may exist as chemical and biological processes, selectivities and/or purifications etc. rarely, if ever, go to absolute completeness). In a chirally pure oligonucleotide, each chiral center is independently defined with respect to its configuration (for a chirally pure oligonucleotide, each internucleotidic linkage is independently stereodefined or chirally controlled). In contrast to chirally controlled and chirally pure oligonucleotides which comprise stereodefined linkage phosphorus, racemic (or "stereorandom", "non-chirally controlled") oligonucleotides comprising chiral linkage phosphorus, e.g., from traditional phosphoramidite oligonucleotide synthesis without stereochemical control during coupling steps in combination with traditional sulfurization (creating stereorandom phosphorothioate internucleotidic linkages), refer to a random mixture of various stereoisomers (typically diastereoisomers (or "diastereomers") as there are multiple chiral centers in an oligonucleotide; e.g., from traditional oligonucleotide preparation using reagents containing no chiral elements other than those in nucleosides and linkage phosphorus). For example, for A*A*A wherein * is a phosphorothioate internucleotidic linkage (which comprises a chiral linkage phosphorus), a racemic oligonucleotide preparation includes four diastereomers [$2^2$=4, considering the two chiral linkage phosphorus, each of which can exist in either of two configurations (Sp or Rp)]: A *S A *S A, A *S A *R A, A *R A *S A, and A *R A *R A, wherein *S represents a Sp phosphorothioate internucleotidic linkage and *R represents a Rp phosphorothioate internucleotidic linkage. For a chirally pure oligonucleotide, e.g., A *S A *S A, it exists in a single stereoisomeric form and it is separated from the other stereoisomers (e.g., the diastereomers A *S A *R A, A *R A *S A, and A *R A *R A). In some embodiments, a Rp phosphorothioate is rendered as *S or * S. In some embodiments, a Rp phosphorothioate is rendered as *R or * R.

In some embodiments, oligonucleotides, e.g., RHO oligonucleotides, comprise 1, 2, 3, 4, 5, 6, 7, 8, 9, 10 or more stereorandom internucleotidic linkages (mixture of Rp and Sp linkage phosphorus at the internucleotidic linkage, e.g., from traditional non-chirally controlled oligonucleotide synthesis). In some embodiments, oligonucleotides, e.g., RHO oligonucleotides, comprise one or more (e.g., 1-50, 1-40, 1-30, 1-25, 1-20, 1, 2, 3, 4, 5, 6, 7, 8, 9, 10, 11, 12, 13, 14, 15, 16, 17, 18, 19, 20, 21, 22, 23, 24, 25 or more) chirally controlled internucleotidic linkages (Rp or Sp linkage phosphorus at the internucleotidic linkage, e.g., from chirally controlled oligonucleotide synthesis). In some embodiments, an internucleotidic linkage is a phosphorothioate internucleotidic linkage. In some embodiments, an internucleotidic linkage is a stereorandom phosphorothioate internucleotidic linkage. In some embodiments, an internucleotidic linkage is a chirally controlled phosphorothioate internucleotidic linkage.

Among other things, the present disclosure provides technologies for preparing chirally controlled (in some embodiments, stereochemically pure) oligonucleotides. In some embodiments, oligonucleotides are stereochemically pure. In some embodiments, oligonucleotides of the present disclosure are about 5%-100%, 10%-100%, 20%-100%, 30%-100%, 40%-100%, 50%-100%, 60%-100%, 70%-100%, 80-100%, 90-100%, 95-100%, 50%-90%, or about 5%, 10%, 15%, 20%, 25%, 30%, 35%, 40%, 45%, 50%, 55%, 60%, 65%, 70%, 75%, 80%, 85%, 90%, 95%, or 100%, or at least about 5%, 10%, 15%, 20%, 25%, 30%, 35%, 40%, 45%, 50%, 55%, 60%, 65%, 70%, 75%, 80%, 85%, 90%, 95%, or 99%, pure. In some embodiments, internucleotidic linkages of oligonucleotides comprise or consist of one or more (e.g., 1-50, 1-40, 1-30, 1-25, 1-20, 5-50, 5-40, 5-30, 5-25, 5-20, 1, 2, 3, 4, 5, 6, 7, 8, 9, 10, 11, 12, 13, 14, 15, 16, 17, 18, 19, 20, 21, 22, 23, 24, 25 or more) chirally controlled chiral internucleotidic linkages, each of which independently has a diastereopurity of at least 80%, 85%, 90%, 91%, 92%, 93%, 94%, 95%, 96%, 97%, 98%, 99% or 99.5%, typically at least 90%, 91%, 92%, 93%, 94%, 95%, 96%, 97%, 98%, 99% or 99.5%. In some embodiments, a chiral internucleotidic linkage has a diastereopurity of at least 95%. In some embodiments, a chiral internucleotidic linkage has a diastereopurity of at least 96%. In some embodiments, a chiral internucleotidic linkage has a diastereopurity of at least 97%. In some embodiments, a chiral internucleotidic linkage has a diastereopurity of at least 98%. In some embodiments, a chiral internucleotidic linkage has a diastereopurity of at least 99%. In some embodiments, oligonucleotides of the present disclosure, e.g., RHO oligonucleotides, have a diastereopurity of $(DS)^{CIL}$, wherein DS is a diastereopurity as described in the present disclosure (e.g., 90%, 91%, 92%, 93%, 94%, 95%, 96%, 97%, 98%, 99% or 99.5% or more) and CIL is the number of chirally controlled internucleotidic linkages (e.g., 1-50, 1-40, 1-30, 1-25, 1-20, 5-50, 5-40, 5-30, 5-25, 5-20, 1, 2, 3, 4, 5, 6, 7, 8, 9, 10, 11, 12, 13, 14, 15, 16, 17, 18, 19, 20, 21, 22, 23, 24, 25 or more). In some embodiments, DS is 95%-100%. In some embodiments, each phosphorothioate internucleotidic linkage is independently chirally controlled. In some embodiments, each internucleotidic linkage is independently chirally controlled. In some embodiments, one or more chiral internucleotidic linkages, e.g., one or more neutral internucleotidic linkages (e.g., n001) is not chirally controlled.

As examples, certain RHO oligonucleotides comprising certain example base sequences, nucleobase modifications and patterns thereof, sugar modifications and patterns thereof, internucleotidic linkages and patterns thereof, linkage phosphorus stereochemistry and patterns thereof, linkers, and/or additional chemical moieties, and compositions thereof, are presented in Tables A1 and A2, below. Among other things, these oligonucleotides and compositions may be utilized to target a RHO transcript, e.g., to reduce the level of a RHO transcript and/or a product thereof, and may be utilized to treat a condition, disorder or disease associated with RHO (e.g., one associated with P23H mutation). In some embodiments, a condition, disorder or disease is retinitis pigmentosa.

TABLE A1

Example RHO Oligonucleotides/Compositions.

| Oligo-nucleotide | Description | Base Sequence | SEQ ID NO | Stereochemistry/ Linkage |
|---|---|---|---|---|
| WV-20791 | Teo*Rm5Ceo*RGeo*RAeo*RAeo*RG*RT*SG*SG*SC*ST*SG*Sm5C*SG*ST*RAeo*Rm5Ceo*Rm5Ceo*RAeo*Rm5Ceo | TCGAAGTGGCTGCGTACCAC | 45 | RRRRR R SSSSS SSSRRRRR |
| WV-20792 | Teo*Rm5Ceo*RGeo*RAeo*RAeo*RG*ST*RG*SG*SC*ST*SG*Sm5C*SG*ST*RAeo*Rm5Ceo*Rm5Ceo*RAeo*Rm5Ceo | TCGAAGTGGCTGCGTACCAC | 46 | RRRRR SR SSSSS SSRRRRR |
| WV-20793 | Teo*Rm5Ceo*RGeo*RAeo*RAeo*RG*ST*SG*RG*SC*ST*SG*Sm5C*SG*ST*RAeo*Rm5Ceo*Rm5Ceo*RAeo*Rm5Ceo | TCGAAGTGGCTGCGTACCAC | 47 | RRRRR SSR SSSSS S RRRRR |
| WV-20794 | m5Ceo*RTeo*Rm5Ceo*RGeo*RAeo*RA*SG*RT*SG*SG*SC*ST*SG*Sm5C*SG*RTeo*RAeo*Rm5Ceo*Rm5Ceo*RAeo | CTCGAAGTGGCTGCGTACCA | 48 | RRRRR SR SSSSS SSRRRRR |

TABLE A1-continued

| Example RHO Oligonucleotides/Compositions. | | | | |
|---|---|---|---|---|
| Oligo-nucleotide | Description | Base Sequence | SEQ ID NO | Stereochemistry/ Linkage |
| WV-20795 | m5Ceo*RTeo*Rm5Ceo*RGeo*RAeo*RA*SG*ST*RG* SG*SC*ST*SG*Sm5C*SG*RTeo*RAeo*Rm5Ceo* Rm5Ceo*RAeo | CTCGAAGTGGC TGCGTACCA | 49 | RRRRR SSR SSSSS S RRRRR |
| WV-20796 | m5Ceo*RTeo*Rm5Ceo*RGeo*RAeo*RA*SG*ST*SG* RG*SC*ST*SG*Sm5C*SG*RTeo*RAeo*Rm5Ceo* Rm5Ceo*RAeo | CTCGAAGTGGC TGCGTACCA | 50 | RRRRR SSSR SSSSS RRRRR |
| WV-20797 | Aeo*Rm5Ceo*RTeo*Rm5Ceo*RGeo*RA*SA*SG*RT* SG*SG*SC*ST*SG*Sm5C*RGeo*RTeo*RAeo*Rm5Ceo *Rm5Ceo | ACTCGAAGTGGC TGCGTACC | 51 | RRRRR SSR SSSSS S RRRRR |
| WV-20798 | Aeo*Rm5Ceo*RTeo*Rm5Ceo*RGeo*RA*SA*SG*ST* RG*SG*SC*ST*SG*Sm5C*RGeo*RTeo*RAeo*Rm5Ceo *Rm5Ceo | ACTCGAAGTGGC TGCGTACC | 52 | RRRRR SSSR SSSSS RRRRR |
| WV-20799 | Aeo*Rm5Ceo*RTeo*Rm5Ceo*RGeo*RA*SA*SG*ST* SG*RG*SC*ST*SG*Sm5C*RGeo*RTeo*RAeo*Rm5Ceo *Rm5Ceo | ACTCGAAGTGGC TGCGTACC | 53 | RRRRR SSSSRSSSS RRRRR |
| WV-20800 | Teo*RAeo*Rm5Ceo*RTeo*Rm5Ceo*RG*SA*SA*SG* RT*SG*SG*SC*ST*SG*Rm5Ceo*RGeo*RTeo*RAeo* Rm5Ceo | TACTCGAAGTGGC TGCGTAC | 54 | RRRRR SSSR SSSSS RRRRR |
| WV-20801 | Teo*RAeo*Rm5Ceo*RTeo*Rm5Ceo*RG*SA*SA*SG* ST*RG*SG*SC*ST*SG*Rm5Ceo*RGeo*RTeo*RAeo* Rm5Ceo | TACTCGAAGTGGC TGCGTAC | 55 | RRRRR SSSSRSSSS RRRRR |
| WV-20802 | Teo*RAeo*Rm5Ceo*RTeo*Rm5Ceo*RG*SA*SA*SG* ST*SG*RG*SC*ST*SG*Rm5Ceo*RGeo*RTeo*RAeo* Rm5Ceo | TACTCGAAGTGGC TGCGTAC | 56 | RRRRR SSSSS RSSS RRRRR |
| WV-20803 | Geo*RTeo*RAeo*Rm5Ceo*RTeo*Rm5C*SG*SA*SA* SG*RT*SG*SG*SC*ST*RGeo*Rm5Ceo*RGeo*RTeo* RAeo | GTACTCGAAGTGG CTGCGTA | 57 | RRRRR SSSSRSSSS RRRRR |
| WV-20804 | Geo*RTeo*RAeo*Rm5Ceo*RTeo*Rm5C*SG*SA*SA* SG*ST*RG*SG*SC*ST*RGeo*Rm5Ceo*RGeo*RTeo* RAeo | GTACTCGAAGTGG CTGCGTA | 58 | RRRRR SSSSS RSSS RRRRR |
| WV-20805 | Geo*RTeo*RAeo*Rm5Ceo*RTeo*Rm5C*SG*SA*SA* SG*ST*SG*RG*SC*ST*RGeo*Rm5Ceo*RGeo*RTeo* RAeo | GTACTCGAAGTGG CTGCGTA | 59 | RRRRR SSSSS SRSS RRRRR |
| WV-20806 | Geo*RGeo*RTeo*RAeo*Rm5Ceo*RT*Sm5C*SG*SA* SA*SG*RT*SG*SG*SC*RTeo*RGeo*Rm5Ceo*RGeo* RTeo | GGTACTCGAA GTGGCTGCGT | 60 | RRRRR SSSSS RSSS RRRRR |
| WV-20807 | Geo*RGeo*RTeo*RAeo*Rm5Ceo*RT*Sm5C*SG*SA* SA*SG*ST*RG*SG*SC*RTeo*RGeo*Rm5Ceo*RGeo* RTeo | GGTACTCGAA GTGGCTGCGT | 61 | RRRRR SSSSS SRSS RRRRR |
| WV-20808 | Geo*RGeo*RTeo*RAeo*Rm5Ceo*RT*Sm5C*SG*SA* SA*SG*ST*SG*RG*SC*RTeo*RGeo*Rm5Ceo*RGeo* RTeo | GGTACTCGAA GTGGCTGCGT | 62 | RRRRR SSSSS SSRS RRRRR |
| WV-20809 | Geo*RGeo*RTeo*RAeo*Rm5Ceo*RT*Sm5C*SG*SA* SA*SG*ST*SG*RG*SC*STeo*RGeo*Rm5Ceo*RGeo* RTeo | GGTACTCGAA GTGGCTGCGT | 63 | RRRRR SSSSSS SRSSR RRR |
| WV-20810 | Teo*Rm5CeoGeoAeoAeo*RG*RT*SG*SG*SC*ST*SG* Sm5C*SG*ST*RAeo*Rm5Ceo*Rm5Ceo*RAeo*Rm5Ceo | TCGAAGTGGC TGCGTACCAC | 64 | ROOORR SSSSS SSS RRRRR |
| WV-20811 | Teo*Rm5CeoGeoAeoAeo*RG*ST*RG*SG*SC*ST*SG* Sm5C*SG*ST*RAeo*Rm5Ceo*Rm5Ceo*RAeo*Rm5Ceo | TCGAAGTGGC TGCGTACCAC | 65 | ROOOR SR SSSSS SSRRRRR |
| WV-20812 | Teo*Rm5CeoGeoAeoAeo*RG*ST*SG*RG*SC*ST*SG* Sm5C*SG*ST*RAeo*Rm5Ceo*Rm5Ceo*RAeo*Rm5Ceo | TCGAAGTGGC TGCGTACCAC | 66 | ROOOR SSR SSSSS S RRRRR |
| WV-20813 | m5Ceo*RTeom5CeoGeoAeo*RA*SG*RT*SG*SG*SC*ST *SG*Sm5C*SG*RTeo*RAeo*Rm5Ceo*Rm5Ceo*RAeo | CTCGAAGTGGC TGCGTACCA | 67 | ROOOR SR SSSSS SSRRRRR |
| WV-20814 | m5Ceo*RTeom5CeoGeoAeo*RA*SG*ST*RG*SG*SC*ST *SG*Sm5C*SG*RTeo*RAeo*Rm5Ceo*Rm5Ceo*RAeo | CTCGAAGTGGC TGCGTACCA | 68 | ROOOR SSR SSSSS S RRRRR |

TABLE A1-continued

Example RHO Oligonucleotides/Compositions.

| Oligo-nucleotide | Description | Base Sequence | SEQ ID NO | Stereochemistry/ Linkage |
| --- | --- | --- | --- | --- |
| WV-20815 | m5Ceo*RTeom5CeoGeoAeo*RA*SG*ST*SG*RG*SC*ST *SG*Sm5C*SG*RTeo*RAeo*Rm5Ceo*Rm5Ceo*RAeo | CTCGAAGTGGC TGCGTACCA | 69 | ROOOR SSSR SSSSS RRRRR |
| WV-20816 | Aeo*Rm5CeoTeom5CeoGeo*RA*SA*SG*RT*SG*SG*SC *ST*SG*Sm5C*RGeo*RTeo*RAeo*Rm5Ceo*Rm5Ceo | ACTCGAAGTGGC TGCGTACC | 70 | ROOOR SSR SSSSS S RRRRR |
| WV-20817 | Aeo*Rm5CeoTeom5CeoGeo*RA*SA*SG*ST*RG*SG*SC *ST*SG*Sm5C*RGeo*RTeo*RAeo*Rm5Ceo*Rm5Ceo | ACTCGAAGTGGC TGCGTACC | 71 | ROOOR SSSR SSSSS RRRRR |
| WV-20818 | Aeo*Rm5CeoTeom5CeoGeo*RA*SA*SG*ST*SG*RG*SC *ST*SG*Sm5C*RGeo*RTeo*RAeo*Rm5Ceo*Rm5Ceo | ACTCGAAGTGGC TGCGTACC | 72 | ROOOR SSSSRSSSS RRRRR |
| WV-20819 | Teo*RAeom5CeoTeom5Ceo*RG*SA*SA*SG*RT*SG*SG *SC*ST*SG*Rm5Ceo*RGeo*RTeo*RAeo*Rm5Ceo | TACTCGAAGTGGC TGCGTAC | 73 | ROOOR SSSR SSSSS RRRRR |
| WV-20820 | Teo*RAeom5CeoTeom5Ceo*RG*SA*SA*SG*ST*RG*SG *SC*ST*SG*Rm5Ceo*RGeo*RTeo*RAeo*Rm5Ceo | TACTCGAAGTGGC TGCGTAC | 74 | ROOOR SSSSRSSSS RRRRR |
| WV-20821 | Teo*RAeom5CeoTeom5Ceo*RG*SA*SA*SG*ST*SG*RG *SC*ST*SG*Rm5Ceo*RGeo*RTeo*RAeo*Rm5Ceo | TACTCGAAGTGGC TGCGTAC | 75 | ROOOR SSSSS RSSS RRRRR |
| WV-20822 | Geo*RTeoAeom5CeoTeo*Rm5C*SG*SA*SA*SG*RT*SG *SG*SC*ST*RGeo*Rm5Ceo*RGeo*RTeo*RAeo | GTACTCGAAGTGG CTGCGTA | 76 | ROOOR SSSSRSSSS RRRRR |
| WV-20823 | Geo*RTeoAeom5CeoTeo*Rm5C*SG*SA*SA*SG*ST*RG *SG*SC*ST*RGeo*Rm5Ceo*RGeo*RTeo*RAeo | GTACTCGAAGTGG CTGCGTA | 77 | ROOOR SSSSS RSSS RRRRR |
| WV-20824 | Geo*RTeoAeom5CeoTeo*Rm5C*SG*SA*SA*SG*ST*SG *RG*SC*ST*RGeo*Rm5Ceo*RGeo*RTeo*RAeo | GTACTCGAAGTGG CTGCGTA | 78 | ROOOR SSSSS SRSS RRRRR |
| WV-20825 | Geo*RGeoTeoAeom5Ceo*RT*Sm5C*SG*SA*SA*SG*RT *SG*SG*SC*RTeo*RGeo*Rm5Ceo*RGeo*RTeo | GGTACTCGAA GTGGCTGCGT | 79 | ROOOR SSSSS RSSS RRRRR |
| WV-20826 | Geo*RGeoTeoAeom5Ceo*RT*Sm5C*SG*SA*SA*SG*ST *RG*SG*SC*RTeo*RGeo*Rm5Ceo*RGeo*RTeo | GGTACTCGAA GTGGCTGCGT | 80 | ROOOR SSSSS SRSS RRRRR |
| WV-20827 | Geo*RGeoTeoAeom5Ceo*RT*Sm5C*SG*SA*SA*SG*ST *SG*RG*SC*RTeo*RGeo*Rm5Ceo*RGeo*RTeo | GGTACTCGAA GTGGCTGCGT | 81 | ROOOR SSSSS SSRS RRRRR |
| WV-20828 | Geo*RGeoTeoAeom5Ceo*RT*Sm5C*SG*SA*SA*SG*ST *SG*RG*SC*STeo*RGeo*Rm5Ceo*RGeo*RTeo | GGTACTCGAA GTGGCTGCGT | 82 | ROOOR SSSSS S SRSSR RRR |
| WV-20829 | Teo*Rm5CeoGeoAeoAeo*RG*RT*SG*SG*SC*ST*SG* Sm5C*SG*ST*RAeom5Ceom5CeoAeo*Rm5Ceo | TCGAAGTGGC TGCGTACCAC | 83 | ROOOR R SSSSS SSSRO OOR |
| WV-20830 | Teo*Rm5CeoGeoAeoAeo*RG*ST*RG*SG*SC*ST*SG* Sm5C*SG*ST*RAeom5Ceom5CeoAeo*Rm5Ceo | TCGAAGTGGC TGCGTACCAC | 84 | ROOOR SR SSSSS SSROO OR |
| WV-20831 | Teo*Rm5CeoGeoAeoAeo*RG*ST*SG*RG*SC*ST*SG* Sm5C*SG*ST*RAeom5Ceom5CeoAeo*Rm5Ceo | TCGAAGTGGC TGCGTACCAC | 85 | ROOOR SSR SSSSS SROOOR |
| WV-20832 | m5Ceo*RTeom5CeoGeoAeo*RA*SG*RT*SG*SG*SC*ST *SG*Sm5C*SG*RTeoAeom5Ceom5Ceo*RAeo | CTCGAAGTGGC TGCGTACCA | 86 | ROOOR SR SSSSS SSROO OR |
| WV-20833 | m5Ceo*RTeom5CeoGeoAeo*RA*SG*ST*RG*SG*SC*ST *SG*Sm5C*SG*RTeoAeom5Ceom5Ceo*RAeo | CTCGAAGTGGC TGCGTACCA | 87 | ROOOR SSR SSSSS SROOOR |
| WV-20834 | m5Ceo*RTeom5CeoGeoAeo*RA*SG*ST*SG*RG*SC*ST *SG*Sm5C*SG*RTeoAeom5Ceom5Ceo*RAeo | CTCGAAGTGGC TGCGTACCA | 88 | ROOOR SSSR SSSSS ROOOR |
| WV-20835 | Aeo*Rm5CeoTeom5CeoGeo*RA*SA*SG*RT*SG*SG*SC *ST*SG*Sm5C*RGeoTeoAeom5Ceo*Rm5Ceo | ACTCGAAGTGGC TGCGTACC | 89 | ROOOR SSR SSSSS SROOOR |
| WV-20836 | Aeo*Rm5CeoTeom5CeoGeo*RA*SA*SG*ST*RG*SG*SC *ST*SG*Sm5C*RGeoTeoAeom5Ceo*Rm5Ceo | ACTCGAAGTGGC TGCGTACC | 90 | ROOOR SSSR SSSSS ROOOR |
| WV-20837 | Aeo*Rm5CeoTeom5CeoGeo*RA*SA*SG*ST*SG*RG*SC *ST*SG*Sm5C*RGeoTeoAeom5Ceo*Rm5Ceo | ACTCGAAGTGGC TGCGTACC | 91 | ROOOR SSSSRS SSSRO OOR |
| WV-20838 | Teo*RAeom5CeoTeom5Ceo*RG*SA*SA*SG*RT*SG*SG *SC*ST*SG*Rm5CeoGeoTeoAeo*Rm5Ceo | TACTCGAAGTGGC TGCGTAC | 92 | ROOOR SSSR SSSSS ROOOR |

TABLE A1-continued

Example RHO Oligonucleotides/Compositions.

| Oligo-nucleotide | Description | Base Sequence | SEQ ID NO | Stereochemistry/ Linkage |
|---|---|---|---|---|
| WV-20839 | Teo*RAeom5CeoTeom5Ceo*RG*SA*SA*SG*ST*RG*SG *SC*ST*SG*Rm5CeoGeoTeoAeo*Rm5Ceo | TACTCGAAGTGGC TGCGTAC | 93 | ROOOR SSSSRS SSSRO OOR |
| WV-20840 | Teo*RAeom5CeoTeom5Ceo*RG*SA*SA*SG*ST*SG*RG *SC*ST*SG*Rm5CeoGeoTeoAeo*Rm5Ceo | TACTCGAAGTGGC TGCGTAC | 94 | ROOOR SSSSS RSSSR OOOR |
| WV-20841 | Geo*RTeoAeom5CeoTeo*Rm5C*SG*SA*SA*SG*RT*SG *SG*SC*ST*RGeom5CeoGeoTeo*RAeo | GTACTCGAAGTGG CTGCGTA | 95 | ROOOR SSSSRS SSSRO OOR |
| WV-20842 | Geo*RTeoAeom5CeoTeo*Rm5C*SG*SA*SA*SG*ST*RG *SG*SC*ST*RGeom5CeoGeoTeo*RAeo | GTACTCGAAGTGG CTGCGTA | 96 | ROOOR SSSSS RSSSR OOOR |
| WV-20843 | Geo*RTeoAeom5CeoTeo*Rm5C*SG*SA*SA*SG*ST*SG *RG*SC*ST*RGeom5CeoGeoTeo*RAeo | GTACTCGAAGTGG CTGCGTA | 97 | ROOOR SSSSS SRSSR OOOR |
| WV-20844 | Geo*RGeoTeoAeom5Ceo*RT*Sm5C*SG*SA*SA*SG*RT *SG*SG*SC*RTeoGeom5CeoGeo*RTeo | GGTACTCGAA GTGGCTGCGT | 98 | ROOOR SSSSS RSSSR OOOR |
| WV-20845 | Geo*RGeoTeoAeom5Ceo*RT*Sm5C*SG*SA*SA*SG*ST *RG*SG*SC*RTeoGeom5CeoGeo*RTeo | GGTACTCGAA GTGGCTGCGT | 99 | ROOOR SSSSS SRSSR OOOR |
| WV-20846 | Geo*RGeoTeoAeom5Ceo*RT*Sm5C*SG*SA*SA*SG*ST *SG*RG*SC*RTeoGeom5CeoGeo*RTeo | GGTACTCGAA GTGGCTGCGT | 100 | ROOOR SSSSS SSRSROOOR |
| WV-20847 | Geo*RGeoTeoAeom5Ceo*RT*Sm5C*SG*SA*SA*SG*ST *SG*RG*SC*STeoGeom5CeoGeo*RTeo | GGTACTCGAA GTGGCTGCGT | 101 | ROOOR SSSSS SSRSSOOOR |
| WV-20848 | Teo*Rm5CeoGeoAeoAeo*RG*RT*SG*SG*SC*ST*SG* Sm5C*SG*ST*SmA*SmC*SmC*SmA*SmC | TCGAAGTGGC TGCGTACCAC | 102 | ROOORRSSSSS SSSSS SSS |
| WV-20849 | Teo*Rm5CeoGeoAeoAeo*RG*ST*RG*SG*SC*ST*SG* Sm5C*SG*ST*SmA*SmC*SmC*SmA*SmC | TCGAAGTGGC TGCGTACCAC | 103 | ROOOR SR SSSSS SSSSS SS |
| WV-20850 | Teo*Rm5CeoGeoAeoAeo*RG*ST*SG*RG*SC*ST*SG* Sm5C*SG*ST*SmA*SmC*SmC*SmA*SmC | TCGAAGTGGC TGCGTACCAC | 104 | ROOOR SSR SSSSS SSSSSS |
| WV-20851 | m5Ceo*RTeom5CeoGeoAeo*RA*SG*RT*SG*SG*SC*ST *SG*Sm5C*SG*SmU*SmA*SmC*SmC*SmA | CTCGAAGTGGC TGCGUACCA | 105 | ROOOR SR SSSSS SSSSS SS |
| WV-20852 | m5Ceo*RTeom5CeoGeoAeo*RA*SG*ST*RG*SG*SC*ST *SG*Sm5C*SG*SmU*SmA*SmC*SmC*SmA | CTCGAAGTGGC TGCGUACCA | 106 | ROOOR SSR SSSSS SSSSSS |
| WV-20853 | m5Ceo*RTeom5CeoGeoAeo*RA*SG*ST*SG*RG*SC*ST *SG*Sm5C*SG*SmU*SmA*SmC*SmC*SmA | CTCGAAGTGGC TGCGUACCA | 107 | ROOOR SSSR SSSSS SSSSS |
| WV-20854 | Aeo*Rm5CeoTeom5CeoGeo*RA*SA*SG*RT*SG*SG*SC *ST*SG*Sm5C*SmG*SmU*SmA*SmC*SmC | ACTCGAAGTGGC TGCGUACC | 108 | ROOOR SSR SSSSS SSSSSS |
| WV-20855 | Aeo*Rm5CeoTeom5CeoGeo*RA*SA*SG*ST*RG*SG*SC *ST*SG*Sm5C*SmG*SmU*SmA*SmC*SmC | ACTCGAAGTGGC TGCGUACC | 109 | ROOOR SSSR SSSSS SSSSS |
| WV-20856 | Aeo*Rm5CeoTeom5CeoGeo*RA*SA*SG*ST*SG*RG*SC *ST*SG*Sm5C*SmG*SmU*SmA*SmC*SmC | ACTCGAAGTGGC TGCGUACC | 110 | ROOOR SSSSR SSSSS SSSS |
| WV-20857 | Teo*RAeom5CeoTeom5Ceo*RG*SA*SA*SG*RT*SG*SG *SC*ST*SG*SmC*SmG*SmU*SmA*SmC | TACTCGAAGTGGC TGCGUAC | ill | ROOOR SSSR SSSSS SSSSS |
| WV-20858 | Teo*RAeom5CeoTeom5Ceo*RG*SA*SA*SG*ST*RG*SG *SC*ST*SG*SmC*SmG*SmU*SmA*SmC | TACTCGAAGTGGC TGCGUAC | 112 | ROOOR SSSSR SSSSS SSSS |
| WV-20859 | Teo*RAeom5CeoTeom5Ceo*RG*SA*SA*SG*ST*SG*RG *SC*ST*SG*SmC*SmG*SmU*SmA*SmC | TACTCGAAGTGGC TGCGUAC | 113 | ROOOR SSSSS R SSSSS SSS |
| WV-20860 | Geo*RTeoAeom5CeoTeo*Rm5C*SG*SA*SA*SG*RT*SG *SG*SC*ST*SmG*SmC*SmG*SmU*SmA | GTACTCGAAGTGG CTGCGUA | 114 | ROOOR SSSSR SSSSS SSSS |
| WV-20861 | Geo*RTeoAeom5CeoTeo*Rm5C*SG*SA*SA*SG*ST*RG *SG*SC*ST*SmG*SmC*SmG*SmU*SmA | GTACTCGAAGTGG CTGCGUA | 115 | ROOOR SSSSS R SSSSS SSS |
| WV-20862 | Geo*RTeoAeom5CeoTeo*Rm5C*SG*SA*SA*SG*ST*SG *RG*SC*ST*SmG*SmC*SmG*SmU*SmA | GTACTCGAAGTGG CTGCGUA | 116 | ROOOR SSSSS SR SSSSS SS |
| WV-20863 | Geo*RGeoTeoAeom5Ceo*RT*Sm5C*SG*SA*SA*SG*RT *SG*SG*SC*SmU*SmG*SmC*SmG*SmU | GGTACTCGAA GTGGCUGCGU | 117 | ROOOR SSSSS R SSSSS SSS |

TABLE A1-continued

Example RHO Oligonucleotides/Compositions.

| Oligo-nucleotide | Description | Base Sequence | SEQ ID NO | Stereochemistry/ Linkage |
|---|---|---|---|---|
| WV-20864 | Geo*RGeoTeoAeom5Ceo*RT*Sm5C*SG*SA*SA*SG*ST *RG*SG*SC*SmU*SmG*SmC*SmG*SmU | GGTACTCGAA GTGGCUGCGU | 118 | ROOOR SSSSS SR SSSSS SS |
| WV-20865 | Geo*RGeoTeoAeom5Ceo*RT*Sm5C*SG*SA*SA*SG*ST *SG*RG*SC*SmU*SmG*SmC*SmG*SmU | GGTACTCGAA GTGGCUGCGU | 119 | ROOOR SSSSS SSRSSSSS S |
| WV-20866 | Geo*Geo*Teo*Aeo*m5Ceo*t*C*G*A*A*G*T*G* G*C*Teo*Geo*m5Ceo*Geo*Teo | GGTACTCGAA GTGGCTGCGT | 120 | XXXXX XXXXX XXXXX XXXX |
| WV-20867 | Geo*GeoTeoAeom5Ceo*T*m5C*G*A*A*G*T*G*G* C*Teo*Geo*m5Ceo*Geo*Teo | GGTACTCGAA GTGGCTGCGT | 121 | XOOO XXXXX XXXXX XXXXX |
| WV-20868 | Geo*GeoTeoAeom5Ceo*T*m5C*G*A*A*G*T*G*G* C*TeoGeom5CeoGeo*Teo | GGTACTCGAA GTGGCTGCGT | 122 | XOOO XXXXX XXXXX XOOOX |
| WV-20869 | Geo*GeoTeoAeom5Ceo*T*m5C*G*A*A*G*T*G*G* C*mU*mG*mC*mG*mU | GGTACTCGAA GTGGCUGCGU | 123 | XOOO XXXXX XXXXX XXXXX |
| WV-20870 | lT*lA*m5lC*t*C*G*A*A*G*T*G*G*C*lT*lG* m5lC | TACTCGAAGTGGC TGC | 124 | XXXXX XXXXX XXXXX |
| WV-21106 | rGrUrGrGrUrArCrGrCrArGrCrCrArCrUrUrCrGrArGrUrAr CrC | GUGGUACGCA GCCACUUCGA GUACC | 125 | OOOOO OOOOO OOOOO OOOOO OOOO |
| WV-21107 | rGrUrGrGrUrArCrGrCrArGrCrCrCrCrUrUrCrGrArGrUrAr CrC | GUGGUACGCA GCCCCUUCGA GUACC | 126 | OOOOO OOOOO OOOOO OOOOO OOOO |
| WV-21503 | Geo*SGeoTeoAeom5Ceo*RT*Sm5C*SG*SA*SA*SG*ST *SG*RG*SC*STeoGeom5CeoGeo*STeo | GGTACTCGAA GTGGCTGCGT | 127 | SOOOR SSSSS SSRSSOOOS |
| WV-21504 | Geo*SGeoTeoAeom5Ceo*RT*Sm5C*SG*SA*SA*SG*ST *SG*RG*SC*SmU*SmG*SmC*SmG*SmU | GGTACTCGAA GTGGCUGCGU | 128 | SOOOR SSSSS SSRSSSSS S |
| WV-21505 | Geo*SGeoTeoAeom5Ceo*RT*Sm5C*SG*SA*SA*SG*ST *SG*RG*SC*SmU*SmG*Sm5mC*SmG*SmU | GGTACTCGAA GTGGCUGCGU | 129 | SOOOR SSSSS SSRSSSSS S |
| WV-23415 | lT*lA*m5lC*T*m5C*G*A*A*G*T*G*G*$_m$5C*lT* lG*m5lC | TACTCGAAGTGGC TGC | 130 | XXXXX XXXXX XXXXX |
| WV-23651 | Geo*SGeoTeoAeom5Ceo*RT*Rm5C*SG*SA*SA*SG*ST *SG*SG*Sm5C*STeoGeom5CeoGeo*STeo | GGTACTCGAA GTGGCTGCGT | 131 | SOOOR R SSSSS S SSSOO OS |
| WV-23652 | Geo*SGeoTeoAeom5Ceo*RT*Sm5C*RG*SA*SA*SG*ST *SG*SG*Sm5C*STeoGeom5CeoGeo*STeo | GGTACTCGAA GTGGCTGCGT | 132 | SOOOR SR SSSSS SSSOO OS |
| WV-23653 | Geo*SGeoTeoAeom5Ceo*RT*Sm5C*SG*RA*SA*SG*ST *SG*SG*Sm5C*STeoGeom5CeoGeo*STeo | GGTACTCGAA GTGGCTGCGT | 133 | SOOOR SSR SSSSS SSOOOS |
| WV-23654 | Geo*SGeoTeoAeom5Ceo*RT*Sm5C*SG*SA*RA*SG*ST *SG*SG*Sm5C*STeoGeom5CeoGeo*STeo | GGTACTCGAA GTGGCTGCGT | 134 | SOOOR SSSR SSSSS SOOOS |
| WV-23655 | Geo*SGeoTeoAeom5Ceo*RT*Sm5C*SG*SA*SA*RG*ST *SG*SG*Sm5C*STeoGeom5CeoGeo*STeo | GGTACTCGAA GTGGCTGCGT | 135 | SOOOR SSSSR SSSSS OOOS |
| WV-23656 | Geo*SGeoTeoAeom5Ceo*RT*Sm5C*SG*SA*SA*SG*RT *SG*SG*Sm5C*STeoGeom5CeoGeo*STeo | GGTACTCGAA GTGGCTGCGT | 136 | SOOOR SSSSS RS SSSOO OS |
| WV-23657 | Geo*SGeoTeoAeom5Ceo*RT*Sm5C*SG*SA*SA*SG*ST *RG*SG*Sm5C*STeoGeom5CeoGeo*STeo | GGTACTCGAA GTGGCTGCGT | 137 | SOOOR SSSSS SR SSSOO OS |
| WV-23658 | Geo*SGeoTeoAeom5Ceo*RT*Sm5C*SG*SA*SA*SG*ST *SG*RG*Sm5C*STeoGeom5CeoGeo*STeo | GGTACTCGAA GTGGCTGCGT | 138 | SOOOR SSSSS SSRSSOOOS |
| WV-23659 | Geo*SGeoTeoAeom5Ceo*RT*Sm5C*SG*SA*SA*SG*ST *SG*SG*Rm5C*STeoGeom5CeoGeo*STeo | GGTACTCGAA GTGGCTGCGT | 139 | SOOOR SSSSS SSSRSOOOS |
| WV-23660 | Geo*SGeoTeoAeom5Ceo*RT*Sm5C*SG*SA*SA*SG*ST *SG*SG*Sm5C*RTeoGeom5CeoGeo*STeo | GGTACTCGAA GTGGCTGCGT | 140 | SOOOR SSSSS S SSSRO OOS |
| WV-23661 | Geo*SGeoTeoAeom5Ceo*RT*Rm5C*SG*SA*SA*SG*ST *SG*SG*Sm5C*SmU*SmG*Sm5mC*SmG*SmU | GGTACTCGAA GTGGCUGCGU | 141 | SOOOR R SSSSS SSSSS SSS |
| WV-23662 | Geo*SGeoTeoAeom5Ceo*RT*Sm5C*RG*SA*SA*SG*ST *SG*SG*Sm5C*SmU*SmG*Sm5mC*SmG*SmU | GGTACTCGAA GTGGCUGCGU | 142 | SOOOR SR SSSSS SSSSS SS |

TABLE A1-continued

Example RHO Oligonucleotides/Compositions.

| Oligo-nucleotide | Description | Base Sequence | SEQ ID NO | Stereochemistry/ Linkage |
|---|---|---|---|---|
| WV-23663 | Geo*SGeoTeoAeom5Ceo*RT*Sm5C*SG*RA*SA*SG*ST *SG*SG*Sm5C*SmU*SmG*Sm5mC*SmG*SmU | GGTACTCGAA GTGGCUGCGU | 143 | SOOOR SSR SSSSS SSSSS S |
| WV-23664 | Geo*SGeoTeoAeom5Ceo*RT*Sm5C*SG*SA*RA*SG*ST *SG*SG*Sm5C*SmU*SmG*Sm5mC*SmG*SmU | GGTACTCGAA GTGGCUGCGU | 144 | SOOOR SSSR SSSSS SSSSS |
| WV-23665 | Geo*SGeoTeoAeom5Ceo*RT*Sm5C*SG*SA*SA*RG*ST *SG*SG*Sm5C*SmU*SmG*Sm5mC*SmG*SmU | GGTACTCGAA GTGGCUGCGU | 145 | SOOOR SSSSR SSSSS SSSS |
| WV-23666 | Geo*SGeoTeoAeom5Ceo*RT*Sm5C*SG*SA*SA*SG*RT *SG*SG*Sm5C*SmU*SmG*Sm5mC*SmG*SmU | GGTACTCGAA GTGGCUGCGU | 146 | SOOOR SSSSS R SSSSS SSS |
| WV-23667 | Geo*SGeoTeoAeom5Ceo*RT*Sm5C*SG*SA*SA*SG*ST *RG*SG*Sm5C*SmU*SmG*Sm5mC*SmG*SmU | GGTACTCGAA GTGGCUGCGU | 147 | SOOOR SSSSS SR SSSSS SS |
| WV-23668 | Geo*SGeoTeoAeom5Ceo*RT*Sm5C*SG*SA*SA*SG*ST *SG*RG*Sm5C*SmU*SmG*Sm5mC*SmG*SmU | GGTACTCGAA GTGGCUGCGU | 148 | SOOOR SSSSS SSRSSSSS S |
| WV-23669 | Geo*SGeoTeoAeom5Ceo*RT*Sm5C*SG*SA*SA*SG*ST *SG*SG*Rm5C*SmU*SmG*Sm5mC*SmG*SmU | GGTACTCGAA GTGGCUGCGU | 149 | SOOOR SSSSS SSSRSSSSS |
| WV-23670 | Geo*SGeoTeoAeom5Ceo*RT*Sm5C*SG*SA*SA*SG*ST *SG*SG*Sm5C*RmU*SmG*Sm5mC*SmG*SmU | GGTACTCGAA GTGGCUGCGU | 150 | SOOOR SSSSS SSSSRSSSS |
| WV-23671 | Geo*SGeoTeoAeom5Ceo*RT*Rm5C*SG*SA*SA*SG*ST *SG*RG*Sm5C*STeoGeom5CeoGeo*STeo | GGTACTCGAA GTGGCTGCGT | 151 | SOOOR R SSSSS SRSSOOOS |
| WV-23672 | Geo*SGeoTeoAeom5Ceo*RT*Sm5C*RG*SA*SA*SG*ST *SG*RG*Sm5C*STeoGeom5CeoGeo*STeo | GGTACTCGAA GTGGCTGCGT | 152 | SOOOR SR SSSSS RSSOOOS |
| WV-23673 | Geo*SGeoTeoAeom5Ceo*RT*Sm5C*SG*RA*SA*SG*ST *SG*RG*Sm5C*STeoGeom5CeoGeo*STeo | GGTACTCGAA GTGGCTGCGT | 153 | SOOOR SSRSSSSRSSOOOS |
| WV-23674 | Geo*SGeoTeoAeom5Ceo*RT*Sm5C*SG*SA*RA*SG*ST *SG*RG*Sm5C*STeoGeom5CeoGeo*STeo | GGTACTCGAA GTGGCTGCGT | 154 | SOOOR SSS RSSSRSSOOOS |
| WV-23675 | Geo*SGeoTeoAeom5Ceo*RT*Sm5C*SG*SA*SA*RG*ST *SG*RG*Sm5C*STeoGeom5CeoGeo*STeo | GGTACTCGAA GTGGCTGCGT | 155 | SOOORSSS SRSSR SSOOOS |
| WV-23676 | Geo*SGeoTeoAeom5Ceo*RT*Sm5C*SG*SA*SA*SG*RT *SG*RG*Sm5C*STeoGeom5CeoGeo*STeo | GGTACTCGAA GTGGCTGCGT | 156 | SOOOR SSSSS RSRSSOOOS |
| WV-23677 | Geo*SGeoTeoAeom5Ceo*RT*Sm5C*SG*SA*SA*SG*ST *RG*RG*Sm5C*STeoGeom5CeoGeo*STeo | GGTACTCGAA GTGGCTGCGT | 157 | SOOOR SSSSS SRRSSOOOS |
| WV-23678 | Geo*SGeoTeoAeom5Ceo*RT*Sm5C*SG*SA*SA*SG*ST *SG*RG*Rm5C*STeoGeom5CeoGeo*STeo | GGTACTCGAA GTGGCTGCGT | 158 | SOOOR SSSSS SSRRSOOOS |
| WV-23679 | Geo*SGeoTeoAeom5Ceo*RT*Sm5C*SG*SA*SA*SG*ST *SG*RG*Sm5C*RTeoGeom5CeoGeo*STeo | GGTACTCGAA GTGGCTGCGT | 159 | SOOOR SSSSS SSRSROOOS |
| WV-23680 | Geo*SGeoTeoAeom5Ceo*RT*Rm5C*SG*SA*SA*SG*ST *SG*RG*Sm5C*SmU*SmG*Sm5mC*SmG*SmU | GGTACTCGAA GTGGCUGCGU | 160 | SOOOR R SSSSS SR SSSSS S |
| WV-23681 | Geo*SGeoTeoAeom5Ceo*RT*Sm5C*RG*SA*SA*SG*ST *SG*RG*Sm5C*SmU*SmG*Sm5mC*SmG*SmU | GGTACTCGAA GTGGCUGCGU | 161 | SOOOR SR SSSSS RSSSSS S |
| WV-23682 | Geo*SGeoTeoAeom5Ceo*RT*Sm5C*SG*RA*SA*SG*ST *SG*RG*Sm5C*SmU*SmG*Sm5mC*SmG*SmU | GGTACTCGAA GTGGCUGCGU | 162 | SOOOR SSRSSSSR SSSSS S |
| WV-23683 | Geo*SGeoTeoAeom5Ceo*RT*Sm5C*SG*SA*RA*SG*ST *SG*RG*Sm5C*SmU*SmG*Sm5mC*SmG*SmU | GGTACTCGAA GTGGCUGCGU | 163 | SOOORSSS RSSSR SSSSS S |
| WV-23684 | Geo*SGeoTeoAeom5Ceo*RT*Sm5C*SG*SA*SA*RG*ST *SG*RG*Sm5C*SmU*SmG*Sm5mC*SmG*SmU | GGTACTCGAA GTGGCUGCGU | 164 | SOOORSSS SRSSR SSSSS S |
| WV-23685 | Geo*SGeoTeoAeom5Ceo*RT*Sm5C*SG*SA*SA*SG*RT *SG*RG*Sm5C*SmU*SmG*Sm5mC*SmG*SmU | GGTACTCGAA GTGGCUGCGU | 165 | SOOOR SSSSS RSR SSSSS S |
| WV-23686 | Geo*SGeoTeoAeom5Ceo*RT*Sm5C*SG*SA*SA*SG*ST *RG*RG*Sm5C*SmU*SmG*Sm5mC*SmG*SmU | GGTACTCGAA GTGGCUGCGU | 166 | SOOOR SSSSS SRR SSSSS S |
| WV-23687 | Geo*SGeoTeoAeom5Ceo*RT*Sm5C*SG*SA*SA*SG*ST *SG*RG*Rm5C*SmU*SmG*Sm5mC*SmG*SmU | GGTACTCGAA GTGGCUGCGU | 167 | SOOOR SSSSS SSRR SSSSS |

TABLE A1-continued

| Example RHO Oligonucleotides/Compositions. | | | | |
|---|---|---|---|---|
| Oligo-nucleotide | Description | Base Sequence | SEQ ID NO | Stereochemistry/ Linkage |
| WV-23688 | Geo*SGeoTeoAeom5Ceo*RT*Sm5C*SG*SA*SA*SG*ST *SG*RG*Sm5C*RmU*SmG*Sm5mC*SmG*SmU | GGTACTCGAA GTGGCUGCGU | 168 | SOOOR SSSSS SSRSRSSSS |
| WV-24004 | lG*lG*lT*A*m5C*T*m5C*G*A*A*G*T*G*lG* m5lC*lT | GGTACTCGAA GTGGCT | 169 | XXXXX XXXXX XXXXX |
| WV-24174 | Teo*Sm5CeoGeoAeoAeo*RG*RG*SG*SG*SC*ST*SC* Sm5C*SG*SC*SmA*SmC*SmC*SmA*SmC | TCGAAGGGGC TCCGCACCAC | 170 | SOOOR R SSSSS SSSSS SSS |
| WV-24175 | Teo*Sm5CeoGeoAeoAeo*RG*SG*RG*SG*SC*ST*SC* Sm5C*SG*SC*SmA*SmC*SmC*SmA*SmC | TCGAAGGGGC TCCGCACCAC | 171 | SOOOR SR SSSSS SSSSS SS |
| WV-24176 | Teo*Sm5CeoGeoAeoAeo*RG*SG*SG*RG*SC*ST*SC* Sm5C*SG*SC*SmA*SmC*SmC*SmA*SmC | TCGAAGGGGC TCCGCACCAC | 172 | SOOOR SSR SSSSS SSSSS S |
| WV-24177 | Teo*Sm5CeoGeoAeoAeo*RG*SG*SG*SG*RC*ST*SC* Sm5C*SG*SC*SmA*SmC*SmC*SmA*SmC | TCGAAGGGGC TCCGCACCAC | 173 | SOOORSSSR SSSSS SSSSS |
| WV-24178 | Teo*Sm5CeoGeoAeoAeo*RG*SG*SG*SG*SC*RT*SC* Sm5C*SG*SC*SmA*SmC*SmC*SmA*SmC | TCGAAGGGGC TCCGCACCAC | 174 | SOOORSSSSR SSSSS SSSS |
| WV-24179 | Teo*Sm5CeoGeoAeoAeo*RG*SG*SG*SG*SC*ST*RC* Sm5C*SG*SC*SmA*SmC*SmC*SmA*SmC | TCGAAGGGGC TCCGCACCAC | 175 | SOOOR SSSSS R SSSSS SSS |
| WV-24180 | Teo*Sm5CeoGeoAeoAeo*RG*SG*SG*SG*SC*ST*SC* Rm5C*SG*SC*SmA*SmC*SmC*SmA*SmC | TCGAAGGGGC TCCGCACCAC | 176 | SOOOR SSSSS SR SSSSS SS |
| WV-24181 | Teo*Sm5CeoGeoAeoAeo*RG*SG*SG*SG*SC*ST*SC* Sm5C*RG*SC*SmA*SmC*SmC*SmA*SmC | TCGAAGGGGC TCCGCACCAC | 177 | SOOOR SSSSS SSRSSSSS S |
| WV-24182 | Teo*Sm5CeoGeoAeoAeo*RG*SG*SG*SG*SC*ST*SC* Sm5C*SG*RC*SmA*SmC*SmC*SmA*SmC | TCGAAGGGGC TCCGCACCAC | 178 | SOOOR SSSSS SSSRSSSSS |
| WV-24183 | Teo*Sm5CeoGeoAeoAeo*RG*SG*SG*SG*SC*ST*SC* Sm5C*SG*SC*RmA*SmC*SmC*SmA*SmC | TCGAAGGGGC TCCGCACCAC | 179 | SOOOR SSSSS SSSSRSSSS |
| WV-24184 | m5Ceo*STeom5CeoGeoAeo*RA*RG*SG*SG*SG*SC*ST *SC*Sm5C*SG*SmC*SmA*SmC*SmC*SmA | CTCGAAGGGG CTCCGCACCA | 180 | SOOOR R SSSSS SSSSS SSS |
| WV-24185 | m5Ceo*STeom5CeoGeoAeo*RA*SG*RG*SG*SG*SC*ST *SC*Sm5C*SG*SmC*SmA*SmC*SmC*SmA | CTCGAAGGGG CTCCGCACCA | 181 | SOOOR SR SSSSS SSSSS SS |
| WV-24186 | m5Ceo*STeom5CeoGeoAeo*RA*SG*SG*RG*SG*SC*ST *SC*Sm5C*SG*SmC*SmA*SmC*SmC*SmA | CTCGAAGGGG CTCCGCACCA | 182 | SOOOR SSR SSSSS SSSSS S |
| WV-24187 | m5Ceo*STeom5CeoGeoAeo*RA*SG*SG*SG*RG*SC*ST *SC*Sm5C*SG*SmC*SmA*SmC*SmC*SmA | CTCGAAGGGG CTCCGCACCA | 183 | SOOORSSSR SSSSS SSSSS |
| WV-24188 | m5Ceo*STeom5CeoGeoAeo*RA*SG*SG*SG*SG*RC*ST *SC*Sm5C*SG*SmC*SmA*SmC*SmC*SmA | CTCGAAGGGG CTCCGCACCA | 184 | SOOORSSSSR SSSSS SSSS |
| WV-24189 | m5Ceo*STeom5CeoGeoAeo*RA*SG*SG*SG*SG*SC*RT *SC*Sm5C*SG*SmC*SmA*SmC*SmC*SmA | CTCGAAGGGG CTCCGCACCA | 185 | SOOOR SSSSS R SSSSS SSS |
| WV-24190 | m5Ceo*STeom5CeoGeoAeo*RA*SG*SG*SG*SG*SC*ST *RC*Sm5C*SG*SmC*SmA*SmC*SmC*SmA | CTCGAAGGGG CTCCGCACCA | 186 | SOOOR SSSSS SR SSSSS SS |
| WV-24191 | m5Ceo*STeom5CeoGeoAeo*RA*SG*SG*SG*SG*SC*ST *SC*Rm5C*SG*SmC*SmA*SmC*SmC*SmA | CTCGAAGGGG CTCCGCACCA | 187 | SOOOR SSSSS SSRSSSSS S |
| WV-24192 | m5Ceo*STeom5CeoGeoAeo*RA*SG*SG*SG*SG*SC*ST *SC*Sm5C*RG*SmC*SmA*SmC*SmC*SmA | CTCGAAGGGG CTCCGCACCA | 188 | SOOOR SSSSS SSSRSSSSS |
| WV-24193 | m5Ceo*STeom5CeoGeoAeo*RA*SG*SG*SG*SG*SC*ST *SC*Sm5C*SG*RmC*SmA*SmC*SmC*SmA | CTCGAAGGGG CTCCGCACCA | 189 | SOOOR SSSSS SSSSRSSSS |
| WV-24194 | Geo*Sm5CeoTeom5CeoGeo*RA*RA*SG*SG*SG*SG*SC *ST*SC*Sm5C*SmG*SmC*SmA*SmC*SmC | GCTCGAAGGG GCTCCGCACC | 190 | SOOOR R SSSSS SSSSS SSS |
| WV-24195 | Geo*Sm5CeoTeom5CeoGeo*RA*SA*RG*SG*SG*SG*SC *ST*SC*Sm5C*SmG*SmC*SmA*SmC*SmC | GCTCGAAGGG GCTCCGCACC | 191 | SOOOR SRSSSSS SSSSS SS |
| WV-24196 | Geo*Sm5CeoTeom5CeoGeo*RA*SA*SG*RG*SG*SG*SC *ST*SC*Sm5C*SmG*SmC*SmA*SmC*SmC | GCTCGAAGGG GCTCCGCACC | 192 | SOOOR SSRSSSSS SSSSS S |

TABLE A1-continued

| Example RHO Oligonucleotides/Compositions. | | | | |
|---|---|---|---|---|
| Oligo-nucleotide | Description | Base Sequence | SEQ ID NO | Stereochemistry/ Linkage |
| WV-24197 | Geo*Sm5CeoTeom5CeoGeo*RA*SA*SG*SG*RG*SG*SC *ST*SC*Sm5C*SmG*SmC*SmA*SmC*SmC | GCTCGAAGGG GCTCCGCACC | 193 | SOOOR SSSR SSSSS SSSSS |
| WV-24198 | Geo*Sm5CeoTeom5CeoGeo*RA*SA*SG*SG*SG*RG*SC *ST*SC*Sm5C*SmG*SmC*SmA*SmC*SmC | GCTCGAAGGG GCTCCGCACC | 194 | SOOOR SSSSR SSSSS SSSS |
| WV-24199 | Geo*Sm5CeoTeom5CeoGeo*RA*SA*SG*SG*SG*SG*RC *ST*SC*Sm5C*SmG*SmC*SmA*SmC*SmC | GCTCGAAGGG GCTCCGCACC | 195 | SOOOR SSSSS R SSSSS SSS |
| WV-24200 | Geo*Sm5CeoTeom5CeoGeo*RA*SA*SG*SG*SG*SG*SC *RT*SC*Sm5C*SmG*SmC*SmA*SmC*SmC | GCTCGAAGGG GCTCCGCACC | 196 | SOOOR SSSSS SR SSSSS SS |
| WV-24201 | Geo*Sm5CeoTeom5CeoGeo*RA*SA*SG*SG*SG*SG*SC *ST*RC*Sm5C*SmG*SmC*SmA*SmC*SmC | GCTCGAAGGG GCTCCGCACC | 197 | SOOOR SSSSS SSRSSSSS S |
| WV-24202 | Geo*Sm5CeoTeom5CeoGeo*RA*SA*SG*SG*SG*SG*SC *ST*SC*Rm5C*SmG*SmC*SmA*SmC*SmC | GCTCGAAGGG GCTCCGCACC | 198 | SOOOR SSSSS SSSRSSSSS |
| WV-24203 | Geo*Sm5CeoTeom5CeoGeo*RA*SA*SG*SG*SG*SG*SC *ST*SC*Sm5C*RmG*SmC*SmA*SmC*SmC | GCTCGAAGGG GCTCCGCACC | 199 | SOOOR SSSSS SSSSRSSSS |
| WV-24204 | Teo*SGeom5CeoTeom5Ceo*RG*RA*SA*SG*SG*SG*SG *SC*ST*SC*Sm5mC*SmG*SmC*SmA*SmC | TGCTCGAAGG GGCTCCGCAC | 200 | SOOOR R SSSSS SSSSS SSS |
| WV-24205 | Teo*SGeom5CeoTeom5Ceo*RG*SA*RA*SG*SG*SG*SG *SC*ST*SC*Sm5mC*SmG*SmC*SmA*SmC | TGCTCGAAGG GGCTCCGCAC | 201 | SOOOR SRSSSSS SSSSS SS |
| WV-24206 | Teo*SGeom5CeoTeom5Ceo*RG*SA*SA*RG*SG*SG*SG *SC*ST*SC*Sm5mC*SmG*SmC*SmA*SmC | TGCTCGAAGG GGCTCCGCAC | 202 | SOOOR SSRSSSSS SSSSS S |
| WV-24207 | Teo*SGeom5CeoTeom5Ceo*RG*SA*SA*SG*RG*SG*SG *SC*ST*SC*Sm5mC*SmG*SmC*SmA*SmC | TGCTCGAAGG GGCTCCGCAC | 203 | SOOOR SSSR SSSSS SSSSS |
| WV-24208 | Teo*SGeom5CeoTeom5Ceo*RG*SA*SA*SG*SG*RG*SG *SC*ST*SC*Sm5mC*SmG*SmC*SmA*SmC | TGCTCGAAGG GGCTCCGCAC | 204 | SOOOR SSSSR SSSSS SSSS |
| WV-24209 | Teo*SGeom5CeoTeom5Ceo*RG*SA*SA*SG*SG*SG*RG *SC*ST*SC*Sm5mC*SmG*SmC*SmA*SmC | TGCTCGAAGG GGCTCCGCAC | 205 | SOOOR SSSSS R SSSSS SSS |
| WV-24210 | Teo*SGeom5CeoTeom5Ceo*RG*SA*SA*SG*SG*SG*SG *RC*ST*SC*Sm5mC*SmG*SmC*SmA*SmC | TGCTCGAAGG GGCTCCGCAC | 206 | SOOOR SSSSS SR SSSSS SS |
| WV-24211 | Teo*SGeom5CeoTeom5Ceo*RG*SA*SA*SG*SG*SG*SG *SC*RT*SC*Sm5mC*SmG*SmC*SmA*SmC | TGCTCGAAGG GGCTCCGCAC | 207 | SOOOR SSSSS SSRSSSSS S |
| WV-24212 | Teo*SGeom5CeoTeom5Ceo*RG*SA*SA*SG*SG*SG*SG *SC*ST*RC*Sm5mC*SmG*SmC*SmA*SmC | TGCTCGAAGG GGCTCCGCAC | 208 | SOOOR SSSSS SSSRSSSSS |
| WV-24213 | Teo*SGeom5CeoTeom5Ceo*RG*SA*SA*SG*SG*SG*SG *SC*ST*SC*Rm5mC*SmG*SmC*SmA*SmC | TGCTCGAAGG GGCTCCGCAC | 209 | SOOOR SSSSS SSSSRSSSS |
| WV-24214 | m5Ceo*STeoGeom5CeoTeo*Rm5C*RG*SA*SA*SG*SG* SG*SG*SC*ST*SmC*Sm5mC*SmG*SmC*SmA | CTGCTCGAAG GGGCTCCGCA | 210 | SOOOR R SSSSS SSSSS SSS |
| WV-24215 | m5Ceo*STeoGeom5CeoTeo*Rm5C*SG*RA*SA*SG*SG* SG*SG*SC*ST*SmC*Sm5mC*SmG*SmC*SmA | CTGCTCGAAG GGGCTCCGCA | 211 | SOOOR SR SSSSS SSSSS SS |
| WV-24216 | m5Ceo*STeoGeom5CeoTeo*Rm5C*SG*SA*RA*SG*SG* SG*SG*SC*ST*SmC*Sm5mC*SmG*SmC*SmA | CTGCTCGAAG GGGCTCCGCA | 212 | SOOOR SSR SSSSS SSSSS S |
| WV-24217 | m5Ceo*STeoGeom5CeoTeo*Rm5C*SG*SA*SA*RG*SG* SG*SG*SC*ST*SmC*Sm5mC*SmG*SmC*SmA | CTGCTCGAAG GGGCTCCGCA | 213 | SOOOR SSSR SSSSS SSSSS |
| WV-24218 | m5Ceo*STeoGeom5CeoTeo*Rm5C*SG*SA*SA*SG*RG* SG*SG*SC*ST*SmC*Sm5mC*SmG*SmC*SmA | CTGCTCGAAG GGGCTCCGCA | 214 | SOOOR SSSSR SSSSS SSSS |
| WV-24219 | m5Ceo*STeoGeom5CeoTeo*Rm5C*SG*SA*SA*SG*SG* RG*SG*SC*ST*SmC*Sm5mC*SmG*SmC*SmA | CTGCTCGAAG GGGCTCCGCA | 215 | SOOOR SSSSS R SSSSS SSS |
| WV-24220 | m5Ceo*STeoGeom5CeoTeo*Rm5C*SG*SA*SA*SG*SG* SG*RG*SC*ST*SmC*Sm5mC*SmG*SmC*SmA | CTGCTCGAAG GGGCTCCGCA | 216 | SOOOR SSSSS SR SSSSS SS |
| WV-24221 | m5Ceo*STeoGeom5CeoTeo*Rm5C*SG*SA*SA*SG*SG* SG*SG*RC*ST*SmC*Sm5mC*SmG*SmC*SmA | CTGCTCGAAG GGGCTCCGCA | 217 | SOOOR SSSSS SSRSSSSS S |

TABLE A1-continued

Example RHO Oligonucleotides/Compositions.

| Oligo-nucleotide | Description | Base Sequence | SEQ ID NO | Stereochemistry/ Linkage |
|---|---|---|---|---|
| WV-24222 | m5Ceo*STeoGeom5CeoTeo*Rm5C*SG*SA*SA*SG*SG*SG*SG*SC*RT*SmC*Sm5mC*SmG*SmC*SmA | CTGCTCGAAGGGGCTCCGCA | 218 | SOOOR SSSSS SSSRSSSSS |
| WV-24223 | m5Ceo*STeoGeom5CeoTeo*Rm5C*SG*SA*SA*SG*SG*SG*SG*SC*ST*RmC*Sm5mC*SmG*SmC*SmA | CTGCTCGAAGGGGCTCCGCA | 219 | SOOOR SSSSS SSSSRSSSS |
| WV-24224 | Geo*Sm5CeoTeoGeom5Ceo*RT*Rm5C*SG*SA*SA*SG*SG*SG*SG*SC*SmU*SmC*Sm5mC*SmG*SmC | GCTGCTCGAAGGGGCUCCGC | 220 | SOOOR R SSSSS SSSSS SSS |
| WV-24225 | Geo*Sm5CeoTeoGeom5Ceo*RT*Sm5C*RG*SA*SA*SG*SG*SG*SG*SC*SmU*SmC*Sm5mC*SmG*SmC | GCTGCTCGAAGGGGCUCCGC | 221 | SOOOR SR SSSSS SSSSS SS |
| WV-24226 | Geo*Sm5CeoTeoGeom5Ceo*RT*Sm5C*SG*RA*SA*SG*SG*SG*SG*SC*SmU*SmC*Sm5mC*SmG*SmC | GCTGCTCGAAGGGGCUCCGC | 222 | SOOOR SSR SSSSS SSSSS S |
| WV-24227 | Geo*Sm5CeoTeoGeom5Ceo*RT*Sm5C*SG*SA*RA*SG*SG*SG*SG*SC*SmU*SmC*Sm5mC*SmG*SmC | GCTGCTCGAAGGGGCUCCGC | 223 | SOOOR SSSR SSSSS SSSSS |
| WV-24228 | Geo*Sm5CeoTeoGeom5Ceo*RT*Sm5C*SG*SA*SA*RG*SG*SG*SG*SC*SmU*SmC*Sm5mC*SmG*SmC | GCTGCTCGAAGGGGCUCCGC | 224 | SOOOR SSSSR SSSSS SSSS |
| WV-24229 | Geo*Sm5CeoTeoGeom5Ceo*RT*Sm5C*SG*SA*SA*SG*RG*SG*SG*SC*SmU*SmC*Sm5mC*SmG*SmC | GCTGCTCGAAGGGGCUCCGC | 225 | SOOOR SSSSS R SSSSS SSS |
| WV-24230 | Geo*Sm5CeoTeoGeom5Ceo*RT*Sm5C*SG*SA*SA*SG*SG*RG*SG*SC*SmU*SmC*Sm5mC*SmG*SmC | GCTGCTCGAAGGGGCUCCGC | 226 | SOOOR SSSSS SR SSSSS SS |
| WV-24231 | Geo*Sm5CeoTeoGeom5Ceo*RT*Sm5C*SG*SA*SA*SG*SG*SG*RG*SC*SmU*SmC*Sm5mC*SmG*SmC | GCTGCTCGAAGGGGCUCCGC | 227 | SOOOR SSSSS SSRSSSSS S |
| WV-24232 | Geo*Sm5CeoTeoGeom5Ceo*RT*Sm5C*SG*SA*SA*SG*SG*SG*SG*RC*SmU*SmC*Sm5mC*SmG*SmC | GCTGCTCGAAGGGGCUCCGC | 228 | SOOOR SSSSS SSSRSSSSS |
| WV-24233 | Geo*Sm5CeoTeoGeom5Ceo*RT*Sm5C*SG*SA*SA*SG*SG*SG*SG*SC*RmU*SmC*Sm5mC*SmG*SmC | GCTGCTCGAAGGGGCUCCGC | 229 | SOOOR SSSSS SSSSRSSSS |
| WV-24234 | Teo*Sm5CeoGeoAeoAeo*RG*RT*SG*SG*SC*ST*SC*Sm5C*SG*SC*SmA*SmC*SmC*SmA*SmC | TCGAAGTGGCTCCGCACCAC | 230 | SOOOR R SSSSS SSSSS SSS |
| WV-24235 | Teo*Sm5CeoGeoAeoAeo*RG*ST*RG*SG*SC*ST*SC*Sm5C*SG*SC*SmA*SmC*SmC*SmA*SmC | TCGAAGTGGCTCCGCACCAC | 231 | SOOOR SR SSSSS SSSSS SS |
| WV-24236 | Teo*Sm5CeoGeoAeoAeo*RG*ST*SG*RG*SC*ST*SC*Sm5C*SG*SC*SmA*SmC*SmC*SmA*SmC | TCGAAGTGGCTCCGCACCAC | 232 | SOOOR SSRSSSSS SSSSS S |
| WV-24237 | Teo*Sm5CeoGeoAeoAeo*RG*ST*SG*SG*RC*ST*SC*Sm5C*SG*SC*SmA*SmC*SmC*SmA*SmC | TCGAAGTGGCTCCGCACCAC | 233 | SOOOR SSSR SSSSS SSSSS |
| WV-24238 | Teo*Sm5CeoGeoAeoAeo*RG*ST*SG*SG*SC*RT*SC*Sm5C*SG*SC*SmA*SmC*SmC*SmA*SmC | TCGAAGTGGCTCCGCACCAC | 234 | SOOOR SSSSR SSSSS SSSS |
| WV-24239 | Teo*Sm5CeoGeoAeoAeo*RG*ST*SG*SG*SC*ST*RC*Sm5C*SG*SC*SmA*SmC*SmC*SmA*SmC | TCGAAGTGGCTCCGCACCAC | 235 | SOOOR SSSSS R SSSSS SSS |
| WV-24240 | Teo*Sm5CeoGeoAeoAeo*RG*ST*SG*SG*SC*ST*SC*Rm5C*SG*SC*SmA*SmC*SmC*SmA*SmC | TCGAAGTGGCTCCGCACCAC | 236 | SOOOR SSSSS SR SSSSS SS |
| WV-24241 | Teo*Sm5CeoGeoAeoAeo*RG*ST*SG*SG*SC*ST*SC*Sm5C*RG*SC*SmA*SmC*SmC*SmA*SmC | TCGAAGTGGCTCCGCACCAC | 237 | SOOOR SSSSS SSRSSSSS S |
| WV-24242 | Teo*Sm5CeoGeoAeoAeo*RG*ST*SG*SG*SC*ST*SC*Sm5C*SG*RC*SmA*SmC*SmC*SmA*SmC | TCGAAGTGGCTCCGCACCAC | 238 | SOOOR SSSSS SSSRSSSSS |
| WV-24243 | Teo*Sm5CeoGeoAeoAeo*RG*ST*SG*SG*SC*ST*SC*Sm5C*SG*SC*RmA*SmC*SmC*SmA*SmC | TCGAAGTGGCTCCGCACCAC | 239 | SOOOR SSSSS SSSSRSSSS |
| WV-24244 | m5Ceo*STeom5CeoGeoAeo*RA*RG*ST*SG*SG*SC*ST*SC*Sm5C*SG*SmC*SmA*SmC*SmC*SmA | CTCGAAGTGGCTCCGCACCA | 240 | SOOOR R SSSSS SSSSS SSS |
| WV-24245 | m5Ceo*STeom5CeoGeoAeo*RA*SG*RT*SG*SG*SC*ST*SC*Sm5C*SG*SmC*SmA*SmC*SmC*SmA | CTCGAAGTGGCTCCGCACCA | 241 | SOOOR SR SSSSS SSSSS SS |
| WV-24246 | m5Ceo*STeom5CeoGeoAeo*RA*SG*ST*RG*SG*SC*ST*SC*Sm5C*SG*SmC*SmA*SmC*SmC*SmA | CTCGAAGTGGCTCCGCACCA | 242 | SOOOR SSRSSSSS SSSSS S |

TABLE A1-continued

Example RHO Oligonucleotides/Compositions.

| Oligo-nucleotide | Description | Base Sequence | SEQ ID NO | Stereochemistry/ Linkage |
|---|---|---|---|---|
| WV-24247 | m5Ceo*STeom5CeoGeoAeo*RA*SG*ST*SG*RG*SC*ST *SC*Sm5C*SG*SmC*SmA*SmC*SmC*SmA | CTCGAAGTGGC TCCGCACCA | 243 | SOOOR SSSR SSSSS SSSSS |
| WV-24248 | m5Ceo*STeom5CeoGeoAeo*RA*SG*ST*SG*SG*RC*ST *SC*Sm5C*SG*SmC*SmA*SmC*SmC*SmA | CTCGAAGTGGC TCCGCACCA | 244 | SOOOR SSSSR SSSSS SSSS |
| WV-24249 | m5Ceo*STeom5CeoGeoAeo*RA*SG*ST*SG*SG*SC*RT *SC*Sm5C*SG*SmC*SmA*SmC*SmC*SmA | CTCGAAGTGGC TCCGCACCA | 245 | SOOOR SSSSS R SSSSS SSS |
| WV-24250 | m5Ceo*STeom5CeoGeoAeo*RA*SG*ST*SG*SG*SC*ST *RC*Sm5C*SG*SmC*SmA*SmC*SmC*SmA | CTCGAAGTGGC TCCGCACCA | 246 | SOOOR SSSSS SR SSSSS SS |
| WV-24251 | m5Ceo*STeom5CeoGeoAeo*RA*SG*ST*SG*SG*SC*ST *SC*Rm5C*SG*SmC*SmA*SmC*SmC*SmA | CTCGAAGTGGC TCCGCACCA | 247 | SOOOR SSSSS SSRSSSSS S |
| WV-24252 | m5Ceo*STeom5CeoGeoAeo*RA*SG*ST*SG*SG*SC*ST *SC*Sm5C*RG*SmC*SmA*SmC*SmC*SmA | CTCGAAGTGGC TCCGCACCA | 248 | SOOOR SSSSS SSSRSSSSS |
| WV-24253 | m5Ceo*STeom5CeoGeoAeo*RA*SG*ST*SG*SG*SC*ST *SC*Sm5C*SG*RmC*SmA*SmC*SmC*SmA | CTCGAAGTGGC TCCGCACCA | 249 | SOOOR SSSSS SSSSRSSSS |
| WV-24254 | Geo*Sm5CeoTeom5CeoGeo*RA*RA*SG*ST*SG*SG*SC *ST*SC*Sm5C*SmG*SmC*SmA*SmC*SmC | GCTCGAAGTG GCTCCGCACC | 250 | SOOOR R SSSSS SSSSS SSS |
| WV-24255 | Geo*Sm5CeoTeom5CeoGeo*RA*SA*RG*ST*SG*SG*SC *ST*SC*Sm5C*SmG*SmC*SmA*SmC*SmC | GCTCGAAGTG GCTCCGCACC | 251 | SOOOR SR SSSSS SSSSS SS |
| WV-24256 | Geo*Sm5CeoTeom5CeoGeo*RA*SA*SG*RT*SG*SG*SC *ST*SC*Sm5C*SmG*SmC*SmA*SmC*SmC | GCTCGAAGTG GCTCCGCACC | 252 | SOOOR SSR SSSSS SSSSS S |
| WV-24257 | Geo*Sm5CeoTeom5CeoGeo*RA*SA*SG*ST*RG*SG*SC *ST*SC*Sm5C*SmG*SmC*SmA*SmC*SmC | GCTCGAAGTG GCTCCGCACC | 253 | SOOOR SSSR SSSSS SSSSS |
| WV-24258 | Geo*Sm5CeoTeom5CeoGeo*RA*SA*SG*ST*SG*RG*SC *ST*SC*Sm5C*SmG*SmC*SmA*SmC*SmC | GCTCGAAGTG GCTCCGCACC | 254 | SOOOR SSSSR SSSSS SSSS |
| WV-24259 | Geo*Sm5CeoTeom5CeoGeo*RA*SA*SG*ST*SG*SG*RC *ST*SC*Sm5C*SmG*SmC*SmA*SmC*SmC | GCTCGAAGTG GCTCCGCACC | 255 | SOOOR SSSSS R SSSSS SSS |
| WV-24260 | Geo*Sm5CeoTeom5CeoGeo*RA*SA*SG*ST*SG*SG*SC *RT*SC*Sm5C*SmG*SmC*SmA*SmC*SmC | GCTCGAAGTG GCTCCGCACC | 256 | SOOOR SSSSS SR SSSSS SS |
| WV-24261 | Geo*Sm5CeoTeom5CeoGeo*RA*SA*SG*ST*SG*SG*SC *ST*RC*Sm5C*SmG*SmC*SmA*SmC*SmC | GCTCGAAGTG GCTCCGCACC | 257 | SOOOR SSSSS SSRSSSSS S |
| WV-24262 | Geo*Sm5CeoTeom5CeoGeo*RA*SA*SG*ST*SG*SG*SC *ST*SC*Rm5C*SmG*SmC*SmA*SmC*SmC | GCTCGAAGTG GCTCCGCACC | 258 | SOOOR SSSSS SSSRSSSSS |
| WV-24263 | Geo*Sm5CeoTeom5CeoGeo*RA*SA*SG*ST*SG*SG*SC *ST*SC*Sm5C*RmG*SmC*SmA*SmC*SmC | GCTCGAAGTG GCTCCGCACC | 259 | SOOOR SSSSS SSSSRSSSS |
| WV-24264 | Teo*SGeom5CeoTeom5Ceo*RG*RA*SA*SG*ST*SG*SG *SC*ST*SC*Sm5mC*SmG*SmC*SmA*SmC | TGCTCGAAGT GGCTCCGCAC | 260 | SOOOR R SSSSS SSSSS SSS |
| WV-24265 | Teo*SGeom5CeoTeom5Ceo*RG*SA*RA*SG*ST*SG*SG *SC*ST*SC*Sm5mC*SmG*SmC*SmA*SmC | TGCTCGAAGT GGCTCCGCAC | 261 | SOOOR SR SSSSS SSSSS SS |
| WV-24266 | Teo*SGeom5CeoTeom5Ceo*RG*SA*SA*RG*ST*SG*SG *SC*ST*SC*Sm5mC*SmG*SmC*SmA*SmC | TGCTCGAAGT GGCTCCGCAC | 262 | SOOOR SSR SSSSS SSSSS S |
| WV-24267 | Teo*SGeom5CeoTeom5Ceo*RG*SA*SA*SG*RT*SG*SG *SC*ST*SC*Sm5mC*SmG*SmC*SmA*SmC | TGCTCGAAGT GGCTCCGCAC | 263 | SOOORSSSR SSSSS SSSSS |
| WV-24268 | Teo*SGeom5CeoTeom5Ceo*RG*SA*SA*SG*ST*RG*SG *SC*ST*SC*Sm5mC*SmG*SmC*SmA*SmC | TGCTCGAAGT GGCTCCGCAC | 264 | SOOORSSSSR SSSSS SSSS |
| WV-24269 | Teo*SGeom5CeoTeom5Ceo*RG*SA*SA*SG*ST*SG*RG *SC*ST*SC*Sm5mC*SmG*SmC*SmA*SmC | TGCTCGAAGT GGCTCCGCAC | 265 | SOOOR SSSSS R SSSSS SSS |
| WV-24270 | Teo*SGeom5CeoTeom5Ceo*RG*SA*SA*SG*ST*SG*SG *RC*ST*SC*Sm5mC*SmG*SmC*SmA*SmC | TGCTCGAAGT GGCTCCGCAC | 266 | SOOOR SSSSS SR SSSSS SS |
| WV-24271 | Teo*SGeom5CeoTeom5Ceo*RG*SA*SA*SG*ST*SG*SG *SC*RT*SC*Sm5mC*SmG*SmC*SmA*SmC | TGCTCGAAGT GGCTCCGCAC | 267 | SOOOR SSSSS SSRSSSSS S |

TABLE A1-continued

| Example RHO Oligonucleotides/Compositions. | | | | |
|---|---|---|---|---|
| Oligo-nucleotide | Description | Base Sequence | SEQ ID NO | Stereochemistry/ Linkage |
| WV-24272 | Teo*SGeom5CeoTeom5Ceo*RG*SA*SA*SG*ST*SG*SG *SC*ST*RC*Sm5mC*SmG*SmC*SmA*SmC | TGCTCGAAGT GGCTCCGCAC | 268 | SOOOR SSSSS SSSRSSSSS |
| WV-24273 | Teo*SGeom5CeoTeom5Ceo*RG*SA*SA*SG*ST*SG*SG *SC*ST*SC*Rm5mC*SmG*SmC*SmA*SmC | TGCTCGAAGT GGCTCCGCAC | 269 | SOOOR SSSSS SSSSRSSSS |
| WV-24274 | m5Ceo*STeoGeom5CeoTeo*Rm5C*RG*SA*SA*SG*ST* SG*SG*SC*ST*SmC*Sm5mC*SmG*SmC*SmA | CTGCTCGAAG TGGCTCCGCA | 270 | SOOOR R SSSSS SSSSS SSS |
| WV-24275 | m5Ceo*STeoGeom5CeoTeo*Rm5C*SG*RA*SA*SG*ST* SG*SG*SC*ST*SmC*Sm5mC*SmG*SmC*SmA | CTGCTCGAAG TGGCTCCGCA | 271 | SOOOR SR SSSSS SSSSS SS |
| WV-24276 | m5Ceo*STeoGeom5CeoTeo*Rm5C*SG*SA*RA*SG*ST* SG*SG*SC*ST*SmC*Sm5mC*SmG*SmC*SmA | CTGCTCGAAG TGGCTCCGCA | 272 | SOOOR SSR SSSSS SSSSS S |
| WV-24277 | m5Ceo*STeoGeom5CeoTeo*Rm5C*SG*SA*SA*RG*ST* SG*SG*SC*ST*SmC*Sm5mC*SmG*SmC*SmA | CTGCTCGAAG TGGCTCCGCA | 273 | SOOORSSSR SSSSS SSSSS |
| WV-24278 | m5Ceo*STeoGeom5CeoTeo*Rm5C*SG*SA*SA*SG*RT* SG*SG*SC*ST*SmC*Sm5mC*SmG*SmC*SmA | CTGCTCGAAG TGGCTCCGCA | 274 | SOOORSSSSR SSSSS SSSS |
| WV-24279 | m5Ceo*STeoGeom5CeoTeo*Rm5C*SG*SA*SA*SG*ST* RG*SG*SC*ST*SmC*Sm5mC*SmG*SmC*SmA | CTGCTCGAAG TGGCTCCGCA | 275 | SOOOR SSSSS R SSSSS SSS |
| WV-24280 | m5Ceo*STeoGeom5CeoTeo*Rm5C*SG*SA*SA*SG*ST* SG*RG*SC*ST*SmC*Sm5mC*SmG*SmC*SmA | CTGCTCGAAG TGGCTCCGCA | 276 | SOOOR SSSSS SR SSSSS SS |
| WV-24281 | m5Ceo*STeoGeom5CeoTeo*Rm5C*SG*SA*SA*SG*ST* SG*SG*RC*ST*SmC*Sm5mC*SmG*SmC*SmA | CTGCTCGAAG TGGCTCCGCA | 277 | SOOOR SSSSS SSRSSSSS S |
| WV-24282 | m5Ceo*STeoGeom5CeoTeo*Rm5C*SG*SA*SA*SG*ST* SG*SG*SC*RT*SmC*Sm5mC*SmG*SmC*SmA | CTGCTCGAAG TGGCTCCGCA | 278 | SOOOR SSSSS SSSRSSSSS |
| WV-24283 | m5Ceo*STeoGeom5CeoTeo*Rm5C*SG*SA*SA*SG*ST* SG*SG*SC*ST*RmC*Sm5mC*SmG*SmC*SmA | CTGCTCGAAG TGGCTCCGCA | 279 | SOOOR SSSSS SSSSRSSSS |
| WV-24284 | Geo*Sm5CeoTeoGeom5Ceo*RT*Rm5C*SG*SA*SA*SG* SG*ST*SG*SC*SmU*SmC*Sm5mC*SmG*SmC | GCTGCTCGAA GGTGCUCCGC | 280 | SOOOR R SSSSS SSSSS SSS |
| WV-24285 | Geo*Sm5CeoTeoGeom5Ceo*RT*Sm5C*RG*SA*SA*SG* SG*ST*SG*SC*SmU*SmC*Sm5mC*SmG*SmC | GCTGCTCGAA GGTGCUCCGC | 281 | SOOOR SRSSSSS SSSSS SS |
| WV-24286 | Geo*Sm5CeoTeoGeom5Ceo*RT*Sm5C*SG*RA*SA*SG* SG*ST*SG*SC*SmU*SmC*Sm5mC*SmG*SmC | GCTGCTCGAA GGTGCUCCGC | 282 | SOOOR SSRSSSSS SSSSS S |
| WV-24287 | Geo*Sm5CeoTeoGeom5Ceo*RT*Sm5C*SG*SA*RA*SG* SG*ST*SG*SC*SmU*SmC*Sm5mC*SmG*SmC | GCTGCTCGAA GGTGCUCCGC | 283 | SOOOR SSSR SSSSS SSSSS |
| WV-24288 | Geo*Sm5CeoTeoGeom5Ceo*RT*Sm5C*SG*SA*SA*RG* SG*ST*SG*SC*SmU*SmC*Sm5mC*SmG*SmC | GCTGCTCGAA GGTGCUCCGC | 284 | SOOOR SSSSR SSSSS SSSS |
| WV-24289 | Geo*Sm5CeoTeoGeom5Ceo*RT*Sm5C*SG*SA*SA*SG* RG*ST*SG*SC*SmU*SmC*Sm5mC*SmG*SmC | GCTGCTCGAA GGTGCUCCGC | 285 | SOOOR SSSSS R SSSSS SSS |
| WV-24290 | Geo*Sm5CeoTeoGeom5Ceo*RT*Sm5C*SG*SA*SA*SG* SG*RT*SG*SC*SmU*SmC*Sm5mC*SmG*SmC | GCTGCTCGAA GGTGCUCCGC | 286 | SOOOR SSSSS SR SSSSS SS |
| WV-24291 | Geo*Sm5CeoTeoGeom5Ceo*RT*Sm5C*SG*SA*SA*SG* SG*ST*RG*SC*SmU*SmC*Sm5mC*SmG*SmC | GCTGCTCGAA GGTGCUCCGC | 287 | SOOOR SSSSS SSRSSSSS S |
| WV-24292 | Geo*Sm5CeoTeoGeom5Ceo*RT*Sm5C*SG*SA*SA*SG* SG*ST*SG*RC*SmU*SmC*Sm5mC*SmG*SmC | GCTGCTCGAA GGTGCUCCGC | 288 | SOOOR SSSSS SSSRSSSSS |
| WV-24293 | Geo*Sm5CeoTeoGeom5Ceo*RT*Sm5C*SG*SA*SA*SG* SG*ST*SG*SC*RmU*SmC*Sm5mC*SmG*SmC | GCTGCTCGAA GGTGCUCCGC | 289 | SOOOR SSSSS SSSSRSSSS |
| WV-24653 | Geo*SGeon001Teon001Aeon001m5Ceo*RT*Sm5C*SG*SA* SA*SG*ST*SG*RG*Sm5C*STeoGeom5CeoGeo*STeo | GGTACTCGAA GTGGCTGCGT | 290 | S nX nX nX R SSSSS SSRSSOOOS |
| WV-24654 | Geo*SGeon001TeoAeon001m5Ceo*RT*Sm5C*SG*SA*SA* SG*ST*SG*RG*Sm5C*STeon001Geom5CeoGeo*STeo | GGTACTCGAA GTGGCTGCGT | 291 | S nX O nX R SSSSS SSRSS nX OOS |

TABLE A1-continued

Example RHO Oligonucleotides/Compositions.

| Oligo-nucleotide | Description | Base Sequence | SEQ ID NO | Stereochemistry/ Linkage |
|---|---|---|---|---|
| WV-24655 | Geo*SGeon001TeoAeon001m5Ceo*RT*Sm5C*SG*SA*SA*SG*ST*SG*RG*Sm5C*STeoGeon001m5CeoGeo*STeo | GGTACTCGAAGTGGCTGCGT | 292 | S nX O nX R SSSSS SSRSSO nX OS |
| WV-24656 | Geo*SGeon001TeoAeon001m5Ceo*RT*Sm5C*SG*SA*SA*SG*ST*SG*RG*Sm5C*STeoGeom5Ceon001Geo*STeo | GGTACTCGAAGTGGCTGCGT | 293 | S nX O nX R SSSSS SSRSSOO nX S |
| WV-24657 | Geo*SGeon001TeoAeon001m5Ceo*RT*Sm5C*SG*SA*SA*SG*ST*SG*RG*Sm5C*STeoGeom5CeoGeon001Teo | GGTACTCGAAGTGGCTGCGT | 294 | S nX O nX R SSSSS SSRSSOOO nX |
| WV-24658 | Geo*SGeon001TeoAeon001m5Ceo*RT*Sm5C*SG*SA*SA*SG*ST*SG*RG*Sm5C*STeoGeom5CeoGeo*STeo | GGTACTCGAAGTGGCTGCGT | 295 | S nX O nX R SSSSS SSRSSOOOS |
| WV-24659 | Geo*SGeon001Teon001Aeon001m5Ceo*RT*Sm5C*SG*SA*SA*SG*ST*SG*RG*Sm5C*SmU*SmG*Sm5mC*SmG*SmU | GGTACTCGAAGTGGCUGCGU | 296 | S nX nX nX R SSSSS SSRSSSSS S |
| WV-24660 | Geo*SGeon001TeoAeon001m5Ceo*RT*Sm5C*SG*SA*SA*SG*ST*SG*RG*Sm5C*SmUn001mG*Sm5mC*SmG*SmU | GGTACTCGAAGTGGCUGCGU | 297 | S nX O nX R SSSSS SSRSS nX SSS |
| WV-24661 | Geo*SGeon001TeoAeon001m5Ceo*RT*Sm5C*SG*SA*SA*SG*ST*SG*RG*Sm5C*SmU*SmGn001m5mC*SmG*SmU | GGTACTCGAAGTGGCUGCGU | 298 | S nX O nX R SSSSS SSRSSS nX SS |
| WV-24662 | Geo*SGeon001TeoAeon001m5Ceo*RT*Sm5C*SG*SA*SA*SG*ST*SG*RG*Sm5C*SmU*SmG*SmCn001mG*SmU | GGTACTCGAAGTGGCUGCGU | 299 | S nX O nX R SSSSS SSRSSSS nX S |
| WV-24663 | Geo*SGeon001TeoAeon001m5Ceo*RT*Sm5C*SG*SA*SA*SG*ST*SG*RG*Sm5C*SmU*SmG*Sm5mC*SmGn001mU | GGTACTCGAAGTGGCUGCGU | 300 | S nX O nX R SSSSS SSR SSSSS nX |
| WV-24664 | Geo*SGeon001TeoAeon001m5Ceo*RT*Sm5C*SG*SA*SA*SG*ST*SG*RG*Sm5C*SmU*SmG*Sm5mC*SmG*SmU | GGTACTCGAAGTGGCUGCGU | 301 | S nX O nX R SSSSS SSRSSSSS S |
| WV-24665 | Geo*SGeoTeoAeom5Ceo*RT*Sm5C*SG*SA*SA*SG*ST*SG*RG*Sm5C*SmU*SmG*Sm5Ceo*SmG*SmU | GGTACTCGAAGTGGCUGCGU | 302 | SOOOR SSSSS SSRSSSSS S |
| WV-24666 | Geo*SGeoTeoAeom5Ceo*RT*Sm5C*SG*SA*SA*SG*ST*SG*RG*Sm5C*SmU*SmG*Sm5Ceo*RmG*SmU | GGTACTCGAAGTGGCUGCGU | 303 | SOOOR SSSSS SSRSSSSRS |
| WV-24667 | Geo*SGeoTeoAeom5Ceo*RT*Sm5C*SG*SA*SA*SG*ST*SG*RG*Sm5C*SmU*SmG*Sm5CeomG*SmU | GGTACTCGAAGTGGCUGCGU | 304 | SOOOR SSSSS SSRSSSSOS |
| WV-24668 | Geo*SGeon001Teon001Aeon001m5Ceo*RT*Sm5C*SG*SA*SA*SG*ST*SG*RG*Sm5C*SmU*SmG*Sm5Ceo*SmG*SmU | GGTACTCGAAGTGGCUGCGU | 305 | S nX nX nX R SSSSS SSR SSSSS S |
| WV-24669 | Geo*SGeon001Teon001Aeon001m5Ceo*RT*Sm5C*SG*SA*SA*SG*ST*SG*RG*Sm5C*SmU*SmG*Sm5Ceo*RmG*SmU | GGTACTCGAAGTGGCUGCGU | 306 | S nX nX nX R SSSSS SSRSSSSRS |
| WV-24670 | Geo*SGeon001Teon001Aeon001m5Ceo*RT*Sm5C*SG*SA*SA*SG*ST*SG*RG*Sm5C*SmU*SmG*Sm5CeomG*SmU | GGTACTCGAAGTGGCUGCGU | 307 | S nX nX nX R SSSSS SSRSSSSOS |

TABLE A2

Example RHQ Oligonucleotides/Compositions.

| Oligo-nucleotide | Description | Base Sequence | SEQ ID NO | Stereochemistry/ Linkage |
|---|---|---|---|---|
| WV-15309 | mC*Sm5CeoTeoTeomC*SC*SC*RT*SG*SA*RA*SG*SG*RT*ST*SmC* SmC*SmU*SmC*SmC | CCTTCCCTGAAGGTT CCUCC | 308 | SOOOSSRSSRSSRSS SSSS |
| WV-21503 | Geo*SGeoTeoAeom5Ceo*RT*Sm5C*SG*SA*SA*SG*ST*SG*RG*SC* STeoGeom5CeoGeo*STeo | GGTACTCGAAGTGG CTGCGT | 309 | SOOORSSSSSSSRSS OOOS |
| WV-21505 | Geo*SGeoTeoAeom5Ceo*RT*Sm5C*SG*SA*SA*SG*ST*SG*RG*SC* SmU*SmG*Sm5mC*SmG*SmU | GGTACTCGAAGTGG CUGCGU | 310 | SOOORSSSSSSSRSS SSSS |
| WV-23658 | Geo*SGeoTeoAeom5Ceo*RT*Sm5C*SG*SA*SA*SG*ST*SG*RG*Sm 5C*STeoGeom5CeoGeo*STeo | GGTACTCGAAGTGG CTGCGT | 311 | SOOORSSSSSSSRSS OOOS |
| WV-24004 | lG*lG*lT*A*m5C*T*m5C*G*A*A*G*T*G*lG*m5lC*lT | GGTACTCGAAGTGG CT | 312 | XXXXXXXXXXXXXXX |
| WV-24653 | Geo*SGeon001Teon001Aeon001m5Ceo*RT*Sm5C*SG*SA*SA*SG* ST*SG*RG*Sm5C*STeoGeom5CeoGeo*STeo | GGTACTCGAAGTGG CTGCGT | 313 | SnXnXnXRSSSSSSSR SSOOOS |
| WV-24654 | Geo*SGeon001TeoAeon001m5Ceo*RT*Sm5C*SG*SA*SA*SG*ST*S G*RG*Sm5C*STeon001Geom5CeoGeo*STeo | GGTACTCGAAGTGG CTGCGT | 314 | SnXOnXRSSSSSSSRS SnXOOS |
| WV-24655 | Geo*SGeon001TeoAeon001m5Ceo*RT*Sm5C*SG*SA*SA*SG*ST*S G*RG*Sm5C*STeoGeon001m5CeoGeo*STeo | GGTACTCGAAGTGG CTGCGT | 315 | SnXOnXRSSSSSSSRS SOnXOS |
| WV-24656 | Geo*SGeon001TeoAeon001m5Ceo*RT*Sm5C*SG*SA*SA*SG*ST*S G*RG*Sm5C*STeoGeom5Ceon001Geo*STeo | GGTACTCGAAGTGG CTGCGT | 316 | SnXOnXRSSSSSSSRS SOOnXS |
| WV-24657 | Geo*SGeon001TeoAeon001m5Ceo*RT*Sm5C*SG*SA*SA*SG*ST*S G*RG*Sm5C*STeoGeom5CeoGeon001Teo | GGTACTCGAAGTGG CTGCGT | 317 | SnXOnXRSSSSSSSRS SOOOnX |
| WV-24658 | Geo*SGeon001TeoAeon001m5Ceo*RT*Sm5C*SG*SA*SA*SG*ST*S G*RG*Sm5C*STeoGeom5CeoGeo*STeo | GGTACTCGAAGTGG CTGCGT | 318 | SnXOnXRSSSSSSSRS SOOOS |
| WV-24665 | Geo*SGeoTeoAeom5Ceo*RT*Sm5C*SG*SA*SA*SG*ST*SG*RG*Sm 5C*SmU*SmG*Sm5Ceo*SmG*SmU | GGTACTCGAAGTGG CUGCGU | 319 | SOOORSSSSSSSRSS SSSS |
| WV-24668 | Geo*SGeon001Teon001Aeon001m5Ceo*RT*Sm5C*SG*SA*SA*SG* ST*SG*RG*Sm5C*SmU*SmG*Sm5Ceo*SmG*SmU | GGTACTCGAAGTGG CUGCGU | 320 | SnXnXnXRSSSSSSSR ssssss |
| WV-28093 | Geo*SGeoTeoAeom5Ceo*ST*Sm5C*SG*SA*SA*SG*ST*SG*RG*Sm5 C*STeoGeom5CeoGeo*STeo | GGTACTCGAAGTGG CTGCGT | 321 | SOOOSSSSSSSSRSS OOOS |
| WV-28094 | Geo*SGeoTeoAeom5Ceo*ST*Sm5C*SG*SA*SA*SG*ST*SG*RG*Sm5 C*SmU*SmG*Sm5mC*SmG*SmU | GGTACTCGAAGTGG CUGCGU | 322 | SOOOSSSSSSSSRSS SSSS |

TABLE A2-continued

Example RHQ Oligonucleotides/Compositions.

| Oligo-nucleotide | Description | Base Sequence | SEQ ID NO | Stereochemistry/ Linkage |
|---|---|---|---|---|
| WV-30204 | Geo*SGeoTeoAeom5Ceo*ST*Sm5C*SG*SA*SA*SG*ST*SG*RG*Sm5C*SmU*SmG*Sm5Ceo*SmG*SmU | GGTACTCGAAGTGGCUGCGU | 323 | SOOOSSSSSSSSRSSSSSS |
| WV-34283 | Geo*SGeon001Teon001Aeon001m5Ceo*ST*Sm5C*SG*SA*SA*SG*ST*SG*RG*Sm5C*STeoGeom5CeoGeo*STeo | GGTACTCGAAGTGGCTGCGT | 324 | SnXnXnXSSSSSSSSRSSOOOS |
| WV-34284 | Geo*SGeon001TeoAeon001m5Ceo*ST*Sm5C*SG*SA*SA*SG*ST*SG*RG*Sm5C*STeoGeom5CeoGeo*STeo | GGTACTCGAAGTGGCTGCGT | 325 | SnXOnXSSSSSSSSRSSOOOS |
| WV-34285 | Geo*SGeon001TeoAeon001m5Ceo*ST*Sm5C*SG*SA*SA*SG*ST*SG*RG*Sm5C*STeon001Geom5CeoGeo*STeo | GGTACTCGAAGTGGCTGCGT | 326 | SnXOnXSSSSSSSSRSSnXOOS |
| WV-34286 | Geo*SGeon001TeoAeon001m5Ceo*ST*Sm5C*SG*SA*SA*SG*ST*SG*RG*Sm5C*STeoGeon001m5CeoGeo*STeo | GGTACTCGAAGTGGCTGCGT | 327 | SnXOnXSSSSSSSSRSSOnXOS |
| WV-34287 | Geo*SGeon001TeoAeon001m5Ceo*ST*Sm5C*SG*SA*SA*SG*ST*SG*RG*Sm5C*STeoGeom5Ceon001Geo*STeo | GGTACTCGAAGTGGCTGCGT | 328 | SnXOnXSSSSSSSSRSSOOnXS |
| WV-34288 | Geo*SGeon001TeoAeon001m5Ceo*ST*Sm5C*SG*SA*SA*SG*ST*SG*RG*Sm5C*STeoGeom5CeoGeon001Teo | GGTACTCGAAGTGGCTGCGT | 329 | SnXOnXSSSSSSSSRSSOOOnX |
| WV-34289 | Geo*SGeon001Teon001Aeon001m5Ceo*RT*Sm5C*SG*SA*SA*SG*ST*SG*RG*SC*STeoGeom5CeoGeo*STeo | GGTACTCGAAGTGGCTGCGT | 330 | SnXnXnXRSSSSSSSRSSOOOS |
| WV-34290 | Geo*SGeon001TeoAeon001m5Ceo*RT*Sm5C*SG*SA*SA*SG*ST*SG*RG*SC*STeoGeom5CeoGeo*STeo | GGTACTCGAAGTGGCTGCGT | 331 | SnXOnXRSSSSSSSRSSOOOS |
| WV-34291 | Geo*SGeon001TeoAeon001m5Ceo*RT*Sm5C*SG*SA*SA*SG*ST*SG*RG*SC*STeon001Geom5CeoGeo*STeo | GGTACTCGAAGTGGCTGCGT | 332 | SnXOnXRSSSSSSSRSSnXOOS |
| WV-34292 | Geo*SGeon001TeoAeon001m5Ceo*RT*Sm5C*SG*SA*SA*SG*ST*SG*RG*SC*STeoGeon001m5CeoGeo*STeo | GGTACTCGAAGTGGCTGCGT | 333 | SnXOnXRSSSSSSSRSSOnXOS |
| WV-34293 | Geo*SGeon001TeoAeon001m5Ceo*RT*Sm5C*SG*SA*SA*SG*ST*SG*RG*SC*STeoGeom5Ceon001Geo*STeo | GGTACTCGAAGTGGCTGCGT | 334 | SnXOnXRSSSSSSSRSSOOnXS |
| WV-34294 | Geo*SGeon001TeoAeon001m5Ceo*RT*Sm5C*SG*SA*SA*SG*ST*SG*RG*SC*STeoGeom5CeoGeon001Teo | GGTACTCGAAGTGGCTGCGT | 335 | SnXOnXRSSSSSSSRSSOOOnX |
| WV-34295 | Geo*SGeoTeoAeom5Ceo*ST*Sm5C*SG*SA*SA*SG*ST*SG*RG*SC*STeoGeom5CeoGeo*STeo | GGTACTCGAAGTGGCTGCGT | 336 | SOOOSSSSSSSSRSSOOOS |
| WV-34296 | Geo*SGeon001Teon001Aeon001m5Ceo*ST*Sm5C*SG*SA*SA*SG*ST*SG*RG*SC*STeoGeom5CeoGeo*STeo | GGTACTCGAAGTGGCTGCGT | 337 | SnXnXnXSSSSSSSSRSSOOOS |
| WV-34297 | Geo*SGeon001TeoAeon001m5Ceo*ST*Sm5C*SG*SA*SA*SG*ST*SG*RG*SC*STeoGeom5CeoGeo*STeo | GGTACTCGAAGTGGCTGCGT | 338 | SnXOnXSSSSSSSSRSSOOOS |

TABLE A2-continued

| Oligo-nucleotide | Description | Base Sequence | SEQ ID NO | Stereochemistry/ Linkage |
|---|---|---|---|---|
| Example RHQ Oligonucleotides/Compositions. | | | | |
| WV-34298 | Geo*SGeon001TeoAeon001m5Ceo*ST*Sm5C*SG*SA*SA*SG*ST*S G*RG*SC*STeon001Geom5CeoGeo*STeo | GGTACTCGAAGTGG CTGCGT | 339 | SnXOnXSSSSSSSSRS SnXOOS |
| WV-34299 | Geo*SGeon001TeoAeon001m5Ceo*ST*Sm5C*SG*SA*SA*SG*ST*S G*RG*SC*STeoGeon001m5CeoGeo*STeo | GGTACTCGAAGTGG CTGCGT | 340 | SnXOnXSSSSSSSSRS SOnXOS |
| WV-34300 | Geo*SGeon001TeoAeon001m5Ceo*ST*Sm5C*SG*SA*SA*SG*ST*S G*RG*SC*STeoGeom5Ceon001Geo*STeo | GGTACTCGAAGTGG CTGCGT | 341 | SnXOnXSSSSSSSSRS SOOnXS |
| WV-34301 | Geo*SGeon001TeoAeon001m5Ceo*ST*Sm5C*SG*SA*SA*SG*ST*S G*RG*SC*STeoGeom5CeoGeon001Teo | GGTACTCGAAGTGG CTGCGT | 342 | SnXOnXSSSSSSSSRS SOOOnX |
| WV-34302 | Geo*SGeon001TeoAeon001m5Ceo*RT*Sm5C*SG*SA*SA*SG*ST*S G*RG*Sm5C*SmU*SmG*Sm5Ceo*SmG*SmU | GGTACTCGAAGTGG CUGCGU | 343 | SnXOnXRSSSSSSSRS SSSSS |
| WV-34303 | Geo*SGeon001TeoAeon001m5Ceo*RT*Sm5C*SG*SA*SA*SG*ST*S G*RG*Sm5C*SmUn001mG*Sm5Ceo*SmG*SmU | GGTACTCGAAGTGG CUGCGU | 344 | SnXOnXRSSSSSSSRS SnXSSS |
| WV-34304 | Geo*SGeon001TeoAeon001m5Ceo*RT*Sm5C*SG*SA*SA*SG*ST*S G*RG*Sm5C*SmU*SmGn001m5Ceo*SmG*SmU | GGTACTCGAAGTGG CUGCGU | 345 | SnXOnXRSSSSSSSRS SSnXSS |
| WV-34305 | Geo*SGeon001TeoAeon001m5Ceo*RT*Sm5C*SG*SA*SA*SG*ST*S G*RG*Sm5C*SmU*SmG*Sm5Ceon001mG*SmU | GGTACTCGAAGTGG CUGCGU | 346 | SnXOnXRSSSSSSSRS SSSnXS |
| WV-34306 | Geo*SGeon001TeoAeon001m5Ceo*RT*Sm5C*SG*SA*SA*SG*ST*S G*RG*Sm5C*SmU*SmG*Sm5Ceo*SmGn001mU | GGTACTCGAAGTGG CUGCGU | 347 | SnXOnXRSSSSSSSRS SSSSnX |
| WV-34307 | Geo*SGeon001Teon001Aeon001m5Ceo*ST*Sm5C*SG*SA*SA*SG* ST*SG*RG*Sm5C*SmU*SmG*Sm5Ceo*SmG*SmU | GGTACTCGAAGTGG CUGCGU | 348 | SnXnXnXSSSSSSSSR ssssss |
| WV-34308 | Geo*SGeon001TeoAeon001m5Ceo*ST*Sm5C*SG*SA*SA*SG*ST*S G*RG*Sm5C*SmU*SmG*Sm5Ceo*SmG*SmU | GGTACTCGAAGTGG CUGCGU | 349 | SnXOnXSSSSSSSSRS SSSSS |
| WV-34309 | Geo*SGeon001TeoAeon001m5Ceo*ST*Sm5C*SG*SA*SA*SG*ST*S G*RG*Sm5C*SmUn001mG*Sm5Ceo*SmG*SmU | GGTACTCGAAGTGG CUGCGU | 350 | SnXOnXSSSSSSSSRS SnXSSS |
| WV-34310 | Geo*SGeon001TeoAeon001m5Ceo*ST*Sm5C*SG*SA*SA*SG*ST*S G*RG*Sm5C*SmU*SmGn001m5Ceo*SmG*SmU | GGTACTCGAAGTGG CUGCGU | 351 | SnXOnXSSSSSSSSRS SSnXSS |
| WV-34311 | Geo*SGeon001TeoAeon001m5Ceo*ST*Sm5C*SG*SA*SA*SG*ST*S G*RG*Sm5C*SmU*SmG*Sm5Ceon001mG*SmU | GGTACTCGAAGTGG CUGCGU | 352 | SnXOnXSSSSSSSSRS SSSnXS |
| WV-34312 | Geo*SGeon001TeoAeon001m5Ceo*ST*Sm5C*SG*SA*SA*SG*ST*S G*RG*Sm5C*SmU*SmG*Sm5Ceo*SmGn001mU | GGTACTCGAAGTGG CUGCGU | 353 | SnXOnXSSSSSSSSRS SSSSnX |
| WV-34313 | Geo*SGeoTeoAeom5Ceo*RT*Sm5C*SG*SA*SA*SG*ST*SG*RG*SC* SmU*SmG*Sm5Ceo*SmG*SmU | GGTACTCGAAGTGG CUGCGU | 354 | SOOORSSSSSSSRSS ssss |

TABLE A2-continued

| Example RHQ Oligonucleotides/Compositions. | | | | |
|---|---|---|---|---|
| Oligo-nucleotide | Description | Base Sequence | SEQ ID NO | Stereochemistry/ Linkage |
| WV-34314 | Geo*SGeon001Teon001Aeon001m5Ceo*RT*Sm5C*SG*SA*SA*SG*ST*SG*RG*SC*SmU*SmG*Sm5Ceo*SmG*SmU | GGTACTCGAAGTGGCUGCGU | 355 | SnXnXnXRSSSSSSSRssssss |
| WV-34315 | Geo*SGeon001TeoAeon001m5Ceo*RT*Sm5C*SG*SA*SA*SG*ST*SG*RG*SC*SmU*SmG*Sm5Ceo*SmG*SmU | GGTACTCGAAGTGGCUGCGU | 356 | SnXOnXRSSSSSSSRSsssss |
| WV-34316 | Geo*SGeon001TeoAeon001m5Ceo*RT*Sm5C*SG*SA*SA*SG*ST*SG*RG*SC*SmUn001mG*Sm5Ceo*SmG*SmU | GGTACTCGAAGTGGCUGCGU | 357 | SnXOnXRSSSSSSSRSSnXSSS |
| WV-34317 | Geo*SGeon001TeoAeon001m5Ceo*RT*Sm5C*SG*SA*SA*SG*ST*SG*RG*SC*SmU*SmGn001m5Ceo*SmG*SmU | GGTACTCGAAGTGGCUGCGU | 358 | SnXOnXRSSSSSSSRSSSnXSS |
| WV-34318 | Geo*SGeon001TeoAeon001m5Ceo*RT*Sm5C*SG*SA*SA*SG*ST*SG*RG*SC*SmU*SmG*Sm5Ceon001mG*SmU | GGTACTCGAAGTGGCUGCGU | 359 | SnXOnXRSSSSSSSRSSSSnXS |
| WV-34319 | Geo*SGeon001TeoAeon001m5Ceo*RT*Sm5C*SG*SA*SA*SG*ST*SG*RG*SC*SmU*SmG*Sm5Ceo*SmGn001mU | GGTACTCGAAGTGGCUGCGU | 360 | SnXOnXRSSSSSSSRSSSSSnX |
| WV-34320 | Geo*SGeoTeoAeom5Ceo*ST*Sm5C*SG*SA*SA*SG*ST*SG*RG*SC*SmU*SmG*Sm5mC*SmG*SmU | GGTACTCGAAGTGGCUGCGU | 361 | SOOOSSSSSSSSRSSSSSS |
| WV-34321 | Geo*SGeoTeoAeom5Ceo*ST*Sm5C*SG*SA*SA*SG*ST*SG*RG*SC*SmU*SmG*Sm5Ceo*SmG*SmU | GGTACTCGAAGTGGCUGCGU | 362 | SOOOSSSSSSSSRSSSSSS |
| WV-34322 | Geo*SGeon001Teon001Aeon001m5Ceo*ST*Sm5C*SG*SA*SA*SG*ST*SG*RG*SC*SmU*SmG*Sm5Ceo*SmG*SmU | GGTACTCGAAGTGGCUGCGU | 363 | SnXnXnXSSSSSSSSRSSSSSS |
| WV-34323 | Geo*SGeon001TeoAeon001m5Ceo*ST*Sm5C*SG*SA*SA*SG*ST*SG*RG*SC*SmU*SmG*Sm5Ceo*SmG*SmU | GGTACTCGAAGTGGCUGCGU | 364 | SnXOnXSSSSSSSSRSSSSSS |
| WV-34324 | Geo*SGeon001TeoAeon001m5Ceo*ST*Sm5C*SG*SA*SA*SG*ST*SG*RG*SC*SmUn001mG*Sm5Ceo*SmG*SmU | GGTACTCGAAGTGGCUGCGU | 365 | SnXOnXSSSSSSSSRSSnXSSS |
| WV-34325 | Geo*SGeon001TeoAeon001m5Ceo*ST*Sm5C*SG*SA*SA*SG*ST*SG*RG*SC*SmU*SmGn001m5Ceo*SmG*SmU | GGTACTCGAAGTGGCUGCGU | 366 | SnXOnXSSSSSSSSRSSSnXSS |
| WV-34326 | Geo*SGeon001TeoAeon001m5Ceo*ST*Sm5C*SG*SA*SA*SG*ST*SG*RG*SC*SmU*SmG*Sm5Ceon001mG*SmU | GGTACTCGAAGTGGCUGCGU | 367 | SnXOnXSSSSSSSSRSSSSnXS |
| WV-34327 | Geo*SGeon001TeoAeon001m5Ceo*ST*Sm5C*SG*SA*SA*SG*ST*SG*RG*SC*SmU*SmG*Sm5Ceo*SmGn001mU | GGTACTCGAAGTGGCUGCGU | 368 | SnXOnXSSSSSSSSRSSSSSnX |

Notes:

Spaces in Table A1 and Table A2 are utilized for formatting and readability, e.g., S nX nX nX R SSSSS SSRSSSSOS illustrates the same Stereochemistry/Linkage as SnXnXnXRSSSSSSSRSSSSOS; * S and *S both indicate a phosphorothioate internucleotidic linkage wherein the linkage phosphorus has Sp configuration (S); etc.

Description, Base Sequence and Stereochemistry/Linkage, due to their length, may be divided into multiple lines in Table A1 and Table A2. Unless otherwise specified, all oligonucleotides in Table A1 and Table A2 are single-stranded. As appreciated by those skilled in the art, nucleoside units are unmodified and contain unmodified nucleobases and 2'-deoxy sugars unless otherwise indicated with modifications (e.g., modified with r, m, m5, eo, etc.); linkages, unless otherwise indicated, are natural phosphate linkages; and acidic/basic groups may independently exist in their salt forms. Moieties and modifications in oligonucleotides (or other compounds, e.g., those useful for preparing provided oligonucleotides comprising these moieties or modifications):

l: LNA sugar;

m: 2'-OMe;

m5 (or m5C): methyl at 5-position of C (nucleobase is 5-methylcytosine);

m51C: methyl at 5-position of C (nucleobase is 5-methylcytosine), nucleobase is C, and sugar is 1 (LNA);

m5Ceo: 5-methyl 2'-O-methoxyethyl C;

eo: 2'-MOE (2'-$OCH_2CH_2OCH_3$);

r: 2'-OH;

O, PO: phosphodiester (phosphate). It can be an end group (or a component thereof), or a linkage, e.g., a linkage between a linker and an oligonucleotide chain, an internucleotidic linkage (a natural phosphate linkage), etc. Phosphodiesters are typically indicated with "O" in the Stereochemistry/Linkage column and are typically not marked in the Description column (if it is an end group, e.g., a 5'-end group, it is indicated in the Description and typically not in Stereochemistry/Linkage); if no linkage is indicated in the Description column, it is typically a phosphodiester unless otherwise indicated. Note that a phosphate linkage between a linker (e.g., L001) and an oligonucleotide chain may not be marked in the Description column, and may not be indicated with "O" in the Stereochemistry/Linkage column;

*, PS: Phosphorothioate. It can be an end group (if it is an end group, e.g., a 5'-end group, it is indicated in the Description and typically not in Stereochemistry/Linkage), or a linkage, e.g., a linkage between linker (e.g., L001) and an oligonucleotide chain, an internucleotidic linkage (a phosphorothioate internucleotidic linkage), etc; * (as opposed to * R or * S) indicates a phosphorothioate which is not chirally controlled;

R, Rp: Phosphorothioate in the Rp configuration. Note that * R in Description indicates a single phosphorothioate linkage in the Rp configuration;

S, Sp: Phosphorothioate in the Sp configuration. Note that * S in Description indicates a single phosphorothioate linkage in the Sp configuration;

X: stereorandom phosphorothioate;

n001:

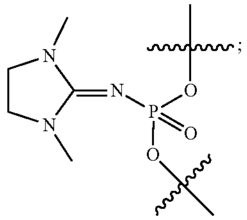 [SMILES: *OP(=O)(N=C1N(C)CCN1C)O*]

and nX stereorandom n001.

Lengths

As appreciated by those skilled in the art, oligonucleotides can be of various lengths to provide desired properties and/or activities for various uses. Many technologies for assessing, selecting and/or optimizing oligonucleotide length are available in the art and can be utilized in accordance with the present disclosure. As demonstrated herein, in many embodiments, provided oligonucleotides are of suitable lengths to hybridize with their targets and reduce levels of their targets and/or an encoded product thereof. In some embodiments, an oligonucleotide is long enough to recognize a target nucleic acid (e.g., a RHO mRNA). In some embodiments, an oligonucleotide is sufficiently long to distinguish between a target nucleic acid and other nucleic acids (e.g., a nucleic acid having a base sequence which is not RHO) to reduce off-target effects. In some embodiments, an oligonucleotide, e.g., a RHO oligonucleotide, is sufficiently short to reduce complexity of manufacture or production and to reduce cost of products.

In some embodiments, the base sequence of an oligonucleotide is about 10-500 nucleobases in length. In some embodiments, a base sequence is about 10-500 nucleobases in length. In some embodiments, a base sequence is about 10-50 nucleobases in length. In some embodiments, a base sequence is about 15-50 nucleobases in length. In some embodiments, a base sequence is from about 15 to about 30 nucleobases in length. In some embodiments, a base sequence is from about 10 to about 25 nucleobases in length. In some embodiments, a base sequence is from about 15 to about 22 nucleobases in length. In some embodiments, a base sequence is about 10, 11, 12, 13, 14, 15, 16, 17, 18, 19, 20, 21, 22, 23, 24, or 25 nucleobases in length. In some embodiments, a base sequence is at least 12 nucleobases in length. In some embodiments, a base sequence is at least 13 nucleobases in length. In some embodiments, a base sequence is at least 14 nucleobases in length. In some embodiments, a base sequence is at least 15 nucleobases in length. In some embodiments, a base sequence is at least 16 nucleobases in length. In some embodiments, a base sequence is at least 17 nucleobases in length. In some embodiments, a base sequence is at least 18 nucleobases in length. In some embodiments, a base sequence is at least 19 nucleobases in length. In some embodiments, a base sequence is at least 20 nucleobases in length. In some embodiments, a base sequence is at least 21 nucleobases in length. In some embodiments, a base sequence is at least 22 nucleobases in length. In some embodiments, a base sequence is at least 23 nucleobases in length. In some embodiments, a base sequence is at least 24 nucleobases in length. In some embodiments, a base sequence is at least 25 nucleobases in length. In some embodiments, a base sequence is 15 nucleobases in length. In some embodiments, a base sequence is 16 nucleobases in length. In some embodiments, a base sequence is 17 nucleobases in length.

In some embodiments, a base sequence is 18 nucleobases in length. In some embodiments, a base sequence is 19 nucleobases in length. In some embodiments, a base sequence is 20 nucleobases in length. In some embodiments, a base sequence is 21 nucleobases in length. In some embodiments, a base sequence is 22 nucleobases in length. In some embodiments, a base sequence is 23 nucleobases in length. In some embodiments, a base sequence is 24 nucleobases in length. In some embodiments, a base sequence is 25 nucleobases in length. In some other embodiments, a base sequence is at least 30 nucleobases in length. In some other embodiments, a base sequence is a duplex of complementary strands of at least 18 nucleobases in length. In some other embodiments, a base sequence is a duplex of complementary strands of at least 21 nucleobases in length. In some embodiments, each nucleobase independently comprises an optionally substituted monocyclic, bicyclic or polycyclic ring wherein at least one ring atom is nitrogen. In some embodiments, each nucleobase is independently optionally substituted adenine, cytosine, guanosine, thymine, or uracil, or an optionally substituted tautomer of adenine, cytosine, guanosine, thymine, or uracil.

Regions, Wings and Cores

In some embodiments, an oligonucleotide, e.g., a RHO oligonucleotide, comprises several regions, each of which independently comprises one or more consecutive nucleosides and optionally one or more internucleotidic linkages. In some embodiments, a region differs from its neighboring region(s) in that it contains one or more structural feature that are different from those corresponding structural features of its neighboring region(s). Example structural features include nucleobase modifications and patterns thereof, sugar modifications and patterns thereof, internucleotidic linkages and patterns thereof (which can be internucleotidic linkage types (e.g., phosphate, phosphorothioate, phosphorothioate triester, neutral internucleotidic linkage, etc.) and patterns thereof, linkage phosphorus modifications (backbone phosphorus modifications) and patterns thereof (e.g., pattern of —$XLR^1$ if internucleotidic linkages having the structure of formula I), backbone chiral center (linkage phosphorus) stereochemistry and patterns thereof [e.g., combination of Rp and/or Sp of chirally controlled internucleotidic linkages (sequentially from 5' to 3'), optionally with non-chirally controlled internucleotidic linkages and/or natural phosphate linkages, if any (e.g., SnX-OnXRSSSSSSSRSSSnXSS)]. In some embodiments, a region comprises a chemical modification (e.g., a sugar modification, base modification, internucleotidic linkage, or stereochemistry of internucleotidic linkage) not present in its neighboring region(s). In some embodiments, a region lacks a chemical modification present in its neighboring regions(s).

In some embodiments, an oligonucleotide, e.g., a RHO oligonucleotide, comprises or consists of two or more regions. In some embodiments, an oligonucleotide comprises or consists of three or more regions. In some embodiments, an oligonucleotide comprises or consists of two neighboring regions, wherein one region is designated as a wing region and the other a core region. The structure of such an oligonucleotide comprises or consists of a wing-core or core-wing structure. In some embodiments, an oligonucleotide comprises or consists of three neighboring regions, wherein one region is flanked by two neighboring regions. In some embodiments, the middle region is designated as the core region, and each of the flanking region a wing region (a 5'-wing if connected to the 5'-end of the core, a 3'-wing if connected to the 3'-end of the core). The structure of such an oligonucleotide comprises or consists of a wing-core-wing structure.

In some embodiments, a first region (e.g., a wing) differs from a second region (e.g., a core) in that the first region contains sugar modification(s) or pattern thereof absent from the second region. In some embodiments, a first (e.g., wing) region comprises a sugar modification absent from a second (e.g., core) region. In some embodiments, a sugar modification is a 2'-modification. In some embodiments, a 2'-modification is 2'-OR, wherein R is optionally substituted $C_{1-6}$ aliphatic. In some embodiments, a 2'-modification is 2'-OR, wherein R is optionally substituted $C_{1-6}$ alkyl. In some embodiments, a 2'-modification is 2'-MOE. In some embodiments, a 2'-modification is 2'-OMe. In some embodiments, a modified sugar is a bicyclic sugar, e.g., a LNA sugar. In some embodiments, each sugar in a region is independently modified. In some embodiments, each sugar of a region (e.g., a wing) independently comprises a modification, which can be the same or different from each other. In some embodiments, each sugar of a region (e.g., a wing) comprises the same modification, e.g., 2'-modification as described in the present disclosure. In some embodiments, sugars of a region (e.g., a core) are not modified. In some embodiments, each sugar of a region (e.g., a core) is a non-modified DNA sugar (with two —H at the 2'-position). In some embodiments, the structure of a provided oligonucleotide comprises or consists of a wing-core, core-wing, or wing-core-wing structure, wherein each wing independently comprises one or more sugar modifications, and each sugar in the core is a natural DNA sugar (with two —H at the 2'-position).

Additionally or alternatively, a first region (e.g., a wing) can contain internucleotidic linkage(s) or pattern thereof that differs from another region (e.g., a core or another wing). In some embodiments, a region (e.g., a wing) comprises two or more consecutive natural phosphate linkages. In some embodiments, a region (e.g., a core) comprises no consecutive natural phosphate linkages. In some embodiments, the structure of a provided oligonucleotide comprises or consists of a wing-core, core-wing, or wing-core-wing structure, wherein at least one wing independently comprises two or more consecutive natural phosphate linkages, and the core comprises no consecutive natural phosphate linkages. In some embodiments, in a wing-core-wing structure, each wing independently comprises two or more consecutive internucleotidic linkages. Unless otherwise noted, for the purpose of stereochemistry of wing-core-wing structures, internucleotidic linkages connecting a core with a wing are included in the core (e.g., see above).

In some embodiments, a region is a 5'-wing, a 3'-wing, or a core. In some embodiments, the 5'-wing is to the 5' end of the oligonucleotide, the 3'-wing is to the 3'-end of the oligonucleotide and the core is between the 5'-wing and the 3'-wing, and the oligonucleotide comprises or consists of a wing-core-wing structure or format. In some embodiments, a core comprises a span of contiguous natural DNA sugars (2'-deoxyribose). In some embodiments, a core comprises a span of at least 5 contiguous natural DNA sugars (2'-deoxyribose). In some embodiments, a core comprises a span of at least 10 contiguous natural DNA sugars (2'-deoxyribose). In some embodiments, a core is referenced as a gap. In some embodiments, an oligonucleotide which comprises or consists of a wing-core-wing structure is described as a gapmer. In some embodiments, the structure of a provided oligonucleotide comprises or consists of a wing-core structure. In some embodiments, the structure of a provided oligonucleotide comprises or consists of a core-wing structure. Non-limiting examples of oligonucleotides having a core-wing structure include WV-20847, WV-20846, WV-20865, WV-20828, WV-21503, WV-21505, WV-23658, and WV-23668. In some embodiments, the structure of an oligonucleotide comprises or consists of an oligonucleotide chain which comprises or consists of wing-core-wing, wing-core, or wing-core, wherein the oligonucleotide chain is conjugated to an additional chemical moiety optionally through a linker as described in the present disclosure. In some embodiments, the present disclosure provides oligonucleotides that target RHO and have a structure that comprises one or two wings and a core, and comprise or consist of a wing-core-wing, core-wing, or wing-core structure.

Ribonuclease H (RNase H, e.g., RNase H1, RNase H2, etc.) reportedly recognizes a structure comprising a hybrid of RNA and DNA (e.g., a heteroduplex), and cleaves the RNA. In some embodiments, an oligonucleotide comprising a span of contiguous natural DNA sugars (2'-deoxyribose, e.g., in a core region) is capable of annealing to a RNA such as a mRNA to form a heteroduplex; and this heteroduplex structure is capable of being recognized by RNase H and the RNA cleaved by RNase H. In some embodiments, a core of a provide oligonucleotide comprises 1, 2, 3, 4, 5, 6, 7, 8, 9, 10 or more contiguous natural DNA sugars, and the core is capable of annealing specifically to a target transcript [e.g., a RHO transcript (e.g., pre-mRNA, mature mRNA, etc.)]; and the formed structure is capable of being recognized by RNase H and the transcript cleaved by RNase H. In some embodiments, a core of a provided oligonucleotide comprises 5 or more contiguous DNA sugars.

Regions, e.g., wings, cores, etc., can be of various suitable lengths. In some embodiments, a region (e.g., a wing, a core, etc.) contains 1, 2, 3, 4, 5, 6, 7, 8, 9, 10, 11, 12, 13, 14, 15, 16, 17, 18, 19, 20, 21, 22, 23, 24, 25 or more nucleobases. As described in the present disclosure, in some embodiments, each nucleobase independently comprises an optionally substituted monocyclic, bicyclic or polycyclic ring, which ring has at least one nitrogen ring atom; in some embodiments, each nucleobase is independently optionally substituted A, T, C, G or U, or a substituted tautomer of A, T, C, G or U. In some embodiments, the number is 1, 2, 3, 4, 5, 6, 7, 8, 9, or 10 for a wing. In some embodiments, the number is 1 for a wing. In some embodiments, the number is 2 for a wing. In some embodiments, the number is 3 for a wing. In some embodiments, the number is 4 for a wing. In some embodiments, the number is 5 for a wing. In some embodiments, the number is 6 for a wing. In some embodiments, the number is 7 for a wing. In some embodiments, the number is 8 for a wing. In some embodiments, the number is 9 for a wing. In some embodiments, the number is 10 for a wing. In some embodiments, each wing of a wing-core-wing structure independently has a length as described in the present disclosure. In some embodiments, the two wings are of the same length. In some embodiments, the two wings are of different length. In some embodiments, the number is 1, 2, 3, 4, 5, 6, 7, 8, 9, 10, 11, 12, 13, 14, 15 or more for a core. In some embodiments, the number is 1 for a core. In some embodiments, the number is 2 for a core. In some embodiments, the number is 3 for a core. In some embodiments, the number is 4 for a core. In some embodiments, the number is 5 for a core. In some embodiments, the number is 6 for a core. In some embodiments, the number is 7 for a core. In some embodiments, the number is 8 for a core. In some embodiments, the number is 9 for a core. In some embodiments, the number is 10 for a core. In some embodiments, the number is 11 for a core. In some embodiments, the number is 12 for a core. In some embodiments, the number is 13 for a core. In some embodiments, the number is 14 for a core. In some embodiments, the number is 15 for a core.

In some embodiments, a wing-core-wing is described as "X-Y-Z", where "X" represents the length of the 5' wing (as number of nucleobases), "Y" represents the length of the core (as number of nucleobases), and "Z" represents the length of the 3' wing (as number of nucleobases). Example embodiments of X, Y, and Z include those lengths described as numbers (e.g., above) and exemplified in oligonucleotide species (e.g., in Table A1/A2). In some embodiments, the two wings are of the same or different lengths and/or have the same or different modifications or patterns of modifications. In some preferred embodiments, Y is between 8 and 15. In some embodiments, X, Y or Z can each independently be 1, 2, 3, 4, 5, 6, 7, 8, 9, 10, 11, 12, 13, 14, 15, 16, 17, 18, 19, 20, 25, 30 or more. In some embodiments, each of X, Y and Z is independently 1-30. In some embodiments, X-Z-Z is 5-10-5, 5-10-4, 4-10-4, 4-10-3, 3-10-3, 2-10-2, 5-9-5, 5-9-4, 4-9-5, 5-8-5, 5-8-4, 4-8-5, 5-7-5, 4-7-5, 5-7-4, or 4-7-4. In some embodiments, the structure of a provided oligonucleotide comprises or is a wing-core or core-wing structure of, for example, 5-10, 8-4, 4-12, 12-4, 3-14, 16-2, 18-1, 10-3, 2-10, 1-10, 8-2, 2-13, 5-13, 5-8, or 6-8. In some embodiments, a wing or a core is a block, and a wing-core, core-wing, or wing-core-wing structure is a blockmer comprising two or three blocks.

In some embodiments, the structure of a provided oligonucleotide comprises or is a wing-core-wing-structure, wherein the length (in nucleobases) of the first wing is represented by X, the length of the core is represented by Y and the length of the second wing is represented by Z, wherein X-Y-Z is 1-5-1, 1-6-1, 1-7-1, 1-8-1, 1-9-1, 1-10-1, 1-11-1, 1-12-1, 1-13-1, 1-14-1, 1-15-1, 1-16-1, 1-17-1, 1-18-1, 1-19-1, 1-20-1, 1-5-2, 1-6-2, 1-7-2, 1-8-2, 1-9-2, 1-10-2, 1-11-2, 1-12-2, 1-13-2, 1-14-2, 1-15-2, 1-16-2, 1-17-2, 1-18-2, 1-19-2, 1-20-2, 1-5-3, 1-6-3, 1-7-3, 1-8-3, 1-9-3, 1-10-3, 1-11-3, 1-12-3, 1-13- 3, 1-14-3, 1-15-3, 1-16-3, 1-17-3, 1-18-3, 1-19-3, 1-20-3, 1-5-4, 1-6-4, 1-7-4, 1-8-4, 1-9-4, 1-10-4, 1-11-4, 1-12-4, 1-13-4, 1-14-4, 1-15-4, 1-16-4, 1-17-4, 1-18-4, 1-19-4, 1-20-4, 1-5-5, 1-6-5, 1-7-5, 1-8-5, 1-9-5, 1-10-5, 1-11-5, 1-12-5, 1-13-5, 1-14-5, 1-15-5, 1-16-5, 1-17-5, 1-18-5, 1-19-5, 1-20-5, 2-5-1, 2-6-1, 2-7-1, 2-8-1, 2-9-1, 2-10-1, 2-12-1, 2-12-1, 2-13-1, 2-14-1, 2-15-1, 2-16-1, 2-17-1, 2-18-1, 2-19-1, 2-20-1, 2-5-2, 2-6-2, 2-7-2, 2-8-2, 2-9-2, 2-10-2, 2-12-2, 2-12-2, 2-13-2, 2-14-2, 2-15-2, 2-16-2, 2-17-2, 2-18-2, 2-19-2, 2-20-2, 2-5-3, 2-6-3, 2-7-3, 2-8-3, 2-9-3, 2-10-3, 2-12-3, 2-12-3, 2-13-3, 2-14-3, 2-15-3, 2-16-3, 2-17-3, 2-18-3, 2-19-3, 2-20-3, 2-5-4, 2-6-4, 2-7-4, 2-8-4, 2-9-4, 2-10-4, 2-12-4, 2-12-4, 2-13-4, 2-14-4, 2-15-4, 2-16-4, 2-17-4, 2-18-4, 2-19-4, 2-20-4, 2-5-5, 2-6-5, 2-7-5, 2-8-5, 2-9-5, 2-10-5, 2-12-5, 2-12-5, 2-13-5, 2-14-5, 2-15-5, 2-16-5, 2-17-5, 2-18-5, 2-19-5, 2-20-5, 3-5-1, 3-6-1, 3-7-1, 3-8-1, 3-9-1, 3-10-1, 3-13-1, 3-14-1, 3-13-1, 3-14-1, 3-15-1, 3-16-1, 3-17-1, 3-18-1, 3-19-1, 3-20-1, 3-5-2, 3-6-2, 3-7-2, 3-8-2, 3-9-2, 3-10-2, 3-13-2, 3-14-2, 3-13-2, 3-14-2, 3-15-2, 3-16-2, 3-17-2, 3-18-2, 3-19-2, 3-20-2, 3-5-3, 3-6-3, 3-7-3, 3-8-3, 3-9-3, 3-10-3, 3-13-3, 3-14-3, 3-13-3, 3-14-3, 3-15-3, 3-16-3, 3-17-3, 3-18-3, 3-19-3, 3-20-3, 3-5-4, 3-6-4, 3-7-4, 3-8-4, 3-9-4, 3-10-4, 3-13-4, 3-14-4, 3-13-4, 3-14-4, 3-15-4, 3-16-4, 3-17-4, 3-18-4, 3-19-4, 3-20-4, 3-5-5, 3-6-5, 3-7-5, 3-8-5, 3-9-5, 3-10-5, 3-13-5, 3-14-5, 3-13-5, 3-14-5, 3-15-5, 3-16-5, 3-17-5, 3-18-5, 3-19-5, 3-20-5, 4-5-1, 4-6-1, 4-7-1, 4-8-1, 4-9-1, 4-10-1, 4-14-1, 4-14-1, 4-13-1, 4-14-1, 4-15-1, 4-16-1, 4-17-1, 4-18-1, 4-19-1, 4-20-1, 4-5-2, 4-6-2, 4-7-2, 4-8-2, 4-9-2, 4-10-2, 4-14-2, 4-14-2, 4-13-2, 4-14-2, 4-15-2, 4-16-

2, 4-17-2, 4-18-2, 4-19-2, 4-20-2, 4-5-3, 4-6-3, 4-7-3, 4-8-3, 4-9-3, 4-10-3, 4-14-3, 4-14-3, 4-13-3, 4-14-3, 4-15-3, 4-16-3, 4-17-3, 4-18-3, 4-19-3, 4-20-3, 4-5-4, 4-6-4, 4-7-4, 4-8-4, 4-9-4, 4-10-4, 4-14-4, 4-14-4, 4-13-4, 4-14-4, 4-15-4, 4-16-4, 4-17-4, 4-18-4, 4-19-4, 4-20-4, 4-5-5, 4-6-5, 4-7-5, 4-8-5, 4-9-5, 4-10-5, 4-14-5, 4-14-5, 4-13-5, 4-14-5, 4-15-5, 4-16-5, 4-17-5, 4-18-5, 4-19-5, 4-20-5, 5-5-1, 5-6-1, 5-7-1, 5-8-1, 5-9-1, 5-10-1, 5-15-1, 5-12-1, 5-13-1, 5-14-1, 5-15-1, 5-16-1, 5-17-1, 5-18-1, 5-19-1, 5-20-1, 5-5-2, 5-6-2, 5-7-2, 5-8-2, 5-9-2, 5-10-2, 5-15-2, 5-12-2, 5-13-2, 5-14-2, 5-15-2, 5-16-2, 5-17-2, 5-18-2, 5-19-2, 5-20-2, 5-5-3, 5-6-3, 5-7-3, 5-8-3, 5-9-3, 5-10-3, 5-15-3, 5-12-3, 5-13-3, 5-14-3, 5-15-3, 5-16-3, 5-17-3, 5-18-3, 5-19-3, 5-20-3, 5-5-4, 5-6-4, 5-7-4, 5-8-4, 5-9-4, 5-10-4, 5-15-4, 5-12-4, 5-13-4, 5-14-4, 5-15-4, 5-16-4, 5-17-4, 5-18-4, 5-19-4, 5-20-4, 5-5-5, 5-6-5, 5-7-5, 5-8-5, 5-9-5, 5-10-5, 5-15-5, 5-12-5, 5-13-5, 5-14-5, 5-15-5, 5-16-5, 5-17-5, 5-18-5, 5-19-5, 5-20-5, 1-5-6, 1-6-6, 1-7-6, 1-8-6, 1-9-6, 1-10-6, 1-11-6, 1-12-6, 1-13-6, 1-14-6, 1-15-6, 1-16-6, 1-17-6, 1-18-6, 1-19-6, 1-20-6, 2-5-6, 2-6-6, 2-7-6, 2-8-6, 2-9-6, 2-10-6, 2-11-6, 2-12-6, 2-13-6, 2-14-6, 2-15-6, 2-16-6, 2-17-6, 2-18-6, 2-19-6, 2-20-6, 3-5-6, 3-6-6, 3-7-6, 3-8-6, 3-9-6, 3-10-6, 3-11-6, 3-12-6, 3-13-6, 3-14-6, 3-15-6, 3-16-6, 3-17-6, 3-18-6, 3-19-6, 3-20-6, 4-5-6, 4-6-6, 4-7-6, 4-8-6, 4-9-6, 4-10-6, 4-11-6, 4-12-6, 4-13-6, 4-14-6, 4-15-6, 4-16-6, 4-17-6, 4-18-6, 4-19-6, 4-20-6, 5-5-6, 5-6-6, 5-7-6, 5-8-6, 5-9-6, 5-10-6, 5-11-6, 5-12-6, 5-13-6, 5-14-6, 5-15-6, 5-16-6, 5-17-6, 5-18-6, 5-19-6, 5-20-6, 6-5-6, 6-6-6, 6-7-6, 6-8-6, 6-9-6, 6-10-6, 6-11-6, 6-12-6, 6-13-6, 6-14-6, 6-15-6, 6-16-6, 6-17-6, 6-18-6, 6-19-6, 6-20-6, 7-5-6, 7-6-6, 7-7-6, 7-8-6, 7-9-6, 7-10-6, 7-11-6, 7-12-6, 7-13-6, 7-14-6, 7-15-6, 7-16-6, 7-17-6, 7-18-6, 7-19-6, 7-20-6, 1-5-7, 1-6-7, 1-7-7, 1-8-7, 1-9-7, 1-10-7, 1-11-7, 1-12-7, 1-13-7, 1-14-7, 1-15-7, 1-16-7, 1-17-7, 1-18-7, 1-19-7, 1-20-7, 2-5-7, 2-6-7, 2-7-7, 2-8-7, 2-9-7, 2-10-7, 2-11-7, 2-12-7, 2-13-7, 2-14-7, 2-15-7, 2-16-7, 2-17-7, 2-18-7, 2-19-7, 2-20-7, 3-5-7, 3-6-7, 3-7-7, 3-8-7, 3-9-7, 3-10-7, 3-11-7, 3-12-7, 3-13-7, 3-14-7, 3-15-7, 3-16-7, 3-17-7, 3-18-7, 3-19-7, 3-20-7, 4-5-7, 4-6-7, 4-7-7, 4-8-7, 4-9-7, 4-10-7, 4-11-7, 4-12-7, 4-13-7, 4-14-7, 4-15-7, 4-16-7, 4-17-7, 4-18-7, 4-19-7, 4-20-7, 5-5-7, 5-6-7, 5-7-7, 5-8-7, 5-9-7, 5-10-7, 5-11-7, 5-12-7, 5-13-7, 5-14-7, 5-15-7, 5-16-7, 5-17-7, 5-18-7, 5-19-7, 5-20-7, 6-5-7, 6-6-7, 6-7-7, 6-8-7, 6-9-7, 6-10-7, 6-11-7, 6-12-7, 6-13-7, 6-14-7, 6-15-7, 6-16-7, 6-17-7, 6-18-7, 6-19-7, 6-20-7, 7-5-7, 7-6-7, 7-7-7, 7-8-7, 7-9-7, 7-10-7, 7-11-7, 7-12-7, 7-13-7, 7-14-7, 7-15-7, 7-16-7, 7-17-7, 7-18-7, 7-19-7, or 7-20-7.

In some embodiments, a wing comprises one or more sugar modifications. In some embodiments, each sugar in a wing is independently modified. In some embodiments, each wing sugar in an oligonucleotide is independently modified. In some embodiments, each modified sugar independently comprises a 2'-modification (e.g., 2'-OR wherein R is optionally substituted $C_{1-6}$ aliphatic, a LNA sugar, etc.). In some embodiments, a first wing comprises a sugar modification that is absent from a second wing (in some embodiments, a first wing is a 5'-wing and a second wing is a 3'-wing; in some embodiments, a first wing is a 3'-wing and a second wing is a 5'-wing). In some embodiments, each sugar modification in a wing is the same. In some embodiments, a wing comprises different sugar modifications, e.g., different 2'-modifications. In some embodiments, a wing comprises different 2'-OR modifications, wherein each R is independently optionally substituted $C_{1-6}$ aliphatic. In some embodiments, 2'-OR is 2'-OMe. In some embodiments, 2'-OR is 2'-MOE. In some embodiments, each sugar in a wing is a 2'-MOE modified sugar (e.g., 5'-wings in certain oligonucleotides in the Tables). In some embodiments, each sugar in a wing is a 2'-OMe modified sugar. In some embodiments, a wing comprises one or more 2'-OMe modified sugars and one or more 2'-MOE modified sugars. In some embodiments, a wing is a 5'-wing. In some embodiments, a wing is a 3'-wing.

In some embodiments, the two wings of a wing-core-wing structure comprise different sugar modifications (and the oligonucleotide has or comprises an "asymmetric" format). In some embodiments, sugar modifications provide improved stability and/or annealing properties compared to absence of sugar modifications.

In some embodiments, certain sugar modifications, e.g., 2'-MOE, provide more stability under certain conditions than other sugar modifications, e.g., 2'-OMe. In some embodiments, a wing comprises 2'-MOE modifications. In some embodiments, each nucleoside unit of a wing comprising a pyrimidine base (e.g., C, U, T, etc.) comprises a 2'-MOE modification. In some embodiments, each sugar unit of a wing comprises a 2'-MOE modification. In some embodiments, each nucleoside unit of a wing comprising a purine base (e.g., A, G, etc.) comprises no 2'-MOE modification (e.g., each such nucleoside unit comprises 2'-OMe, or no 2'-modification, etc.). In some embodiments, each nucleoside unit of a wing comprising a purine base comprises a 2'-OMe modification. In some embodiments, each internucleotidic linkage at the 3'-position of a sugar unit comprising a 2'-MOE modification is a natural phosphate linkage.

In some embodiments, a wing comprises no 2'-MOE modifications. In some embodiments, a wing comprises 2'-OMe modifications. In some embodiments, each nucleoside unit of a wing independently comprises a 2'-OMe modification.

In some embodiments, the structure of a RHO oligonucleotide comprises a wing-core-wing structure, wherein one wing comprises a 2'-OMe sugar modification and the other wing comprises a bicyclic sugar. In some embodiments, the structure of a RHO oligonucleotide comprises a wing-core-wing structure, wherein one wing comprises 2'-OMe and the other wing comprises a bicyclic sugar, and the majority of the sugars in the core are natural DNA sugars (with no substitution at the 2'-position).

In some embodiments, the structure of a RHO oligonucleotide comprises a wing-core-wing structure, wherein the majority of the sugars in one wing comprise 2'-OMe and the majority of the sugars in the other wing are independently bicyclic sugars. In some embodiments, the structure of a RHO oligonucleotide comprises a wing-core-wing structure, wherein the majority of the sugars in one wing comprise 2'-OMe and the majority of the sugars in the other wing are independently bicyclic sugars, and the majority of the sugars in the core are natural DNA sugars.

In some embodiments, the structure of a RHO oligonucleotide comprises a wing-core-wing structure, wherein the majority of the sugars in one wing comprise 2'-OMe and, in the other wing, at least one sugar is a bicyclic sugar and at least one sugar comprises 2'-OMe. In some embodiments, the structure of a RHO oligonucleotide comprises a wing-core-wing structure, wherein the majority of the sugars in one wing comprise 2'-OMe and, in the other wing, at least one sugar is a bicyclic sugar and at least one sugar comprises 2'-OMe, and the majority of the sugars in the core are natural DNA sugars.

In some embodiments, the structure of a RHO oligonucleotide comprises a wing-core-wing structure, wherein the majority of the sugars in one wing are bicyclic sugars and, in the other wing, at least one sugar is a bicyclic sugar and at least one sugar comprises 2'-OMe. In some embodiments, the structure of a RHO oligonucleotide comprises a wing-core-wing structure, wherein the majority of the sugars in one wing are independently bicyclic sugars and, in the other wing, at least one sugar is a bicyclic sugar and at least one sugar comprises 2'-OMe, and the majority of the sugars in the core are natural DNA sugars.

In some embodiments, the structure of a RHO oligonucleotide comprises a wing-core-wing structure, wherein each sugar in one wing comprises 2'-OMe and each sugar in the other wing is independently a bicyclic sugar. In some embodiments, the structure of a RHO oligonucleotide comprises a wing-core-wing structure, wherein each sugar in one wing comprises 2'-OMe and each sugar in the other wing is independently a bicyclic sugar, and the majority of the sugars in the core are natural DNA sugars.

In some embodiments, the structure of a RHO oligonucleotide comprises a wing-core-wing structure, wherein each sugar in one wing is independently a bicyclic sugar, each sugar in the other wing comprises 2'-OMe, and each sugar in the core is a natural DNA sugar.

In some embodiments, the structure of a RHO oligonucleotide comprises a wing-core-wing structure, wherein one wing comprises a bicyclic sugar and the other wing comprises 2'-MOE. In some embodiments, the structure of a RHO oligonucleotide comprises a wing-core-wing structure, wherein one wing comprises a bicyclic sugar and the other wing comprises 2'-MOE, and the majority of the sugars in the core are natural DNA sugars.

In some embodiments, the structure of a RHO oligonucleotide comprises a wing-core-wing structure, wherein the majority of the sugars in one wing are independently bicyclic sugars and the majority of the sugars in the other wing comprise 2'-MOE. In some embodiments, the structure of a RHO oligonucleotide comprises a wing-core-wing structure, wherein the majority of the sugars in one wing comprise are independently bicyclic sugars and the majority of the sugars in the other wing comprise 2'-MOE, and the majority of the sugars in the core are natural DNA sugars.

In some embodiments, the structure of a RHO oligonucleotide comprises a wing-core-wing structure, wherein the majority of the sugars in one wing are independently bicyclic sugars and, in the other wing, at least one sugar comprises 2'-MOE and at least one sugar is a bicyclic sugar. In some embodiments, the structure of a RHO oligonucleotide comprises a wing-core-wing structure, wherein the majority of the sugars in one wing are independently bicyclic sugars and, in the other wing, at least one sugar comprises 2'-MOE and at least one sugar is a bicyclic sugar, and the majority of the sugars in the core are natural DNA sugars.

In some embodiments, the structure of a RHO oligonucleotide comprises a wing-core-wing structure, wherein the majority of the sugars in one wing comprise 2'-MOE and, in the other wing, at least one sugar comprises 2'-MOE and at least one sugar is a bicyclic sugar. In some embodiments, the structure of a RHO oligonucleotide comprises a wing-core-wing structure, wherein the majority of the sugars in one wing comprise 2'-MOE and, in the other wing, at least one sugar comprises 2'-MOE and at least one sugar is a bicyclic sugar, and the majority of the sugars in the core are natural DNA sugars.

In some embodiments, the structure of a RHO oligonucleotide comprises a wing-core-wing structure, wherein each sugar in one wing is independently a bicyclic sugar and each sugar in the other wing independently comprises 2'-MOE. In some embodiments, the structure of a RHO oligonucleotide comprises a wing-core-wing structure, wherein each sugar in one wing is independently a bicyclic sugar and each sugar in the other wing of the oligonucleotide comprises 2'-MOE, and the majority of the sugars in the core are natural DNA sugars.

In some embodiments, the structure of a RHO oligonucleotide comprises a wing-core-wing structure, wherein each sugar in one wing comprises 2'-MOE, each sugar in the other wing is independently a bicyclic sugar, and each sugar in the core is a natural DNA sugar.

In some embodiments, a bicyclic sugar is a LNA, a cEt or a BNA sugar.

In some embodiments, an oligonucleotide, e.g., a RHO oligonucleotide, has a wing-core-wing structure. In some embodiments, a core comprises 1 or more natural DNA sugars. In some embodiments, a core comprises 5 or more consecutive natural DNA sugars. In some embodiments, the core comprises 5-10, 5-15, 5-20, 5-25, 5-30, or 5, 6, 7, 8, 9, 10, 11, 12, 13, 14, 15 or more natural DNA sugars which are optionally consecutive. In some embodiments, the core comprises 5, 6, 7, 8, 9, 10, 11, 12, 13, 14, 15 or more consecutive natural DNA sugars. In some embodiments, a core comprises 10 or more natural DNA sugars. In some embodiments, a core comprises 10 or more consecutive natural DNA sugars. In some embodiments, the core is able to hybridize to a target mRNA, forming a duplex structure recognizable by RNaseH, such that RNaseH is able to cleave the mRNA.

In some embodiments, an oligonucleotide, e.g., a RHO oligonucleotide, has a wing-core-wing structure and has an asymmetrical format.

In some embodiments, in an oligonucleotide having an asymmetrical format, one wing differs from another in the sugar modifications or pattern thereof, or the backbone internucleotidic linkages or pattern thereof, or the backbone chiral centers or pattern thereof. In some embodiments, an oligonucleotide, e.g., a RHO oligonucleotide, has an asymmetrical format in that one wing comprises a different sugar modification than the other wing. In some embodiments, an oligonucleotide, e.g., a RHO oligonucleotide, has an asymmetrical format in that one wing comprises a different pattern of sugar modifications than the other wing.

In some embodiments, a mixmer is an oligonucleotide wherein the various sugars of the oligonucleotide comprise at least two different types of sugars, wherein the regions comprising one type of sugar are not readily divided by sugar type into two or three distinct regions (e.g., a wing-core or wing-core-wing), as the types of sugars are mixed. In some embodiments, an oligonucleotide, e.g., a RHO oligonucleotide, is a mixmer. In some embodiments, an oligonucleotide comprising at least one chirally controlled internucleotidic linkage is a mixmer.

In some embodiments, the pattern of sugars in an oligonucleotide is or comprises a sequence of: D~~D~~D~~D~~, D~~DD~~D, DDD~~D~~, DD~~D~~D, D~~D~~DD, ~~D~~DDD, ~~D~~DD~~D~~, ~~DD~~DD, ~~D~~D~~D~~D, D~~D~~D~~D~~, DDDD, ~~DDDD~~, DD~~D~~D, DD~~DD~~, ~~DDD~~, ~~D~~D~~DD~~, ~~DD~~D~~D~~, ~~DDD~~D, ~~DD~~D~~D~~, ~~DD~~D~~D~~D, ~~DD~~D~~D~~DD, ~~DD~~D~~D~~DD~~D~~, ~~DD~~, ~~DD~~D~~D~~DD~~D~~D~~D~~, ~~DD~~D~~D~~DD~~D~~D~~D~~D, ~~DD~~D~~D~~DD~~D~~D~~D~~DD, ~~DD~~D~~D~~DD~~D~~D~~D~~DD~~D~~, ~~DD~~, D~~DD~~, DD~~DD~~, ~~D~~DD~~DD~~, D~~D~~DD~~DD~~, ~~D~~D~~D~~DD~~DD~~, D~~D~~D~~D~~DD~~DD~~, DD~~D~~D~~D~~DD~~DD~~, D~~D~~DD~~D~~D~~D~~DD~~DD~~, ~~D~~D~~D~~DD~~D~~D~~D~~DD~~DD~~, ~~DD~~D~~D~~DD~~D~~D~~D~~DD~~DD~~, wherein D is 2'-deoxyribose (unmodified DNA sugar) and D is a sugar which is not a 2'-deoxyribose.

In some embodiments, the pattern of sugars in an oligonucleotide is or comprises a sequence of: DLDL, DLLD, DDDL, DDLD, DLDD, LDDD, LDDL, LLDD, LDLD, DLDL, DDDD, LLLL, DDLD, DDLL, DLLL, LDLL, LLDL, LLLD, LLDL, LLDLD, LLDLDD, LLDLDDL, LLDLDDLD, LLDLDDLDL, LLDLDDLDLD, LLDLD-DLDLDD, LLDLDDLDLDDL, LL, DLL, DDLL, LDDLL, DLDDLL, LDLDDLL, DLDLDDLL, DDLDLDDLL, DDLDLDDLL, DLDDLDLDDLL, LDLDDLDLDDLL, LLDLDDLDLDDLL, LLDLDDLDLDDLL, wherein L is LNA sugar modification, and D is 2'-deoxyribose (unmodified DNA sugar).

Among other things, 2'-modifications and/or modified internucleotidic linkages can be utilized either individually or in combination to fine-tune properties, e.g., stability, and/or activities of oligonucleotides. In some embodiments, modified (non-natural) internucleotidic linkages (which are not natural phosphate linkage or salt forms thereof), such as phosphorothioate linkages (phosphorothioate diester linkages), can be utilized to improve properties, e.g., stability (e.g., by using Sp phosphorothioate linkages), of an oligonucleotide. In some embodiments, in an oligonucleotide, e.g., a RHO oligonucleotide, a particular modified internucleotidic linkage can be used in combination with a particular sugar to achieve desired properties and/or activities. In some embodiments, a wing comprises no 2'-MOE modifications, and each internucleotidic linkage between nucleoside units of the wing is a modified internucleotidic linkage. In some embodiments, a wing comprises no 2'-MOE modifications, each nucleoside unit of the wing comprise a 2'-OMe modification, and each internucleotidic linkage between nucleoside units of the wing is a modified internucleotidic linkage. In some embodiments, a modified internucleotidic linkage is a phosphorothioate linage. In some embodiments, a modified internucleotidic linkage is a chirally controlled internucleotidic linkage. In some embodiments, a modified internucleotidic linkage is a chirally controlled internucleotidic linkage wherein the linkage phosphorus is of Sp configuration. In some embodiments, a modified internucleotidic linkage is a chirally controlled internucleotidic linkage wherein the linkage phosphorus is of Rp configuration. In some embodiments, a modified internucleotidic linkage is a Sp phosphorothioate linkage. In some embodiments, a modified internucleotidic linkage is a Rp phosphorothioate linkage. In some embodiments, such a wing is a 5'-wing. In some embodiments, such a wing is a 3'-wing.

In some embodiments, a region, e.g., a wing, of an oligonucleotide, e.g., a RHO oligonucleotide, comprises one or more, e.g., 1, 2, 3, 4, 5, 6 or more, natural phosphate linkages. In some embodiments, a wing comprises one or more, e.g., 1, 2, 3, 4, 5, 6 or more, consecutive natural phosphate linkages. In some embodiments, the number of natural phosphate linkage is 1. In some embodiments, the number of natural phosphate linkages is 2. In some embodiments, the number of natural phosphate linkages is 3. In some embodiments, the number of natural phosphate linkages is 4. In some embodiments, the number of natural phosphate linkages is 5. In some embodiments, the number of natural phosphate linkages is 6. In some embodiments, 2 natural phosphate linkages are consecutive. In some embodiments, 3 natural phosphate linkages are consecutive. In some embodiments, 4 natural phosphate linkages are consecutive. In some embodiments, 5 natural phosphate linkages are consecutive. In some embodiments, 6 natural phosphate linkages are consecutive. In some embodiments, all natural phosphate linkages in a wing are consecutive. In some embodiments, a wing comprises one or more natural phosphate linkages (in some embodiments, one or more consecutive natural phosphate linkages as described herein) and one or more modified internucleotidic linkages. In some embodiments, the first internucleotidic linkage and/or the last internucleotidic linkage of a wing is a modified internucleotidic linkage. In some embodiments, the first internucleotidic linkage (counting from 5' to 3') of a 5' wing (to the 5'-end of a core) is a modified internucleotidic linkage. In some embodiments, the last internucleotidic linkage (counting from 5' to 3') of a 3' wing (to the 3'-end of a core) is a modified internucleotidic linkage. In some embodiments, a wing contains one and no more than one modified internucleotidic linkage (all the other internucleotidic linkages are natural phosphate linkages). In some embodiments, the single modified internucleotidic linkage is the first internucleotidic linkage of a wing if the wing is a 5'-wing, or the last internucleotidic linkage of the wing if the wing is a 3'-wing. In some embodiments, the single modified internucleotidic linkage of a wing is the first internucleotidic linkage of the oligonucleotide if the wing is a 5'-wing, and/or the last internucleotidic linkage of the oligonucleotide if the wing is a 3'-wing. In some embodiments, the last internucleotidic linkage of a 5'-wing is a natural phosphate linkage, and/or the first internucleotidic linkage of a 3'-wing is a natural phosphate linkage. In some embodiments, a modified internucleotidic linkage is Sp. In some embodiments, a modified internucleotidic linkage is Rp. In some embodiments, a modified internucleotidic linkage is a phosphorothioate linkage. In some embodiments, a modified internucleotidic linkage is a Sp phosphorothioate linkage. In some embodiments, a modified internucleotidic linkage is a Rp phosphorothioate linkage. In some embodiments, a natural phosphate linkage is bonded to at least one sugar which is a bicyclic sugar or a sugar comprising 2'-MOE. In some embodiments, a natural phosphate linkage is bonded to two sugars each of which is independently a bicyclic sugar or a sugar comprising 2'-MOE. In some embodiments, one or both sugars bonded to a natural phosphate linkage are independently bicyclic sugars. In some embodiments, one or both sugars bonded to a natural phosphate linkage independently comprise 2'-MOE.

In some embodiments, a wing comprises one and only one modified internucleotidic linkages, and each other internucleotidic linkages linking two wing nucleosides in independently a natural phosphate linkage. In some embodiments, in a 5'-wing (to the 5' of a core), the first internucleotidic linkage from the 5'-end is a modified internucleotidic linkage. In some embodiments, in a 3'-wing (to the 3' of a core), the first internucleotidic linkage from the 3'-end is a modified internucleotidic linkage. In some embodiments, a modified internucleotidic linkage is chirally controlled and is Sp. In some embodiments, a modified internucleotidic linkage is chirally controlled and is Rp. In some embodiments, a modified internucleotidic linkage is a chirally controlled Sp phosphorothioate internucleotidic linkage. In some embodiments, a modified internucleotidic linkage is a chirally controlled Rp phosphorothioate internucleotidic linkage. Among other things, the present disclosure demonstrates that Rp internucleotidic linkages can be utilized as the 5'-end and/or the 3'-end internucleotidic linkages despite that in some cases they are less stable than corresponding Sp internucleotidic linkages, e.g., toward nuclease activities.

In some embodiments, each internucleotidic linkage linking two sugars comprising 2'-OR', wherein R' is optionally substituted alkyl, is independently a natural phosphate linkage, except the 5'-end and the 3'-end internucleotidic linkages, which are independently optionally chirally controlled modified internucleotidic linkages (e.g., in some embodiments, chirally controlled phosphorothioate internucleotidic linkages). In some embodiments, each wing sugar modification, if any, is independently 2'-OR', wherein R' is optionally $C_{1-6}$ substituted alkyl. In some embodiments, each wing sugar independently comprises a 2'-OR' modification, wherein R' is optionally $C_{1-6}$ substituted alkyl. In some embodiments, each sugar comprising a 2'-OR' modification, wherein R' is optionally $C_{1-6}$ substituted alkyl, is a sugar in a wing. In some embodiments, each modified sugar of an oligonucleotide independently comprises a 2'-OR' modification, wherein R' is optionally $C_{1-6}$ substituted alkyl. In some embodiments, R' is methyl.

In some embodiments, a wing comprises one or more modified internucleotidic linkages. In some embodiments, a wing comprises one or more modified internucleotidic linkages in addition to one or more natural phosphate linkages. In some embodiments, 1, 2, 3, 4, 5, 6, 7, 8, 9, or 10 or more, or 10%, 20%, 30%, 40%, 50%, 60%, 70%, 80%, or 90% or more, or all internucleotidic linkages that are bonded to two wing sugars are independently modified internucleotidic linkages. In some embodiments, a modified internucleotidic linkage is a phosphorothioate internucleotidic linkage. In some embodiments, a wing comprises 1, 2, 3, 4, 5, 6, 7, 8, 9, 10 or more phosphorothioate internucleotidic linkages. In some embodiments, a modified internucleotidic linkage is a non-negatively charged internucleotidic linkage as described herein. In some embodiments, a wing comprises 1, 2, 3, 4, 5, 6, 7, 8, 9, 10 or more non-negatively charged internucleotidic linkages. In some embodiments, a wing comprises 1, 2, 3, 4, 5, 6, 7, 8, 9, 10 or more phosphorothioate internucleotidic linkages and 1, 2, 3, 4, 5, 6, 7, 8, 9, 10 or more non-negatively charged internucleotidic linkages. In some embodiments, each internucleotidic linkage bonded to two wing sugars is independently selected from a phosphorothioate internucleotidic linkage, a non-negatively charged internucleotidic linkage and a natural phosphate linkage. In some embodiments, each internucleotidic linkage bonded to two wing sugars is independently selected from a phosphorothioate internucleotidic linkage and a non-negatively charged internucleotidic linkage. In some embodiments, a non-negatively charged internucleotidic linkage is a neutral internucleotidic linkage. In some embodiments, a non-negatively charged internucleotidic linkage is n001. In some embodiments, each phosphorothioate internucleotidic linkage is independently chirally controlled. In some embodiments, one or more or all non-negatively charged internucleotidic linkages are not chirally controlled.

In some embodiments, the first internucleotidic linkage of a 5'-wing is a phosphorothioate internucleotidic linkage. In some embodiments, the first internucleotidic linkage of a 5'-wing is a phosphorothioate internucleotidic linkage which is chirally controlled and is Sp. In some embodiments, an internucleotidic linkage between two internal 5'-wing nucleosides (not the first and the last) is a non-negatively charged internucleotidic linkage. In some embodiments, an internucleotidic linkage between two internal 5'-wing nucleosides (not the first and the last) is a natural phosphate linkage. In some embodiments, each 5'-wing internucleotidic linkage is independently selected from a phosphorothioate internucleotidic linkage, a non-negatively charged internucleotidic linkage (e.g., n001) and a natural phosphate linkage. In some embodiments, the first internucleotidic linkage is the only phosphorothioate internucleotidic linkage in a 5'-wing. In some embodiments, it is Sp. In some embodiments, the last internucleotidic linkage of a 3'-wing is a phosphorothioate internucleotidic linkage. In some embodiments, the last internucleotidic linkage of a 3'-wing is a phosphorothioate internucleotidic linkage which is chirally controlled and is Sp. In some embodiments, the last internucleotidic linkage of a 3'-wing is a non-negatively charged internucleotidic linkage, e.g., n001.

In some embodiments, a wing comprises one or more Sp chirally controlled modified internucleotidic linkages. In some embodiments, at least 50%, 60%, 70%, 80%, or 90%, or all chirally controlled phosphorothioate internucleotidic linkages are Sp. In some embodiments, at least 50%, 60%, 70%, 80%, or 90%, or all phosphorothioate internucleotidic linkages are chirally controlled and are Sp. In some embodiments, a wing comprises one or more Rp chirally controlled phosphorothioate internucleotidic linkages. In some embodiments, at least 50%, 60%, 70%, 80%, or 90%, or all chirally controlled non-negatively charged internucleotidic linkages, e.g., n001, are Rp. In some embodiments, at least 50%, 60%, 70%, 80%, or 90%, or all non-negatively charged internucleotidic linkages, e.g., n001, are chirally controlled and are Rp. In some embodiments, at least 50%, 60%, 70%, 80%, or 90%, or all non-negatively charged internucleotidic linkages, e.g., n001, are not chirally controlled.

In some embodiments, an internucleotidic linkage bonded to a modified sugar and a natural DNA sugar is a modified internucleotidic linkage as described herein. In some embodiments, an internucleotidic linkage bonded to a wing sugar and a core sugar is a modified internucleotidic linkage as described herein. In some embodiments, as described herein, a modified internucleotidic linkage is a phosphorothioate internucleotidic linkage. In some embodiments, it is chirally controlled and is Rp. In some embodiments, it is chirally controlled and is Sp. In some embodiments, an internucleotidic linkage bonded to a 5'-wing sugar and a core sugar is chirally controlled and is Rp. In some embodiments, an internucleotidic linkage bonded to a 5'-wing sugar and a core sugar is chirally controlled and is Sp. In some embodiments, an internucleotidic linkage bonded to a 3'-wing sugar and a core sugar is chirally controlled and is Rp. In some embodiments, an internucleotidic linkage bonded to a 3'-wing sugar and a core sugar is chirally controlled and is Sp. In some embodiments, an internucleotidic linkage bonded to a wing sugar and a core sugar is included in a pattern of backbone chiral centers (linkage phosphorus) of a core.

In some embodiments, a core is differentiated from a first or second wing by the modification(s) of sugar(s) or combination(s) or pattern(s) thereof.

In some embodiments, an internucleotidic linkage bonded to a wing nucleoside and a core nucleoside is considered one of the core internucleotidic linkages, for example, when describing types, modifications, numbers, and/or patterns of core internucleotidic linkages. In some embodiments, each internucleotidic linkage bonded to a wing nucleoside and a core nucleoside is considered one of the core internucleotidic linkages, for example, when describing types, modifications, numbers, and/or patterns of core internucleotidic linkages.

In some embodiments, a wing comprises no natural phosphate linkages, and each internucleotidic linkage of the wing is independently a modified internucleotidic linkage. In some embodiments, a modified internucleotidic linkage is chiral and chirally controlled. In some embodiments, a modified internucleotidic linkage is a phosphorothioate linkage. In some embodiments, a modified internucleotidic linkage is a phosphorothioate linkage. In some embodiments, each internucleotidic linkage in a wing is a modified internucleotidic linkage. In some embodiments, each internucleotidic linkage in a wing is a phosphorothioate linkage. In some embodiments, each internucleotidic linkage in a wing is a Sp phosphorothioate internucleotidic linkage. In some embodiments, a modified internucleotidic linkage is a Sp phosphorothioate linkage. In some embodiments, in a wing-core-wing structure, one wing (e.g., the 5' wing) comprises one or more natural phosphate linkages as described in the present disclosure (in some embodiments, one or more consecutive natural phosphate linkages), and the other wing (e.g., the 3'-wing) contains no natural phosphate linkages as described in the present disclosure.

In some embodiments, the structure of a RHO oligonucleotide comprises or consists of a wing-core-wing structure, wherein one wing comprises 2'-OR modifications wherein R is optionally substituted $C_{1-6}$ alkyl (e.g., 2'-MOE), while the other wing comprises no modifications of the same structure as a modification of the first wing, or a lower level (e.g., by number and/or percentage) of such modifications; additionally or alternatively, one wing comprises natural phosphate linkages while the other wing comprises no natural phosphate linkages or a lower level (e.g., by number and/or percentage) of natural phosphate linkages; additionally or alternatively, one wing may comprise a certain type of modified internucleotidic linkages (e.g., phosphorothioate internucleotidic linkage) while the other wing comprises no such type of modified internucleotidic linkages or a lower level (e.g., by number and/or percentage) of the type of modified internucleotidic linkages; additionally or alternatively, one wing may comprise chiral modified internucleotidic linkages comprising linkage phosphorus atoms of a particular configuration (e.g., Rp or Sp), while the other wing comprises no or a lower level of chiral modified internucleotidic linkages comprising linkage phosphorus atoms of the particular configuration; alternatively or additionally, each wing may comprise a different pattern of sugar modification, internucleotidic linkages, and/or backbone chiral centers. In some embodiments, one wing comprises one or more natural phosphate linkages and one or more 2'-OR modifications wherein R is not —H or -Me, and the other wing comprises no natural phosphate linkages and no 2'-OR modifications wherein R is not —H or -Me. In some embodiments, one wing comprises one or more natural phosphate linkages and one or more 2'-MOE modifications, and each internucleotidic linkage in the other wing is a phosphorothioate linkage and each sugar of the other wing comprises a 2'-OMe modification. In some embodiments, one wing comprises one or more natural phosphate linkages and one or more 2'-MOE modifications, and each internucleotidic linkage in the other wing is a Sp phosphorothioate linkage and each sugar of the other wing comprises 2'-OMe modification.

In some embodiments, the structure of a RHO oligonucleotide comprises or consists of a wing-core-wing structure in an asymmetrical format, wherein a first wing and a second wing independently has a pattern of internucleotidic linkages which is or comprises PS, PO, PS—PS, PS—PO, PO—PS, PO—PO, PO—PS—PS, PS—PO—PO—PO—PS, PS—PO—PO—PS, PS—PS—PS—PS, PS—PS—PS—PS—PS, PS-nX-nX-nX-PS, or a pattern of internucleotidic linkages of a wing of an oligonucleotide in Table A1 or A2, wherein the patterns of internucleotidic linkages of the first and second wing are different, wherein PS represents a phosphorothioate linkage, PO represents a natural phosphate linkage, and nX (or Xn) represents a non-negatively charged internucleotidic linkage. In some embodiments, the structure of an oligonucleotide comprises or consists of a wing-core-wing structure in an asymmetrical format, wherein a first wing and a second wing independently has a pattern of stereochemistry of internucleotidic linkages which is or comprises O, SR, Sp, Rp, Sp-O, Rp-O, O-Sp, O-Rp, O—O—O, Sp-O—O, Rp-O—O, Rp-O—O—O-Rp, Rp-O—O-Rp-Rp, Rp-O-Rp-O-Rp, Rp-Rp-O—O-Rp, Sp-O—O—O-Sp, Sp-Sp-Sp-Sp, Sp-Sp-Sp-Sp, Sp-Sp-Sp-Sp-Sp, Sp-nX-nX-nX-Sp, SR—O—O—O—SR, SR—SR—SR—SR, SR—SR—SR—SR—SR, SR-nX-nX-nX-SR, or a pattern of stereochemistry of internucleotidic linkages of a wing of an oligonucleotide in Table A1 or A2, wherein the pattern of stereochemistry of internucleotidic linkages of the first and second wing are different, and wherein SR represents a linkage phosphorus of an internucleotidic linkage being stereorandom (e.g., not chirally controlled), O represents a linkage phosphorus of a natural phosphate linkage being achiral, Sp represents an internucleotidic linkage being in the Sp configuration, Rp represents an internucleotidic linkage being in the Rp configuration, and each nX independently represents stereochemistry of the linkage phosphorus of a non-negatively charged internucleotidic linkage which is independently chirally controlled (in the Rp or Sp configuration) or stereorandom. In some embodiments of an oligonucleotide having an asymmetrical format, the first wing is the 5' wing and the second wing is the 3'-wing. In some embodiments of an oligonucleotide having an asymmetrical format, the first wing is the 3' wing and the second wing is the 5'-wing. In some embodiments, the first and second wings are of the same or different lengths.

In some embodiments, an oligonucleotide, e.g., a RHO oligonucleotide, having an asymmetrical structure (e.g., wherein one wing differs chemically from another wing in sugar modifications and/or patterns thereof, internucleotidic linkage types and/or stereochemistry, etc.) has improved properties and/or activities compared to an oligonucleotide having the same base sequence but a different structure (e.g., a symmetric structure wherein both wings have the same pattern of chemical modifications, or a different asymmetrical structure). As used in the present disclosure, in some embodiments, improved activity includes improved decrease of the expression, activity, and/or level or a gene or gene product. In some embodiments, improved activity is improved delivery to a cellular nucleus. In some embodiments, improved activity is improved delivery to a cellular nucleus and one wing in an oligonucleotide having an asymmetrical structure comprises 2'-F or two or more 2'-F. In some embodiments, improved activity is improved delivery to a cellular nucleus and one wing in an oligonucleotide having an asymmetrical structure comprises 2'-MOE or two or more 2'-MOE. In some embodiments, improved activity is improved delivery to a cellular nucleus and one wing in an oligonucleotide having an asymmetrical structure comprises 2'-OMe or two or more 2'-OMe. In some embodiments, improved activity is improved delivery to a cellular nucleus and one wing in an oligonucleotide having an asymmetrical structure comprises a bicyclic sugar or two or more bicyclic sugars. In some embodiments, the other wing does not contain such sugar modifications.

In some embodiments, a core of an oligonucleotide, e.g., a RHO oligonucleotide, comprises no more than 1, 2, 3, 4, or 5, or no more than 10%, 20%, 30%, 40%, or 50%, or no sugars comprising a 2'-OR modification wherein R is optionally substituted $C_{1-6}$ aliphatic. In some embodiments, a core of an oligonucleotide, e.g., a RHO oligonucleotide, comprises no 2'-substitution, and each sugar is a natural sugar found in natural unmodified DNA.

In some embodiments, no less than 70%, 80%, 90% or 100% of internucleotidic linkages in a core are independently modified internucleotidic linkages. In some embodiments, no less than 60%, 70%, 80%, or 90% of internucleotidic linkages in a core are independently modified internucleotidic linkages of Sp configuration, and the core comprises 1, 2, 3, 4, 5, or 6 internucleotidic linkages independently selected from modified internucleotidic linkages of Rp configuration and natural phosphate linkages. In some embodiments, a core comprises 1 or 2 internucleotidic linkages independently selected from modified internucleotidic linkages of Rp configuration and natural phosphate linkages. In some embodiments, a core comprises 1 and no more than 1 internucleotidic linkage selected from a modified internucleotidic linkage of Rp configuration and a natural phosphate linkage, and the rest internucleotidic linkages of the core are independently modified internucleotidic linkages of Sp configuration. In some embodiments, a core comprises 2 and no more than 2 internucleotidic linkages each independently selected from a modified internucleotidic linkage of Rp configuration and a natural phosphate linkage, and the rest internucleotidic linkages of the core are independently modified internucleotidic linkages of Sp configuration. In some embodiments, a core comprises 1 and no more than 1 natural phosphate linkage, and the rest internucleotidic linkages in the core are independently modified internucleotidic linkages of Sp configuration. In some embodiments, a core comprises 2 and no more than 2 natural phosphate linkages, and the rest internucleotidic linkages are independently modified internucleotidic linkages of Sp configuration. In some embodiments, a core comprises 1 and no more than 1 modified internucleotidic linkage of Rp configuration, and the rest internucleotidic linkages are independently modified internucleotidic linkages of Sp configuration. In some embodiments, a core comprises 2 and no more than 2 modified internucleotidic linkages of Rp configuration, and the rest internucleotidic linkages are independently modified internucleotidic linkages of Sp configuration. In some embodiments, internucleotidic linkages that are not modified internucleotidic linkages of Sp configuration (e.g., each and every pair of two natural phosphate linkages, two modified internucleotidic linkages of Rp configuration, or one natural phosphate linkage and one modified internucleotidic linkage) are separated by two or more modified internucleotidic linkages of Sp configuration. For example, in RSSRSSSSRSS, the Rp internucleotidic linkages (R) are separated by at least two Sp internucleotidic linkages (S). In some embodiments, a modified internucleotidic linkage is a phosphorothioate linkage.

In some embodiments, as described herein, patterns of backbone chiral centers of a core or of an oligonucleotide comprises one or more RpSpSp or (Sp)tRp(Sp)m units, wherein each of t and m is independently as described herein. In some embodiments, m is 2 or more. In some embodiments, each of t and m is independently 2 or more. In some embodiments, at least one or each Rp internucleotidic linkage of such units is independently bonded to two core sugars. In some embodiments, an Rp of an RpSpSp or (Sp)tRp(Sp)m unit is at a +1, +2, +3, −1, −2, or −3 position relative to a differentiating position (a position whose nucleobase or whose complementary nucleobase can differentiate a target sequence (e.g., comprising Rho P23H mutation) from other sequences (e.g., comprising no Rho P23H mutation such as a wild type sequence)). Unless otherwise specified, for Rp internucleotidic linkage positioning, "−" is counting from the nucleoside at a differentiating position toward the 5'-end of an oligonucleotide with the internucleotidic linkage at the −1 position being the internucleotidic linkage bonded to the 5'-carbon of the nucleoside at the differentiating position, and "+" is counting from the nucleoside at a differentiating position toward the 3'-end of an oligonucleotide with the internucleotidic linkage at the +1 position being the internucleotidic linkage bonded to the 3'-carbon of the nucleoside at the differentiating position. In some embodiments, a pattern of backbone chiral centers of an oligonucleotide or a portion (e.g., a core) thereof is or comprises Rp(Sp)m, wherein the Rp is at +1 position and m is 2 or more. In some embodiments, a pattern of backbone chiral centers of an oligonucleotide or a portion (e.g., a core) thereof is or comprises Rp(Sp)m, wherein the Rp is at +2 position and m is 2 or more. In some embodiments, a pattern of backbone chiral centers of an oligonucleotide or a portion (e.g., a core) thereof is or comprises Rp(Sp)m, wherein the Rp is at +3 position and m is 2 or more. In some embodiments, a pattern of backbone chiral centers of an oligonucleotide or a portion (e.g., a core) thereof is or comprises Rp(Sp)m, wherein the Rp is at −1 position and m is 2 or more. In some embodiments, a pattern of backbone chiral centers of an oligonucleotide or a portion (e.g., a core) thereof is or comprises Rp(Sp)m, wherein the Rp is at −2 position and m is 2 or more. In some embodiments, a pattern of backbone chiral centers of an oligonucleotide or a portion (e.g., a core) thereof is or comprises Rp(Sp)m, wherein the Rp is at −3 position and m is 2 or more. In some embodiments, a pattern of backbone chiral centers of an oligonucleotide or a portion (e.g., a core) thereof is or comprises (Sp)tRp(Sp)m, wherein the Rp is at +1 position and m is 2 or more. In some embodiments, a pattern of backbone chiral centers of an oligonucleotide or a portion (e.g., a core) thereof is or comprises (Sp)tRp(Sp)m, wherein the Rp is at +2 position and m is 2 or more. In some embodiments, a pattern of backbone chiral centers of an oligonucleotide or a portion (e.g., a core) thereof is or comprises (Sp)tRp(Sp)m, wherein the Rp is at +3 position and m is 2 or more. In some embodiments, a pattern of backbone chiral centers of an oligonucleotide or a portion (e.g., a core) thereof is or comprises (Sp)tRp(Sp)m, wherein the Rp is at −1 position and m is 2 or more. In some embodiments, a pattern of backbone chiral centers of an oligonucleotide or a portion (e.g., a core) thereof is or comprises (Sp)tRp(Sp)m, wherein the Rp is at −2 position and m is 2 or more. In some embodiments, a pattern of backbone chiral centers of an oligonucleotide or a portion (e.g., a core) thereof is or comprises (Sp)tRp(Sp)m, wherein the Rp is at −3 position and m is 2 or more. In some embodiments, t is 1. In some embodiments, t is 2. In some embodiments, t is 2 or more. In some embodiments, t is 1-10 (e.g., 1, 2, 3, 4, 5, 6, 7, 8, 9, or 10). In some embodiments, m is 2. In some embodiments, m is 2 or more. In some embodiments, m is 2–10 (e.g., 2, 3, 4, 5, 6, 7, 8, 9, or 10). In some embodiments, Rp of Rp(Sp)m or (Sp)tRp(Sp)m is the $1^{st}$, $2^{nd}$, $3^{rd}$, $4^{th}$, $5^{th}$, $6^{th}$, $7^{th}$, $8^{th}$, $9^{th}$, $10^{th}$, $11^{th}$, $12^{th}$, $13^{th}$, $14^{th}$, $15^{th}$, $16^{th}$, $17^{th}$, $18^{th}$, $19^{th}$, or $20^{th}$ internucleotidic linkage of an oligonucleotide or a portion (e.g., a core) thereof. In some embodiments, it is the $3^{rd}$, $4^{th}$, $5^{th}$, $6^{th}$, $7^{th}$, $8^{th}$, $9^{th}$, $10^{th}$ $11^{th}$, $12^{th}$, $13^{th}$, $14^{th}$, $15^{th}$, $16^{th}$, $17^{th}$, $18^{th}$, $19^{th}$, or $20^{th}$ internucleotidic linkage of a core (the $1^{st}$ internucleotidic linkage being the internucleotidic linkage bonded to a 5'-wing sugar and a core sugar). In some embodiments, it is the $5^{th}$ of a core. In some embodiments, it is the $6^{th}$ of a core. In some embodiments, it is the $7^{th}$ of a core. In some embodiments, it is the $8^{th}$ of a core. In some embodiments, it is the $9^{th}$ of a core. In some embodiments, it is the $10^{th}$ of a core. In some embodiments, it is the $5^{th}$ of an oligonucleotide. In some embodiments, it is the $6^{th}$ of an oligonucleotide. In some embodiments, it is the $7^{th}$ of an oligonucleotide. In some embodiments, it is the $8^{th}$ of an oligonucleotide. In some embodiments, it is the $9^{th}$ of an oligonucleotide. In some embodiments, it is the $10^{th}$ of an oligonucleotide. In some embodiments, it is the $11^{th}$ of an oligonucleotide. In some embodiments, it is the $12^{th}$ of an oligonucleotide. In some embodiments, it is the $13^{th}$ of an oligonucleotide. In some embodiments, it is the $14^{th}$ of an oligonucleotide. In some embodiments, it is the $15^{th}$ of an oligonucleotide.

In some embodiments, a nucleobase at a differentiating position is complementary to a differentiating element/characteristic sequence element in a target sequence (e.g., a particular SNP allele, a mutation, etc.) is at position 2, 3, 4, 5, 6, 7, 8, 9, 10, 11, 12, 13, 14, or 15 of a core (from 5' to 3', the first nucleobase of the core is at position 1). In some embodiments, a position is 5. In some embodiments, a position is 6. In some embodiments, a position is 7. In some embodiments, a position is 8. In some embodiments, a position is 9. In some embodiments, a position is 10. In some embodiments, such a nucleobase is at position 5, 6, 7, 8, 9, 10, 11, 12, 13, 14, 15, 16, 17, 18, 19, or 20 of an oligonucleotide (the first nucleobase from the 5'-end of an oligonucleotide is at position 1). In some embodiments, a position is 5. In some embodiments, a position is 6. In some embodiments, a position is 7. In some embodiments, a position is 8. In some embodiments, a position is 9. In some embodiments, a position is 10. In some embodiments, a position is 11. In some embodiments, a position is 12. In some embodiments, a position is 13. In some embodiments, a position is 14. In some embodiments, a position is 15. In some embodiments, a position is 16. In some embodiments, a position is 17. In some embodiments, a position is 18. In some embodiments, a position is 19. In some embodiments, a position is 20.

As described herein, core and wings can be of various lengths. In some embodiments, a core comprises no less than 5, 6, 7, 8, 9, 10, 11, 12, 13, 14, 15, 16, 17, 18, 19, or 20 nucleobases. In some embodiments, a wing comprises no less than 1, 2, 3, 4, 5, 6, 7, 8, 9, or 10 nucleobases. In some embodiments, a wing comprises no more than 2, 3, 4, 5, 6, 7, 8, 9, or 10 nucleobases. In some embodiments, for a wing-core-wing structure, both wings are of the same length, for example, of 5 nucleobases. In some embodiments, the two wings are of different lengths. In some embodiments, a core is no less than 40%, 45%, 50%, 60%, 70%, 80%, or 90% of total oligonucleotide length as measured by percentage of nucleoside units within the core over all nucleoside units of the oligonucleotide chain. In some embodiments, a core is no less than 50% of total oligonucleotide length.

In some embodiments, a region, e.g., a wing, a core, etc. is a block. In some embodiments, a region is a sugar modification block in that all sugars in the region are the same.

In some embodiments, an oligonucleotide, e.g., a RHO oligonucleotide, is a gapmer.

In some embodiments, an oligonucleotide, e.g., a RHO oligonucleotide, is a hemimer. In some embodiments, a hemimer is an oligonucleotide wherein a 5'-end or a 3'-end region has a sequence that possesses a structure feature that the rest of the oligonucleotide does not have. In some embodiments, a 5'-end or a 3'-end region comprises 2 to 20 nucleosides. In some embodiments, the number of nucleosides in a 5'-end or a 3'-end region is 2 to 20. In some embodiments, a structural feature is a base modification. In some embodiments, a structural feature is a sugar modification. In some embodiments, a structural feature is a P-modification. In some embodiments, a structural feature is stereochemistry of linkage phosphorus. In some embodiments, a structural feature is or comprises a base modification, a sugar modification, a P-modification, or linkage phosphorus stereochemistry, or combinations thereof. In some embodiments, a hemimer is an oligonucleotide in which each sugar moiety of the 5'-end region shares a common modification. In some embodiments, a hemimer is an oligonucleotide in which each sugar moiety of the 3'-end region shares a common modification. In some embodiments, a common sugar modification of the 5' or 3'-end region is not shared by any other sugar moieties in the oligonucleotide. In some embodiments, an example hemimer is an oligonucleotide comprising a sequence of substituted or unsubstituted 2'-O-alkyl sugar modified nucleosides, bicyclic sugar modified nucleosides, β-D-ribonucleosides or D-D-deoxyribonucleosides (for example 2'-MOE modified nucleosides, and LNA™ or ENA™ bicyclic sugar modified nucleosides) at one terminus region and a sequence of nucleosides with a different sugar moiety (such as a substituted or unsubstituted 2'-O-alkyl sugar modified nucleosides, bicyclic sugar modified nucleosides or natural ones) at the other terminus region. In some embodiments, an oligonucleotide, e.g., a RHO oligonucleotide, or a portion thereof comprises one or more: unimer, altmer, blockmer, gapmer, hemimer, and/or skipmer. In some embodiments, an oligonucleotide, e.g., a RHO oligonucleotide, is or comprises a combination of one or more: unimer, altmer, blockmer, gapmer, and/or skipmer. In some embodiments, an altmer is a stereoaltmer, P-modification altmer, or linkage altmer. In some embodiments, an altmer is a sugar modification altmer, which comprises two alternating types of sugars, wherein either: (a) one type of sugar comprises no modification and the other type comprises a modification; or (b) the two alternating types comprise different modifications. In some embodiments, a unimer is a stereounimer, P-modification unimer, linkage unimer, or sugar modification unimer. For instance, in some embodiments, an oligonucleotide, e.g., a RHO oligonucleotide, is both an altmer and a gapmer. In some embodiments, a provided nucleotide is both a gapmer and a skipmer. One of skill in the art will recognize that numerous other combinations of patterns are available. In some embodiments, a hemimer structure provides advantageous benefits. In some embodiments, provided oligonucleotides are 5'-hemimers that comprises modified sugars in a 5'-end sequence. In some embodiments, provided oligonucleotides are 5'-hemimers that comprises modified 2'-modified sugars in a 5'-end sequence.

In some embodiments, an oligonucleotide consists of a wing-core-wing structure, wherein the core comprises 2, 3, 4, 5, 6, 7, 8, 9, 10, 11, 12, 13, 14, 15, 16, 17, 18, 19, 20 or more consecutive natural DNA sugars and each sugar in the core is a natural DNA sugar, each of the 5' and 3' wings independently comprises 1, 2, 3, 4, 5, 6, 7, 8, 9, 10 or more modified sugars and each sugar in the wings is independently a modified sugar, and the oligonucleotide optionally comprises one or more additional chemical moieties optionally linked to the oligonucleotide chain (e.g., at sugar, nucleobase, and/or internucleotidic linkage) through one or more linkers. In some embodiments, each sugar modification in a wing is the same. In some embodiments, all wing sugar modifications are the same.

In some embodiments, a wing is 2'-MOE wing in which each sugar independently comprises 2'-MOE modification. In some embodiments, in a wing each sugar is

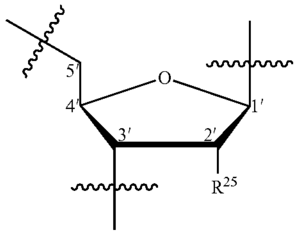

wherein $R^{2s}$ is —$OCH_2CH_2OCH_3$. In some embodiments, such a wing is a 5'-wing. In some embodiments, such a wing is a 3'-wing. In some embodiments, in a 5'-wing each internucleotidic linkage linking two wing sugars is independently a natural phosphate linkage, except that the internucleotidic linkage linking the first and second sugars from the 5'-end of a 5'-wing is a modified internucleotidic linkage, optionally chirally controlled. In some embodiments, the internucleotidic linkage linking the first and second sugars from the 5'-end of a 5'-wing is a chirally controlled phosphorothioate internucleotidic linkage. In some embodiments, it is Rp. In some embodiments, it is Sp. In some embodiments, in a 3'-wing each internucleotidic linkage linking two wing sugars is independently a natural phosphate linkage, except that the internucleotidic linkage linking the first and second sugars from the 3'-end of a 3'-wing is a modified internucleotidic linkage, optionally chirally controlled. In some embodiments, the internucleotidic linkage linking the first and second sugars from the 3'-end of a 3'-wing is a chirally controlled phosphorothioate internucleotidic linkage. In some embodiments, it is Rp. In some embodiments, it is Sp. In some embodiments, each 5'-wing sugar is independently

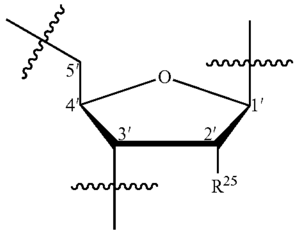

wherein $R^{2s}$ is —OR, wherein R is as described herein and is not —H. In some embodiments, each 5'-wing sugar is independently

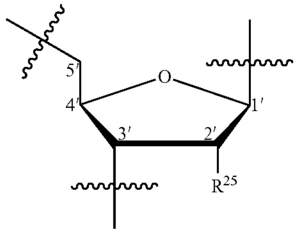

wherein $R^{2s}$ is —$OCH_2CH_2OCH_3$. In some embodiments, each 3'-wing sugar is independently

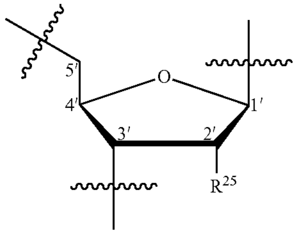

wherein $R^{2s}$ is —OR, wherein R is as described herein and is not —H. In some embodiments, $R^{2s}$ is —$OCH_2CH_2OCH_3$. In some embodiments, $R^{2s}$ is —OMe. In some embodiments, each internucleotidic linkage linking two wing sugars wherein $R^{2s}$ is —OMe is independently a modified internucleotidic linkage. In some embodiments, a modified internucleotidic linkage is a chirally controlled internucleotidic linkage. In some embodiments, it is a chirally controlled phosphorothioate internucleotidic linkage. In some embodiments, it is a chirally controlled Sp phosphorothioate internucleotidic linkage. In some embodiments, each core sugar is independently

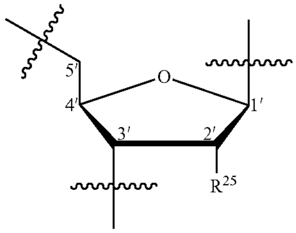

wherein $R^{2s}$ is —H.

In some embodiments, the internucleotidic linkage linking a 5'-wing sugar and a core sugar is a chirally controlled internucleotidic linkage. In some embodiments, it is a chirally controlled phosphorothioate internucleotidic linkage. In some embodiments, it is Rp. In some embodiments, it is Sp. In some embodiments, the internucleotidic linkage linking a 3'-wing sugar and a core sugar is a chirally controlled internucleotidic linkage. In some embodiments, it is a chirally controlled phosphorothioate internucleotidic linkage. In some embodiments, it is Rp. In some embodiments, it is Sp.

Non-limiting examples of oligonucleotides having a wing-core-wing format include: WV-20847, WV-20846, WV-20865, WV-20828, WV-21503, WV-21505, WV-23658, and WV-23668.

Non-limiting examples of oligonucleotides having a wing-core-wing format, wherein the first wing comprises a sugar modification which is also present in the second wing, include: WV-20791, WV-20792, WV-20793, WV-20794, WV-20795, WV-20796, WV-20797, WV-20798, WV-20799, WV-20800, WV-20801, WV-20802, WV-20803, WV-20804, WV-20805, WV-20806, WV-20807, WV-20808, WV-20809, WV-20810, WV-20811, WV-20812, WV-20813, WV-20814, and WV-20815.

In some embodiments, the structure of a RHO oligonucleotide is or comprise a wing-core structure. Non-limiting examples of such a RHO oligonucleotide include but are not limited to: WV-20832, WV-20833, WV-20834, WV-20835, WV-20836, WV-20837, WV-20838, WV-20839, WV-20840, WV-20841, WV-20842, WV-20843, WV-20844, WV-20845, WV-20846, WV-20847, WV-20848, WV-20849, WV-20850, WV-20851, WV-20852, WV-20853, WV-20854, WV-20855, WV-20856, WV-20857, and WV-20858.

In some embodiments, the structure of a RHO oligonucleotide is or comprises a wing-core-wing structure, wherein the first or second wings each independently comprise at least one 2'-OMe. Non-limiting examples of such a RHO oligonucleotide include but are not limited to: WV-23662, WV-23663, WV-23664, WV-23665, WV-23666, WV-23667, WV-23668, and WV-23669.

In some embodiments, the structure of a RHO oligonucleotide is or comprises a wing-core-wing structure, wherein the first and second wings each independently comprise at least one 2'-MOE. Non-limiting examples of such a RHO oligonucleotide include but are not limited to: WV-20830, WV-20831, WV-20832, WV-20833, WV-20834, WV-20835, WV-20836, WV-20837, WV-20838, WV-20839, WV-20840, WV-20841, WV-20842, WV-20843, WV-20844, WV-20845, WV-20846, and WV-20847.

In some embodiments, the structure of a RHO oligonucleotide is or comprises a wing-core-wing structure, wherein the first or second wings each independently comprise at least one 2'-MOE. Non-limiting examples of such a RHO oligonucleotide include but are not limited to: WV-23662, WV-23663, WV-23664, WV-23665, WV-23666, WV-23667, WV-23668, and WV-23669.

In some embodiments, the structure of a RHO oligonucleotide comprises or consists of an asymmetrical format. Non-limiting examples of such a RHO oligonucleotide include but are not limited to: WV-23661, WV-23662, WV-23663, WV-23664, WV-23665, WV-23666, WV-23667, WV-23668, WV-23669, WV-23670, WV-20865, WV-21504, and WV-21505.

In some embodiments, the structure of a RHO oligonucleotide is or comprises a wing-core-wing structure, wherein a first wing comprises at least one 2'-MOE and no 2'-OMe and a second wing comprises at least one 2'-OMe. In some embodiments, the structure of a RHO oligonucleotide is or comprises a wing-core-wing structure, wherein a first wing comprises at least one 2'-MOE and no 2'-OMe and a second wing comprises at least one 2'-OMe and no 2'-MOE. Non-limiting examples of such a RHO oligonucleotide include but are not limited to: WV-23661, WV-23662, WV-23663, WV-23664, WV-23665, WV-23666, WV-23667, WV-23668, WV-23669, WV-23670, WV-20865, WV-21504, and WV-21505.

In some embodiments, the structure of a RHO oligonucleotide is or comprises a wing-core-wing structure, wherein a first wing comprises at least one 2'-MOE and a second wing comprises at least one 2'-OMe and at least one 2'-MOE. In some embodiments, the structure of a RHO oligonucleotide is or comprises a wing-core-wing structure, wherein a first wing comprises at least one 2'-MOE and no 2'-OMe and a second wing comprises at least one 2'-OMe and at least one 2'-MOE. In some embodiments, a first wing comprises one or more phosphorothioate internucleotidic linkages and one or more non-negatively charged internucleotidic linkages (e.g., neutral internucleotidic linkages such as n001). In some embodiments, a first wing comprises one or more natural phosphate linkages, one or more phosphorothioate internucleotidic linkages and one or more non-negatively charged internucleotidic linkages (e.g., neutral internucleotidic linkages such as n001).

In some embodiments, the structure of a RHO oligonucleotide comprises or consists of a symmetrical format. Non-limiting examples of such a RHO oligonucleotide include but are not limited to: WV-23651, WV-23652, WV-23653, WV-23654, WV-23655, WV-23656, WV-23657, WV-23658, WV-23659, and WV-23660.

In some embodiments, the structure of a RHO oligonucleotide is or comprises an asymmetrical format, wherein the structure of the oligonucleotide is a wing-core-wing structure, wherein the format of the first wing is different from that of the second wing. In some embodiments, the structure of a RHO oligonucleotide is or comprises an asymmetrical format, wherein the structure of the oligonucleotide is a wing-core-wing structure, wherein the first and second wings differ in sugar modification (or combinations or patterns thereof) and/or in internucleotidic linkages (or combinations or patterns thereof). In some embodiments, the structure of a RHO oligonucleotide is or comprises an asymmetrical format, wherein the structure of the oligonucleotide is a wing-core-wing structure, wherein the first and second wings differ in sugar modification (or combinations or patterns thereof).

In some embodiments, the structure of a RHO oligonucleotide is or comprises a wing-core-wing structure, wherein one wing comprises one type of sugar, and the other comprises that type and a second type. In some embodiments, this is a non-limiting example of a RHO oligonucleotide having an asymmetrical format.

In some embodiments, the structure of a RHO oligonucleotide is or comprises a wing-core-wing structure, wherein one wing comprises a first type of sugar but not a second type of sugar, and the other comprises the second type of sugar but not the first type of sugar. In some embodiments, this is a non-limiting example of a RHO oligonucleotide having an asymmetrical format.

In some embodiments, the structure of a RHO oligonucleotide is or comprises a wing-core-wing structure, wherein one wing comprises a neutral or non-negatively charged internucleotidic linkage and the other wing does not comprise a neutral or non-negatively charged internucleotidic linkage. Non-limiting examples of such a RHO oligonucleotide include but are not limited to: WV-24653, WV-24658, WV-24659, WV-24664, WV-24669, and WV-24670.

In some embodiments, the structure of a RHO oligonucleotide is or comprises a wing-core-wing structure, wherein the first and second wings each independently comprise at least one neutral or non-negatively charged internucleotidic linkage. Non-limiting examples of such a RHO oligonucleotide include but are not limited to: WV-24654, WV-24655, WV-24656, WV-24657, WV-24660, WV-24661, WV-24662, and WV-24663.

In some embodiments, the structure of a RHO oligonucleotide is or comprises a wing-core-wing structure, wherein at least one wing comprises a neutral or non-negatively charged internucleotidic linkage. Non-limiting examples of such a RHO oligonucleotide include but are not limited to: WV-24653, WV-24654, WV-24655, WV-24656, WV-24657, WV-24658, WV-24659, WV-24660, WV-24661, WV-24662, WV-24663, WV-24664, WV-24668, WV-24669, WV-24670.

In some embodiments, a RHO oligonucleotide comprises at least one neutral or non-negatively charged internucleotidic linkage. Non-limiting examples of such a RHO oligonucleotide include but are not limited to: WV-24653, WV-24654, WV-24655, WV-24656, WV-24657, WV-24658, WV-24659, WV-24660, WV-24661, WV-24662, WV-24663, WV-24664, WV-24668, WV-24669, WV-24670.

In some embodiments, a RHO oligonucleotide comprises at least two adjacent neutral or non-negatively charged internucleotidic linkages. Non-limiting examples of such a RHO oligonucleotide include but are not limited to: WV-24653, WV-24659, WV-24668, WV-24669, WV-24670.

In some embodiments, a RHO oligonucleotide comprises at least two non-adjacent neutral or non-negatively charged internucleotidic linkages. Non-limiting examples of such a RHO oligonucleotide include but are not limited to: WV-24654, WV-24655, WV-24656, WV-24657, WV-24658, WV-24659, WV-24660, WV-24661, WV-24662, WV-24663, WV-24664. In some embodiments, a neutral or non-negatively charged internucleotidic linkage is referenced as a PN. In some embodiments, a series or string of two or more non-adjacent (e.g., non-contiguous) neutral or non-negatively charged internucleotidic linkages (PN) is referenced as a broken string of PN or broken PN.

In some embodiments, the structure of a RHO oligonucleotide comprises a core and at least one wing, wherein the core comprises 2, 3, 4, 5, 6, 7, 8, 9, 10, 11, 12, 13, 14, 15, 16, 17, 18, 19, 20, or more consecutive 2'-deoxyribose sugars.

In some embodiments, the structure of a RHO oligonucleotide comprises a core and at least one wing, wherein the core comprises at least 5 consecutive 2'-deoxyribose sugars. Non-limiting examples of such a RHO oligonucleotide include but are not limited to: WV-20828, WV-20846, WV-20847, WV-20865, WV-21503, WV-21505, WV-23658, WV-23668, WV-20808, WV-20827, WV-20843, WV-20845, WV-23654, WV-23655, WV-23657, WV-23661, WV-23664, WV-23665, WV-23667, WV-23675, WV-23676, WV-23677, WV-23678, WV-23679, WV-23683, WV-23684, WV-23685, WV-23686, WV-23687, WV-23680, WV-23671, WV-23674, WV-23651, WV-24653, WV-24654, WV-24655, WV-24656, WV-24657, WV-24658, and WV-24659.

In some embodiments, the structure of a RHO oligonucleotide comprises a core and at least one wing, wherein the core comprises at least 6 consecutive 2'-deoxyribose sugars. Non-limiting examples of such a RHO oligonucleotide include but are not limited to: WV-24653, WV-24654, WV-24655, WV-24656, WV-24657, WV-24658, WV-20828, WV-20846, WV-20847, WV-20865, WV-21503, WV-21505, WV-23658, WV-23668, WV-20808, WV-20827, WV-20843, WV-20845, WV-23654, WV-23655, WV-23657, WV-23661, WV-23664, WV-23665, WV-23667, WV-23675, WV-23676, WV-23677, WV-23678, WV-23679, WV-23683, WV-23684, WV-23685, WV-23686, WV-23687, WV-23680, WV-23671, WV-23674, WV-23651, WV-24659, WV-24660, WV-24661, WV-24662, WV-24663, WV-24664, WV-24668, WV-24669, and WV-24670.

In some embodiments, the structure of a RHO oligonucleotide comprises a core and at least one wing, wherein the core comprises at least 7 consecutive 2'-deoxyribose sugars. Non-limiting examples of such a RHO oligonucleotide include but are not limited to: WV-20828, WV-20846, WV-20847, WV-20865, WV-21503, WV-21505, WV-23658, WV-23668, WV-20808, WV-20827, WV-20843, WV-20845, WV-23654, WV-23655, WV-23657, WV-23661, WV-23664, WV-23665, WV-23667, WV-23675, WV-23676, WV-23677, WV-23678, WV-23679, WV-23683, WV-23684, WV-23685, WV-23686, WV-23687, WV-23680, WV-23671, WV-23674, and WV-23651.

In some embodiments, the structure of a RHO oligonucleotide comprises a core and at least one wing, wherein the core comprises at least 8 consecutive 2'-deoxyribose sugars. Non-limiting examples of such a RHO oligonucleotide include but are not limited to: WV-24653, WV-24654, WV-24655, WV-24656, WV-24657, WV-24658, WV-24659, WV-24660, WV-24661, WV-24662, WV-24663, WV-24664, WV-24668, WV-24669, WV-20828, WV-20846, WV-20847, WV-20865, WV-21503, WV-21505, WV-23658, WV-23668, WV-20808, WV-20827, WV-20843, WV-20845, WV-23654, WV-23655, WV-23657, WV-23661, WV-23664, WV-23665, WV-23667, WV-23675, WV-23676, WV-23677, WV-23678, WV-23679, WV-23683, WV-23684, WV-23685, WV-23686, WV-23687, WV-23680, WV-23671, WV-23674, WV-23651, and WV-24670.

In some embodiments, the structure of a RHO oligonucleotide comprises a core and at least one wing, wherein the core comprises at least 9 consecutive 2'-deoxyribose sugars. Non-limiting examples of such a RHO oligonucleotide include but are not limited to: WV-20828, WV-20846, WV-20847, WV-20865, WV-21503, WV-21505, WV-23658, WV-23668, WV-20808, WV-20827, WV-20843, WV-20845, WV-23654, WV-23655, WV-23657, WV-23661, WV-23664, WV-23665, WV-23667, WV-23675, WV-23676, WV-23677, WV-23678, WV-23679, WV-23683, WV-23684, WV-23685, WV-23686, WV-23687, WV-23680, WV-23671, WV-23674, and WV-23651.

In some embodiments, the structure of a RHO oligonucleotide comprises a core and at least one wing, wherein the core comprises at least 10 consecutive 2'-deoxyribose sugars. Non-limiting examples of such a RHO oligonucleotide include but are not limited to: WV-20828, WV-20846, WV-20847, WV-20865, WV-21503, WV-21505, WV-23658, WV-23668, WV-20808, WV-20827, WV-20843, WV-20845, WV-23654, WV-23655, WV-23657, WV-23661, WV-23664, WV-23665, WV-23667, WV-23675, WV-23676, WV-23677, WV-23678, WV-23679, WV-23683, WV-23684, WV-23685, WV-23686, WV-23687, WV-23680, WV-23671, WV-23674, and WV-23651.

In some embodiments, the structure of a RHO oligonucleotide is or comprises a wing-core-wing structure, wherein the oligonucleotide comprises at least one neutral or non-negatively charged internucleotidic linkage. Non-limiting examples of such a RHO oligonucleotide include but are not limited to: WV-24653, WV-24654, WV-24655, WV-24656, WV-24657, WV-24658, WV-24659, WV-24660, WV-24661, WV-24662, WV-24663, WV-24664, WV-24668, WV-24669, and WV-24670.

In some embodiments, a RHO oligonucleotide comprises at least three different types of internucleotidic linkages. Non-limiting examples of such a RHO oligonucleotide include but are not limited to: WV-24653, WV-24654, WV-24655, WV-24656, WV-24657, and WV-24658.

In some embodiments, a RHO oligonucleotide comprises: at least one natural phosphate internucleotidic linkage; at least one phosphorothioate; and at least one neutral or non-negatively charged internucleotidic linkage. Non-limiting examples of such a RHO oligonucleotide include but are not limited to: WV-24653, WV-24654, WV-24655, WV-24656, WV-24657, and WV-24658.

In some embodiments, a RHO oligonucleotide comprises: at least one natural phosphate internucleotidic linkage; at least one phosphorothioate which is chirally controlled; and at least one neutral or non-negatively charged internucleotidic linkage. Non-limiting examples of such a RHO oligonucleotide include but are not limited to: WV-24653, WV-24654, WV-24655, WV-24656, WV-24657, and WV-24658.

In some embodiments, a RHO oligonucleotide comprises: at least one natural phosphate internucleotidic linkage; at least one phosphorothioate; and at least one neutral or non-negatively charged internucleotidic linkage which is chirally controlled.

In some embodiments, a RHO oligonucleotide comprises: at least one natural phosphate internucleotidic linkage; at least one phosphorothioate which is chirally controlled; and at least one neutral or non-negatively charged internucleotidic linkage which is chirally controlled.

In some embodiments, the structure of a RHO oligonucleotide comprises a core and at least one wing, wherein the core comprises at least 12 consecutive 2'-deoxyribose sugars.

In some embodiments, the structure of a RHO oligonucleotide comprises a core and at least one wing, wherein the core comprises at least 14 consecutive 2'-deoxyribose sugars.

In some embodiments, the structure of a RHO oligonucleotide is or comprises a wing-core-wing structure, wherein the first and second wing each comprise at least 2 different types of sugars.

In some embodiments, the structure of a RHO oligonucleotide is or comprises a wing-core-wing structure, wherein the first and second wing each comprise 2'-DNA sugar (a natural 2'-deoxyribose) and a sugar comprising 2'-modification.

In some embodiments, the structure of a RHO oligonucleotide is or comprises a wing-core-wing structure, wherein the first and second wing each comprise 2'-DNA sugar (a natural 2'-deoxyribose) and a 2'-OMe sugar.

In some embodiments, a RHO oligonucleotide comprises at least one natural 2'-deoxyribose sugar (unmodified DNA sugar), at least one LNA sugar and at least one 2'-MOE sugar.

In some embodiments, the structure of a RHO oligonucleotide is or comprises a wing-core-wing structure, wherein the first and second wing each comprise a natural 2'-deoxyribose (unmodified DNA sugar), a LNA sugar and 2'-MOE sugar.

In some embodiments, a RHO oligonucleotide comprises at least one natural 2'-deoxyribose (unmodified DNA sugar), at least one LNA sugar and at least one 2'-OMe sugar.

In some embodiments, the structure of a RHO oligonucleotide is or comprises a wing-core-wing structure, wherein the first and second wing each comprise a natural 2'-deoxyribose (unmodified DNA sugar), a LNA sugar and 2'-OMe sugar.

In some embodiments, the structure of a RHO oligonucleotide is or comprises a wing-core-wing structure, wherein the first and second wing each comprise at least 3 different types of sugars (e.g., selected from unmodified sugars and modified sugars with various modifications).

In some embodiments, the structure of a RHO oligonucleotide is or comprises a wing-core-wing structure, wherein one wing comprises at least one 2'-F sugar and the other wing comprises at least one 2'-MOE sugar.

In some embodiments, the structure of a RHO oligonucleotide is or comprises a wing-core-wing structure, wherein at least one wing comprises one or more (1, 2, 3, 4, 5, 6, 7, 8, 9, or 10) LNA sugars.

In some embodiments, the structure of a RHO oligonucleotide is or comprises a wing-core-wing structure, wherein the first and second wing each comprise one or more 2'-MOE sugars and one or more LNA sugars.

In some embodiments, the structure of a RHO oligonucleotide is or comprises a wing-core-wing structure, wherein the first and second wing each comprise one or more LNA sugars.

In some embodiments, the structure of a RHO oligonucleotide is or comprises a wing-core-wing structure, wherein one wing comprises one or more LNA sugars and one or more 2'-MOE sugars and the other wing comprises one or more LNA sugars and one or more 2'-OMe sugars.

In some embodiments, the structure of a RHO oligonucleotide is or comprises a wing-core-wing structure, wherein one wing comprises 2'-MOE and 2'-F sugars, and the other wing comprises a 2'-MOE sugar.

In some embodiments, the structure of a RHO oligonucleotide is or comprises a wing-core-wing structure, wherein one wing comprises a natural 2'-deoxyribose (unmodified DNA sugar), a LNA sugar, and a 2'-MOE sugar.

In some embodiments, the structure of a RHO oligonucleotide is or comprises a wing-core-wing structure, wherein one wing comprises at least 3 different types of sugars.

In some embodiments, the structure of a RHO oligonucleotide is or comprises a wing-core-wing structure, wherein the first and second wing each comprise a natural 2'-deoxyribose (unmodified DNA sugar) and at least 1 modified sugar (compared to 2'-deoxyribose (unmodified DNA sugar)).

In some embodiments, the structure of a RHO oligonucleotide is or comprises a wing-core-wing structure, wherein the first and second wing each comprise a natural 2'-deoxyribose (unmodified DNA sugar) and at least 2 sugar modifications.

In some embodiments, the structure of a RHO oligonucleotide is or comprises a wing, wherein the wing comprises at least 3 different types of sugars.

In some embodiments, the structure of a RHO oligonucleotide comprises a wing, wherein the wing comprises at least 1 base(s).

In some embodiments, the structure of a RHO oligonucleotide comprises a wing, wherein the wing comprises at least 2 base(s).

In some embodiments, the structure of a RHO oligonucleotide comprises a wing, wherein the wing comprises at least 3 base(s).

In some embodiments, the structure of a RHO oligonucleotide comprises a wing, wherein the wing comprises at least 4 base(s).

In some embodiments, the structure of a RHO oligonucleotide comprises a wing, wherein the wing is 5 base(s).

In some embodiments, the structure of a RHO oligonucleotide comprises a wing, wherein the wing comprises at least 6 base(s).

In some embodiments, the structure of a RHO oligonucleotide comprises a wing, wherein the wing comprises at least 7 base(s).

In some embodiments, the structure of a RHO oligonucleotide comprises a wing, wherein the wing is an 8 base(s).

In some embodiments, the structure of a RHO oligonucleotide is or comprises a wing-core-wing structure, wherein the first and second wing each comprise two different types of sugars.

In some embodiments, the structure of a RHO oligonucleotide is or comprises a wing-core-wing structure, wherein one wing comprises at least one 2'-MOE sugar and the other wing comprises at least one 2'-OMe sugar.

In some embodiments, the structure of a RHO oligonucleotide is or comprises a wing-core-wing structure, wherein one wing comprises a 2'-F sugar and one wing comprises a 2'-OMe sugar.

In some embodiments, the structure of a RHO oligonucleotide is or comprises a wing-core-wing structure, wherein one wing comprises a natural 2'-deoxyribose (unmodified DNA sugar) and at least one modified sugar.

In some embodiments, the structure of a RHO oligonucleotide is or comprises a wing-core-wing structure, wherein one wing comprises a natural 2'-deoxyribose (unmodified DNA sugar) and at least two modified sugars.

In some embodiments, a core region comprises a sequence complementary to a characteristic sequence element which differentiates a target nucleic acid sequence from other sequences, e.g., one allele of a differentiating position, e.g., a SNP location, a mutation site, etc. In some embodiments, a core region comprises a sequence complementary to one allele of a SNP or a mutation (e.g., disease-associated mutation(s) in a RHO gene) but is not complementary to other alleles of a SNP or the wild type or another form of mutation which is not or is less associated with a condition, disorder or disease. In some embodiments, for SNP or a point mutation such a sequence is one nucleobase. In some embodiments, a core region comprises a nucleobase complementary to an allele of a SNP which is on the same strand/chromosome as disease-associated mutation(s) in a RHO gene. In some embodiments, a core region comprises a nucleobase complementary to a mutation (e.g., a RHO mutation (e.g., P23H)) which is associated with a condition, disorder or disease. Among other things, the present disclosure demonstrates that properties and/or activities of oligonucleotides may be modulated through positioning of such a nucleobase. In some embodiments, a position of such a nucleobase is position 4, 5, 6, 7 or 8 counting from the 5'-end of a core region (the first nucleoside of the core region from the 5'-end being position 1). In some embodiments, a position is position 4 from the 5'-end of a core region. In some embodiments, a position is position 5 from the 5'-end of a core region. In some embodiments, a position is position 6 from the 5'-end of a core region. In some embodiments, a position is position 7 from the 5'-end of a core region. In some embodiments, a position is position 8 from the 5'-end of a core region. In some embodiments, a position of such a nucleobase is position 7, 8, 9, 10, 11 or 12 counting from the 5'-end of an oligonucleotide (the first nucleoside of the oligonucleotide from the 5'-end being position 1). In some embodiments, a position is position 7 from the 5'-end of an oligonucleotide. In some embodiments, a position is position 8 from the 5'-end of an oligonucleotide. In some embodiments, a position is position 9 from the 5'-end of an oligonucleotide. In some embodiments, a position is position 10 from the 5'-end of an oligonucleotide. In some embodiments, a position is position 11 from the 5'-end of an oligonucleotide. In some embodiments, an oligonucleotide comprises a 5'-end wing comprising 5 and no more than 5 nucleosides. In some embodiments, each wing sugar is 2'-modified. In some embodiments, each wing sugar is 2'-OMe modified. In some embodiments, each core sugar independently comprises no 2'-OR modification, wherein R is as described in the present disclosure. In some embodiments, each core sugar is independently an unmodified DNA sugar.

In some embodiments, a wing may comprise one or more high-affinity sugars. In some embodiments, a 3'-wing comprises a high-affinity sugar. In some embodiments, each sugar in a 3'-wing is independently a high-affinity sugar. High-affinity sugars are widely known in the art and may be utilized in accordance with the present disclosure. In some embodiments, a high affinity sugar is a 2'-MOE modified sugar. In some embodiments, a high-affinity sugar is a LNA sugar. In some embodiments, compared to a 3'-wing, a 5'-wing comprises no or fewer high-affinity sugars. In some embodiments, compared to a 3'-wing, a 5'-wing comprises no or fewer high-affinity sugars present in the 3'-wing. For example, in some embodiments, a 5'-wing comprises no 2'-MOE modified sugar while each 3'-wing sugar is 2'-MOE modified. In some embodiments, each 5'-wing sugar is 2'-OMe modified, while each 3'-wing sugar is 2'-MOE modified.

In some embodiments, an oligonucleotide, e.g., a RHO oligonucleotide, may comprise any first wing, core and/or second wing, as described herein or known in the art.

In some embodiments, an oligonucleotide which has a base sequence which is, comprises or comprises a span of a RHO oligonucleotide sequence disclosed herein can comprise a first wing, core and/or second wing, as described herein or known in the art.

Internucleotidic Linkages

In some embodiments, oligonucleotides comprise base modifications, sugar modifications, and/or internucleotidic linkage modifications. Various internucleotidic linkages can be utilized in accordance with the present disclosure to link units comprising nucleobases, e.g., nucleosides. In some embodiments, RHO oligonucleotides comprise both one or more modified internucleotidic linkages and one or more natural phosphate linkages. As widely known by those skilled in the art, natural phosphate linkages are widely found in natural DNA and RNA molecules; they have the structure of —OP(O)(OH)O—, connect sugars in the nucleosides in DNA and RNA, and may be in various salt forms, for example, at physiological pH (about 7.4), natural phosphate linkages are predominantly exist in salt forms with the anion being —OP(O)($O^-$)O—. A modified internucleotidic linkage, or a non-natural phosphate linkage, is an internucleotidic linkage that is not natural phosphate linkage or a salt form thereof. Modified internucleotidic linkages, depending on their structures, may also be in their salt forms. For example, as appreciated by those skilled in the art, phosphorothioate internucleotidic linkages which have the structure of —OP(O)(SH)O— may be in various salt forms, e.g., at physiological pH (about 7.4) with the anion being —OP(O)($S^-$)O—.

In some embodiments, an oligonucleotide comprises an internucleotidic linkage which is a modified internucleotidic linkage, e.g., phosphorothioate, phosphorodithioate, methylphosphonate, phosphoroamidate, thiophosphate, 3'-thiophosphate, or 5'-thiophosphate.

In some embodiments, a modified internucleotidic linkage is a chiral internucleotidic linkage which comprises a chiral linkage phosphorus. In some embodiments, a chiral internucleotidic linkage is a phosphorothioate linkage. In some embodiments, a chiral internucleotidic linkage is a non-negatively charged internucleotidic linkage. In some embodiments, a chiral internucleotidic linkage is a neutral internucleotidic linkage. In some embodiments, a chiral internucleotidic linkage is chirally controlled with respect to its chiral linkage phosphorus. In some embodiments, a chiral internucleotidic linkage is stereochemically pure with respect to its chiral linkage phosphorus. In some embodiments, a chiral internucleotidic linkage is not chirally controlled. In some embodiments, a pattern of backbone chiral centers comprises or consists of positions and linkage phosphorus configurations of chirally controlled internucleotidic linkages (Rp or Sp) and positions of achiral internucleotidic linkages (e.g., natural phosphate linkages).

In some embodiments, an oligonucleotide comprises a modified internucleotidic linkage (e.g., a modified internucleotidic linkage having the structure of Formula I, I-a, I-b, or I-c, I-n-1, I-n-2, I-n-3, I-n-4, II, II-a-1, II-a-2, II-b-1, II-b-2, II-c-1, II-c-2, II-d-1, II-d-2, etc., or a salt form thereof) as described in U.S. Pat. Nos. 9,394,333, 9,744,183, 9,605,019, 9,598,458, 9,982,257, U.S. Ser. No. 10/160,969, U.S. Ser. No. 10/479,995, US 2020/0056173, US 2018/0216107, US 2019/0127733, U.S. Ser. No. 10/450,568, US 2019/0077817, US 2019/0249173, US 2019/0375774, WO 2018/223056, WO 2018/223073, WO 2018/223081, WO 2018/237194, WO 2019/032607, WO 2019/055951, WO 2019/075357, WO 2019/200185, WO 2019/217784, and/or WO 2019/032612, the internucleotidic linkages (e.g., those of Formula I, I-a, I-b, or I-c, I-n-1, I-n-2, I-n-3, I-n-4, II, II-a-1, II-a-2, II-b-1, II-b-2, II-c-1, II-c-2, II-d-1, II-d-2, etc.) of each of which are independently incorporated herein by reference. In some embodiments, a modified internucleotidic linkage is a non-negatively charged internucleotidic linkage. In some embodiments, provided oligonucleotides comprise one or more non-negatively charged internucleotidic linkages. In some embodiments, a non-negatively charged internucleotidic linkage is a positively charged internucleotidic linkage. In some embodiments, a non-negatively charged internucleotidic linkage is a neutral internucleotidic linkage. In some embodiments, the present disclosure provides oligonucleotides comprising one or more neutral internucleotidic linkages. In some embodiments, a non-negatively charged internucleotidic linkage or a neutral internucleotidic linkage (e.g., one of Formula I-n-1, I-n-2, I-n-3, I-n-4, II, II-a-1, II-a-2, II-b-1, II-b-2, II-c-1, II-c-2, II-d-1, II-d-2, etc.) is as described in U.S. Pat. Nos. 9,394,333, 9,744,183, 9,605,019, 9,598,458, 9,982,257, U.S. Ser. No. 10/160,969, U.S. Ser. No. 10/479,995, US 2020/0056173, US 2018/0216107, US 2019/0127733, U.S. Ser. No. 10/450,568, US 2019/0077817, US 2019/0249173, US 2019/0375774, WO 2018/223056, WO 2018/223073, WO 2018/223081, WO 2018/237194, WO 2019/032607, WO 2019/055951, WO 2019/075357, WO 2019/200185, WO 2019/217784, and/or WO 2019/032612. In some embodiments, a non-negatively charged internucleotidic linkage or neutral internucleotidic linkage is one of Formula I-n-1, I-n-2, I-n-3, I-n-4, II, II-a-1, II-a-2, II-b-1, II-b-2, II-c-1, II-c-2, II-d-1, II-d-2, etc. as described in WO 2018/223056, WO 2019/032607, WO 2019/075357, WO 2019/032607, WO 2019/075357, WO 2019/200185, WO 2019/217784, and/or WO 2019/032612, such internucleotidic linkages of each of which are independently incorporated herein by reference.

In some embodiments, provided oligonucleotides comprise one or more non-negatively charged internucleotidic linkages. In some embodiments, a non-negatively charged internucleotidic linkage can improve the delivery and/or activity (e.g., ability to decrease the level, activity and/or expression of a target gene or a gene product thereof) of an oligonucleotide.

In some embodiments, a non-negatively charged internucleotidic linkage has the structure of $—OP(=W)(—N=C(R'')_2)—O—$ or $—OP(=W)(—N(R'')_2)—O—$, wherein:

W is O or S;

each R'' is independently R' or $—N(R')_2$;

each R' is independently —R, —C(O)R, —C(O)OR, or $—S(O)_2R$;

each R is independently —H, or an optionally substituted group selected from $C_{1-30}$ aliphatic, $C_{1-30}$ heteroaliphatic having 1-10 heteroatoms, $C_{6-30}$ aryl, $C_{6-30}$ arylaliphatic, $C_{6-30}$ arylheteroaliphatic having 1-10 heteroatoms, 5-30 membered heteroaryl having 1-10 heteroatoms, and 3-30 membered heterocyclyl having 1-10 heteroatoms, or:

two R groups are optionally and independently taken together to form a covalent bond, or:

two or more R groups on the same atom are optionally and independently taken together with the atom to form an optionally substituted, 3-30 membered monocyclic, bicyclic or polycyclic ring having, in addition to the atom, 0-10 heteroatoms, or:

two or more R groups on two or more atoms are optionally and independently taken together with their intervening atoms to form an optionally substituted, 3-30 membered monocyclic, bicyclic or polycyclic ring having, in addition to the intervening atoms, 0-10 heteroatoms.

In some embodiments, W is O. In some embodiments, W is S.

In some embodiments, R'' is R'. In some embodiments, R'' is $—N(R')_2$.

In some embodiments, a non-negatively charged internucleotidic linkage has the structure of $—OP(=O)(—N=C(N(R')_2)_2—O—$. In some embodiments, a R' group of one $N(R')_2$ is R, a R' group of the other $N(R')_2$ is R, and the two R groups are taken together with their intervening atoms to form an optionally substituted ring, e.g., a 5-membered ring as in n001. In some embodiments, each R' is independently R, wherein each R is independently optionally substituted $C_{1-6}$ aliphatic.

In some embodiments, a non-negatively charged internucleotidic linkage has the structure of $—OP(=W)(—N(R')_2)—O—$.

In some embodiments, R' is R. In some embodiments, R' is H. In some embodiments, R' is —C(O)R. In some embodiments, R' is —C(O)OR. In some embodiments, R' is $—S(O)_2R$.

In some embodiments, R'' is —NHR'. In some embodiments, $—N(R')_2$ is —NHR'.

As described herein, some embodiments, R is H. In some embodiments, R is optionally substituted $C_{1-6}$ aliphatic. In some embodiments, R is optionally substituted $C_{1-6}$ alkyl. In some embodiments, R is methyl. In some embodiments, R is substituted methyl. In some embodiments, R is ethyl. In some embodiments, R is substituted ethyl.

In some embodiments, as described herein, a non-negatively charged internucleotidic linkage is a neutral internucleotidic linkage.

In some embodiments, a modified internucleotidic linkage (e.g., a non-negatively charged internucleotidic linkage) comprises optionally substituted triazolyl. In some embodiments, a modified internucleotidic linkage (e.g., a non-negatively charged internucleotidic linkage) comprises optionally substituted alkynyl. In some embodiments, a modified internucleotidic linkage comprises a triazole or alkyne moiety. In some embodiments, a triazole moiety, e.g., a triazolyl group, is optionally substituted. In some embodiments, a triazole moiety, e.g., a triazolyl group) is substituted. In some embodiments, a triazole moiety is unsubstituted. In some embodiments, a modified internucleotidic linkage comprises an optionally substituted cyclic guanidine moiety. In some embodiments, a modified internucleotidic linkage comprises an optionally substituted cyclic guanidine moiety and has the structure of

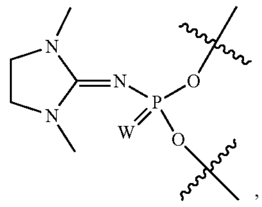,
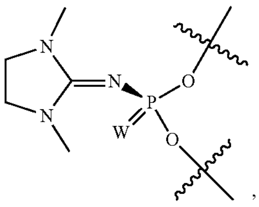, or
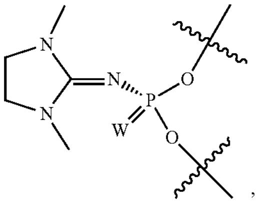, wherein W is O or S. In some embodiments, W is O. In some embodiments, W is S. In some embodiments, a non-negatively charged internucleotidic linkage is stereochemically controlled.

In some embodiments, a non-negatively charged internucleotidic linkage or a neutral internucleotidic linkage is an internucleotidic linkage comprising a triazole moiety. In some embodiments, a non-negatively charged internucleotidic linkage or a non-negatively charged internucleotidic linkage comprises an optionally substituted triazolyl group. In some embodiments, an internucleotidic linkage comprising a triazole moiety (e.g., an optionally substituted triazolyl group) has the structure of

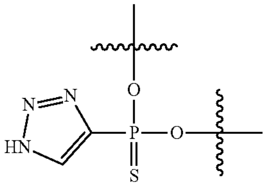.

In some embodiments, an internucleotidic linkage comprising a triazole moiety has the structure of

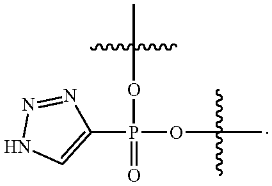 [SMILES: *OP(=O)(O*)c1c[nH]nn1].

In some embodiments, an internucleotidic linkage, e.g., a non-negatively charged internucleotidic linkage, a neutral internucleotidic linkage, comprises a cyclic guanidine moiety. In some embodiments, an internucleotidic linkage comprising a cyclic guanidine moiety has the structure of

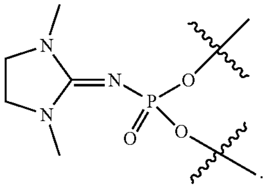 [SMILES: *OP(=O)(N=C1N(C)CCN1C)O*].

In some embodiments, a non-negatively charged internucleotidic linkage, or a neutral internucleotidic linkage, is or comprising a structure selected from

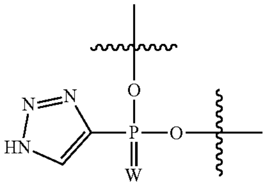,
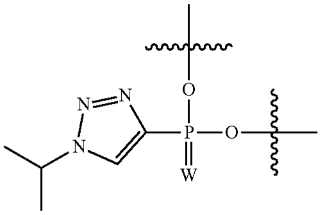,
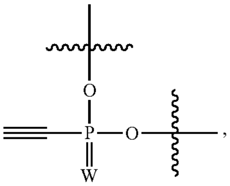, or
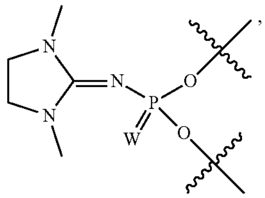, wherein W is O or S.

In some embodiments, an internucleotidic linkage comprises a Tmg group (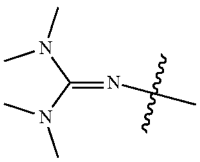).

In some embodiments, an internucleotidic linkage comprises a Tmg group and has the structure of

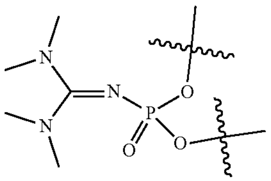 [SMILES: *OP(=O)(N=C(N(C)C)N(C)C)O*]

(the "Tmg internucleotidic linkage"). In some embodiments, neutral internucleotidic linkages include internucleotidic linkages of PNA and PMO, and an Tmg internucleotidic linkage.

In some embodiments, a non-negatively charged internucleotidic linkage comprises an optionally substituted 3-20 membered heterocyclyl or heteroaryl group having 1-10 heteroatoms. In some embodiments, a non-negatively charged internucleotidic linkage comprises an optionally substituted 3-20 membered heterocyclyl or heteroaryl group having 1-10 heteroatoms, wherein at least one heteroatom is nitrogen. In some embodiments, such a heterocyclyl or heteroaryl group is of a 5-membered ring. In some embodiments, such a heterocyclyl or heteroaryl group is of a 6-membered ring.

In some embodiments, a non-negatively charged internucleotidic linkage comprises an optionally substituted 5-20 membered heteroaryl group having 1-10 heteroatoms. In some embodiments, a non-negatively charged internucleotidic linkage comprises an optionally substituted 5-20 membered heteroaryl group having 1-10 heteroatoms, wherein at least one heteroatom is nitrogen. In some embodiments, a non-negatively charged internucleotidic linkage comprises an optionally substituted 5-6 membered heteroaryl group having 1-4 heteroatoms, wherein at least one heteroatom is nitrogen. In some embodiments, a non-negatively charged internucleotidic linkage comprises an optionally substituted 5-membered heteroaryl group having 1-4 heteroatoms, wherein at least one heteroatom is nitrogen. In some embodiments, a heteroaryl group is directly bonded to a linkage phosphorus. In some embodiments, a non-negatively charged internucleotidic linkage comprises an optionally substituted triazolyl group. In some embodiments, a non-negatively charged internucleotidic linkage comprises an unsubstituted triazolyl group, e.g.,

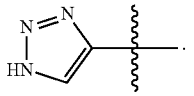

In some embodiments, a non-negatively charged internucleotidic linkage comprises a substituted triazolyl group, e.g.,

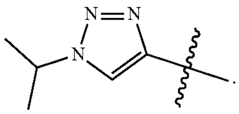 [SMILES: *c1cn(C(C)C)nn1]

In some embodiments, a non-negatively charged internucleotidic linkage comprises an optionally substituted 5-20 membered heterocyclyl group having 1-10 heteroatoms. In some embodiments, a non-negatively charged internucleotidic linkage comprises an optionally substituted 5-20 membered heterocyclyl group having 1-10 heteroatoms, wherein at least one heteroatom is nitrogen. In some embodiments, a non-negatively charged internucleotidic linkage comprises an optionally substituted 5-6 membered heterocyclyl group having 1-4 heteroatoms, wherein at least one heteroatom is nitrogen. In some embodiments, a non-negatively charged internucleotidic linkage comprises an optionally substituted 5-membered heterocyclyl group having 1-4 heteroatoms, wherein at least one heteroatom is nitrogen. In some embodiments, at least two heteroatoms are nitrogen. In some embodiments, a heterocyclyl group is directly bonded to a linkage phosphorus. In some embodiments, a heterocyclyl group is bonded to a linkage phosphorus through a linker, e.g., =N— when the heterocyclyl group is part of a guanidine moiety who directed bonded to a linkage phosphorus through its =N—. In some embodiments, a non-negatively charged internucleotidic linkage comprises an optionally substituted

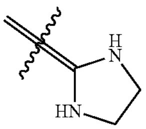 [SMILES: *=C1NCCN1]

group. In some embodiments, a non-negatively charged internucleotidic linkage comprises an substituted

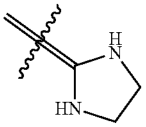 [SMILES: *=C1NCCN1]

group. In some embodiments, a non-negatively charged internucleotidic linkage comprises a

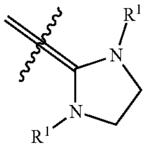

group. In some embodiments, each $R^1$ is independently optionally substituted $C_{1-6}$ alkyl. In some embodiments, each $R^1$ is independently methyl.

In some embodiments, a modified internucleotidic linkage, e.g., a non-negatively charged internucleotidic linkage, comprises a triazole or alkyne moiety, each of which is optionally substituted. In some embodiments, a modified internucleotidic linkage comprises a triazole moiety. In some embodiments, a modified internucleotidic linkage comprises a unsubstituted triazole moiety. In some embodiments, a modified internucleotidic linkage comprises a substituted triazole moiety. In some embodiments, a modified internucleotidic linkage comprises an alkyl moiety. In some embodiments, a modified internucleotidic linkage comprises an optionally substituted alkynyl group. In some embodiments, a modified internucleotidic linkage comprises an unsubstituted alkynyl group. In some embodiments, a modified internucleotidic linkage comprises a substituted alkynyl group. In some embodiments, an alkynyl group is directly bonded to a linkage phosphorus.

In some embodiments, an oligonucleotide comprises different types of internucleotidic phosphorus linkages. In some embodiments, a chirally controlled oligonucleotide comprises at least one natural phosphate linkage and at least one modified (non-natural) internucleotidic linkage. In some embodiments, an oligonucleotide comprises at least one natural phosphate linkage and at least one phosphorothioate. In some embodiments, an oligonucleotide comprises at least one non-negatively charged internucleotidic linkage. In some embodiments, an oligonucleotide comprises at least one natural phosphate linkage and at least one non-negatively charged internucleotidic linkage. In some embodiments, an oligonucleotide comprises at least one phosphorothioate internucleotidic linkage and at least one non-negatively charged internucleotidic linkage. In some embodiments, an oligonucleotide comprises at least one phosphorothioate internucleotidic linkage, at least one natural phosphate linkage, and at least one non-negatively charged internucleotidic linkage. In some embodiments, oligonucleotides comprise one or more, e.g., 1-50, 1-40, 1-30, 1-20, 1-15, 1-10, 1, 2, 3, 4, 5, 6, 7, 8, 9, 10, 11, 12, 13, 14, 15, 16, 17, 18, 19, 20 or more non-negatively charged internucleotidic linkages. In some embodiments, a non-negatively charged internucleotidic linkage is not negatively charged in that at a given pH in an aqueous solution less than 50%, 40%, 40%, 30%, 20%, 10%, 5%, or 1% of the internucleotidic linkage exists in a negatively charged salt form. In some embodiments, a pH is about pH 7.4. In some embodiments, a pH is about 4-9. In some embodiments, the percentage is less than 10%. In some embodiments, the percentage is less than 5%. In some embodiments, the percentage is less than 1%. In some embodiments, an internucleotidic linkage is a non-negatively charged internucleotidic linkage in that the neutral form of the internucleotidic linkage has no pKa that is no more than about 1, 2, 3, 4, 5, 6, or 7 in water. In some embodiments, no pKa is 7 or less. In some embodiments, no pKa is 6 or less. In some embodiments, no pKa is 5 or less. In some embodiments, no pKa is 4 or less. In some embodiments, no pKa is 3 or less. In some embodiments, no pKa is 2 or less. In some embodiments, no pKa is 1 or less. In some embodiments, pKa of the neutral form of an internucleotidic linkage can be represented by pKa of the neutral form of a compound having the structure of $CH_3$—the internucleotidic linkage-$CH_3$. For example, pKa of

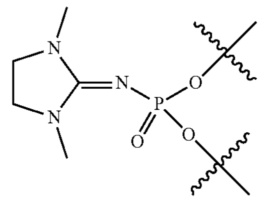 [SMILES: *OP(=O)(N=C1N(C)CCN1C)O*]

can be represented by pKa

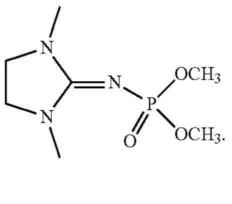

In some embodiments, a non-negatively charged internucleotidic linkage is a neutral internucleotidic linkage. In some embodiments, a non-negatively charged internucleotidic linkage is a positively-charged internucleotidic linkage. In some embodiments, a non-negatively charged internucleotidic linkage comprises a guanidine moiety. In some embodiments, a non-negatively charged internucleotidic linkage comprises a heteroaryl base moiety. In some embodiments, a non-negatively charged internucleotidic linkage comprises a triazole moiety. In some embodiments, a non-negatively charged internucleotidic linkage comprises an alkynyl moiety.

Without wishing to be bound by any particular theory, the present disclosure notes that a neutral internucleotidic linkage can be more hydrophobic than a phosphorothioate internucleotidic linkage (PS), which can be more hydrophobic than a natural phosphate linkage (PO). Typically, unlike a PS or PO, a neutral internucleotidic linkage bears less charge. Without wishing to be bound by any particular theory, the present disclosure notes that incorporation of one or more neutral internucleotidic linkages into an oligonucleotide may increase oligonucleotides' ability to be taken up by a cell and/or to escape from endosomes. Without wishing to be bound by any particular theory, the present disclosure notes that incorporation of one or more neutral internucleotidic linkages can be utilized to modulate melting temperature of duplexes formed between an oligonucleotide and its target nucleic acid.

Without wishing to be bound by any particular theory, the present disclosure notes that incorporation of one or more non-negatively charged internucleotidic linkages, e.g., neutral internucleotidic linkages, into an oligonucleotide may be able to increase the oligonucleotide's ability to mediate a function such as gene knockdown. In some embodiments, an oligonucleotide, e.g., a RHO oligonucleotide capable of mediating knockdown of level of a nucleic acid or a product encoded thereby comprises one or more non-negatively charged internucleotidic linkages. In some embodiments, an oligonucleotide, e.g., a RHO oligonucleotide capable of mediating knockdown of expression of a target gene comprises one or more non-negatively charged internucleotidic linkages.

In many embodiments, as demonstrated extensively, oligonucleotides of the present disclosure comprise two or more different internucleotidic linkages. In some embodiments, an oligonucleotide comprises a phosphorothioate internucleotidic linkage and a non-negatively charged internucleotidic linkage. In some embodiments, an oligonucleotide comprises a phosphorothioate internucleotidic linkage, a non-negatively charged internucleotidic linkage, and a natural phosphate linkage. In some embodiments, a non-negatively charged internucleotidic linkage is a neutral internucleotidic linkage. In some embodiments, a non-negatively charged internucleotidic linkage is n001. In some embodiments, each phosphorothioate internucleotidic linkage is independently chirally controlled. In some embodiments, each chiral modified internucleotidic linkage is independently chirally controlled. In some embodiments, at least 5, 6, 7, 8, 9, 10, 11, 12, 13, 14, 15, 16, 17, 18, 19, or 20 chiral internucleotidic linkage are independently chirally controlled.

A typical connection, as in natural DNA and RNA, is that an internucleotidic linkage forms bonds with two sugars (which can be either unmodified or modified as described herein). In many embodiments, as exemplified herein an internucleotidic linkage forms bonds through its oxygen atoms or heteroatoms with one optionally modified ribose or deoxyribose at its 5' carbon, and the other optionally modified ribose or deoxyribose at its 3' carbon. In some embodiments, each nucleoside units connected by an internucleotidic linkage independently comprises a nucleobase which is independently an optionally substituted A, T, C, G, or U, or an optionally substituted tautomer of A, T, C, G or U.

In some embodiments, a modified internucleotidic linkage has the structure of —O—P(═O)(—R)—O—, wherein R is as described herein. In some embodiments, R is optionally substituted $C_{1-6}$ alipatic. In some embodiments, R is methyl. In some embodiments, R is ethyl.

As appreciated by those skilled in the art, many other types of internucleotidic linkages may be utilized in accordance with the present disclosure, for example, those described in U.S. Pat. Nos. 3,687,808; 4,469,863; 4,476,301; 5,177,195; 5,023,243; 5,034,506; 5,166,315; 5,185,444; 5,188,897; 5,214,134; 5,216,141; 5,235,033; 5,264,423; 5,264,564; 5,276,019; 5,278,302; 5,286,717; 5,321,131; 5,399,676; 5,405,938; 5,405,939; 5,434,257; 5,453,496; 5,455,233; 5,466,677; 5,466,677; 5,470,967; 5,476,925; 5,489,677; 5,519,126; 5,536,821; 5,541,307; 5,541,316; 5,550,111; 5,561,225; 5,563,253; 5,571,799; 5,587,361; 5,596,086; 5,602,240; 5,608,046; 5,610,289; 5,618,704; 5,623,070; 5,625,050; 5,633,360; 5,64,562; 5,663,312; 5,677,437; 5,677,439; 6,160,109; 6,239,265; 6,028,188; 6,124,445; 6,169,170; 6,172,209; 6,277,603; 6,326,199; 6,346,614; 6,444,423; 6,531,590; 6,534,639; 6,608,035; 6,683,167; 6,858,715; 6,867,294; 6,878,805; 7,015,315; 7,041,816; 7,273,933; 7,321,029; or RE39464. In some embodiments, a modified internucleotidic linkage is one described in U.S. Pat. Nos. 9,394,333, 9,744,183, 9,605,019, 9,598,458, 9,982,257, U.S. Ser. No. 10/160,969, U.S. Ser. No. 10/479,995, US 2020/0056173, US 2018/0216107, US 2019/0127733, U.S. Ser. No. 10/450,568, US 2019/0077817, US 2019/0249173, US 2019/0375774, WO 2018/223056, WO 2018/223073, WO 2018/223081, WO 2018/237194, WO 2019/032607, WO 2019/055951, WO 2019/075357, WO 2019/200185, WO 2019/217784, and/or WO 2019/032612, the nucleobases, sugars, internucleotidic linkages, chiral auxiliaries/reagents, and technologies for oligonucleotide synthesis (reagents, conditions, cycles, etc.) of each of which is independently incorporated herein by reference.

In some embodiments, an oligonucleotide comprises one or more nucleotides that independently comprise a phosphorus modification prone to "autorelease" under certain conditions. That is, under certain conditions, a particular phosphorus modification is designed such that it self-cleaves from the oligonucleotide to provide, e.g., a natural phosphate linkage. Certain examples of such phosphorus modification groups can be found in U.S. Pat. No. 9,982,257. In some embodiments, an autorelease group is characterized by the ability to deliver an agent to the internucleotidic phosphorus linker, which agent facilitates further modification of the phosphorus atom such as, e.g., desulfurization. In some embodiments, the agent is water and the further modification is hydrolysis to form a natural phosphate linkage.

In some embodiments, provided oligonucleotides or regions thereof comprises alternating phosphodiester (PO) and phosphorothioate (PS) internucleotidic linkages, e.g., [(PO)(PS)]x, [(PS)(PO)]x, etc., wherein x is 1-50. In some embodiments, an oligonucleotide or a region thereof, e.g., a 5'-wing, comprises or consists of a pattern of backbone linkages (internucleotidic linkages) of (PM)(PO/PN)t, (PM)(PO)t, or (PM)(PN)t, wherein each PM is independently a modified internucleotidic linkage, each PN is independently a non-negatively charged internucleotidic linkage, and t is 1-50. In some embodiments, an oligonucleotide or a region thereof, e.g., a 3'-wing, comprises or consists of a pattern of backbone linkages (internucleotidic linkages) of (PO/PN)m(PM), (PO)m(PM), or (PN)m(PM), wherein m is 1-50, and each other variable is independently as described in the present disclosure. In some embodiments, an oligonucleotide comprises or consists of a pattern of backbone linkages (internucleotidic linkages) of (PM)(PO/PN)t(PM)n(PO/PN)m(PM), (PM)(PN)t(PM)n(PO)m(PM), (PM)(PO)t(PM)n(PN)m(PM), (PM)(PO)t(PM)n(PO)m(PM), or (PM)(PN)t(PM)n(PN)m(PM), wherein n is 1-50, and each other variable is as described in the present disclosure. In some embodiments, a PM is a PS. In some embodiments, each PM is a PS. In some embodiments, a PN is n001. In some embodiments, each PN is n001.

In some embodiments, t is 1, 2, 3, 4, 5, 6, 7, 8, 9, 10, 11, 12, 13, 14, 15, 16, 17, 18, 19, 20, 21, 22, 23, 24, or 25. In some embodiments, t is 1, 2, 3, 4, 5, 6, 7, 8, 9, or 10. In some embodiments, t is 1-10, 1-15, 1-20, 1-25, 1-30, 2-10, 2-15, 2-20, 2-25, 2-30, 5-10, 5-15, 5-20, 5-25, 5-30, 8-10, 8-15, 8-20, 8-25, 8-30, 10-15, 10-20, 10-25, or 10-30. In some embodiments, t is 1-3, 1-4, 1-5, 1-10, 2-3, 2-5, 2-6, or 2-10. In some embodiments, t is 1. In some embodiments, t is 2. In some embodiments, t is 3. In some embodiments, t is 4. In some embodiments, t is 5. In some embodiments, t is 6. In some embodiments, t is 7. In some embodiments, t is 8. In some embodiments, t is 9. In some embodiments, t is 10. In some embodiments, t is 11. In some embodiments, t is 12. In some embodiments, t is 13. In some embodiments, t is 14. In some embodiments, t is 15. In some embodiments, t is 16. In some embodiments, t is 17. In some embodiments, t is 18. In some embodiments, t is 19. In some embodiments, t is 20.

In some embodiments, m is 1, 2, 3, 4, 5, 6, 7, 8, 9, 10, 11, 12, 13, 14, 15, 16, 17, 18, 19, 20, 21, 22, 23, 24, or 25. In some embodiments, m is 1, 2, 3, 4, 5, 6, 7, 8, 9, or 10. In some embodiments, m is 1-10, 1-15, 1-20, 1-25, 1-30, 2-10, 2-15, 2-20, 2-25, 2-30, 5-10, 5-15, 5-20, 5-25, 5-30, 8-10, 8-15, 8-20, 8-25, 8-30, 10-15, 10-20, 10-25, or 10-30. In some embodiments, m is 1-3, 1-4, 1-5, 1-10, 2-3, 2-5, 2-6, or 2-10. In some embodiments, m is 1. In some embodiments, m is 2. In some embodiments, m is 3. In some embodiments, m is 4. In some embodiments, m is 5. In some embodiments, m is 6. In some embodiments, m is 7. In some embodiments, m is 8. In some embodiments, m is 9. In some embodiments, m is 10. In some embodiments, m is 11. In some embodiments, m is 12. In some embodiments, m is 13. In some embodiments, m is 14. In some embodiments, m is 15. In some embodiments, m is 16. In some embodiments, m is 17. In some embodiments, m is 18. In some embodiments, m is 19. In some embodiments, m is 20.

In some embodiments, t=m. In some embodiments, t>m. In some embodiments, t<m. In some embodiments, n is 1-10, 1-15, 1-20, 1-25, 1-30, 2-10, 2-15, 2-20, 2-25, 2-30, 5-10, 5-15, 5-20, 5-25, 5-30, 8-10, 8-15, 8-20, 8-25, 8-30, 10-15, 10-20, 10-25, or 10-30. In some embodiments, n is 1, 2, 3, 4, 5, 6, 7, 8, 9, 10, 11, 12, 13, 14, 15, 16, 17, 18, 19, 20, 21, 22, 23, 24, or 25. In some embodiments, n is 1. In some embodiments, n is 2. In some embodiments, n is 3. In some embodiments, n is 4. In some embodiments, n is 5. In some embodiments, n is 6. In some embodiments, n is 7. In some embodiments, n is 8. In some embodiments, n is 9. In some embodiments, n is 10. In some embodiments, n is 11. In some embodiments, n is 12. In some embodiments, n is 13. In some embodiments, n is 14. In some embodiments, n is 15. In some embodiments, n is 16. In some embodiments, n is 17. In some embodiments, n is 18. In some embodiments, n is 19. In some embodiments, n is 20.

Examples of certain patterns can be found, e.g., in oligonucleotides in Table A1 or A2.

Various types of internucleotidic linkages may be utilized in combination of other structural elements, e.g., sugars, to achieve desired oligonucleotide properties and/or activities. For example, the present disclosure routinely utilizes modified internucleotidic linkages and modified sugars, optionally with natural phosphate linkages and natural sugars, in designing oligonucleotides. In some embodiments, the present disclosure provides an oligonucleotide comprising one or more modified sugars. In some embodiments, the present disclosure provides an oligonucleotide comprising one or more modified sugars and one or more modified internucleotidic linkages, one or more of which are natural phosphate linkages.

Oligonucleotide Compositions

Among other things, the present disclosure provides various oligonucleotide compositions. In some embodiments, the present disclosure provides oligonucleotide compositions of oligonucleotides described herein. In some embodiments, an oligonucleotide composition, e.g., a RHO oligonucleotide composition, comprises a plurality of an oligonucleotide described in the present disclosure. In some embodiments, an oligonucleotide composition, e.g., a RHO oligonucleotide composition, is chirally controlled. In some embodiments, an oligonucleotide composition, e.g., a RHO oligonucleotide composition, is not chirally controlled (stereorandom).

Linkage phosphorus of natural phosphate linkages is achiral. Linkage phosphorus of many modified internucleotidic linkages, e.g., phosphorothioate internucleotidic linkages, are chiral. In some embodiments, during preparation of oligonucleotide compositions (e.g., in traditional phosphoramidite oligonucleotide synthesis), configurations of chiral linkage phosphorus are not purposefully designed or controlled, creating non-chirally controlled (stereorandom) oligonucleotide compositions (substantially racemic preparations) which are complex, random mixtures of various stereoisomers (diastereoisomers)—for oligonucleotides with n chiral internucleotidic linkages (linkage phosphorus being chiral), typically $2^n$ stereoisomers (e.g., when n is 10, $2^{10}=1,032$; when n is 20, $2^{20}=1,048,576$). These stereoisomers have the same constitution, but differ with respect to the pattern of stereochemistry of their linkage phosphorus.

In some embodiments, stereorandom oligonucleotide compositions have sufficient properties and/or activities for certain purposes and/or applications. In some embodiments, stereorandom oligonucleotide compositions can be cheaper, easier and/or simpler to produce than chirally controlled oligonucleotide compositions. However, stereoisomers within stereorandom compositions may have different properties, activities, and/or toxicities, resulting in inconsistent therapeutic effects and/or unintended side effects by stereorandom compositions, particularly compared to certain chirally controlled oligonucleotide compositions of oligonucleotides of the same constitution.

In some embodiments, the present disclosure encompasses technologies for designing and preparing chirally controlled oligonucleotide compositions. In some embodiments, the present disclosure provides chirally controlled oligonucleotide compositions, e.g., of many oligonucleotides in Table A1 or A2 which contain S and/or R in their stereochemistry/linkage. In some embodiments, a chirally controlled oligonucleotide composition comprises a controlled/pre-determined (not random as in stereorandom compositions) level of a plurality of oligonucleotides, wherein the oligonucleotides share the same linkage phosphorus stereochemistry at one or more chiral internucleotidic linkages (chirally controlled internucleotidic linkages). In some embodiments, the oligonucleotides share the same pattern of backbone chiral centers (stereochemistry of linkage phosphorus). In some embodiments, a pattern of backbone chiral centers is as described in the present disclosure. In some embodiments, the oligonucleotides are structural identical.

In some embodiments, an oligonucleotide composition is a chirally controlled oligonucleotide composition comprising a plurality of oligonucleotides, wherein the oligonucleotides share:

1) a common base sequence,
2) a common pattern of backbone linkages, and
3) the same linkage phosphorus stereochemistry at one or more (e.g., 1-50, 1-40, 1-30, 1-25, 1-20, 1-15, 1-10, 5-50, 5-40, 5-30, 5-25, 5-20, 5-15, 5-10, 1, 2, 3, 4, 5, 6, 7, 8, 9, 10, 11, 12, 13, 14, 15, 16, 17, 18, 19, 20, or more) chiral internucleotidic linkages (chirally controlled internucleotidic linkages), wherein the composition is enriched, relative to a substantially racemic preparation of oligonucleotides sharing the common base sequence and pattern of backbone linkages, for oligonucleotides of the plurality.

In some embodiments, an oligonucleotide composition is a chirally controlled oligonucleotide composition comprising a plurality of oligonucleotides, wherein the oligonucleotides share:

1) a common base sequence,
2) a common patter of backbone linkages, and
3) a common pattern of backbone chiral centers, which pattern comprises at least one Sp, wherein the composition is enriched, relative to a substantially racemic preparation of oligonucleotides sharing the common base sequence and pattern of backbone linkages, for oligonucleotides of the plurality.

In some embodiments, an oligonucleotide composition is a chirally controlled oligonucleotide composition comprising a plurality of oligonucleotides, wherein the oligonucleotides share:

1) a common base sequence,
2) a common patter of backbone linkages, and
3) a common pattern of backbone chiral centers, which pattern comprises at least one Rp, wherein the composition is enriched, relative to a substantially racemic preparation of oligonucleotides sharing the common base sequence and pattern of backbone linkages, for oligonucleotides of the plurality.

In some embodiments, oligonucleotides of a plurality are of the same constitution. In some embodiments, the present disclosure provides a chirally controlled oligonucleotide composition comprising a plurality of oligonucleotides, wherein the oligonucleotides are of a common constitution, and share the same linkage phosphorus stereochemistry at one or more (e.g., 1-50, 1-40, 1-30, 1-25, 1-20, 1, 2, 3, 4, 5, 6, 7, 8, 9, 10, 11, 12, 13, 14, 15, 16, 17, 18, 19, 20, 21, 22, 23, 24, 25 or more) chiral internucleotidic linkages (chirally controlled internucleotidic linkages), wherein the composition is enriched, relative to a substantially racemic preparation of oligonucleotides of the common constitution, for oligonucleotides of the plurality.

In some embodiments, oligonucleotides of a plurality are structurally identical. In some embodiments, the present disclosure provides a chirally controlled oligonucleotide composition comprising a plurality of oligonucleotides, wherein the oligonucleotides are structurally identical, and share the same linkage phosphorus stereochemistry at one or more (e.g., 1-50, 1-40, 1-30, 1-25, 1-20, 1, 2, 3, 4, 5, 6, 7, 8, 9, 10, 11, 12, 13, 14, 15, 16, 17, 18, 19, 20, 21, 22, 23, 24, 25 or more) chiral internucleotidic linkages (chirally controlled internucleotidic linkages), wherein the composition is enriched, relative to a substantially racemic preparation of oligonucleotides of the same constitution as the oligonucleotides of the plurality, for oligonucleotides of the plurality.

In some embodiments, they share the same stereochemistry independently 5-50 or more, e.g., 5, 6, 7, 8, 9, 10, 11, 12, 13, 14, 15, 16, 17, 18, 19, 20, 21, 22, 23, 24, or 25 or more chiral internucleotidic linkages. In some embodiments, oligonucleotides of the plurality share the same stereochemistry at each phosphorothioate internucleotidic linkage.

In some embodiments, an enrichment relative to a substantially racemic preparation is that at least about 5%, 10%, 20%, 30%, 40%, 50%, 60%, 70%, 80%, 85%, 90%, 91%, 92%, 93%, 94%, 95%, 96%, 97%, 98%, or 99% of all oligonucleotides in the composition are oligonucleotide of the plurality. In some embodiments, an enrichment relative to a substantially racemic preparation is that at least about 5%, 10%, 20%, 30%, 40%, 50%, 60%, 70%, 80%, 85%, 90%, 91%, 92%, 93%, 94%, 95%, 96%, 97%, 98%, or 99% of all oligonucleotides in the composition that share the common base sequence are oligonucleotides of the plurality. In some embodiments, an enrichment relative to a substantially racemic preparation is that at least about 5%, 10%, 20%, 30%, 40%, 50%, 60%, 70%, 80%, 85%, 90%, 91%, 92%, 93%, 94%, 95%, 96%, 97%, 98%, or 99% of all oligonucleotides in the composition that share the common constitution are oligonucleotides of the plurality. In some embodiments, the percentage is at least about 10%. In some embodiments, the percentage is at least about 20%. In some embodiments, the percentage is at least about 30%. In some embodiments, the percentage is at least about 40%. In some embodiments, the percentage is at least about 50%. In some embodiments, the percentage is at least about 60%. In some embodiments, the percentage is at least about 70%. In some embodiments, the percentage is at least about 75%. In some embodiments, the percentage is at least about 80%. In some embodiments, the percentage is at least about 85%. In some embodiments, the percentage is at least about 90%. In some embodiments, the percentage is at least about 91%. In some embodiments, the percentage is at least about 92%. In some embodiments, the percentage is at least about 93%. In some embodiments, the percentage is at least about 94%. In some embodiments, the percentage is at least about 95%. In some embodiments, the percentage is at least about 96%. In some embodiments, the percentage is at least about 97%. In some embodiments, the percentage is at least about 98%. In some embodiments, the percentage is at least about 99%. As appreciated by those skilled in the art, various forms of an oligonucleotide may be properly considered to have the same constitution and/or structure, and various forms of oligonucleotides sharing the same constitution may be properly considered to have the same constitution.

Levels of oligonucleotides of a plurality in chirally controlled oligonucleotide compositions are controlled. In contrast, in non-chirally controlled (or stereorandom, racemic) oligonucleotide compositions (or preparations), levels of oligonucleotides are random and not controlled. In some embodiments, a level of the oligonucleotides of a plurality in a chirally controlled oligonucleotide composition is about 1%-100%, (e.g., about 5%-100%, 10%-100%, 20%-100%, 30%-100%, 40%-100%, 50%-100%, 60%-100%, 70%-100%, 80-100%, 90-100%, 95-100%, 50%-90%, or about 5%, 10%, 20%, 30%, 40%, 50%, 60%, 70%, 80%, 85%, 90%, 91%, 92%, 93%, 94%, 95%, 96%, 97%, 98%, or 99%, or at least 5%, 10%, 20%, 30%, 40%, 50%, 60%, 70%, 80%, 85%, 90%, 91%, 92%, 93%, 94%, 95%, 96%, 97%, 98%, or 99%) of all oligonucleotides in the chirally controlled oligonucleotide composition, or of all oligonucleotides in the chirally controlled oligonucleotide composition that share the common base sequence as the oligonucleotides of the plurality, or of all oligonucleotides in the chirally controlled oligonucleotide composition that share the common base sequence and pattern of backbone linkages as the oligonucleotides of the plurality, or of all oligonucleotides in the chirally controlled oligonucleotide composition that share the common base sequence, pattern of backbone linkages as and pattern of backbone phosphorus modifications as the oligonucleotides of the plurality, or of all oligonucleotides in the chirally controlled oligonucleotide composition that share the same constitution as oligonucleotides of the plurality. In some embodiments, an enrichment relative to a substantially racemic preparation is a level described herein.

In some embodiments, a level as a percentage (e.g., a controlled level, a pre-determined level, an enrichment) is or is at least $(DS)^{nc}$, wherein DS is 90%-100%, and nc is the number of chirally controlled internucleotidic linkages as described in the present disclosure (e.g., 5, 6, 7, 8, 9, 10, 11, 12, 13, 14, 15, 16, 17, 18, 19, 20 or more). In some embodiments, each chiral internucleotidic linkage is chirally controlled, and nc is the number of chiral internucleotidic linkage. In some embodiments, DS is 90%, 91%, 92%, 93%, 94%, 95%, 96%, 97%, 98%, 99% or 99.5% or more. In some embodiments, DS is or is at least 90%. In some embodiments, DS is or is at least 91%. In some embodiments, DS is or is at least 92%. In some embodiments, DS is or is at least 93%. In some embodiments, DS is or is at least 94%. In some embodiments, DS is or is at least 95%. In some embodiments, DS is or is at least 96%. In some embodiments, DS is or is at least 97%. In some embodiments, DS is or is at least 98%. In some embodiments, DS is or is at least 99%. In some embodiments, a level (e.g., a controlled level, a pre-determined level, an enrichment) is a percentage of all oligonucleotides in a composition that share the same constitution, wherein the percentage is or is at least $(DS)^{nc}$. For example, when DS is 99% and nc is 10, the percentage is or is at least 90% ($(99\%)^{10}\approx 0.90=90\%$). As appreciated by those skilled in the art, in a stereorandom preparation the percentage is typically about $1/2^{nc}$—when nc is 10, the percentage is about $1/2^{10}\approx 0.001=0.1\%$.

In some embodiments, an oligonucleotide composition is a chirally controlled oligonucleotide composition comprising a plurality of oligonucleotides, wherein the oligonucleotides share:

1) a common base sequence,
2) a common pattern of backbone linkages, and
3) the same linkage phosphorus stereochemistry at one or more (e.g., 1-50, 1-40, 1-30, 1-25, 1-20, 1-15, 1-10, 5-50, 5-40, 5-30, 5-25, 5-20, 5-15, 5-10, 1, 2, 3, 4, 5, 6, 7, 8, 9, 10, 11, 12, 13, 14, 15, 16, 17, 18, 19, 20, or more) chiral internucleotidic linkages (chirally controlled internucleotidic linkages), wherein the percentage of the oligonucleotides of the plurality within all oligonucleotides in the composition that share the common base sequence and pattern of backbone linkages is at least $(DS)^{nc}$, wherein DS is 90%-100%, and nc is the number of chirally controlled internucleotidic linkages.

In some embodiments, an oligonucleotide composition is a chirally controlled oligonucleotide composition comprising a plurality of oligonucleotides, wherein the oligonucleotides share:

1) a common base sequence,
2) a common patter of backbone linkages, and
3) a common pattern of backbone chiral centers, which pattern comprises at least one Sp, wherein the percentage of the oligonucleotides of the plurality within all oligonucleotides in the composition that share the common base sequence and pattern of backbone linkages is at least $(DS)^{nc}$, wherein DS is 90%-100%, and nc is the number of chirally controlled internucleotidic linkages.

In some embodiments, an oligonucleotide composition is a chirally controlled oligonucleotide composition comprising a plurality of oligonucleotides, wherein the oligonucleotides share:

1) a common base sequence,
2) a common patter of backbone linkages, and
3) a common pattern of backbone chiral centers, which pattern comprises at least one Rp, wherein the percentage of the oligonucleotides of the plurality within all oligonucleotides in the composition that share the common base sequence and pattern of backbone linkages is at least $(DS)^{nc}$, wherein DS is 90%-100%, and nc is the number of chirally controlled internucleotidic linkages.

In some embodiments, the present disclosure provides a chirally controlled oligonucleotide composition comprising a plurality of oligonucleotides, wherein the oligonucleotides are of a common constitution, and share the same linkage phosphorus stereochemistry at one or more (e.g., 1-50, 1-40, 1-30, 1-25, 1-20, 1-15, 1-10, 5-50, 5-40, 5-30, 5-25, 5-20, 5-15, 5-10, 1, 2, 3, 4, 5, 6, 7, 8, 9, 10, 11, 12, 13, 14, 15, 16, 17, 18, 19, 20, or more) chiral internucleotidic linkages (chirally controlled internucleotidic linkages), wherein the percentage of the oligonucleotides of the plurality within all oligonucleotides of the same constitution in the composition is at least $(DS)^{nc}$, wherein DS is 90%-100%, and nc is the number of chirally controlled internucleotidic linkages.

In some embodiments, oligonucleotides of the plurality are of different salt forms. In some embodiments, oligonucleotides of the plurality comprise one or more forms, e.g., various pharmaceutically acceptable salt forms, of a single oligonucleotide. In some embodiments, oligonucleotides of the plurality comprise one or more forms, e.g., various pharmaceutically acceptable salt forms, of two or more oligonucleotides. In some embodiments, oligonucleotides of the plurality comprise one or more forms, e.g., various pharmaceutically acceptable salt forms, of $2^{NCC}$ oligonucleotides, wherein NCC is the number of non-chirally controlled chiral internucleotidic linkages. In some embodiments, the $2^{NCC}$ oligonucleotides have relatively similar levels within a composition as, e.g., none of them are specifically enriched using chirally controlled oligonucleotide synthesis.

In some embodiments, the present disclosure provides a chirally controlled oligonucleotide composition comprising a plurality of oligonucleotides, wherein the oligonucleotides are structurally identical, and share the same linkage phosphorus stereochemistry at one or more (e.g., 1-50, 1-40, 1-30, 1-25, 1-20, 1-15, 1-10, 5-50, 5-40, 5-30, 5-25, 5-20, 5-15, 5-10, 1, 2, 3, 4, 5, 6, 7, 8, 9, 10, 11, 12, 13, 14, 15, 16, 17, 18, 19, 20, or more) chiral internucleotidic linkages (chirally controlled internucleotidic linkages), wherein the percentage of the oligonucleotides of the plurality within all oligonucleotides of the same constitution as the oligonucleotides of the plurality in the composition is at least $(DS)^{nc}$, wherein DS is 90%-100%, and nc is the number of chirally controlled internucleotidic linkages.

In some embodiments, level of a plurality of oligonucleotides in a composition can be determined as the product of the diastereopurity of each chirally controlled internucleotidic linkage in the oligonucleotides. In some embodiments, diastereopurity of an internucleotidic linkage connecting two nucleosides in an oligonucleotide (or nucleic acid) is represented by the diastereopurity of an internucleotidic linkage of a dimer connecting the same two nucleosides, wherein the dimer is prepared using comparable conditions, in some instances, identical synthetic cycle conditions (e.g., for the linkage between Nx and Ny in an oligonucleotide . . . NxNy . . . , the dimer is NxNy).

In some embodiments, all chiral internucleotidic linkages are chiral controlled, and the composition is a completely chirally controlled oligonucleotide composition. In some embodiments, not all chiral internucleotidic linkages are chiral controlled internucleotidic linkages, and the composition is a partially chirally controlled oligonucleotide composition. In some embodiments, at least 10%, 20%, 30%, 40%, 50%, 60%, 70%, 80%, 85%, 90%, 91%, 92%, 93%, 94%, 95%, 96%, 97%, 98%, or 99% of all chiral internucleotidic linkages are chirally controlled. In some embodiments, at least 50%, 60%, 70%, 80%, 85%, 90%, 91%, 92%, 93%, 94%, 95%, 96%, 97%, 98%, or 99% of all chiral internucleotidic linkages are chirally controlled.

Oligonucleotides may comprise or consist of various patterns of backbone chiral centers (patterns of stereochemistry of chiral linkage phosphorus). Certain useful patterns of backbone chiral centers are described in the present disclosure. In some embodiments, a plurality of oligonucleotides share a common pattern of backbone chiral centers, which is or comprises a pattern described in the present disclosure (e.g., as in "Linkage Phosphorus Stereochemistry and Patterns Thereof", a pattern of backbone chiral centers of a chirally controlled oligonucleotide in Table A1 or A2, etc.).

In some embodiments, a chirally controlled oligonucleotide composition is chirally pure (or stereopure, stereochemically pure) oligonucleotide composition, wherein the oligonucleotide composition comprises a plurality of oligonucleotides, wherein the oligonucleotides are identical [including that each chiral element of the oligonucleotides, including each chiral linkage phosphorus, is independently defined (stereodefined)], and the composition does not contain other stereoisomers. A chirally pure (or stereopure, stereochemically pure) oligonucleotide composition of an oligonucleotide stereoisomer does not contain other stereoisomers (as appreciated by those skilled in the art, one or more unintended stereoisomers may exist as impurities—example purities are descried in the present disclosure).

Chirally controlled oligonucleotide compositions can demonstrate a number of advantages over stereorandom oligonucleotide compositions. Among other things, chirally controlled oligonucleotide compositions are more uniform than corresponding stereorandom oligonucleotide compositions with respect to oligonucleotide structures. By controlling stereochemistry, compositions of individual stereoisomers can be prepared and assessed, so that chirally controlled oligonucleotide composition of stereoisomers with desired properties and/or activities can be developed. In some embodiments, chirally controlled oligonucleotide compositions provides better delivery, stability, clearance, activity, selectivity, and/or toxicity profiles compared to, e.g., corresponding stereorandom oligonucleotide compositions. In some embodiments, chirally controlled oligonucleotide compositions provide better efficacy, fewer side effects, and/or more convenient and effective dosage regimens. Among other things, patterns of backbone chiral centers as described herein can be utilized to provide controlled cleavage of oligonucleotide targets (e.g., transcripts such as pre-mRNA, mature mRNA, etc; including control of cleavage sites, rate and/or extent of cleavage at cleavage sites, and/or overall rate and extent of cleavage, etc.) and greatly increased target selectivity. In some embodiments, chirally controlled oligonucleotide compositions of oligonucleotides comprising certain patterns of backbone chiral centers can differentiate sequences with nucleobase difference at very few positions, in some embodiments, at single position (e.g., at SNP site, point mutation site, etc.).

In some embodiments, the present disclosure provides a stereorandom oligonucleotide composition, e.g., a stereorandom RHO oligonucleotide composition. In some embodiments, the present disclosure provides a stereorandom RHO oligonucleotide composition which is capable of decreasing the level, activity or expression of a RHO gene or a gene product thereof. In some embodiments, the present disclosure provides a stereorandom RHO oligonucleotide composition which is capable of decreasing the level, activity or expression of a RHO gene or a gene product thereof, and wherein the base sequence of the RHO oligonucleotides is, comprises, or comprises a span (e.g., at least 10 or 15 contiguous bases) of a base sequence disclosed herein (e.g., a base sequence in Table A1 or A2, wherein each T may be independently replaced with U and vice versa). In some embodiments, the present disclosure provides a stereorandom RHO oligonucleotide composition which is capable of decreasing the level, activity or expression of a RHO gene or a gene product thereof, and wherein the base sequence of the RHO oligonucleotides is or comprises a base sequence disclosed herein (e.g., a base sequence in Table A1 or A2, wherein each T may be independently replaced with U and vice versa). In some embodiments, the present disclosure provides a stereorandom RHO oligonucleotide composition which is capable of decreasing the level, activity or expression of a RHO gene or a gene product thereof, and wherein the base sequence of the RHO oligonucleotides is a base sequence disclosed herein (e.g., a base sequence in Table A1 or A2, wherein each T may be independently replaced with U and vice versa).

Non-limiting examples of stereorandom oligonucleotide compositions, e.g., stereorandom RHO oligonucleotide compositions are described herein, including but not limited to: WV-20866, WV-20867, WV-20868, WV-20869, and WV-20870.

Non-limiting examples of stereopure (or chirally controlled) oligonucleotide compositions, e.g., stereopure (or chirally controlled) RHO oligonucleotide compositions, are described herein, including but not limited to: WV-24270, WV-24271, WV-24272, WV-24273, WV-24274, WV-24275, WV-24276, WV-24277, WV-24278, WV-24279, WV-24280, WV-24281, WV-24282, WV-24283, WV-24284, WV-24285, WV-24286, WV-24287, WV-24288, WV-24289, WV-24290, WV-24291, WV-24292, WV-24293, WV-24653, WV-24654, WV-24655, WV-24656, and WV-24657.

In some embodiments, an oligonucleotide composition comprises a plurality of oligonucleotides, one or more internucleotidic linkages of which are stereocontrolled (chirally controlled) and one or more internucleotidic linkages which are stereorandom. In some embodiments, a RHO oligonucleotide composition comprises a plurality of oligonucleotides, one or more internucleotidic linkages of which are stereocontrolled (chirally controlled) and one or more internucleotidic linkages which are stereorandom.

In some embodiments, an oligonucleotide composition comprises a plurality of oligonucleotides, one or more internucleotidic linkages of which are stereocontrolled (e.g., chirally controlled) and one or more internucleotidic linkages which are stereorandom.

As understood by a person having ordinary skill in the art, stereorandom or (substantially) racemic preparations/non-chirally controlled oligonucleotide compositions are typically prepared without chiral control, e.g., without using chiral auxiliaries, chiral modification reagents, and/or chiral catalysts that can provide high stereoselectivity (e.g., 90%, 91%, 92%, 93%, 94%, 95%, 96%, 97%, 98%, 99% or 99.5% or more; in some embodiments, 95%, 96%, 97%, 98%, 99% or 99.5% or more; in some embodiments, 97%, 98%, 99% or 99.5% or more; in some embodiments, 98%, 99% or 99.5% or more) at linkage phosphorus during oligonucleotide synthesis. In some embodiments, in a substantially racemic (or chirally uncontrolled) preparation of oligonucleotides, coupling steps are not chirally controlled in that the coupling steps are not specifically conducted to provide enhanced stereoselectivity. An example substantially racemic preparation of oligonucleotides/non-chirally controlled oligonucleotide composition is a preparation of phosphorothioate oligonucleotides through traditional phosphoramidite oligonucleotide synthesis and sulfurization with non-chiral sulfurization reagents such as tetraethylthiuram disulfide or (TETD), 3H-1, 2-bensodithiol-3-one 1, 1-dioxide (BDTD), etc., which are well-known processes. Various methods for making stereorandom oligonucleotide compositions/substantially racemic preparations of oligonucleotides are widely known and practiced in the art and can be utilized for preparing such compositions and preparations of the present disclosure.

In some embodiments, the present disclosure provides a chirally controlled oligonucleotide composition, e.g., chirally controlled RHO oligonucleotide composition. In some embodiments, provided chirally controlled oligonucleotide compositions comprise a plurality of oligonucleotides, e.g., RHO oligonucleotides, of the same constitution, and have one or more (e.g., 1-50, 1-40, 1-30, 1-25, 1-20, 1-15, 1-10, 5-50, 5-40, 5-30, 5-25, 5-20, 5-15, 5-10, 1, 2, 3, 4, 5, 6, 7, 8, 9, 10, 11, 12, 13, 14, 15, 16, 17, 18, 19, 20, or more) internucleotidic linkages. In some embodiments, a plurality of oligonucleotides, e.g., in a chirally controlled oligonucleotide composition, is a plurality of an oligonucleotide selected from Table A1 or A2, wherein the oligonucleotide comprises at least one Rp or Sp linkage phosphorus in a chirally controlled internucleotidic linkage. In some embodiments, a plurality of oligonucleotides, e.g., in a chirally controlled oligonucleotide composition, is a plurality of an oligonucleotide selected from Table A1 or A2, wherein each phosphorothioate internucleotidic linkage in the oligonucleotide is independently chirally controlled (each phosphorothioate internucleotidic linkage is independently Rp or Sp). In some embodiments, an oligonucleotide composition, e.g., a RHO oligonucleotide composition is a substantially pure preparation of a single oligonucleotide in that oligonucleotides in the composition that are not the single oligonucleotide are impurities from the preparation process of the single oligonucleotide, in some case, after certain purification procedures. In some embodiments, a single oligonucleotide is an oligonucleotide of Table A1 or A2, wherein each chiral internucleotidic linkage of the oligonucleotide is chirally controlled (e.g., indicated as S or R but not X in "Stereochemistry/Linkage").

In some embodiments, a chirally controlled oligonucleotide composition can have, relative to a corresponding stereorandom oligonucleotide composition, increased activity and/or stability, increased delivery, and/or decreased ability to elicit adverse effects such as complement, TLR9 activation, etc. In some embodiments, a stereorandom (non-chirally controlled) oligonucleotide composition differs from a chirally controlled oligonucleotide composition in that its corresponding plurality of oligonucleotides do not contain any chirally controlled internucleotidic linkages but the stereorandom oligonucleotide composition is otherwise identical to the chirally controlled oligonucleotide composition.

In some embodiments, the present disclosure pertains to a chirally controlled RHO oligonucleotide composition which is capable of decreasing the level, activity or expression of a RHO gene or a gene product thereof.

In some embodiments, the present disclosure provides a chirally controlled RHO oligonucleotide composition which is capable of decreasing the level, activity or expression of a RHO gene or a gene product thereof, and comprises a plurality of oligonucleotides which share a common base sequence that is, comprises, or comprises a span (e.g., at least 10 or 15 contiguous bases) of abase sequence disclosed herein (e.g., in Table A1 or A2, wherein each T may be independently replaced with U and vice versa). In some embodiments, the present disclosure provides a chirally controlled RHO oligonucleotide composition which is capable of decreasing the level, activity or expression of a RHO gene or a gene product thereof, and comprises a plurality of oligonucleotides which share a common base sequence that is or comprises a base sequence disclosed herein (e.g., in Table A1 or A2, wherein each T may be independently replaced with U and vice versa). In some embodiments, the present disclosure provides a chirally controlled RHO oligonucleotide composition which is capable of decreasing the level, activity or expression of a RHO gene or a gene product thereof, and comprises a plurality of oligonucleotides which share a common base sequence that is a base sequence disclosed herein (e.g., in Table A1 or A2, wherein each T may be independently replaced with U and vice versa).

In some embodiments, a provided chirally controlled oligonucleotide composition is a chirally controlled RHO oligonucleotide composition comprising a plurality of RHO oligonucleotides. In some embodiments, a chirally controlled oligonucleotide composition is a chirally pure (or "stereochemically pure") oligonucleotide composition. In some embodiments, the present disclosure provides a chirally pure oligonucleotide composition of an oligonucleotide in Table A1 or A2, wherein each chiral internucleotidic linkage of the oligonucleotide is independently chirally controlled (Rp or Sp, e.g., can be determined from R or S but not X in "Stereochemistry/Linkage"). As appreciated by those skilled in the art, in a chirally controlled or chirally pure composition of an oligonucleotide, the percentage of the oligonucleotide in the composition is significantly higher [e.g., 10, 11, 12, 13, 14, 15, 16, 17, 18, 19, 20, 21, 22, 23, 24, 25, 30, 35, 40, 45, 50, 60, 70, 80, 90, 100, $10^3$, $\mathbf{10^4}$, $\mathbf{10^5}$ or more, or $10^{nc}$, $\mathbf{15^{nc}}$, $\mathbf{20^{nc}}$, $\mathbf{25^{nc}}$, $\mathbf{30^{nc}}$, $\mathbf{35^{nc}}$, $\mathbf{40^{nc}}$, $\mathbf{45^{nc}}$, $\mathbf{50^{nc}}$, $\mathbf{60^{nc}}$, $\mathbf{70^{nc}}$, $\mathbf{80^{nc}}$, $\mathbf{90^{nc}}$, $\mathbf{100^{nc}}$ or more, fold of the percentage of another stereoisomer, wherein nc is the number of chirally controlled internucleotidic linkage(s)] than any other possible stereoisomers, which may exist in the composition as impurities. As one of ordinary skill in the art will understand, chemical selectivity rarely, if ever, achieves completeness (absolute 100%). In some embodiments, a chirally pure oligonucleotide composition comprises a plurality of oligonucleotides, wherein oligonucleotides of the plurality are structurally identical and all have the same structure (the same stereoisomeric form; in the context of oligonucleotide, typically the same diastereomeric form as typically multiple chiral centers exist in an oligonucleotide), and the chirally pure oligonucleotide composition does not contain any other stereoisomers (in the context of oligonucleotide, typically diastereomers as typically multiple chiral centers exist in an oligonucleotide; to the extent, e.g., achievable by stereoselective preparation). As appreciated by those skilled in the art, stereorandom (or "racemic", "non-chirally controlled") oligonucleotide compositions are random mixtures of many stereoisomers (e.g., $2^n$ diastereoisomers wherein n is the number of chiral linkage phosphorus for oligonucleotides in which other chiral centers (e.g., carbon chiral centers in sugars) are chirally controlled each independently existing in one configuration and only chiral linkage phosphorus centers are not chirally controlled).

Certain data showing properties and/or activities of chirally controlled oligonucleotide composition, e.g., chirally controlled RHO oligonucleotide compositions in decreasing the level, activity and/or expression of a RHO target gene or a gene product thereof, are shown in, for example, the Examples section of this document.

In some embodiments, the present disclosure provides an oligonucleotide composition comprising oligonucleotides that comprise at least one chiral linkage phosphorus. In some embodiments, the present disclosure provides a RHO oligonucleotide composition comprising RHO oligonucleotides that comprise at least one chiral linkage phosphorus. In some embodiments, the present disclosure provides a RHO oligonucleotide composition in which the RHO oligonucleotides comprise a chirally controlled phosphorothioate internucleotidic linkage, wherein the linkage phosphorus has a Rp configuration. In some embodiments, the present disclosure provides a RHO oligonucleotide composition in which the RHO oligonucleotides comprise a chirally controlled phosphorothioate internucleotidic linkage, wherein the linkage phosphorus has a Sp configuration.

In some embodiments, compared to reference oligonucleotide compositions, provided chirally controlled oligonucleotide compositions (e.g., chirally controlled RHO oligonucleotide compositions) are surprisingly effective. In some embodiments, desired biological effects (e.g., as measured by decreased levels of mRNA, proteins, etc. whose levels are targeted for reduction) can be enhanced by more than 5, 10, 15, 20, 25, 30, 40, 50, or 100 fold (e.g., as measured by remaining levels of mRNA, proteins, etc.). In some embodiments, a change is measured by decrease of an undesired mRNA level compared to a reference condition. In some embodiments, a change is measured by increase of a desired mRNA level compared to a reference condition. In some embodiments, a change is measured by decrease of an undesired mRNA level compared to a reference condition. In some embodiments, a reference condition is absence of treatment, e.g., by a chirally controlled oligonucleotide composition. In some embodiments, a reference condition is a corresponding stereorandom composition of oligonucleotides having the same constitution.

In some embodiments, the present disclosure provides a chirally controlled oligonucleotide composition, e.g., a chirally controlled RHO oligonucleotide composition, wherein the linkage phosphorus of at least one chirally controlled internucleotidic linkage is Sp. In some embodiments, the present disclosure provides a chirally controlled oligonucleotide composition, e.g., a chirally controlled RHO oligonucleotide composition, wherein the majority of linkage phosphorus of chirally controlled internucleotidic linkages are Sp. In some embodiments, about 50%-100%, 55%-100%, 60%-100%, 65%-100%, 70%-100%, 75%-100%, 80%-100%, 85%-100%, 90%-100%, 55%-95%, 60%-95%, 65%-95%, or about 55%, 60%, 65%, 70%, 75%, 80%, 85%, 90%, 95%, 97%, 99% or more, of all chirally controlled internucleotidic linkages (or of all chiral internucleotidic linkages, or of all internucleotidic linkages) are Sp. In some embodiments, the present disclosure provides a chirally controlled oligonucleotide composition, e.g., a chirally controlled RHO oligonucleotide composition, wherein the majority of chiral internucleotidic linkages are chirally controlled and are Sp at their linkage phosphorus. In some embodiments, the present disclosure provides a chirally controlled oligonucleotide composition, e.g., a chirally controlled RHO oligonucleotide composition, wherein each chiral internucleotidic linkage is chirally controlled and each chiral linkage phosphorus is Sp. In some embodiments, the present disclosure provides a chirally controlled oligonucleotide composition, e.g., chirally controlled RHO oligonucleotide composition, wherein at least one chirally controlled internucleotidic linkage has a Rp linkage phosphorus. In some embodiments, the present disclosure provides a chirally controlled oligonucleotide composition, e.g., a chirally controlled RHO oligonucleotide composition, wherein at least one chirally controlled internucleotidic linkage comprises a Rp linkage phosphorus and at least one chirally controlled internucleotidic linkage comprises a Sp linkage phosphorus.

In some embodiments, the present disclosure provides a chirally controlled oligonucleotide composition, wherein at least two chirally controlled internucleotidic linkages have different linkage phosphorus stereochemistry and/or different P-modifications relative to one another, wherein a P-modification is a modification at a linkage phosphorus. In some embodiments, the present disclosure provides a chirally controlled oligonucleotide composition, wherein at least two chirally controlled internucleotidic linkages have different stereochemistry relative to one another, and the pattern of the backbone chiral centers of the oligonucleotides is characterized by a repeating pattern of alternating stereochemistry.

In certain embodiments, the present disclosure provides a chirally controlled oligonucleotide composition comprising a plurality of oligonucleotides, wherein with in each of the oligonucleotides at least two individual internucleotidic linkages have different P-modifications relative to one another. In certain embodiments, the present disclosure provides a chirally controlled oligonucleotide composition comprising a plurality of oligonucleotides, wherein with in each of the oligonucleotides at least two individual internucleotidic linkages have different P-modifications relative to one another, and each of the oligonucleotide comprises a natural phosphate linkage. In certain embodiments, the present disclosure provides a chirally controlled oligonucleotide composition comprising a plurality of oligonucleotides, wherein with in each of the oligonucleotides at least two individual internucleotidic linkages have different P-modifications relative to one another, and each of the oligonucleotide comprises a phosphorothioate internucleotidic linkage. In certain embodiments, the present disclosure provides a chirally controlled oligonucleotide composition comprising a plurality of oligonucleotides, wherein with in each of the oligonucleotides at least two individual internucleotidic linkages have different P-modifications relative to one another, and each of the oligonucleotide comprises a natural phosphate linkage and a phosphorothioate internucleotidic linkage. In certain embodiments, the present disclosure provides a chirally controlled oligonucleotide composition comprising a plurality of oligonucleotides, wherein with in each of the oligonucleotides at least two individual internucleotidic linkages have different P-modifications relative to one another, and each of the oligonucleotide comprises a phosphorothioate triester internucleotidic linkage. In certain embodiments, the present disclosure provides a chirally controlled oligonucleotide composition comprising a plurality of oligonucleotides, wherein with in each of the oligonucleotides at least two individual internucleotidic linkages have different P-modifications relative to one another, and each of the oligonucleotide comprises a natural phosphate linkage and a phosphorothioate triester internucleotidic linkage. In certain embodiments, the present disclosure provides a chirally controlled oligonucleotide composition comprising a plurality of oligonucleotides, wherein with in each of the oligonucleotides at least two individual internucleotidic linkages have different P-modifications relative to one another, and each of the oligonucleotide comprises a phosphorothioate internucleotidic linkage and a phosphorothioate triester internucleotidic linkage.

In some embodiments, the present disclosure provides a chirally controlled oligonucleotide composition, e.g., a chirally controlled RHO oligonucleotide composition, comprising a plurality of oligonucleotides which share a common base sequence that is the base sequence of an oligonucleotide disclosed herein, wherein at least one internucleotidic linkage is chirally controlled. In some embodiments, the present disclosure provides a chirally controlled oligonucleotide composition, e.g., a chirally controlled RHO oligonucleotide composition, comprising a plurality of oligonucleotides which share a common base sequence that is the base sequence of an oligonucleotide disclosed herein, wherein at least one internucleotidic linkage is chirally controlled, and at least one internucleotidic linkage has the structure of formula I or a salt form thereof. In some embodiments, the present disclosure provides a chirally controlled oligonucleotide composition, e.g., a chirally controlled RHO oligonucleotide composition, comprising a plurality of oligonucleotides which share a common base sequence that is the base sequence of an oligonucleotide disclosed herein, wherein at least one internucleotidic linkage is chirally controlled, and each chirally controlled internucleotidic linkage has the structure of formula I or a salt form thereof. In some embodiments, the present disclosure provides a chirally controlled oligonucleotide composition, e.g., a chirally controlled RHO oligonucleotide composition, comprising a plurality of oligonucleotides which share a common base sequence that is the base sequence of an oligonucleotide disclosed herein, wherein each modified internucleotidic linkage has the structure of formula I or a salt form thereof. In some embodiments, at least one internucleotidic linkage has the structure of Formula I-c. In some embodiments, each modified internucleotidic linkage independently has the structure of Formula I-c. In some embodiments, each internucleotidic linkage has the structure of formula I-c. In some embodiments, a chirally controlled internucleotidic linkage is a chirally controlled phosphorothioate internucleotidic linkage. In some embodiments, each chirally controlled internucleotidic linkage is a chirally controlled phosphorothioate internucleotidic linkage.

Stereochemistry and Patterns of Backbone Chiral Centers

In contrast to natural phosphate linkages, linkage phosphorus of chiral modified internucleotidic linkages, e.g., phosphorothioate internucleotidic linkages, are chiral. Among other things, the present disclosure provides technologies (e.g., oligonucleotides, compositions, methods, etc.) comprising control of stereochemistry of chiral linkage phosphorus in chiral internucleotidic linkages. In some embodiments, as demonstrated herein, control of stereochemistry can provide improved properties and/or activities, including desired stability, reduced toxicity, improved reduction of target nucleic acids, etc. In some embodiments, the present disclosure provides useful patterns of backbone chiral centers for oligonucleotides and/or regions thereof, which pattern is a combination of stereochemistry of each chiral linkage phosphorus (Rp or Sp) of chiral linkage phosphorus, indication of each achiral linkage phosphorus (Op, if any), etc. from 5' to 3'. In some embodiments, patterns of backbone chiral centers can control cleavage patterns of target nucleic acids when they are contacted with provided oligonucleotides or compositions thereof in a cleavage system (e.g., in vitro assay, cells, tissues, organs, organisms, subjects, etc.). In some embodiments, patterns of backbone chiral centers improve cleavage efficiency and/or selectivity of target nucleic acids when they are contacted with provided oligonucleotides or compositions thereof in a cleavage system.

In some embodiments, a pattern of backbone chiral centers of an oligonucleotide, e.g., a RHO oligonucleotide, or a region thereof comprises or is (Np)n(Op)m, wherein Np is Rp or Sp, Op represents a linkage phosphorus being achiral (e.g., as for the linkage phosphorus of natural phosphate linkages), and each of n and m is independently as defined and described in the present disclosure. In some embodiments, a pattern of backbone chiral centers of an oligonucleotide or a region thereof comprises or is (Sp)n(Op)m, wherein each variable is independently as defined and described in the present disclosure. In some embodiments, a pattern of backbone chiral centers of an oligonucleotide or a region thereof comprises or is (Rp)n(Op)m, wherein each variable is independently as defined and described in the present disclosure. In some embodiments, n is 1. In some embodiments, a pattern of backbone chiral centers of an oligonucleotide or a region thereof comprises or is (Sp)(Op)m, wherein m is 1, 2, 3, 4, 5, 6, 7, 8, 9, or 10. In some embodiments, a pattern of backbone chiral centers of an oligonucleotide or a region thereof comprises or is (Rp)(Op)m, wherein m is 1, 2, 3, 4, 5, 6, 7, 8, 9, or 10. In some embodiments, the pattern of backbone chiral centers of a 5'-wing is or comprises (Np)n(Op)m. In some embodiments, the pattern of backbone chiral centers of a 5'-wing is or comprises (Sp)n(Op)m. In some embodiments, the pattern of backbone chiral centers of a 5'-wing is or comprises (Rp)n(Op)m. In some embodiments, the pattern of backbone chiral centers of a 5'-wing is or comprises (Sp)(Op)m. In some embodiments, the pattern of backbone chiral centers of a 5'-wing is or comprises (Rp)(Op)m. In some embodiments, the pattern of backbone chiral centers of a 5'-wing is (Sp)(Op)m. In some embodiments, the pattern of backbone chiral centers of a 5'-wing is (Rp)(Op)m. In some embodiments, the pattern of backbone chiral centers of a 5'-wing is (Sp)(Op)m, wherein Sp is the linkage phosphorus configuration of the first internucleotidic linkage of the oligonucleotide from the 5'-end. In some embodiments, the pattern of backbone chiral centers of a 5'-wing is (Rp)(Op)m, wherein Rp is the linkage phosphorus configuration of the first internucleotidic linkage of the oligonucleotide from the 5'-end. In some embodiments, as described in the present disclosure, m is 2; in some embodiments, m is 3; in some embodiments, m is 4; in some embodiments, m is 5; in some embodiments, m is 6.

In some embodiments, a pattern of backbone chiral centers of an oligonucleotide, e.g., a RHO oligonucleotide, or a region thereof comprises or is (Op)m(Np)n, wherein Np is Rp or Sp, Op represents a linkage phosphorus being achiral (e.g., as for the linkage phosphorus of natural phosphate linkages), and each of n and m is independently as defined and described in the present disclosure. In some embodiments, a pattern of backbone chiral centers of an oligonucleotide or a region thereof comprises or is (Op)m(Sp)n, wherein each variable is independently as defined and described in the present disclosure. In some embodiments, a pattern of backbone chiral centers of an oligonucleotide or a region thereof comprises or is (Op)m(Rp)n, wherein each variable is independently as defined and described in the present disclosure. In some embodiments, n is 1. In some embodiments, a pattern of backbone chiral centers of an oligonucleotide or a region thereof comprises or is (Op)m(Sp), wherein m is 1, 2, 3, 4, 5, 6, 7, 8, 9, or 10. In some embodiments, a pattern of backbone chiral centers of an oligonucleotide or a region thereof comprises or is (Op)m(Rp), wherein m is 1, 2, 3, 4, 5, 6, 7, 8, 9, or 10. In some embodiments, the pattern of backbone chiral centers of a 3'-wing is or comprises (Op)m(Np)n. In some embodiments, the pattern of backbone chiral centers of a 3'-wing is or comprises (Op)m(Sp)n. In some embodiments, the pattern of backbone chiral centers of a 3'-wing is or comprises (Op)m(Rp)n. In some embodiments, the pattern of backbone chiral centers of a 3'-wing is or comprises (Op)m(Sp). In some embodiments, the pattern of backbone chiral centers of a 3'-wing is or comprises (Op)m(Rp). In some embodiments, the pattern of backbone chiral centers of a 3'-wing is (Op)m(Sp). In some embodiments, the pattern of backbone chiral centers of a 3'-wing is (Op)m(Rp). In some embodiments, the pattern of backbone chiral centers of a 3'-wing is (Op)m(Sp), wherein Sp is the linkage phosphorus configuration of the last internucleotidic linkage of the oligonucleotide from the 5'-end. In some embodiments, the pattern of backbone chiral centers of a 3'-wing is (Op)m(Rp), wherein Rp is the linkage phosphorus configuration of the last internucleotidic linkage of the oligonucleotide from the 5'-end. In some embodiments, as described in the present disclosure, m is 2; in some embodiments, m is 3; in some embodiments, m is 4; in some embodiments, m is 5; in some embodiments, m is 6.

In some embodiments, a pattern of backbone chiral centers of an oligonucleotide, e.g., a RHO oligonucleotide, or a region thereof (e.g., a core) comprises or is (Sp)m(Rp/Op)n or (Rp/Op)n(Sp)m, wherein each variable is independently as described in the present disclosure. In some embodiments, a pattern of backbone chiral centers of an oligonucleotide or a region thereof (e.g., a core) comprises or is (Sp)m(Rp)n or (Rp)n(Sp)m, wherein each variable is independently as described in the present disclosure. In some embodiments, a pattern of backbone chiral centers of an oligonucleotide or a region thereof (e.g., a core) comprises (Sp)m(Rp)n, wherein each variable is independently as described in the present disclosure. For example, in some embodiments, n is 1; in some embodiments, n is 2; in some embodiments, m is 1; in some embodiments, m is greater than 1; in some embodiments, m is 1, 2, 3, 4, 5, 6, 7, 8, 9, 10 or more. In some embodiments, a pattern of backbone chiral centers of an oligonucleotide or a region thereof (e.g., a core) comprises (Rp)n(Sp)m, wherein each variable is independently as described in the present disclosure. For example, in some embodiments, n is 1; in some embodiments, n is 2; in some embodiments, m is 1; in some embodiments, m is greater than 1; in some embodiments, m is 1, 2, 3, 4, 5, 6, 7, 8, 9, 10 or more. In some embodiments, a pattern of backbone chiral centers of an oligonucleotide or a region thereof (e.g., a core) comprises or is (Sp)m(Op)n or (Op)n(Sp)m, wherein each variable is independently as described in the present disclosure. In some embodiments, a pattern of backbone chiral centers of an oligonucleotide, e.g., a RHO oligonucleotide, or a region thereof (e.g., a core) comprises or is (Np)t[(Rp/Op)n(Sp)m]y or [(Rp/Op)n(Sp)m]y(Np)t, wherein y is 1-50, and each other variable is independently as described in the present disclosure. In some embodiments, a pattern of backbone chiral centers of an oligonucleotide or a region thereof (e.g., a core) comprises or is (Np)t[(Rp)n(Sp)m]y or [(Rp)n(Sp)m]y(Np)t, wherein each variable is independently as described in the present disclosure. In some embodiments, a pattern of backbone chiral centers of an oligonucleotide, e.g., a RHO oligonucleotide, or a region thereof (e.g., a core) comprises or is [(Rp/Op)n(Sp)m]y(Rp)k, [(Rp/Op)n(Sp)m]y, (Sp)t[(Rp/Op)n(Sp)m]y, (Sp)t[(Rp/Op)n(Sp)m]y(Rp)k, wherein k is 1-50, and each other variable is independently as described in the present disclosure. In some embodiments, a pattern of backbone chiral centers of an oligonucleotide or a region thereof (e.g., a core) comprises or is [(Op)n(Sp)m]y(Rp)k, [(Op)n(Sp)m]y, (Sp)t[(Op)n(Sp)m]y, (Sp)t[(Op)n(Sp)m]y(Rp)k, wherein each variable is independently as described in the present disclosure. In some embodiments, a pattern of backbone chiral centers of an oligonucleotide or a region thereof (e.g., a core) comprises or is [(Rp)n(Sp)m]y(Rp)k, [(Rp)n(Sp)m]y, (Sp)t[(Rp)n(Sp)m]y, (Sp)t[(Rp)n(Sp)m]y(Rp)k, wherein each variable is independently as described in the present disclosure. In some embodiments, an oligonucleotide comprises a core region. In some embodiments, an oligonucleotide comprises a core region, wherein each sugar in the core region does not contain a 2'-$OR^1$, wherein $R^1$ is as described in the present disclosure. In some embodiments, an oligonucleotide comprises a core region, wherein each sugar in the core region is independently a natural DNA sugar. In some embodiments, the pattern of backbone chiral centers of the core comprises or is (Rp)(Sp)m. In some embodiments, the pattern of backbone chiral centers of the core comprises or is (Op)(Sp)m. In some embodiments, the pattern of backbone chiral centers of the core comprises or is (Np)t[(Rp/Op)n(Sp)m]y or [(Rp/Op)n(Sp)m]y(Np)t. In some embodiments, the pattern of backbone chiral centers of the core comprises or is (Np)t[(Rp/Op)n(Sp)m]y or [(Rp/Op)n(Sp)m]y(Np)t. In some embodiments, the pattern of backbone chiral centers of the core comprises or is (Np)t[(Rp)n(Sp)m]y or [(Rp)n(Sp)m]y(Np)t. In some embodiments, the pattern of backbone chiral centers of a core comprises or is [(Rp/Op)n(Sp)m]y(Rp)k, [(Rp/Op)n(Sp)m]y, (Sp)t[(Rp/Op)n(Sp)m]y, (Sp)t[(Rp/Op)n(Sp)m]y(Rp)k. In some embodiments, a pattern of backbone chiral centers of a core comprises or is [(Op)n(Sp)m]y(Rp)k, [(Op)n(Sp)m]y, (Sp)t[(Op)n(Sp)m]y, (Sp)t[(Op)n(Sp)m]y(Rp)k. In some embodiments, a pattern of backbone chiral centers of a core comprises or is [(Rp)n(Sp)m]y(Rp)k, [(Rp)n(Sp)m]y, (Sp)t[(Rp)n(Sp)m]y, or (Sp)t[(Rp)n(Sp)m]y(Rp)k. In some embodiments, a pattern of backbone chiral centers of a core comprises [(Rp)n(Sp)m]y(Rp)k. In some embodiments, a pattern of backbone chiral centers of a core comprises [(Rp)n(Sp)m]y(Rp). In some embodiments, a pattern of backbone chiral centers of a core comprises [(Rp)n(Sp)m]y. In some embodiments, a pattern of backbone chiral centers of a core comprises (Sp)t[(Rp)n(Sp)m]y. In some embodiments, a pattern of backbone chiral centers of a core comprises (Sp)t[(Rp)n(Sp)m]y(Rp)k. In some embodiments, a pattern of backbone chiral centers of a core comprises (Sp)t[(Rp)n(Sp)m]y(Rp). In some embodiments, a pattern of backbone chiral centers of a core is [(Rp)n(Sp)m]y(Rp)k. In some embodiments, a pattern of backbone chiral centers of a core is [(Rp)n(Sp)m]y(Rp). In some embodiments, a pattern of backbone chiral centers of a core is [(Rp)n(Sp)m]y. In some embodiments, a pattern of backbone chiral centers of a core is (Sp)t[(Rp)n(Sp)m]y. In some embodiments, a pattern of backbone chiral centers of a core is (Sp)t[(Rp)n(Sp)m]y(Rp)k. In some embodiments, a pattern of backbone chiral centers of a core is (Sp)t[(Rp)n(Sp)m]y(Rp). In some embodiments, each n is 1. In some embodiments, each t is 1. In some embodiments, t is 2, 3, 4, 5, 6, 7, 8, 9, or 10. In some embodiments, each of t and n is 1. In some embodiments, each m is 2 or more. In some embodiments, k is 1. In some embodiments, k is 2-10.

In some embodiments, a pattern of backbone chiral centers comprises or is (Sp)m(Rp)n, (Rp)n(Sp)m, (Np)t(Rp)n(Sp)m, (Sp)t(Rp)n(Sp)m, (Np)t[(Rp)n(Sp)m]2, (Sp)t[(Rp)n(Sp)m]2, (Np)t(Op)n(Sp)m, (Sp)t(Op)n(Sp)m, (Np)t[(Op)n(Sp)m]2, or (Sp)t[(Op)n(Sp)m]2. In some embodiments, a pattern is (Np)t(Op/Rp)n(Sp)m(Op/Rp)n(Sp)m. In some embodiments, a pattern is (Np)t(Op/Rp)n(Sp)1-5(Op/Rp)n(Sp)m. In some embodiments, a pattern is (Np)t(Op/Rp)n(Sp)2-5(Op/Rp)n(Sp)m. In some embodiments, a pattern is (Np)t(Op/Rp)n(Sp)2(Op/Rp)n(Sp)m. In some embodiments, a pattern is (Np)t(Op/Rp)n(Sp)3(Op/Rp)n(Sp)m. In some embodiments, a pattern is (Np)t(Op/Rp)n(Sp)4(Op/Rp)n(Sp)m. In some embodiments, a pattern is (Np)t(Op/Rp)n(Sp)5(Op/Rp)n(Sp)m.

In some embodiments, Np is Sp. In some embodiments, (Op/Rp) is Op. In some embodiments, (Op/Rp) is Rp. In some embodiments, Np is Sp and (Op/Rp) is Rp. In some embodiments, Np is Sp and (Op/Rp) is Op. In some embodiments, Np is Sp and at least one (Op/Rp) is Rp, and at least one (Op/Rp) is Op. In some embodiments, a pattern of backbone chiral centers comprises or is (Rp)n(Sp)m, (Np)t(Rp)n(Sp)m, or (Sp)t(Rp)n(Sp)m, wherein m>2. In some embodiments, a pattern of backbone chiral centers comprises or is (Rp)n(Sp)m, (Np)t(Rp)n(Sp)m, or (Sp)t(Rp)n(Sp)m, wherein n is 1, at least one t>1, and at least one m>2.

In some embodiments, oligonucleotides comprising core regions whose patterns of backbone chiral centers starting with Rp can provide high activities and/or improved properties. In some embodiments, oligonucleotides comprising core regions whose patterns of backbone chiral centers ending with Rp can provide high activities and/or improved properties. In some embodiments, oligonucleotides comprising core regions whose patterns of backbone chiral centers starting with Rp provide high activities (e.g., target cleavage) without significantly impacting its properties, e.g., stability. In some embodiments, oligonucleotides comprising core regions whose patterns of backbone chiral centers ending with Rp provide high activities (e.g., target cleavage) without significantly impacting its properties, e.g., stability. In some embodiments, patterns of backbone chiral centers start with Rp and end with Sp. In some embodiments, patterns of backbone chiral centers start with Rp and end with Rp. In some embodiments, patterns of backbone chiral centers start with Sp and end with Rp. Typically, for patterns of backbone chiral centers internucleotidic linkages connecting core nucleosides and wing nucleosides are included in the patterns of the core regions. In many embodiments as described in the present disclosure (e.g., various oligonucleotides in Table A1 or A2), the wing sugar connected by such a connecting internucleotidic linkage has a different structure than the core sugar connected by the same connecting internucleotidic linkage (e.g., in some embodiments, the wing sugar comprises a 2'-modification while the core sugar does not contain the same 2'-modification or have two —H at the 2' position). In some embodiments, the wing sugar comprises a sugar modification that the core sugar does not contain. In some embodiments, the wing sugar is a modified sugar while the core sugar is a natural DNA sugar. In some embodiments, the wing sugar comprises a sugar modification at the 2' position (less than two —H at the 2' position), and the core sugar has no modification at the 2'-position (two —H at the 2' position).

As demonstrated herein, in some embodiments, introducing additional Rp internucleotidic linkages (e.g., in addition to a Rp linkage linking two core sugars, which are optionally unmodified and are optionally at or near characteristic sequence, e.g., a SNP site) can improve activity and/or selectivity of an oligonucleotide. In some embodiments, as demonstrated herein, an additional Rp internucleotidic linkage links a sugar containing no 2'-substituent (e.g., a core sugar) and a sugar comprising a 2'-modification (e.g., 2'-OR', wherein R' is optionally substituted $C_{1-6}$ aliphatic (e.g., 2'-OMe, 2'-MOE, etc.), which can be a wing sugar). In some embodiments, an internucleotidic linkage linking a sugar containing no 2'-substituent to the 5'-end (e.g., to the 3'-carbon of the sugar) and a sugar comprising a 2'-modification to the 3'-end (e.g., to the 5'-carbon of the sugar) is a Rp internucleotidic linkage. In some embodiments, an internucleotidic linkage linking a sugar containing no 2'-substituent to the 3'-end (e.g., to the 5'-carbon of the sugar) and a sugar comprising a 2'-modification to the 5'-end (e.g., to the 3'-carbon of the sugar) is a Rp internucleotidic linkage. In some embodiments, each internucleotidic linkage linking a sugar containing no 2'-substituent and a sugar comprising a 2'-modification is independently a Rp internucleotidic linkage. In some embodiments, a Rp internucleotidic linkage is a Rp phosphorothioate internucleotidic linkage.

In some embodiments, a pattern of backbone chiral centers of an oligonucleotide, e.g., a RHO oligonucleotide, or a region thereof (e.g., a core) comprises or is (Op)[(Rp/Op)n(Sp)m]y(Rp)k(Op), (Op)[(Rp/Op)n(Sp)m]y(Op), (Op)(Sp)t[(Rp/Op)n(Sp)m]y(Op), or (Op)(Sp)t[(Rp/Op)n(Sp)m]y(Rp)k(Op), wherein k is 1-50, and each other variable is independently as described in the present disclosure. In some embodiments, a pattern of backbone chiral centers of an oligonucleotide, e.g., a RHO oligonucleotide, comprises or is (Op)[(Rp/Op)n(Sp)m]y(Rp)k(Op), (Op)[(Rp/Op)n(Sp)m]y(Op), (Op)(Sp)t[(Rp/Op)n(Sp)m]y(Op), or (Op)(Sp)t[(Rp/Op)n(Sp)m]y(Rp)k(Op), wherein each of f, g, h and j is independently 1-50, and each other variable is independently as described in the present disclosure, and the oligonucleotide comprises a core region whose pattern of backbone chiral centers comprises or is [(Rp/Op)n(Sp)m]y(Rp)k, [(Rp/Op)n(Sp)m]y, (Sp)t[(Rp/Op)n(Sp)m]y, or (Sp)t[(Rp/Op)n(Sp)m]y(Rp)k as described in the present disclosure. In some embodiments, a pattern of backbone chiral centers is or comprises (Op)[(Rp/Op)n(Sp)m]y(Rp)k(Op). In some embodiments, a pattern of backbone chiral centers is or comprises (Op)[(Rp/Op)n(Sp)m]y(Rp)(Op). In some embodiments, a pattern of backbone chiral centers is or comprises (Op)[(Rp/Op)n(Sp)m]y(Op). In some embodiments, a pattern of backbone chiral centers is or comprises (Op)(Sp)t[(Rp/Op)n(Sp)m]y(Op). In some embodiments, a pattern of backbone chiral centers is or comprises (Op)(Sp)t[(Rp/Op)n(Sp)m]y(Rp)k(Op). In some embodiments, a pattern of backbone chiral centers is or comprises (Op)(Sp)t[(Rp/Op)n(Sp)m]y(Rp)(Op). In some embodiments, a pattern of backbone chiral centers is or comprises (Op)[(Rp)n(Sp)m]y(Rp)k(Op). In some embodiments, a pattern of backbone chiral centers is or comprises (Op)[(Rp)n(Sp)m]y(Rp)(Op). In some embodiments, a pattern of backbone chiral centers is or comprises (Op)[(Rp)n(Sp)m]y(Op). In some embodiments, a pattern of backbone chiral centers is or comprises (Op)(Sp)t[(Rp)n(Sp)m]y(Op). In some embodiments, a pattern of backbone chiral centers is or comprises (Op)(Sp)t[(Rp)n(Sp)m]y(Rp)k(Op). In some embodiments, a pattern of backbone chiral centers is or comprises (Op)(Sp)t[(Rp)n(Sp)m]y(Rp)(Op). In some embodiments, each n is 1. In some embodiments, k is 1. In some embodiments, k is 2-10.

In some embodiments, a pattern of backbone chiral centers of an oligonucleotide, e.g., a RHO oligonucleotide, or a region thereof (e.g., a core) comprises or is (Np)f(Op)g[(Rp/Op)n(Sp)m]y(Rp)k(Op)h(Np)j, (Np)f(Op)g[(Rp/Op)n(Sp)m]y(Op)h(Np)j, (Np)f(Op)g(Sp)t[(Rp/Op)n(Sp)m]y(Op)h(Np)j, or (Np)f(Op)g(Sp)t[(Rp/Op)n(Sp)m]y(Rp)k(Op)h(Np)j, wherein each of f, g, h and j is independently 1-50, and each other variable is independently as described in the present disclosure. In some embodiments, a pattern of backbone chiral centers of an oligonucleotide, e.g., a RHO oligonucleotide, comprises or is (Np)f(Op)g[(Rp/Op)n(Sp)m]y(Rp)k(Op)h(Np)j, (Np)f(Op)g[(Rp/Op)n(Sp)m]y(Op)h(Np)j, (Np)f(Op)g(Sp)t[(Rp/Op)n(Sp)m]y(Op)h(Np)j, or (Np)f(Op)g(Sp)t[(Rp/Op)n(Sp)m]y(Rp)k(Op)h(Np)j, and the oligonucleotide comprises a core region whose pattern of backbone chiral centers comprises or is [(Rp/Op)n(Sp)m]y(Rp)k, [(Rp/Op)n(Sp)m]y, (Sp)t[(Rp/Op)n(Sp)m]y, or (Sp)t[(Rp/Op)n(Sp)m]y(Rp)k as described in the present disclosure. In some embodiments, a pattern of backbone chiral centers of an oligonucleotide, e.g., a RHO oligonucleotide, is (Np)f(Op)g[(Rp/Op)n(Sp)m]y(Rp)k(Op)h(Np)j, (Np)f(Op)g[(Rp/Op)n(Sp)m]y(Op)h(Np)j, (Np)f(Op)g(Sp)t[(Rp/Op)n(Sp)m]y(Op)h(Np)j, or (Np)f(Op)g(Sp)t[(Rp/Op)n(Sp)m]y(Rp)k(Op)h(Np)j, and the oligonucleotide comprises a core region whose pattern of backbone chiral centers comprises or is [(Rp/Op)n(Sp)m]y(Rp)k, [(Rp/Op)n(Sp)m]y, (Sp)t[(Rp/Op)n(Sp)m]y, or (Sp)t[(Rp/Op)n(Sp)m]y(Rp)k as described in the present disclosure. In some embodiments, a pattern of backbone chiral centers is or comprises (Np)f(Op)g[(Rp/Op)n(Sp)m]y(Rp)k(Op)h(Np)j. In some embodiments, a pattern of backbone chiral centers is or comprises (Np)f(Op)g[(Rp/Op)n(Sp)m]y(Rp)(Op)h(Np)j. In some embodiments, a pattern of backbone chiral centers is or comprises (Np)f(Op)g[(Rp/Op)n(Sp)m]y(Op)h(Np)j. In some embodiments, a pattern of backbone chiral centers is or comprises (Np)f(Op)g(Sp)t[(Rp/Op)n(Sp)m]y(Op)h(Np)j. In some embodiments, a pattern of backbone chiral centers is or comprises (Np)f(Op)g(Sp)t[(Rp/Op)n(Sp)m]y(Rp)k(Op)h(Np)j. In some embodiments, a pattern of backbone chiral centers is or comprises (Np)f(Op)g(Sp)t[(Rp/Op)n(Sp)m]y(Rp)(Op)h(Np)j. In some embodiments, a pattern of backbone chiral centers is or comprises (Np)f(Op)g[(Rp)n(Sp)m]y(Rp)k(Op)h(Np)j. In some embodiments, a pattern of backbone chiral centers is or comprises (Np)f(Op)g[(Rp)n(Sp)m]y(Rp)(Op)h(Np)j. In some embodiments, a pattern of backbone chiral centers is or comprises (Np)f(Op)g[(Rp)n(Sp)m]y(Op)h(Np)j. In some embodiments, a pattern of backbone chiral centers is or comprises (Np)f(Op)g(Sp)t[(Rp)n(Sp)m]y(Op)h(Np)j. In some embodiments, a pattern of backbone chiral centers is or comprises (Np)f(Op)g(Sp)t[(Rp)n(Sp)m]y(Rp)k(Op)h(Np)j. In some embodiments, a pattern of backbone chiral centers is or comprises (Np)f(Op)g(Sp)t[(Rp)n(Sp)m]y(Rp)(Op)h(Np)j. In some embodiments, at least one Np is Sp. In some embodiments, at least one Np is Rp. In some embodiments, the 5' most Np is Sp. In some embodiments, the 3' most Np is Sp. In some embodiments, each Np is Sp. In some embodiments, (Np)f(Op)g[(Rp/Op)n(Sp)m]y(Rp)k(Op)h(Np)j is (Sp)(Op)g

[(Rp)n(Sp)m]y(Rp)k(Op)h(Sp). In some embodiments, (Np)f(Op)g[(Rp/Op)n(Sp)m]y(Rp)k(Op)h(Np)j is (Sp)(Op)g[(Rp)n(Sp)m]y(Rp)(Op)h(Sp). In some embodiments, a pattern of backbone chiral center of an oligonucleotide is or comprises (Sp)(Op)g[(Rp)n(Sp)m]y(Rp)(Op)h(Sp). In some embodiments, a pattern of backbone chiral center of an oligonucleotide is (Sp)(Op)g[(Rp)n(Sp)m]y(Rp)(Op)h(Sp). In some embodiments, (Np)f(Op)g[(Rp/Op)n(Sp)m]y(Op)h(Np)j is (Sp)(Op)g[(Rp)n(Sp)m]y(Op)h(Sp). In some embodiments, a pattern of backbone chiral center of an oligonucleotide is or comprises (Sp)(Op)g[(Rp)n(Sp)m]y(Op)h(Sp). In some embodiments, a pattern of backbone chiral center of an oligonucleotide is (Sp)(Op)g[(Rp)n(Sp)m]y(Op)h(Sp). In some embodiments, (Np)f(Op)g(Sp)t[(Rp/Op)n(Sp)m]y(Op)h(Np)j is (Sp)(Op)g(Sp)t[(Rp)n(Sp)m]y(Op)h(Sp). In some embodiments, a pattern of backbone chiral center of an oligonucleotide is or comprises (Sp)(Op)g(Sp)t[(Rp)n(Sp)m]y(Op)h(Sp). In some embodiments, a pattern of backbone chiral center of an oligonucleotide is (Sp)(Op)g(Sp)t[(Rp)n(Sp)m]y(Op)h(Sp). In some embodiments, (Np)f(Op)g(Sp)t[(Rp/Op)n(Sp)m]y(Rp)k(Op)h(Np)j is (Sp)(Op)g(Sp)t[(Rp)n(Sp)m]y(Rp)k(Op)h(Sp). In some embodiments, (Np)f(Op)g(Sp)t[(Rp/Op)n(Sp)m]y(Rp)k(Op)h(Np)j is (Sp)(Op)g(Sp)t[(Rp)n(Sp)m]y(Rp)(Op)h(Sp). In some embodiments, a pattern of backbone chiral center of an oligonucleotide is or comprises (Sp)(Op)g(Sp)t[(Rp)n(Sp)m]y(Rp)(Op)h(Sp). In some embodiments, a pattern of backbone chiral center of an oligonucleotide is (Sp)(Op)g(Sp)t[(Rp)n(Sp)m]y(Rp)(Op)h(Sp). In some embodiments, each n is 1. In some embodiments, f is 1. In some embodiments, g is 1. In some embodiments, g is greater than 1. In some embodiments, g is 2. In some embodiments, g is 3. In some embodiments, g is 4. In some embodiments, g is 5. In some embodiments, g is 6. In some embodiments, g is 7. In some embodiments, g is 8. In some embodiments, g is 9. In some embodiments, g is 10. In some embodiments, h is 1. In some embodiments, h is greater than 1. In some embodiments, h is 2. In some embodiments, h is 3. In some embodiments, h is 4. In some embodiments, h is 5. In some embodiments, h is 6. In some embodiments, h is 7. In some embodiments, h is 8. In some embodiments, h is 9. In some embodiments, h is 10. In some embodiments, j is 1. In some embodiments, k is 1. In some embodiments, k is 2-10.

In some embodiments, a pattern of backbone chiral centers of an oligonucleotide, e.g., a RHO oligonucleotide, or a region thereof (e.g., a core) comprises or is [(Rp/Op)n(Sp)m]y, (Sp)t[(Rp/Op)n(Sp)m]y, (Sp)t[(Rp/Op)n(Sp)m]yRp, [(Rp/Op)n(Sp)m]y(Rp)k, (Sp)t[(Rp/Op)n(Sp)m]y(Rp)k, (Sp)t[(Rp/Op)n(Sp)m]y(Rp)k(Op)h, (Sp)t[(Rp/Op)n(Sp)m]y(Rp)k(Op)h(Np)j, wherein each variable is independently as described in the present disclosure.

In some embodiments, in a provided pattern of backbone chiral centers, at least one (Rp/Op) is Rp. In some embodiments, at least one (Rp/Op) is Op. In some embodiments, each (Rp/Op) is Rp. In some embodiments, each (Rp/Op) is Op. In some embodiments, at least one of [(Rp)n(Sp)m]y or [(Rp/Op)n(Sp)m]y of a pattern is RpSp. In some embodiments, at least one of [(Rp)n(Sp)m]y or [(Rp/Op)n(Sp)m]y of a pattern is or comprises RpSpSp. In some embodiments, at least one of [(Rp)n(Sp)m]y or [(Rp/Op)n(Sp)m]y in a pattern is RpSp, and at least one of [(Rp)n(Sp)m]y or [(Rp/Op)n(Sp)m]y in a pattern is or comprises RpSpSp. For example, in some embodiments, [(Rp)n(Sp)m]y in a pattern is (RpSp)[(Rp)n(Sp)m]$_{(y-1)}$; in some embodiments, [(Rp)n(Sp)m]y in a pattern is (RpSp)[RpSpSp(Sp)$_{(m-2)}$][(Rp)n(Sp)m]$_{(y-2)}$. In some embodiments, (Sp)t[(Rp)n(Sp)m]y(Rp) is (Sp)t(RpSp)[(Rp)n(Sp)m]$_{(y-1)}$(Rp). In some embodiments, (Sp)t[(Rp)n(Sp)m]y(Rp) is (Sp)t(RpSp)[RpSpSp(Sp)$_{(m-2)}$][(Rp)n(Sp)m]$_{(y-2)}$(Rp). In some embodiments, each [(Rp/Op)n(Sp)m] is independently [Rp(Sp)m]. In some embodiments, the first Sp of (Sp)t represents linkage phosphorus stereochemistry of the first internucleotidic linkage of an oligonucleotide from 5' to 3'. In some embodiments, the first Sp of (Sp)t represents linkage phosphorus stereochemistry of the first internucleotidic linkage of a region from 5' to 3', e.g., a core. In some embodiments, the last Np of (Np)j represents linkage phosphorus stereochemistry of the last internucleotidic linkage of the oligonucleotide from 5' to 3'. In some embodiments, the last Np is Sp.

In some embodiments, a pattern of backbone chiral centers of an oligonucleotide or a region (e.g., of a 5'-wing) is or comprises Sp$(Op)_3$. In some embodiments, a pattern of backbone chiral centers of an oligonucleotide or a region (e.g., of a 5'-wing) is or comprises Rp$(Op)_3$. In some embodiments, a pattern of backbone chiral centers of an oligonucleotide or a region (e.g., of a 3'-wing) is or comprises $(Op)_3$Sp. In some embodiments, a pattern of backbone chiral centers of an oligonucleotide or a region (e.g., of a 3'-wing) is or comprises $(Op)_3$Rp. In some embodiments, a pattern of backbone chiral centers of an oligonucleotide or a region (e.g., of a core) is or comprises Rp$(Sp)_4$Rp$(Sp)_4$Rp. In some embodiments, a pattern of backbone chiral centers of an oligonucleotide or a region (e.g., of a core) is or comprises $(Sp)_5$Rp$(Sp)_4$Rp. In some embodiments, a pattern of backbone chiral centers of an oligonucleotide or a region (e.g., of a core) is or comprises $(Sp)_5$Rp$(Sp)_5$. In some embodiments, a pattern of backbone chiral centers of an oligonucleotide or a region (e.g., of a core) is or comprises Rp$(Sp)_4$Rp$(Sp)_5$. In some embodiments, a pattern of backbone chiral centers of an oligonucleotide is or comprises Np$(Op)_3$Rp$(Sp)_4$Rp$(Sp)_4$Rp$(Op)_3$Np. In some embodiments, a pattern of backbone chiral centers of an oligonucleotide is or comprises Np$(Op)_3(Sp)_5$Rp$(Sp)_4$Rp$(Op)_3$Np. In some embodiments, a pattern of backbone chiral centers of an oligonucleotide is or comprises Np$(Op)_3(Sp)_5$Rp$(Sp)_5(Op)_3$Np. In some embodiments, a pattern of backbone chiral centers of an oligonucleotide is or comprises Np$(Op)_3$Rp$(Sp)_4$Rp$(Sp)_5(Op)_3$Np. In some embodiments, a pattern of backbone chiral centers of an oligonucleotide is or comprises Sp$(Op)_3$Rp$(Sp)_4$Rp$(Sp)_4$Rp$(Op)_3$Sp. In some embodiments, a pattern of backbone chiral centers of an oligonucleotide is or comprises Sp$(Op)_3(Sp)_5$Rp$(Sp)_4$Rp$(Op)_3$Sp. In some embodiments, a pattern of backbone chiral centers of an oligonucleotide is or comprises Sp$(Op)_3(Sp)_5$Rp$(Sp)_5(Op)_3$Sp. In some embodiments, a pattern of backbone chiral centers of an oligonucleotide is or comprises Sp$(Op)_3$Rp$(Sp)_4$Rp$(Sp)_5(Op)_3$Sp. In some embodiments, a pattern of backbone chiral centers of an oligonucleotide is or comprises Rp$(Op)_3$Rp$(Sp)_4$Rp$(Sp)_4$Rp$(Op)_3$Rp. In some embodiments, a pattern of backbone chiral centers of an oligonucleotide is or comprises Rp$(Op)_3(Sp)_5$Rp$(Sp)_4$Rp$(Op)_3$Rp. In some embodiments, a pattern of backbone chiral centers of an oligonucleotide is or comprises Rp$(Op)_3(Sp)_5$Rp$(Sp)_5(Op)_3$Rp. In some embodiments, a pattern of backbone chiral centers of an oligonucleotide is or comprises Rp$(Op)_3$Rp$(Sp)_4$Rp$(Sp)_5(Op)_3$Rp. In some embodiments, for an Rp immediately preceding or after Op, that Rp internucleotidic linkage is bonded to a sugar comprising a 2'-MOE modification.

In some embodiments, m is 1, 2, 3, 4, 5, 6, 7, 8, 9, 10, 11, 12, 13, 14, 15, 16, 17, 18, 19, 20, 21, 22, 23, 24, or 25. In some embodiments, in a pattern of backbone chiral centers each m is independently 2 or more. In some embodiments, each m is independently 2, 3, 4, 5, 6, 7, 8, 9, or 10. In some embodiments, each m is independently 2-3, 2-5, 2-6, or 2-10. In some embodiments, m is 2. In some embodiments, m is 3. In some embodiments, m is 4. In some embodiments, m is 5. In some embodiments, m is 6. In some embodiments, m is 7. In some embodiments, m is 8. In some embodiments, m is 9. In some embodiments, m is 10. In some embodiments, where there are two or more occurrences of m, they can be the same or different, and each of them is independently as described in the present disclosure.

In some embodiments, y is 1, 2, 3, 4, 5, 6, 7, 8, 9, 10, 11, 12, 13, 14, 15, 16, 17, 18, 19, 20, 21, 22, 23, 24, or 25. In some embodiments, y is 1, 2, 3, 4, 5, 6, 7, 8, 9, or 10. In some embodiments, y is 1. In some embodiments, y is 2. In some embodiments, y is 3. In some embodiments, y is 4. In some embodiments, y is 5. In some embodiments, y is 6. In some embodiments, y is 7. In some embodiments, y is 8. In some embodiments, y is 9. In some embodiments, y is 10.

In some embodiments, t is 1, 2, 3, 4, 5, 6, 7, 8, 9, 10, 11, 12, 13, 14, 15, 16, 17, 18, 19, 20, 21, 22, 23, 24, or 25. In some embodiments, each t is independently 1, 2, 3, 4, 5, 6, 7, 8, 9, or 10. In some embodiments, t is 2 or more. In some embodiments, t is 1. In some embodiments, t is 2. In some embodiments, t is 3. In some embodiments, t is 4. In some embodiments, t is 5. In some embodiments, t is 6. In some embodiments, t is 7. In some embodiments, t is 8. In some embodiments, t is 9. In some embodiments, t is 10. In some embodiments, where there are two or more occurrences of t, they can be the same or different, and each of them is independently as described in the present disclosure.

In some embodiments, n is 1, 2, 3, 4, 5, 6, 7, 8, 9, 10, 11, 12, 13, 14, 15, 16, 17, 18, 19, 20, 21, 22, 23, 24, or 25. In some embodiments, n is 1. In some embodiments, n is 2. In some embodiments, n is 3. In some embodiments, n is 4. In some embodiments, n is 5. In some embodiments, n is 6. In some embodiments, n is 7. In some embodiments, n is 8. In some embodiments, n is 9. In some embodiments, n is 10. In some embodiments, where there are two or more occurrences of n, they can be the same or different, and each of them is independently as described in the present disclosure. In many embodiments, in a pattern of backbone chiral centers, at least one occurrence of n is 1; in some cases, each n is 1.

In some embodiments, k is 1, 2, 3, 4, 5, 6, 7, 8, 9, 10, 11, 12, 13, 14, 15, 16, 17, 18, 19, 20, 21, 22, 23, 24, or 25. In some embodiments, k is 1. In some embodiments, k is 2. In some embodiments, k is 3. In some embodiments, k is 4. In some embodiments, k is 5. In some embodiments, k is 6. In some embodiments, k is 7. In some embodiments, k is 8. In some embodiments, k is 9. In some embodiments, k is 10.

In some embodiments, f is 1-20. In some embodiments, f is 1-10. In some embodiments, f is 1-5. In some embodiments, f is 1, 2, 3, 4, 5, 6, 7, 8, 9, 10, 11, 12, 13, 14, 15, 16, 17, 18, 19, 20, 21, 22, 23, 24, or 25. In some embodiments, f is 1. In some embodiments, f is 2. In some embodiments, f is 3. In some embodiments, f is 4. In some embodiments, f is 5. In some embodiments, f is 6. In some embodiments, f is 7. In some embodiments, f is 8. In some embodiments, f is 9. In some embodiments, f is 10.

In some embodiments, g is 1-20. In some embodiments, g is 1-10. In some embodiments, g is 1-5. In some embodiments, g is 2-10. In some embodiments, g is 2-5. In some embodiments, g is 1, 2, 3, 4, 5, 6, 7, 8, 9, 10, 11, 12, 13, 14, 15, 16, 17, 18, 19, 20, 21, 22, 23, 24, or 25. In some embodiments, g is 1. In some embodiments, g is 2. In some embodiments, g is 3. In some embodiments, g is 4. In some embodiments, g is 5. In some embodiments, g is 6. In some embodiments, g is 7. In some embodiments, g is 8. In some embodiments, g is 9. In some embodiments, g is 10.

In some embodiments, h is 1-20. In some embodiments, h is 1-10. In some embodiments, h is 1-5. In some embodiments, h is 2-10. In some embodiments, h is 2-5. In some embodiments, h is 1, 2, 3, 4, 5, 6, 7, 8, 9, 10, 11, 12, 13, 14, 15, 16, 17, 18, 19, 20, 21, 22, 23, 24, or 25. In some embodiments, h is 1. In some embodiments, h is 2. In some embodiments, h is 3. In some embodiments, h is 4. In some embodiments, h is 5. In some embodiments, h is 6. In some embodiments, h is 7. In some embodiments, h is 8. In some embodiments, h is 9. In some embodiments, h is 10.

In some embodiments, j is 1-20. In some embodiments, j is 1-10. In some embodiments, j is 1-5. In some embodiments, j is 1, 2, 3, 4, 5, 6, 7, 8, 9, 10, 11, 12, 13, 14, 15, 16, 17, 18, 19, 20, 21, 22, 23, 24, or 25. In some embodiments, j is 1. In some embodiments, j is 2. In some embodiments, j is 3. In some embodiments, j is 4. In some embodiments, j is 5. In some embodiments, j is 6. In some embodiments, j is 7. In some embodiments, j is 8. In some embodiments, j is 9. In some embodiments, j is 10.

In some embodiments, at least one n is 1, and at least one m is no less than 2. In some embodiments, at least one n is 1, at least one t is no less than 2, and at least one m is no less than 3. In some embodiments, each n is 1. In some embodiments, t is 1. In some embodiments, at least one t>1. In some embodiments, at least one t>2. In some embodiments, at least one t>3. In some embodiments, at least one t>4. In some embodiments, at least one m>1. In some embodiments, at least one m>2. In some embodiments, at least one m>3. In some embodiments, at least one m>4. In some embodiments, a pattern of backbone chiral centers comprises one or more achiral natural phosphate linkages. In some embodiments, the sum of m, t, and n (or m and n if no t in a pattern) is no less than 5, 6, 7, 8, 9, 10, 11, 12, 13, 14, 15, 16, 17, 18, 19 or 20. In some embodiments, the sum is 5. In some embodiments, the sum is 6. In some embodiments, the sum is 7. In some embodiments, the sum is 8. In some embodiments, the sum is 9. In some embodiments, the sum is 10. In some embodiments, the sum is 11. In some embodiments, the sum is 12. In some embodiments, the sum is 13. In some embodiments, the sum is 14. In some embodiments, the sum is 15.

In some embodiments, a number of linkage phosphorus in chirally controlled internucleotidic linkages are Sp. In some embodiments, at least 10%, 20%, 25%, 30%, 35%, 40%, 45%, 50%, 55%, 60%, 65%, 70%, 75%, 80%, 85%, 90% or 95% of chirally controlled internucleotidic linkages have Sp linkage phosphorus. In some embodiments, at least 10%, 20%, 25%, 30%, 35%, 40%, 45%, 50%, 55%, 60%, 65%, 70%, 75%, 80%, 85%, 90% or 95% of chirally controlled phosphorothioate internucleotidic linkages have Sp linkage phosphorus. In some embodiments, at least 10%, 20%, 25%, 30%, 35%, 40%, 45%, 50%, 55%, 60%, 65%, 70%, 75%, 80%, 85%, 90% or 95% of all chiral internucleotidic linkages are chirally controlled internucleotidic linkages having Sp linkage phosphorus. In some embodiments, at least 10%, 20%, 25%, 30%, 35%, 40%, 45%, 50%, 55%, 60%, 65%, 70%, 75%, 80%, 85%, 90% or 95% of all chiral internucleotidic linkages are chirally controlled phosphorothioate internucleotidic linkages having Sp linkage phosphorus. In some embodiments, at least 10%, 20%, 25%, 30%, 35%, 40%, 45%, 50%, 55%, 60%, 65%, 70%, 75%, 80%, 85%, 90% or 95% of all internucleotidic linkages are chirally controlled internucleotidic linkages having Sp linkage phosphorus. In some embodiments, the percentage is at least 20%. In some embodiments, the percentage is at least 30%. In some embodiments, the percentage is at least 40%. In some embodiments, the percentage is at least 50%. In some embodiments, the percentage is at least 60%. In some embodiments, the percentage is at least 65%. In some embodiments, the percentage is at least 70%. In some embodiments, the percentage is at least 75%. In some embodiments, the percentage is at least 80%. In some embodiments, the percentage is at least 90%. In some embodiments, the percentage is at least 95%. In some embodiments, at least 1, 2, 3, 4, 5, 6, 7, 8, 9, 10, 11, 12, 13, 14, 15, 16, 17, 18, 19, 20, 21, 22, 23, 24, or 25 internucleotidic linkages are chirally controlled internucleotidic linkages having Sp linkage phosphorus. In some embodiments, at least 5 internucleotidic linkages are chirally controlled internucleotidic linkages having Sp linkage phosphorus. In some embodiments, at least 6 internucleotidic linkages are chirally controlled internucleotidic linkages having Sp linkage phosphorus. In some embodiments, at least 7 internucleotidic linkages are chirally controlled internucleotidic linkages having Sp linkage phosphorus. In some embodiments, at least 8 internucleotidic linkages are chirally controlled internucleotidic linkages having Sp linkage phosphorus. In some embodiments, at least 9 internucleotidic linkages are chirally controlled internucleotidic linkages having Sp linkage phosphorus. In some embodiments, at least 10 internucleotidic linkages are chirally controlled internucleotidic linkages having Sp linkage phosphorus. In some embodiments, at least 11 internucleotidic linkages are chirally controlled internucleotidic linkages having Sp linkage phosphorus. In some embodiments, at least 12 internucleotidic linkages are chirally controlled internucleotidic linkages having Sp linkage phosphorus. In some embodiments, at least 13 internucleotidic linkages are chirally controlled internucleotidic linkages having Sp linkage phosphorus. In some embodiments, at least 14 internucleotidic linkages are chirally controlled internucleotidic linkages having Sp linkage phosphorus. In some embodiments, at least 15 internucleotidic linkages are chirally controlled internucleotidic linkages having Sp linkage phosphorus. In some embodiments, at least 1, 2, 3, 4, 5, 6, 7, 8, 9, 10, 11, 12, 13, 14, 15, 16, 17, 18, 19, 20, 21, 22, 23, 24, or 25 internucleotidic linkages are chirally controlled internucleotidic linkages having Rp linkage phosphorus. In some embodiments, no more than 1, 2, 3, 4, 5, 6, 7, 8, 9, 10, 11, 12, 13, 14, 15, 16, 17, 18, 19, 20, 21, 22, 23, 24, or 25 internucleotidic linkages are chirally controlled internucleotidic linkages having Rp linkage phosphorus. In some embodiments, one and no more than one internucleotidic linkage in an oligonucleotide is a chirally controlled internucleotidic linkage having Rp linkage phosphorus. In some embodiments, 2 and no more than 2 internucleotidic linkages in an oligonucleotide are chirally controlled internucleotidic linkages having Rp linkage phosphorus. In some embodiments, 3 and no more than 3 internucleotidic linkages in an oligonucleotide are chirally controlled internucleotidic linkages having Rp linkage phosphorus. In some embodiments, 4 and no more than 4 internucleotidic linkages in an oligonucleotide are chirally controlled internucleotidic linkages having Rp linkage phosphorus. In some embodiments, 5 and no more than 5 internucleotidic linkages in an oligonucleotide are chirally controlled internucleotidic linkages having Rp linkage phosphorus.

In some embodiments, all, essentially all or most of the internucleotidic linkages in an oligonucleotide are in the Sp configuration (e.g., about 50%-100%, 55%-100%, 60%-100%, 65%-100%, 70%-100%, 75%-100%, 80%-100%, 85%-100%, 90%-100%, 55%-95%, 60%-95%, 65%-95%, or about 55%, 60%, 65%, 70%, 75%, 80%, 85%, 90%, 95%, 97%, 99% or more of all chirally controlled internucleotidic linkages, or of all chiral internucleotidic linkages, or of all internucleotidic linkages in the oligonucleotide) except for one or a minority of internucleotidic linkages (e.g., 1, 2, 3, 4, or 5, and/or less than 50%, 45%, 40%, 35%, 30%, 25%, 20%, 15%, 10%, or 5% of all chirally controlled internucleotidic linkages, or of all chiral internucleotidic linkages, or of all internucleotidic linkages in the oligonucleotide) being in the Rp configuration. In some embodiments, all, essentially all or most of the internucleotidic linkages in a core are in the Sp configuration (e.g., about 50%-100%, 55%-100%, 60%-100%, 65%-100%, 70%-100%, 75%-100%, 80%-100%, 85%-100%, 90%-100%, 55%-95%, 60%-95%, 65%-95%, or about 55%, 60%, 65%, 70%, 75%, 80%, 85%, 90%, 95%, 97%, 99% or more of all chirally controlled internucleotidic linkages, or of all chiral internucleotidic linkages, or of all internucleotidic linkages, in the core) except for one or a minority of internucleotidic linkages (e.g., 1, 2, 3, 4, or 5, and/or less than 50%, 45%, 40%, 35%, 30%, 25%, 20%, 15%, 10%, or 5% of all chirally controlled internucleotidic linkages, or of all chiral internucleotidic linkages, or of all internucleotidic linkages, in the core) being in the Rp configuration. In some embodiments, all, essentially all or most of the internucleotidic linkages in the core are a phosphorothioate in the Sp configuration (e.g., about 50%-100%, 55%-100%, 60%-100%, 65%-100%, 70%-100%, 75%-100%, 80%-100%, 85%-100%, 90%-100%, 55%-95%, 60%-95%, 65%-95%, or about 55%, 60%, 65%, 70%, 75%, 80%, 85%, 90%, 95%, 97%, 99% or more of all chirally controlled internucleotidic linkages, or of all chiral internucleotidic linkages, or of all internucleotidic linkages, in the core) except for one or a minority of internucleotidic linkages (e.g., 1, 2, 3, 4, or 5, and/or less than 50%, 45%, 40%, 35%, 30%, 25%, 20%, 15%, 10%, or 5% of all chirally controlled internucleotidic linkages, or of all chiral internucleotidic linkages, or of all internucleotidic linkages, in the core) being a phosphorothioate in the Rp configuration. In some embodiments, each internucleotidic linkage in the core is a phosphorothioate in the Sp configuration except for one phosphorothioate in the Rp configuration. In some embodiments, each internucleotidic linkage in the core is a phosphorothioate in the Sp configuration except for one phosphorothioate in the Rp configuration.

In some embodiments, an oligonucleotide comprises one or more Rp internucleotidic linkages. In some embodiments, an oligonucleotide comprises one and no more than one Rp internucleotidic linkages. In some embodiments, an oligonucleotide comprises two or more Rp internucleotidic linkages. In some embodiments, an oligonucleotide comprises three or more Rp internucleotidic linkages. In some embodiments, an oligonucleotide comprises four or more Rp internucleotidic linkages. In some embodiments, an oligonucleotide comprises five or more Rp internucleotidic linkages. In some embodiments, about 5%-50% of all chirally controlled internucleotidic linkages in an oligonucleotide are Rp. In some embodiments, about 5%-40% of all chirally controlled internucleotidic linkages in an oligonucleotide are Rp. In some embodiments, about 10%-40% of all chirally controlled internucleotidic linkages in an oligonucleotide are Rp. In some embodiments, about 15%-40% of all chirally controlled internucleotidic linkages in an oligonucleotide are Rp. In some embodiments, about 20%-40% of all chirally controlled internucleotidic linkages in an oligonucleotide are Rp. In some embodiments, about 25%-40% of all chirally controlled internucleotidic linkages in an oligonucleotide are Rp. In some embodiments, about 30%-

40% of all chirally controlled internucleotidic linkages in an oligonucleotide are Rp. In some embodiments, about 35%-40% of all chirally controlled internucleotidic linkages in an oligonucleotide are Rp.

In some embodiments, the base sequence of an oligonucleotide or a region thereof, e.g., a core region, comprises a sequence that is complementary to a characteristic sequence element which differentiates a target nucleic acid sequence from other sequences, e.g., one allele of a differentiating position, e.g., a SNP, a mutation, etc. In some embodiments, such a complementary sequence consists of one nucleobase, e.g., for a differentiating single nucleobase such as SNP, point mutation, single nucleobase sequence difference (e.g., between two different genes), etc. In some embodiments, a characteristic sequence element corresponds to P23H mutation in RHO. Among other things, the present disclosure demonstrates that positioning of Rp internucleotidic linkages relative to a differentiating position (and/or complementary sequences thereof) can improve one or more of activities, properties and/or selectivities of oligonucleotides. In some embodiments, the present disclosure provides useful positioning of Rp internucleotidic linkages. In some embodiments, an Rp internucleotidic linkage is at position −4, −3, −2, −1, +1, +2, +3, or +4 relative to a sequence that is complementary to a characteristic sequence element, e.g., one allele of a differentiating position, a point mutation, etc. In some embodiments, an Rp internucleotidic linkage is at position −4, −3, −2, −1, +1, +2, +3, or +4 relative to a nucleobase (counting 5' to 3', the internucleotidic linkage bonded to 5'-carbon of the nucleobase is −1, and 3'-carbon +1) that is complementary to a differentiating nucleobase (e.g., of a SNP, a point mutation, etc.). In some embodiments, Rp is at −4. In some embodiments, Rp is at −3. In some embodiments, Rp is at −2. In some embodiments, Rp is at −1. In some embodiments, Rp is at +1. In some embodiments, Rp is at +2. In some embodiments, Rp is at +3. In some embodiments, Rp is at +4. In some embodiments, each internucleotidic linkage in the core is a phosphorothioate in the Sp configuration except for one phosphorothioate in the Rp configuration, and the one phosphorothioate in the Rp configuration has a position relative to the SNP/mutation in the core (e.g., −1, +1, +2, +3, etc.). In some embodiments, an Rp internucleotidic linkage is at position −4, −3, −2, −1, +1, +2, +3, or +4 relative to a nucleobase that is complementary to an allele of an SNP at the SNP position or a point mutation. In some embodiments, the position is −4. In some embodiments, the position is −3. In some embodiments, the position is −2. In some embodiments, the position is −1. In some embodiments, the position is +1. In some embodiments, the position is +2. In some embodiments, the position is +3. In some embodiments, the position is +4. In some embodiments, such an Rp internucleotidic linkage is in a core region. In some embodiments, the position of an Rp internucleotidic linkage in a core is −4, −3, −2, −1, +1, +2, +3, or +4 (counting 5' to 3') relative to the nucleobase which is or recognizes (e.g., is complementary to) a SNP rs104893768 variant (e.g., A). In some embodiments, the position of an Rp internucleotidic linkage in a core is −1, +1, +2, or +3 (counting 5' to 3') relative to the nucleobase which is or recognizes a SNP rs104893768 variant. In some embodiments, the position of an Rp internucleotidic linkage in a core is −1 (counting 5' to 3') relative to the nucleobase which is or recognizes a SNP rs104893768 variant. In some embodiments, the position of an Rp internucleotidic linkage in a core is +1 (counting 5' to 3') relative to the nucleobase which is or recognizes a SNP rs104893768 variant. In some embodiments, the position of an Rp internucleotidic linkage in a core is +2 (counting 5' to 3') relative to the nucleobase which is or recognizes a SNP rs104893768 variant. In some embodiments, the position of an Rp internucleotidic linkage in a core is +3 (counting 5' to 3') relative to the nucleobase which is or recognizes a SNP rs104893768 variant. In some embodiments, an Rp internucleotidic linkage is an Rp phosphorothioate internucleotidic linkage. In some embodiments, as demonstrated herein, an oligonucleotide is complementary to an allele of a SNP that is associated with a condition, disorder or disease and not complementary to other alleles that is not associated or less associated with the condition, disorder or disease. In some embodiments, a SNP is a SNP in RHO. In some embodiments, a SNP is a SNP in RHO as described herein. In some embodiments, a SNP is a SNP in RHO, and an oligonucleotide is complementary to an allele of a SNP that is associated with a RHO-related condition, disorder or disease, e.g., retinopathy (e.g, retinal degeneration, retinal degenerative disease, retinal degenerative disorder, inherited retinal degenerative disorder, retinitis pigmentosa, autosomal dominant retinitis pigmentosa, etc.) (such allele in many cases is on the same DNA strand/chromosome of disease-associated mutation(s)). In some embodiments, a SNP is rsSNP rs104893768. In some embodiments, a SNP is rs104893768. In some embodiments, a SNP rs104893768 variant is A. Other SNPs that may be targeted are described herein and/or known in the art. In some embodiments, a Rp is the Rp of Rp(Sp)m wherein m is 2 or more as described herein, and wherein Rp(Sp)m is, or is a portion of, a pattern of backbone chiral centers of an oligonucleotide or a portion thereof (e.g., a core). In some embodiments, a Rp is the Rp of Rp(Sp)2 wherein Rp(Sp)2 is, or is a portion of, a pattern of backbone chiral centers of an oligonucleotide or a portion thereof (e.g., a core). In some embodiments, a Rp is the Rp of (Sp)tRp(Sp)m wherein m is 2 or more as described herein, t is as described herein, and (Sp)tRp(Sp)m is, or is a portion of, a pattern of backbone chiral centers of an oligonucleotide or a portion thereof (e.g., a core). In some embodiments, a Rp is the Rp of (Sp)tRp(Sp)2 wherein t is as described herein, and (Sp)tRp(Sp)2 is, or is a portion of, a pattern of backbone chiral centers of an oligonucleotide or a portion thereof (e.g., a core). In some embodiments, t is 2. In some embodiments, t is 2 or more. In some embodiments, the present disclosure pertains to a RHO oligonucleotide, wherein the position of an Rp internucleotidic linkage is −3 (counting 5' to 3') relative to the nucleobase which is or which recognizes a SNP rs104893768 variant. Non-limiting examples of such an oligonucleotide include: WV-23654 and WV-23664.

In some embodiments, the present disclosure pertains to a RHO oligonucleotide, wherein the position of an Rp internucleotidic linkage is −2 (counting 5' to 3') relative to the nucleobase which is or which recognizes a SNP rs104893768 variant. Non-limiting examples of such an oligonucleotide include: WV-23655 and WV-23665.

In some embodiments, the present disclosure pertains to a RHO oligonucleotide, wherein the position of an Rp internucleotidic linkage is −1 (counting 5' to 3') relative to the nucleobase which is or which recognizes a SNP rs104893768 variant. Non-limiting examples of such an oligonucleotide include: WV-23656 and WV-23666.

In some embodiments, the present disclosure pertains to a RHO oligonucleotide, wherein the position of an Rp internucleotidic linkage is +1 (counting 5' to 3') relative to the nucleobase which is or which recognizes a SNP rs104893768 variant. Non-limiting examples of such an oligonucleotide include: WV-23657 and WV-23667.

In some embodiments, the present disclosure pertains to a RHO oligonucleotide, wherein the position of an Rp internucleotidic linkage is +2 (counting 5' to 3') relative to the nucleobase which is or which recognizes a SNP rs104893768 variant. Non-limiting examples of such an oligonucleotide include: WV-20847, WV-20846, WV-20865, WV-20828, WV-23658, WV-23668, WV-24653, and WV-24654.

In some embodiments, the present disclosure pertains to a RHO oligonucleotide, wherein the position of an Rp internucleotidic linkage is +3 (counting 5' to 3') relative to the nucleobase which is or which recognizes a SNP rs104893768 variant. Non-limiting examples of such an oligonucleotide include: WV-23669 and WV-23659.

In some embodiments, the core of an oligonucleotide, e.g., a RHO oligonucleotide, having a wing-core-wing structure has a sequence which comprises a SNP (e.g., a nucleobase complementary to a SNP in a target nucleic acid sequence), including but not limited to a SNP described herein, and all, essentially all or most of the internucleotidic linkages in the core (e.g., about 50%-100%, 55%-100%, 60%-100%, 65%-100%, 70%-100%, 75%-100%, 80%-100%, 85%-100%, 90%-100%, 55%-95%, 60%-95%, 65%-95%, or about 55%, 60%, 65%, 70%, 75%, 80%, 85%, 90%, 95%, 97%, 99% or more of all chirally controlled internucleotidic linkages, or of all chiral internucleotidic linkages, or of all internucleotidic linkages, in the core) are in the Sp configuration except for one or a minority of internucleotidic linkages (e.g., 1, 2, 3, 4, or 5, and/or less than 50%, 45%, 40%, 35%, 30%, 25%, 20%, 15%, 10%, or 5% of all chirally controlled internucleotidic linkages, or of all chiral internucleotidic linkages, or of all internucleotidic linkages, in the core) which are in the Rp configuration. In some embodiments, the core of an oligonucleotide, e.g., a RHO oligonucleotide, having a wing-core-wing structure has a sequence which comprises a SNP, including but not limited to a SNP described herein, and all, essentially all or most of the internucleotidic linkages in the core are a phosphorothioate in the Sp configuration except for one or a minority of internucleotidic linkages which are a phosphorothioate in the Rp configuration. In some embodiments, the core of an oligonucleotide, e.g., a RHO oligonucleotide, having a wing-core-wing structure has a sequence which comprises a SNP, including but not limited to a SNP described herein, and each internucleotidic linkage in the core is a phosphorothioate in the Sp configuration except for one phosphorothioate in the Rp configuration. In some embodiments, the core of an oligonucleotide, e.g., a RHO oligonucleotide, having a wing-core-wing structure has a sequence which comprises a SNP, including but not limited to a SNP described herein, and each internucleotidic linkage in the core is a phosphorothioate in the Sp configuration except for one phosphorothioate in the Rp configuration. In some embodiments, the core of an oligonucleotide, e.g., a RHO oligonucleotide, having a wing-core-wing structure has a sequence which comprises a SNP, including but not limited to a SNP described herein, and each internucleotidic linkage in the core is a phosphorothioate in the Sp configuration except for one phosphorothioate in the Rp configuration, and the one phosphorothioate in the Rp configuration has a position relative to the SNP in the core (e.g., the Rp is −1, +1, +2, +3, etc. to the SNP). In some embodiments, the core of an oligonucleotide, e.g., a RHO oligonucleotide, having a wing-core-wing structure has a sequence which comprises a SNP, including but not limited to a SNP described herein, and the position of the an internucleotidic linkage in the Rp configuration in the core is −4, −3, −2, −1, +1, +2, +3, or +4 (counting 5' to 3') relative to the nucleobase which is or recognizes a SNP rs104893768 variant. In some embodiments, the core of an oligonucleotide, e.g., a RHO oligonucleotide, having a wing-core-wing structure has a sequence which comprises a SNP, including but not limited to a SNP described herein, and the position of a phosphorothioate internucleotidic linkage in the Rp configuration in the core is −4, −3, −2, −1, +1, +2, +3, or +4 (counting 5' to 3') relative to the nucleobase which is or recognizes a SNP rs104893768 variant. In some embodiments, the position is −1, +1, +2, or +3 (counting 5' to 3') relative to the nucleobase which is or recognizes a SNP rs104893768 variant. In some embodiments, the core of an oligonucleotide, e.g., a RHO oligonucleotide, having a wing-core-wing structure has a sequence which comprises a SNP, including but not limited to a SNP described herein, and the position of a phosphorothioate in the Rp configuration in the core is −1 (counting 5' to 3') relative to the nucleobase which is or recognizes a SNP rs104893768 variant. In some embodiments, the core of an oligonucleotide, e.g., a RHO oligonucleotide, having a wing-core-wing structure has a sequence which comprises a SNP, including but not limited to a SNP described herein, and the position of a phosphorothioate in the Rp configuration in the core is +1 (counting 5' to 3') relative to the nucleobase which is or recognizes a SNP rs104893768 variant. In some embodiments, the core of an oligonucleotide, e.g., a RHO oligonucleotide, having a wing-core-wing structure has a sequence which comprises a SNP, including but not limited to a SNP described herein, and the position of a phosphorothioate in the Rp configuration in the core is +2 (counting 5' to 3') relative to the nucleobase which is or recognizes a SNP rs104893768 variant. In some embodiments, the core of an oligonucleotide, e.g., a RHO oligonucleotide, having a wing-core-wing structure has a sequence which comprises a SNP, including but not limited to a SNP described herein, and the position of a phosphorothioate in the Rp configuration in the core is +3 (counting 5' to 3') relative to the nucleobase which is or recognizes a SNP rs104893768 variant.

As demonstrated in the present disclosure, position of Rp, among other things, may improve properties, activities and/or selectivities of oligonucleotides. In some embodiments, as shown herein, improvement of the ability of a RHO oligonucleotide to decrease the level, expression and/or activity of a RHO target gene (or to perform allele-specific knockdown of the level, expression and/or activity of a mutant RHO target gene), or a gene product thereof, was achieved by designed positioning of a single chiral internucleotidic linkage (e.g., a phosphorothioate) in the Rp configuration relative to the SNP. In some cases, a relatively inactive oligonucleotide composition, wherein the base sequence of the core comprises a base which is or targets a SNP rs104893768 variant, and wherein the oligonucleotide composition is stereorandom, can be converted into a more active or highly active oligonucleotide composition by converting the oligonucleotide, including the core, into a chirally controlled or stereopure composition, wherein all, essentially all, or most of the internucleotidic linkages are in the Sp configuration except for one or a minority of internucleotidic linkages in the Rp configuration as described herein. In some cases, an oligonucleotide comprising a core, wherein the base sequence of the core comprises a base which is or targets a SNP rs104893768 variant, and all, essentially all, or most of the internucleotidic linkages in the core are in the Sp configuration except for one or a minority of internucleotidic linkages in the Rp configuration, can be converted into a more active or highly active oligonucleotide by altering the position of one or more (in some cases, one) internucleotidic linkages in the Rp configuration relative to the SNP. In some cases, a relatively inactive oligonucleotide comprising a core, wherein the base sequence of the core comprises a base which is or targets a SNP rs104893768 variant, and all of the internucleotidic linkages in the core are in the Sp configuration except for one internucleotidic linkage in the Rp configuration, can be converted into a more active or highly active oligonucleotide by moving the placement of the one internucleotidic linkage in the Rp configuration relative to the SNP.

In some embodiments, instead of an Rp internucleotidic linkage, a natural phosphate linkage may be similarly utilized, optionally with a modification, e.g., a sugar modification (e.g., a 5'-modification such as $R^{5s}$ as described herein). In some embodiments, a modification improves stability of a natural phosphate linkage.

In some embodiments, the present disclosure provides an oligonucleotide having a pattern of backbone chiral centers as described herein. In some embodiments, oligonucleotides in a chirally controlled oligonucleotide composition share a common pattern of backbone chiral centers as described herein.

In some embodiments, at least about 25% of the internucleotidic linkages of an oligonucleotide, e.g., a RHO oligonucleotide, are chirally controlled and have Sp linkage phosphorus. In some embodiments, at least about 30% of the internucleotidic linkages of an oligonucleotide are chirally controlled and have Sp linkage phosphorus. In some embodiments, at least about 40% of the internucleotidic linkages of a provided oligonucleotide are chirally controlled and have Sp linkage phosphorus. In some embodiments, at least about 50% of the internucleotidic linkages of a provided oligonucleotide are chirally controlled and have Sp linkage phosphorus. In some embodiments, at least about 60% of the internucleotidic linkages of a provided oligonucleotide are chirally controlled and have Sp linkage phosphorus. In some embodiments, at least about 65% of the internucleotidic linkages of a provided oligonucleotide are chirally controlled and have Sp linkage phosphorus. In some embodiments, at least about 70% of the internucleotidic linkages of a provided oligonucleotide are chirally controlled and have Sp linkage phosphorus. In some embodiments, at least about 75% of the internucleotidic linkages of a provided oligonucleotide are chirally controlled and have Sp linkage phosphorus. In some embodiments, at least about 80% of the internucleotidic linkages of a provided oligonucleotide are chirally controlled and have Sp linkage phosphorus. In some embodiments, at least about 85% of the internucleotidic linkages of a provided oligonucleotide are chirally controlled and have Sp linkage phosphorus. In some embodiments, at least about 90% of the internucleotidic linkages of a provided oligonucleotide are chirally controlled and have Sp linkage phosphorus. In some embodiments, at least about 95% of the internucleotidic linkages of a provided oligonucleotide are chirally controlled and have Sp linkage phosphorus.

In some embodiments, the present disclosure provides chirally controlled oligonucleotide compositions, e.g., chirally controlled RHO oligonucleotide compositions, wherein the composition comprises a non-random or controlled level of a plurality of oligonucleotides, wherein oligonucleotides of the plurality share a common base sequence, and share the same configuration of linkage phosphorus independently at 1-50, 1-40, 1-30, 1-25, 1-20, 1-15, 1-10, 5-50, 5-40, 5-30, 5-25, 5-20, 5-15, 5-10, 1, 2, 3, 4, 5, 6, 7, 8, 9, 10, 11, 12, 13, 14, 15, 16, 17, 18, 19, 20, 21, 22, 23, 24, or 25 or more chiral internucleotidic linkages.

In some embodiments, provided oligonucleotides comprise 2-30 chirally controlled internucleotidic linkages. In some embodiments, provided oligonucleotide compositions comprise 5-30 chirally controlled internucleotidic linkages. In some embodiments, provided oligonucleotide compositions comprise 10-30 chirally controlled internucleotidic linkages. In some embodiments, provided oligonucleotide compositions comprise 1, 2, 3, 4, 5, 6, 7, 8, 9, 10, 11, 12, 13, 14, 15, 16, 17, 18, 19, 20, 21, 22, 23, 24, or 25 or more chirally controlled internucleotidic linkages.

In some embodiments, about 1-100% of all internucleotidic linkages are chirally controlled internucleotidic linkages. In some embodiments, a percentage is about 5%-100%. In some embodiments, a percentage is at least 5%, 10%, 15%, 20%, 25%, 30%, 35%, 40%, 45%, 50%, 55%, 60%, 65%, 70%, 75%, 80%, 85%, 90%, 95%, 965, 96%, 98%, or 99%. In some embodiments, a percentage is about 5%, 10%, 15%, 20%, 25%, 30%, 35%, 40%, 45%, 50%, 55%, 60%, 65%, 70%, 75%, 80%, 85%, 90%, 95%, 965, 96%, 98%, or 99%.

In some embodiments, a pattern of backbone chiral centers in an oligonucleotide, e.g., a RHO oligonucleotide, comprises a pattern of $i^{o}-i^{s}-i^{o}-i^{s}-i^{o}$, $i-i^{o}-i^{s}-i^{s}-i^{s}-i^{o}-i^{s}$, $i^{s}-i^{o}-i^{s}-i^{o}$, $i^{s}-i^{o}-i^{s}-i^{o}$, $i^{s}-i^{s}-i^{o}-i^{s}$, $i^{s}-i^{o}-i^{s}-i^{o}-i^{s}-i^{o}$, $i^{s}-i^{o}-i^{s}-i^{o}-i^{s}-i^{o}-i^{s}-i^{o}$, $i^{s}-i^{o}-i^{s}-i^{s}-i^{s}-i^{o}$, $i^{s}-i^{s}-i^{o}-i^{s}-i^{s}-i^{s}-i^{o}-i^{s}-i^{s}$, $i^{s}-i^{s}-i^{s}-i^{o}-i^{s}-i^{o}-i^{s}-i^{s}-i^{s}$, $i^{s}-i^{s}-i^{s}-i^{s}-i^{o}-i^{s}-i^{o}-i^{s}-i^{s}-i^{s}-i^{s}$, $i^{s}-i^{s}-i^{s}-i^{s}-i^{s}$, $i^{s}-i^{s}-i^{s}-i^{s}-i^{s}-i^{s}$, $i^{s}-i^{s}-i^{s}-i^{s}-i^{s}-i^{s}-i^{s}$, $i^{s}-i^{s}-i^{s}-i^{s}-i^{s}-i^{s}-i^{s}-i^{s}$, $i^{s}-i^{s}-i^{s}-i^{s}-i^{s}-i^{s}-i^{s}-i^{s}-i^{s}$, or $i^{r}-i^{r}-i^{r}$, wherein $i^{s}$ represents an internucleotidic linkage in the Sp configuration; $i^{o}$ represents an achiral internucleotidic linkage; and $i^{r}$ represents an internucleotidic linkage in the Rp configuration.

In some embodiments, an internucleotidic linkage in the Sp configuration (having a Sp linkage phosphorus) is a phosphorothioate internucleotidic linkage. In some embodiments, an achiral internucleotidic linkage is a natural phosphate linkage. In some embodiments, an internucleotidic linkage in the Rp configuration (having a Rp linkage phosphorus) is a phosphorothioate internucleotidic linkage. In some embodiments, each internucleotidic linkage in the Sp configuration is a phosphorothioate internucleotidic linkage. In some embodiments, each achiral internucleotidic linkage is a natural phosphate linkage. In some embodiments, each internucleotidic linkage in the Rp configuration is a phosphorothioate internucleotidic linkage. In some embodiments, each internucleotidic linkage in the Sp configuration is a phosphorothioate internucleotidic linkage, each achiral internucleotidic linkage is a natural phosphate linkage, and each internucleotidic linkage in the Rp configuration is a phosphorothioate internucleotidic linkage.

In some embodiments, a pattern of backbone chiral centers (e.g., a pattern of backbone chiral centers in an oligonucleotide, e.g., a RHO oligonucleotide or in a core or a wing or in two wings of an oligonucleotide, e.g., a RHO oligonucleotide) comprises a pattern of OpSpOpSpOp, OpSpSpSpOp, OpSpSpSpOpSp, SpOpSpOp, SpOpSpOp, SpOpSpOpSp, SpOpSpOpSpOp, SpOpSpOpSpOpSpOp, SpOpSpSpSpOp, SpSpOpSpSpSpOpSpSp, SpSpSpOpSpOpSpSpSp, SpSpSpSpOpSpOpSpSpSpSp, SpSpSpSpSp, SpSpSpSpSpSp, SpSpSpSpSpSpSp, SpSpSpSpSpSpSpSp, SpSpSpSpSpSpSpSpSp, or RpRpRp, wherein each Rp and Sp is independently the linkage phosphorus configuration of a chirally controlled internucleotidic linkage (in some embodiments, each Rp and Sp is independently the linkage phosphorus configuration of a chirally controlled phosphorothioate internucleotidic linkage), and each Op independently represents linkage phosphorus being achiral in a natural phosphate linkage.

In some embodiments, an internucleotidic linkage bonded to a wing nucleoside and a core nucleoside is considered one of the core internucleotidic linkages, for example, when describing types, modifications, numbers, and/or patterns of core internucleotidic linkages. In some embodiments, each internucleotidic linkage bonded to a wing nucleoside and a core nucleoside is considered one of the core internucleotidic linkages, for example, when describing types, modifications, numbers, and/or patterns of core internucleotidic linkages. In some embodiments, a core internucleotidic linkage is bonded to two core nucleosides. In some embodiments, a core internucleotidic linkage is bonded to a core nucleoside and a wing nucleoside. In some embodiments, each core internucleotidic linkage is independently bonded to two core nucleosides, or a core nucleoside and a wing nucleoside. In some embodiments, each wing internucleotidic linkage is independently bonded to two wing nucleosides.

In some embodiments, at least about 25% of the oligonucleotides in a composition share a common base sequence, a common pattern of backbone linkages, and a common pattern of backbone chiral centers. In some embodiments, at least about 30% of the oligonucleotides in a composition share a common base sequence, a common pattern of backbone linkages, and a common pattern of backbone chiral centers. In some embodiments, at least about 50% of the oligonucleotides in a composition share a common base sequence, a common pattern of backbone linkages, and a common pattern of backbone chiral centers. In some embodiments, at least about 60% of the oligonucleotides in a composition share a common base sequence, a common pattern of backbone linkages, and a common pattern of backbone chiral centers. In some embodiments, at least about 70% of the oligonucleotides in a composition share a common base sequence, a common pattern of backbone linkages, and a common pattern of backbone chiral centers. In some embodiments, at least about 80% of the oligonucleotides in a composition share a common base sequence, a common pattern of backbone linkages, and a common pattern of backbone chiral centers. In some embodiments, at least about 85% of the oligonucleotides in a composition share a common base sequence, a common pattern of backbone linkages, and a common pattern of backbone chiral centers. In some embodiments, at least about 90% of the oligonucleotides in a composition share a common base sequence, a common pattern of backbone linkages, and a common pattern of backbone chiral centers. In some embodiments, at least about 92% of the oligonucleotides in a composition share a common base sequence, a common pattern of backbone linkages, and a common pattern of backbone chiral centers. In some embodiments, at least about 94% of the oligonucleotides in a composition share a common base sequence, a common pattern of backbone linkages, and a common pattern of backbone chiral centers. In some embodiments, at least about 95% of the oligonucleotides in a composition share a common base sequence, a common pattern of backbone linkages, and a common pattern of backbone chiral centers. In some embodiments, at least about 91%, 92%, 93%, 94%, 95%, 96%, 97%, 98%, or 99% of the oligonucleotides in a composition share a common base sequence, a common pattern of backbone linkages, and a common pattern of backbone chiral centers. In some embodiments, greater than about 99% of the oligonucleotides in a composition share a common base sequence, a common pattern of backbone linkages, and a common pattern of backbone chiral centers. In some embodiments, purity of a composition may be expressed as the percentage of oligonucleotides in a composition that share a common base sequence, a common pattern of backbone linkages, and a common pattern of backbone chiral centers.

In some embodiments, provided oligonucleotides, e.g., RHO oligonucleotides, in chirally controlled oligonucleotide compositions each comprise different types of internucleotidic linkages. In some embodiments, provided oligonucleotides comprise at least one natural phosphate linkage and at least one modified internucleotidic linkage. In some embodiments, provided oligonucleotides comprise at least one natural phosphate linkage and at least two modified internucleotidic linkages. In some embodiments, provided oligonucleotides comprise at least one natural phosphate linkage and at least three modified internucleotidic linkages. In some embodiments, provided oligonucleotides comprise at least one natural phosphate linkage and at least four modified internucleotidic linkages. In some embodiments, provided oligonucleotides comprise at least one natural phosphate linkage and at least five modified internucleotidic linkages. In some embodiments, provided oligonucleotides comprise at least one natural phosphate linkage and 1, 2, 3, 4, 5, 6, 7, 8, 9, 10, 11, 12, 13, 14, 15, 16, 17, 18, 19, 20, 21, 22, 23, 24, or 25 modified internucleotidic linkages. In some embodiments, a modified internucleotidic linkage is a phosphorothioate internucleotidic linkage. In some embodiments, each modified internucleotidic linkage is a phosphorothioate internucleotidic linkage. In some embodiments, a modified internucleotidic linkage is a non-negatively charged internucleotidic linkage. In some embodiments, a modified internucleotidic linkage is a neutral internucleotidic linkage. In some embodiments, a modified internucleotidic linkage is n001. In some embodiments, each modified internucleotidic linkage is independently phosphorothioate or a neutral internucleotidic linkage. In some embodiments, each modified internucleotidic linkage is independently phosphorothioate or n001. In some embodiments, provided oligonucleotides comprise at least one natural phosphate linkage and at least 2, 3, 4, 5, 6, 7, 8, 9, 10, 11, 12, 13, 14, 15, 16, 17, 18, 19, 20, 21, 22, 23, 24, or 25 consecutive modified internucleotidic linkages. In some embodiments, provided oligonucleotides comprise at least one natural phosphate linkage and at least 2, 3, 4, 5, 6, 7, 8, 9, 10, 11, 12, 13, 14, 15, 16, 17, 18, 19, 20, 21, 22, 23, 24, or 25 consecutive phosphorothioate internucleotidic linkages.

In some embodiments, oligonucleotides comprise two or more types of internucleotidic linkages. In some embodiments, oligonucleotides comprise two or more types of modified internucleotidic linkages. In some embodiments, oligonucleotides comprise one or more natural phosphate linkages and one or more types of modified internucleotidic linkages. In some embodiments, modified internucleotidic linkages are independently chiral internucleotidic linkages. In some embodiments, oligonucleotides comprises natural phosphate linkages and two or more types of modified internucleotidic linkages. In some embodiments, modified internucleotidic linkages are phosphorothioate internucleotidic linkages. In some embodiments, modified internucleotidic linkages are non-negatively charged internucleotidic linkages. In some embodiments, modified internucleotidic linkages are neutral internucleotidic linkages. In some embodiments, non-negatively charged internucleotidic linkages or neutral internucleotidic linkages are n001. In some embodiments, oligonucleotides comprises one or more natural phosphate linkages and one or more phosphorothioate internucleotidic linkages. In some embodiments, oligonucleotide comprises one or more natural phosphate linkages, one or more negatively charged modified internucleotidic linkages (e.g., phosphorothioate internucleotidic linkages) and one or more non-negatively charged internucleotidic linkages (e.g., neutral internucleotidic linkages such as n001). In some embodiments, each chiral internucleotidic linkage is independently chirally controlled. In some embodiments, each phosphorothioate internucleotidic linkage is independently chirally controlled. In some embodiments, one or more chiral internucleotidic linkages, e.g., n001, are not chirally controlled.

In some embodiments, a modified linkage comprises a chiral auxiliary, which, for example, is used to control the stereoselectivity of a reaction, e.g., a coupling reaction in an oligonucleotide synthesis cycle.

In some embodiments, oligonucleotides are linked to a solid support. In some embodiments, a solid support is a support for oligonucleotide synthesis. In some embodiments, a solid support comprises glass. In some embodiments, a solid support is CPG (controlled pore glass). In some embodiments, a solid support is polymer. In some embodiments, a solid support is polystyrene. In some embodiments, the solid support is Highly Crosslinked Polystyrene (HCP). In some embodiments, the solid support is hybrid support of Controlled Pore Glass (CPG) and Highly Cross-linked Polystyrene (HCP). In some embodiments, a solid support is a metal foam. In some embodiments, a solid support is a resin. In some embodiments, oligonucleotides are cleaved from a solid support.

In some embodiments, purity, particularly stereochemical purity, and particularly diastereomeric purity of many oligonucleotides and compositions thereof wherein all other chiral centers in the oligonucleotides but the chiral linkage phosphorus centers have been stereodefined (e.g., carbon chiral centers in the sugars, which are defined in, e.g., phosphoramidites for oligonucleotide synthesis), can be controlled by stereoselectivity (as appreciated by those skilled in this art, diastereoselectivity in many cases of oligonucleotide synthesis wherein the oligonucleotide comprise more than one chiral centers) at chiral linkage phosphorus in coupling steps when forming chiral internucleotidic linkages. In some embodiments, a coupling step has a stereoselectivity (diastereoselectivity when there are other chiral centers) of 60% at the linkage phosphorus. After such a coupling step, the new internucleotidic linkage formed may be referred to have a 60% stereochemical purity (for oligonucleotides, typically diastereomeric purity in view of the existence of other chiral centers). In some embodiments, each coupling step independently has a stereoselectivity of at least 60%. In some embodiments, each coupling step independently has a stereoselectivity of at least 70%. In some embodiments, each coupling step independently has a stereoselectivity of at least 80%. In some embodiments, each coupling step independently has a stereoselectivity of at least 85%. In some embodiments, each coupling step independently has a stereoselectivity of at least 90%. In some embodiments, each coupling step independently has a stereoselectivity of at least 91%. In some embodiments, each coupling step independently has a stereoselectivity of at least 92%. In some embodiments, each coupling step independently has a stereoselectivity of at least 93%. In some embodiments, each coupling step independently has a stereoselectivity of at least 94%. In some embodiments, each coupling step independently has a stereoselectivity of at least 95%. In some embodiments, each coupling step independently has a stereoselectivity of at least 96%. In some embodiments, each coupling step independently has a stereoselectivity of at least 97%. In some embodiments, each coupling step independently has a stereoselectivity of at least 98%. In some embodiments, each coupling step independently has a stereoselectivity of at least 99%. In some embodiments, each coupling step independently has a stereoselectivity of at least 99.5%. In some embodiments, each coupling step independently has a stereoselectivity of virtually 100%. In some embodiments, a coupling step has a stereoselectivity of virtually 100% in that each detectable product from the coupling step analyzed by an analytical method (e.g., NMR, HPLC, etc.) has the intended stereoselectivity. In some embodiments, a chirally controlled internucleotidic linkage is typically formed with a stereoselectivity of at least 90%, 91%, 92%, 93%, 94%, 95%, 96%, 97%, 98%, 99.5% or virtually 100% (in some embodiments, at least 90%; in some embodiments, at least 95%; in some embodiments, at least 96%; in some embodiments, at least 97%; in some embodiments, at least 98%; in some embodiments, at least 99%). In some embodiments, a chirally controlled internucleotidic linkage has a stereochemical purity (typically diastereomeric purity for oligonucleotides with multiple chiral centers) of at least 90%, 91%, 92%, 93%, 94%, 95%, 96%, 97%, 98%, 99.5% or virtually 100% (in some embodiments, at least 90%; in some embodiments, at least 95%; in some embodiments, at least 96%; in some embodiments, at least 97%; in some embodiments, at least 98%; in some embodiments, at least 99%) at its chiral linkage phosphorus. In some embodiments, each chirally controlled internucleotidic linkage independently has a stereochemical purity (typically diastereomeric purity for oligonucleotides with multiple chiral centers) of at least 90%, 91%, 92%, 93%, 94%, 95%, 96%, 97%, 98%, 99.5% or virtually 100% (in some embodiments, at least 90%; in some embodiments, at least 95%; in some embodiments, at least 96%; in some embodiments, at least 97%; in some embodiments, at least 98%; in some embodiments, at least 99%) at its chiral linkage phosphorus. In some embodiments, a non-chirally controlled internucleotidic linkage is typically formed with a stereoselectivity of less than 60%, 70%, 80%, 85%, or 90% (in some embodiments, less than 60%; in some embodiments, less than 70%; in some embodiments, less than 80%; in some embodiments, less than 85%; in some embodiments, less than 90%). In some embodiments, each non-chirally controlled internucleotidic linkage is independently formed with a stereoselectivity of less than 60%, 70%, 80%, 85%, or 90% (in some embodiments, less than 60%; in some embodiments, less than 70%; in some embodiments, less than 80%; in some embodiments, less than 85%; in some embodiments, less than 90%). In some embodiments, a non-chirally controlled internucleotidic linkage has a stereochemical purity (typically diastereomeric purity for oligonucleotides with multiple chiral centers) of less than 60%, 70%, 80%, 85%, or 90% (in some embodiments, less than 60%; in some embodiments, less than 70%; in some embodiments, less than 80%; in some embodiments, less than 85%; in some embodiments, less than 90%) at its chiral linkage phosphorus. In some embodiments, each non-chirally controlled internucleotidic linkage independently has a stereochemical purity (typically diastereomeric purity for oligonucleotides with multiple chiral centers) of less than 60%, 70%, 80%, 85%, or 90% (in some embodiments, less than 60%; in some embodiments, less than 70%; in some embodiments, less than 80%; in some embodiments, less than 85%; in some embodiments, less than 90%) at its chiral linkage phosphorus.

In some embodiments, at least 1, 2, 3, 4, 5, 6, 7, 8, 9, or 10 couplings of a monomer (as appreciated by those skilled in the art in many embodiments a phosphoramidite for oligonucleotide synthesis) independently have a stereoselectivity less than about 60%, 70%, 80%, 85%, or 90% [for oligonucleotide synthesis, typically diastereoselectivity with respect to formed linkage phosphorus chiral center(s)]. In some embodiments, at least one coupling has a stereoselectivity less than about 60%, 70%, 80%, 85%, or 90%. In some embodiments, at least two couplings independently have a stereoselectivity less than about 60%, 70%, 80%, 85%, or 90%. In some embodiments, at least three couplings independently have a stereoselectivity less than about 60%, 70%, 80%, 85%, or 90%. In some embodiments, at least four couplings independently have a stereoselectivity less than about 60%, 70%, 80%, 85%, or 90%. In some embodiments, at least five couplings independently have a stereoselectivity less than about 60%, 70%, 80%, 85%, or 90%. In some embodiments, each coupling independently has a stereoselectivity less than about 60%, 70%, 80%, 85%, or 90%. In some embodiments, each non-chirally controlled internucleotidic linkage is independently formed with a stereoselectivity less than about 60%, 70%, 80%, 85%, or 90%. In some embodiments, a stereoselectivity is less than about 60%. In some embodiments, a stereoselectivity is less than about 70%. In some embodiments, a stereoselectivity is less than about 80%. In some embodiments, a stereoselectivity is less than about 90%. In some embodiments, at least 1, 2, 3, 4, 5, 6, 7, 8, 9, 10, 11, 12, 13, 14, 15, 16, 17, 18, 19, 20, 21, 22, 23, 24, or 25 couplings independently have a stereoselectivity less than about 90%. In some embodiments, at least one coupling has a stereoselectivity less than about 90%. In some embodiments, at least two couplings have a stereoselectivity less than about 90%. In some embodiments, at least three couplings have a stereoselectivity less than about 90%. In some embodiments, at least four couplings have a stereoselectivity less than about 90%. In some embodiments, at least five couplings have a stereoselectivity less than about 90%. In some embodiments, each coupling independently has a stereoselectivity less than about 90%. In some embodiments, at least 1, 2, 3, 4, 5, 6, 7, 8, 9, 10, 11, 12, 13, 14, 15, 16, 17, 18, 19, 20, 21, 22, 23, 24, or 25 couplings independently have a stereoselectivity less than about 85%. In some embodiments, each coupling independently has a stereoselectivity less than about 85%. In some embodiments, at least 1, 2, 3, 4, 5, 6, 7, 8, 9, 10, 11, 12, 13, 14, 15, 16, 17, 18, 19, 20, 21, 22, 23, 24, or 25 couplings independently have a stereoselectivity less than about 80%. In some embodiments, each coupling independently has a stereoselectivity less than about 80%. In some embodiments, at least 1, 2, 3, 4, 5, 6, 7, 8, 9, 10, 11, 12, 13, 14, 15, 16, 17, 18, 19, 20, 21, 22, 23, 24, or 25 couplings independently have a stereoselectivity less than about 70%. In some embodiments, each coupling independently has a stereoselectivity less than about 70%.

In some embodiments, in stereorandom (or racemic) preparations (or stereorandom/non-chirally controlled oligonucleotide compositions), at least 1, 2, 3, 4, 5, 6, 7, 8, 9, 10, 11, 12, 13, 14, 15, 16, 17, 18, 19, 20, 21, 22, 23, 24, or 25 chiral internucleotidic linkages of the oligonucleotides independently have a stereochemical purity (typically diastereomeric purity for oligonucleotides comprising multiple chiral centers) less than about 60%, 70%, 80%, 85%, or 90% with respect to chiral linkage phosphorus of the internucleotidic linkage(s). In some embodiments, at least one internucleotidic linkage has a diastereomeric purity less than about 60%, 70%, 80%, 85%, or 90%. In some embodiments, at least two internucleotidic linkages independently have a diastereomeric purity less than about 60%, 70%, 80%, 85%, or 90%. In some embodiments, at least three internucleotidic linkages independently have a diastereomeric purity less than about 60%, 70%, 80%, 85%, or 90%. In some embodiments, at least four internucleotidic linkages independently have a diastereomeric purity less than about 60%, 70%, 80%, 85%, or 90%. In some embodiments, at least five internucleotidic linkages independently have a diastereomeric purity less than about 60%, 70%, 80%, 85%, or 90%. In some embodiments, each internucleotidic linkages independently has a diastereomeric purity less than about 60%, 70%, 80%, 85%, or 90%. In some embodiments, a diastereomeric purity is less than about 60%. In some embodiments, a diastereomeric purity is less than about 70%. In some embodiments, a diastereomeric purity is less than about 80%. In some embodiments, a diastereomeric purity is less than about 85%. In some embodiments, a diastereomeric purity is less than about 90%. In some embodiments, at least 1, 2, 3, 4, 5, 6, 7, 8, 9, 10, 11, 12, 13, 14, 15, 16, 17, 18, 19, 20, 21, 22, 23, 24, or 25 internucleotidic linkages independently have a diastereomeric purity less than about 90%. In some embodiments, at least one internucleotidic linkage has a diastereomeric purity less than about 90%. In some embodiments, at least two internucleotidic linkages independently have a diastereomeric purity less than about 90%. In some embodiments, at least three internucleotidic linkages independently have a diastereomeric purity less than about 90%. In some embodiments, at least four internucleotidic linkages independently have a diastereomeric purity less than about 90%. In some embodiments, at least five internucleotidic linkages independently have a diastereomeric purity less than about 90%. In some embodiments, each chiral internucleotidic linkage internucleotidic linkage independently has a diastereomeric purity less than about 90%. In some embodiments, at least 1, 2, 3, 4, 5, 6, 7, 8, 9, 10, 11, 12, 13, 14, 15, 16, 17, 18, 19, 20, 21, 22, 23, 24, or 25 internucleotidic linkages independently have a diastereomeric purity less than about 85%. In some embodiments, each chiral internucleotidic linkage independently has a diastereomeric purity less than about 85%. In some embodiments, at least 1, 2, 3, 4, 5, 6, 7, 8, 9, 10, 11, 12, 13, 14, 15, 16, 17, 18, 19, 20, 21, 22, 23, 24, or 25 internucleotidic linkages independently have a diastereomeric purity less than about 80%. In some embodiments, each chiral internucleotidic linkage independently has a diastereomeric purity less than about 80%.

In some embodiments, at least 5%-100% of all chiral elements of provided oligonucleotides each independently have a diastereomeric purity as described herein. In some embodiments, at least 5%, 10%, 15%, 20%, 25%, 30%, 40%, 45%, 50%, 55% 60%, 65%, 70%, 75%, 80%, 85%, 90%, 95%, or 100% of all chiral elements each independently have a diastereomeric purity as described herein. In some embodiments, at least 5%-100% of all chiral phosphorus centers each independently have a diastereomeric purity as described herein. In some embodiments, at least 5%, 10%, 15%, 20%, 25%, 30%, 40%, 45%, 50%, 55%, 60%, 65%, 70%, 75%, 80%, 85%, 90%, 95%, or 100% of all chiral linkage phosphorus each independently have a diastereomeric purity as described herein. In some embodiments, provided oligonucleotides, e.g., oligonucleotides of a plurality in provided chirally controlled oligonucleotide compositions have a diastereomeric purity as described herein.

In some embodiments, a stereochemical purity, e.g., diastereomeric purity, is about 60%-100%. In some embodiments, a diastereomeric purity, is about 60%-100%. In some embodiments, the percentage is at least 60%, 65%, 70%, 75%, 80%, 85%, 90%, 91%, 92%, 93%, 93%, 95%, 96%, 97%, 98%, or 99%. In some embodiments, the percentage is at least 80%, 85%, 90%, 91%, 92%, 93%, 93%, 95%, 96%, 97%, 98%, or 99%. In some embodiments, the percentage is at least 90%, 91%, 92%, 93%, 93%, 95%, 96%, 97%, 98%, or 99%. In some embodiments, a diastereomeric purity is at least 60%. In some embodiments, a diastereomeric purity is at least 70%. In some embodiments, a diastereomeric purity is at least 80%. In some embodiments, a diastereomeric purity is at least 85%. In some embodiments, a diastereomeric purity is at least 90%. In some embodiments, a diastereomeric purity is at least 91%. In some embodiments, a diastereomeric purity is at least 92%. In some embodiments, a diastereomeric purity is at least 93%. In some embodiments, a diastereomeric purity is at least 94%. In some embodiments, a diastereomeric purity is at least 95%. In some embodiments, a diastereomeric purity is at least 96%. In some embodiments, a diastereomeric purity is at least 97%. In some embodiments, a diastereomeric purity is at least 98%. In some embodiments, a diastereomeric purity is at least 99%. In some embodiments, a diastereomeric purity is at least 99.5%.

In some embodiments, compounds of the present disclosure (e.g., oligonucleotides, chiral auxiliaries, etc.) comprise multiple chiral elements (e.g., multiple carbon and/or phosphorus (e.g., linkage phosphorus of chiral internucleotidic linkages) chiral centers). In some embodiments, at least 1, 2, 3, 4, 5, 6, 7, 8, 9 or more chiral elements of a provided compound (e.g., an oligonucleotide) each independently have a diastereomeric purity as described herein. In some embodiments, at least 1, 2, 3, 4, 5, 6, 7, 8, 9 or more chiral carbon centers of a provided compound each independently have a diastereomeric purity as described herein. In some embodiments, at least 1, 2, 3, 4, 5, 6, 7, 8, 9 or more chiral phosphorus centers of a provided compound each independently have a diastereomeric purity as described herein. In some embodiments, each chiral element independently has a diastereomeric purity as described herein. In some embodiments, each chiral center independently has a diastereomeric purity as described herein. In some embodiments, each chiral carbon center independently has a diastereomeric purity as described herein. In some embodiments, each chiral phosphorus center independently has a diastereomeric purity as described herein. In some embodiments, each chiral phosphorus center independently has a diastereomeric purity of at least 90%, 91%, 92%, 93%, 93%, 95%, 96%, 97%, 98%, or 99% or more.

As understood by a person having ordinary skill in the art, in some embodiments, diastereoselectivity of a coupling or diastereomeric purity of a chiral linkage phosphorus center can be assessed through the diastereoselectivity of a dimer formation or diastereomeric purity of a dimer prepared under the same or comparable conditions, wherein the dimer has the same 5'- and 3'-nucleosides and internucleotidic linkage.

Various technologies can be utilized for identifying or confirming stereochemistry of chiral elements (e.g., configuration of chiral linkage phosphorus) and/or patterns of backbone chiral centers, and/or for assessing stereoselectivity (e.g., diastereoselectivity of couple steps in oligonucleotide synthesis) and/or stereochemical purity (e.g., diastereomeric purity of internucleotidic linkages, compounds (e.g., oligonucleotides), etc.). Example technologies include NMR [e.g., 1D (one-dimensional) and/or 2D (two-dimensional) $^{1}H$-$^{31}P$ HETCOR (heteronuclear correlation spectroscopy)], HPLC, RP-HPLC, mass spectrometry, LC-MS, and cleavage of internucleotidic linkages by stereospecific nucleases, etc., which may be utilized individually or in combination. Example useful nucleases include benzonase, micrococcal nuclease, and svPDE (snake venom phosphodiesterase), which are specific for certain internucleotidic linkages with Rp linkage phosphorus (e.g., a Rp phosphorothioate linkage); and nuclease P1, mung bean nuclease, and nuclease S1, which are specific for internucleotidic linkages with Sp linkage phosphorus (e.g., a Sp phosphorothioate linkage). Without wishing to be bound by any particular theory, the present disclosure notes that, in at least some cases, cleavage of oligonucleotides by a particular nuclease may be impacted by structural elements, e.g., chemical modifications (e.g., 2'-modifications of a sugars), base sequences, or stereochemical contexts. For example, it is observed that in some cases, benzonase and micrococcal nuclease, which are specific for internucleotidic linkages with Rp linkage phosphorus, were unable to cleave an isolated Rp phosphorothioate internucleotidic linkage flanked by Sp phosphorothioate internucleotidic linkages.

In some embodiments, oligonucleotides sharing a common base sequence, a common pattern of backbone linkages, and a common pattern of backbone chiral centers share a common pattern of backbone phosphorus modifications and a common pattern of base modifications. In some embodiments, oligonucleotide compositions sharing a common base sequence, a common pattern of backbone linkages, and a common pattern of backbone chiral centers share a common pattern of backbone phosphorus modifications and a common pattern of nucleoside modifications. In some embodiments, oligonucleotides share a common base sequence, a common pattern of backbone linkages, and a common pattern of backbone chiral centers have identical structures. In some embodiments, in a composition an oligonucleotide exists in one form, e.g., a pharmaceutically acceptable salt form such as a sodium salt form. In some embodiments, in a composition an oligonucleotide exists in two or more forms, e.g., two or more pharmaceutically acceptable salt forms.

In some embodiments, the present disclosure provides an oligonucleotide composition comprising a plurality of oligonucleotides capable of directing RHO knockdown, wherein oligonucleotides of the plurality are of a particular oligonucleotide type, which composition is chirally controlled in that it is enriched, relative to a substantially racemic preparation of oligonucleotides having the same base sequence, for oligonucleotides of the particular oligonucleotide type.

In some embodiments, oligonucleotides having a common base sequence, a common pattern of backbone linkages, and a common pattern of backbone chiral centers have a common pattern of backbone phosphorus modifications and a common pattern of base modifications. In some embodiments, oligonucleotides having a common base sequence, a common pattern of backbone linkages, and a common pattern of backbone chiral centers have a common pattern of backbone phosphorus modifications and a common pattern of nucleoside modifications. In some embodiments, oligonucleotides having a common base sequence, a common pattern of backbone linkages, and a common pattern of backbone chiral centers have identical structures.

In some embodiments, the present disclosure provides RHO oligonucleotide compositions comprising a plurality of oligonucleotides. In some embodiments, the present disclosure provides RHO oligonucleotide compositions comprising a plurality of oligonucleotides, wherein at least one oligonucleotide comprises a chirally controlled internucleotidic linkage. In some embodiments, the present disclosure provides RHO oligonucleotide compositions comprising a plurality of oligonucleotides, wherein none of the oligonucleotides comprises a chirally controlled internucleotidic linkage. In some embodiments, the present disclosure provides chirally controlled oligonucleotide compositions of RHO oligonucleotides. In some embodiments, the present disclosure provides a RHO oligonucleotide whose base sequence is or is complementary to a RHO sequence disclosed herein or a portion thereof (e.g., various bases sequences in Table A1 or A2, wherein each T may be independently replaced with U and vice versa). In some embodiments, the present disclosure provides a RHO oligonucleotide whose base sequence comprises a base sequence that is or is complementary to a RHO sequence disclosed herein or a portion thereof (e.g., various bases sequences in Table A1 or A2). In some embodiments, the present disclosure provides a RHO oligonucleotide whose base sequence comprises 15 contiguous bases of a base sequence that is or is complementary to a RHO sequence disclosed herein or a portion thereof (e.g., various bases sequences in Table A1 or A2, wherein each T may be independently replaced with U and vice versa). In some embodiments, the present disclosure provides a RHO oligonucleotide which has a base sequence comprising 15 contiguous bases with 0-3 mismatches of a base sequence that is or is complementary to a RHO sequence disclosed herein or a portion thereof (e.g., various bases sequences in Table A1 or A2, wherein each T may be independently replaced with U and vice versa). In some embodiments, the present disclosure provides a RHO oligonucleotide composition wherein the RHO oligonucleotides comprise at least one chiral internucleotidic linkage which is not chirally controlled. In some embodiments, the present disclosure provides a RHO oligonucleotide comprising a non-chirally controlled chiral internucleotidic linkage, wherein the base sequence of the RHO oligonucleotide comprises a base sequence that is or is complementary to a RHO sequence disclosed herein or a portion thereof (e.g., various bases sequences in Table A1 or A2, wherein each T may be independently replaced with U and vice versa). In some embodiments, the present disclosure provides a RHO oligonucleotide composition comprising a non-chirally controlled chiral internucleotidic linkage, wherein the base sequence of the RHO oligonucleotide is a base sequence that is or is complementary to a RHO sequence disclosed herein or a portion thereof (e.g., various bases sequences in Table A1 or A2, wherein each T may be independently replaced with U and vice versa). In some embodiments, the present disclosure provides a RHO oligonucleotide comprising a non-chirally controlled chiral internucleotidic linkage, wherein the base sequence of the RHO oligonucleotide comprises 15 contiguous bases of a base sequence that is or is complementary to a RHO sequence disclosed herein or a portion thereof (e.g., various bases sequences in Table A1 or A2, wherein each T may be independently replaced with U and vice versa). In some embodiments, the present disclosure provides a RHO oligonucleotide comprising a non-chirally controlled chiral internucleotidic linkage, wherein the base sequence of the RHO oligonucleotides comprises 15 contiguous bases with 0-3 mismatches of a base sequence that is or is complementary to a RHO sequence disclosed herein or a portion thereof (e.g., various bases sequences in Table A1 or A2, wherein each T may be independently replaced with U and vice versa). In some embodiments, the present disclosure provides a RHO oligonucleotide comprising a chirally controlled chiral internucleotidic linkage, wherein the base sequence of the RHO oligonucleotide comprises a base sequence that is or is complementary to a RHO sequence disclosed herein or a portion thereof (e.g., various bases sequences in Table A1 or A2, wherein each T may be independently replaced with U and vice versa). In some embodiments, the present disclosure provides a RHO oligonucleotide composition comprising a chirally controlled chiral internucleotidic linkage, wherein the base sequence of the RHO oligonucleotide is a base sequence that is or is complementary to a RHO sequence disclosed herein or a portion thereof (e.g., various bases sequences in Table A1 or A2, wherein each T may be independently replaced with U and vice versa). In some embodiments, the present disclosure provides a RHO oligonucleotide comprising a chirally controlled chiral internucleotidic linkage, wherein the base sequence of the RHO oligonucleotide comprises 15 contiguous bases of abase sequence that is or is complementary to a RHO sequence disclosed herein or a portion thereof (e.g., various bases sequences in Table A1 or A2, wherein each T may be independently replaced with U and vice versa). In some embodiments, the present disclosure provides a RHO oligonucleotide comprising a chirally controlled chiral internucleotidic linkage, wherein the base sequence of the RHO oligonucleotides comprises 15 contiguous bases with 0-3 mismatches of a base sequence that is or is complementary to a RHO sequence disclosed herein or a portion thereof (e.g., various bases sequences in Table A1 or A2, wherein each T may be independently replaced with U and vice versa).

In some embodiments, oligonucleotides of the same oligonucleotide type have a common pattern of backbone phosphorus modifications and a common pattern of nucleoside modifications. In some embodiments, oligonucleotides of the same oligonucleotide type have a common pattern of sugar modifications. In some embodiments, oligonucleotides of the same oligonucleotide type have a common pattern of base modifications. In some embodiments, oligonucleotides of the same oligonucleotide type have a common pattern of nucleoside modifications. In some embodiments, oligonucleotides of the same oligonucleotide type have the same constitution. In many embodiments, oligonucleotides of the same oligonucleotide type are identical.

In some embodiments, a plurality of oligonucleotides or oligonucleotides of a particular oligonucleotide type in a provided oligonucleotide composition are RHO oligonucleotides. In some embodiments, the present disclosure provides a chirally controlled RHO oligonucleotide composition comprising a plurality of RHO oligonucleotides, wherein the oligonucleotides share:

1) a common base sequence;
2) a common pattern of backbone linkages; and
3) the same linkage phosphorus stereochemistry at one or more (e.g., 1-50, 1-40, 1-30, 1-25, 1-20, 1-15, 1-10, 5-50, 5-40, 5-30, 5-25, 5-20, 5-15, 5-10, 1, 2, 3, 4, 5, 6, 7, 8, 9, 10, 11, 12, 13, 14, 15, 16, 17, 18, 19, 20, or more) chiral internucleotidic linkages (chirally controlled internucleotidic linkages), wherein the composition is enriched, relative to a substantially racemic preparation of oligonucleotides sharing the common base sequence and pattern of backbone linkages, for oligonucleotides of the plurality.

In some embodiments, as used herein, "one or more" or "at least one" is 1-50, 1-40, 1-30, 1-25, 1-20, 1-15, 1-10, 5-50, 5-40, 5-30, 5-25, 5-20, 5-15, 5-10, 1, 2, 3, 4, 5, 6, 7, 8, 9, 10, 11, 12, 13, 14, 15, 16, 17, 18, 19, 20, or more.

In some embodiments, the present disclosure provides a chirally controlled RHO oligonucleotide composition comprising a plurality of oligonucleotides, wherein the oligonucleotides share:

1) a common base sequence;
2) a common pattern of backbone linkages; and
3) a common pattern of backbone chiral centers, which composition is a substantially pure preparation of a single oligonucleotide in that at least about 10%, 15%, 20%, 25%, 30%, 35%, 40%, 45%, 50%, 55%, 60%, 65%, 70%, 75%, 80%, 85%, 90%, 91%, 92%, 93%, 93%, 95%, 96%, 97%, 98%, or 99% of the oligonucleotides in the composition have the common base sequence, the common pattern of backbone linkages, and the common pattern of backbone chiral centers.

In some embodiments, an oligonucleotide type is further defined by: 4) additional chemical moiety, if any.

In some embodiments, the percentage is at least about 10%. In some embodiments, the percentage is at least about 20%. In some embodiments, the percentage is at least about 30%. In some embodiments, the percentage is at least about 40%. In some embodiments, the percentage is at least about 50%. In some embodiments, the percentage is at least about 60%. In some embodiments, the percentage is at least about 70%. In some embodiments, the percentage is at least about 75%. In some embodiments, the percentage is at least about 80%. In some embodiments, the percentage is at least about 85%. In some embodiments, the percentage is at least about 90%. In some embodiments, the percentage is at least about 91%. In some embodiments, the percentage is at least about 92%. In some embodiments, the percentage is at least about 93%. In some embodiments, the percentage is at least about 94%. In some embodiments, the percentage is at least about 95%. In some embodiments, the percentage is at least about 96%. In some embodiments, the percentage is at least about 97%. In some embodiments, the percentage is at least about 98%. In some embodiments, the percentage is at least about 99%. In some embodiments, the percentage is or is greater than $(DS)^{nc}$, wherein DS and nc are each independently as described in the present disclosure.

In some embodiments, a plurality of oligonucleotides, e.g., RHO oligonucleotides, share the same constitution. In some embodiments, a plurality of oligonucleotides, e.g., RHO oligonucleotides, are identical (the same stereoisomer). In some embodiments, a chirally controlled oligonucleotide composition, e.g., a chirally controlled RHO oligonucleotide composition, is a stereopure oligonucleotide composition wherein oligonucleotides of the plurality are identical (the same stereoisomer), and the composition does not contain any other stereoisomers. Those skilled in the art will appreciate that one or more other stereoisomers may exist as impurities as processes, selectivities, purifications, etc. may not achieve completeness.

In some embodiments, a provided composition is characterized in that when it is contacted with a target nucleic acid [e.g., a RHO transcript (e.g., pre-mRNA, mature mRNA, other types of RNA, etc. that hybridizes with oligonucleotides of the composition)], levels of the target nucleic acid and/or a product encoded thereby is reduced compared to that observed under a reference condition. In some embodiments, a reference condition is selected from the group consisting of absence of the composition, presence of a reference composition, and combinations thereof. In some embodiments, a reference condition is absence of the composition. In some embodiments, a reference condition is presence of a reference composition. In some embodiments, a reference composition is a composition whose oligonucleotides do not hybridize with the target nucleic acid. In some embodiments, a reference composition is a composition whose oligonucleotides do not comprise a sequence that is sufficiently complementary to the target nucleic acid. In some embodiments, a provided composition is a chirally controlled oligonucleotide composition and a reference composition is a non-chirally controlled oligonucleotide composition which is otherwise identical but is not chirally controlled (e.g., a racemic preparation of oligonucleotides of the same constitution as oligonucleotides of a plurality in the chirally controlled oligonucleotide composition).

In some embodiments, the present disclosure provides a chirally controlled RHO oligonucleotide composition comprising a plurality of RHO oligonucleotides capable of directing RHO knockdown, wherein the oligonucleotides share:

1) a common base sequence,
2) a common pattern of backbone linkages, and
3) the same linkage phosphorus stereochemistry at one or more (e.g., 1-50, 1-40, 1-30, 1-25, 1-20, 1-15, 1-10, 5-50, 5-40, 5-30, 5-25, 5-20, 5-15, 5-10, 1, 2, 3, 4, 5, 6, 7, 8, 9, 10, 11, 12, 13, 14, 15, 16, 17, 18, 19, 20, or more) chiral internucleotidic linkages (chirally controlled internucleotidic linkages), wherein the composition is enriched, relative to a substantially racemic preparation of oligonucleotides sharing the common base sequence and pattern of backbone linkages, for oligonucleotides of the plurality, the oligonucleotide composition being characterized in that, when it is contacted with a RHO transcript in a RHO knockdown system, knockdown of the transcript is improved relative to that observed under reference conditions selected from the group consisting of absence of the composition, presence of a reference composition, and combinations thereof.

As noted above and understood in the art, in some embodiments, the base sequence of an oligonucleotide may refer to the identity and/or modification status of nucleoside residues (e.g., of sugar and/or base components, relative to standard naturally occurring nucleotides such as adenine, cytosine, guanosine, thymine, and uracil) in the oligonucleotide and/or to the hybridization character (i.e., the ability to hybridize with particular complementary residues) of such residues.

As demonstrated herein, oligonucleotide structural elements (e.g., patterns of sugar modifications, backbone linkages, backbone chiral centers, backbone phosphorus modifications, etc.) and combinations thereof can provide surprisingly improved properties and/or bioactivities.

In some embodiments, oligonucleotide compositions are capable of reducing the expression, level and/or activity of a target gene or a gene product thereof. In some embodiments, oligonucleotide compositions are capable of reducing in the expression, level and/or activity of a target gene or a gene product thereof by sterically blocking translation after annealing to a target gene mRNA, by cleaving mRNA (pre-mRNA or mature mRNA), and/or by altering or interfering with mRNA splicing. In some embodiments, provided RHO oligonucleotide compositions are capable of reducing the expression, level and/or activity of a RHO target gene or a gene product thereof. In some embodiments, provided RHO oligonucleotide compositions are capable of reducing in the expression, level and/or activity of a RHO target gene or a gene product thereof by sterically blocking translation after annealing to a RHO target gene mRNA, by cleaving RHO mRNA (pre-mRNA or mature mRNA), and/or by altering or interfering with mRNA splicing.

In some embodiments, an oligonucleotide composition, e.g., a RHO oligonucleotide composition, is a substantially pure preparation of a single oligonucleotide stereoisomer, e.g., a RHO oligonucleotide stereoisomer, in that oligonucleotides in the composition that are not of the oligonucleotide stereoisomer are impurities from the preparation process of said oligonucleotide stereoisomer, in some case, after certain purification procedures.

In some embodiments, the present disclosure provides oligonucleotides and oligonucleotide compositions that are chirally controlled, and in some embodiments, stereopure. For instance, in some embodiments, a provided composition contains non-random or controlled levels of one or more individual oligonucleotide types. In some embodiments, oligonucleotides of the same oligonucleotide type are identical.

Sugars

Various sugars, including modified sugars, can be utilized in accordance with the present disclosure. In some embodiments, the present disclosure provides sugar modifications and patterns thereof optionally in combination with other structural elements (e.g., internucleotidic linkage modifications and patterns thereof, pattern of backbone chiral centers thereof, etc.) that when incorporated into oligonucleotides can provide improved properties and/or activities.

The most common naturally occurring nucleosides comprise ribose sugars (e.g., in RNA) or deoxyribose sugars (e.g., in DNA) linked to the nucleobases adenosine (A), cytosine (C), guanine (G), thymine (T) or uracil (U). In some embodiments, a sugar, e.g., various sugars in many oligonucleotides in Table 1 or A2 (unless otherwise notes), is a natural DNA sugar (in DNA nucleic acids or oligonucleotides, having the structure of

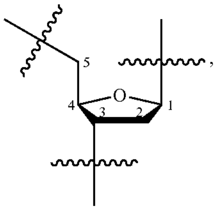

wherein a nucleobase is attached to the 1' position, and the 3' and 5' positions are connected to internucleotidic linkages (as appreciated by those skilled in the art, if at the 5'-end of an oligonucleotide, the 5' position may be connected to a 5'-end group (e.g., —OH), and if at the 3'-end of an oligonucleotide, the 3' position may be connected to a 3'-end group (e.g., —OH). In some embodiments, a sugar is a natural RNA sugar (in RNA nucleic acids or oligonucleotides, having the structure of

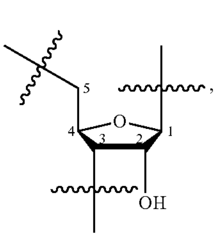

wherein a nucleobase is attached to the 1' position, and the 3' and 5' positions are connected to internucleotidic linkages (as appreciated by those skilled in the art, if at the 5'-end of an oligonucleotide, the 5' position may be connected to a 5'-end group (e.g., —OH), and if at the 3'-end of an oligonucleotide, the 3' position may be connected to a 3'-end group (e.g., —OH). In some embodiments, a sugar is a modified sugar in that it is not a natural DNA sugar or a natural RNA sugar. Among other things, modified sugars may provide improved stability. In some embodiments, modified sugars can be utilized to alter and/or optimize one or more hybridization characteristics. In some embodiments, modified sugars can be utilized to alter and/or optimize target recognition. In some embodiments, modified sugars can be utilized to optimize Tm. In some embodiments, modified sugars can be utilized to improve oligonucleotide activities.

Sugars can be bonded to internucleotidic linkages at various positions. As non-limiting examples, internucleotidic linkages can be bonded to the 2', 3', 4' or 5' positions of sugars. In some embodiments, as most commonly in natural nucleic acids, an internucleotidic linkage connects with one sugar at the 5' position and another sugar at the 3' position unless otherwise indicated.

In some embodiments, a sugar is an optionally substituted natural DNA or RNA sugar. In some embodiments, a sugar is optionally substituted

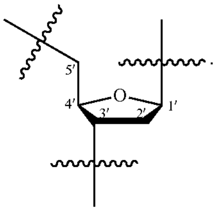

In some embodiments, the 2' position is optionally substituted. In some embodiments, a sugar is

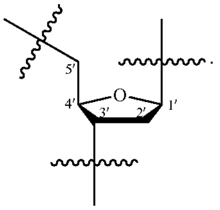

In some embodiments, a sugar has the structure of

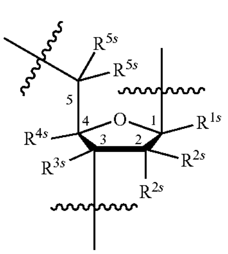

or

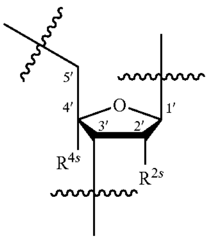

, wherein each of $R^{1s}$, $R^{2s}$, $R^{3s}$, $R^{4s}$, and $R^{5s}$ is independently —H, a suitable substituent or suitable sugar modification (e.g., those described in U.S. Pat. Nos. 9,394,333, 9,744, 183, 9,605,019, 9,982,257, US 20170037399, US 20180216108, US 20180216107, U.S. Pat. No. 9,598,458, WO 2017/062862, WO 2018/067973, WO 2017/160741, WO 2017/192679, WO 2017/210647, WO 2018/098264, WO 2018/022473, WO 2018/223056, WO 2018/223073, WO 2018/223081, WO 2018/237194, WO 2019/032607, WO2019/032612, WO 2019/055951, and/or WO 2019/075357, the substituents, sugar modifications, descriptions of $R^{1s}$, $R^{2s}$, $R^{3s}$, $R^{4s}$, and $R^{5s}$, and modified sugars of each of which are independently incorporated herein by reference). In some embodiments, each of $R^{1s}$, $R^{2s}$, $R^{5s}$, $R^{4s}$, and $R^{5s}$ is independently $R^s$, wherein each $R^s$ is independently —F, —Cl, —Br, —I, —CN, —$N_3$, —NO, —$NO_2$, -$L^s$-R', -$L^s$-OR', -$L^s$-SR, -$L^s$-N(R')$_2$, —O-$L^s$-OR', —O-$L^s$-SR', or —O-$L^s$-N(R')$_2$, wherein each R' is independently as described herein, and $L^s$ is a covalent bond or optionally substituted bivalent $C_{1-6}$ aliphatic or heteroaliphatic having 1-4 heteroatoms. In some embodiments, a sugar has the structure of

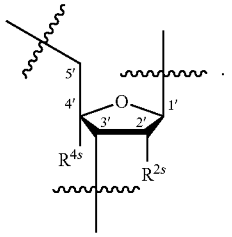

In some embodiments, $R^{4s}$ is —H. In some embodiments, a sugar has the structure of

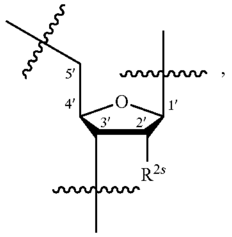

wherein $R^{2s}$ is —H, halogen, or —OR, wherein R is optionally substituted $C_{1-6}$ aliphatic. In some embodiments, $R^{2s}$ is —H. In some embodiments, $R^{2s}$ is —F. In some embodiments, $R^{2s}$ is —OMe. In some embodiments, $R^{2s}$ is —$OCH_2CH_2OMe$.

In some embodiments, a sugar has the structure of

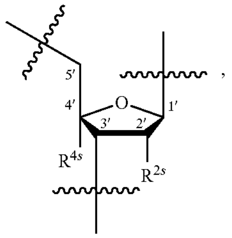

wherein $R^{2s}$ and $R^{4s}$ are taken together to form -$L^s$-, wherein $L^s$ is a covalent bond or optionally substituted bivalent $C_{1-6}$ aliphatic or heteroaliphatic having 1-4 heteroatoms. In some embodiments, each heteroatom is independently selected from nitrogen, oxygen or sulfur). In some embodiments, $L^s$ is optionally substituted C2-O—$CH_2$—C4. In some embodiments, $L^s$ is C2-O—$CH_2$—C4. In some embodiments, $L^s$ is $C_{2-0}$—(R)—CH($CH_2CH_3$)—C4. In some embodiments, $L^s$ is C2-O—(S)—CH($CH_2CH_3$)—C4.

In some embodiments, a modified sugar contains one or more substituents at the 2' position (typically one substituent, and often at the axial position) independently selected from —F; —$CF_3$, —CN, —$N_3$, —NO, —$NO_2$, —OR', —SR', or —N(R')$_2$, wherein each R' is independently described in the present disclosure, and in some embodiments, optionally substituted $C_{1-10}$ aliphatic; —O—($C_1$-$C_{10}$ alkyl), —S—($C_1$-$C_{10}$ alkyl), —NH—($C_1$-$C_{10}$ alkyl), or —N($C_1$-$C_{10}$ alkyl)$_2$; —O—($C_2$-$C_{10}$ alkenyl), —S—($C_2$-$C_{10}$ alkenyl), —NH—($C_2$-$C_{10}$ alkenyl), or —N($C_2$-$C_{10}$ alkenyl)$_2$; —O—($C_2$-$C_{10}$ alkynyl), —S—($C_2$-$C_{10}$ alkynyl), —NH—($C_2$-$C_{10}$ alkynyl), or —N($C_2$-$C_{10}$ alkynyl)$_2$; or —O—($C_1$-$C_{10}$ alkylene)-O—($C_1$-$C_{10}$ alkyl), —O—($C_1$-$C_{10}$ alkylene)-NH—($C_1$-$C_{10}$ alkyl) or —O—($C_1$-$C_{10}$ alkylene)-NH($C_1$-$C_{10}$ alkyl)$_2$, —NH—($C_1$-$C_{10}$ alkylene)-O—($C_1$-$C_{10}$ alkyl), or —N($C_1$-$C_{10}$ alkyl)-($C_1$-$C_{10}$ alkylene)-O—($C_1$-$C_{10}$ alkyl), wherein each of the alkyl, alkylene, alkenyl and alkynyl is independently and optionally substituted. In some embodiments, a substituent is —O($CH_2$), $OCH_3$, —O($CH_2$)$_n$$NH_2$, MOE, DMAOE, or DMAEOE, wherein n is from 1 to about 10.

In some embodiments, the 2'-OH of a ribose is replaced with a group selected from —H, —F; —$CF_3$, —CN, —$N_3$, —NO, —$NO_2$, —OR', —SR', or —N(R')$_2$, wherein each R' is independently described in the present disclosure; —O—($C_1$-$C_{10}$ alkyl), —S—($C_1$-$C_{10}$ alkyl), —NH—($C_1$-$C_{10}$ alkyl), or —N($C_1$-$C_{10}$ alkyl)$_2$; —O—($C_2$-$C_{10}$ alkenyl), —S—($C_2$-$C_{10}$ alkenyl), —NH—($C_2$-$C_{10}$ alkenyl), or —N($C_2$-$C_{10}$ alkenyl)$_2$; —O—($C_2$-$C_{10}$ alkynyl), —S—($C_2$-$C_{10}$ alkynyl), —NH—($C_2$-$C_{10}$ alkynyl), or —N($C_2$-$C_{10}$ alkynyl)$_2$; or —O—($C_1$-$C_{10}$ alkylene)-O—($C_1$-$C_{10}$ alkyl), —O—($C_1$-$C_{10}$ alkylene)-NH—($C_1$-$C_{10}$ alkyl) or —O—($C_1$-$C_{10}$ alkylene)-NH($C_1$-$C_{10}$ alkyl)$_2$, —NH—($C_1$-$C_{10}$ alkylene)-O—($C_1$-$C_{10}$ alkyl), or —N($C_1$-$C_{10}$ alkyl)-($C_1$-$C_{10}$ alkylene)-O—($C_1$-$C_{10}$ alkyl), wherein each of the alkyl, alkylene, alkenyl and alkynyl is independently and optionally substituted. In some embodiments, the 2'-OH is replaced with —H (deoxyribose). In some embodiments, the 2'-OH is replaced with —F. In some embodiments, the 2'-OH is replaced with —OR'. In some embodiments, the 2'-OH is replaced with —OMe. In some embodiments, the 2'-OH is replaced with —$OCH_2CH_2OMe$.

In some embodiments, a sugar modification is a 2'-modification. In some embodiments, 2'-modifications include but are not limited to 2'-OR, wherein R is as described herein. In some embodiments, R is optionally substituted $C_{1-6}$ aliphatic. In some embodiments, a modification is 2'-OR, wherein R is optionally substituted $C_{1-6}$ alkyl. In some embodiments, a modification is 2'-OMe. In some embodiments, a modification is 2'-MOE. In some embodiments, a 2'-modification is S-cEt. In some embodiments, a modified sugar is an LNA sugar. In some embodiments, a 2'-modification is —F.

In some embodiments, a sugar modification replaces a sugar moiety with another cyclic or acyclic moiety. Examples of such moieties are widely known in the art, including but not limited to those used in morpholino (optionally with its phosphorodiamidate linkage), glycol nucleic acids, etc.

In some embodiments, one or more of the sugars of an RHO oligonucleotide are modified. In some embodiments, each sugar of an oligonucleotide or a portion thereof (e.g., a wing) is independently modified. In some embodiments, a modified sugar comprises a 2'-modification. In some embodiments, each modified sugar independently comprises a 2'-modification. In some embodiments, a 2'-modification is 2'-OR, wherein R is optionally substituted $C_{1-6}$ aliphatic. In some embodiments, a 2'-modification is a 2'-OMe. In some embodiments, a 2'-modification is a 2'-MOE. In some embodiments, a 2'-modification is an LNA sugar modification. In some embodiments, a 2'-modification is 2'-F. In some embodiments, each sugar modification is independently a 2'-modification. In some embodiments, each sugar modification is independently 2'-OR. In some embodiments, each sugar modification is independently 2'-OR, wherein R is optionally substituted $C_{1-6}$ alkyl. In some embodiments, each sugar modification is 2'-OMe. In some embodiments, each sugar modification is 2'-MOE. In some embodiments, each sugar modification is independently 2'-OMe or 2'-MOE. In some embodiments, each sugar modification is independently 2'-OMe, 2'-MOE, or a LNA sugar.

As those skilled in the art will appreciate, modifications of sugars, nucleobases, internucleotidic linkages, etc. can and are often utilized in combination in oligonucleotides, e.g., see various oligonucleotides in Table 1 or A2. For example, a combination of sugar modification and nucleobase modification is 2'-F (sugar) 5-methyl (nucleobase) modified nucleosides. In some embodiments, a combination is replacement of a ribosyl ring oxygen atom with S and substitution at the 2'-position.

In some embodiments, a sugar is one described in U.S. Pat. Nos. 9,394,333, 9,744,183, 9,605,019, 9,598,458, 9,982,257, U.S. Ser. No. 10/160,969, U.S. Ser. No. 10/479,995, US 2020/0056173, US 2018/0216107, US 2019/0127733, U.S. Ser. No. 10/450,568, US 2019/0077817, US 2019/0249173, US 2019/0375774, WO 2018/223056, WO 2018/223073, WO 2018/223081, WO 2018/237194, WO 2019/032607, WO 2019/055951, WO 2019/075357, WO 2019/200185, WO 2019/217784, and/or WO 2019/032612, the sugars of each of which is incorporated herein by reference.

Various additional sugars useful for preparing oligonucleotides or analogs thereof are known in the art and may be utilized in accordance with the present disclosure.

Nucleobases

Various nucleobases may be utilized in provided oligonucleotides in accordance with the present disclosure. In some embodiments, a nucleobase is a natural nucleobase, the most commonly occurring ones being A, T, C, G and U. In some embodiments, a nucleobase is a modified nucleobase in that it is not A, T, C, G or U. In some embodiments, a nucleobase is optionally substituted A, T, C, G or U, or a substituted tautomer of A T, C, G or U. In some embodiments, a nucleobase is optionally substituted A, T, C, G or U, e.g., 5mC, 5-hydroxymethyl C, etc. In some embodiments, a nucleobase is alkyl-substituted A, T, C, G or U. In some embodiments, a nucleobase is A. In some embodiments, a nucleobase is T. In some embodiments, a nucleobase is C. In some embodiments, a nucleobase is G. In some embodiments, a nucleobase is U. In some embodiments, a nucleobase is 5mC. In some embodiments, a nucleobase is substituted A, T, C, G or U. In some embodiments, a nucleobase is a substituted tautomer of A, T, C, G or U. In some embodiments, substitution protects certain functional groups in nucleobases to minimize undesired reactions during oligonucleotide synthesis. Suitable technologies for nucleobase protection in oligonucleotide synthesis are widely known in the art and may be utilized in accordance with the present disclosure. In some embodiments, modified nucleobases improves properties and/or activities of oligonucleotides. For example, in many cases, 5mC may be utilized in place of C to modulate certain undesired biological effects, e.g., immune responses. In some embodiments, when determining sequence identity, a substituted nucleobase having the same hydrogen-bonding pattern is treated as the same as the unsubstituted nucleobase, e.g., 5mC may be treated the same as C [e.g., an oligonucleotide having 5mC in place of C (e.g., AT5mCG) is considered to have the same base sequence as an oligonucleotide having C at the corresponding location(s) (e.g., ATCG)].

In some embodiments, an oligonucleotide comprises one or more A, T, C, G or U. In some embodiments, an oligonucleotide comprises one or more optionally substituted A, T, C, G or U. In some embodiments, an oligonucleotide comprises one or more 5-methylcytidine, 5-hydroxymethylcytidine, 5-formylcytosine, or 5-carboxylcytosine. In some embodiments, an oligonucleotide comprises one or more 5-methylcytidine. In some embodiments, each nucleobase in an oligonucleotide is selected from the group consisting of optionally substituted A, T, C, G and U, and optionally substituted tautomers of A, T, C, G and U. In some embodiments, each nucleobase in an oligonucleotide is optionally protected A, T, C, G and U. In some embodiments, each nucleobase in an oligonucleotide is optionally substituted A, T, C, G or U. In some embodiments, each nucleobase in an oligonucleotide is selected from the group consisting of A, T, C, G, U, and 5mC.

In some embodiments, a nucleobase is optionally substituted 2AP or DAP. In some embodiments, a nucleobase is optionally substituted 2AP. In some embodiments, a nucleobase is optionally substituted DAP. In some embodiments, a nucleobase is 2AP. In some embodiments, a nucleobase is DAP.

In some embodiments, a nucleobase is a natural nucleobase or a modified nucleobase derived from a natural nucleobase. Examples include uracil, thymine, adenine, cytosine, and guanine optionally having their respective amino groups protected by acyl protecting groups, 2-fluorouracil, 2-fluorocytosine, 5-bromouracil, 5-iodouracil, 2,6-diaminopurine, azacytosine, pyrimidine analogs such as pseudoisocytosine and pseudouracil and other modified nucleobases such as 8-substituted purines, xanthine, or hypoxanthine (the latter two being the natural degradation products). Certain examples of modified nucleobases are disclosed in Chiu and Rana, R N A, 2003, 9, 1034-1048, Limbach et al. Nucleic Acids Research, 1994, 22, 2183-2196 and Revankar and Rao, Comprehensive Natural Products Chemistry, vol. 7, 313. In some embodiments, a modified nucleobase is substituted uracil, thymine, adenine, cytosine, or guanine. In some embodiments, a modified nucleobase is a functional replacement, e.g., in terms of hydrogen bonding and/or base pairing, of uracil, thymine, adenine, cytosine, or guanine. In some embodiments, a nucleobase is optionally substituted uracil, thymine, adenine, cytosine, 5-methylcytosine, or guanine. In some embodiments, a nucleobase is uracil, thymine, adenine, cytosine, 5-methylcytosine, or guanine.

In some embodiments, a provided oligonucleotide comprises one or more 5-methylcytosine. In some embodiments, the present disclosure provides an oligonucleotide whose base sequence is disclosed herein, e.g., in Table 1 or A2, wherein each T may be independently replaced with U and vice versa, and each cytosine is optionally and independently replaced with 5-methylcytosine or vice versa. As appreciated by those skilled in the art, in some embodiments, 5mC may be treated as C with respect to base sequence of an oligonucleotide—such oligonucleotide comprises a nucleobase modification at the C position (e.g., see various oligonucleotides in Table 1 or A2). In description of oligonucleotides, typically unless otherwise noted, nucleobases, sugars and internucleotidic linkages are non-modified.

In some embodiments, a modified base is optionally substituted adenine, cytosine, guanine, thymine, or uracil, or a tautomer thereof. In some embodiments, a modified nucleobase is a modified adenine, cytosine, guanine, thymine or uracil, modified by one or more modifications by which:

(1) a nucleobase is modified by one or more optionally substituted groups independently selected from acyl, halogen, amino, azide, alkyl, alkenyl, alkynyl, aryl, heteroalkyl, heteroalkenyl, heteroalkynyl, heterocyclyl, heteroaryl, carboxyl, hydroxyl, biotin, avidin, streptavidin, substituted silyl, and combinations thereof, (2) one or more atoms of a nucleobase are independently replaced with a different atom selected from carbon, nitrogen and sulfur;

(3) one or more double bonds in a nucleobase are independently hydrogenated; or (4) one or more aryl or heteroaryl rings are independently inserted into a nucleobase.

In some embodiments, a modified nucleobase is a modified nucleobase known in the art, e.g., WO2017/210647. In some embodiments, modified nucleobases are expanded-size nucleobases in which one or more aryl and/or heteroaryl rings, such as phenyl rings, have been added. In some embodiments, a modified nucleobase is a protected A, T, C, G, U, 5mC, etc., which are suitable for oligonucleotide synthesis. Various nucleobase protection technologies are available and can be utilized in accordance with the present disclosure.

In some embodiments, a modified nucleobase is selected from 5-substituted pyrimidines, 6-azapyrimidines, alkyl or alkynyl substituted pyrimidines, alkyl substituted purines, and N-2, N-6 and 0-6 substituted purines. In certain embodiments, modified nucleobases are selected from 2-aminopropyladenine, 5-hydroxymethyl cytosine, xanthine, hypoxanthine, 2-aminoadenine, 6-N-methylguanine, 6-N-methyladenine, 2-propyladenine, 2-thiouracil, 2-thiothymine and 2-thiocytosine, 5-propynyl ($-C\equiv C\equiv CH_3$) uracil, 5-propynylcytosine, 6-azouracil, 6-azocytosine, 6-azothymine, 5-ribosyluracil (pseudouracil), 4-thiouracil, 8-halo, 8-amino, 8-thiol, 8-thioalkyl, 8-hydroxyl, 8-aza and other 8-substituted purines, 5-halo, particularly 5-bromo, 5-trifluoromethyl, 5-halouracil, and 5-halocytosine, 7-methylguanine, 7-methyladenine, 2-F-adenine, 2-aminoadenine, 7-deazaguanine, 7-deazaadenine, 3-deazaguanine, 3-deazaadenine, 6-N-benzoyladenine, 2-N-isobutyrylguanine, 4-N-benzoylcytosine, 4-N-benzoyluracil, 5-methyl 4-N-benzoylcytosine, 5-methyl 4-N-benzoyluracil, universal bases, hydrophobic bases, promiscuous bases, size-expanded bases, and fluorinated bases. In some embodiments, modified nucleobases are tricyclic pyrimidines, such as 1,3-diazaphenoxazine-2-one, 1,3-diazaphenothiazine-2-one or 9-(2-aminoethoxy)-1,3-diazaphenoxazine-2-one (G-clamp). In some embodiments, modified nucleobases are those in which the purine or pyrimidine base is replaced with other heterocycles, for example, 7-deazaadenine, 7-deazaguanosine, 2-aminopyridine or 2-pyridone.

In some embodiments, a modified nucleobase is substituted. In some embodiments, a modified nucleobase is substituted such that it contains, e.g., heteroatoms, alkyl groups, or linking moieties connected to fluorescent moieties, biotin or avidin moieties, or other protein or peptides. In some embodiments, a modified nucleobase is a "universal base" that is not a nucleobase in the most classical sense, but that functions similarly to a nucleobase. One example of a universal base is 3-nitropyrrole.

In some embodiments, nucleosides that can be utilized in provided technologies comprise modified nucleobases and/or modified sugars, e.g., 4-acetylcytidine; 5-(carboxyhydroxylmethyl)uridine; 2'-O-methylcytidine; 5-carboxymethylaminomethyl-2-thiouridine; 5-carboxymethylaminomethyluridine; dihydrouridine; 2'-O-methylpseudouridine; beta,D-galactosylqueosine; 2'-O-methylguanosine; $N^6$-isopentenyladenosine; 1-methyladenosine; 1-methylpseudouridine; 1-methylguanosine; 1-methylinosine; 2,2-dimethylguanosine; 2-methyladenosine; 2-methylguanosine; $N^7$-methylguanosine; 3-methylcytidine; 5-methylcytidine; 5-hydroxymethylcytidine; 5-formylcytosine; 5-carboxylcytosine; $N^6$-methyladenosine; 7-methylguanosine; 5-methylaminoethyluridine; 5-methoxyaminomethyl-2-thiouridine; beta,D-mannosylqueosine; 5-methoxycarbonylmethyluridine; 5-methoxyuridine; 2-methylthio-$N^6$-isopentenyladenosine; N-((9-beta,D-ribofuranosyl-2-methylthiopurine-6-yl)carbamoyl)threonine; N-((9-beta,D-ribofuranosylpurine-6-yl)-N-methylcarbamoyl)threonine; uridine-5-oxyacetic acid methylester; uridine-5-oxyacetic acid (v); pseudouridine; queosine; 2-thiocytidine; 5-methyl-2-thiouridine; 2-thiouridine; 4-thiouridine; 5-methyluridine; 2'-O-methyl-5-methyluridine; and 2'-O-methyluridine.

In some embodiments, a nucleobase, e.g., a modified nucleobase comprises one or more biomolecule binding moieties such as e.g., antibodies, antibody fragments, biotin, avidin, streptavidin, receptor ligands, or chelating moieties. In other embodiments, a nucleobase is 5-bromouracil, 5-iodouracil, or 2,6-diaminopurine. In some embodiments, a nucleobase comprises substitution with a fluorescent or biomolecule binding moiety. In some embodiments, a substituent is a fluorescent moiety. In some embodiments, a substituent is biotin or avidin.

In some embodiments, a nucleobase is one described in U.S. Pat. Nos. 9,394,333, 9,744,183, 9,605,019, 9,598,458, 9,982,257, U.S. Ser. No. 10/160,969, U.S. Ser. No. 10/479,995, US 2020/0056173, US 2018/0216107, US 2019/0127733, U.S. Ser. No. 10/450,568, US 2019/0077817, US 2019/0249173, US 2019/0375774, WO 2018/223056, WO 2018/223073, WO 2018/223081, WO 2018/237194, WO 2019/032607, WO 2019/055951, WO 2019/075357, WO 2019/200185, WO 2019/217784, and/or WO 2019/032612, the nucleobases of each of which is incorporated herein by reference.

Additional Chemical Moieties

In some embodiments, a RHO oligonucleotide comprises one or more additional chemical moieties. Various additional chemical moieties, e.g., targeting moieties, carbohydrate moieties, lipid moieties, etc. are known in the art and can be utilized in accordance with the present disclosure to modulate properties and/or activities of RHO oligonucleotides, e.g., stability, half life, activities, delivery, pharmacodynamics properties, pharmacokinetic properties, etc. In some embodiments, certain additional chemical moieties facilitate delivery of oligonucleotides to desired cells, tissues and/or organs, including but not limited the cells of the central nervous system. In some embodiments, certain additional chemical moieties facilitate internalization of oligonucleotides. In some embodiments, certain additional chemical moieties increase oligonucleotide stability. In some embodiments, the present disclosure provides technologies for incorporating various additional chemical moieties into oligonucleotides.

In some embodiments, an additional chemical moiety is capable of improving the stability and/or delivery of a RHO oligonucleotide, e.g., to a particular tissue, organ or body part, or throughout the entire patient's body.

In some embodiments, additional chemical moieties are carbohydrate moieties, targeting moieties, etc., which, when incorporated into oligonucleotides, can improve one or more properties. In some embodiments, an additional chemical moiety is selected from glucose, GluNAc (N-acetyl amine glucosamine) and anisamide moieties.

In some embodiments, an additional chemical moiety is a targeting moiety. In some embodiments, an additional chemical moiety is or comprises a carbohydrate moiety. In some embodiments, an additional chemical moiety is or comprises a lipid moiety. In some embodiments, an additional chemical moiety is or comprises a ligand moiety for, e.g., cell receptors such as a sigma receptor, an asialoglycoprotein receptor, etc. In some embodiments, a ligand moiety is or comprises an anisamide moiety, which may be a ligand moiety for a sigma receptor. In some embodiments, an additional chemical moiety is or comprises a ligand moiety for an asialoglycoprotein receptor.

In some embodiments, an additional chemical moiety is or comprises a GalNAc moiety.

Certain useful additional chemical moieties are described in U.S. Pat. Nos. 9,394,333, 9,744,183, 9,605,019, 9,598,458, 9,982,257, U.S. Ser. No. 10/160,969, U.S. Ser. No. 10/479,995, US 2020/0056173, US 2018/0216107, US 2019/0127733, U.S. Ser. No. 10/450,568, US 2019/0077817, US 2019/0249173, US 2019/0375774, WO 2018/223056, WO 2018/223073, WO 2018/223081, WO 2018/237194, WO 2019/032607, WO 2019/055951, WO 2019/075357, WO 2019/200185, WO 2019/217784, and/or WO 2019/032612, the additional chemical moieties of each of which are incorporated herein by reference.

Production of Oligonucleotides and Compositions

Various methods can be utilized for production of oligonucleotides and compositions and can be utilized in accordance with the present disclosure. For example, traditional phosphoramidite chemistry can be utilized to prepare stereorandom oligonucleotides and compositions, and certain reagents and chirally controlled technologies can be utilized to prepare chirally controlled oligonucleotide compositions, e.g., as described in U.S. Pat. No. 9,982,257, US 20170037399, US 20180216108, US 20180216107, U.S. Pat. No. 9,598,458, WO 2017/062862, WO 2018/067973, WO 2017/160741, WO 2017/192679, WO 2017/210647, WO 2018/098264, WO 2018/223056, WO 2018/237194, or WO 2019/055951, the reagents and methods of each of which is incorporated herein by reference.

In some embodiments, chirally controlled/stereoselective preparation of oligonucleotides and compositions thereof comprise utilization of a chiral auxiliary, e.g., as part of monomeric phosphoramidites. Examples of such chiral auxiliary reagents and phosphoramidites are described in U.S. Pat. No. 9,982,257, US 20170037399, US 20180216108, US 20180216107, U.S. Pat. No. 9,598,458, WO 2017/062862, WO 2018/067973, WO 2017/160741, WO 2017/192679, WO 2017/210647, WO 2018/098264, WO 2018/223056, WO 2018/237194, or WO 2019/055951, the chiral auxiliary reagents and phosphoramidites of each of which are independently incorporated herein by reference. In some embodiments, a chiral auxiliary is

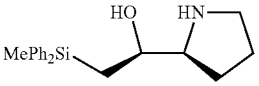

or

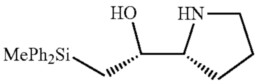

(DPSE chiral auxiliaries). In some embodiments, a chiral auxiliary is

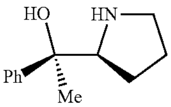

or

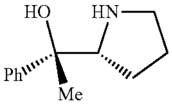

.

In some embodiments, a chiral auxiliary is

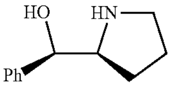

or

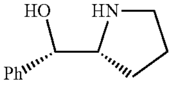

.

In some embodiments, a chiral auxiliary is

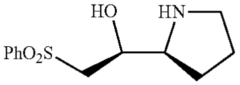

or

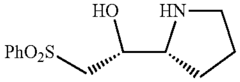

(PSM chiral auxiliaries).

In some embodiments, chirally controlled preparation technologies, including oligonucleotide synthesis cycles, reagents and conditions are described in U.S. Pat. No. 9,982,257, US 20170037399, US 20180216108, US 20180216107, U.S. Pat. No. 9,598,458, WO 2017/062862, WO 2018/067973, WO 2017/160741, WO 2017/192679, WO 2017/210647, WO 2018/237194, or WO 2019/055951, the oligonucleotide synthesis methods, cycles, reagents (including various phosphoramidites for chirally controlled and non-chirally controlled synthesis) and conditions of each of which are independently incorporated herein by reference. In some embodiments, a useful oligonucleotide synthesis cycle using DPSE chiral auxiliaries is depicted below, wherein each of $BA_1$, $BA_2$ and $BA_3$ is independently a suitable nucleobase (in some embodiments, protected for oligonucleotide synthesis), $R^{LP}$ is $-L^s-R$, and each other variables is independently as described in the present disclosure. In some embodiments, H—$OR^{LP}$ is a chiral auxiliary as described herein. In some embodiments, H—$OR^{LP}$ is a chiral auxiliary as described herein, wherein —NH— is replaced with —N(—C(O)—R)—, wherein R is as described herein. In some embodiments, R is optionally substituted $C_{1-6}$ aliphatic. In some embodiments, R is methyl.

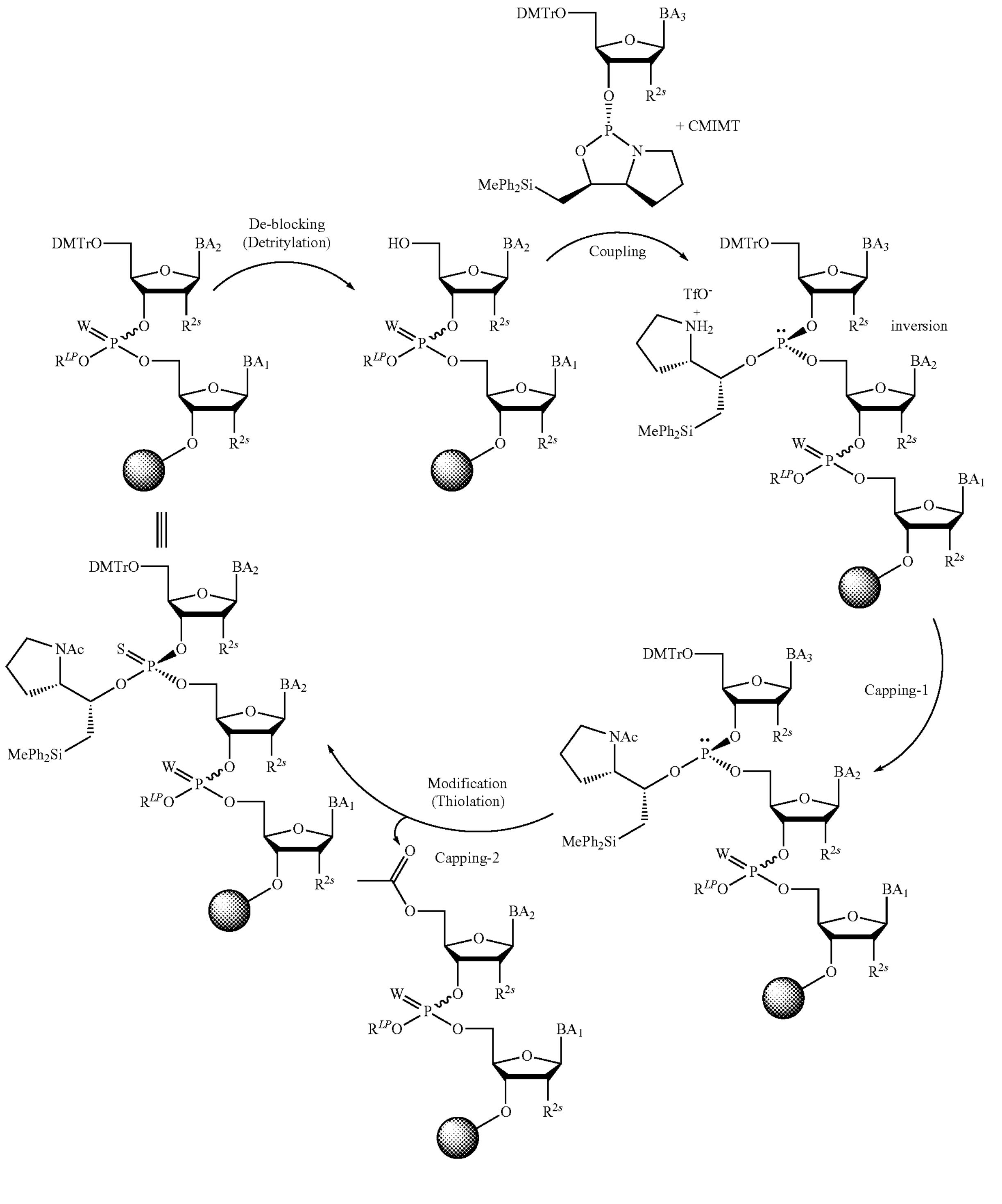

Once synthesized, provided oligonucleotides and compositions are typically further purified. Suitable purification technologies are widely known and practiced by those skilled in the art, including but not limited to those described in U.S. Pat. No. 9,982,257, US 20170037399, US 20180216108, US 20180216107, U.S. Pat. No. 9,598,458, WO 2017/062862, WO 2018/067973, WO 2017/160741, WO 2017/192679, WO 2017/210647, WO 2018/098264, WO 2018/223056, WO 2018/237194, or WO 2019/055951, the purification technologies of each of which are independently incorporated herein by reference.

In some embodiments, a cycle comprises or consists of coupling, capping, modification and deblocking. In some embodiments, a cycle comprises or consists of coupling, capping, modification, capping and deblocking. These steps are typically performed in the order they are listed, but in some embodiments, as appreciated by those skilled in the art, the order of certain steps, e.g., capping and modification, may be altered. If desired, one or more steps may be repeated to improve conversion, yield and/or purity as those skilled in the art often perform in syntheses. For example, in some embodiments, coupling may be repeated; in some embodiments, modification (e.g., oxidation to install =O, sulfurization to install =S, etc.) may be repeated; in some embodiments, coupling is repeated after modification which can convert a P(III) linkage to a P(V) linkage which can be more stable under certain circumstances, and coupling is routinely followed by modification to convert newly formed P(III) linkages to P(V) linkages. In some embodiments, when steps are repeated, different conditions may be employed (e.g., concentration, temperature, reagent, time, etc.).

Technologies for formulating provided oligonucleotides and/or preparing pharmaceutical compositions, e.g., for administration to subjects via various routes, are readily available in the art and can be utilized in accordance with the present disclosure, e.g., those described in U.S. Pat. No. 9,982,257, US 20170037399, US 20180216108, US 20180216107, U.S. Pat. No. 9,598,458, WO 2017/062862, WO 2018/067973, WO 2017/160741, WO 2017/192679, WO 2017/210647, WO 2018/098264, WO 2018/223056, WO 2018/237194, or WO 2019/055951 and references cited therein.

Biological Applications

As appreciated by those skilled in the art, oligonucleotides are useful for multiple purposes. In some embodiments, provided technologies (e.g., oligonucleotides, compositions, methods, etc.) are useful for reducing levels and/or activities of various transcripts (e.g., RNA) and/or products encoded thereby (e.g., proteins). In some embodiments, provided technologies reduce levels and/or activities RNA, e.g., RHO RNA transcripts. In some embodiments, provided oligonucleotides and compositions provide improved knockdown of transcripts, e.g., RHO transcripts, compared to a reference condition selected from the group consisting of absence of the oligonucleotide or composition, presence of a reference oligonucleotide or composition, and combinations thereof. Certain example applications and/or methods for using and making various oligonucleotides are described in U.S. Pat. Nos. 9,394,333, 9,744,183, 9,605,019, 9,982,257, US 20170037399, US 20180216108, US 20180216107, U.S. Pat. No. 9,598,458, WO 2017/062862, WO 2018/067973, WO 2017/160741, WO 2017/192679, WO 2017/210647, WO 2018/098264, WO 2018/223056, or WO 2018/237194.

For example, in some embodiments, a provided oligonucleotide is a RHO oligonucleotide capable of mediating a decrease in the expression, activity and/or level of a RHO gene product. An improvement mediated by a RHO oligonucleotide can be an improvement of any desired biological functions, including but not limited to treatment and/or prevention of a RHO-related disorder or a symptom thereof.

In some embodiments, a provided compound, e.g., oligonucleotide, and/or compositions thereof, can modulate activities and/or functions of a target gene. In some embodiments, a target gene is a gene with respect to which expression and/or activity of one or more gene products (e.g., RNA and/or protein products) are intended to be altered. In many embodiments, a target gene is intended to be inhibited. Thus, when an oligonucleotide as described herein acts on a particular target gene, presence and/or activity of one or more gene products of that gene are altered when the oligonucleotide is present as compared with when it is absent. In some embodiments, a target gene is RHO.

In some embodiments, a target sequence is a sequence of a gene or a transcript thereof to which an oligonucleotide hybridizes. In some embodiments, a target sequence is fully complementary or substantially complementary to a sequence of an oligonucleotide, or of consecutive residues therein (e.g., an oligonucleotide includes a target-binding sequence that is an exact complement of a target sequence). In some embodiments, a small number of differences/mismatches is tolerated between (a relevant portion of) an oligonucleotide and its target sequence. In many embodiments, a target sequence is present within a target gene. In many embodiments, a target sequence is present within a transcript (e.g., an mRNA and/or a pre-mRNA) produced from a target gene. In some embodiments, a target sequence is a RHO target sequence which is a sequence of a RHO gene or a transcript thereof to which a RHO oligonucleotide hybridizes.

In some embodiments, provided oligonucleotides and compositions are useful for treating various conditions, disorders or diseases, by reducing levels and/or activities of transcripts and/or products encoded thereby that are associated with the conditions, disorders or diseases. In some embodiments, the present disclosure provides methods for preventing or treating a condition, disorder or disease, comprising administering to a subject susceptible to or suffering from a condition, disorder or disease a provided oligonucleotide or composition thereof. In some embodiments, a provided oligonucleotide or oligonucleotides in a provided composition are of a base sequence that is or is complementary to a portion of a transcript, which transcript is associated with a condition, disorder or disease. In some embodiments, a base sequence is such that it selectively bind to a transcript, e.g., a RHO transcript, associated with a condition, disorder or disease over other transcripts that are not associated with the same condition, disorder or disease. In some embodiments, a condition, disorder or disease is associated with RHO. In some embodiments, a condition, disorder or disease is retinitis pigmentosa.

In some embodiments, in a method of treating a disease by administering a composition comprising a plurality of oligonucleotides sharing a common base sequence, which base sequence is complementary to a target sequence in a target transcript, the present disclosure provides an improvement that comprises administering as the oligonucleotide composition a chirally controlled oligonucleotide composition as described in the present disclosure, characterized in that, when it is contacted with the target transcript in a knockdown system, knockdown of the transcript is improved relative to that observed under a reference condition selected from the group consisting of absence of the composition, presence of a reference composition, and combinations thereof. In some embodiments, a reference composition is a racemic preparation of oligonucleotides of the same sequence or constitution. In some embodiments, a target transcript is a RHO transcript.

In some embodiments, provided oligonucleotides can bind to a transcript, and improve knockdown of the transcript (e.g., a RHO RNA). In some embodiments, provided oligonucleotides, e.g., RHO oligonucleotides, improve knockdown, e.g., RHO knockdown, with efficiency greater than a comparable oligonucleotide under one or more suitable conditions.

In some embodiments, a provided improved knockdown, e.g., of a RHO transcript, is at least 10%, 20%, 30%, 40%, 50%, 60%, 70%, 80%, 90%, 100%, 110%, 120%, 130%, 140%, 150%, 160%, 170%, 180%, 190% more than, or 2, 3, 4, 5, 6, 7, 8, 9, 10, 11, 12, 13, 14, 15, 16, 17, 18, 19, 20, 30, 40, 50 or more fold of, that of a comparable oligonucleotide or composition (e.g., one with no chiral control of linkage phosphorus stereochemistry) under one or more suitable conditions. In some embodiments, knockdown efficiency is measured by remaining target transcript.

In some embodiments, expression or level of a target gene or a gene product thereof is decreased by at least about 10%, 15%, 20%, 25%, 30%, 35%, 40%, 45%, 50%, 60%, 70%, 75%, 80%, 85%, 90%, or 95% by administration of a provided oligonucleotide or composition thereof, e.g., at certain oligonucleotide concentrations (e.g., 1 nM, 5 nM, 10 nM, 100 nM, 500 nM, 1 uM, 5 uM, etc.) in, e.g., various suitable assay (e.g., in vitro cell-based assays, assays described in the Examples, etc.). In some embodiments, expression or level of a target gene, e.g., RHO, or a gene product thereof is decreased by at least about 10%, 15%, 20%, 25%, 30%, 35%, 40%, 45%, 50%, 60%, 70%, 75%, 80%, 85%, 90%, or 95% by administration of an oligonucleotide, e.g., a RHO oligonucleotide, or a composition thereof. In some embodiments, expression or level of a target gene, e.g., RHO, or a gene product thereof is decreased by at least about 10%, 15%, 20%, 25%, 30%, 35%, 40%, 45%, 50%, 60%, 70%, 75%, 80%, 85%, 90%, or 95% by knockdown directed by an oligonucleotide, e.g., a RHO oligonucleotide, or a composition thereof. In some embodiments, expression or level of a target gene, e.g., RHO, or a gene product thereof is decreased by at least about 10%, 15%, 20%, 25%, 30%, 35%, 40%, 45%, 50%, 60%, 70%, 75%, 80%, 85%, 90%, or 95% by RNase H-mediated knockdown directed by an oligonucleotide, e.g., a RHO oligonucleotide or a composition thereof. In some embodiments, expression or level of a target gene, e.g., RHO, or a gene product thereof is decreased by at least about 10%, 15%, 20%, 25%, 30%, 35%, 40%, 45%, 50%, 60%, 70%, 75%, 80%, 85%, 90%, or 95% by administration of an oligonucleotide, e.g., a RHO oligonucleotide, in vitro. In some embodiments, expression or level of a target gene, e.g., RHO, or a gene product thereof is decreased by at least about 10%, 15%, 20%, 25%, 30%, 35%, 40%, 45%, 50%, 60%, 70%, 75%, 80%, 85%, 90%, or 95% by knockdown directed by an oligonucleotide, e.g., a RHO oligonucleotide, or a composition thereof in vitro. In some embodiments, expression or level of a target gene, e.g., RHO, or a gene product thereof is decreased by at least about 10%, 15%, 20%, 25%, 30%, 35%, 40%, 45%, 50%, 60%, 70%, 75%, 80%, 85%, 90%, or 95% by RNase H-mediated knockdown directed by an oligonucleotide, e.g., a RHO oligonucleotide, or a composition thereof in vitro. In some embodiments, expression or level of a target gene, e.g., RHO, or a gene product thereof is decreased by at least about 10%, 15%, 20%, 25%, 30%, 35%, 40%, 45%, 50%, 60%, 70%, 75%, 80%, 85%, 90%, or 95% by administration of an oligonucleotide, e.g., a RHO oligonucleotide, or a composition thereof in a cell(s) in vitro. In some embodiments, expression or level of a target gene, e.g., RHO, or a gene product thereof is decreased by at least about 10%, 15%, 20%, 25%, 30%, 35%, 40%, 45%, 50%, 60%, 70%, 75%, 80%, 85%, 90%, or 95% by knockdown directed by an oligonucleotide, e.g., a RHO oligonucleotide, or a composition thereof in a cell(s) in vitro. In some embodiments, expression or level of a target gene, e.g., RHO, or a gene product thereof is decreased by at least about 10%, 15%, 20%, 25%, 30%, 35%, 40%, 45%, 50%, 60%, 70%, 75%, 80%, 85%, 90%, or 95% by RNase H-mediated knockdown directed by an oligonucleotide, e.g., a RHO oligonucleotide, or a composition thereof in a cell(s) in vitro. In some embodiments, expression or level of a target gene, e.g., RHO, or a gene product thereof is decreased by at least about 10%, 15%, 20%, 25%, 30%, 35%, 40%, 45%, 50%, 60%, 70%, 75%, 80%, 85%, 90%, or 95% by administration of an oligonucleotide, e.g., a RHO oligonucleotide, or a composition thereof at an oligonucleotide, e.g., a RHO oligonucleotide, concentration of 1 uM or less in a cell(s) in vitro. In some embodiments, expression or level of a target gene, e.g., RHO, or a gene product thereof is decreased by at least about 10%, 15%, 20%, 25%, 30%, 35%, 40%, 45%, 50%, 60%, 70%, 75%, 80%, 85%, 90%, or 95% by knockdown directed by an oligonucleotide, e.g., a RHO oligonucleotide, or a composition thereof at an oligonucleotide, e.g., a RHO oligonucleotide, concentration of 1 uM or less in a cell(s) in vitro. In some embodiments, expression or level of a target gene, e.g., RHO, or a gene product thereof is decreased by at least about 10%, 15%, 20%, 25%, 30%, 35%, 40%, 45%, 50%, 60%, 70%, 75%, 80%, 85%, 90%, or 95% by RNase H-mediated knockdown directed by an oligonucleotide, e.g., a RHO oligonucleotide, or a composition thereof at an oligonucleotide, e.g., a RHO oligonucleotide, concentration of 1 uM or less in a cell(s) in vitro. In some embodiments, expression or level of a target gene, e.g., RHO, or a gene product thereof is decreased by at least about 10%, 15%, 20%, 25%, 30%, 35%, 40%, 45%, 50%, 60%, 70%, 75%, 80%, 85%, 90%, or 95% by administration of an oligonucleotide, e.g., a RHO oligonucleotide, or a composition thereof at an oligonucleotide, e.g., a RHO oligonucleotide, concentration of 10 uM or less in a cell(s) in vitro. In some embodiments, expression or level of a target gene, e.g., RHO, or a gene product thereof is decreased by at least about 10%, 15%, 20%, 25%, 30%, 35%, 40%, 45%, 50%, 60%, 70%, 75%, 80%, 85%, 90%, or 95% by knockdown directed by an oligonucleotide, e.g., a RHO oligonucleotide, or a composition thereof at an oligonucleotide, e.g., a RHO oligonucleotide, concentration of 10 uM or less in a cell(s) in vitro. In some embodiments, expression or level of a target gene, e.g., RHO, or a gene product thereof is decreased by at least about 10%, 15%, 20%, 25%, 30%, 35%, 40%, 45%, 50%, 60%, 70%, 75%, 80%, 85%, 90%, or 95% by RNase H-mediated knockdown directed by an oligonucleotide, e.g., a RHO oligonucleotide, or a composition thereof at an oligonucleotide, e.g., a RHO oligonucleotide, concentration of 10 uM or less in a cell(s) in vitro. In some embodiments, an oligonucleotide, e.g., a RHO oligonucleotide, or a composition thereof is capable of mediating a decrease in the expression or level of a target gene, e.g., RHO, or a gene product thereof at an oligonucleotide, e.g., a RHO oligonucleotide, concentration of 1 nm or less in a cell in vitro. In some embodiments, an oligonucleotide, e.g., a RHO oligonucleotide, or a composition thereof is capable of mediating a decrease in the expression or level of a target gene, e.g., RHO, or a gene product thereof at an oligonucleotide, e.g., a RHO oligonucleotide, concentration of 5 nm or less in a cell in vitro. In some embodiments, an oligonucleotide, e.g., a RHO oligonucleotide, or a composition thereof is capable of mediating a decrease in the expression or level of a target gene, e.g., RHO, or a gene product thereof at an oligonucleotide, e.g., a RHO oligonucleotide, concentration of 10 nm or less in a cell in vitro.

In some embodiments, activity of a provided oligonucleotide or oligonucleotide composition may be assessed by IC50 which is the inhibitory concentration to decrease expression or level of a target gene or a gene product thereof by 50% in a suitable condition, e.g., cell-based in vitro assays, assays described in the Examples, etc. In some embodiments, provided oligonucleotides or compositions have an IC50 no more than 0.001, 0.01, 0.1, 0.5, 1, 2, 5, 10, 50, 100, 200, 500 or 1000 nM. In some embodiments, an oligonucleotide, e.g., a RHO oligonucleotide, has an IC50 of no more than about 10 nM in a cell(s) in vitro. In some embodiments, an oligonucleotide, e.g., a RHO oligonucleotide, has an IC50 of no more than about 5 nM in a cell(s) in vitro. In some embodiments, an oligonucleotide, e.g., a RHO oligonucleotide, has an IC50 of no more than about 2 nM in a cell(s) in vitro. In some embodiments, an oligonucleotide, e.g., a RHO oligonucleotide, has an IC50 of no more than about 1 nM in a cell(s) in vitro. In some embodiments, an oligonucleotide, e.g., a RHO oligonucleotide, has an IC50 of no more than about 0.5 nM in a cell(s) in vitro. In some embodiments, an oligonucleotide, e.g., a RHO oligonucleotide, has an IC50 of no more than about 0.1 nM in a cell(s) in vitro. In some embodiments, an oligonucleotide, e.g., a RHO oligonucleotide, has an IC50 of no more than about 0.01 nM in a cell(s) in vitro. In some embodiments, an oligonucleotide, e.g., a RHO oligonucleotide, has an IC50 of no more than about 0.001 nM in a cell(s) in vitro.

In some embodiments, the pattern of stereochemistry of a provided RHO oligonucleotide comprises a pattern of stereochemistry described herein or any portion thereof. In some embodiments, an oligonucleotide comprises a pattern of stereochemistry described herein and is capable of directing RNase H-mediated knockdown. In some embodiments, a provided RHO oligonucleotide comprises a pattern of stereochemistry described herein and is capable of directing RNase H-mediated RHO knockdown.

In some embodiments, a provided RHO oligonucleotide comprises a modification or pattern of modification described herein. In some embodiments, a provided RHO oligonucleotide comprises a pattern of modification described herein and is capable of directing RNase H-mediated RHO knockdown. In some embodiments, a modification or pattern of modification is a modification or pattern of modification of sugar modifications, e.g., modifications at the 2' position of sugars (e.g., 2'-F, 2'-OMe, 2'-MOE, etc.).

Among other things, provided technologies can provide high selectivity (e.g., among various alleles, among nucleic acids from different genetic locations (and/or transcripts thereof) but sharing similar sequences, etc.). As demonstrated herein, in some embodiments, technologies of the present disclosure provides allele specificity. For example, in some embodiments, provided technologies can selectively reduce levels of transcripts from a particular allele over another allele of the same sequence. In some embodiments, the present disclosure provides a method for suppression of a transcript from a target nucleic acid sequence for which one or more similar nucleic acid sequences exist within a population, each of the target and similar sequences contains a specific characteristic sequence element that defines the target sequence relative to the similar sequences, the method comprising contacting a sample comprising transcripts of the target nucleic acid sequence with an oligonucleotide, or an oligonucleotide composition comprising a plurality of oligonucleotides sharing a common base sequence, wherein the base sequence of the oligonucleotide, or the common base sequence of the plurality of oligonucleotide, is or comprises a sequence that is complementary to the characteristic sequence element that defines the target nucleic acid sequence. In some embodiments, wherein when the oligonucleotide, or the oligonucleotide composition, is contacted with a system comprising transcripts of both the target nucleic acid sequence and a similar nucleic acid sequences, transcripts of the target nucleic acid sequence are suppressed at a greater level than a level of suppression observed for a similar nucleic acid sequence. In some embodiments, suppression of the transcripts of the target nucleic acid sequence is 1.1-100, 2-100, 1.5, 2, 2.5, 3, 4, 5, 6, 7, 8, 9, or 10, or more fold of suppression observed for a similar nucleic acid sequence (e.g., a different allele, a different gene, etc., and/or transcripts thereof). In some embodiments, a target nucleic acid sequence is a RHO sequence. In some embodiments, a target sequence comprises P23H mutation. In some embodiments, a target nucleic acid sequence is associated with (or more associated with compared to a similar nucleic acid sequence) a condition, disorder or disease as described herein, e.g. retinopathy. In some embodiments, the present disclosure provides a method for allele-specific suppression of a transcript from a target nucleic acid sequence for which a plurality of alleles exist within a population, each of which contains a specific characteristic sequence element that defines the allele relative to other alleles of the same target sequence, the method comprising contacting a sample comprising transcripts of the target nucleic acid sequence with an oligonucleotide or an oligonucleotide composition comprising a plurality of oligonucleotides sharing a common base sequence, wherein the base sequence of the oligonucleotide, or the common base sequence of the plurality of oligonucleotide, is or comprises a sequence that is complementary to the characteristic sequence element that defines a particular allele. In some embodiments, when the oligonucleotide, or the oligonucleotide composition, is contacted with a system comprising transcripts of both the target allele and another allele of the same nucleic acid sequence, transcripts of the particular allele are suppressed at a greater level than a level of suppression observed for another allele of the same nucleic acid sequence. In some embodiments, suppression of the transcripts of the particularly allele is 1.1-100, 2-100, 1.5, 2, 2.5, 3, 4, 5, 6, 7, 8, 9, or 10, or more fold of suppression observed for another allele. In some embodiments, a target nucleic acid sequence is a RHO sequence. In some embodiments, transcripts of the particular allele are associated with (or more associated with compared to transcripts of another allele) a condition, disorder or disease as described herein, e.g. retinopathy. In some embodiments, a characteristic sequence element comprises a SNP. In some embodiments, a SNP is SNP rs104893768. In some embodiments, a SNP is rs104893768. As those skilled in the art will appreciate, selective reduction of transcripts (and/or products thereof) associated with conditions, disorders or diseases while maintaining those that are not, or are less, associated with conditions, disorders or diseases can provide a number of advantages, for example, providing disease prevention and/or treatment while maintaining one or more desired biological functions (which may provide, among other things, fewer or less severe side effects).

In some embodiments, as demonstrated herein, selectivity is at least 10 fold, or 20, 30, 40, 50, 60, 70, 80, 90, 100, 200, 500, 1000, 2000, 5000 fold or more in a system, e.g. a reporter assay or other assays (e.g., cell-based asssays) described herein. In some embodiments, selectivity is assessed by ratio of an IC50 for one nucleic acid (e.g., a wild-type transcript or a transcript less associated with a condition, disorder or disease (e.g., a RHO transcript without P23H mutation)) and an IC50 for a target nucleic acid (e.g., a transcript associated with a condition, disorder or disease (e.g., a RHO transcript comprising P23H mutation)) under comparable conditions. In some embodiments, provided technologies (e.g., oligonucleotides, compositions, methods, etc.) can provide unexpectedly high selectivity compared to a reference technology (e.g., comparable oligonucleotides and/or compositions with no chiral control). In some embodiments, oligonucleotides in a reference composition, or reference oligonucleotides, have similar or identical base sequences as those in provided technologies but are not chirally controlled. In some embodiments, oligonucleotides in a reference composition, or reference oligonucleotides, share the same base sequences as those in provided technologies but are not chirally controlled. In some embodiments, oligonucleotides in a reference composition, or reference oligonucleotides, share the same constitutions as those in provided technologies but are not chirally controlled. In some embodiments, selectivity of a provided technology is at least 2, 3, 4, 5, 10, 20, 30, 40, 50, 60, 70, 80, 90, 100, 200, 500, 1000, 2000, 5000 or more fold compared to a reference technology (e.g., as measured by the ratio of a selectivity of a provided technology to that of a reference technology under comparable conditions; e.g., if selectivity of a provided technology is 1000 (e.g., if IC50 for a target mutant nucleic acid is 1 nm, and IC50 for a wild-type non-target nucleic acid is 1000 nm), that of a reference technology is 10, the fold is 100). In some embodiments, a fold is at least 2. In some embodiments, a fold is at least 5. In some embodiments, a fold is at least 10. In some embodiments, a fold is at least 50. In some embodiments, a fold is at least 100. In some embodiments, a provided oligonucleotide or composition thereof can effectively reduce levels of mutant RHO protein (e.g., at least 50%, 60%, 70% or more reduction of a mutant RHO protein) while maintaining levels of wild-type RHO protein (e.g. at least 70%, 75%, 80%, 85%, 90%, 95%, or more wild-type RHO protein remaining) in a system (e.g. in retinopathy-affected cell). In some embodiments, provided oligonucleotides are stable in various biological systems, e.g. in mouse brain homogenates (e.g., at least 70%, 75%, 80%, 85%, 90%, 95%, or more remaining after 1, 2, 3, 4, 5, 6, 7, or 8 days). In some embodiments, provided oligonucleotides are of low toxicity. In some embodiments, provided oligonucleotides and compositions thereof, e.g., chirally controlled oligonucleotides and compositions thereof, do not significant activate TLR9 (e.g., when compared to reference oligonucleotides and compositions thereof (e.g., corresponding stereorandom oligonucleotides and compositions thereof)). In some embodiments, provided oligonucleotides and compositions thereof, e.g., chirally controlled oligonucleotides and compositions thereof, do not significant induce complement activation (e.g., when compared to reference oligonucleotides and compositions thereof (e.g., corresponding stereorandom oligonucleotides and compositions thereof)).

Targeting a Disease-associated Allele by Targeting an Associated SNP

Among other things, oligonucleotides of the present disclosure can provide high specificity. For example, in some embodiments, an oligonucleotide targeting RHO is capable of mediating allele-specific knockdown, wherein the mutant, disease-associated allele of RHO (or a gene product thereof) is knocked down to a greater extent than an allele that is not associated or less associated, e.g., a wild-type allele. In some embodiments, a disease-associated allele comprises disease-associated mutation(s), e.g., P23H in RHO. In some embodiments, allele-specific knockdown is achieved with a RHO oligonucleotide which targets the disease-associated mutation of the disease-associated RHO allele.

In some embodiments, for the treatment of an autosomal dominant disease, such as retinopathy (e.g, retinal degeneration, retinal degenerative disease, retinal degenerative disorder, inherited retinal degenerative disorder, retinitis pigmentosa, autosomal dominant retinitis pigmentosa, etc.), in which one mutated copy of a gene is sufficient to cause disease, selectively targeting transcripts, e.g., mRNA, corresponding to the disease-causing allele is preferred. In some embodiments, a strategy to achieve this end involves using an oligonucleotide, e.g., a RHO oligonucleotide, capable of targeting a SNP, e.g., a RHO SNP, where one variant of a SNP associates with a condition, disorder or disease at high frequency. In some embodiments, a variant of a SNP associated with a condition, disorder or disease may be referred to as a mutation.

In some embodiments, a SNP is a variation in a single nucleotide that occurs at a specific position in the genome, where each variation is present to some appreciable degree within a population (e.g., >1%). In some embodiments, the terms "single nucleotide polymorphism" and "SNP", as used herein, refer to a single nucleotide variation among genomes of individuals of the same species. For example, at a specific base position in the human genome, the base C may appear in most individuals, but in an appreciable minority of individuals, the position is occupied by base A. There is an SNP at this specific base position, and the two possible nucleotide variations—C or A—are said to be alleles (or variants or isoforms) for this base position. In some embodiments, there are only two different alleles. In some embodiments, a SNP is triallelic in which three different base variations may coexist within a population. Hodgkinson et al. 2009 Genetics 1. doi:10.4172/2157-7145.1000107. In some embodiments, a SNP may be a single nucleotide deletion or insertion. In general, SNPs may occur relatively frequently in genomes and contribute to genetic diversity. In some embodiments, the location of a SNP is flanked by highly conserved sequences. In some embodiments, an individual may be homozygous or heterozygous for an allele at each SNP site. A heterozygous SNP allele can be a differentiating polymorphism. A SNP may be targeted, optionally with selectivity as demonstrated herein, with an oligonucleotide.

Large collections of confirmed and annotated SNPs are publicly available (e.g., The SNP Consortium, National Center for Biotechnology Information, Cold Spring Harbor Laboratory) [Sachidanandam et al. 2001 Nature 409: 928-933; The 1000 Genomes Project Consortium 2010 Nature 467: 1061-73 and Corrigendum; Kay et al. 2015 Mol. Ther. 23: 1759-1771].

Many SNPs in the RHO gene (e.g., RHO SNPs) are reportedly associated with disease chromosomes and have strong linkage associations with the deleterious, disease-associated mutation(s). It has been reported that many SNPs highly associated with a disease-associated mutation(s) do not segregate independently and are in Linkage Disequilibrium with each other. Among other things, the present disclosure recognizes that strong association between specific RHO SNPs and/or mutation(s) and various conditions, disorders or diseases provides an attractive therapeutic opportunity for the treatment of such conditions, disorders or diseases (e.g., retinopathy (e.g, retinal degeneration, retinal degenerative disease, retinal degenerative disorder, inherited retinal degenerative disorder, retinitis pigmentosa, autosomal dominant retinitis pigmentosa, etc.), e.g., through antisense therapy. Furthermore, the association of specific SNPs combined with high rates of heterozygosity in retinopathy patients provides suitable targets for allele-specific knockdown of the mutant gene product.

In some embodiments, one variant of a RHO SNP may be more associated with a condition, disorder or disease. In some embodiments, a variant of a SNP is also designated an isoform of a SNP. In some embodiments, a RHO oligonucleotide targets a variant of a SNP which is more associated with a condition, disorder or disease, and the RHO oligonucleotide is capable of mediating allele-specific inhibition (or suppression), wherein the level, expression and/or activity of the mutant RHO allele [comprising a disease-associated mutation(s)] is decreased preferentially relative to the level, expression and/or activity of the wild-type RHO allele (which does not comprise a disease-associated mutation(s)).

In some embodiments, prior to treating a subject with a RHO oligonucleotide which targets a particular variant of a particular SNP or a mutation, and which is capable of mediating allele-specific knockdown of the mutant RHO, a genetic analysis of the subject is performed to determine which variant of the targeted SNP the subject has, or whether the subject has the targeted mutation.

At a given gene locus on a pair of autosomal chromosomes, a diploid organism (e.g., a human being) inherits one allele of the gene from the mother and another allele of the gene from the father. At a heterozygous gene locus, two parents contribute different alleles (e.g., one A and one a). Without additional processing, it may be impossible to tell which parent contributed which allele. Such genotype data that is not attributed to a particular parent is referred to as unphased genotype data. Typically, initial genotype readings obtained from genotyping chips are often in an unphased form.

Many sequencing procedures can reveal that an individual has sequence variability at particular positions. For example, at one position (e.g., a SNP), the individual may have a C in one copy of the gene and a G on the other. For a separate position (e.g., a different SNP), the individual may have an A in one copy and a U in the other. Because many sequencing techniques involve fragmentation of the nucleic acid template, depending on the sequencing technique used, it may not be possible to determine, for example, if the C and A or C and U are on the same chromosome. Phasing information will provide information on the arrangement of the different alleles on the different chromosomes.

As noted by Laver et al., phasing is also important in pharmacogenetics, transplant HLA typing and disease association mapping. Laver et al. 2016 Nature Scientific Reports 6:21746 DOI: 10.1038/srep21746. Phasing of allelic variants is important for clinical interpretation of the genome, population genetic analysis, and functional genomic analysis of allelic activity. The phasing of rare and de novo variants is crucial for identifying putative causal variants in clinical genetics applications, for example by distinguishing compound heterozygotes from two variants on the same allele.

In some embodiments, a RHO oligonucleotide targets a portion of a RHO transcript, e.g., mRNA, comprising a position of a SNP. Many RHO SNPs are known in the art. In some embodiments, a provided oligonucleotide, e.g., a RHO oligonucleotide, targets a portion of a RHO transcript comprising a mutation, e.g., P23H (P [CCC]>H [CAC]). In some embodiments, a provided oligonucleotide is complementary to the mutation [A] but not to [C].

In some embodiments of a method for treatment of retinopathy (e.g, retinal degeneration, retinal degenerative disease, retinal degenerative disorder, inherited retinal degenerative disorder, retinitis pigmentosa, autosomal dominant retinitis pigmentosa, etc.), a patient is afflicted with retinopathy (e.g, retinal degeneration, retinal degenerative disease, retinal degenerative disorder, inherited retinal degenerative disorder, retinitis pigmentosa, autosomal dominant retinitis pigmentosa, etc.) characterized by a disease-associated mutation(s) in one allele of the RHO gene, and the patient is administered a therapeutically effective amount of a RHO oligonucleotide, wherein the RHO targets a RHO SNP (e.g., a portion of a RHO mRNA comprising the position of a SNP) variant which is associated with the condition, disorder or disease.

In some embodiments, an oligonucleotide comprises a sequence that is complementary to an SNP allele associated with a condition, disorder or disease. In some embodiments, a RHO oligonucleotide targets a RHO site which is SNP rs104893768. In some embodiments, an oligonucleotide is complementary to the A allele of SNP rs104893768. In some embodiments, an oligonucleotide comprises a sequence that is complementary to a point mutation, e.g., P23H (P [CCC]>H [CAC]) in RHO.

In some embodiments, a RHO oligonucleotide targets a RHO site which is selected from any of the following SNPs: rs104893768.

In some embodiments, a RHO oligonucleotide targets a RHO site which is selected from any of the following SNPs: rs104893768.

At least one of SNPs has been reported as being difficult to target with an oligonucleotide to reduce expression, level and/or activity of RHO or a product thereof, especially with selectivity for mutant RHO. Among other things, the present disclosure provides technologies, e.g., oligonucleotides, compositions, methods, etc., for targeting such difficult SNPs (and others) to reduce expression, level and/or activity of RHO or a product thereof, in many cases, selectively of mutant RHO or a product thereof.

In some embodiments, a targeted RHO SNP is rs104893768.

In some embodiments, RHO oligonucleotides targeting SNP rs104893768 (or the corresponding wild-type position) include, as non-limiting examples: WV-20847, WV-20846, WV-20865, WV-20828, WV-21503, WV-21505, WV-23658, and WV-23668, and any oligonucleotide comprising at least 10 consecutive bases of the sequence of any of these oligonucleotides which spans the SNP (or the corresponding wild-type position).

In some embodiments, RHO oligonucleotides targeting SNP rs104893768 (or the corresponding wild-type position) include, as non-limiting examples: WV-20847, WV-20846, WV-20865, WV-20828, WV-21503, WV-21505, WV-23658, and WV-23668, and any oligonucleotide comprising at least 10 consecutive bases of the sequence of any of these oligonucleotides which spans the SNP (or the corresponding wild-type position).

In some embodiments, a targeted RHO SNP is intronic. In some embodiments, a targeted RHO SNP is exonic.

In some embodiments, a RHO oligonucleotide targets a SNP which is intronic.

In some embodiments, a RHO oligonucleotide targets an intronic RHO SNP and has a base sequence comprising the SNP (or the complement of a base sequence comprising the SNP) or has a base sequence comprising a wild-type base corresponding to the SNP (or the complement thereof).

In some embodiments, a base basepairing to a base at a SNP site (a SNP base; a base basepairing to a SNP base a SNP-pairing base) in a transcript, e.g., a RHO mRNA, can be located at various position of an oligonucleotide, e.g., a RHO oligonucleotide. In some embodiments, a SNP-pairing base is located at position 1, 2, 3, 4, 5, 6, 7, 8, 9, 19, 11, 12, 13, 14, 15, 16, 17, 18, 19, 20, 21, 22, 23, 24, 25, 26, 27, 28, 29 or 30 (counting from the 5' end) of an oligonucleotide. In some embodiments, the position 1 (counting from the 5' end) is also designated P1; the position 2 (counting from the 5' end) is also designated P2; etc. In some embodiments, an oligonucleotide, e.g., a RHO oligonucleotide, comprises a SNP-pairing base at position 1, 2, 3, 4, 5, 6, 7, 8, 9, 19, 11, 12, 13, 14, 15, 16, 17, 18, 19, 20, 21, 22, 23, 24, 25, 26, 27, 28, 29 or 30 (counting from the 5' end).

In some embodiments, a RHO oligonucleotide has a SNP at position 12 (counting from 5' to 3'). Non-limiting examples of such oligonucleotides include, but are not limited to: WV-23652, WV-23653, WV-23654, WV-23655, WV-23660, WV-23661, WV-23662, WV-23663, WV-23664, WV-23672, WV-23673, WV-23674, WV-23675, WV-23676, WV-23677, WV-23678, WV-23679, WV-23680, WV-23681, WV-23682, WV-23683, WV-23684, WV-23685, WV-23686, WV-23687, and WV-23688.

In some embodiments, a RHO oligonucleotide has a SNP at position 11 (counting from 5' to 3'). Non-limiting examples of such oligonucleotides include, but are not limited to: WV-20803, WV-20804, WV-20805, WV-20822, WV-20823, WV-20824, WV-20841, WV-20842, WV-20843, WV-20860, WV-20861, and WV-20862.

In some embodiments, a RHO oligonucleotide has a SNP at position 10 (counting from 5' to 3'). Non-limiting examples of such oligonucleotides include, but are not limited to: WV-20870, WV-23415, WV-20800, WV-20801, WV-20802, WV-20819, WV-20820, WV-20821, WV-20838, WV-20839, WV-20840, WV-20857, WV-20858, and WV-20859.

In some embodiments, a RHO oligonucleotide has a SNP at position 9 (counting from 5' to 3'). Non-limiting examples of such oligonucleotides include, but are not limited to: WV-20797, WV-20798, WV-20799, WV-20816, WV-20817, WV-20818, WV-20835, WV-20836, WV-20837, WV-20854, WV-20855, and WV-20856.

In some embodiments, a RHO oligonucleotide has a SNP at position 8 (counting from 5' to 3'). Non-limiting examples of such oligonucleotides include, but are not limited to: WV-20794, WV-20795, WV-20796, WV-20813, WV-20814, WV-20815, WV-20832, WV-20833, WV-20834, WV-20851, WV-20852, and WV-20853.

In some embodiments, a RHO oligonucleotide has a SNP at position 7 (counting from 5' to 3'). Non-limiting examples of such oligonucleotides include, but are not limited to: WV-20791, WV-20792, WV-20793, WV-20810, WV-20811, WV-20812, WV-20829, WV-20830, WV-20831, WV-20848, WV-20849, and WV-20850.

In some embodiments, a base that base-pairs to a nucleic acid at a SNP can be considered either a SNP-pairing base or a SNP. For example, if a SNP is A in the gene, a gene transcript having a T in the corresponding position can be considered either a SNP or a SNP-pairing base. An oligonucleotide having A at that position can be considered to be a SNP-pairing base (as it can base-pair with the gene transcript having a T at the corresponding position), or it may simply be considered a SNP. In some embodiments, a SNP-pairing base is a SNP.

In some embodiments, an oligonucleotide, e.g., a RHO oligonucleotide, comprises a SNP-pairing base at Position P1 (of the oligonucleotide, wherein the position is counted as a number of bases from 5' to 3'). In some embodiments, an oligonucleotide, e.g., a RHO oligonucleotide, comprises a SNP-pairing base at Position P2 (e.g., the second position of the oligonucleotide, wherein the position is counted as a number of bases from 5' to 3'). In some embodiments, an oligonucleotide, e.g., a RHO oligonucleotide, comprises a SNP-pairing base at Position P3. In some embodiments, an oligonucleotide, e.g., a RHO oligonucleotide, comprises a SNP-pairing base at Position P4. In some embodiments, an oligonucleotide, e.g., a RHO oligonucleotide, comprises a SNP-pairing base at Position P5. In some embodiments, an oligonucleotide, e.g., a RHO oligonucleotide, comprises a SNP-pairing base at Position P6. In some embodiments, an oligonucleotide, e.g., a RHO oligonucleotide, comprises a SNP-pairing base at Position P7. In some embodiments, an oligonucleotide, e.g., a RHO oligonucleotide, comprises a SNP-pairing base at Position P8. In some embodiments, an oligonucleotide, e.g., a RHO oligonucleotide, comprises a SNP-pairing base at Position P9. In some embodiments, an oligonucleotide, e.g., a RHO oligonucleotide, comprises a SNP-pairing base at Position P10. In some embodiments, an oligonucleotide, e.g., a RHO oligonucleotide, comprises a SNP-pairing base at Position P11. In some embodiments, an oligonucleotide, e.g., a RHO oligonucleotide, comprises a SNP-pairing base at Position P12. In some embodiments, an oligonucleotide, e.g., a RHO oligonucleotide, comprises a SNP-pairing base at Position P13. In some embodiments, an oligonucleotide, e.g., a RHO oligonucleotide, comprises a SNP-pairing base at Position P14. In some embodiments, an oligonucleotide, e.g., a RHO oligonucleotide, comprises a SNP-pairing base at Position P15. In some embodiments, an oligonucleotide, e.g., a RHO oligonucleotide, comprises a SNP-pairing base at Position P16. In some embodiments, an oligonucleotide, e.g., a RHO oligonucleotide, comprises a SNP-pairing base at Position P17. In some embodiments, an oligonucleotide, e.g., a RHO oligonucleotide, comprises a SNP-pairing base at Position P18. In some embodiments, an oligonucleotide, e.g., a RHO oligonucleotide, comprises a SNP-pairing base at Position P19. In some embodiments, an oligonucleotide, e.g., a RHO oligonucleotide, comprises a SNP-pairing base at Position P20. In some embodiments, an oligonucleotide, e.g., a RHO oligonucleotide, comprises a SNP-pairing base at Position P21. In some embodiments, an oligonucleotide, e.g., a RHO oligonucleotide, comprises a SNP-pairing base at Position P22. In some embodiments, an oligonucleotide, e.g., a RHO oligonucleotide, comprises a SNP-pairing base at Position P23. In some embodiments, an oligonucleotide, e.g., a RHO oligonucleotide, comprises a SNP-pairing base at Position P24. In some embodiments, an oligonucleotide, e.g., a RHO oligonucleotide, comprises a SNP-pairing base at Position P25. In some embodiments, an oligonucleotide, e.g., a RHO oligonucleotide, comprises a SNP-pairing base at Position P26. In some embodiments, an oligonucleotide, e.g., a RHO oligonucleotide, comprises a SNP-pairing base at Position P27. In some embodiments, an oligonucleotide, e.g., a RHO oligonucleotide, comprises a SNP-pairing base at Position P28. In some embodiments, an oligonucleotide, e.g., a RHO oligonucleotide, comprises a SNP-pairing base at Position P29. In some embodiments, an oligonucleotide, e.g., a RHO oligonucleotide, comprises a SNP-pairing base at Position P30.

In some embodiments, an oligonucleotide, e.g., a RHO oligonucleotide, comprises a SNP-pairing base at Position P7. Non-limiting examples include but are not limited to: WV-20791, WV-20792, WV-20793, WV-20810, WV-20811, WV-20812, WV-20829, WV-20830, WV-20831, WV-20848, WV-20849, WV-20850.

In some embodiments, an oligonucleotide, e.g., a RHO oligonucleotide, comprises a SNP-pairing base at Position P8. Non-limiting examples include but are not limited to: WV-20794, WV-20795, WV-20796, WV-20813, WV-20814, WV-20815, WV-20832, WV-20833, WV-20834, WV-20851, WV-20852, WV-20853.

In some embodiments, an oligonucleotide, e.g., a RHO oligonucleotide, comprises a SNP-pairing base at Position P9. Non-limiting examples include but are not limited to: WV-20797, WV-20798, WV-20799, WV-20816, WV-20817, WV-20818, WV-20835, WV-20836, WV-20837, WV-20854, WV-20855, WV-20856.

In some embodiments, an oligonucleotide, e.g., a RHO oligonucleotide, comprises a SNP-pairing base at Position P10. Non-limiting examples include but are not limited to: WV-20870, WV-23415, WV-20800, WV-20801, WV-20802, WV-20819, WV-20820, WV-20821, WV-20838, WV-20839, WV-20840, WV-20857, WV-20858, WV-20859.

In some embodiments, an oligonucleotide, e.g., a RHO oligonucleotide, comprises a SNP-pairing base at Position P11. Non-limiting examples include but are not limited to: WV-20803, WV-20804, WV-20805, WV-20822, WV-20823, WV-20824, WV-20841, WV-20842, WV-20843, WV-20860, WV-20861, WV-20862.

In some embodiments, an oligonucleotide, e.g., a RHO oligonucleotide, comprises a SNP-pairing base at Position P12. Non-limiting examples include but are not limited to: WV-20806, WV-20807, WV-20808, WV-20809, WV-20825, WV-20826, WV-20827, WV-20828, WV-20844, WV-20845, WV-20846, WV-20847, WV-20863, WV-20864, WV-20865, WV-20866, WV-20867, WV-20868, WV-20869, WV-21503, WV-21504, WV-21505, WV-23651, WV-23652, WV-23653, WV-23654, WV-23655, WV-23656, WV-23657, WV-23658, WV-23659, WV-23660, WV-23661, WV-23662.

In some embodiments, the present disclosure pertains to any oligonucleotide comprising a sequence of any oligonucleotide or comprising a span of 10 or more consecutive bases of the sequence of any oligonucleotide disclosed herein, wherein any one or more bases is replaced by inosine.

Phasing

Various techniques can be used to determine if a particular SNP allele is on the same chromosome as a disease-associated sequence, e.g., disease-associated mutation(s) for RHO. Typically, if the SNP allele and the disease-associated mutation(s) are on the same chromosome, a RHO oligonucleotide that targets that SNP allele can also "target" the disease-associated mutation(s), thereby allowing a decrease in the expression, level and/or activity of the RHO allele with the disease-associated mutation(s). In such a way, for example, a RHO oligonucleotide can be used in a treatment for a RHO-related disorder such as retinopathy (e.g, retinal degeneration, retinal degenerative disease, retinal degenerative disorder, inherited retinal degenerative disorder, retinitis pigmentosa, autosomal dominant retinitis pigmentosa, etc.). A RHO oligonucleotide targeting a SNP can thus preferentially decrease the expression, level and/or activity of a mutant allele of RHO compared to the wild-type allele.

Humans, among other living things, are diploid, and determining the linkage of alleles of genetic loci on the same or different chromosomes is desirable for phasing techniques. The sequences on corresponding chromosomes are known as haplotypes. The process of determining which alleles are on which chromosomes is known as phasing, haplotype phasing or haplotyping. Phasing information is useful in patient stratification, forensics and various other applications in the treatment of RHO-related diseases and disorders such as retinopathy (e.g, retinal degeneration, retinal degenerative disease, retinal degenerative disorder, inherited retinal degenerative disorder, retinitis pigmentosa, autosomal dominant retinitis pigmentosa, etc.)s. For additional general information about phasing, see, for example: Twehey et al. 2011 Nat. Rev. Genet. 12: 215-223; and Glusman et al. 2014 Genome Med. 6:73.

Phasing data can be important in allele-specific therapies for diseases such as retinopathy (e.g, retinal degeneration, retinal degenerative disease, retinal degenerative disorder, inherited retinal degenerative disorder, retinitis pigmentosa, autosomal dominant retinitis pigmentosa, etc.). In some diseases, a genetic lesion such as a deleterious repeat, deletion, insertion, inversion or other mutation has been identified, such as a mutant (and disease-associated) RHO allele(s). In some patients, one allele of a gene such as RHO can comprise a disease-associated mutation(s) at a genetic locus, while the other allele is normal, wild-type or otherwise not disease-associated. In some embodiments, an allele-specific therapy can target an allele of RHO comprising a disease-associated mutation(s), but not the corresponding wild-type allele. In some embodiments, an allele-specific therapy can target a RHO allele comprising a disease-associated mutation(s) at a particular locus, such as a disease-associated mutation(s) (or a disease-associated mutation(s)), but not by directly targeting the locus, but rather by targeting a different locus on the mutant allele. As a non-limiting example, an allele-specific therapy can target an allele comprising a disease-associated mutation(s) at a locus by targeting a different locus in the same allele, such as a SNP (single nucleotide polymorphism) in the same gene.

As a non-limiting example, some disease-associated genetic lesions may be difficult to target or otherwise not readily amenable to targeting. As a non-limiting example, some genes such as mutant RHO comprise a disease-associated (deleterious) mutation; in some cases, such as retinopathy (e.g, retinal degeneration, retinal degenerative disease, retinal degenerative disorder, inherited retinal degenerative disorder, retinitis pigmentosa, autosomal dominant retinitis pigmentosa, etc.). However, if a particular SNP variant exists on the same allele as the disease-associated mutation but not on the wild-type allele, that SNP variant can be used to target an allele-specific therapy which targets the mutant allele but not the wild-type allele.

As a non-limiting example, phasing data for an individual indicates if a particular SNP is in phase (e.g., on the same chromosome) as the lesion and thus that SNP can be targeted with a therapeutic nucleic acid. The therapeutic can then target the mutant gene, while not targeting the wild-type allele. Obtaining the phasing data to target only the mutant allele can be especially useful if expression of the wild-type allele is essential.

As another non-limiting example, phasing information is useful if it is known that an individual has both a wild-type and a mutant allele of each of two genetic loci on the same gene. Phasing information will reveal if both copies of the gene each have one mutant allele, or if one copy of the gene has two mutations, while the other is wild-type at both alleles.

In some embodiments, the present disclosure presents, inter alia, various methods for phasing genetic loci on a nucleic acid template. As non-limiting examples, the present disclosure presents methods for phasing a genetic locus such as a genetic lesion (such as an inversion, fusion, deletion, insertion or other mutation) and another genetic locus (such as a SNP) on a chromosome; the two genetic loci can be in the same gene, or in different genes.

In a non-limiting example, an example patient may have retinopathy (e.g, retinal degeneration, retinal degenerative disease, retinal degenerative disorder, inherited retinal degenerative disorder, retinitis pigmentosa, autosomal dominant retinitis pigmentosa, etc.), which is linked to a a disease-associated mutation in the RHO gene. In some embodiments, the patient may be under consideration for treatment with an allele-specific therapeutic (e.g., an antisense oligonucleotide or RNAi agent) which recognizes a particular allelic variant of a genetic locus in the RHO gene (which is outside a deleterious or pathogenic mutation), as a non-limiting example, a SNP. If phasing reveals that the same chromosome of the patient comprises both the delerious or pathogenic mutation and the particular allelic variant of a genetic locus (e.g., a SNP) recognized by the allele-specific therapeutic, then the patient is eligible for treatment with the allele-specific therapeutic.

In some embodiments, phasing is performed using blood samples. In one procedure, blood samples were obtained from 3 healthy donors, and peripheral blood mononuclear cells (PBMCs) were isolated.

In some embodiments, phasing of a SNP allele and a disease-associated mutation can be performed using sequencing.

Various methods for phasing are known in the art, including but not limited to those described in: WO2018/022473; and Berger et al. 2015 Res. Comp. Mol. Biol. 9029: 28-29; Castel et al. 2015 Genome Biol. 16: 195; Castel et al. 2016 phASER: Long range phasing and haplotypic expression from RNA sequencing, doi: http://dx.doi.org/10.1101/039529; Delaneau et al. 2012 Nat. Methods 9: 179-181; Garg et al. 2016 Read-Based Phasing of Related Individuals; Hickey et al. 2011 Genet. Select. Evol. 43:12; Kuleshov et al. 2014 Nat. Biotech. 32: 261-266; Laver et al. 2016 Nature Scientific Reports 16:21746 DOI: 10.1038/srep21746; O'Connell et al. 2014 PLoS ONE 10: e1004234; Regan et al. 2015 PloS ONE 10: e0118270; Roach et al. 2011 Am. J. Hum. Genet. 89: 382-397; and Yang et al. 2013 Bioinformatics 29: 2245-2252. In some embodiments, sequencing, particularly sequencing that can produce long single reads, can be utilized for phasing.

Pan-Specific RHO Oligonucleotides

In some embodiments, a RHO oligonucleotide can effectively reduce expression, level, and/or activity of transcripts from two or more or all alleles and/or products thereof (e.g., by targeting a shared base sequence). In some embodiments, a RHO oligonucleotide can effectively reduce expression, level, and/or activity of both mutant and wild-type RHO transcripts and/or products thereof. In some embodiments, a RHO oligonucleotide reduces expression, level, and/or activity of both mutant and wild-type RHO alleles or products thereof without significant selectivity. In some embodiments, a RHO oligonucleotide does not target a region comprising a SNP; e.g., the RHO oligonucleotide is completely complementary to a sequence in a RHO gene or mRNA which is present in all, essentially all, or nearly all human beings. In some embodiments, a RHO oligonucleotide targets a sequence shared by both wild-type and mutant RHO. In some embodiments, a RHO oligonucleotide is complementary to a sequence shared by both wild-type and mutant RHO.

Such a RHO oligonucleotide can be considered as a pan-specific RHO oligonucleotide. While a pan-specific RHO oligonucleotide does not distinguish significantly between the wild-type and mutant alleles of RHO with significant selectivity (e.g., 2 or more fold), it may be useful in sufficiently lowering the expression, level and/or activity of the mutant RHO allele (while, in at least some cases, concomitantly lowering the expression, level and/or activity of the wild-type RHO allele). In some embodiments, a pan-specific RHO oligonucleotide is capable of mediating a decrease in the expression, level and/or activity of a mutant RHO gene or a gene product thereof which is sufficient to ameliorate, prevent, or delay the onset of retinopathy (e.g, retinal degeneration, retinal degenerative disease, retinal degenerative disorder, inherited retinal degenerative disorder, retinitis pigmentosa, autosomal dominant retinitis pigmentosa, etc.) or at least one symptom thereof, while simultaneously the pan-specific RHO oligonucleotide does not decrease the expression, level and/or activity of the wild-type gene or a gene product enough to cause a deleterious effect in the subject or patient.

Example reductions in levels, activities and/or expression of a RHO target gene or a gene product thereof as mediated by various RHO oligonucleotides, some of which are pan-specific, are described herein.

In some embodiments, a RHO oligonucleotide does not target a SNP or mutation. In some embodiments, a base sequence does not comprise a SNP or mutation, or a sequence complementary to a SNP or mutation.

In some embodiments, a RHO oligonucleotide has a base sequence which is not characterized by a known SNP or mutation; in some embodiments, such an oligonucleotide can knock down both wild-type and mutant RHO, and in some embodiments, such an oligonucleotide is a pan-specific oligonucleotide.

In some embodiments, the present disclosure pertains to an oligonucleotide composition comprising a plurality of oligonucleotides, wherein the oligonucleotides are pan-specific RHO oligonucleotides which comprise at least one chirally controlled internucleotidic linkage. In some embodiments, a chirally controlled internucleotidic linkage is a chirally controlled phosphorothioate internucleotidic linkage. In some embodiments, a chirally controlled internucleotidic linkage is a Sp chirally controlled phosphorothioate internucleotidic linkage. In some embodiments, a chirally controlled internucleotidic linkage is a Rp chirally controlled phosphorothioate internucleotidic linkage. In some embodiments, the oligonucleotides comprise at least one Sp chirally controlled phosphorothioate internucleotidic linkage, and at least one Rp chirally controlled internucleotidic linkage.

Characterization and Assessment

In some embodiments, properties and/or activities of provided oligonucleotides, e.g., RHO oligonucleotides, and compositions thereof can be characterized and/or assessed using various technologies available to those skilled in the art, e.g., biochemical assays (e.g., RNase H assays), cell based assays, animal models, clinical trials, etc.

In some embodiments, a method of identifying and/or characterizing an oligonucleotide composition, e.g., a RHO oligonucleotide composition, comprises steps of:

providing at least one composition comprising a plurality of oligonucleotides; and assessing delivery relative to a reference composition.

In some embodiments, the present disclosure provides a method of identifying and/or characterizing an oligonucleotide composition, e.g., a RHO oligonucleotide composition, comprises steps of:

providing at least one composition comprising a plurality of oligonucleotides; and assessing cellular uptake relative to a reference composition.

In some embodiments, the present disclosure provides a method of identifying and/or characterizing an oligonucleotide composition, e.g., a RHO oligonucleotide composition, comprises steps of:

providing at least one composition comprising a plurality of oligonucleotides; and assessing reduction of transcripts of a target gene and/or a product encoded thereby relative to a reference composition.

In some embodiments, properties and/or activities of oligonucleotides, e.g., RHO oligonucleotides, and compositions thereof are compared to reference oligonucleotides and compositions thereof, respectively.

In some embodiments, a reference oligonucleotide composition is a stereorandom oligonucleotide composition. In some embodiments, a reference oligonucleotide composition is a stereorandom composition of oligonucleotides of which all internucleotidic linkages are phosphorothioate. In some embodiments, a reference oligonucleotide composition is a DNA oligonucleotide composition with all phosphate linkages. In some embodiments, a reference composition comprise a plurality of reference oligonucleotides, which share the same constitution as oligonucleotides of a plurality in a provided chirally controlled oligonucleotide composition but have fewer or no chirally controlled internucleotidic linkages. In some embodiments, a reference composition comprise a plurality of reference oligonucleotides, which share the same constitution as oligonucleotides of a plurality in a provided chirally controlled oligonucleotide composition but have a different pattern of backbone chiral centers. In some embodiments, a reference oligonucleotide composition is otherwise identical to a provided chirally controlled oligonucleotide composition except that it is not chirally controlled. In some embodiments, a reference oligonucleotide composition is otherwise identical to a provided chirally controlled oligonucleotide composition except that it has a different pattern of stereochemistry. In some embodiments, a reference oligonucleotide composition is similar to a provided oligonucleotide composition except that it has a different modification of one or more sugar, base, and/or internucleotidic linkage, or pattern of modifications. In some embodiments, an oligonucleotide composition is stereorandom and a reference oligonucleotide composition is also stereorandom, but they differ in regards to sugar and/or base modification(s) or patterns thereof.

In some embodiments, a reference composition is a composition of oligonucleotides having the same base sequence and the same chemical modifications. In some embodiments, a reference composition is a composition of oligonucleotides having the same base sequence and the same pattern of chemical modifications. In some embodiments, a reference composition is a non-chirally controlled (or stereorandom) composition of oligonucleotides having the same base sequence and chemical modifications. In some embodiments, a reference composition is a non-chirally controlled (or stereorandom) composition of oligonucleotides of the same constitution but is otherwise identical to a provided chirally controlled oligonucleotide composition.

In some embodiments, the suffix “r” is appended to the designation of a stereorandom oligonucleotide composition. In some embodiments, the suffix “p” is appended to the designation of a chirally-controlled (or stereopure) oligonucleotide composition. The suffixes “r” and “p” are optional.

In some embodiments, a reference composition is a composition of oligonucleotides having the same base sequence but different chemical modifications, including but not limited to chemical modifications described herein. In some embodiments, a reference composition is a composition of oligonucleotides having the same base sequence but different patterns of internucleotidic linkages and/or stereochemistry of internucleotidic linkages and/or chemical modifications.

Various methods are known in the art for detection of gene products, the expression, level and/or activity of which may be altered after introduction or administration of a provided oligonucleotide. For example, transcripts and their knockdown can be detected and quantified with qPCR, and protein levels can be determined via Western blot.

In some embodiments, assessment of efficacy of oligonucleotides can be performed in biochemical assays or in vitro in cells. In some embodiments, provided oligonucleotides can be introduced to cells via various methods available to those skilled in the art, e.g., gymnotic delivery, transfection, lipofection, etc.

In some embodiments, the efficacy of a putative RHO oligonucleotide can be tested in vitro.

In some embodiments, the efficacy of a putative RHO oligonucleotide can be tested in vitro using any known method of testing the expression, level and/or activity of a RHO gene or gene product thereof.

In some embodiments, a RHO oligonucleotide is tested in a cell or animal model of retinopathy.

In some embodiments, a cell model of retinopathy is a cell comprising a wild-type and/or mutant RHO gene. In some embodiments, a cell model or animal model which comprises a wild-type RHO gene can be used as a control in an experiment involving the knockdown of a mutant RHO gene in a corresponding cell model or animal model. In some embodiments, wherein a RHO oligonucleotide is designed to knock down both wild-type and mutant RHO alleles (e.g., a pan-specific RHO oligonucleotide), a cell model and/or animal model comprising a wild-type and/or mutant RHO allele can be used to evaluate the ability of the RHO oligonucleotide to knock down RHO.

In some embodiments, a cell is retinopathy patient-derived cell.

In some embodiments, a cell is retinopathy patient-derived fibroblast.

In some embodiments, a cell is a COS-7 cells expressing RHO P23H.

In some embodiments, a cell is a human retinal pigmented epithelial cell line (ARPE-19).

In some embodiments, a RHO gene or protein that is used in various studies and evaluations is a fluorescently tagged Rhodopsin, Rho-EGFP.

Many technologies for assessing activities and/or properties of oligonucleotides in animals are known and practiced by those skilled in the art and can be utilized in accordance with the present disclosure. In some embodiments, evaluation of an oligonucleotide can be performed in an animal. Various animals may be used to assess properties and activities of provided oligonucleotides and compositions thereof.

Identification of the RHO gene has allowed for the development of animal models of the disease, including transgenic RHO rats and mice carrying mutated human or mouse forms of the gene. Models include mice carrying at least a portion of the human gene, which contains the disease-associated mutation(s) (or the wild-type equivalent). Animal models typically have at least some shared features with the human disease. These mice have allowed for the testing of a number of different therapeutic agents for the prevention, amelioration and treatment of retinopathy using a number of endpoints. Useful compounds may function by a number of different mechanisms.

Various animal models of retinopathy have been reported in the literature. For information related to cells, cell lines, animal models, including but not limited to mice, rats and flies, and various experimental procedures suitable for the study of RHO, and/or the analysis of RHO oligonucleotides, see those noted herein or in the relevant art. Various model organisms have reportedly been used in the study of RHO function. Any of these model organisms can be used to analyze the activity or other properties of a RHO oligonucleotide.

RHO animal models (including those with both or either wild-type RHO and RHO P23H) include:

Homozygous breeders of transgenic rats carrying RHO mutation P23H (line 2, albino); and heterozygous P23H rats produced by mating homozygous breeders with wild-type Sprague Dawley rats.

A RHO P23H line-3 rat model.

A Sprague-Dawley rat comprising a wild-type RHO or RHO P23H gene.

A knock-in RHO P23H mouse model.

A transgenic mouse model which comprises a normal RHO, e.g., NHR-A or NHR-E.

A transgenic *Xenopus laevis* model of RP.

A genetically modified pig expressing RHO P23H.

A nematode model comprising a wild-type RHO or RHO P23H gene.

In some embodiments, wherein an oligonucleotide, e.g., a RHO oligonucleotide, which targets a particular SNP variant, it may be desirable to test the oligonucleotide in a particular test animal. However, it may also be the case that the test animal may not have in its genome the complement of that SNP variant. In such a case, it may be desirable to construct an oligonucleotide which is identical to the RHO oligonucleotide to be tested except that it has a SNP variant which is complementary to the SNP variant in the test animal. Such an oligonucleotide can be termed, for example, a surrogate of the RHO oligonucleotide to be tested. In some embodiments, a provided RHO oligonucleotide is identical to any RHO oligonucleotide described herein, or any oligonucleotide which comprises at least 10 contiguous bases thereof, except that the oligonucleotide comprises a different SNP variant than that described herein.

In some embodiments, an animal model administered an oligonucleotide, e.g., a RHO oligonucleotide, can be evaluated for safety and/or efficacy.

In some embodiments, the effect(s) of administration of an oligonucleotide to an animal can be evaluated, including any effects on behavior, inflammation, and toxicity. In some embodiments, following dosing, animals can be observed for signs of toxicity including trouble grooming, lack of food consumption, and any other signs of lethargy. In some embodiments, in a mouse model of retinopathy (e.g, retinal degeneration, retinal degenerative disease, retinal degenerative disorder, inherited retinal degenerative disorder, retinitis pigmentosa, autosomal dominant retinitis pigmentosa, etc.), following administration of a RHO oligonucleotide, the animals can be monitored for timing of onset of a rear paw clasping phenotype.

In some embodiments, following administration of a RHO oligonucleotide to an animal, the animal can be sacrificed and analysis of tissues or cells can be performed to determine changes in mutant or wild-type RHO, or other biochemical or other changes. In some embodiments, following necropsy, liver, heart, lung, kidney, and spleen can be collected, fixed, and processed for histopathological evaluation (standard light microscopic examination of hematoxylin and eosin-stained tissue slides).

In some embodiments, following administration of an oligonucleotide, e.g., a RHO oligonucleotide, to an animal, behavioral changes can be monitored or assessed. In some embodiments, such an assessment can be performed using a technique described in the scientific literature.

Various effects of testing in animals described herein can also be monitored in human subjects or patients following administration of a RHO oligonucleotide.

In addition, the efficacy of a RHO oligonucleotide in a human patient can be measured by evaluating, after administration of the oligonucleotide, any of various parameters known in the art, including but not limited to a reduction in a symptom of retinopathy, or a decrease in the rate of worsening of a symptom of retinopathy.

In some embodiments, following human treatment with an oligonucleotide, or contacting a cell or tissue in vitro with an oligonucleotide, cells and/or tissues are collected for analysis.

In some embodiments, in various cells and/or tissues, target nucleic acid levels can be quantitated by methods available in the art, many of which can be accomplished with commercially available kits and materials. Such methods include, e.g., Northern blot analysis, competitive polymerase chain reaction (PCR), quantitative real-time PCR, etc. RNA analysis can be performed on total cellular RNA or poly(A)+ mRNA. Probes and primers are designed to hybridize to a nucleic acid to be detected. Methods for designing real-time PCR probes and primers are well known and widely practiced in the art. For example, to detect and quantify RHO RNA, an example method comprises isolation of total RNA (e.g., including mRNA) from a cell or animal treated with an oligonucleotide or a composition and subjecting the RNA to reverse transcription and/or quantitative real-time PCR, for example, as described herein, or in: Moon et al. 2012 Cell Metab. 15: 240-246.

In some embodiments, protein levels can be evaluated or quantitated in various methods known in the art, e.g., enzyme-linked immunosorbent assay (ELISA), Western blot analysis (immunoblotting), immunocytochemistry, fluorescence-activated cell sorting (FACS), immunohistochemistry, immunoprecipitation, protein activity assays (for example, caspase activity assays), and quantitative protein assays. Antibodies useful for the detection of mouse, rat, monkey, and human proteins are commercially available or can be generated if needed. For example, various RHO antibodies have been reported in the literature. Antibodies to RHO are also commercially available, e.g., from GeneTex (Irvine, Calif.), LifeSpan BioSciences (Seattle, WA), Abcam (Cambridge, MA), etc.

Various technologies are available and/or known in the art for detecting levels of oligonucleotides or other nucleic acids. Such technologies are useful for detecting provided oligonucleotides, e.g., RHO oligonucleotides, when administered to assess, e.g., delivery, cell uptake, stability, distribution, etc.

In some embodiments, selection criteria are used to evaluate the data resulting from various assays and to select particularly desirable oligonucleotides, e.g., desirable RHO oligonucleotides, with certain properties and activities. In some embodiments, selection criteria include an $IC_{50}$ of less than about 10 nM, less than about 5 nM or less than about 1 nM. In some embodiments, selection criteria for a stability assay include at least 50% stability [at least 50% of an oligonucleotide is still remaining and/or detectable] at Day 1. In some embodiments, selection criteria for a stability assay include at least 50% stability at Day 2. In some embodiments, selection criteria for a stability assay include at least 50% stability at Day 3. In some embodiments, selection criteria for a stability assay include at least 50% stability at Day 4. In some embodiments, selection criteria for a stability assay include at least 50% stability at Day 5. In some embodiments, selection criteria for a stability assay include at least 80% [at least 80% of the oligonucleotide remains] at Day 5.

In some embodiments, a target gene, e.g., RHO, is a wild-type gene. In some embodiments, a target gene comprises one or more mutations. In some embodiments, a target gene comprises a mutation associated with a disorder. In some embodiments, a mutation is a single nucleotide polymorphism (SNP). In some embodiments, base sequences of provided oligonucleotides are complementary to target sequences in transcripts comprising a mutation or SNP associated with a condition, disorder or disease. In some embodiments, provided oligonucleotides and compositions selectively reduce levels of transcripts comprising a mutation or SNP associated with a condition, disorder or disease and/or products encoded thereby relative to wild-type transcripts and/or transcripts less associated with a condition, disorder or disease and/or products encoded thereby. In many embodiments, provided oligonucleotides are complementary to transcripts comprising mutations or SNPs associated with conditions, disorders or diseases at the mutation or SNP sites while they have mismatches when hybridizing to wild-type or less associated transcripts at the sites corresponding to the mutations or SNPs. In some embodiments, a mutation or SNP is located 0, 1, 2, 3 or 4 internucleotidic linkages from a Rp or Op internucleotidic linkage when a transcript comprising the mutation or SNP is hybridized with a provided oligonucleotide.

In some embodiments, efficacy of a RHO oligonucleotide is assessed directly or indirectly by monitoring, measuring or detecting a change in a condition, disorder or disease or a biological pathway associated with RHO.

In some embodiments, efficacy of a RHO oligonucleotide is assessed directly or indirectly by monitoring, measuring or detecting a change in a biochemical phenomenon associated with retinopathy (e.g, retinal degeneration, retinal degenerative disease, retinal degenerative disorder, inherited retinal degenerative disorder, retinitis pigmentosa, autosomal dominant retinitis pigmentosa, etc.), including but not limited to accumulation of complexes comprising mutant RHO protein comprising a P23H mutation, or fragments thereof.

In some embodiments, efficacy of a RHO oligonucleotide is assessed directly or indirectly by monitoring, measuring or detecting a change in a response to be affected by RHO knockdown.

In some embodiments, a provided oligonucleotide (e.g., a RHO oligonucleotide) can by analyzed by a sequence analysis to determine what other genes [e.g., genes which are not a target gene (e.g., RHO)] have a sequence which is complementary to the base sequence of the provided oligonucleotide (e.g., the RHO oligonucleotide) or which have 0, 1, 2 or more mismatches from the base sequence of the provided oligonucleotide (e.g., the RHO oligonucleotide). Knockdown, if any, by the oligonucleotide of these potential off-targets can be determined to evaluate potential off-target effects of an oligonucleotide (e.g., a RHO oligonucleotide). In some embodiments, an off-target effect is also termed an unintended effect and/or related to hybridization to a bystander (non-target) sequence or gene.

Oligonucleotides which have been evaluated and tested for efficacy in knocking down RHO have various uses, e.g., in treatment or prevention of a RHO-related condition, disorder or disease or a symptom thereof.

In some embodiments, a RHO oligonucleotide which has been evaluated and tested for its ability to provide a particular biological effect (e.g., reduction of level, expression and/or activity of a RHO target gene or a gene product thereof) can be used to treat, ameliorate and/or prevent a RHO-related condition, disorder or disease.

RHO-Related Conditions, Disorders or Diseases

In some embodiments, provided oligonucleotides and compositions thereof are capable of providing a decrease in the expression and/or level of a mutant RHO target gene or a gene product thereof. In some embodiments, a provided oligonucleotide or composition targets a RHO gene and is useful for treatment of RHO-related conditions, disorders or diseases. In some embodiments, the present disclosure provides oligonucleotides and compositions for preventing and/or treating RHO-related conditions, disorders or diseases. In some embodiments, the present disclosure provides methods for preventing and/or treating RHO-related conditions, disorders or diseases, comprising administering to a subject susceptible thereto or suffering therefrom a therapeutically effective amount of a provided RHO oligonucleotide or a composition thereof. RHO-related conditions, disorders or diseases are extensively described in the art. In some embodiments, RHO-related conditions, disorders or diseases are associated with P23H mutation P [CCC]>H [CAC]. In some embodiments, a RHO-related condition, disorder or disease is retinitis pigmentosa.

In some embodiments, a mutant RHO gene, gene target, protein, or other gene product, has the mutation P23H or RHO P23H. In some embodiments, the RHO P23H mutation (also referenced as RhoP23H or the RhoP23H allele) leads to a misfolded protein that is characterized by abnormal glycosylation pattern, abnormal disulfide bond formation and oligomerization. In RP patients with the RHO P23H allele, retinal degeneration is characterized by the initial disorganization and shortening of rod outer segments, followed by the loss of rod photoreceptors and the ensuing death of cone cells. Similar findings are observed in various RhoP23H animal models.

In some embodiments, a RHO-related condition, disorder or disease is a condition, disorder or disease that is related to, caused by and/or associated with abnormal or excessive activity, level and/or expression, or abnormal tissue or inter- or intracellular distribution, of a RHO gene or a gene product thereof. In some embodiments, a RHO-related condition, disorder or disease is associated with RHO if the presence, level and/or form of transcription of a RHO region, a RHO transcript and/or a product encoded thereby correlates with incidence of and/or susceptibility to the condition, disorder or disease (e.g., across a relevant population). In some embodiments, a RHO-related condition, disorder or disease is a condition, disorder or disease in which reduction of the level, expression and/or activity of a RHO gene or a product thereof ameliorates, prevents and/or reduces the severity of the condition, disorder or disease.

Examples of RHO-related conditions, disorders or diseases include retinopathy (e.g, retinal degeneration, retinal degenerative disease, retinal degenerative disorder, inherited retinal degenerative disorder, retinitis pigmentosa, autosomal dominant retinitis pigmentosa, etc.).

In some embodiments, retinitis pigmentosa includes but is not limited to autosomal dominant retinitis pigmentosa (adRP or ADRP), or X-linked retinitis pigmentosa (xlRP or XLRP or XRP).

Two classes of adRP were reported. Class A patients reportedly lost retinal function over the entire retina and reported the onset of night blindness early in life. In contrast, class B patients reportedly exhibited a milder phenotype, normal rod activation kinetics, and preserved rod outer segment length, with anomalies in the rod visual cycle that were mutation specific. Photoreceptor degeneration in subclass B1 was reportedly not homogenous, and some patients showed an inferior to superior progression of disease.

Among other things, the present disclosure provides methods of using oligonucleotides disclosed herein which are capable of targeting RHO for treating and/or manufacturing a treatment for a RHO-related condition, disorder or disease. In some embodiments, a base sequence of a RHO oligonucleotide or a single-stranded RNAi agent can comprise or consist of a base sequence which has a specified maximum number of mismatches (e.g., 1, 2, 3, etc.) from a specified base sequence.

Treatment of RHO-Related Conditions, Disorders or Diseases

In some embodiments, the present disclosure provides a RHO oligonucleotide which targets RHO (e.g., a RHO oligonucleotide comprising a RHO target sequence or a sequence complementary to a RHO target sequence). In some embodiments, the present disclosure provides a RHO oligonucleotide which directs target-specific knockdown of RHO. In some embodiments, the present disclosure provides a RHO oligonucleotide which directs target-specific knockdown of RHO mediated by RNaseH and/or RNA interference. Various oligonucleotides capable of targeting RHO are provided herein. In some embodiments, the present disclosure provides methods for preventing and/or treating RHO-related conditions, disorders or diseases using provided RHO oligonucleotides and compositions thereof. In some embodiments, the present disclosure provides oligonucleotides and compositions thereof for use as medicaments, e.g., for RHO-related conditions, disorders or diseases. In some embodiments, the present disclosure provides oligonucleotides and compositions thereof for use in the treatment of RHO-related conditions, disorders or diseases. In some embodiments, the present disclosure provides oligonucleotides and compositions thereof for the manufacture of medicaments for the treatment of RHO-related conditions, disorders or diseases.

In some embodiments, the present disclosure provides a method for preventing, treating or ameliorating a RHO-related condition, disorder or disease in a subject susceptible thereto or suffering therefrom, comprising administering to the subject a therapeutically effective amount of a RHO oligonucleotide or a pharmaceutical composition thereof.

In some embodiments, the present disclosure provides a method for treating or ameliorating a RHO-related condition, disorder or disease in a subject suffering therefrom, comprising administering to the subject a therapeutically effective amount of a RHO oligonucleotide or a pharmaceutical composition thereof.

In some embodiments, the present disclosure provides methods for preventing or treating retinitis pigmentosa, comprising administering to a subject susceptible thereto or suffering therefrom a provided oligonucleotide or a composition thereof.

In some embodiments, an oligonucleotide or composition is administered as a pharmaceutical composition comprising an effective amount of an oligonucleotide or composition and a pharmaceutically acceptable carrier. In some embodiments, a composition is chirally controlled. In some embodiments, a composition comprises one or more pharmaceutically acceptable salt forms of an oligonucleotide. In some embodiments, a composition is a liquid composition. In some embodiments, a liquid composition has an about neutral pH (e.g., around pH 7). In some embodiments, a liquid composition has a pH of about 7.4. In some embodiments, a liquid composition comprises a buffer.

In some embodiments, a RHO-related condition, disorder or disease is retinopathy (e.g, retinal degeneration, retinal degenerative disease, retinal degenerative disorder, inherited retinal degenerative disorder, retinitis pigmentosa, autosomal dominant retinitis pigmentosa, etc.).

In some embodiments, the present disclosure provides a method for reducing RHO gene expression in a cell, comprising: contacting the cell with a RHO oligonucleotide or a composition thereof. In some embodiments, the present disclosure provides a method for reducing the level of a RHO transcript in a cell, comprising: contacting the cell with a RHO oligonucleotide or a composition thereof. In some embodiments, the present disclosure provides a method for reducing the level of a RHO protein in a cell, comprising: contacting the cell with a RHO oligonucleotide or a composition thereof. In some embodiments, provided methods selectively reduce levels of RHO transcripts and/or products encoded thereby that are related to conditions, disorders or diseases.

In some embodiments, the present disclosure provides a method for decreasing RHO gene expression in a mammal in need thereof, comprising administering to the mammal a nucleic acid-lipid particle comprising a provided RHO oligonucleotide or a composition thereof.

In some embodiments, the present disclosure provides a method for in vivo delivery of a RHO oligonucleotide, comprising administering to a mammal a RHO oligonucleotide or a composition thereof.

In some embodiments, a mammal is a human. In some embodiments, a mammal is susceptible to or afflicted with and/or suffering from a RHO-related condition, disorder or disease. In some embodiments, a mammal susceptible to a RHO-related condition, disorder or disease has a familial history of such a condition, disorder or disease, and/or has been genetically tested and determined to comprise a disease-associated mutation in the RHO gene.

In some embodiments, a subject or patient suitable for treatment of a RHO-related condition, disorder or disease, such as retinopathy (e.g, retinal degeneration, retinal degenerative disease, retinal degenerative disorder, inherited retinal degenerative disorder, retinitis pigmentosa, autosomal dominant retinitis pigmentosa, etc.), can be identified or diagnosed by a health care professional.

In some embodiments, a symptom of retinopathy (e.g, retinal degeneration, retinal degenerative disease, retinal degenerative disorder, inherited retinal degenerative disorder, retinitis pigmentosa, autosomal dominant retinitis pigmentosa, etc.) is any symptom listed herein.

In some embodiments, a provided oligonucleotide or a composition thereof prevents, treats, ameliorates, or slows progression of a RHO-related condition, disorder or disease, or at least one symptom of a RHO-related condition, disorder or disease.

In some embodiments, a method of the present disclosure is for the treatment of retinopathy (e.g, retinal degeneration, retinal degenerative disease, retinal degenerative disorder, inherited retinal degenerative disorder, retinitis pigmentosa, autosomal dominant retinitis pigmentosa, etc.) in a subject wherein the method comprises administering to a subject a therapeutically effective amount of a RHO oligonucleotide or a pharmaceutical composition thereof.

In some embodiments, a provided method reduces at least one symptom of retinopathy (e.g, retinal degeneration, retinal degenerative disease, retinal degenerative disorder, inherited retinal degenerative disorder, retinitis pigmentosa, autosomal dominant retinitis pigmentosa, etc.) wherein the method comprises administering to a subject a therapeutically effective amount of a RHO oligonucleotide or a pharmaceutical composition thereof.

In some embodiments, the present disclosure provides a method for treating and/or ameliorating one or more symptoms associated with a RHO-related condition, disorder or disease in a mammal in need thereof, the method comprising administering to the mammal a therapeutically effective amount of a RHO oligonucleotide or a composition thereof. In some embodiments, the present disclosure provides a method for reducing susceptibility to a RHO-related condition, disorder or disease in a mammal in need thereof, the method comprising: administering to the mammal a therapeutically effective amount of a RHO oligonucleotide or a composition thereof. In some embodiments, the present disclosure provides a method for preventing or delaying the onset of a RHO-related condition, disorder or disease in a mammal in need thereof, the method comprising: administering to the mammal a therapeutically effective amount of a RHO oligonucleotide or a composition thereof. In some embodiments, the present disclosure provides a method for treating and/or ameliorating one or more symptoms associated with a RHO-related condition, disorder or disease in a mammal in need thereof, the method comprising: administering to the mammal a therapeutically effective amount of a nucleic acid-lipid particle comprising a RHO oligonucleotide. In some embodiments, the present disclosure provides a method for reducing susceptibility to a RHO-related condition, disorder or disease in a mammal in need thereof, the method comprising: administering to the mammal a therapeutically effective amount of a nucleic acid-lipid particle comprising a RHO oligonucleotide. In some embodiments, the present disclosure provides a method for preventing or delaying the onset of a RHO-related condition, disorder or disease in a mammal in need thereof, the method comprising: administering to the mammal a therapeutically effective amount of a nucleic acid-lipid particle comprising a RHO oligonucleotide. In some embodiments, a mammal is a human. In some embodiments, a mammal is susceptible to, afflicted with and/or suffering from a RHO-related condition, disorder or disease.

In some embodiments, administration of a RHO oligonucleotide to a patient or subject is capable of mediating any one or more of: slowing retinopathy (e.g, retinal degeneration, retinal degenerative disease, retinal degenerative disorder, inherited retinal degenerative disorder, retinitis pigmentosa, autosomal dominant retinitis pigmentosa, etc.) progression, delaying the onset of retinopathy or at least one symptom thereof, improving one or more indicators of retinopathy, and/or increasing the survival time or lifespan of the patient or subject.

In some embodiments, slowing disease progression relates to the prevention of, or delay in, a clinically undesirable change in one or more clinical parameters in an individual susceptible to or suffering from retinopathy, such as those described herein. It is well within the abilities of a physician to identify a slowing of disease progression in an individual susceptible to or suffering from retinopathy, using one or more of the disease assessment tests described herein. Additionally, it is understood that a physician may administer to the individual diagnostic tests other than those described herein to assess the rate of disease progression in an individual susceptible to or suffering from retinopathy.

In some embodiments, delaying the onset of retinopathy or a symptom thereof relates to delaying one or more undesirable changes in one or more indicators of retinopathy that are negative for retinopathy. A physician may use family history of retinopathy or comparisons to other retinopathy patients with similar genetic profile to determine an expected approximate age of retinopathy onset to retinopathy to determine if onset of retinopathy is delayed.

In some embodiments, indicators of retinopathy include parameters employed by a medical professional, such as a physician, to diagnose or measure the progression of retinopathy.

In some embodiments, an improvement in an indicator of retinopathy relates to the absence of an undesirable change, or the presence of a desirable change, in one or more indicators of retinopathy. In one embodiment, an improvement in an indicator of retinopathy is evidenced by the absence of a measurable change in one or more indicators of retinopathy. In another embodiment, an improvement in an indicator of retinopathy is evidenced by a desirable change in one or more indicators of retinopathy.

In some embodiments, a slowing of disease progression may further comprise an increase in survival time in an individual susceptible to or suffering from retinopathy. In some embodiments, an increase in survival time relates to mean increasing the survival of an individual suffering from retinopathy, relative to an approximate survival time based upon retinopathy progression and/or family history of retinopathy. A physician can use one or more of the disease assessment tests described herein to predict an approximate survival time of an individual susceptible to or suffering from retinopathy. A physician may additionally use the family history of an individual susceptible to or suffering from retinopathy or comparisons to other retinopathy patients with similar genetic profile (e.g., disease-associated mutation(s)) to predict expected survival time.

In some embodiments, the present disclosure provides a method of inhibiting RHO expression in a cell, the method comprising: (a) contacting the cell with a RHO oligonucleotide; and (b) maintaining the cell produced in step (a) for a time sufficient to obtain degradation of a mRNA transcript of a RHO gene, thereby inhibiting expression of the RHO gene in the cell. In some embodiments, RHO expression is inhibited by at least 30%.

In some embodiments, the present disclosure provides a method of treating a condition, disorder or disease mediated by RHO expression comprising administering to a human susceptible to or suffering therefrom a therapeutically effective amount of a RHO oligonucleotide or a composition thereof. In some embodiments, administration causes a decrease in the expression, activity and/or level of a RHO transcript. In some embodiments, administration is associated with a decrease in the expression, activity and/or level of a RHO transcript. In some embodiments, administration is followed by a decrease in the expression, activity and/or level of a RHO transcript.

In some embodiments, the present disclosure provides a RHO oligonucleotide for use in a subject to treat a RHO-related condition, disorder or disease. In some embodiments, a RHO-related condition, disorder or disease is selected from retinopathy (e.g, retinal degeneration, retinal degenerative disease, retinal degenerative disorder, inherited retinal degenerative disorder, retinitis pigmentosa, autosomal dominant retinitis pigmentosa, etc.).

In some embodiments, a subject is administered an oligonucleotide, e.g., a RHO oligonucleotide, or a composition thereof and an additional agent and/or method, e.g., an additional therapeutic agent and/or method.

In some embodiments, an additional therapeutic agent and/or method is any described or referenced in: Nguyen et al. 2014 Retinal Degenerative Diseases pp 471-476, or WO/2019/075320, WO/2019/009265, WO/2018/232227, WO/2018/213278, WO/2018/208703, WO/2018/201146, WO/2018/182527, WO/2018/172961, WO/2018/169090, WO/2018/167510, WO/2018/107226, WO/2018/100054, WO/2018/096196, WO/2018/085644, WO/2018/030389, WO/2018/009562, WO/2018/002873, WO/2017/201425, WO/2017/151823, WO/2017/144611, WO/2017/123710, WO/2017/121766, WO/2017/106364, WO/2017/048731, WO/2017/044649, WO/2017/042584, WO/2016/191645, WO/2016/145345, WO/2016/144892, WO/2016/138353, WO/2016/130460, WO/2016/077467, WO/2016/077422, WO/2016/073931, WO/2016/073829, WO/2016/017980, WO/2016/017831, WO/2016/014353, WO/2016/001693, WO/2015/160893, WO/2015/143418, WO/2015/134812, WO/2015/126972, WO/2015/110556, WO/2015/105064, WO/2015/042281, WO/2015/020522, WO/2015/001379, WO/2014/180996, WO/2014/130869, WO/2014/129466, WO/2014/100361, WO/2014/066836, WO/2014/066835, WO/2014/058464, WO/2014/011210, WO/2013/134867, WO/2013/112448, WO/2013/053719, WO/2012/167109, WO/2012/148994, WO/2012/148930, WO/2012/145708, WO/2012/135498, WO/2012/100142, WO/2012/043891, WO/2012/024404, WO/2011/149012, WO/2011/149010, WO/2011/133964, WO/2011/095475, WO/2011/025734, WO/2010/150564, WO/2010/130418, WO/2010/099436, WO/2010/097201, WO/2010/032073, WO/2010/005533, WO/2009/111169, WO/2009/102021, WO/2009/089399, WO/2009/083188, WO/2009/083185, WO/2009/047640, WO/2009/046446, WO/2009/018333, WO/2008/135536, WO/2008/125908, WO/2008/124151, WO/2008/111497, WO/2008/013983, WO/2007/131180, WO/2007/094669, WO/2007/014327, WO/2007/011880, WO/2007/011674, WO/2006/101634, WO/2006/086452, WO/2006/077824, WO/2005/120544, WO/2005/110114, WO/2005/079815, WO/2005/074981, WO/2005/023311, WO/2004/096146, WO/2004/043480, WO/2004/030693, WO/2003/105678, WO/2003/082081, WO/2003/047525, or WO/2003/007979, WO/2003/004058.

In some embodiments, an oligonucleotide or composition thereof can be administered alone or in combination with one or more additional therapeutic agents and/or treatment. When administered in combination each component may be administered at the same time or sequentially in any order at different points in time. In some embodiments, each component may be administered separately but sufficiently closely in time so as to provide the desired therapeutic effect. In some embodiments, provided oligonucleotides and additional therapeutic components are administered concurrently. In some embodiments, provided oligonucleotides and additional therapeutic components are administered as one composition. In some embodiments, at a time point a subject being administered is exposed to both provided oligonucleotides and additional components at the same time.

In some embodiments, an additional therapeutic agent or method is capable of preventing, treating, ameliorating or slowing the progress of a neurological condition, disorder or disease. In some embodiments, an additional therapeutic agent or method is capable of preventing, treating, ameliorating or slowing the progress of a RHO-related condition, disorder or disease. In some embodiments, an additional therapeutic agent or method may "indirectly" decrease the expression, activity and/or level of RHO, e.g., by knocking down a gene or gene product which can increases the expression, activity and/or level of RHO.

In some embodiments, an additional therapeutic agent is physically conjugated to an oligonucleotide, e.g., a RHO oligonucleotide. In some embodiments, an additional agent is a RHO oligonucleotide. In some embodiments, a provided oligonucleotide is physically conjugated with an additional agent which is a RHO oligonucleotide. In some embodiments, additional agent oligonucleotides have base sequences, sugars, nucleobases, internucleotidic linkages, patterns of sugar, nucleobase, and/or internucleotidic linkage modifications, patterns of backbone chiral centers, etc., or any combinations thereof, as described in the present disclosure, wherein each T may be independently replaced with U and vice versa. In some embodiments, an additional oligonucleotide targets RHO. In some embodiments, a RHO oligonucleotide is physically conjugated to a second oligonucleotide which can decrease (directly or indirectly) the expression, activity and/or level of RHO, or which is useful for treating a RHO-related condition, disorder or disease. In some embodiments, a first RHO oligonucleotide is physically conjugated to a second RHO oligonucleotide, which can be identical to the first RHO oligonucleotide or not identical, and which can target a different or the same or an overlapping sequence as the first RHO oligonucleotide.

In some embodiments, a provided oligonucleotide, e.g., a RHO oligonucleotide, may be administered with one or more additional (or second) therapeutic agent for retinopathy.

In some embodiments, an additional therapeutic agent comprises a treatment for one or more symptoms of retinopathy.

In some embodiments, an additional treatment is a treatment intended to reduce or eliminate a symptom of retinopathy, including but not limited to a symptom listed herein.

In some embodiments, a subject is administered a RHO oligonucleotide and an additional therapeutic agent, wherein the additional therapeutic agent is an agent described herein or known in the art which is useful for treatment of a RHO-related condition, disorder or disease.

In some embodiments, an additional therapeutic agent is, as a non-limiting example: a traditional medicine used in China or other locations in Asia for treatment of blindness and other eye ailments.

In some embodiments, an additional therapeutic agent is, as a non-limiting example: a compound derived from bear bile.

In some embodiments, an additional therapeutic agent is, as a non-limiting example: tauroursodeoxycholic acid.

In some embodiments, an additional therapeutic agent is, as a non-limiting example: Valproic acid.

In some embodiments, RP is associated with inflammation.

In some embodiments, an additional therapeutic agent is, as a non-limiting example: an agent which reduces inflammation.

In some embodiments, an additional therapeutic agent is, as a non-limiting example: gene therapy.

In some embodiments, an additional therapeutic agent is, as a non-limiting example: encapsulating cells releasing a neurotrophic factor(s).

In some embodiments, an additional therapeutic agent is, as a non-limiting example: stem cell transplantation.

In some embodiments, an additional therapeutic agent is, as a non-limiting example: $LEDGF_{1-326}$.

In some embodiments, an additional therapeutic agent is, as a non-limiting example: an inhibitor of mitochondrial μ-calpain.

In some embodiments, an additional therapeutic agent is, as a non-limiting example: a peptide inhibitor of mitochondrial μ-calpain.

In some embodiments, an additional therapeutic agent is, as a non-limiting example: Tat-μCL (HIV-Nμ)

In some embodiments, an additional therapeutic agent is, as a non-limiting example: a composition or compound which reduces protein aggregation.

In some embodiments, an additional therapeutic agent is, as a non-limiting example: a composition or compound which reduces aggregation of wild-type or mutant Rho protein.

In some embodiments, an additional therapeutic agent is, as a non-limiting example: Curcumin.

In some embodiments, an additional therapeutic agent is, as a non-limiting example: a chaperone.

In some embodiments, an additional therapeutic agent is, as a non-limiting example: Grp78/BiP.

In some embodiments, an additional therapeutic agent is, as a non-limiting example: proinsulin.

In some embodiments, an additional therapeutic agent is, as a non-limiting example: a ribozyme or other small nucleic acid (e.g., an antisense oligonucleotide, single- or double-stranded siRNA or RNAi agent, etc.) targeting opsin.

In some embodiments, an additional therapeutic agent is, as a non-limiting example: an rAAV delivered ribozyme targeting opsin.

In some embodiments, an additional therapeutic agent is, as a non-limiting example: Transplantation of Photoreceptor and Total Neural Retina.

In some embodiments, an additional therapeutic agent is, as a non-limiting example: Gene therapy.

In some embodiments, an additional therapeutic agent is, as a non-limiting example: Transplantation of syngeneic Schwann cells to the retina.

In some embodiments, an additional therapeutic agent is, as a non-limiting example: CRISPR/Cas9 genome surgery.

In some embodiments, an additional therapeutic agent is, as a non-limiting example: tauroursodeoxycholic acid.

In some embodiments, an additional therapeutic agent is, as a non-limiting example: tauroursodeoxycholic acid or a derivative thereof.

In some embodiments, an additional therapeutic agent is, as a non-limiting example: 11-cis-retinal or a derivative thereof.

In some embodiments, an additional therapeutic agent is, as a non-limiting example: 11-cis-retinal or a derivative thereof or a compound described in WO/2018/201146.

In some embodiments, an additional therapeutic agent is, as a non-limiting example: a meganuclease.

In some embodiments, an additional therapeutic agent is, as a non-limiting example: an indene derivative.

In some embodiments, an additional therapeutic agent is, as a non-limiting example: an indene derivative described in EP3176163.

In some embodiments, an additional therapeutic agent is, as a non-limiting example: a Pyrazolopyridazine or a derivative thereof.

In some embodiments, an additional therapeutic agent is, as a non-limiting example: a Pyrazolopyridazine or a derivative thereof described in U.S. Pat. No. 9,925,187.

In some embodiments, an additional therapeutic agent is, as a non-limiting example: gasdermin, gasdermin A, gasdermin B, gasdermin C, gasdermin D, DFNA5 or DFNB59 (or pejvakin), or a derivative of any of these compounds.

In some embodiments, an additional therapeutic agent is, as a non-limiting example: a methanone derivative and/or a benzo-thiophene derivative.

In some embodiments, an additional therapeutic agent is, as a non-limiting example: a methanone derivative described in WO/2016/017831.

In some embodiments, an additional therapeutic agent is, as a non-limiting example: a RDCVF1 or a RDCVF2 protein or a nucleic acid encoding the same.

In some embodiments, an additional therapeutic agent is, as a non-limiting example: a PRO polypeptide.

In some embodiments, an additional therapeutic agent is, as a non-limiting example: a beta- or gamma-diketone or an analog or derivative thereof.

In some embodiments, an additional therapeutic agent is, as a non-limiting example: a retinoic acid receptor agonistic action (such as tamibarotene, tamibarotene methyl ester, tamibarotene ethyl ester, tazarotene, tazarotenic acid, adapalene, palovalotene, retinol, isotretinoin, alitretinoin, etretinate, acitretin, and bexarotene) or a salt thereof.

In some embodiments, an additional therapeutic agent is, as a non-limiting example: a tetra- or pentapeptide.

In some embodiments, an additional therapeutic agent is, as a non-limiting example: a tetra- or pentapeptide described in US20180353565.

In some embodiments, an additional therapeutic agent is, as a non-limiting example: a compound capable of inhibiting YHL/Vhl.

In some embodiments, an additional therapeutic agent is, as a non-limiting example: N— acetylcysteine amide.

In some embodiments, an additional therapeutic agent is, as a non-limiting example: 1,2,4-oxadiazole benzoic acid compounds.

In some embodiments, an additional therapeutic agent is, as a non-limiting example: 3-[5-(2-fluorophenyl)-[1,2,4]oxadiazol-3-yl]benzoic acid.

In some embodiments, an additional therapeutic agent is, as a non-limiting example: 7,8-dihydroxyflavone (DHF).

In some embodiments, an additional therapeutic agent is, as a non-limiting example: 9- or 11-cis retinyl ester.

In some embodiments, an additional therapeutic agent is, as a non-limiting example: a benzaldehyde compound.

In some embodiments, an additional therapeutic agent is, as a non-limiting example: a compound described in U.S. Pat. App. No. US20110224200.

In some embodiments, an additional therapeutic agent is, as a non-limiting example: a compound described in WO2010150564.

In some embodiments, an additional therapeutic agent is, as a non-limiting example: a compound or a combination of lutein, zeaxanthin, glutathione, and/or alpha lipoic acid.

In some embodiments, an additional therapeutic agent is, as a non-limiting example: a compound or medicament described in Chinese Patent App. No. 201510118534.9.

In some embodiments, an additional therapeutic agent is, as a non-limiting example: a method or composition described in US20160058825.

In some embodiments, an additional therapeutic agent is, as a non-limiting example: a phthalazinone pyrazole derivative.

In some embodiments, an additional therapeutic agent is, as a non-limiting example: a proteasomal inhibitor selected from the group consisting of MG-132, lactocystin, clasto-lactocystin beta lactone, PSI, MG-115, MG101, N-acetyl-Leu-Leu-Met-CHO, N-carbobenzoyl-Gly-Pro-Phe-Leu-CHO, N-carbobenzoyl-Gly-Pro-Ala-Phe-CHO, or N-carbobenzoyl-Leu-Leu-Phe-CHO or a salt thereof.

In some embodiments, an additional therapeutic agent is, as a non-limiting example: a proteasomal inhibitor selected from the group consisting of MG-132, lactocystin, clasto-lactocystin beta lactone, PSI, MG-115, MG101, N-acetyl-Leu-Leu-Met-CHO, N-carbobenzoyl-Gly-Pro-Phe-Leu-CHO, N-carbobenzoyl-Gly-Pro-Ala-Phe-CHO, or N-carbobenzoyl-Leu-Leu-Phe-CHO or a salt thereof, in combination with a compound selected from the group consisting of 11-cis-retinal, 9-cis-retinal or a 7-ring locked isomer of 11-cis retinal.

In some embodiments, an additional therapeutic agent is, as a non-limiting example: a pyridine-3-carbaldehyde-O-(piperidin-1-yl-propyl)-oxime derivative.

In some embodiments, an additional therapeutic agent is, as a non-limiting example: a senne palmitoyltransferase inhibitor.

In some embodiments, an additional therapeutic agent is, as a non-limiting example: an alphal receptor blocker.

In some embodiments, an additional therapeutic agent is, as a non-limiting example: an apoptosis suppressing agent.

In some embodiments, an additional therapeutic agent is, as a non-limiting example: an apoptosis suppressing agent containing (R)-1-(benzofuran-2-yl)-2-propylaminopentane or its pharmacologically permissible salt, hydrate or solvate.

In some embodiments, an additional therapeutic agent is, as a non-limiting example: an aromatic-cationic peptide.

In some embodiments, an additional therapeutic agent is, as a non-limiting example: an aromatic-cationic peptide represented by the formula D-Arg-2',6'-Dmt-Lys-Phe-NH2 (SS-31) or Phe-D-Arg-Phe-Lys-NH2 (SS-20).

In some embodiments, an additional therapeutic agent is, as a non-limiting example: an IL-6 inhibitor, an APOE inhibitor and/or a Fas activator.

In some embodiments, an additional therapeutic agent is, as a non-limiting example: an indazole derivative.

In some embodiments, an additional therapeutic agent is, as a non-limiting example: an Inhibitor of TGF-R-signaling.

In some embodiments, an additional therapeutic agent is, as a non-limiting example: an isoquinoline sulfonyl derivative.

In some embodiments, an additional therapeutic agent is, as a non-limiting example: an opioid antagonist.

In some embodiments, an additional therapeutic agent is, as a non-limiting example: an SIP receptor agonist.

In some embodiments, an additional therapeutic agent is, as a non-limiting example: an SIP receptor agonist such as 2-amino-2-[2-(4-octylphenyl)ethyl]propane-1,3-diol and (2R)-2-amino-4-[3-(4-cyclohexyloxybutyl)-benzo[b]thien-6-yl]-2-methylbutan-1-ol.

In some embodiments, an additional therapeutic agent is, as a non-limiting example: benzo-thiophene derivative.

In some embodiments, an additional therapeutic agent is, as a non-limiting example: dopamine and/or serotonin receptor antagonist.

In some embodiments, an additional therapeutic agent is, as a non-limiting example: fragments of the histone deacetylase 4 (HDAC4) gene lacking the enzymatic domain.

In some embodiments, an additional therapeutic agent is, as a non-limiting example: geranylgeranylacetone.

In some embodiments, an additional therapeutic agent is, as a non-limiting example: insulin, IGF-1, and/or chlorin e6.

In some embodiments, an additional therapeutic agent is, as a non-limiting example: N— acetylcysteine amide (NACA).

In some embodiments, an additional therapeutic agent is, as a non-limiting example: nut and/or seed oils, walnut oil, almond oil, avocado oil, pistachio oil and/or flaxseed oil, or any combination thereof.

In some embodiments, an additional therapeutic agent is, as a non-limiting example: pigment epithelium-derived factor (PEDF) and/or docosahexaenoic acid (DHA).

In some embodiments, an additional therapeutic agent is, as a non-limiting example: somatostatin-28, somatostatin-14, somatostatin-13, prosomatostatin, octreotide, lanreotide, vapreotide, pasireotide, seglitide, or cortistatin or any of their pharmaceutically acceptable salts.

In some embodiments, an additional therapeutic agent is, as a non-limiting example: xanthophyll.

In some embodiments, an additional therapeutic agent is, as a non-limiting example: A composition capable of preventing, delaying and/or decreasing any symptom of a retinopathy.

In some embodiments, an additional therapeutic agent is, as a non-limiting example: A siRNA. In some embodiments, an additional therapeutic agent is a siRNA delivered into the eye. In some embodiments, an oligonucleotide and/or an additional therapeutic agent is delivered by intravitreal injection.

In some embodiments, prior to the dose administration, a mydriatic (1% tropicamide) is instilled in the eye, followed by a topical anesthetic.

In some embodiments, an additional therapeutic treatment is, as a non-limiting example: a method of editing a RHO gene. In some embodiments, an additional therapeutic treatment is, as a non-limiting example: a method of editing a RHO gene in a cell, comprising the steps of: introducing into the cell one or more DNA endonucleases to effect one or more single-strand or double-strand breaks within or near the RHO gene that result(s) in permanent deletion of a P23H mutation in the RHO gene or replacement of one or more nucleotide bases, or one or more exons and/or introns within or near the RHO gene, thereby restoring the RHO gene function.

In some embodiments, an additional therapeutic agent is, as a non-limiting example: An oligonucleotide.

In some embodiments, a second or additional therapeutic agent is administered to a subject prior, simultaneously with, or after, a RHO oligonucleotide. In some embodiments, a second or additional therapeutic agent is administered multiple times to a subject, and a RHO oligonucleotide is also administered multiple times to a subject, and the administrations are in any order.

In some embodiments, an improvement may include decreasing the expression, activity and/or level of a gene or gene product which is too high in a disease state; increasing the expression, activity and/or level of a gene or gene product which is too low in the disease state; and/or decreasing the expression, activity and/or level of a mutant and/or disease-associated variant of a gene or gene product.

In some embodiments, a RHO oligonucleotide useful for treating, ameliorating and/or preventing a RHO-related condition, disorder or disease can be administered (e.g., to a subject) via any method described herein or known in the art.

In some embodiments, provided oligonucleotides, e.g., RHO oligonucleotides are administered as pharmaceutical composition, e.g., for treating, ameliorating and/or preventing RHO-related conditions, disorders or diseases. In some embodiments, provided oligonucleotides comprise at least one chirally controlled internucleotidic linkage. In some embodiments, provided oligonucleotide compositions are chirally controlled.

In some cases, patients with retinopathy (e.g, retinal degeneration, retinal degenerative disease, retinal degenerative disorder, inherited retinal degenerative disorder, retinitis pigmentosa, autosomal dominant retinitis pigmentosa, etc.) reportedly can further suffer from an additional, associated disorder or disease or complication, such as pulmonary complications, including but not limited to pneumonia, difficulties with vision and/or locomotion, and/or cachexia.

In some embodiments, an additional therapeutic agent includes a treatment for an additional, associated disorder or disease or complication.

In some cases, patients who have been administered an oligonucleotide as a medicament may experience certain side effects or adverse effects, including: thrombocytopenia, renal toxicity, glomerulonephritis, and/or coagulation abnormalities; genotoxicity, repeat-dose toxicity of target organs and pathologic effects; dose response and exposure relationships; chronic toxicity; juvenile toxicity; reproductive and developmental toxicity; cardiovascular safety; injection site reactions; cytokine response complement effects; immunogenicity; and/or carcinogenicity. In some embodiments, an additional therapeutic agent is administered to counter-act a side effect or adverse effect of administration of a RHO oligonucleotide. In some embodiments, a particular RHO oligonucleotide has a reduced capability of eliciting a side effect or adverse effect, compared to a different RHO oligonucleotide.

In some embodiments, an additional therapeutic agent can be administered to the patient in order to control or alleviate one or more side effects or adverse effects associated with administration of an oligonucleotide.

In some embodiments, an oligonucleotide and one or more additional therapeutic agent are administered to a patient (in any order), wherein the additional therapeutic agent can be administered to the patient in order to control or alleviate one or more side effects or adverse effects associated with administration of the oligonucleotide.

In some embodiments, an oligonucleotide and one or more additional therapeutic agent are administered to a patient (in any order), wherein the additional therapeutic agent can be administered to the patient in order to control or alleviate one or more side effects or adverse effects associated with administration of the oligonucleotide, and wherein the oligonucleotide targets RHO.

In some embodiments, an oligonucleotide composition and one or more additional therapeutic agent are administered to a patient (in any order), wherein the additional therapeutic agent can be administered to the patient in order to control or alleviate one or more side effects or adverse effects associated with administration of the oligonucleotide composition, and wherein the oligonucleotide composition is chirally controlled or comprises at least one chirally controlled internucleotidic linkage (including but not limited to a chirally controlled phosphorothioate).

Administration of Oligonucleotides and Compositions Thereof

Many delivery methods, regimen, etc. can be utilized in accordance with the present disclosure for administering provided oligonucleotides and compositions thereof (typically pharmaceutical compositions for therapeutic purposes), including various technologies known in the art.

In some embodiments, a RHO oligonucleotide or composition is delivered to an eye. In some embodiments, oligonucleotides and compositions are administered to one or both eyes of a subject.

In some embodiments, a RHO oligonucleotide (and, optionally, an additional therapeutic agent, is delivery to the eye or the retina using any method, device or composition described herein or known in the art. Non-limiting examples of documents describing various methods, devices and compositions useful for delivering a RHO oligonucleotide (and optionally, an additional therapeutic agent) to the eye or the retina include: patents and patent applications U.S. Pat. Nos. 6,416,777, 6,299,895, 5,725,493, 5,443,505, EP1473003, US20170073674, US20170173183, US20180169131, US20180250370, WO2018055134. In some embodiments, a RHO oligonucleotide (and, optionally, an additional therapeutic agent, is delivery to the eye or the retina using any method, device or composition described herein or known in the art, including but not limited to: a drug delivery device, an ophthalmic drug delivery device, a device and method for treating ophthalmic diseases, a method of intravitreal medicine delivery, or a biocompatible ocular implant. In some embodiments, delivery of a RHO oligonucleotide (and, optionally, an additional therapeutic agent) to the retina is by injection of a RHO oligonucleotide (and, optionally, an additional therapeutic agent) to the sub-retinal space of the retina. In some embodiments, a RHO oligonucleotide (and, optionally, an additional therapeutic agent) are administered in one or more locations in the sub-retinal space of the retina. In some embodiments, systemic modes of administration of a RHO oligonucleotide (and, optionally, an additional therapeutic agent) include oral and parenteral routes. In some embodiments, parenteral routes include, as non-limiting examples: intravenous, intrarterial, intramuscular, intradermal, subcutaneous, intranasal, and intraperitoneal routes. In some embodiments, an oligonucleotide or additional therapeutic agent administered systemically may be modified or formulated to target the an oligonucleotide and an optional additional therapeutic agent to the eye. In some embodiments, local modes of administration of a RHO oligonucleotide (and, optionally, an additional therapeutic agent) include, as non-limiting examples, intraocular, intraorbital, subconjuctival, intravitreal, subretinal, transscleral or intracochlear routes. In some embodiments, significantly smaller amounts of the RHO oligonucleotide (and, optionally, an additional therapeutic agent) may exert an effect when administered locally (for example, intravitreally) compared to when administered systemically (for example, intravenously). In some embodiments, local modes of administration can reduce or eliminate the incidence of potentially toxic side effects that may occur when therapeutically effective amounts of a component are administered systemically. In some embodiments, an oligonucleotide and an optional additional therapeutic agent are delivered subretinally, e.g., by subretinal injection. In some embodiments, subretinal injections may be made directly into the macular, e.g., submacular injection. In some embodiments, an oligonucleotide and an optional additional therapeutic agent are delivered by intravitreal injection. In some embodiments, intravitreal injection reportedly has a relatively low risk of retinal detachment. In some embodiments, nanoparticle or viral, e.g., AAV vector, is delivered intravitreally. In some embodiments, an AAV vector with multiple tyrosine-to-phenylalanine modifications can reportedly infect many cell types following intravitreal or subretinal injection. In some embodiments, intracochlear injections may be made in the vicinity of inner and/or outer hair cells. In some embodiments, methods for administration of agents to the eye are known in the medical arts and can be used to administer an oligonucleotide and an optional additional therapeutic agent. Exemplary methods include intraocular injection (e.g., retrobulbar, subretinal, submacular, intravitreal and intrachoridal), iontophoresis, eye drops, intraocular implantation (e.g., intravitreal, sub-Tenons and subconjunctival) and intracochlear injection. In some embodiments, administration may be provided as a periodic bolus (for example, subretinally, intravenously, intravitreally or by intracochlear injection) or as continuous infusion from an internal reservoir (for example, from an implant disposed at an intra- or extra-ocular location (see, U.S. Pat. Nos. 5,443,505 and 5,766,242)) or from an external reservoir (for example, from an intravenous bag). Components may be administered locally, for example, by continuous release from a sustained release drug delivery device immobilized to an inner wall of the eye or via targeted transscleral controlled release into the choroid (see, for example, PCT/USOO/00207, PCT/US02/14279, Ambati et al. (2000) INVEST. OPHTHALMOL. VIS. SCI.41: 1181-1185, and Ambati et al. (2000) INVEST. OPHTHALMOL. VIS. SCI.41: 1186-1191). A variety of devices suitable for administering an oligonucleotide and an optional additional therapeutic agent locally to the inside of the eye are known in the art. See, for example, U.S. Pat. Nos. 6,251,090, 6,299,895, 6,416,777, 6,413,540, and PCT/USOO/28187. In some embodiments, an oligonucleotide and an optional additional therapeutic agent can be formulated to permit release over a prolonged period of time. In some embodiments, a release system can include a matrix of a biodegradable material or a material which releases the incorporated an oligonucleotide and an optional additional therapeutic agent by diffusion. In some embodiments, the an oligonucleotide and an optional additional therapeutic agent can be homogeneously or heterogeneously distributed within the release system. In some embodiments, a variety of release systems may be useful, however, the choice of the appropriate system will depend upon rate of release required by a particular application. In some embodiments, a non-degradable or degradable release systems is used. In some embodiments, suitable release systems include polymers and polymeric matrices, non-polymeric matrices, or inorganic and organic excipients and diluents such as, but not limited to, calcium carbonate and sugar (for example, trehalose). In some embodiments, release systems may be natural or synthetic. In some embodiments, the release system material can be selected so that an oligonucleotide and an optional additional therapeutic agent having different molecular weights are released by diffusion through or degradation of the material. In some embodiments, synthetic, biodegradable polymers include as non-limiting examples: polyamides such as poly(amino acids) and poly(peptides); polyesters such as poly(lactic acid), poly(glycolic acid), poly(lactic-co-glycolic acid), and poly(caprolactone); poly(anhydrides); polyorthoesters; polycarbonates; and chemical derivatives thereof (substitutions, additions of chemical groups, for example, alkyl, alkylene, hydroxylations, oxidations, and other modifications routinely made by those skilled in the art), copolymers and mixtures thereof. In some embodiments, synthetic, non-degradable polymers include, as non-limiting examples: polyethers such as poly(ethylene oxide), poly(ethylene glycol), and poly(tetramethylene oxide); vinyl polymers-polyacrylates and polymethacrylates such as methyl, ethyl, other alkyl, hydroxyethyl methacrylate, acrylic and methacrylic acids, and others such as poly(vinyl alcohol), poly(vinyl pyrolidone), and poly(vinyl acetate); poly(urethanes); cellulose and its derivatives such as alkyl, hydroxyalkyl, ethers, esters, nitrocellulose, and various cellulose acetates; polysiloxanes; and any chemical derivatives thereof (substitutions, additions of chemical groups, for example, alkyl, alkylene, hydroxylations, oxidations, and other modifications routinely made by those skilled in the art), copolymers and mixtures thereof. In some embodiments, poly(lactide-co-glycolide) microsphere can also be used for intraocular injection. In some embodiments, the microspheres are composed of a polymer of lactic acid and glycolic acid, which are structured to form hollow spheres. In some embodiments, the spheres can be approximately 15-30 microns in diameter and can be loaded with an oligonucleotide and an optional additional therapeutic agent.

In some embodiments, an oligonucleotide composition, e.g., a RHO oligonucleotide composition, is administered at a dose and/or frequency lower than that of an otherwise comparable reference oligonucleotide composition and has comparable or improved effects. In some embodiments, a chirally controlled oligonucleotide composition is administered at a dose and/or frequency lower than that of a comparable, otherwise identical stereorandom reference oligonucleotide composition and with comparable or improved effects, e.g., in improving the knockdown of the target transcript.

In some embodiments, the present disclosure recognizes that properties and activities, e.g., knockdown activity, stability, toxicity, etc. of oligonucleotides and compositions thereof can be modulated and optimized by chemical modifications and/or stereochemistry. In some embodiments, the present disclosure provides methods for optimizing oligonucleotide properties and/or activities through chemical modifications and/or stereochemistry. In some embodiments, the present disclosure provides oligonucleotides and compositions thereof with improved properties and/or activities. Without wishing to be bound by any theory, due to, e.g., their better activity, stability, delivery, distribution, toxicity, pharmacokinetic, pharmacodynamics and/or efficacy profiles, Applicant notes that provided oligonucleotides and compositions thereof in some embodiments can be administered at lower dosage and/or reduced frequency to achieve comparable or better efficacy, and in some embodiments can be administered at higher dosage and/or increased frequency to provide enhanced effects.

In some embodiments, provided technologies can provide long-lasting effects, e.g., for 1, 2, 3, 4, 5, 6 or more months after administration (e.g., intravitreal injection). In some embodiments, reduction of levels and/or activities of target transcripts and/or products encoded thereby may be observed 1, 2, 3, 4, 5, 6 or more months after administration (e.g., intravitreal injection). In some embodiments, provided technologies can be administered with no more than two doses per year. In some embodiments, provided technologies are administered two doses per year. In some embodiments, provided technologies are administered through intravitreal injection.

In some embodiments, it was observed that provided oligonucleotides and compositions thereof did not significantly induce TLR3 and/or TLR9 activation.

In some embodiments, the present disclosure provides, in a method of administering an oligonucleotide composition comprising a plurality of oligonucleotides sharing a common base sequence, the improvement comprising administering an oligonucleotide comprising a plurality of oligonucleotides that is characterized by improved delivery relative to a reference oligonucleotide composition of the same common base sequence.

In some embodiments, provided oligonucleotides, compositions and methods provide improved delivery. In some embodiments, provided oligonucleotides, compositions and methods provide improved cytoplasmatic delivery. In some embodiments, improved delivery is to a population of cells. In some embodiments, improved delivery is to a tissue. In some embodiments, improved delivery is to an organ. In some embodiments, improved delivery is to an organism, e.g., a patient or subject. Example structural elements (e.g., chemical modifications, stereochemistry, combinations thereof, etc.), oligonucleotides, compositions and methods that provide improved delivery are extensively described in the present disclosure.

Various dosing regimens can be utilized to administer oligonucleotides and compositions of the present disclosure. In some embodiments, multiple unit doses are administered, separated by periods of time. In some embodiments, a given composition has a recommended dosing regimen, which may involve one or more doses. In some embodiments, a dosing regimen comprises a plurality of doses each of which are separated from one another by a time period of the same length; in some embodiments, a dosing regimen comprises a plurality of doses and at least two different time periods separating individual doses. In some embodiments, all doses within a dosing regimen are of the same unit dose amount. In some embodiments, different doses within a dosing regimen are of different amounts. In some embodiments, a dosing regimen comprises a first dose in a first dose amount, followed by one or more additional doses in a second dose amount different from the first dose amount. In some embodiments, a dosing regimen comprises a first dose in a first dose amount, followed by one or more additional doses in a second (or subsequent) dose amount that is the same as or different from the first dose (or another prior dose) amount. In some embodiments, a dosing regimen comprises administering at least one unit dose for at least one day. In some embodiments, a dosing regimen comprises administering more than one dose over a time period of at least one day, and sometimes more than one day. In some embodiments, a dosing regimen comprises administering multiple doses over a time period of at least a week. In some embodiments, the time period is at least 2, 3, 4, 5, 6, 7, 8, 9, 10, 11, 12, 13, 14, 15, 16, 17, 18, 19, 20, 21, 22, 23 24, 25, 26, 27, 28, 29, 30, 31, 32, 33, 34, 35, 36, 37, 38, 39, 40 or more (e.g., about 45, 50, 55, 60, 65, 70, 75, 80, 85, 90, 95, 100 or more) weeks. In some embodiments, a dosing regimen comprises administering one dose per week for more than one week. In some embodiments, a dosing regimen comprises administering one dose per week for 2, 3, 4, 5, 6, 7, 8, 9, 10, 11, 12, 13, 14, 15, 16, 17, 18, 19, 20, 21, 22, 23 24, 25, 26, 27, 28, 29, 30, 31, 32, 33, 34, 35, 36, 37, 38, 39, 40 or more (e.g., about 45, 50, 55, 60, 65, 70, 75, 80, 85, 90, 95, 100 or more) weeks. In some embodiments, a dosing regimen comprises administering one dose every two weeks for more than two week period. In some embodiments, a dosing regimen comprises administering one dose every two weeks over a time period of 2, 3, 4, 5, 6, 7, 8, 9, 10, 11, 12, 13, 14, 15, 16, 17, 18, 19, 20, 21, 22, 23 24, 25, 26, 27, 28, 29, 30, 31, 32, 33, 34, 35, 36, 37, 38, 39, 40 or more (e.g., about 45, 50, 55, 60, 65, 70, 75, 80, 85, 90, 95, 100 or more) weeks. In some embodiments, a dosing regimen comprises administering one dose per month for one month. In some embodiments, a dosing regimen comprises administering one dose per month f or more than one month. In some embodiments, a dosing regimen comprises administering one dose per month for 2, 3, 4, 5, 6, 7, 8, 9, 10, 11, 12, or more months. In some embodiments, a dosing regimen comprises administering one dose per week for about 10 weeks. In some embodiments, a dosing regimen comprises administering one dose per week for about 20 weeks. In some embodiments, a dosing regimen comprises administering one dose per week for 26 weeks. In some embodiments, a dosing regimen comprises administering one dose per week for about 30 weeks. In some embodiments, a chirally controlled oligonucleotide composition is administered according to a dosing regimen that differs from that utilized for a non-chirally controlled (e.g., stereorandom) oligonucleotide composition of the same sequence, and/or of a different chirally controlled oligonucleotide composition of the same sequence. In some embodiments, a chirally controlled oligonucleotide composition is administered according to a dosing regimen that is reduced as compared with that of a chirally uncontrolled (e.g., stereorandom) oligonucleotide composition of the same sequence in that it achieves a lower level of total exposure over a given unit of time, involves one or more lower unit doses, and/or includes a smaller number of doses over a given unit of time. In some embodiments, a chirally uncontrolled oligonucleotide is administered according to a dosing regimen that extends for a longer period of time than does that of a chirally uncontrolled (e.g., stereorandom) oligonucleotide composition of the same sequence Without wishing to be limited by theory, Applicant notes that in some embodiments, the shorter dosing regimen, and/or longer time periods between doses, may be due to the improved stability, bioavailability, and/or efficacy of a chirally controlled oligonucleotide composition. In some embodiments, with their improved delivery (and other properties), provided compositions can be administered in lower dosages and/or with lower frequency to achieve biological effects, for example, clinical efficacy.

Pharmaceutical Compositions

In some embodiments, the present disclosure provides pharmaceutical compositions comprising a provided compound, e.g., an oligonucleotide, or a pharmaceutically acceptable salt thereof, and a pharmaceutical carrier. In some embodiments, for therapeutic and clinical purposes, oligonucleotides of the present disclosure are provided as pharmaceutical compositions.

In some embodiments, the present disclosure pertains to a RHO oligonucleotide or oligonucleotide composition comprising a pharmaceutically acceptable carrier suitable for delivery to the eye.

In some embodiments, an oligonucleotide is delivered by intravitreal injection. In some embodiments, prior to intravitreal injection, a mydriatic (e.g., 1% tropicamide) is instilled in the eye, followed by a topical anesthetic.

As appreciated by those skilled in the art, oligonucleotides of the present disclosure can be provided in their acid, base and/or salt forms. In some embodiments, oligonucleotides can be in acid forms, e.g., for natural phosphate linkages, in the form of —OP(O)(OH)O—; for phosphorothioate internucleotidic linkages, in the form of —OP(O)(SH)O—; etc. In some embodiments, provided oligonucleotides can be in salt forms, e.g., for natural phosphate linkages, in the form of —OP(O)(ONa)O— in sodium salts; for phosphorothioate internucleotidic linkages, in the form of —OP(O)(SNa)O— in sodium salts; etc. Unless otherwise noted, oligonucleotides of the present disclosure can exist in acid, base and/or salt forms.

When used as therapeutics, a provided oligonucleotide, e.g., a RHO oligonucleotide, or oligonucleotide composition thereof is typically administered as a pharmaceutical composition. In some embodiments, a pharmaceutical composition is suitable for administration of an oligonucleotide to an area of a body affected by a condition, disorder or disease. In some embodiments, a pharmaceutical composition comprises a therapeutically effective amount of a provided oligonucleotide or a pharmaceutically acceptable salt thereof, and a pharmaceutically acceptable inactive ingredient. In some embodiments, a pharmaceutically acceptable inactive ingredient is selected from pharmaceutically acceptable diluents, pharmaceutically acceptable excipients, and pharmaceutically acceptable carriers. In some embodiments, a pharmaceutically acceptable inactive ingredient is a pharmaceutically acceptable carrier.

In some embodiments, a provided oligonucleotide is formulated for administration to and/or contact with a body cell and/or tissue expressing its target. For example, in some embodiments, a provided RHO oligonucleotide is formulated for administration to a body cell and/or tissue expressing RHO. In some embodiments, such a body cell and/or tissue are a neuron or a cell and/or tissue of the eye. In some embodiments, broad distribution of oligonucleotides and compositions may be achieved with intraparenchymal administration, intrathecal administration, or intracerebroventricular administration.

In some embodiments, the pharmaceutical composition is formulated for intravenous injection, oral administration, buccal administration, inhalation, nasal administration, topical administration, ophthalmic administration or otic administration. In some embodiments, the pharmaceutical composition is a tablet, a pill, a capsule, a liquid, an inhalant, a nasal spray solution, a suppository, a suspension, a gel, a colloid, a dispersion, a suspension, a solution, an emulsion, an ointment, a lotion, an eye drop or an ear drop.

In some embodiments, the present disclosure provides a pharmaceutical composition comprising chirally controlled oligonucleotide or composition thereof, in admixture with a a pharmaceutically acceptable inactive ingredient (e.g., a pharmaceutically acceptable excipient, a pharmaceutically acceptable carrier, etc.). One of skill in the art will recognize that the pharmaceutical compositions include pharmaceutically acceptable salts of provided oligonucleotide or compositions. In some embodiments, a pharmaceutical composition is a chirally controlled oligonucleotide composition. In some embodiments, a pharmaceutical composition is a stereopure oligonucleotide composition.

In some embodiments, the present disclosure provides salts of oligonucleotides and pharmaceutical compositions thereof. In some embodiments, a salt is a pharmaceutically acceptable salt. In some embodiments, a pharmaceutical composition comprises an oligonucleotide, optionally in its salt form, and a sodium salt. In some embodiments, a pharmaceutical composition comprises an oligonucleotide, optionally in its salt form, and sodium chloride. In some embodiments, each hydrogen ion of an oligonucleotide that may be donated to a base (e.g., under conditions of an aqueous solution, a pharmaceutical composition, etc.) is replaced by a non-$H^+$ cation. For example, in some embodiments, a pharmaceutically acceptable salt of an oligonucleotide is an all-metal ion salt, wherein each hydrogen ion (for example, of —OH, —SH, etc.) of each internucleotidic linkage (e.g., a natural phosphate linkage, a phosphorothioate internucleotidic linkage, etc.) is replaced by a metal ion. Various suitable metal salts for pharmaceutical compositions are widely known in the art and can be utilized in accordance with the present disclosure. In some embodiments, a pharmaceutically acceptable salt is a sodium salt. In some embodiments, a pharmaceutically acceptable salt is magnesium salt. In some embodiments, a pharmaceutically acceptable salt is a calcium salt. In some embodiments, a pharmaceutically acceptable salt is a potassium salt. In some embodiments, a pharmaceutically acceptable salt is an ammonium salt (cation $N(R)_4^+$). In some embodiments, a pharmaceutically acceptable salt comprises one and no more than one types of cation. In some embodiments, a pharmaceutically acceptable salt comprises two or more types of cation. In some embodiments, a cation is $Li^+$, $Na^+$, $K^+$, $Mg^{2+}$ or $Ca^{2+}$. In some embodiments, a pharmaceutically acceptable salt is an all-sodium salt. In some embodiments, a pharmaceutically acceptable salt is an all-sodium salt, wherein each internucleotidic linkage which is a natural phosphate linkage (acid form —O—P(O)(OH)—O—), if any, exists as its sodium salt form (—O—P(O)(ONa)—O—), and each internucleotidic linkage which is a phosphorothioate internucleotidic linkage (acid form —O—P(O)(SH)—O—), if any, exists as its sodium salt form (—O—P(O)(SNa)—O—).

Various technologies for delivering nucleic acids and/or oligonucleotides are known in the art can be utilized in accordance with the present disclosure. For example, a variety of supramolecular nanocarriers can be used to deliver nucleic acids. Example nanocarriers include, but are not limited to liposomes, cationic polymer complexes and various polymeric compounds. Complexation of nucleic acids with various polycations is another approach for intracellular delivery; this includes use of PEGylated polycations, polyethyleneamine (PEI) complexes, cationic block co-polymers, and dendrimers. Several cationic nanocarriers, including PEI and polyamidoamine dendrimers help to release contents from endosomes. Other approaches include use of polymeric nanoparticles, microspheres, liposomes, dendrimers, biodegradable polymers, conjugates, prodrugs, inorganic colloids such as sulfur or iron, antibodies, implants, biodegradable implants, biodegradable microspheres, osmotically controlled implants, lipid nanoparticles, emulsions, oily solutions, aqueous solutions, biodegradable polymers, poly(lactide-coglycolic acid), poly (lactic acid), liquid depot, polymer micelles, quantum dots and lipoplexes. In some embodiments, an oligonucleotide is conjugated to another molecule.

In therapeutic and/or diagnostic applications, compounds, e.g., oligonucleotides, of the disclosure can be formulated for a variety of modes of administration, including systemic and topical or localized administration. Techniques and formulations generally may be found in Remington, The Science and Practice of Pharmacy ($20^{th}$ ed. 2000).

Provided oligonucleotides and compositions thereof are effective over a wide dosage range. For example, in the treatment of adult humans, dosages from about 0.01 to about 1000 mg, from about 0.5 to about 100 mg, from about 1 to about 50 mg per day, and from about 5 to about 100 mg per day are examples of dosages that may be used. Exact dosages may depend upon routes of administration, forms in which provided compounds, e.g., oligonucleotides, are administered, subjects to be treated, conditions, disorders or diseases to be treated, body weights of the subjects to be treated, and/or preferences and experiences of physicians.

Pharmaceutically acceptable salts for basic moieties are generally well known to those of ordinary skill in the art, and may include, e.g., acetate, benzenesulfonate, besylate, benzoate, bicarbonate, bitartrate, bromide, calcium edetate, camsylate, carbonate, citrate, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isethionate, lactate, lactobionate, malate, maleate, mandelate, mesylate, mucate, napsylate, nitrate, pamoate (embonate), pantothenate, phosphate/diphosphate, polygalacturonate, salicylate, stearate, subacetate, succinate, sulfate, tannate, tartrate, or teoclate. Other pharmaceutically acceptable salts may be found in, for example, Remington, The Science and Practice of Pharmacy ($20^{th}$ ed. 2000). Preferred pharmaceutically acceptable salts include, for example, acetate, benzoate, bromide, carbonate, citrate, gluconate, hydrobromide, hydrochloride, maleate, mesylate, napsylate, pamoate (embonate), phosphate, salicylate, succinate, sulfate, or tartrate.

In some embodiments, provided oligonucleotides are formulated in pharmaceutical compositions described in WO 2005/060697, WO 2011/076807 or WO 2014/136086.

Depending on the specific conditions, disorders or diseases being treated, provided agents, e.g., oligonucleotides, may be formulated into liquid or solid dosage forms and administered systemically or locally. Provided oligonucleotides may be delivered, for example, in a timed- or sustained-low release form as is known to those skilled in the art. Techniques for formulation and administration may be found in Remington, The Science and Practice of Pharmacy ($20^{th}$ ed. 2000). Suitable routes may include oral, buccal, by inhalation spray, sublingual, rectal, transdermal, vaginal, transmucosal, nasal or intestinal administration; parenteral delivery, including intramuscular, subcutaneous, intramedullary injections, as well as intrathecal, direct intraventricular, intravenous, intra-articular, intra-stemal, intra-synovial, intra-hepatic, intralesional, intracranial, intraperitoneal, intranasal, or intraocular injections or another mode of delivery.

For injection, provided agents, e.g., oligonucleotides may be formulated and diluted in aqueous solutions, such as in physiologically compatible buffers such as Hank's solution, Ringer's solution, or physiological saline buffer. For such transmucosal administration, penetrants appropriate to the barrier to be permeated are used in the formulations. Such penetrants are generally known in the art and can be utilized in accordance with the present disclosure.

Use of pharmaceutically acceptable carriers to formulate compounds, e.g., provided oligonucleotides, for the practice of the disclosure into dosages suitable for various mods of administration is well known in the art. With proper choice of carrier and suitable manufacturing practice, compositions of the present disclosure, e.g., those formulated as solutions, may be administered via various routes, e.g., parenterally, such as by intravenous injection.

In some embodiments, a composition comprising an oligonucleotide, e.g., a RHO oligonucleotide, further comprises any or all of: calcium chloride dihydrate, magnesium chloride hexahydrate, potassium chloride, sodium chloride, sodium phosphate dibasic anhydrous, sodium phosphate, monobasic dihydrate, and/or water for Injection. In some embodiments, a composition further comprises any or all of: calcium chloride dihydrate (0.21 mg) USP, magnesium chloride hexahydrate (0.16 mg) USP, potassium chloride (0.22 mg) USP, sodium chloride (8.77 mg) USP, sodium phosphate dibasic anhydrous (0.10 mg) USP, sodium phosphate monobasic dihydrate (0.05 m g) USP, and Water for Injection USP.

In some embodiments, a composition comprising an oligonucleotide further comprises any or all of: cholesterol, (6Z,9Z,28Z,31Z)-heptatriaconta-6,9,28,31-tetraen-19-yl-4-(dimethylamino) butanoate(DLin-MC3-DMA), 1,2-distearoyl-sn-glycero-3-phosphocholine (DSPC), alpha-(3'-{[1,2-di(myristyloxy)propanoxy] carbonylamino}propyl)-omega-methoxy, polyoxyethylene(PEG2000-C-DMG), potassium phosphate monobasic anhydrous NF, sodium chloride, sodium phosphate dibasic heptahydrate, and Water for Injection. In some embodiments, the pH of a composition comprising an oligonucleotide, e.g., a RHO oligonucleotide, is ~7.0. In some embodiments, a composition comprising an oligonucleotide further comprises any or all of: 6.2 mg cholesterol USP, 13.0 mg (6Z,9Z,28Z,31Z)-heptatriaconta-6,9,28,31-tetraen-19-yl-4-(dimethylamino) butanoate(DLin-MC3-DMA), 3.3 mg 1,2-distearoyl-sn-glycero-3-phosphocholine (DSPC), 1.6 mg α-(3'-{[1,2-di(myristyloxy)propanoxy]carbonylamino}propyl)-ω-methoxy, polyoxyethylene(PEG2000-C-DMG), 0.2 mg potassium phosphate monobasic anhydrous NF, 8.8 mg sodium chloride USP, 2.3 mg sodium phosphate dibasic heptahydrate USP, and Water for Injection USP, in an approximately 1 mL total volume.

Provided compounds, e.g., oligonucleotides, can be formulated readily using pharmaceutically acceptable carriers well known in the art into dosages suitable for oral administration. In some embodiments, such carriers enable provided oligonucleotides to be formulated as tablets, pills, capsules, liquids, gels, syrups, slurries, suspensions and the like, for, e.g., oral ingestion by a subject (e.g., patient) to be treated.

For nasal or inhalation delivery, provided compounds, e.g., oligonucleotides, may be formulated by methods known to those of skill in the art, and may include, e.g., examples of solubilizing, diluting, or dispersing substances such as saline, preservatives, such as benzyl alcohol, absorption promoters, and fluorocarbons.

In certain embodiments, oligonucleotides and compositions are delivered to the CNS. In certain embodiments, oligonucleotides and compositions are delivered to the cerebrospinal fluid. In certain embodiments, oligonucleotides and compositions are administered to the brain parenchyma. In certain embodiments, oligonucleotides and compositions are delivered to an animal/subject by intrathecal administration, or intracerebroventricular administration. Broad distribution of oligonucleotides and compositions may be achieved with methods of administration described herein and/or known in the art.

In certain embodiments, parenteral administration is by injection, by, e.g., a syringe, a pump, etc. In certain embodiments, an injection is abolus injection. In certain embodiments, an injection is administered directly to a tissue or location, such as striatum, caudate, cortex, hippocampus and/or cerebellum.

In certain embodiments, methods of specifically localizing provided compounds, e.g., oligonucleotides, such as by bolus injection, may decrease median effective concentration (EC50) by a factor of 20, 25, 30, 35, 40, 45 or 50. In certain embodiments, a targeted tissue is brain tissue. In certain embodiments, a targeted tissue is striatal tissue. In certain embodiments, decreasing EC50 is desirable because it reduces the dose required to achieve a pharmacological result in a patient in need thereof.

In certain embodiments, a provided oligonucleotide is delivered by injection or infusion once every month, every two months, every 90 days, every 3 months, every 6 months, twice a year or once a year.

Pharmaceutical compositions suitable for use in the present disclosure include compositions wherein the active ingredients, e.g., oligonucleotides, are contained in effective amounts to achieve their intended purposes. Determination of the effective amounts is well within the capability of those skilled in the art, especially in light of the detailed disclosure provided herein.

In addition to active ingredients, pharmaceutical compositions may contain suitable pharmaceutically acceptable carriers comprising excipients and auxiliaries which facilitate processing of an active compound into preparations which can be used pharmaceutically. Preparations formulated for oral administration may be in the form of tablets, dragees, capsules, or solutions.

In some embodiments, pharmaceutical compositions for oral use can be obtained by combining an active compound with solid excipients, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol;

cellulose preparations, for example, maize starch, wheat starch, rice starch, potato starch, gelatin, gum tragacanth, methyl cellulose, hydroxypropylmethyl-cellulose, sodium carboxymethyl-cellulose (CMC), and/or polyvinylpyrrolidone (PVP: povidone). If desired, disintegrating agents may be added, such as the cross-linked polyvinylpyrrolidone, agar, or alginic acid or a salt thereof such as sodium alginate.

In some embodiments, dragee cores are provided with suitable coatings. For this purpose, concentrated sugar solutions may be used, which may optionally contain gum arabic, talc, polyvinylpyrrolidone, carbopol gel, polyethylene glycol (PEG), and/or titanium dioxide, lacquer solutions, and suitable organic solvents or solvent mixtures. Dye-stuffs or pigments may be added to the tablets or dragee coatings for identification or to characterize different combinations of active compound doses.

Pharmaceutical preparations that can be used orally include push-fit capsules made of gelatin, as well as soft, sealed capsules made of gelatin, and a plasticizer, such as glycerol or sorbitol. Push-fit capsules can contain active ingredients, e.g., oligonucleotides, in admixture with fillers such as lactose, binders such as starches, and/or lubricants such as talc or magnesium stearate and, optionally, stabilizers. In soft capsules, active compounds, e.g., oligonucleotides, may be dissolved or suspended in suitable liquids, such as fatty oils, liquid paraffin, or liquid polyethylene glycols (PEGs). In addition, stabilizers may be added.

In some embodiments, a provided composition comprises a lipid. In some embodiments, a lipid is conjugated to an active compound, e.g., an oligonucleotide. In some embodiments, a lipid is not conjugated to an active compound. In some embodiments, a lipid comprises a $C_{10}$-$C_{40}$ linear, saturated or partially unsaturated, aliphatic chain. In some embodiments, a lipid comprises a $C_{10}$-$C_{40}$ linear, saturated or partially unsaturated, aliphatic chain, optionally substituted with one or more $C_{1-4}$ aliphatic group. In some embodiments, the lipid is selected from the group consisting of lauric acid, myristic acid, palmitic acid, stearic acid, oleic acid, linoleic acid, alpha-linolenic acid, gamma-linolenic acid, docosahexaenoic acid (cis-DHA), turbinaric acid and dilinoleyl alcohol. In some embodiments, an active compound is a provided oligonucleotide. In some embodiments, a composition comprises a lipid and an active compound, and further comprises another component which is another lipid or a targeting compound or moiety. In some embodiments, a lipid is an amino lipid; an amphipathic lipid; an anionic lipid; an apolipoprotein; a cationic lipid; a low molecular weight cationic lipid; a cationic lipid such as CLinDMA and DLinDMA; an ionizable cationic lipid; a cloaking component; a helper lipid; a lipopeptide; a neutral lipid; a neutral zwitterionic lipid; a hydrophobic small molecule; a hydrophobic vitamin; a PEG-lipid; an uncharged lipid modified with one or more hydrophilic polymers; phospholipid; a phospholipid such as 1,2-dioleoyl-sn-glycero-3-phosphoethanolamine; a stealth lipid; a sterol; a cholesterol; a targeting lipid; or another lipid described herein or reported in the art suitable for pharmaceutical uses. In some embodiments, a composition comprises a lipid and a portion of another lipid capable of mediating at least one function of another lipid. In some embodiments, a targeting compound or moiety is capable of targeting a compound (e.g., an oligonucleotide) to a particular cell or tissue or subset of cells or tissues. In some embodiments, a targeting moiety is designed to take advantage of cell- or tissue-specific expression of particular targets, receptors, proteins, or another subcellular component. In some embodiments, a targeting moiety is a ligand (e.g., a small molecule, antibody, peptide, protein, carbohydrate, aptamer, etc.) that targets a composition to a cell or tissue, and/or binds to a target, receptor, protein, or another subcellular component.

Certain example lipids for delivery of an active compound, e.g., an oligonucleotide, allow (e.g., do not prevent or interfere with) the function of an active compound. In some embodiments, a lipid is lauric acid, myristic acid, palmitic acid, stearic acid, oleic acid, linoleic acid, alpha-linolenic acid, gamma-linolenic acid, docosahexaenoic acid (cis-DHA), turbinaric acid or dilinoleyl alcohol.

As described in the present disclosure, lipid conjugation, such as conjugation with fatty acids, may improve one or more properties of oligonucleotides.

In some embodiments, a composition for delivery of an active compound, e.g., an oligonucleotide, is capable of targeting an active compound to particular cells or tissues as desired. In some embodiments, a composition for delivery of an active compound is capable of targeting an active compound to a muscle cell or tissue. In some embodiments, the present disclosure provides compositions and methods related to delivery of active compounds, wherein the compositions comprise an active compound and a lipid. In various embodiments to a muscle cell or tissue, a lipid is selected from lauric acid, myristic acid, palmitic acid, stearic acid, oleic acid, linoleic acid, alpha-linolenic acid, gamma-linolenic acid, docosahexaenoic acid (cis-DHA), turbinaric acid and dilinoleyl alcohol.

In some embodiments, a RHO oligonucleotide is delivered to the eye, or a cell or tissue or portion thereof, via a delivery method or composition designed for delivery of nucleic acids to the eye, or a cell or tissue or portion thereof.

In some embodiments, a RHO oligonucleotide is delivered via a method or composition described in any of: Buyens et al. J. Control Release 2012, 158; 362-70; Couto L B, High K A. Viral vector-mediated RNA interference. Curr. Opin. Pharmacol. 2010, 5; 534-542; Gomes da Silva et al. Acc. Chem. Res. 2012, 45; 1163-71; Grijalvo et al. 2014 Expert Opinion on Therapeutic Patents 24(7); Montana et al. Bioconjug. Chem. 2007, 18; 302-8; Moshfeghi et al. Expert Opin. Investig. Drugs 2005, 14; 671-682; Müller et al. Curr. Drug Discov. Technol. 2011, 8; 207-27; Semple et al. Nat. Biotechnol. 2010, 28; 172-6; Soutschek et al. Nature 2004, 432; 173-8; Templeton N. Cationic liposomes as in vivo delivery vehicles. Biosci. Rep. 2002, 22; 283-95; Trabulo et al. Curr. Pharm. Des. 2013, 19; 2895-923; Troiber et al. Bioconjug. Chem. 2011, 22; 1737-52; Yousefi et al. J. Control Release 2013, 170; 209-18; Zhi et al. Bioconjug. Chem. 2013, 24; 487-519; Zhou et al. Pharmaceuticals 2013, 6; 85-107; Zimmermann et al. Nature 2006. 441; 111-4; Khorkova et al. Nature Biotechnology volume 35, pages 249-263 (2017); Kritika Goyal, Veena Koul, Yashveer Singh, and Akshay Anand, Central Nervous System Agents in Medicinal Chemistry 14, 2014, 43-59; Aviñó et al. J Nucleic Acids. 2011; 2011: 586935; Passini et al. Sci. Transl. Med. 2011 Mar. 2; 3(72): 72ra18; Chen et al. Front. Neurosci. 30 Aug. 2017; Juliano et al. Nucleic Acids Research, Volume 44, Issue 14, 19 Aug. 2016, Pages 6518-6548; and/or any of the published patent applications: EP2822600; US 20090264506; US 20170080100; US20100144845; US 20180030443; US20100055168; US20100055169; US20100254901 US2010234282; US2010311654; US2011003754; US20110281787; US2012027861; US2012142765; US20122007795; US2012230938; US20130183379; US2013281658; U.S. Pat. No. 9,938,526; WO2010017328; WO2010039088; WO2010045584; WO2010056403; WO2010085665; WO2010088565;

WO2010111466; WO2010129672 WO2010135207; WO2011005566; WO2011017456; WO2011022460; WO2011028850; WO2011045747; WO2011053989; WO2011055888; WO2011064552; WO2011109698; WO2011115555; WO2011115862; WO2011116152; WO2011120053; WO2011120953; WO2011126937 WO2011126974; WO2011135138; WO2011135141; WO2011143008; WO2011153120; WO2011163121; WO201153493; WO2012009448; WO2012024396; WO2012030745; WO2012044638; WO2012054365; WO2012061259; WO2012061402; WO2012068187; WO2012082574; WO2012089352; WO2012099755; WO2012101235; WO2012113846; WO2012119051; WO2012142480; WO2012150960; WO2012162210; WO2012173994; WO2012176138; WO2013016157; WO2013030569; WO2013032643; WO2013040295; WO2013044116; WO2013049328; WO2013070010; WO2013075035; WO2013082286; WO2013086207; WO2013086322; WO2013086354; WO2013101983; WO2013110679; WO2013110679; WO2013110680; WO2013116126; WO2013123217; WO2013126564; WO2013148541; WO2013148736; WO2013155493; WO2013158579; WO2013160773; WO2013166121; and/or WO2013170386.

In some embodiments, a RHO oligonucleotide is delivered via a composition comprising any one or more of, or a method of delivery involving the use of any one or more of: transferrin receptor-targeted nanoparticle; cationic liposome-based delivery strategy; cationic liposome; polymeric nanoparticle; viral carrier; retrovirus; adeno-associated virus; stable nucleic acid lipid particle; polymer; cell-penetrating peptide; lipid; dendrimer; neutral lipid; cholesterol; lipid-like molecule; fusogenic lipid; hydrophilic molecule; polyethylene glycol (PEG) or a derivative thereof; shielding lipid; PEGylated lipid; PEG-C-DMSO; PEG-C-DMSA; DSPC; ionizable lipid; a guanidinium-based cholesterol derivative; ion-coated nanoparticle; metal-ion coated nanoparticle; manganese ion-coated nanoparticle; angubindin-1; nanogel; incorporation of the RHO into a branched nucleic acid structure; and/or incorporation of the RHO into a branched nucleic acid structure comprising 2, 3, 4 or more oligonucleotides.

In some embodiments, a composition comprising an oligonucleotide is lyophilized. In some embodiments, a composition comprising an oligonucleotide is lyophilized, and the lyophilized oligonucleotide is in a vial. In some embodiments, the vial is back filled with nitrogen. In some embodiments, the lyophilized oligonucleotide composition is reconstituted prior to administration. In some embodiments, the lyophilized oligonucleotide composition is reconstituted with a sodium chloride solution prior to administration. In some embodiments, the lyophilized oligonucleotide composition is reconstituted with a 0.9% sodium chloride solution prior to administration. In some embodiments, reconstitution occurs at the clinical site for administration. In some embodiments, in a lyophilized composition, an oligonucleotide composition is chirally controlled or comprises at least one chirally controlled internucleotidic linkage and/or the oligonucleotide targets RHO.

EXEMPLIFICATION

Certain examples of provided technologies (compounds (oligonucleotides, reagents, etc.), compositions, methods (methods of preparation, use, assessment, etc.), etc.) were presented herein.

Example 1. Oligonucleotide Synthesis

Various technologies for preparing oligonucleotides and oligonucleotide compositions (both stereorandom and chirally controlled) are known and can be utilized in accordance with the present disclosure, including, for example, those in U.S. Pat. Nos. 9,394,333, 9,744,183, 9,605,019, 9,598,458, 9,982,257, U.S. Ser. No. 10/160,969, U.S. Ser. No. 10/479,995, US 2020/0056173, US 2018/0216107, US 2019/0127733, U.S. Ser. No. 10/450,568, US 2019/0077817, US 2019/0249173, US 2019/0375774, WO 2018/223056, WO 2018/223073, WO 2018/223081, WO 2018/237194, WO 2019/032607, WO 2019/055951, WO 2019/075357, WO 2019/200185, WO 2019/217784, and/or WO 2019/032612, the methods and reagents of each of which are incorporated herein by reference.

In some embodiments, oligonucleotides were prepared using suitable chiral auxiliaries, e.g., DPSE and PSM chiral auxiliaries. Various oligonucleotides, e.g., those in Table 1A and Table 1B, and compositions thereof, were prepared in accordance with the present disclosure.

Example 2. Provided Oligonucleotides can Effectively Reduce Levels of their Targets Various technologies can be utilized to assess properties and/or activities of provided oligonucleotides and compositions thereof. Some such technologies are described in this Example. Those skilled in the art appreciate that many other technologies can be readily utilized. As demonstrated herein, provided oligonucleotides and compositions, among other things, can be highly active, e.g., in reducing levels of their target nucleic acids.

Various RHO oligonucleotides were designed and constructed. A number of RHO oligonucleotides were tested, including testing knockdown of RHO in vitro in cells at one or a range of concentrations, and $IC_{50}$. Various experiments were performed to evaluate the activity of certain oligonucleotides and compositions. Some results are shown in the following Tables. In some of these Tables, results of replicate experiments are shown. In some of these Tables, not all controls may be shown (data not shown). Certain RHO oligonucleotides and compositions target SNP rs104893768. For this SNP, in many instances there is a C in the wild-type RHO mRNA, and A in the mutant RHO mRNA. The C to A mutation in the mutant gives rise to a P23H mutation in the RHO protein.

In various Tables, knockdown represents knockdown of RHO transcripts (wt, mt (P23H), or total) relative to control, unless otherwise noted. Various experiments were performed in vitro unless otherwise noted. RHO oligonucleotides were tested in vitro for ability to knock down the wild-type (wt) and the mutant (m or mt) RHO corresponding to the SNP. Results from replicate data are shown. Numbers indicate the % of remaining luciferase signal, corresponding to RHO remaining (relative to control) at the indicated oligonucleotide concentrations. The unit of the concentrations is nM in some tables, or Log (dose nM) in some tables. The correspondence of the Log (dose nM) and dose nM is described in Table 23A and Table 23B, below.

RHO wt is the amount (%) of wild-type RHO transcripts (without the SNP (e.g., SNP rs104893768) allele that leads to P23H) remaining after treatment with an oligonucleotide composition. RHO P23H or RHO mt is the amount (%) mutant transcripts (e.g., comprising an allele of SNP rs104893768 that leads to P23H) remaining after treatment with an oligonucleotide composition. Various oligonucleotide compositions in various tables were evaluated for their ability to reduce the wt (wild-type) mt RHO transcripts; certain data are presented herein as examples. 100.0 would represent 100% RHO level (0% knockdown) and 0.0 would represent 0% RHO level (100% knock down).

TABLE 1A

Activities of certain oligonucleotide compositions. Certain oligonucleotide compositions were tested in a luciferase reporting assay (procedures as shown in Example 3). Oligonucleotide were tested at a concentration of 5 nM (wt) and 1 nm (mt). WV-993 is non-targeting.

| ID | 5 nM Wt | | 1 nm Mt | |
|---|---|---|---|---|
| H2O | 118.07 | 104.72 | 95.96 | 102.34 |
| WV-993 | 105.57 | 100.50 | 105.54 | 105.98 |
| WV-20866 | 58.40 | 58.41 | 72.77 | 75.09 |
| WV-20791 | 111.24 | 94.08 | 88.88 | 103.48 |
| WV-20792 | 86.48 | 82.33 | 83.92 | 79.49 |
| WV-20793 | 82.39 | 82.69 | 69.86 | 79.17 |
| WV-20794 | 79.86 | 90.02 | 94.96 | 85.39 |
| WV-20795 | 105.50 | 97.85 | 85.80 | 89.25 |
| WV-20796 | 96.49 | 89.85 | 77.52 | 80.81 |
| WV-20797 | 84.06 | 68.30 | 92.51 | 79.36 |
| WV-20798 | 95.14 | 96.83 | 102.59 | 93.22 |
| WV-20799 | 107.42 | 91.26 | 78.04 | 81.65 |
| WV-20800 | 72.58 | 69.44 | 84.63 | 83.93 |
| WV-20801 | 96.39 | 89.24 | 83.89 | 98.21 |
| WV-20803 | 78.28 | 59.85 | 69.45 | 71.99 |
| WV-20804 | 90.77 | 95.06 | 73.63 | 85.65 |
| WV-20805 | 105.04 | 84.28 | 70.02 | 67.80 |
| WV-20806 | 75.85 | 73.32 | 78.62 | 92.84 |
| WV-20807 | 96.04 | 80.57 | 73.75 | 81.82 |
| WV-20808 | 94.83 | 86.34 | 68.08 | 77.10 |

TABLE 1B

Activities of certain oligonucleotide compositions. Certain oligonucleotide compositions were tested in a luciferase reporting assay (procedures as shown in Example 3). Oligonucleotide were tested at a concentration of 5 nM (wt) and 1 nm (mt). WV-993 is non-targeting.

| ID | 5 nM Wt | | 1 nm Mt | |
|---|---|---|---|---|
| H2O | 118.07 | 104.72 | 95.96 | 102.34 |
| WV-993 | 105.57 | 100.50 | 105.54 | 105.98 |
| WV-20867 | 58.92 | 61.70 | 56.74 | 56.49 |
| WV-20810 | 73.89 | 85.93 | 81.06 | 85.69 |
| WV-20811 | 84.21 | 81.64 | 86.26 | 84.88 |
| WV-20812 | 79.92 | 86.20 | 81.97 | 69.13 |
| WV-20813 | 82.60 | 81.50 | 91.50 | 86.34 |
| WV-20814 | 86.07 | 87.84 | 87.93 | 104.68 |
| WV-20815 | 87.74 | 87.39 | 93.70 | 98.21 |
| WV-20816 | 71.18 | 70.19 | 78.94 | 81.09 |
| WV-20817 | 88.60 | 79.75 | 78.07 | 88.08 |
| WV-20818 | 83.94 | 81.38 | 73.55 | 78.85 |
| WV-20819 | 80.11 | 81.07 | 95.80 | 81.19 |
| WV-20820 | 91.95 | 84.50 | 78.73 | 87.11 |
| WV-20821 | 94.07 | 91.00 | 83.79 | 86.12 |
| WV-20822 | 48.79 | 53.49 | 72.52 | 66.12 |
| WV-20823 | 99.58 | 88.01 | 70.37 | 75.67 |
| WV-20824 | 95.27 | 106.47 | 63.41 | 56.95 |
| WV-20825 | 49.82 | 52.38 | 63.47 | 66.34 |
| WV-20826 | 79.46 | 77.70 | 63.08 | 60.70 |
| WV-20827 | 90.11 | 108.10 | 54.42 | 58.05 |
| WV-20828 | 111.68 | 103.78 | 43.34 | 39.60 |

TABLE 1C

Activities of oligonucleotide compositions. Certain oligonucleotide compositions were tested in a luciferase reporting assay (procedures as shown in Example 3). Oligonucleotide were tested at a concentration of 5 nM (wt) and 1 nm (mt). WV-993 is non-targeting.

| ID | 5 nM Wt | | 1 nM Mt | |
|---|---|---|---|---|
| H2O | 101.39 | 99.86 | 92.56 | 90.46 |
| WV-993 | 118.07 | 104.72 | 95.96 | 102.34 |
| WV-20868 | 63.54 | 55.86 | 69.76 | 50.96 |
| WV-20829 | 80.05 | 67.79 | 72.53 | 73.60 |
| WV-20830 | 58.65 | 74.13 | 68.83 | 85.29 |
| WV-20831 | 65.40 | 64.21 | 68.54 | 61.17 |
| WV-20832 | 72.16 | 74.14 | 77.21 | 76.80 |
| WV-20833 | 87.29 | 73.56 | 70.23 | 83.69 |
| WV-20834 | 76.50 | 71.71 | 68.36 | 68.49 |
| WV-20835 | 69.14 | 69.97 | 81.56 | 78.78 |
| WV-20836 | 81.12 | 73.19 | 73.43 | 71.33 |
| WV-20837 | 76.83 | 69.43 | 68.34 | 72.37 |
| WV-20838 | 61.76 | 72.94 | 92.33 | 99.89 |
| WV-20839 | 102.32 | 84.49 | 86.06 | 86.45 |
| WV-20840 | 93.30 | 81.73 | 76.70 | 85.42 |
| WV-20841 | 48.35 | 45.17 | 67.11 | 71.62 |
| WV-20842 | 72.93 | 85.73 | 67.00 | 70.31 |
| WV-20843 | 103.87 | 98.98 | 65.44 | 60.43 |
| WV-20844 | 52.33 | 48.13 | 51.20 | 52.95 |
| WV-20845 | 97.90 | 82.06 | 50.09 | 58.79 |
| WV-20846 | 109.20 | 108.96 | 47.66 | 45.90 |
| WV-20847 | 124.68 | 102.96 | 30.67 | 32.83 |

TABLE 1D

Activities of certain oligonucleotide compositions. Certain oligonucleotide compositions were tested in a luciferase reporting assay (procedures as shown in Example 3). Oligonucleotide were tested at a concentration of 5 nM (wt) and 1 nm (mt). WV-993 is non-targeting.

| ID | 5 nM Wt | | 1 nm Mt | |
|---|---|---|---|---|
| H2O | 101.39 | 99.86 | 92.56 | 90.46 |
| WV-993 | 118.07 | 104.72 | 95.96 | 102.34 |
| WV-20869 | 58.84 | 64.52 | 63.34 | 66.62 |
| WV-20849 | 77.77 | 75.41 | 72.08 | 81.66 |
| WV-20850 | 66.95 | 81.49 | 66.18 | 73.22 |
| WV-20851 | 90.51 | 86.64 | 101.49 | 94.20 |
| WV-20852 | 83.63 | 79.56 | 78.53 | 76.49 |
| WV-20853 | 90.84 | 84.38 | 80.86 | 75.49 |
| WV-20854 | 71.00 | 77.61 | 85.86 | 88.04 |
| WV-20855 | 77.75 | 67.35 | 75.73 | 84.22 |
| WV-20856 | 94.33 | 89.60 | 78.35 | 73.57 |
| WV-20857 | 93.92 | 79.25 | 81.02 | 99.64 |
| WV-20858 | 77.67 | 79.67 | 100.57 | 98.34 |
| WV-20859 | 88.18 | 84.42 | 92.45 | 89.54 |
| WV-20860 | 89.71 | 92.94 | 92.69 | 80.09 |
| WV-20861 | 112.70 | 85.19 | 71.74 | 103.13 |
| WV-20862 | 87.73 | 90.56 | 82.44 | 79.57 |
| WV-20863 | 101.26 | 75.85 | 73.80 | 74.43 |
| WV-20864 | 74.94 | 81.10 | 70.00 | 60.61 |
| WV-20865 | 89.59 | 74.30 | 44.72 | 52.56 |

TABLE 2

Activities of certain oligonucleotide compositions. Certain oligonucleotide compositions were tested in a luciferase reporting assay (procedures as shown in Example 3). Oligonucleotide were tested at a concentration of 5 nM (wt) and 1 nm (mt).

| ID | 5 nM Wt | | 1 nm Mt | |
|---|---|---|---|---|
| H2O | 118.07 | 104.72 | 95.96 | 102.34 |
| WV-993 | 105.57 | 100.50 | 105.54 | 105.98 |
| WV-20870 | 63.86 | 66.30 | 82.59 | 73.72 |

TABLE 2-continued

Activities of certain oligonucleotide compositions. Certain oligonucleotide compositions were tested in a luciferase reporting assay (procedures as shown in Example 3). Oligonucleotide were tested at a concentration of 5 nM (wt) and 1 nm (mt).

| ID | 5 nM Wt | | 1 nm Mt | |
|---|---|---|---|---|
| WV-20866 | 58.40 | 58.41 | 72.77 | 75.09 |
| WV-20807 | 96.04 | 80.57 | 73.75 | 81.82 |
| WV-20808 | 94.83 | 86.34 | 68.08 | 77.10 |
| WV-20809 | | | | |
| WV-20867 | 58.92 | 61.70 | 56.74 | 56.49 |
| WV-20826 | 79.46 | 77.70 | 63.08 | 60.70 |
| WV-20827 | 90.11 | 108.10 | 54.42 | 58.05 |
| WV-20828 | 111.68 | 103.78 | 43.34 | 39.60 |

TABLE 2-continued

Activities of certain oligonucleotide compositions. Certain oligonucleotide compositions were tested in a luciferase reporting assay (procedures as shown in Example 3). Oligonucleotide were tested at a concentration of 5 nM (wt) and 1 nm (mt).

| ID | 5 nM Wt | | 1 nm Mt | |
|---|---|---|---|---|
| WV-20868 | 63.54 | 55.86 | 69.76 | 50.96 |
| WV-20845 | 97.90 | 82.06 | 50.09 | 58.79 |
| WV-20846 | 109.20 | 108.96 | 47.66 | 45.90 |
| WV-20847 | 124.68 | 102.96 | 30.67 | 32.83 |
| WV-20869 | 58.84 | 64.52 | 63.34 | 66.62 |
| WV-20864 | 74.94 | 81.10 | 70.00 | 60.61 |
| WV-20865 | 89.59 | 74.30 | 44.72 | 52.56 |

TABLE 3

Activities of certain oligonucleotide compositions. Certain oligonucleotide compositions were tested in a luciferase reporting assay (procedures as shown in Example 3). Oligonucleotide were tested at multiple concentrations (shown as Log dose nM).

| | Conc. [Log (dose nM)] | Rho-Wt | | | RhoP23H | | |
|---|---|---|---|---|---|---|---|
| WV-993 | 0.92 | 112.24 | 118.31 | 123.72 | 114.67 | 119.46 | 108.34 |
| | 0.44 | 112.49 | 115.00 | 135.04 | 121.79 | 115.23 | 105.74 |
| | −0.03 | 103.60 | 107.55 | 143.20 | 98.18 | 117.39 | 108.30 |
| | −0.51 | 117.23 | 117.68 | 132.45 | 115.81 | 118.15 | 91.21 |
| | −0.99 | 115.28 | 121.35 | 111.13 | 103.65 | 109.66 | 100.58 |
| | −1.46 | 109.25 | 115.30 | 116.44 | 110.89 | 111.02 | 108.64 |
| | −1.94 | 114.90 | 118.15 | 108.76 | 119.04 | 110.88 | 114.86 |
| WV-20845 | 0.92 | 111.17 | 108.31 | 135.94 | 12.58 | 14.26 | 12.72 |
| | 0.44 | 96.43 | 93.27 | 116.38 | 15.02 | 18.93 | 18.80 |
| | −0.03 | 81.47 | 90.97 | 97.97 | 30.66 | 39.18 | 36.03 |
| | −0.51 | 95.47 | 83.12 | 114.01 | 59.04 | 64.03 | 62.74 |
| | −0.99 | 103.33 | 96.57 | 103.33 | 83.80 | 89.13 | 85.41 |
| | −1.46 | 107.14 | 107.03 | 105.79 | 90.03 | 94.24 | 98.06 |
| | −1.94 | 100.26 | 102.15 | 107.99 | 107.93 | 100.94 | 99.01 |
| WV-20870 | 0.92 | 34.24 | 40.84 | 42.27 | 10.10 | 10.98 | 10.84 |
| | 0.44 | 53.99 | 53.53 | 62.83 | 17.63 | 20.29 | 21.37 |
| | −0.03 | 61.46 | 74.88 | 92.26 | 36.20 | 48.55 | 47.00 |
| | −0.51 | 91.15 | 91.75 | 107.05 | 68.41 | 78.52 | 68.12 |
| | −0.99 | 105.05 | 100.76 | 119.32 | 81.48 | 93.61 | 86.98 |
| | −1.46 | 115.17 | 124.40 | 112.83 | 97.96 | 100.38 | 106.58 |
| | −1.94 | 112.82 | 117.58 | 95.93 | 100.59 | 107.23 | 101.87 |
| WV-20865 | 1.40 | 148.49 | 143.40 | 150.67 | 8.91 | 8.31 | 6.65 |
| | 0.92 | 100.21 | 97.09 | 118.11 | 2.03 | 2.73 | 2.79 |
| | 0.44 | 96.14 | 94.40 | 111.89 | 5.63 | 6.87 | 8.06 |
| | −0.03 | 97.94 | 103.47 | 122.46 | 15.40 | 21.33 | 25.17 |
| | −0.51 | 92.27 | 95.84 | 109.87 | 40.60 | 48.74 | 50.64 |
| | −0.99 | 101.14 | 105.63 | 114.33 | 68.31 | 78.67 | 77.33 |
| | −1.46 | 117.20 | 108.66 | 100.37 | 82.61 | 94.92 | 96.38 |
| | −1.94 | 96.16 | 101.93 | 105.60 | 97.29 | 105.18 | 102.01 |

TABLE 4

Activities of certain oligonucleotide compositions. Certain oligonucleotide compositions were tested in a luciferase reporting assay (procedures as shown in Example 3). Oligonucleotide were tested at multiple concentrations (shown as Log dose nM).

| ID | Conc. [Log (dose nM)] | Rho-Wt | | | RhoP23H | | |
|---|---|---|---|---|---|---|---|
| WV-20808 | 0.92 | 127.15 | 109.39 | 141.59 | 44.44 | 45.07 | 48.12 |
| | 0.44 | 107.33 | 112.27 | 119.10 | 52.44 | 53.57 | 56.73 |
| | −0.03 | 81.48 | 90.59 | 95.50 | 54.93 | 62.13 | 64.57 |
| | −0.51 | 92.14 | 95.56 | 106.41 | 74.15 | 77.24 | 70.41 |
| | −0.99 | 96.55 | 102.96 | 105.44 | 94.51 | 89.38 | 84.86 |

TABLE 4-continued

Activities of certain oligonucleotide compositions. Certain oligonucleotide compositions were tested in a luciferase reporting assay (procedures as shown in Example 3). Oligonucleotide were tested at multiple concentrations (shown as Log dose nM).

| ID | Conc. [Log (dose nM)] | Rho-Wt | | | RhoP23H | | |
|---|---|---|---|---|---|---|---|
| | −1.46 | 97.63 | 98.54 | 92.55 | 87.58 | 101.19 | 98.93 |
| | −1.94 | 91.39 | 101.84 | 108.29 | 99.08 | 95.48 | 89.22 |
| WV-20827 | 0.92 | 140.10 | 125.18 | 146.21 | 15.34 | 13.43 | 14.31 |
| | 0.44 | 110.25 | 115.49 | 136.86 | 18.11 | 18.74 | 21.34 |
| | −0.03 | 92.05 | 97.48 | 106.19 | 26.75 | 33.45 | 31.27 |
| | −0.51 | 95.77 | 98.86 | 98.53 | 50.54 | 52.16 | 54.16 |
| | −0.99 | 95.06 | 98.94 | 104.33 | 75.33 | 80.15 | 74.96 |
| | −1.46 | 99.52 | 108.13 | 99.37 | 90.01 | 87.37 | 94.54 |
| | −1.94 | 98.53 | 94.86 | 91.70 | 96.68 | 94.84 | 89.74 |
| WV-20828 | 0.92 | 179.98 | 132.57 | 181.12 | 5.58 | 5.56 | 3.74 |
| | 0.44 | 159.51 | 134.53 | 147.88 | 4.78 | 5.44 | 6.49 |
| | −0.03 | 111.08 | 116.32 | 124.46 | 12.25 | 17.27 | 15.62 |
| | −0.51 | 93.52 | 94.29 | 100.96 | 34.21 | 41.86 | 42.17 |
| | −0.99 | 99.12 | 98.53 | 103.99 | 65.62 | 60.62 | 63.95 |
| | −1.46 | 96.52 | 106.92 | 95.03 | 77.31 | 93.83 | 81.82 |
| | −1.94 | 96.89 | 104.61 | 106.12 | 93.62 | 96.85 | 88.85 |

TABLE 5

Activities of certain oligonucleotide compositions. Certain oligonucleotide compositions were tested in a luciferase reporting assay (procedures as shown in Example 3). Oligonucleotide were tested at multiple concentrations (shown as Log dose nM).

| ID | Conc. [Log (dose nM)] | Rho-Wt | | | RhoP23H | | |
|---|---|---|---|---|---|---|---|
| WV-20843 | 0.92 | 152.68 | 124.61 | 154.99 | 3.45 | 3.73 | 4.08 |
| | 0.44 | 110.27 | 105.17 | 131.63 | 8.57 | 10.05 | 11.93 |
| | −0.03 | 109.33 | 102.25 | 109.12 | 26.92 | 38.34 | 37.23 |
| | −0.51 | 103.76 | 102.56 | 107.36 | 57.00 | 63.86 | 62.76 |
| | −0.99 | 106.94 | 116.57 | 103.68 | 83.19 | 83.52 | 85.61 |
| | −1.46 | 103.73 | 111.91 | 96.59 | 90.43 | 94.19 | 104.68 |
| | −1.94 | 99.84 | 91.81 | 109.39 | 99.50 | 108.28 | 104.37 |
| WV-20844 | 0.92 | 45.97 | 40.32 | 50.47 | 12.69 | 14.14 | 12.67 |
| | 0.44 | 46.62 | 43.95 | 53.27 | 14.00 | 17.54 | 21.77 |
| | −0.03 | 53.54 | 55.72 | 57.07 | 26.18 | 30.22 | 33.31 |
| | −0.51 | 75.41 | 73.58 | 86.80 | 52.19 | 56.17 | 56.50 |
| | −0.99 | 93.58 | 91.26 | 91.76 | 76.31 | 83.33 | 74.66 |
| | −1.46 | 101.11 | 94.97 | 103.44 | 96.80 | 98.88 | 92.78 |
| | −1.94 | 100.36 | 96.25 | 99.55 | 95.66 | 98.45 | 100.35 |
| WV-20845 | 0.92 | 111.17 | 108.31 | 135.94 | 12.58 | 14.26 | 12.72 |
| | 0.44 | 96.43 | 93.27 | 116.38 | 15.02 | 18.93 | 18.80 |
| | −0.03 | 81.47 | 90.97 | 97.97 | 30.66 | 39.18 | 36.03 |
| | −0.51 | 95.47 | 83.12 | 114.01 | 59.04 | 64.03 | 62.74 |
| | −0.99 | 103.33 | 96.57 | 103.33 | 83.80 | 89.13 | 85.41 |
| | −1.46 | 107.14 | 107.03 | 105.79 | 90.03 | 94.24 | 98.06 |
| | −1.94 | 100.26 | 102.15 | 107.99 | 107.93 | 100.94 | 99.01 |
| WV-20846 | 0.92 | 157.94 | 119.55 | 178.55 | 6.52 | 5.77 | 4.91 |
| | 0.44 | 119.58 | 112.64 | 135.30 | 7.54 | 8.27 | 9.21 |
| | −0.03 | 96.35 | 100.73 | 117.65 | 16.64 | 22.60 | 23.69 |
| | −0.51 | 105.28 | 92.58 | 110.66 | 43.61 | 53.64 | 48.81 |
| | −0.99 | 111.14 | 114.71 | 116.89 | 68.30 | 76.29 | 79.83 |
| | −1.46 | 102.24 | 106.17 | 104.93 | 91.08 | 89.02 | 91.96 |
| | −1.94 | 94.72 | 101.23 | 103.25 | 93.96 | 97.62 | 106.56 |
| WV-20847 | 0.92 | 143.17 | 121.18 | 167.72 | 3.76 | 4.10 | 4.96 |
| | 0.44 | 127.94 | 125.33 | 150.87 | 3.38 | 2.89 | 4.34 |
| | −0.03 | 112.70 | 119.50 | 133.95 | 10.21 | 13.61 | 13.07 |
| | −0.51 | 109.49 | 104.39 | 105.30 | 32.69 | 38.64 | 36.03 |
| | −0.99 | 108.28 | 117.62 | 118.23 | 60.56 | 63.66 | 68.98 |
| | −1.46 | 101.43 | 108.02 | 102.92 | 78.51 | 82.01 | 96.86 |
| | −1.94 | 90.86 | 95.38 | 104.21 | 99.81 | 112.11 | 96.62 |

TABLE 6

Activities of certain oligonucleotide compositions. Certain oligonucleotide compositions were tested in a luciferase reporting assay (procedures as shown in Example 3). Oligonucleotide were tested at multiple concentrations (shown as Log dose nM).

| ID | Conc. [Log (dose nM)] | Rho-Wt | | | RhoP23H | | |
|---|---|---|---|---|---|---|---|
| WV-20865 | 0.92 | 100.21 | 97.09 | 118.11 | 2.03 | 2.73 | 2.79 |
| | 0.44 | 96.14 | 94.40 | 111.89 | 5.63 | 6.87 | 8.06 |
| | −0.03 | 97.94 | 103.47 | 122.46 | 15.40 | 21.33 | 25.17 |
| | −0.51 | 92.27 | 95.84 | 109.87 | 40.60 | 48.74 | 50.64 |
| | −0.99 | 101.14 | 105.63 | 114.33 | 68.31 | 78.67 | 77.33 |
| | −1.46 | 117.20 | 108.66 | 100.37 | 82.61 | 94.92 | 96.38 |
| | −1.94 | 96.16 | 101.93 | 105.60 | 97.29 | 105.18 | 102.01 |

TABLE 7A

Activities of certain oligonucleotide compositions. Certain oligonucleotide compositions were tested in a luciferase reporting assay (procedures as shown in Example 3) for RHO wt. Oligonucleotide were tested at multiple concentrations (shown as Log dose nM).

| | WV-21503 | | WV-21504 | | WV-21505 | | WV-23415 | | WV-993 | |
|---|---|---|---|---|---|---|---|---|---|---|
| 1.00 | 80.52 | 90.65 | 76.88 | 101.18 | 76.73 | 88.73 | 32.82 | 50.67 | 100.52 | 116.33 |
| 0.60 | 85.93 | 93.12 | 78.15 | 78.47 | 74.27 | 82.80 | 36.03 | 30.81 | 95.43 | 96.05 |
| 0.20 | 86.00 | 93.59 | 76.94 | 88.31 | 77.65 | 90.50 | 41.28 | 39.76 | 100.04 | 103.48 |
| −0.19 | 81.10 | 91.57 | 77.42 | 95.69 | 90.53 | 89.74 | 60.25 | 61.71 | 91.89 | 100.21 |
| −0.59 | 79.93 | 86.60 | 72.43 | 88.95 | 84.41 | 99.42 | 58.36 | 63.79 | 78.88 | 101.93 |
| −0.99 | 76.21 | 91.37 | 86.98 | 96.72 | 87.38 | 103.69 | 79.29 | 77.95 | 86.79 | 99.78 |
| −1.39 | 79.17 | 100.31 | 80.59 | 104.10 | 88.96 | 96.11 | 89.18 | 94.28 | 93.00 | 100.40 |
| −1.79 | 78.69 | 96.05 | 89.24 | 101.20 | 73.37 | 102.62 | 84.52 | 94.46 | 104.12 | 114.65 |
| −2.18 | 85.05 | 109.69 | 104.16 | 109.75 | 87.42 | 117.78 | 87.28 | 102.69 | 89.39 | 110.45 |
| −2.58 | 89.39 | 113.27 | 95.07 | 114.89 | 97.61 | 102.58 | 98.64 | 110.97 | 101.85 | 105.65 |
| −2.98 | 102.60 | 103.14 | 107.89 | 119.34 | 100.75 | 127.91 | 105.93 | 110.99 | 101.26 | 119.01 |

TABLE 7B

Activities of certain oligonucleotide compositions. Certain oligonucleotide compositions were tested in a luciferase reporting assay (procedures as shown in Example 3) for RHO mt (P23H). Oligonucleotide were tested at multiple concentrations (shown as Log dose nM).

| | WV-21503 | | WV-21504 | | WV-21505 | | WV-23415 | | WV-993 | |
|---|---|---|---|---|---|---|---|---|---|---|
| 1.00 | 8.25 | 6.07 | 1.63 | 1.43 | 1.52 | 1.48 | 13.47 | 10.98 | 104.58 | 98.45 |
| 0.60 | 3.32 | 3.42 | 3.42 | 3.65 | 3.37 | 3.60 | 9.42 | 12.23 | 99.07 | 94.47 |
| 0.20 | 5.75 | 6.75 | 11.13 | 11.01 | 9.13 | 9.91 | 14.77 | 19.21 | 92.02 | 92.86 |
| −0.19 | 14.24 | 17.44 | 26.16 | 25.71 | 22.99 | 21.31 | 29.79 | 37.66 | 92.74 | 81.57 |
| −0.59 | 42.99 | 42.02 | 47.64 | 44.32 | 43.24 | 43.81 | 43.98 | 57.56 | 108.61 | 92.10 |
| −0.99 | 57.03 | 62.64 | 62.77 | 60.14 | 58.49 | 60.36 | 64.75 | 77.95 | 90.68 | 97.01 |
| −1.39 | 76.19 | 76.19 | 80.97 | 75.93 | 73.53 | 64.32 | 74.41 | 79.63 | 85.15 | 91.27 |
| −1.79 | 90.29 | 81.44 | 92.29 | 84.13 | 93.89 | 77.39 | 86.67 | 96.95 | 103.87 | 100.28 |
| −2.18 | 94.51 | 94.14 | 89.40 | 90.27 | 96.31 | 88.11 | 91.41 | 107.95 | 102.15 | 89.01 |
| −2.58 | 106.15 | 102.60 | 83.34 | 104.06 | 97.18 | 97.69 | 100.96 | 103.64 | 93.39 | 105.53 |
| −2.98 | 105.47 | 106.16 | 111.21 | 110.48 | 115.54 | 87.98 | 105.11 | 122.12 | 118.54 | 105.50 |

TABLE 7C

Activities of certain oligonucleotide compositions. Certain oligonucleotide compositions were tested in a luciferase reporting assay (procedures as shown in Example 3) for RHO mt (P23H). Oligonucleotide were tested at multiple concentrations, IC50 (nM) is shown in the following table.

| ID | Allele Diff | IC 50 P23H (nM) |
|---|---|---|
| WV-20847 | Yes | 0.14 |
| WV-21503 | Yes | 0.13 |
| WV-21504 | Yes | 0.20 |

TABLE 7C-continued

Activities of certain oligonucleotide compositions. Certain oligonucleotide compositions were tested in a luciferase reporting assay (procedures as shown in Example 3) for RHO mt (P23H). Oligonucleotide were tested at multiple concentrations, IC50 (nM) is shown in the following table.

| ID | Allele Diff | IC 50 P23H (nM) |
|---|---|---|
| WV-21505 | Yes | 0.16 |
| WV-23415 | No | 0.17 |

TABLE 8A

Activities of certain oligonucleotide compositions. Certain oligonucleotide compositions were tested in a luciferase reporting assay (procedures as shown in Example 3) for RHO wt. Oligonucleotide were tested at multiple concentrations (shown as Log dose nM).

| Conc. [Log (dose nM)] | WV-23651 | | WV-23652 | | WV-23653 | | WV-23654 | | WV-23655 | |
|---|---|---|---|---|---|---|---|---|---|---|
| 0.95 | 127.37 | 108.66 | 25.77 | 20.88 | 14.07 | 14.52 | 96.24 | 104.34 | 88.00 | 94.65 |
| 0.48 | 75.07 | 101.27 | 28.40 | 33.60 | 19.74 | 20.27 | 82.19 | 80.26 | 78.42 | 68.64 |
| 0.00 | 90.97 | 86.36 | 47.73 | 46.47 | 38.95 | 36.50 | 84.88 | 80.46 | 93.78 | 77.19 |
| −0.48 | 78.99 | 93.84 | 62.90 | 70.42 | 60.78 | 53.97 | 85.93 | 77.01 | 83.73 | 74.78 |
| −0.95 | 96.59 | 97.59 | 70.50 | 84.45 | 60.32 | 77.25 | 75.44 | 77.56 | 76.29 | 79.71 |
| −1.43 | 99.25 | 109.34 | 101.87 | 93.12 | 80.38 | 89.82 | 92.72 | 99.41 | 93.36 | 92.14 |
| −1.91 | 93.92 | 112.69 | 89.52 | 116.34 | 92.90 | 89.58 | 95.56 | 79.32 | 91.80 | 86.96 |
| −2.39 | 103.24 | 93.16 | 105.65 | 84.56 | 109.86 | 81.38 | 107.01 | 90.13 | 100.30 | 95.39 |

| Conc. [Log (dose nM)] | WV-23656 | | WV-23657 | | WV-23658 | | WV-23659 | | WV-23660 | |
|---|---|---|---|---|---|---|---|---|---|---|
| 0.95 | 51.01 | 50.51 | 93.43 | 111.35 | 134.05 | 133.14 | 94.98 | 78.37 | 84.80 | 76.53 |
| 0.48 | 45.17 | 46.05 | 75.33 | 75.36 | 115.37 | 123.76 | 63.34 | 77.03 | 78.84 | 80.50 |
| 0.00 | 54.56 | 60.86 | 87.42 | 89.53 | 102.92 | 95.68 | 90.59 | 82.88 | 93.36 | 89.47 |
| −0.48 | 69.04 | 67.05 | 80.10 | 97.22 | 110.82 | 92.96 | 106.37 | 84.49 | 125.62 | 86.25 |
| −0.95 | 68.09 | 66.40 | 68.83 | 84.97 | 80.45 | 81.36 | 76.61 | 81.93 | 86.23 | 87.34 |
| −1.43 | 89.62 | 83.18 | 80.71 | 86.74 | 99.27 | 83.69 | 90.38 | 98.68 | 95.14 | 86.99 |
| −1.91 | 95.10 | 95.67 | 103.03 | 105.63 | 98.31 | 94.71 | 86.78 | 102.97 | 99.96 | 95.27 |
| −2.39 | 97.78 | 89.51 | 96.35 | 89.58 | 95.78 | 79.44 | 107.69 | 98.48 | 93.22 | 95.74 |

TABLE 8B

Activities of certain oligonucleotide compositions. Certain oligonucleotide compositions were tested in a luciferase reporting assay (procedures as shown in Example 3) for RHO mt (P23H). Oligonucleotide were tested at multiple concentrations (shown as Log dose nM).

| Conc. [Log (dose nM)] | WV-23651 | | WV-23652 | | WV-23653 | | WV-23654 | | WV-23655 | |
|---|---|---|---|---|---|---|---|---|---|---|
| 0.95 | 28.04 | 30.90 | 2.10 | 1.73 | 2.51 | 2.54 | 3.85 | 2.97 | 26.92 | 26.95 |
| 0.48 | 33.69 | 32.81 | 5.39 | 4.16 | 6.60 | 5.55 | 7.74 | 6.78 | 36.43 | 27.41 |
| 0.00 | 51.95 | 52.84 | 18.55 | 18.52 | 21.93 | 17.81 | 27.31 | 22.45 | 52.20 | 40.93 |
| −0.48 | 73.71 | 62.37 | 45.73 | 35.85 | 45.81 | 35.25 | 46.61 | 47.08 | 64.69 | 60.37 |
| −0.95 | 90.07 | 87.68 | 66.48 | 65.27 | 78.48 | 56.10 | 63.21 | 67.32 | 92.25 | 75.95 |
| −1.43 | 94.79 | 89.34 | 89.34 | 78.57 | 81.31 | 71.84 | 80.26 | 73.82 | 91.69 | 70.16 |
| −1.91 | 103.37 | 91.20 | 89.23 | 94.62 | 101.97 | 89.01 | 91.76 | 99.77 | 86.04 | 86.90 |
| −2.39 | 95.35 | 88.52 | 101.22 | 73.20 | 93.26 | 82.79 | 93.37 | 80.85 | 95.76 | 81.34 |

| Conc. [Log (dose nM)] | WV-23656 | | WV-23657 | | WV-23658 | | WV-23659 | | WV-23660 | |
|---|---|---|---|---|---|---|---|---|---|---|
| 0.95 | 14.40 | 13.77 | 11.88 | 13.74 | 5.24 | 5.23 | 49.51 | 50.35 | 59.58 | 51.32 |
| 0.48 | 21.71 | 17.66 | 17.06 | 19.69 | 6.18 | 6.32 | 46.74 | 48.66 | 59.96 | 57.48 |
| 0.00 | 42.63 | 35.80 | 40.88 | 39.01 | 18.07 | 16.56 | 58.44 | 49.31 | 74.87 | 84.62 |
| −0.48 | 52.94 | 59.30 | 62.05 | 60.38 | 42.42 | 40.23 | 83.91 | 86.22 | 94.17 | 77.43 |
| −0.95 | 77.69 | 65.79 | 87.08 | 71.67 | 65.54 | 68.84 | 94.62 | 87.32 | 103.85 | 98.50 |
| −1.43 | 87.04 | 75.51 | 88.53 | 78.28 | 80.68 | 82.04 | 89.55 | 96.27 | 90.10 | 116.26 |

TABLE 8B-continued

Activities of certain oligonucleotide compositions. Certain oligonucleotide compositions were tested in a luciferase reporting assay (procedures as shown in Example 3) for RHO mt (P23H). Oligonucleotide were tested at multiple concentrations (shown as Log dose nM).

| | | | | | | | | | | |
|---|---|---|---|---|---|---|---|---|---|---|
| −1.91 | 94.14 | 96.13 | 102.77 | 94.43 | 95.25 | 89.22 | 107.54 | 90.59 | 107.90 | 95.72 |
| −2.39 | 108.01 | 87.24 | 97.22 | 84.39 | 99.01 | 75.49 | 112.61 | 88.05 | 100.91 | 87.83 |

TABLE 9

Activities of certain oligonucleotide compositions. Certain oligonucleotide compositions were tested in a luciferase reporting assay (procedures as shown in Example 3). Oligonucleotide were tested at multiple concentrations (shown as Log dose nM).

| | Conc. [Log (dose nM)] | Rho Wt | | RhoP23H | |
|---|---|---|---|---|---|
| WV-23651 | 0.95 | 127.37 | 108.66 | 28.04 | 30.90 |
| | 0.48 | 75.07 | 101.27 | 33.69 | 32.81 |
| | 0.00 | 90.97 | 86.36 | 51.95 | 52.84 |
| | −0.48 | 78.99 | 93.84 | 73.71 | 62.37 |
| | −0.95 | 96.59 | 97.59 | 90.07 | 87.68 |
| | −1.43 | 99.25 | 109.34 | 94.79 | 89.34 |
| | −1.91 | 93.92 | 112.69 | 103.37 | 91.20 |
| | −2.39 | 103.24 | 93.16 | 95.35 | 88.52 |
| WV-23652 | 0.95 | 25.77 | 20.88 | 2.10 | 1.73 |
| | 0.48 | 28.40 | 33.60 | 5.39 | 4.16 |
| | 0.00 | 47.73 | 46.47 | 18.55 | 18.52 |
| | −0.48 | 62.90 | 70.42 | 45.73 | 35.85 |
| | −0.95 | 70.50 | 84.45 | 66.48 | 65.27 |
| | −1.43 | 101.87 | 93.12 | 89.34 | 78.57 |
| | −1.91 | 89.52 | 116.34 | 89.23 | 94.62 |
| | −2.39 | 105.65 | 84.56 | 101.22 | 73.20 |
| WV-23653 | 0.95 | 14.07 | 14.52 | 2.51 | 2.54 |
| | 0.48 | 19.74 | 20.27 | 6.60 | 5.55 |
| | 0.00 | 38.95 | 36.50 | 21.93 | 17.81 |
| | −0.48 | 60.78 | 53.97 | 45.81 | 35.25 |
| | −0.95 | 60.32 | 77.25 | 78.48 | 56.10 |
| | −1.43 | 80.38 | 89.82 | 81.31 | 71.84 |
| | −1.91 | 92.90 | 89.58 | 101.97 | 89.01 |
| | −2.39 | 109.86 | 81.38 | 93.26 | 82.79 |
| WV-23654 | 0.95 | 96.24 | 104.34 | 3.85 | 2.97 |
| | 0.48 | 82.19 | 80.26 | 7.74 | 6.78 |
| | 0.00 | 84.88 | 80.46 | 27.31 | 22.45 |
| | −0.48 | 85.93 | 77.01 | 46.61 | 47.08 |
| | −0.95 | 75.44 | 77.56 | 63.21 | 67.32 |
| | −1.43 | 92.72 | 99.41 | 80.26 | 73.82 |
| | −1.91 | 95.56 | 79.32 | 91.76 | 99.77 |
| | −2.39 | 107.01 | 90.13 | 93.37 | 80.85 |
| WV-23655 | 0.95 | 88.00 | 94.65 | 26.92 | 26.95 |
| | 0.48 | 78.42 | 68.64 | 36.43 | 27.41 |
| | 0.00 | 93.78 | 77.19 | 52.20 | 40.93 |
| | −0.48 | 83.73 | 74.78 | 64.69 | 60.37 |
| | −0.95 | 76.29 | 79.71 | 92.25 | 75.95 |
| | −1.43 | 93.36 | 92.14 | 91.69 | 70.16 |
| | −1.91 | 91.80 | 86.96 | 86.04 | 86.90 |
| | −2.39 | 100.30 | 95.39 | 95.76 | 81.34 |

TABLE 9-continued

Activities of certain oligonucleotide compositions. Certain oligonucleotide compositions were tested in a luciferase reporting assay (procedures as shown in Example 3). Oligonucleotide were tested at multiple concentrations (shown as Log dose nM).

| | Conc. [Log (dose nM)] | Rho Wt | | RhoP23H | |
|---|---|---|---|---|---|
| WV-23656 | 0.95 | 51.01 | 50.51 | 14.40 | 13.77 |
| | 0.48 | 45.17 | 46.05 | 21.71 | 17.66 |
| | 0.00 | 54.56 | 60.86 | 42.63 | 35.80 |
| | −0.48 | 69.04 | 67.05 | 52.94 | 59.30 |
| | −0.95 | 68.09 | 66.40 | 77.69 | 65.79 |
| | −1.43 | 89.62 | 83.18 | 87.04 | 75.51 |
| | −1.91 | 95.10 | 95.67 | 94.14 | 96.13 |
| | −2.39 | 97.78 | 89.51 | 108.01 | 87.24 |
| WV-23657 | 0.95 | 93.43 | 111.35 | 11.88 | 13.74 |
| | 0.48 | 75.33 | 75.36 | 17.06 | 19.69 |
| | 0.00 | 87.42 | 89.53 | 40.88 | 39.01 |
| | −0.48 | 80.10 | 97.22 | 62.05 | 60.38 |
| | −0.95 | 68.83 | 84.97 | 87.08 | 71.67 |
| | −1.43 | 80.71 | 86.74 | 88.53 | 78.28 |
| | −1.91 | 103.03 | 105.63 | 102.77 | 94.43 |
| | −2.39 | 96.35 | 89.58 | 97.22 | 84.39 |
| WV-23658 | 0.95 | 134.05 | 133.14 | 5.24 | 5.23 |
| | 0.48 | 115.37 | 123.76 | 6.18 | 6.32 |
| | 0.00 | 102.92 | 95.68 | 18.07 | 16.56 |
| | −0.48 | 110.82 | 92.96 | 42.42 | 40.23 |
| | −0.95 | 80.45 | 81.36 | 65.54 | 68.84 |
| | −1.43 | 99.27 | 83.69 | 80.68 | 82.04 |
| | −1.91 | 98.31 | 94.71 | 95.25 | 89.22 |
| | −2.39 | 95.78 | 79.44 | 99.01 | 75.49 |
| WV-23659 | 0.95 | 94.98 | 78.37 | 49.51 | 50.35 |
| | 0.48 | 63.34 | 77.03 | 46.74 | 48.66 |
| | 0.00 | 90.59 | 82.88 | 58.44 | 49.31 |
| | −0.48 | 106.37 | 84.49 | 83.91 | 86.22 |
| | −0.95 | 76.61 | 81.93 | 94.62 | 87.32 |
| | −1.43 | 90.38 | 98.68 | 89.55 | 96.27 |
| | −1.91 | 86.78 | 102.97 | 107.54 | 90.59 |
| | −2.39 | 107.69 | 98.48 | 112.61 | 88.05 |
| WV-23660 | 0.95 | 84.80 | 76.53 | 59.58 | 51.32 |
| | 0.48 | 78.84 | 80.50 | 59.96 | 57.48 |
| | 0.00 | 93.36 | 89.47 | 74.87 | 84.62 |
| | −0.48 | 125.62 | 86.25 | 94.17 | 77.43 |
| | −0.95 | 86.23 | 87.34 | 103.85 | 98.50 |
| | −1.43 | 95.14 | 86.99 | 90.10 | 116.26 |
| | −1.91 | 99.96 | 95.27 | 107.90 | 95.72 |
| | −2.39 | 93.22 | 95.74 | 100.91 | 87.83 |

TABLE 10A

Activities of certain oligonucleotide compositions. Certain oligonucleotide compositions were tested in a luciferase reporting assay (procedures as shown in Example 3) for RHO wt. Oligonucleotide were tested at multiple concentrations (shown as Log dose nM).

| Conc. [Log (dose nM)] | WV-23661 | | WV-23662 | | WV-23663 | | WV-23664 | | WV-23665 | |
|---|---|---|---|---|---|---|---|---|---|---|
| 0.95 | 73.12 | 81.31 | 16.13 | 19.24 | 20.54 | 22.47 | 65.96 | 76.27 | 68.48 | 70.88 |
| 0.48 | 78.02 | 116.66 | 30.65 | 45.98 | 31.87 | 43.68 | 72.68 | 90.92 | 68.25 | 81.71 |
| 0.00 | 105.01 | 95.48 | 59.17 | 54.91 | 53.86 | 60.81 | 89.56 | 88.53 | 76.93 | 91.02 |

TABLE 10A-continued

Activities of certain oligonucleotide compositions. Certain oligonucleotide compositions were tested in a luciferase reporting assay (procedures as shown in Example 3) for RHO wt. Oligonucleotide were tested at multiple concentrations (shown as Log dose nM).

| | | | | | | | | | | |
|---|---|---|---|---|---|---|---|---|---|---|
| −0.48 | 81.80 | 95.26 | 70.92 | 70.65 | 65.89 | 81.94 | 72.50 | 86.34 | 73.13 | 85.76 |
| −0.95 | 89.67 | 130.83 | 79.59 | 113.07 | 88.49 | 109.86 | 86.40 | 84.80 | 78.91 | 93.81 |
| −1.43 | 86.05 | 92.54 | 90.08 | 91.15 | 86.44 | 86.93 | 85.97 | 88.30 | 80.68 | 100.85 |
| −1.91 | 112.48 | 96.66 | 80.98 | 97.03 | 77.92 | 93.55 | 88.16 | 102.58 | 82.86 | 104.37 |
| −2.39 | 85.71 | 109.49 | 105.80 | 101.00 | 90.09 | 100.88 | 103.86 | 103.31 | 92.54 | 108.43 |

| Conc. [Log (dose nM)] | WV-23666 | | WV-23667 | | WV-23668 | | WV-23669 | | WV-23415 | |
|---|---|---|---|---|---|---|---|---|---|---|
| 0.95 | 51.07 | 54.06 | 72.80 | 84.54 | 98.91 | 98.67 | 66.20 | 79.16 | 50.33 | 43.45 |
| 0.48 | 61.70 | 69.06 | 75.77 | 78.62 | 83.27 | 80.93 | 78.71 | 91.23 | 39.50 | 40.79 |
| 0.00 | 81.56 | 85.39 | 93.80 | 85.46 | 99.00 | 86.75 | 84.93 | 85.37 | 49.22 | 67.27 |
| −0.48 | 73.00 | 90.09 | 88.27 | 87.73 | 81.64 | 92.74 | 82.83 | 94.22 | 93.28 | 76.47 |
| −0.95 | 85.81 | 96.03 | 92.08 | 99.75 | 79.12 | 88.24 | 86.57 | 94.34 | 91.16 | 83.99 |
| −1.43 | 88.14 | 96.95 | 85.26 | 94.12 | 93.26 | 84.81 | 84.38 | 91.15 | 85.69 | 87.35 |
| −1.91 | 79.54 | 102.51 | 82.60 | 95.71 | 94.25 | 97.16 | 91.13 | 100.29 | 85.92 | 101.65 |
| −2.39 | 88.37 | 111.11 | 91.19 | 109.01 | 88.66 | 108.10 | 96.25 | 111.94 | 95.41 | 113.82 |

TABLE 10B

Activities of certain oligonucleotide compositions. Certain oligonucleotide compositions were tested in a luciferase reporting assay (procedures as shown in Example 3) for RHO mt (P23H). Oligonucleotide were tested at multiple concentrations (shown as Log dose nM).

| Conc. [Log (dose nM)] | WV-23661 | | WV-23662 | | WV-23663 | | WV-23664 | | WV-23665 | |
|---|---|---|---|---|---|---|---|---|---|---|
| 0.95 | 26.04 | 29.72 | 3.19 | 3.05 | 4.66 | 5.06 | 5.33 | 4.58 | 22.08 | 27.34 |
| 0.48 | 37.88 | 38.24 | 8.76 | 7.70 | 11.84 | 10.54 | 14.75 | 11.43 | 42.41 | 35.29 |
| 0.00 | 55.88 | 62.08 | 25.01 | 26.40 | 27.88 | 32.96 | 32.95 | 30.53 | 56.06 | 54.63 |
| −0.48 | 75.73 | 71.84 | 47.14 | 44.01 | 59.86 | 55.06 | 57.33 | 59.27 | 77.66 | 78.88 |
| −0.95 | 87.18 | 89.85 | 77.30 | 75.81 | 71.27 | 79.05 | 76.31 | 70.46 | 76.65 | 79.23 |
| −1.43 | 87.75 | 95.83 | 82.50 | 81.84 | 86.41 | 82.57 | 75.33 | 85.15 | 84.04 | 97.04 |
| −1.91 | 96.45 | 86.65 | 89.05 | 98.10 | 78.27 | 82.06 | 80.62 | 79.54 | 86.27 | 88.60 |
| −2.39 | 90.97 | 97.61 | 92.03 | 93.98 | 88.76 | 96.48 | 91.18 | 94.04 | 105.48 | 90.64 |

| Conc. [Log (dose nM)] | WV-23666 | | WV-23667 | | WV-23668 | | WV-23669 | | WV-23415 | |
|---|---|---|---|---|---|---|---|---|---|---|
| 0.95 | 18.08 | 19.95 | 11.63 | 13.90 | 3.07 | 3.54 | 33.25 | 44.26 | 13.81 | 21.11 |
| 0.48 | 39.08 | 33.89 | 27.18 | 22.72 | 9.41 | 7.79 | 60.59 | 47.90 | 20.17 | 17.97 |
| 0.00 | 56.53 | 58.54 | 41.92 | 47.87 | 27.35 | 24.63 | 71.49 | 61.26 | 32.14 | 29.18 |
| −0.48 | 77.58 | 70.11 | 71.08 | 65.74 | 49.79 | 49.21 | 83.60 | 81.40 | 49.02 | 47.94 |
| −0.95 | 81.29 | 94.70 | 79.75 | 85.51 | 61.43 | 71.46 | 92.11 | 92.35 | 81.20 | 74.62 |
| −1.43 | 83.07 | 79.13 | 84.81 | 102.43 | 73.26 | 93.66 | 81.52 | 102.56 | 79.05 | 97.05 |
| −1.91 | 89.93 | 82.11 | 94.57 | 81.91 | 79.96 | 92.87 | 83.17 | 85.70 | 79.03 | 93.34 |
| −2.39 | 93.75 | 99.92 | 108.41 | 94.63 | 94.81 | 91.67 | 97.76 | 98.71 | 89.50 | 110.89 |

TABLE 11

Activities of certain oligonucleotide compositions. Certain oligonucleotide compositions were tested in a luciferase reporting assay (procedures as shown in Example 3). Oligonucleotide were tested at multiple concentrations (shown as Log dose nM).

| | Conc. [Log (dose nM)] | RhoWt | | RhoP23H | |
|---|---|---|---|---|---|
| WV-23661 | 0.95 | 73.12 | 81.31 | 26.04 | 29.72 |
| | 0.48 | 78.02 | 116.66 | 37.88 | 38.24 |
| | 0.00 | 105.01 | 95.48 | 55.88 | 62.08 |
| | −0.48 | 81.80 | 95.26 | 75.73 | 71.84 |
| | −0.95 | 89.67 | 130.83 | 87.18 | 89.85 |
| | −1.43 | 86.05 | 92.54 | 87.75 | 95.83 |
| | −1.91 | 112.48 | 96.66 | 96.45 | 86.65 |
| | −2.39 | 85.71 | 109.49 | 90.97 | 97.61 |

TABLE 11-continued

Activities of certain oligonucleotide compositions. Certain oligonucleotide compositions were tested in a luciferase reporting assay (procedures as shown in Example 3). Oligonucleotide were tested at multiple concentrations (shown as Log dose nM).

| | Conc. [Log (dose nM)] | RhoWt | | RhoP23H | |
|---|---|---|---|---|---|
| WV-23662 | 0.95 | 16.13 | 19.24 | 3.19 | 3.05 |
| | 0.48 | 30.65 | 45.98 | 8.76 | 7.70 |
| | 0.00 | 59.17 | 54.91 | 25.01 | 26.40 |
| | −0.48 | 70.92 | 70.65 | 47.14 | 44.01 |
| | −0.95 | 79.59 | 113.07 | 77.30 | 75.81 |
| | −1.43 | 90.08 | 91.15 | 82.50 | 81.84 |
| | −1.91 | 80.98 | 97.03 | 89.05 | 98.10 |
| | −2.39 | 105.80 | 101.00 | 92.03 | 93.98 |

TABLE 11-continued

Activities of certain oligonucleotide compositions. Certain oligonucleotide compositions were tested in a luciferase reporting assay (procedures as shown in Example 3). Oligonucleotide were tested at multiple concentrations (shown as Log dose nM).

| | Conc. [Log (dose nM)] | RhoWt | | RhoP23H | |
|---|---|---|---|---|---|
| WV-23663 | 0.95 | 20.54 | 22.47 | 4.66 | 5.06 |
| | 0.48 | 31.87 | 43.68 | 11.84 | 10.54 |
| | 0.00 | 53.86 | 60.81 | 27.88 | 32.96 |
| | −0.48 | 65.89 | 81.94 | 59.86 | 55.06 |
| | −0.95 | 88.49 | 109.86 | 71.27 | 79.05 |
| | −1.43 | 86.44 | 86.93 | 86.41 | 82.57 |
| | −1.91 | 77.92 | 93.55 | 78.27 | 82.06 |
| | −2.39 | 90.09 | 100.88 | 88.76 | 96.48 |
| WV-23664 | 0.95 | 65.96 | 76.27 | 5.33 | 4.58 |
| | 0.48 | 72.68 | 90.92 | 14.75 | 11.43 |
| | 0.00 | 89.56 | 88.53 | 32.95 | 30.53 |
| | −0.48 | 72.50 | 86.34 | 57.33 | 59.27 |
| | −0.95 | 86.40 | 84.80 | 76.31 | 70.46 |
| | −1.43 | 85.97 | 88.30 | 75.33 | 85.15 |
| | −1.91 | 88.16 | 102.58 | 80.62 | 79.54 |
| | −2.39 | 103.86 | 103.31 | 91.18 | 94.04 |
| WV-23665 | 0.95 | 68.48 | 70.88 | 22.08 | 27.34 |
| | 0.48 | 68.25 | 81.71 | 42.41 | 35.29 |
| | 0.00 | 76.93 | 91.02 | 56.06 | 54.63 |
| | −0.48 | 73.13 | 85.76 | 77.66 | 78.88 |
| | −0.95 | 78.91 | 93.81 | 76.65 | 79.23 |
| | −1.43 | 80.68 | 100.85 | 84.04 | 97.04 |
| | −1.91 | 82.86 | 104.37 | 86.27 | 88.60 |
| | −2.39 | 92.54 | 108.43 | 105.48 | 90.64 |
| WV-23666 | 0.95 | 51.07 | 54.06 | 18.08 | 19.95 |
| | 0.48 | 61.70 | 69.06 | 39.08 | 33.89 |
| | 0.00 | 81.56 | 85.39 | 56.53 | 58.54 |
| | −0.48 | 73.00 | 90.09 | 77.58 | 70.11 |
| | −0.95 | 85.81 | 96.03 | 81.29 | 94.70 |

TABLE 11-continued

Activities of certain oligonucleotide compositions. Certain oligonucleotide compositions were tested in a luciferase reporting assay (procedures as shown in Example 3). Oligonucleotide were tested at multiple concentrations (shown as Log dose nM).

| | Conc. [Log (dose nM)] | RhoWt | | RhoP23H | |
|---|---|---|---|---|---|
| | −1.43 | 88.14 | 96.95 | 83.07 | 79.13 |
| | −1.91 | 79.54 | 102.51 | 89.93 | 82.11 |
| | −2.39 | 88.37 | 111.11 | 93.75 | 99.92 |
| WV-23667 | 0.95 | 72.80 | 84.54 | 11.63 | 13.90 |
| | 0.48 | 75.77 | 78.62 | 27.18 | 22.72 |
| | 0.00 | 93.80 | 85.46 | 41.92 | 47.87 |
| | −0.48 | 88.27 | 87.73 | 71.08 | 65.74 |
| | −0.95 | 92.08 | 99.75 | 79.75 | 85.51 |
| | −1.43 | 85.26 | 94.12 | 84.81 | 102.43 |
| | −1.91 | 82.60 | 95.71 | 94.57 | 81.91 |
| | −2.39 | 91.19 | 109.01 | 108.41 | 94.63 |
| WV-23668 | 0.95 | 98.91 | 98.67 | 3.07 | 3.54 |
| | 0.48 | 83.27 | 80.93 | 9.41 | 7.79 |
| | 0.00 | 99.00 | 86.75 | 27.35 | 24.63 |
| | −0.48 | 81.64 | 92.74 | 49.79 | 49.21 |
| | −0.95 | 79.12 | 88.24 | 61.43 | 71.46 |
| | −1.43 | 93.26 | 84.81 | 73.26 | 93.66 |
| | −1.91 | 94.25 | 97.16 | 79.96 | 92.87 |
| | −2.39 | 88.66 | 108.10 | 94.81 | 91.67 |
| WV-23669 | 0.95 | 66.20 | 79.16 | 33.25 | 44.26 |
| | 0.48 | 78.71 | 91.23 | 60.59 | 47.90 |
| | 0.00 | 84.93 | 85.37 | 71.49 | 61.26 |
| | −0.48 | 82.83 | 94.22 | 83.60 | 81.40 |
| | −0.95 | 86.57 | 94.34 | 92.11 | 92.35 |
| | −1.43 | 84.38 | 91.15 | 81.52 | 102.56 |
| | −1.91 | 91.13 | 100.29 | 83.17 | 85.70 |
| | −2.39 | 96.25 | 111.94 | 97.76 | 98.71 |

TABLE 12

Activities of certain oligonucleotide compositions. Certain oligonucleotide compositions were tested in a luciferase reporting assay (procedures as shown in Example 3). Oligonucleotide were tested at multiple concentrations (shown as Log dose nM).

| Conc. [Log (dose nM)] | RhoWt-23668 | | RhoP23H--23668 | | RhoWt-23658 | | RhoP23H-23658 | |
|---|---|---|---|---|---|---|---|---|
| 0.95 | 98.91 | 98.67 | 3.07 | 3.54 | 134.05 | 133.14 | 5.24 | 5.23 |
| 0.48 | 83.27 | 80.93 | 9.41 | 7.79 | 115.37 | 123.76 | 6.18 | 6.32 |
| 0.00 | 99.00 | 86.75 | 27.35 | 24.63 | 102.92 | 95.68 | 18.07 | 16.56 |
| −0.48 | 81.64 | 92.74 | 49.79 | 49.21 | 110.82 | 92.96 | 42.42 | 40.23 |
| −0.95 | 79.12 | 88.24 | 61.43 | 71.46 | 80.45 | 81.36 | 65.54 | 68.84 |
| −1.43 | 93.26 | 84.81 | 73.26 | 93.66 | 99.27 | 83.69 | 80.68 | 82.04 |
| −1.91 | 94.25 | 97.16 | 79.96 | 92.87 | 98.31 | 94.71 | 95.25 | 89.22 |
| −2.39 | 88.66 | 108.10 | 94.81 | 91.67 | 95.78 | 79.44 | 99.01 | 75.49 |

TABLE 13A

Activities of certain oligonucleotide compositions. Certain oligonucleotide compositions were tested in a luciferase reporting assay (procedures as shown in Example 3) for RHO wt. Oligonucleotide were tested at multiple concentrations (shown as Log dose nM).

| Conc. [Log (dose nM)] | WV-23671 | | WV-23672 | | WV-23673 | | WV-23674 | | WV-23675 | |
|---|---|---|---|---|---|---|---|---|---|---|
| 0.95 | 145.56 | 164.61 | 27.00 | 34.22 | 10.88 | 11.05 | 121.61 | 100.65 | 141.85 | 133.54 |
| 0.48 | 116.24 | 125.45 | 30.94 | 33.40 | 11.34 | 13.82 | 82.95 | 93.79 | 91.06 | 130.26 |
| 0.00 | 102.78 | 105.16 | 41.16 | 42.07 | 20.87 | 28.68 | 76.62 | 85.94 | 79.27 | 82.07 |
| −0.48 | 92.08 | 90.22 | 58.09 | 64.15 | 44.86 | 48.85 | 76.64 | 76.18 | 76.85 | 82.35 |
| −0.95 | 84.33 | 92.28 | 89.78 | 78.13 | 71.16 | 69.47 | 79.26 | 80.41 | 79.06 | 86.68 |

TABLE 13A-continued

Activities of certain oligonucleotide compositions. Certain oligonucleotide compositions were tested in a luciferase reporting assay (procedures as shown in Example 3) for RHO wt. Oligonucleotide were tested at multiple concentrations (shown as Log dose nM).

| | | | | | | | | | | |
|---|---|---|---|---|---|---|---|---|---|---|
| −1.43 | 122.20 | 88.58 | 92.22 | 91.33 | 98.61 | 86.74 | 93.61 | 79.27 | 91.42 | 94.81 |
| −1.91 | 90.11 | 89.19 | 89.86 | 82.48 | 98.70 | 83.59 | 93.73 | 81.33 | 96.35 | 94.94 |
| −2.39 | 102.82 | 112.92 | 107.82 | 115.61 | 97.88 | 102.58 | 88.65 | 100.07 | 128.80 | 97.36 |
| Conc. [Log (dose nM)] | WV-23676 | | WV-23677 | | WV-23678 | | WV-23679 | | WV-24004 | |
| 0.95 | 123.67 | 110.20 | 102.49 | 94.11 | 66.39 | 74.62 | 108.49 | 106.62 | 12.90 | 11.01 |
| 0.48 | 92.06 | 112.24 | 83.22 | 92.81 | 60.34 | 75.39 | 78.98 | 113.51 | 20.51 | 23.39 |
| 0.00 | 75.40 | 79.91 | 83.18 | 86.39 | 71.68 | 93.15 | 79.96 | 86.43 | 50.65 | 40.57 |
| −0.48 | 71.08 | 78.17 | 71.82 | 65.80 | 72.86 | 83.42 | 91.82 | 86.13 | 57.91 | 63.11 |
| −0.95 | 81.02 | 82.40 | 82.86 | 80.60 | 80.85 | 93.89 | 77.08 | 81.07 | 73.80 | 81.89 |
| −1.43 | 85.08 | 95.27 | 93.50 | 88.07 | 85.34 | 102.89 | 89.11 | 95.02 | 71.46 | 86.36 |
| −1.91 | 81.48 | 98.37 | 81.07 | 94.57 | 93.84 | 82.41 | 77.50 | 94.13 | 81.42 | 107.56 |
| −2.39 | 96.41 | 90.39 | 122.64 | 100.61 | 107.98 | 109.82 | 118.32 | 92.27 | 109.58 | 97.43 |

TABLE 13B

Activities of certain oligonucleotide compositions. Certain oligonucleotide compositions were tested in a luciferase reporting assay (procedures as shown in Example 3) for RHO mt (P23H). Oligonucleotide were tested at multiple concentrations (shown as Log dose nM).

| Conc. [Log (dose nM)] | WV-23671 | | WV-23672 | | WV-23673 | | WV-23674 | | WV-23675 | |
|---|---|---|---|---|---|---|---|---|---|---|
| 0.95 | 7.29 | 6.31 | 2.82 | 1.63 | 3.14 | 1.41 | 1.50 | 1.58 | 2.17 | 3.52 |
| 0.48 | 6.80 | 6.80 | 3.49 | 3.71 | 2.25 | 1.62 | 2.26 | 2.58 | 4.43 | 4.95 |
| 0.00 | 18.98 | 17.56 | 14.04 | 10.94 | 9.42 | 10.77 | 13.36 | 13.49 | 19.21 | 22.70 |
| −0.48 | 35.34 | 36.05 | 32.98 | 39.07 | 29.12 | 26.30 | 32.97 | 37.58 | 41.60 | 45.98 |
| −0.95 | 58.22 | 72.42 | 57.51 | 56.53 | 57.79 | 49.47 | 54.53 | 64.87 | 61.58 | 78.27 |
| −1.43 | 70.47 | 91.21 | 69.73 | 74.91 | 58.85 | 74.70 | 69.22 | 83.26 | 71.85 | 90.22 |
| −1.91 | 83.56 | 96.64 | 83.03 | 102.56 | 101.20 | 105.73 | 94.19 | 113.49 | 77.83 | 114.21 |
| −2.39 | 103.33 | 121.98 | 86.17 | 101.78 | 95.50 | 92.41 | 100.90 | 98.25 | 99.94 | 96.19 |
| Conc. [Log (dose nM)] | WV-23676 | | WV-23677 | | WV-23678 | | WV-23679 | | WV-24004 | |
| 0.95 | 3.14 | 3.44 | 4.48 | 4.49 | 19.20 | 15.70 | 8.40 | 7.76 | 4.09 | 3.57 |
| 0.48 | 5.78 | 5.96 | 4.65 | 5.94 | 21.18 | 22.00 | 9.51 | 11.12 | 6.51 | 7.26 |
| 0.00 | 18.66 | 20.55 | 15.98 | 22.92 | 40.23 | 42.11 | 25.97 | 32.50 | 16.70 | 15.88 |
| −0.48 | 46.26 | 43.03 | 44.19 | 49.67 | 52.65 | 64.07 | 50.93 | 51.86 | 37.12 | 26.08 |
| −0.95 | 58.25 | 68.09 | 57.28 | 63.27 | 79.28 | 86.08 | 67.38 | 77.25 | 58.33 | 49.24 |
| −1.43 | 72.16 | 71.35 | 68.29 | 74.52 | 85.01 | 86.44 | 78.59 | 86.19 | 66.48 | 78.49 |
| −1.91 | 85.30 | 107.04 | 98.47 | 107.35 | 91.28 | 111.93 | 102.74 | 95.04 | 87.76 | 90.69 |
| −2.39 | 102.64 | 98.07 | 94.24 | 109.06 | 106.53 | 111.06 | 103.54 | 93.18 | 90.77 | 103.01 |
| WV-23669 | 0.95 | 66.20 | 79.16 | 33.25 | 44.26 | | | | | |
| | 0.48 | 78.71 | 91.23 | 60.59 | 47.90 | | | | | |
| | 0.00 | 84.93 | 85.37 | 71.49 | 61.26 | | | | | |
| | −0.48 | 82.83 | 94.22 | 83.60 | 81.40 | | | | | |
| | −0.95 | 86.57 | 94.34 | 92.11 | 92.35 | | | | | |
| | −1.43 | 84.38 | 91.15 | 81.52 | 102.56 | | | | | |
| | −1.91 | 91.13 | 100.29 | 83.17 | 85.70 | | | | | |
| | −2.39 | 96.25 | 111.94 | 97.76 | 98.71 | | | | | |

TABLE 14A

Activities of certain oligonucleotide compositions. Certain oligonucleotide compositions were tested in a luciferase reporting assay (procedures as shown in Example 3). Oligonucleotide were tested at multiple concentrations (shown as Log dose nM).

| ID | Conc. [Log (dose nM)] | RhoWt | | RhoP23H | |
|---|---|---|---|---|---|
| WV-23671 | 0.95 | 145.56 | 164.61 | 7.29 | 6.31 |
| | 0.48 | 116.24 | 125.45 | 6.80 | 6.80 |
| | 0.00 | 102.78 | 105.16 | 18.98 | 17.56 |

TABLE 14A-continued

Activities of certain oligonucleotide compositions. Certain oligonucleotide compositions were tested in a luciferase reporting assay (procedures as shown in Example 3). Oligonucleotide were tested at multiple concentrations (shown as Log dose nM).

| ID | Conc. [Log (dose nM)] | RhoWt | | RhoP23H | |
|---|---|---|---|---|---|
| | −0.48 | 92.08 | 90.22 | 35.34 | 36.05 |
| | −0.95 | 84.33 | 92.28 | 58.22 | 72.42 |
| | −1.43 | 122.20 | 88.58 | 70.47 | 91.21 |

TABLE 14A-continued

Activities of certain oligonucleotide compositions. Certain oligonucleotide compositions were tested in a luciferase reporting assay (procedures as shown in Example 3). Oligonucleotide were tested at multiple concentrations (shown as Log dose nM).

| ID | Conc. [Log (dose nM)] | RhoWt | | RhoP23H | |
|---|---|---|---|---|---|
| | -1.91 | 90.11 | 89.19 | 83.56 | 96.64 |
| | -2.39 | 102.82 | 112.92 | 103.33 | 121.98 |
| WV-23672 | 0.95 | 27.00 | 34.22 | 2.82 | 1.63 |
| | 0.48 | 30.94 | 33.40 | 3.49 | 3.71 |
| | 0.00 | 41.16 | 42.07 | 14.04 | 10.94 |
| | -0.48 | 58.09 | 64.15 | 32.98 | 39.07 |
| | -0.95 | 89.78 | 78.13 | 57.51 | 56.53 |
| | -1.43 | 92.22 | 91.33 | 69.73 | 74.91 |
| | -1.91 | 89.86 | 82.48 | 83.03 | 102.56 |
| | -2.39 | 107.82 | 115.61 | 86.17 | 101.78 |
| WV-23673 | 0.95 | 10.88 | 11.05 | 3.14 | 1.41 |
| | 0.48 | 11.34 | 13.82 | 2.25 | 1.62 |
| | 0.00 | 20.87 | 28.68 | 9.42 | 10.77 |
| | -0.48 | 44.86 | 48.85 | 29.12 | 26.30 |
| | -0.95 | 71.16 | 69.47 | 57.79 | 49.47 |
| | -1.43 | 98.61 | 86.74 | 58.85 | 74.70 |
| | -1.91 | 98.70 | 83.59 | 101.20 | 105.73 |
| | -2.39 | 97.88 | 102.58 | 95.50 | 92.41 |
| WV-23674 | 0.95 | 121.61 | 100.65 | 1.50 | 1.58 |
| | 0.48 | 82.95 | 93.79 | 2.26 | 2.58 |
| | 0.00 | 76.62 | 85.94 | 13.36 | 13.49 |
| | -0.48 | 76.64 | 76.18 | 32.97 | 37.58 |
| | -0.95 | 79.26 | 80.41 | 54.53 | 64.87 |
| | -1.43 | 93.61 | 79.27 | 69.22 | 83.26 |
| | -1.91 | 93.73 | 81.33 | 94.19 | 113.49 |
| | -2.39 | 88.65 | 100.07 | 100.90 | 98.25 |
| WV-23675 | 0.95 | 141.85 | 133.54 | 2.17 | 3.52 |
| | 0.48 | 91.06 | 130.26 | 4.43 | 4.95 |
| | 0.00 | 79.27 | 82.07 | 19.21 | 22.70 |
| | -0.48 | 76.85 | 82.35 | 41.60 | 45.98 |
| | -0.95 | 79.06 | 86.68 | 61.58 | 78.27 |
| | -1.43 | 91.42 | 94.81 | 71.85 | 90.22 |
| | -1.91 | 96.35 | 94.94 | 77.83 | 114.21 |
| | -2.39 | 128.80 | 97.36 | 99.94 | 96.19 |

TABLE 14A-continued

Activities of certain oligonucleotide compositions. Certain oligonucleotide compositions were tested in a luciferase reporting assay (procedures as shown in Example 3). Oligonucleotide were tested at multiple concentrations (shown as Log dose nM).

| ID | Conc. [Log (dose nM)] | RhoWt | | RhoP23H | |
|---|---|---|---|---|---|
| WV-23676 | 0.95 | 123.67 | 110.20 | 3.14 | 3.44 |
| | 0.48 | 92.06 | 112.24 | 5.78 | 5.96 |
| | 0.00 | 75.40 | 79.91 | 18.66 | 20.55 |
| | -0.48 | 71.08 | 78.17 | 46.26 | 43.03 |
| | -0.95 | 81.02 | 82.40 | 58.25 | 68.09 |
| | -1.43 | 85.08 | 95.27 | 72.16 | 71.35 |
| | -1.91 | 81.48 | 98.37 | 85.30 | 107.04 |
| | -2.39 | 96.41 | 90.39 | 102.64 | 98.07 |
| WV-23677 | 0.95 | 102.49 | 94.11 | 4.48 | 4.49 |
| | 0.48 | 83.22 | 92.81 | 4.65 | 5.94 |
| | 0.00 | 83.18 | 86.39 | 15.98 | 22.92 |
| | -0.48 | 71.82 | 65.80 | 44.19 | 49.67 |
| | -0.95 | 82.86 | 80.60 | 57.28 | 63.27 |
| | -1.43 | 93.50 | 88.07 | 68.29 | 74.52 |
| | -1.91 | 81.07 | 94.57 | 98.47 | 107.35 |
| | -2.39 | 122.64 | 100.61 | 94.24 | 109.06 |
| WV-23678 | 0.95 | 102.49 | 94.11 | 4.48 | 4.49 |
| | 0.48 | 83.22 | 92.81 | 4.65 | 5.94 |
| | 0.00 | 83.18 | 86.39 | 15.98 | 22.92 |
| | -0.48 | 71.82 | 65.80 | 44.19 | 49.67 |
| | -0.95 | 82.86 | 80.60 | 57.28 | 63.27 |
| | -1.43 | 93.50 | 88.07 | 68.29 | 74.52 |
| | -1.91 | 81.07 | 94.57 | 98.47 | 107.35 |
| | -2.39 | 122.64 | 100.61 | 94.24 | 109.06 |
| WV-23679 | 0.95 | 108.49 | 106.62 | 8.40 | 7.76 |
| | 0.48 | 78.98 | 113.51 | 9.51 | 11.12 |
| | 0.00 | 79.96 | 86.43 | 25.97 | 32.50 |
| | -0.48 | 91.82 | 86.13 | 50.93 | 51.86 |
| | -0.95 | 77.08 | 81.07 | 67.38 | 77.25 |
| | -1.43 | 89.11 | 95.02 | 78.59 | 86.19 |
| | -1.91 | 77.50 | 94.13 | 102.74 | 95.04 |
| | -2.39 | 118.32 | 92.27 | 103.54 | 93.18 |

TABLE 14B

Activities of certain oligonucleotide compositions. Certain oligonucleotide compositions were tested in a luciferase reporting assay (procedures as shown in Example 3). Oligonucleotide were tested at multiple concentrations (shown as Log dose nM).

| Conc. [Log (dose nM)] | RhoWt-21503 | | RhoP23H-21503 | | RhoWt-21505 | | RhoP23H-21505 | |
|---|---|---|---|---|---|---|---|---|
| 0.95 | 169.58 | 131.99 | 6.13 | 4.72 | 84.52 | 98.40 | 3.07 | 3.05 |
| 0.48 | 109.43 | 118.75 | 3.47 | 3.76 | 74.60 | 109.94 | 4.78 | 4.12 |
| 0.00 | 106.90 | 105.96 | 9.58 | 12.66 | 98.65 | 88.77 | 16.37 | 17.93 |
| -0.48 | 83.03 | 105.25 | 34.72 | 31.04 | 99.19 | 120.93 | 37.35 | 40.46 |
| -0.95 | 95.67 | 95.84 | 65.58 | 61.93 | 97.90 | 98.59 | 70.94 | 74.53 |
| -1.43 | 102.76 | 91.13 | 83.48 | 73.23 | 102.79 | 137.25 | 88.66 | 80.57 |
| -1.91 | 100.82 | 118.83 | 103.39 | 95.35 | 99.84 | 108.41 | 90.94 | 103.24 |
| -2.39 | 103.89 | 88.34 | 115.85 | 113.82 | 99.46 | 97.21 | 136.78 | 118.22 |

TABLE 15A

Activities of certain oligonucleotide compositions. Certain oligonucleotide compositions were tested in a luciferase reporting assay (procedures as shown in Example 3) for RHO wt. Oligonucleotide were tested at multiple concentrations (shown as Log dose nM).

| Conc. [Log (dose nM)] | WV-23680 | | WV-23681 | | WV-23682 | | WV-23683 | | WV-23684 | |
|---|---|---|---|---|---|---|---|---|---|---|
| 0.95 | 117.73 | 108.61 | 35.66 | 27.90 | 12.62 | 15.49 | 80.25 | 86.59 | 118.47 | 97.93 |
| 0.48 | 85.45 | 86.49 | 35.34 | 34.04 | 18.55 | 22.51 | 67.07 | 71.63 | 74.06 | 78.85 |

TABLE 15A-continued

Activities of certain oligonucleotide compositions. Certain oligonucleotide compositions were tested in a luciferase reporting assay (procedures as shown in Example 3) for RHO wt. Oligonucleotide were tested at multiple concentrations (shown as Log dose nM).

| | | | | | | | | | | |
|---|---|---|---|---|---|---|---|---|---|---|
| 0.00 | 74.88 | 98.97 | 59.64 | 58.12 | 48.73 | 41.54 | 78.73 | 71.00 | 88.86 | 76.69 |
| −0.48 | 76.68 | 90.99 | 69.16 | 85.87 | 68.97 | 71.56 | 83.31 | 97.53 | 96.13 | 77.65 |
| −0.95 | 90.42 | 85.36 | 77.43 | 92.34 | 84.16 | 93.87 | 91.16 | 100.92 | 90.07 | 94.86 |
| −1.43 | 92.45 | 99.80 | 88.92 | 88.32 | 92.18 | 80.83 | 87.19 | 80.91 | 83.93 | 94.12 |
| −1.91 | 97.43 | 97.75 | 91.31 | 104.39 | 91.65 | 99.87 | 95.91 | 103.36 | 108.14 | 102.06 |
| −2.39 | 89.61 | 99.78 | 100.31 | 86.49 | 97.88 | 85.63 | 87.19 | 99.80 | 97.96 | 89.79 |
| Conc. [Log (dose nM)] | WV-23685 | | WV-23686 | | WV-23687 | | WV-21503 | | WV-21505 | |
| 0.95 | 89.09 | 85.13 | 94.31 | 99.18 | 68.31 | 77.65 | 169.59 | 131.99 | 84.52 | 98.40 |
| 0.48 | 81.43 | 69.88 | 78.84 | 68.53 | 65.52 | 66.36 | 109.43 | 118.75 | 74.60 | 109.94 |
| 0.00 | 86.10 | 73.55 | 70.69 | 70.87 | 80.96 | 78.36 | 106.90 | 105.96 | 98.65 | 88.77 |
| −0.48 | 87.96 | 90.65 | 91.80 | 81.35 | 88.23 | 84.79 | 83.03 | 105.25 | 99.19 | 120.93 |
| −0.95 | 91.23 | 103.50 | 99.46 | 94.16 | 83.03 | 107.60 | 95.67 | 95.84 | 97.90 | 98.59 |
| −1.43 | 96.96 | 95.59 | 95.93 | 93.93 | 96.30 | 102.61 | 102.76 | 91.13 | 102.79 | 137.25 |
| −1.91 | 106.85 | 102.03 | 98.15 | 102.67 | 84.71 | 108.04 | 100.82 | 118.83 | 99.84 | 108.41 |
| −2.39 | 100.74 | 106.09 | 115.89 | 89.73 | 102.57 | 98.97 | 103.89 | 88.34 | 99.46 | 97.21 |

TABLE 15B

Activities of certain oligonucleotide compositions. Certain oligonucleotide compositions were tested in a luciferase reporting assay (procedures as shown in Example 3) for RHO mt (P23H). Oligonucleotide were tested at multiple concentrations (shown as Log dose nM).

| Conc. [Log (dose nM)] | WV-23680 | | WV-23681 | | WV-23682 | | WV-23683 | | WV-23684 | |
|---|---|---|---|---|---|---|---|---|---|---|
| 0.95 | 3.18 | 4.10 | 1.98 | 1.96 | 1.78 | 2.58 | 2.12 | 1.11 | 1.99 | 2.54 |
| 0.48 | 5.98 | 10.62 | 1.83 | 2.99 | 2.20 | 4.55 | 2.16 | 2.26 | 6.17 | 6.50 |
| 0.00 | 15.86 | 20.51 | 9.29 | 8.89 | 10.47 | 11.43 | 11.58 | 14.15 | 22.67 | 21.14 |
| −0.48 | 44.81 | 39.32 | 25.62 | 29.33 | 35.43 | 29.45 | 34.95 | 31.48 | 43.73 | 46.32 |
| −0.95 | 67.09 | 68.73 | 58.96 | 60.28 | 63.45 | 55.52 | 65.80 | 55.30 | 78.03 | 66.86 |
| −1.43 | 94.02 | 83.58 | 86.77 | 74.17 | 89.17 | 72.89 | 81.11 | 74.76 | 79.38 | 71.47 |
| −1.91 | 96.69 | 103.49 | 88.79 | 84.48 | 103.11 | 86.64 | 88.78 | 89.20 | 109.32 | 96.01 |
| −2.39 | 131.28 | 92.37 | 109.74 | 94.26 | 129.80 | 97.38 | 121.39 | 100.78 | 118.31 | 98.78 |
| Conc. [Log (dose nM)] | WV-23685 | | WV-23686 | | WV-23687 | | WV-21503 | | WV-21505 | |
| 0.95 | 3.00 | 2.88 | 3.47 | 4.64 | 19.44 | 20.50 | 6.13 | 4.72 | 3.07 | 3.05 |
| 0.48 | 6.96 | 7.27 | 6.79 | 8.19 | 28.47 | 25.31 | 3.47 | 3.76 | 4.78 | 4.12 |
| 0.00 | 27.66 | 24.30 | 22.80 | 20.06 | 45.53 | 46.61 | 9.58 | 12.66 | 16.37 | 17.93 |
| −0.48 | 53.03 | 50.60 | 40.30 | 46.66 | 60.10 | 66.77 | 34.72 | 31.04 | 37.35 | 40.46 |
| −0.95 | 85.42 | 71.05 | 87.37 | 75.83 | 92.36 | 82.02 | 65.58 | 61.93 | 70.94 | 74.53 |
| −1.43 | 86.77 | 74.74 | 89.01 | 69.29 | 107.84 | 86.57 | 83.48 | 73.23 | 88.66 | 80.57 |
| −1.91 | 101.96 | 97.56 | 105.36 | 102.03 | 118.97 | 99.83 | 103.39 | 95.35 | 90.94 | 103.24 |
| −2.39 | 118.10 | 109.31 | 117.71 | 119.63 | 115.75 | 102.79 | 115.85 | 113.82 | 136.78 | 118.22 |

TABLE 16A

Activities of certain oligonucleotide compositions. Certain oligonucleotide compositions were tested in a luciferase reporting assay (procedures as shown in Example 3). Oligonucleotide were tested at multiple concentrations (shown as Log dose nM).

| ID | Conc. [Log (dose nM)] | Rho Wt | | RhoP23H | |
|---|---|---|---|---|---|
| WV-23680 | 0.95 | 117.73 | 108.61 | 3.18 | 4.10 |
| | 0.48 | 85.45 | 86.49 | 5.98 | 10.62 |
| | 0.00 | 74.88 | 98.97 | 15.86 | 20.51 |
| | −0.48 | 76.68 | 90.99 | 44.81 | 39.32 |
| | −0.95 | 90.42 | 85.36 | 67.09 | 68.73 |
| | −1.43 | 92.45 | 99.80 | 94.02 | 83.58 |

TABLE 16A-continued

Activities of certain oligonucleotide compositions. Certain oligonucleotide compositions were tested in a luciferase reporting assay (procedures as shown in Example 3). Oligonucleotide were tested at multiple concentrations (shown as Log dose nM).

| ID | Conc. [Log (dose nM)] | Rho Wt | | RhoP23H | |
|---|---|---|---|---|---|
| | −1.91 | 97.43 | 97.75 | 96.69 | 103.49 |
| | −2.39 | 89.61 | 99.78 | 131.28 | 92.37 |
| WV-23681 | 0.95 | 35.66 | 27.90 | 1.98 | 1.96 |
| | 0.48 | 35.34 | 34.04 | 1.83 | 2.99 |
| | 0.00 | 59.64 | 58.12 | 9.29 | 8.89 |
| | −0.48 | 69.16 | 85.87 | 25.62 | 29.33 |

TABLE 16A-continued

Activities of certain oligonucleotide compositions. Certain oligonucleotide compositions were tested in a luciferase reporting assay (procedures as shown in Example 3). Oligonucleotide were tested at multiple concentrations (shown as Log dose nM).

| ID | Conc. [Log (dose nM)] | Rho Wt | | RhoP23H | |
|---|---|---|---|---|---|
| | −0.95 | 77.43 | 92.34 | 58.96 | 60.28 |
| | −1.43 | 88.92 | 88.32 | 86.77 | 74.17 |
| | −1.91 | 91.31 | 104.39 | 88.79 | 84.48 |
| | −2.39 | 100.31 | 86.49 | 109.74 | 94.26 |
| WV-23682 | 0.95 | 12.62 | 15.49 | 1.78 | 2.58 |
| | 0.48 | 18.55 | 22.51 | 2.20 | 4.55 |
| | 0.00 | 48.73 | 41.54 | 10.47 | 11.43 |
| | −0.48 | 68.97 | 71.56 | 35.43 | 29.45 |
| | −0.95 | 84.16 | 93.87 | 63.45 | 55.52 |
| | −1.43 | 92.18 | 80.83 | 89.17 | 72.89 |
| | −1.91 | 91.65 | 99.87 | 103.11 | 86.64 |
| | −2.39 | 97.88 | 85.63 | 129.80 | 97.38 |
| WV-23683 | 0.95 | 80.25 | 86.59 | 2.12 | 1.11 |
| | 0.48 | 67.07 | 71.63 | 2.16 | 2.26 |
| | 0.00 | 78.73 | 71.00 | 11.58 | 14.15 |
| | −0.48 | 83.31 | 97.53 | 34.95 | 31.48 |
| | −0.95 | 91.16 | 100.92 | 65.80 | 55.30 |
| | −1.43 | 87.19 | 80.91 | 81.11 | 74.76 |
| | −1.91 | 95.91 | 103.36 | 88.78 | 89.20 |
| | −2.39 | 87.19 | 99.80 | 121.39 | 100.78 |
| WV-23684 | 0.95 | 118.47 | 97.93 | 1.99 | 2.54 |
| | 0.48 | 74.06 | 78.85 | 6.17 | 6.50 |
| | 0.00 | 88.86 | 76.69 | 22.67 | 21.14 |
| | −0.48 | 96.13 | 77.65 | 43.73 | 46.32 |
| | −0.95 | 90.07 | 94.86 | 78.03 | 66.86 |
| | −1.43 | 83.93 | 94.12 | 79.38 | 71.47 |
| | −1.91 | 108.14 | 102.06 | 109.32 | 96.01 |
| | −2.39 | 97.96 | 89.79 | 118.31 | 98.78 |
| WV-23685 | 0.95 | 89.09 | 85.13 | 3.00 | 2.88 |
| | 0.48 | 81.43 | 69.88 | 6.96 | 7.27 |
| | 0.00 | 86.10 | 73.55 | 27.66 | 24.30 |
| | −0.48 | 87.96 | 90.65 | 53.03 | 50.60 |
| | −0.95 | 91.23 | 103.50 | 85.42 | 71.05 |
| | −1.43 | 96.96 | 95.59 | 86.77 | 74.74 |
| | −1.91 | 106.85 | 102.03 | 101.96 | 97.56 |
| | −2.39 | 100.74 | 106.09 | 118.10 | 109.31 |
| WV-23686 | 0.95 | 94.31 | 99.18 | 3.47 | 4.64 |
| | 0.48 | 78.84 | 68.53 | 6.79 | 8.19 |
| | 0.00 | 70.69 | 70.87 | 22.80 | 20.06 |
| | −0.48 | 91.80 | 81.35 | 40.30 | 46.66 |
| | −0.95 | 99.46 | 94.16 | 87.37 | 75.83 |
| | −1.43 | 95.93 | 93.93 | 89.01 | 69.29 |
| | −1.91 | 98.15 | 102.67 | 105.36 | 102.03 |
| | −2.39 | 115.89 | 89.73 | 117.71 | 119.63 |
| WV-23687 | 0.95 | 68.31 | 77.65 | 19.44 | 20.50 |
| | 0.48 | 65.52 | 66.36 | 28.47 | 25.31 |
| | 0.00 | 80.96 | 78.36 | 45.53 | 46.61 |
| | −0.48 | 88.23 | 84.79 | 60.10 | 66.77 |
| | −0.95 | 83.03 | 107.60 | 92.36 | 82.02 |
| | −1.43 | 96.30 | 102.61 | 107.84 | 86.57 |
| | −1.91 | 84.71 | 108.04 | 118.97 | 99.83 |
| | −2.39 | 102.57 | 98.97 | 115.75 | 102.79 |

TABLE 16B

Activities of certain oligonucleotide compositions. Certain oligonucleotide compositions were tested in a luciferase reporting assay (procedures as shown in Example 3). Oligonucleotide were tested at multiple concentrations (shown as Log dose nM).

| Conc. [Log (dose nM)] | RhoWt-21503 | | RhoP23H-21503 | | RhoWt-21505 | | RhoP23H-21505 | |
|---|---|---|---|---|---|---|---|---|
| 0.95 | 169.58 | 131.99 | 6.13 | 4.72 | 84.52 | 98.40 | 3.07 | 3.05 |
| 0.48 | 109.43 | 118.75 | 3.47 | 3.76 | 74.60 | 109.94 | 4.78 | 4.12 |
| 0.00 | 106.90 | 105.96 | 9.58 | 12.66 | 98.65 | 88.77 | 16.37 | 17.93 |
| −0.48 | 83.03 | 105.25 | 34.72 | 31.04 | 99.19 | 120.93 | 37.35 | 40.46 |
| −0.95 | 95.67 | 95.84 | 65.58 | 61.93 | 97.90 | 98.59 | 70.94 | 74.53 |
| −1.43 | 102.76 | 91.13 | 83.48 | 73.23 | 102.79 | 137.25 | 88.66 | 80.57 |
| −1.91 | 100.82 | 118.83 | 103.39 | 95.35 | 99.84 | 108.41 | 90.94 | 103.24 |
| −2.39 | 103.89 | 88.34 | 115.85 | 113.82 | 99.46 | 97.21 | 136.78 | 118.22 |

TABLE 17

Activities of certain oligonucleotide compositions. Certain oligonucleotide compositions were tested in a luciferase reporting assay (procedures as shown in Example 3). Oligonucleotide were tested at multiple concentrations (shown as Log dose nM).

| Conc. [Log (dose nM)] | RhoWt-23668 | | RhoP23H-23668 | | RhoWt-23658 | |
|---|---|---|---|---|---|---|
| 0.95 | 98.91 | 98.67 | 3.07 | 3.54 | 134.05 | 133.14 |
| 0.48 | 83.27 | 80.93 | 9.41 | 7.79 | 115.37 | 123.76 |
| 0.00 | 99.00 | 86.75 | 27.35 | 24.63 | 102.92 | 95.68 |
| −0.48 | 81.64 | 92.74 | 49.79 | 49.21 | 110.82 | 92.96 |
| −0.95 | 79.12 | 88.24 | 61.43 | 71.46 | 80.45 | 81.36 |
| −1.43 | 93.26 | 84.81 | 73.26 | 93.66 | 99.27 | 83.69 |
| −1.91 | 94.25 | 97.16 | 79.96 | 92.87 | 98.31 | 94.71 |
| −2.39 | 88.66 | 108.10 | 94.81 | 91.67 | 95.78 | 79.44 |

| Conc. [Log (dose nM)] | RhoP23H-23658 | | RhoWt-23674 | | RhoP23H-23674 | |
|---|---|---|---|---|---|---|
| 0.95 | 5.24 | 5.23 | 121.61 | 100.65 | 1.50 | 1.58 |
| 0.48 | 6.18 | 6.32 | 82.95 | 93.79 | 2.26 | 2.58 |
| 0.00 | 18.07 | 16.56 | 76.62 | 85.94 | 13.36 | 13.49 |
| −0.48 | 42.42 | 40.23 | 76.64 | 76.18 | 32.97 | 37.58 |
| −0.95 | 65.54 | 68.84 | 79.26 | 80.41 | 54.53 | 64.87 |
| −1.43 | 80.68 | 82.04 | 93.61 | 79.27 | 69.22 | 83.26 |
| −1.91 | 95.25 | 89.22 | 93.73 | 81.33 | 94.19 | 113.49 |
| −2.39 | 99.01 | 75.49 | 88.65 | 100.07 | 100.90 | 98.25 |

TABLE 18

Activities of certain oligonucleotide compositions. Certain oligonucleotide compositions were tested in a luciferase reporting assay (procedures as shown in Example 3). Oligonucleotide were tested at multiple concentrations (shown as Log dose nM).

| | Conc. [Log (dose nM)] | Rho-Wt | | RhoP23H | |
|---|---|---|---|---|---|
| WV-23658 | 0.95 | 117.65 | 135.03 | 2.55 | 3.60 |
| | 0.48 | 126.19 | 122.75 | 5.50 | 6.08 |
| | 0.00 | 109.82 | 112.35 | 17.74 | 22.20 |
| | −0.48 | 109.68 | 106.17 | 39.59 | 43.72 |
| | −0.95 | 93.22 | 111.85 | 59.02 | 77.08 |
| | −1.43 | 159.64 | 110.81 | 82.55 | 97.70 |
| | −1.91 | 105.09 | 115.00 | 94.97 | 108.77 |
| | −2.39 | 123.74 | 104.31 | 90.19 | 115.05 |
| WV-23668 | 0.95 | 123.74 | 104.31 | 90.19 | 115.05 |
| | 0.48 | 92.50 | 95.50 | 19.34 | 20.54 |
| | 0.00 | 135.13 | 116.80 | 39.15 | 49.48 |
| | −0.48 | 126.47 | 117.68 | 70.12 | 59.30 |
| | −0.95 | 89.94 | 118.82 | 90.66 | 105.35 |
| | −1.43 | 138.65 | 105.77 | 92.97 | 96.58 |
| | −1.91 | 126.61 | 121.60 | 112.23 | 120.63 |
| | −2.39 | 126.61 | 124.08 | 100.30 | 117.52 |

TABLE 19

Activities of certain oligonucleotide compositions. Certain oligonucleotide compositions were tested in a luciferase reporting assay (procedures as shown in Example 3). Oligonucleotide were tested at multiple concentrations (shown as Log dose nM).

| | Conc. [Log (dose nM)] | Mt RhoP23H | |
|---|---|---|---|
| WV-24653 | 0.95 | 4.66 | 5.37 |
| | 0.48 | 6.35 | 8.72 |
| | 0.00 | 26.47 | 29.03 |
| | −0.48 | 46.43 | 53.64 |
| | −0.95 | 66.42 | 88.62 |
| | −1.43 | 98.79 | 107.50 |
| | −1.91 | 96.64 | 116.93 |
| | −2.39 | 89.31 | 98.99 |

TABLE 19-continued

Activities of certain oligonucleotide compositions. Certain oligonucleotide compositions were tested in a luciferase reporting assay (procedures as shown in Example 3). Oligonucleotide were tested at multiple concentrations (shown as Log dose nM).

| | Conc. [Log (dose nM)] | Mt RhoP23H | |
|---|---|---|---|
| WV-24654 | 0.95 | 3.11 | 4.52 |
| | 0.48 | 7.53 | 11.49 |
| | 0.00 | 30.17 | 34.44 |
| | −0.48 | 44.03 | 59.54 |
| | −0.95 | 73.81 | 84.08 |
| | −1.43 | 87.55 | 104.97 |
| | −1.91 | 85.11 | 101.99 |
| | −2.39 | 87.36 | 121.49 |
| WV-24655 | 0.95 | 4.03 | 5.39 |
| | 0.48 | 8.37 | 11.32 |
| | 0.00 | 36.67 | 39.88 |
| | −0.48 | 43.74 | 67.52 |
| | −0.95 | 83.70 | 86.77 |
| | −1.43 | 90.50 | 117.76 |
| | −1.91 | 104.41 | 105.28 |
| | −2.39 | 84.86 | 112.49 |
| WV-24656 | 0.95 | 2.99 | 4.16 |
| | 0.48 | 6.07 | 11.10 |
| | 0.00 | 31.07 | 32.91 |
| | −0.48 | 43.97 | 57.58 |
| | −0.95 | 64.63 | 81.36 |
| | −1.43 | 79.31 | 95.31 |
| | −1.91 | 91.03 | 118.84 |
| | −2.39 | 88.35 | 114.05 |
| WV-24657 | 0.95 | 2.64 | 3.28 |
| | 0.48 | 6.11 | 10.89 |
| | 0.00 | 29.90 | 35.71 |
| | −0.48 | 39.60 | 61.98 |
| | −0.95 | 64.80 | 83.60 |
| | −1.43 | 76.69 | 97.08 |
| | −1.91 | 94.35 | 124.26 |
| | −2.39 | 98.20 | 105.07 |
| WV-24658 | 0.95 | 2.89 | 2.91 |
| | 0.48 | 5.28 | 8.37 |
| | 0.00 | 26.22 | 33.04 |
| | −0.48 | 47.17 | 48.66 |
| | −0.95 | 59.46 | 75.92 |
| | −1.43 | 81.22 | 89.81 |
| | −1.91 | 92.41 | 104.37 |
| | −2.39 | 87.57 | 109.50 |
| WV-24659 | 0.95 | 2.81 | 3.82 |
| | 0.48 | 5.53 | 7.45 |
| | 0.00 | 26.18 | 31.99 |
| | −0.48 | 41.04 | 50.32 |
| | −0.95 | 57.05 | 68.71 |
| | −1.43 | 77.11 | 96.17 |
| | −1.91 | 90.90 | 104.89 |
| | −2.39 | 83.07 | 124.40 |
| WV-24660 | 0.95 | 2.43 | 3.10 |
| | 0.48 | 5.82 | 6.57 |
| | 0.00 | 27.61 | 28.10 |
| | −0.48 | 42.65 | 45.88 |
| | −0.95 | 63.62 | 81.86 |
| | −1.43 | 95.33 | 99.96 |
| | −1.91 | 79.72 | 114.59 |
| | −2.39 | 81.18 | 109.61 |
| WV-24661 | 0.95 | 2.74 | 4.38 |
| | 0.48 | 8.23 | 10.40 |
| | 0.00 | 25.93 | 34.39 |
| | −0.48 | 46.69 | 66.13 |
| | −0.95 | 76.91 | 85.78 |
| | −1.43 | 93.13 | 104.32 |
| | −1.91 | 92.18 | 118.89 |
| | −2.39 | 88.45 | 126.72 |
| WV-24662 | 0.95 | 3.48 | 3.61 |
| | 0.48 | 7.49 | 12.30 |
| | 0.00 | 27.08 | 34.50 |
| | −0.48 | 51.46 | 53.44 |
| | −0.95 | 72.58 | 87.59 |
| | −1.43 | 87.49 | 94.12 |
| | −1.91 | 106.80 | 100.87 |
| | −2.39 | 109.94 | 94.14 |

TABLE 19-continued

Activities of certain oligonucleotide compositions. Certain oligonucleotide compositions were tested in a luciferase reporting assay (procedures as shown in Example 3). Oligonucleotide were tested at multiple concentrations (shown as Log dose nM).

| | Conc. [Log (dose nM)] | Mt RhoP23H | |
|---|---|---|---|
| WV-24663 | 0.95 | 3.39 | 3.06 |
| | 0.48 | 7.60 | 11.01 |
| | 0.00 | 21.35 | 27.07 |
| | −0.48 | 56.38 | 52.62 |
| | −0.95 | 80.12 | 87.86 |
| | −1.43 | 98.28 | 96.15 |
| | −1.91 | 112.74 | 116.68 |
| | −2.39 | 109.02 | 112.22 |
| WV-24664 | 0.95 | 3.58 | 3.71 |
| | 0.48 | 6.00 | 8.90 |
| | 0.00 | 21.60 | 24.44 |
| | −0.48 | 47.20 | 46.46 |
| | −0.95 | 78.38 | 83.87 |
| | −1.43 | 96.59 | 94.02 |
| | −1.91 | 108.92 | 94.97 |
| | −2.39 | 107.60 | 97.96 |
| WV-24665 | 0.95 | 3.39 | 2.89 |
| | 0.48 | 5.85 | 10.03 |
| | 0.00 | 26.17 | 25.57 |
| | −0.48 | 46.45 | 48.57 |
| | −0.95 | 69.50 | 76.18 |
| | −1.43 | 83.60 | 88.91 |
| | −1.91 | 117.77 | 103.09 |
| | −2.39 | 102.32 | 101.92 |
| WV-24666 | 0.95 | 4.40 | 4.39 |
| | 0.48 | 7.42 | 9.90 |
| | 0.00 | 23.36 | 29.37 |
| | −0.48 | 53.75 | 48.17 |
| | −0.95 | 69.70 | 75.11 |
| | −1.43 | 78.36 | 84.74 |
| | −1.91 | 108.79 | 100.44 |
| | −2.39 | 103.99 | 105.15 |
| WV-24667 | 0.95 | 4.75 | 4.73 |
| | 0.48 | 7.36 | 9.90 |
| | 0.00 | 23.96 | 29.89 |
| | −0.48 | 50.62 | 49.09 |
| | −0.95 | 68.62 | 71.40 |
| | −1.43 | 86.93 | 83.93 |
| | −1.91 | 93.30 | 100.34 |
| | −2.39 | 103.68 | 110.13 |
| WV-24668 | 0.95 | 3.46 | 4.20 |
| | 0.48 | 6.19 | 9.66 |
| | 0.00 | 19.25 | 23.41 |
| | −0.48 | 43.79 | 42.27 |
| | −0.95 | 70.40 | 71.52 |
| | −1.43 | 80.29 | 82.10 |
| | −1.91 | 106.58 | 109.10 |
| | −2.39 | 98.43 | 112.88 |
| WV-24669 | 0.95 | 5.84 | 5.89 |
| | 0.48 | 9.14 | 12.77 |
| | 0.00 | 23.51 | 26.75 |
| | −0.48 | 49.11 | 50.82 |
| | −0.95 | 76.14 | 89.52 |
| | −1.43 | 96.12 | 88.88 |
| | −1.91 | 107.15 | 103.65 |
| | −2.39 | 110.98 | 102.41 |
| WV-24670 | 0.95 | 6.93 | 5.80 |
| | 0.48 | 8.97 | 12.53 |
| | 0.00 | 25.35 | 30.74 |
| | −0.48 | 50.68 | 54.59 |
| | −0.95 | 82.84 | 96.82 |
| | −1.43 | 103.85 | 97.94 |
| | −1.91 | 109.61 | 106.28 |
| | −2.39 | 103.47 | 115.80 |

TABLE 20

Activities of certain oligonucleotide compositions. Certain oligonucleotide compositions were tested in a luciferase reporting assay (procedures as shown in Example 3). Oligonucleotide were tested at multiple concentrations (shown as Log dose nM).

| | Conc. [Log (dose nM)] | Rho-Wt | | RhoP23H | |
|---|---|---|---|---|---|
| WV-24653 | 0.95 | 131.63 | 109.37 | 4.66 | 5.37 |
| | 0.48 | 140.99 | 106.69 | 6.35 | 8.72 |
| | 0.00 | 108.61 | 99.61 | 26.47 | 29.03 |
| | −0.48 | 124.31 | 104.40 | 46.43 | 53.64 |
| | −0.95 | 88.71 | 108.20 | 66.42 | 88.62 |
| | −1.43 | 113.95 | 120.70 | 98.79 | 107.50 |
| | −1.91 | 101.57 | 110.97 | 96.64 | 116.93 |
| | −2.39 | 101.27 | 99.14 | 89.31 | 98.99 |
| WV-24654 | 0.95 | 119.60 | 141.30 | 3.11 | 4.52 |
| | 0.48 | 129.91 | 126.06 | 7.53 | 11.49 |
| | 0.00 | 109.54 | 107.69 | 30.17 | 34.44 |
| | −0.48 | 104.97 | 85.52 | 44.03 | 59.54 |
| | −0.95 | 106.86 | 115.31 | 73.81 | 84.08 |
| | −1.43 | 109.32 | 104.48 | 87.55 | 104.97 |
| | −1.91 | 121.68 | 131.84 | 85.11 | 101.99 |
| | −2.39 | 106.76 | 107.85 | 87.36 | 121.49 |
| WV-24655 | 0.95 | 133.14 | 134.22 | 4.03 | 5.39 |
| | 0.48 | 139.18 | 106.12 | 8.37 | 11.32 |
| | 0.00 | 120.66 | 96.24 | 36.67 | 39.88 |
| | −0.48 | 135.31 | 112.99 | 43.74 | 67.52 |
| | −0.95 | 104.10 | 105.64 | 83.70 | 86.77 |
| | −1.43 | 112.13 | 109.90 | 90.50 | 117.76 |
| | −1.91 | 114.86 | 122.71 | 104.41 | 105.28 |
| | −2.39 | 101.81 | 98.76 | 84.86 | 112.49 |
| WV-24656 | 0.95 | 102.70 | 128.61 | 2.99 | 4.16 |
| | 0.48 | 119.84 | 132.14 | 6.07 | 11.10 |
| | 0.00 | 109.22 | 94.48 | 31.07 | 32.91 |
| | −0.48 | 100.75 | 109.35 | 43.97 | 57.58 |
| | −0.95 | 93.16 | 96.35 | 64.63 | 81.36 |
| | −1.43 | 98.68 | 103.88 | 79.31 | 95.31 |
| | −1.91 | 109.21 | 109.42 | 91.03 | 118.84 |
| | −2.39 | 98.71 | 98.41 | 88.35 | 114.05 |
| WV-24657 | 0.95 | 108.91 | 135.34 | 2.64 | 3.28 |
| | 0.48 | 131.17 | 130.29 | 6.11 | 10.89 |
| | 0.00 | 112.51 | 107.02 | 29.90 | 35.71 |
| | −0.48 | 102.73 | 101.74 | 39.60 | 61.98 |
| | −0.95 | 104.37 | 117.99 | 64.80 | 83.60 |
| | −1.43 | 100.75 | 96.66 | 76.69 | 97.08 |
| | −1.91 | 95.62 | 117.38 | 94.35 | 124.26 |
| | −2.39 | 99.05 | 97.26 | 98.20 | 105.07 |
| WV-24658 | 0.95 | 102.17 | 106.62 | 2.89 | 2.91 |
| | 0.48 | 112.75 | 115.68 | 5.28 | 8.37 |
| | 0.00 | 105.31 | 93.84 | 26.22 | 33.04 |
| | −0.48 | 98.25 | 96.00 | 47.17 | 48.66 |
| | −0.95 | 94.41 | 104.43 | 59.46 | 75.92 |
| | −1.43 | 90.28 | 95.42 | 81.22 | 89.81 |
| | −1.91 | 115.00 | 127.79 | 92.41 | 104.37 |
| | −2.39 | 118.48 | 109.21 | 87.57 | 109.50 |

TABLE 21

Activities of certain oligonucleotide compositions. Certain oligonucleotide compositions were tested in a luciferase reporting assay (procedures as shown in Example 3). Oligonucleotide were tested at multiple concentrations (shown as Log dose nM).

| | Conc. [Log (dose nM)] | Rho-Wt | | RhoP23H | |
|---|---|---|---|---|---|
| WV-24659 | 0.95 | 101.05 | 92.14 | 2.81 | 3.82 |
| | 0.48 | 99.73 | 95.82 | 5.53 | 7.45 |
| | 0.00 | 94.16 | 92.59 | 26.18 | 31.99 |
| | −0.48 | 100.00 | 90.87 | 41.04 | 50.32 |
| | −0.95 | 91.48 | 111.26 | 57.05 | 68.71 |
| | −1.43 | 103.48 | 98.13 | 77.11 | 96.17 |
| | −1.91 | 117.94 | 119.33 | 90.90 | 104.89 |
| | −2.39 | 122.92 | 114.24 | 83.07 | 124.40 |
| WV-24660 | 0.95 | 89.16 | 93.17 | 2.43 | 3.10 |
| | 0.48 | 101.89 | 109.53 | 5.82 | 6.57 |
| | 0.00 | 93.08 | 103.15 | 27.61 | 28.10 |
| | −0.48 | 102.25 | 108.50 | 42.65 | 45.88 |

TABLE 21-continued

Activities of certain oligonucleotide compositions. Certain oligonucleotide compositions were tested in a luciferase reporting assay (procedures as shown in Example 3). Oligonucleotide were tested at multiple concentrations (shown as Log dose nM).

| | Conc. [Log (dose nM)] | Rho-Wt | | RhoP23H | |
|---|---|---|---|---|---|
| | −0.95 | 100.16 | 116.40 | 63.62 | 81.86 |
| | −1.43 | 123.33 | 114.21 | 95.33 | 99.96 |
| | −1.91 | 100.41 | 108.24 | 79.72 | 114.59 |
| | −2.39 | 131.88 | 99.18 | 81.18 | 109.61 |
| WV-24661 | 0.95 | 98.36 | 96.62 | 2.74 | 4.38 |
| | 0.48 | 89.95 | 88.57 | 8.23 | 10.40 |
| | 0.00 | 107.09 | 114.42 | 25.93 | 34.39 |
| | −0.48 | 102.80 | 105.03 | 46.69 | 66.13 |
| | −0.95 | 106.21 | 115.37 | 76.91 | 85.78 |
| | −1.43 | 119.63 | 131.70 | 93.13 | 104.32 |
| | −1.91 | 112.38 | 117.22 | 92.18 | 118.89 |
| | −2.39 | 117.15 | 114.83 | 88.45 | 126.72 |
| WV-24662 | 0.95 | 91.33 | 84.64 | 3.48 | 3.61 |
| | 0.48 | 114.38 | 109.02 | 7.49 | 12.30 |
| | 0.00 | 87.52 | 103.87 | 27.08 | 34.50 |
| | −0.48 | 91.46 | 96.13 | 51.46 | 53.44 |
| | −0.95 | 137.05 | 114.54 | 72.58 | 87.59 |
| | −1.43 | 110.66 | 98.85 | 87.49 | 94.12 |
| | −1.91 | 108.39 | 102.77 | 106.80 | 100.87 |
| | −2.39 | 95.49 | 116.70 | 109.94 | 94.14 |
| WV-24663 | 0.95 | 102.69 | 87.01 | 3.39 | 3.06 |
| | 0.48 | 90.39 | 93.64 | 7.60 | 11.01 |
| | 0.00 | 114.73 | 85.95 | 21.35 | 27.07 |
| | −0.48 | 99.83 | 97.52 | 56.38 | 52.62 |
| | −0.95 | 129.74 | 102.89 | 80.12 | 87.86 |
| | −1.43 | 109.58 | 112.60 | 98.28 | 96.15 |
| | −1.91 | 126.57 | 110.96 | 112.74 | 116.68 |
| | −2.39 | 99.43 | 108.68 | 109.02 | 112.22 |
| WV-24664 | 0.95 | 90.38 | 101.86 | 3.58 | 3.71 |
| | 0.48 | 88.43 | 90.89 | 6.00 | 8.90 |
| | 0.00 | 89.32 | 114.96 | 21.60 | 24.44 |
| | −0.48 | 100.38 | 104.48 | 47.20 | 46.46 |
| | −0.95 | 113.30 | 111.50 | 78.38 | 83.87 |
| | −1.43 | 100.26 | 108.65 | 96.59 | 94.02 |
| | −1.91 | 98.70 | 93.16 | 108.92 | 94.97 |
| | −2.39 | 101.12 | 112.85 | 107.60 | 97.96 |

TABLE 22

Activities of certain oligonucleotide compositions. Certain oligonucleotide compositions were tested in a luciferase reporting assay (procedures as shown in Example 3). Oligonucleotide were tested at multiple concentrations (shown as Log dose nM).

| | Conc. [Log (dose nM)] | Rho-Wt | | RhoP23H | |
|---|---|---|---|---|---|
| WV-24665 | 0.95 | 93.65 | 102.61 | 3.39 | 2.89 |
| | 0.48 | 93.12 | 86.15 | 5.85 | 10.03 |
| | 0.00 | 88.02 | 92.13 | 26.17 | 25.57 |
| | −0.48 | 95.48 | 96.26 | 46.45 | 48.57 |
| | −0.95 | 84.61 | 95.35 | 69.50 | 76.18 |
| | −1.43 | 96.95 | 93.02 | 83.60 | 88.91 |
| | −1.91 | 102.37 | 101.07 | 117.77 | 103.09 |
| | −2.39 | 93.79 | 108.65 | 102.32 | 101.92 |
| WV-24666 | 0.95 | 96.08 | 90.16 | 4.40 | 4.39 |
| | 0.48 | 93.99 | 96.87 | 7.42 | 9.90 |
| | 0.00 | 91.78 | 86.83 | 23.36 | 29.37 |
| | −0.48 | 93.68 | 83.71 | 53.75 | 48.17 |
| | −0.95 | 90.66 | 86.54 | 69.70 | 75.11 |
| | −1.43 | 99.83 | 94.66 | 78.36 | 84.74 |
| | −1.91 | 103.76 | 111.45 | 108.79 | 100.44 |
| | −2.39 | 98.97 | 114.95 | 103.99 | 105.15 |
| WV-24667 | 0.95 | 92.56 | 87.92 | 4.75 | 4.73 |
| | 0.48 | 92.70 | 99.04 | 7.36 | 9.90 |
| | 0.00 | 86.75 | 85.79 | 23.96 | 29.89 |
| | −0.48 | 90.61 | 95.78 | 50.62 | 49.09 |
| | −0.95 | 93.35 | 103.93 | 68.62 | 71.40 |
| | −1.43 | 87.10 | 92.18 | 86.93 | 83.93 |
| | −1.91 | 103.35 | 98.27 | 93.30 | 100.34 |
| | −2.39 | 114.02 | 123.35 | 103.68 | 110.13 |

TABLE 22-continued

Activities of certain oligonucleotide compositions. Certain oligonucleotide compositions were tested in a luciferase reporting assay (procedures as shown in Example 3). Oligonucleotide were tested at multiple concentrations (shown as Log dose nM).

| | Conc. [Log (dose nM)] | Rho-Wt | | RhoP23H | |
|---|---|---|---|---|---|
| WV-24668 | 0.95 | 83.37 | 91.09 | 3.46 | 4.20 |
| | 0.48 | 86.88 | 91.18 | 6.19 | 9.66 |
| | 0.00 | 80.90 | 80.23 | 19.25 | 23.41 |
| | −0.48 | 85.70 | 81.51 | 43.79 | 42.27 |
| | −0.95 | 84.48 | 105.96 | 70.40 | 71.52 |
| | −1.43 | 96.34 | 93.07 | 80.29 | 82.10 |
| | −1.91 | 102.32 | 116.25 | 106.58 | 109.10 |
| | −2.39 | 134.08 | 109.55 | 98.43 | 112.88 |
| WV-24669 | 0.95 | 83.14 | 93.25 | 5.84 | 5.89 |
| | 0.48 | 79.45 | 92.52 | 9.14 | 12.77 |
| | 0.00 | 119.43 | 92.56 | 23.51 | 26.75 |
| | −0.48 | 93.23 | 101.27 | 49.11 | 50.82 |
| | −0.95 | 87.31 | 112.02 | 76.14 | 89.52 |
| | −1.43 | 100.58 | 105.95 | 96.12 | 88.88 |
| | −1.91 | 121.22 | 116.35 | 107.15 | 103.65 |
| | −2.39 | 125.05 | 127.46 | 110.98 | 102.41 |
| WV-24670 | 0.95 | 80.62 | 101.01 | 6.93 | 5.80 |
| | 0.48 | 88.58 | 96.72 | 8.97 | 12.53 |
| | 0.00 | 97.92 | 115.78 | 25.35 | 30.74 |
| | −0.48 | 101.28 | 101.89 | 50.68 | 54.59 |
| | −0.95 | 117.12 | 106.81 | 82.84 | 96.82 |
| | −1.43 | 130.54 | 110.33 | 103.85 | 97.94 |
| | −1.91 | 107.17 | 119.07 | 109.61 | 106.28 |
| | −2.39 | 126.26 | 127.11 | 103.47 | 115.80 |

TABLE 23A

Conc. [Log (dose nM)] and Conc. nM

| Conc. [Log (dose nM)] | Conc. nM |
|---|---|
| 0.92 | 8.32 |
| 0.44 | 2.75 |
| −0.03 | 0.93 |
| −0.51 | 0.31 |
| −0.99 | 0.10 |
| −1.46 | 0.03 |
| −1.94 | 0.01 |
| 0.95 | 8.91 |
| 0.48 | 3.01 |
| 0 | 1 |
| −0.48 | 0.33 |
| −0.95 | 0.11 |
| −1.43 | 0.04 |
| −1.91 | 0.01 |
| −2.39 | 0.004 |

TABLE 24A

Activities of certain oligonucleotide compositions. Certain oligonucleotide compositions were tested in a luciferase reporting assay (procedures as shown in Example 3). Oligonucleotide were tested at a concentrations of 5 nM.

| 5 nm treatment | Wt Rho (5 nM) | | RHO P23H (5 nM) | |
|---|---|---|---|---|
| H2O | 95.17 | 122.11 | 75.31 | 98.70 |
| WV-15309 | 107.76 | 104.82 | 91.45 | 103.04 |
| WV-24004 | 20.52 | 14.98 | 5.16 | 6.11 |
| WV-23658 | 109.54 | 80.61 | 5.25 | 5.48 |
| WV-21503 | 85.47 | 95.86 | 5.07 | 1.81 |
| WV-28093 | 114.66 | 61.71 | 2.54 | 2.86 |
| WV-34295 | 80.42 | 45.13 | 0.51 | 2.02 |
| WV-24653 | 95.80 | 81.90 | 8.10 | 7.67 |
| WV-24654 | 118.78 | 118.90 | 7.36 | 5.25 |
| WV-24655 | 108.19 | 96.18 | 4.36 | 3.25 |
| WV-24656 | 97.82 | 91.65 | 2.45 | 3.85 |
| WV-24657 | 117.77 | 129.54 | 4.43 | 4.74 |

TABLE 24A-continued

Activities of certain oligonucleotide compositions. Certain oligonucleotide compositions were tested in a luciferase reporting assay (procedures as shown in Example 3). Oligonucleotide were tested at a concentrations of 5 nM.

| 5 nm treatment | Wt Rho (5 nM) | | RHO P23H (5 nM) | |
|---|---|---|---|---|
| WV-24658 | 102.28 | 118.28 | 2.91 | 4.48 |
| WV-24668 | 98.95 | 86.99 | 2.50 | 3.40 |
| WV-34283 | 96.98 | 108.81 | 3.54 | 5.67 |
| WV-34284 | 90.27 | 106.64 | 2.05 | 3.65 |
| WV-34285 | 118.21 | 95.56 | 3.50 | 2.83 |
| WV-34286 | 128.38 | 123.63 | 3.16 | 4.72 |
| WV-34287 | 93.55 | 110.46 | 2.44 | 3.70 |
| WV-34288 | 118.55 | 115.47 | 2.05 | 3.28 |
| WV-34289 | 110.09 | 99.63 | 4.45 | 3.31 |
| WV-34290 | 104.58 | 74.49 | 1.69 | 3.62 |
| WV-34291 | 102.11 | 81.88 | 5.79 | 4.60 |
| WV-34292 | 93.45 | 62.84 | 4.96 | 5.18 |
| WV-34293 | 92.18 | 108.33 | 3.02 | 4.03 |
| WV-34294 | 89.30 | 101.98 | 4.69 | 1.55 |
| WV-34296 | 95.06 | 114.49 | 4.40 | 3.38 |
| WV-34297 | 86.07 | 81.16 | 1.79 | 2.94 |
| WV-34298 | 70.41 | 68.58 | 4.09 | 3.68 |
| WV-34299 | 77.36 | 83.68 | 2.34 | 2.41 |
| WV-34300 | 90.54 | 60.23 | 3.95 | 2.18 |
| WV-34301 | 94.77 | 82.53 | 1.77 | 2.91 |

TABLE 24B

Activities of certain oligonucleotide compositions. Certain oligonucleotide compositions were tested in a luciferase reporting assay (procedures as shown in Example 3). Oligonucleotide were tested at a concentrations of 1 nM.

| 1 nM treatment | Wt Rho (1 nM) | | RHO P23H (1 nM) | |
|---|---|---|---|---|
| H2O | 88.64 | 81.07 | 89.03 | 91.98 |
| WV-15309 | 135.10 | 89.26 | 90.37 | 114.12 |
| WV-24004 | 32.30 | 35.51 | 7.18 | 11.46 |
| WV-23658 | 74.76 | 82.40 | 20.95 | 12.77 |
| WV-21503 | 72.82 | 91.53 | 9.18 | 13.05 |
| WV-28093 | 76.09 | 94.86 | 9.60 | 9.27 |
| WV-34295 | 69.23 | 70.04 | 7.89 | 7.93 |
| WV-24653 | 94.66 | 102.69 | 28.09 | 21.83 |
| WV-24654 | 78.47 | 96.78 | 27.24 | 20.71 |
| WV-24655 | 99.17 | 109.09 | 22.49 | 27.22 |
| WV-24656 | 80.49 | 76.96 | 20.99 | 17.36 |
| WV-24657 | 88.66 | 96.28 | 23.35 | 24.26 |
| WV-24658 | 87.43 | 92.06 | 11.38 | 17.87 |
| WV-24668 | 85.38 | 96.51 | 17.76 | 13.23 |
| WV-34283 | 103.04 | 95.12 | 17.37 | 17.10 |
| WV-34284 | 82.39 | 83.00 | 17.18 | 15.25 |
| WV-34285 | 119.22 | 113.43 | 18.23 | 23.07 |
| WV-34286 | 83.20 | 71.29 | 26.46 | 25.39 |
| WV-34287 | 91.50 | 91.85 | 18.54 | 17.11 |
| WV-34288 | 109.02 | 87.04 | 15.87 | 22.28 |
| WV-34289 | 82.72 | 81.83 | 24.89 | 22.96 |
| WV-34290 | 98.11 | 83.03 | 16.40 | 18.45 |
| WV-34291 | 110.40 | 83.78 | 24.32 | 23.72 |
| WV-34292 | 75.95 | 94.75 | 23.16 | 26.10 |
| WV-34293 | 83.37 | 75.50 | 23.28 | 18.82 |
| WV-34294 | 65.01 | 62.80 | 19.04 | 13.85 |
| WV-34296 | 87.97 | 90.16 | 17.15 | 19.65 |
| WV-34297 | 70.77 | 89.06 | 16.76 | 12.90 |
| WV-34298 | 99.09 | 83.45 | 17.13 | 32.88 |
| WV-34299 | 94.33 | 97.86 | 22.29 | 25.54 |
| WV-34300 | 88.48 | 76.83 | 17.31 | 16.53 |
| WV-34301 | 86.61 | 77.69 | 13.74 | 15.40 |

TABLE 24C

Activities of certain oligonucleotide compositions. Certain oligonucleotide compositions were tested in a luciferase reporting assay (procedures as shown in Example 3). Oligonucleotide were tested at a concentrations of 5 nM.

| 5 nm treatment | Wt Rho (5 nM) | | RHO P23H (5 nM) | |
|---|---|---|---|---|
| H2O | 101.66 | 103.11 | 110.13 | 106.24 |
| WV-15309 | 107.76 | 104.82 | 91.45 | 103.04 |
| WV-24004 | 20.52 | 14.98 | 5.16 | 6.11 |
| WV-23668 | 86.80 | 88.08 | 4.31 | 5.80 |
| WV-21505 | 79.47 | 68.82 | 3.87 | 2.61 |
| WV-24665 | 74.45 | 64.99 | 4.43 | 3.40 |
| WV-28094 | 62.89 | 97.18 | 5.36 | 3.16 |
| WV-30204 | 71.79 | 69.46 | 2.02 | 2.76 |
| WV-34313 | 74.04 | 88.23 | 1.71 | 1.82 |
| WV-34320 | 79.66 | 71.68 | 3.82 | 2.88 |
| WV-34321 | 81.04 | 64.95 | 3.94 | 3.38 |
| WV-34302 | 76.86 | 58.51 | 3.78 | |
| WV-34303 | 77.24 | 84.60 | 5.31 | 3.04 |
| WV-34304 | 94.79 | 93.65 | 3.52 | 6.31 |
| WV-34305 | 88.68 | 88.51 | 3.93 | 6.60 |
| WV-34306 | 79.81 | 73.53 | 3.82 | 3.91 |
| WV-34307 | 75.35 | 88.32 | 5.38 | 4.98 |
| WV-34308 | 68.72 | 76.09 | 4.60 | 5.33 |
| WV-34309 | 69.26 | 71.23 | 2.64 | 2.93 |
| WV-34310 | 92.40 | 66.02 | 3.59 | 3.33 |
| WV-34311 | 78.26 | 86.26 | 3.31 | 3.27 |
| WV-34312 | 102.41 | 56.66 | 4.39 | 3.40 |
| WV-34314 | 77.88 | 111.67 | 2.65 | 4.49 |
| WV-34315 | 85.32 | 87.61 | 2.62 | 3.43 |
| WV-34316 | 83.78 | 87.53 | 2.40 | 2.37 |
| WV-34317 | 78.87 | 79.85 | 4.30 | 2.50 |
| WV-34318 | 92.55 | 88.32 | 3.59 | 3.26 |
| WV-34319 | 81.34 | 73.25 | 6.01 | 4.29 |
| WV-34322 | 69.86 | 90.56 | 3.58 | 4.85 |
| WV-34323 | 85.14 | 84.03 | 3.67 | 3.66 |
| WV-34324 | 74.62 | 86.13 | 3.94 | 2.79 |
| WV-34325 | 96.40 | 67.62 | 2.61 | 2.61 |
| WV-34326 | 81.77 | 83.20 | 3.86 | 5.48 |
| WV-34327 | 67.29 | 77.28 | 5.17 | 4.10 |

TABLE 24D

Activities of certain oligonucleotide compositions. Certain oligonucleotide compositions were tested in a luciferase reporting assay (procedures as shown in Example 3). Oligonucleotide were tested at a concentrations of 1 nM.

| 1 nM treatment | Wt Rho (1 nM) | | RHO P23H (1 nM) | |
|---|---|---|---|---|
| H2O | 81.83 | 67.50 | 101.35 | 95.49 |
| WV-15309 | 135.10 | 89.26 | 90.37 | 114.12 |
| WV-24004 | 32.30 | 35.51 | 7.18 | 11.46 |
| WV-23668 | 66.59 | 65.59 | 27.95 | 15.25 |
| WV-21505 | 76.87 | 80.92 | 14.79 | 15.53 |
| WV-24665 | 79.99 | 73.66 | 23.29 | 18.97 |
| WV-28094 | 85.88 | 85.46 | 18.47 | 16.13 |
| WV-30204 | 95.14 | 87.47 | 14.24 | 24.10 |
| WV-34313 | 77.80 | 77.99 | 13.56 | 14.64 |
| WV-34320 | 80.31 | 101.76 | 19.92 | 20.23 |
| WV-34321 | 86.03 | 81.32 | 18.57 | 17.88 |
| WV-34302 | 88.06 | 68.83 | 16.55 | 16.60 |
| WV-34303 | 87.20 | 77.36 | 16.88 | 22.20 |
| WV-34304 | 93.59 | 77.38 | 25.26 | 23.68 |
| WV-34305 | 101.28 | 86.81 | 21.00 | 16.07 |
| WV-34306 | 68.39 | 83.63 | 28.66 | 25.76 |
| WV-34307 | 61.74 | 88.33 | 17.45 | 26.63 |
| WV-34308 | 77.69 | 79.64 | 23.38 | 15.16 |
| WV-34309 | 75.66 | 86.76 | 23.08 | 20.35 |
| WV-34310 | 79.46 | 80.24 | 24.29 | 22.58 |
| WV-34311 | 74.07 | 67.65 | 14.76 | 18.05 |
| WV-34312 | 65.99 | 97.60 | 23.37 | 25.75 |
| WV-34314 | 79.53 | 98.73 | 17.09 | 22.24 |
| WV-34315 | 70.40 | 94.65 | 13.43 | 24.38 |
| WV-34316 | 89.42 | 84.80 | 14.37 | 21.58 |
| WV-34317 | 86.58 | 82.48 | 24.88 | 23.41 |

TABLE 24D-continued

Activities of certain oligonucleotide compositions. Certain oligonucleotide compositions were tested in a luciferase reporting assay (procedures as shown in Example 3). Oligonucleotide were tested at a concentrations of 1 nM.

| 1 nM treatment | Wt Rho (1 nM) | | RHO P23H (1 nM) | |
|---|---|---|---|---|
| WV-34318 | 93.24 | 65.55 | 20.67 | 25.49 |
| WV-34319 | 88.43 | 92.95 | 17.44 | 17.07 |
| WV-34322 | 76.63 | 90.01 | 27.30 | 29.40 |
| WV-34323 | 99.72 | 99.38 | 14.64 | 23.79 |
| WV-34324 | 102.04 | 100.78 | 17.14 | 22.49 |
| WV-34325 | 97.86 | 94.00 | 27.48 | 28.43 |
| WV-34326 | 101.31 | 65.41 | 18.49 | 19.67 |
| WV-34327 | 86.62 | 73.26 | 14.83 | 20.36 |

TABLE 25A

Activities of certain oligonucleotide compositions. Certain oligonucleotide compositions were tested in a luciferase reporting assay (procedures as shown in Example 3). Oligonucleotide were tested at a concentrations of 5 nM.

| 5 nm treatment | Wt Rho (5 nM) | | P23H (5 nM) | |
|---|---|---|---|---|
| WV-15309 | 107.76 | 104.82 | 91.45 | 103.04 |
| WV-34295 | 80.42 | 45.13 | 0.51 | 2.02 |
| WV-24004 | 20.52 | 14.98 | 5.16 | 6.11 |
| WV-23658 | 109.54 | 80.61 | 5.25 | 5.48 |
| WV-34301 | 94.77 | 82.53 | 1.77 | 2.91 |
| WV-24658 | 102.28 | 118.28 | 2.91 | 4.48 |
| WV-34297 | 86.07 | 81.16 | 1.79 | 2.94 |
| WV-24668 | 98.95 | 86.99 | 2.50 | 3.40 |
| WV-34284 | 90.27 | 106.64 | 2.05 | 3.65 |
| WV-34311 | 78.26 | 86.26 | 3.31 | 3.40 |
| WV-34294 | 89.30 | 101.98 | 4.69 | 1.55 |
| WV-34302 | 76.86 | 58.51 | 3.78 | 3.04 |
| WV-34300 | 90.54 | 60.23 | 3.95 | 2.18 |
| WV-34283 | 96.98 | 108.81 | 3.54 | 5.67 |
| WV-34319 | 81.34 | 73.25 | 6.01 | 4.85 |
| WV-34290 | 104.58 | 74.49 | 1.69 | 3.62 |
| WV-34327 | 67.29 | 77.28 | 5.17 | 6.21 |
| WV-34287 | 93.55 | 110.46 | 2.44 | 3.70 |
| WV-34316 | 83.78 | 87.53 | 2.40 | 2.50 |
| WV-34296 | 95.06 | 114.49 | 4.40 | 3.38 |

TABLE 25B

Activities of certain oligonucleotide compositions. Certain oligonucleotide compositions were tested in a luciferase reporting assay (procedures as shown in Example 3). Oligonucleotide were tested at a concentrations of 1 nM.

| 1 nm treatment | Wt Rho (1 nM) | | P23H (1 nM) | |
|---|---|---|---|---|
| WV-15309 | 135.10 | 89.26 | 90.37 | 114.12 |
| WV-34295 | 69.23 | 70.04 | 7.89 | 7.93 |
| WV-24004 | 32.30 | 35.51 | 7.18 | 11.46 |
| WV-23658 | 74.76 | 82.40 | 20.95 | 12.77 |
| WV-34301 | 86.61 | 77.69 | 13.74 | 15.40 |
| WV-24658 | 87.43 | 92.06 | 11.38 | 17.87 |
| WV-34297 | 70.77 | 89.06 | 16.76 | 12.90 |
| WV-24668 | 85.38 | 96.51 | 17.76 | 13.23 |
| WV-34284 | 82.39 | 83.00 | 17.18 | 15.25 |
| WV-34311 | 74.07 | 67.65 | 14.76 | 18.05 |
| WV-34294 | 65.01 | 62.80 | 19.04 | 13.85 |
| WV-34302 | 88.06 | 68.83 | 16.55 | 16.60 |
| WV-34300 | 88.48 | 76.83 | 17.31 | 16.53 |
| WV-34283 | 103.04 | 95.12 | 17.37 | 17.10 |
| WV-34319 | 88.43 | 92.95 | 17.44 | 17.07 |
| WV-34290 | 98.11 | 83.03 | 16.40 | 18.45 |
| WV-34327 | 86.62 | 73.26 | 14.83 | 20.36 |
| WV-34287 | 91.50 | 91.85 | 18.54 | 17.11 |

TABLE 25B-continued

Activities of certain oligonucleotide compositions. Certain oligonucleotide compositions were tested in a luciferase reporting assay (procedures as shown in Example 3). Oligonucleotide were tested at a concentrations of 1 nM.

| 1 nm treatment | Wt Rho (1 nM) | | P23H (1 nM) | |
|---|---|---|---|---|
| WV-34316 | 89.42 | 84.80 | 14.37 | 21.58 |
| WV-34296 | 87.97 | 90.16 | 17.15 | 19.65 |

TABLE 26A

Activities of certain oligonucleotide compositions. Certain oligonucleotide compositions were tested in a luciferase reporting assay (procedures as shown in Example 3). Oligonucleotide were tested at multiple concentrations (shown as nM and Log dose nM).

| | Conc. nM | Conc. [Log (dose nM)] | RhoP23H | |
|---|---|---|---|---|
| WV-24658 | 2.99 | 0.48 | 9.85 | 7.53 |
| | 1.00 | 0.00 | 14.35 | 19.35 |
| | 0.33 | −0.48 | 42.08 | 35.60 |
| | 0.11 | −0.95 | 58.29 | 69.84 |
| | 0.03 | −1.43 | 76.81 | 76.82 |
| | 0.01 | −1.91 | 78.18 | 93.07 |
| | 0.00 | −2.39 | 76.82 | 120.79 |
| | 0.00 | −2.86 | 119.65 | 116.45 |
| WV-34283 | 2.99 | 0.48 | 8.70 | 9.65 |
| | 1.00 | 0.00 | 15.41 | 20.82 |
| | 0.33 | −0.48 | 35.45 | 41.65 |
| | 0.11 | −0.95 | 52.23 | 75.51 |
| | 0.03 | −1.43 | 87.18 | 63.34 |
| | 0.01 | −1.91 | 60.96 | 84.40 |
| | 0.00 | −2.39 | 76.97 | 98.83 |
| | 0.00 | −2.86 | 113.89 | 100.54 |
| WV-34284 | 2.99 | 0.48 | 6.64 | 6.09 |
| | 1.00 | 0.00 | 17.90 | 17.98 |
| | 0.33 | −0.48 | 33.64 | 34.78 |
| | 0.11 | −0.95 | 52.80 | 52.79 |
| | 0.03 | −1.43 | 68.64 | 91.45 |
| | 0.01 | −1.91 | 71.78 | 97.17 |
| | 0.00 | −2.39 | 83.03 | 85.22 |
| | 0.00 | −2.86 | 126.18 | 126.89 |
| WV-34287 | 2.99 | 0.48 | 5.72 | 5.74 |
| | 1.00 | 0.00 | 15.01 | 19.22 |
| | 0.33 | −0.48 | 35.69 | 42.25 |
| | 0.11 | −0.95 | 42.52 | 50.54 |
| | 0.03 | −1.43 | 65.45 | 67.48 |
| | 0.01 | −1.91 | 82.37 | 86.34 |
| | 0.00 | −2.39 | 75.36 | 109.99 |
| | 0.00 | −2.86 | 113.27 | 107.37 |
| WV-34290 | 2.99 | 0.48 | 5.69 | 6.41 |
| | 1.00 | 0.00 | 12.45 | 17.71 |
| | 0.33 | −0.48 | 31.63 | 37.12 |
| | 0.11 | −0.95 | 51.56 | 61.34 |
| | 0.03 | −1.43 | 73.67 | 71.58 |
| | 0.01 | −1.91 | 88.56 | 82.83 |
| | 0.00 | −2.39 | 87.84 | 82.90 |
| | 0.00 | −2.86 | 116.53 | 105.06 |
| WV-34294 | 2.99 | 0.48 | 12.09 | 8.75 |
| | 1.00 | 0.00 | 22.18 | 21.55 |
| | 0.33 | −0.48 | 34.57 | 47.02 |
| | 0.11 | −0.95 | 54.15 | 56.14 |
| | 0.03 | −1.43 | 65.64 | 77.07 |
| | 0.01 | −1.91 | 66.73 | 93.21 |
| | 0.00 | −2.39 | 82.96 | 106.40 |
| | 0.00 | −2.86 | 124.03 | 98.25 |
| WV-34296 | 2.99 | 0.48 | 11.82 | 8.61 |
| | 1.00 | 0.00 | 13.48 | 15.68 |
| | 0.33 | −0.48 | 41.01 | 47.01 |
| | 0.11 | −0.95 | 53.16 | 74.65 |
| | 0.03 | −1.43 | 69.21 | 62.00 |
| | 0.01 | −1.91 | 74.68 | 75.11 |
| | 0.00 | −2.39 | 101.21 | 90.16 |
| | 0.00 | −2.86 | 121.25 | 116.13 |

TABLE 26A-continued

Activities of certain oligonucleotide compositions. Certain oligonucleotide compositions were tested in a luciferase reporting assay (procedures as shown in Example 3). Oligonucleotide were tested at multiple concentrations (shown as nM and Log dose nM).

| | Conc. nM | Conc. [Log (dose nM)] | RhoP23H | |
|---|---|---|---|---|
| WV-34297 | 2.99 | 0.48 | 7.98 | 4.74 |
| | 1.00 | 0.00 | 14.18 | 18.12 |
| | 0.33 | −0.48 | 46.19 | 45.01 |
| | 0.11 | −0.95 | 53.92 | 57.84 |
| | 0.03 | −1.43 | 67.39 | 82.97 |
| | 0.01 | −1.91 | 73.68 | 95.35 |
| | 0.00 | −2.39 | 89.88 | 92.82 |
| | 0.00 | −2.86 | 112.59 | 112.70 |
| WV-34300 | 2.99 | 0.48 | 5.51 | 7.15 |
| | 1.00 | 0.00 | 18.46 | 23.05 |
| | 0.33 | −0.48 | 42.33 | 34.19 |
| | 0.11 | −0.95 | 63.45 | 73.90 |
| | 0.03 | −1.43 | 85.27 | 75.26 |
| | 0.01 | −1.91 | 108.61 | 90.19 |
| | 0.00 | −2.39 | 77.41 | 108.61 |
| | 0.00 | −2.86 | 118.21 | 124.94 |

TABLE 26B

Activities of certain oligonucleotide compositions. Certain oligonucleotide compositions were tested in a luciferase reporting assay (procedures as shown in Example 3). Oligonucleotide were tested at multiple concentrations (shown as nM and Log dose nM).

| | Conc. nM | Conc. [Log (dose nM)] | RhoP23H | |
|---|---|---|---|---|
| WV-24668 | 2.99 | 0.48 | 4.65 | 6.67 |
| | 1.00 | 0.00 | 15.37 | 18.35 |
| | 0.33 | −0.48 | 33.64 | 33.17 |
| | 0.11 | −0.95 | 76.89 | 54.78 |
| | 0.03 | −1.43 | 77.40 | 81.02 |
| | 0.01 | −1.91 | 82.10 | 66.75 |
| | 0.00 | −2.39 | 88.65 | 79.84 |
| | 0.00 | −2.86 | 103.27 | 97.24 |
| WV-34301 | 2.99 | 0.48 | 4.91 | 4.72 |
| | 1.00 | 0.00 | 17.43 | 18.62 |
| | 0.33 | −0.48 | 40.18 | 46.30 |
| | 0.11 | −0.95 | 73.67 | 69.00 |
| | 0.03 | −1.43 | 74.60 | 86.43 |
| | 0.01 | −1.91 | 74.46 | 69.88 |
| | 0.00 | −2.39 | 76.59 | 98.09 |
| | 0.00 | −2.86 | 108.40 | 120.83 |
| WV-34302 | 2.99 | 0.48 | 6.47 | 4.46 |
| | 1.00 | 0.00 | 12.48 | 19.15 |
| | 0.33 | −0.48 | 39.24 | 38.89 |
| | 0.11 | −0.95 | 58.99 | 65.92 |
| | 0.03 | −1.43 | 71.98 | 69.14 |
| | 0.01 | −1.91 | 75.20 | 74.81 |
| | 0.00 | −2.39 | 80.13 | 108.06 |
| | 0.00 | −2.86 | 85.27 | 101.68 |
| WV-34311 | 2.99 | 0.48 | 7.07 | 6.78 |
| | 1.00 | 0.00 | 18.20 | 22.23 |
| | 0.33 | −0.48 | 43.26 | 45.74 |
| | 0.11 | −0.95 | 67.84 | 70.07 |
| | 0.03 | −1.43 | 72.64 | 87.16 |
| | 0.01 | −1.91 | 77.65 | 72.31 |
| | 0.00 | −2.39 | 105.07 | 99.82 |
| | 0.00 | −2.86 | 114.23 | 120.32 |
| WV-34316 | 2.99 | 0.48 | 7.66 | 5.41 |
| | 1.00 | 0.00 | 23.39 | 20.40 |
| | 0.33 | −0.48 | 42.52 | 40.89 |
| | 0.11 | −0.95 | 53.62 | 66.35 |
| | 0.03 | −1.43 | 74.56 | 83.08 |
| | 0.01 | −1.91 | 67.23 | 75.53 |
| | 0.00 | −2.39 | 68.98 | 90.39 |
| | 0.00 | −2.86 | 102.10 | 127.21 |

TABLE 26B-continued

Activities of certain oligonucleotide compositions. Certain oligonucleotide compositions were tested in a luciferase reporting assay (procedures as shown in Example 3). Oligonucleotide were tested at multiple concentrations (shown as nM and Log dose nM).

| | Conc. nM | Conc. [Log (dose nM)] | RhoP23H | |
|---|---|---|---|---|
| WV-34319 | 2.99 | 0.48 | 5.58 | 7.00 |
| | 1.00 | 0.00 | 19.66 | 27.74 |
| | 0.33 | −0.48 | 44.50 | 52.57 |
| | 0.11 | −0.95 | 67.61 | 69.55 |
| | 0.03 | −1.43 | 67.62 | 85.42 |
| | 0.01 | −1.91 | 68.43 | 68.53 |
| | 0.00 | −2.39 | 98.89 | 87.48 |
| | 0.00 | −2.86 | 100.03 | 107.19 |
| WV-34327 | 2.99 | 0.48 | 7.67 | 6.11 |
| | 1.00 | 0.00 | 14.55 | 23.36 |
| | 0.33 | −0.48 | 51.29 | 54.22 |
| | 0.11 | −0.95 | 67.22 | 62.91 |
| | 0.03 | −1.43 | 71.86 | 79.94 |
| | 0.01 | −1.91 | 75.78 | 80.81 |
| | 0.00 | −2.39 | 113.70 | 97.08 |
| | 0.00 | −2.86 | 92.86 | 111.90 |

TABLE 26C

Activities of certain oligonucleotide compositions. Certain oligonucleotide compositions were tested in a luciferase reporting assay (procedures as shown in Example 3). Oligonucleotide were tested at multiple concentrations (shown as nM and Log dose nM).

| | Conc. nM | Conc. [Log (dose nM)] | RhoP23H | |
|---|---|---|---|---|
| WV-23658 | 2.99 | 0.48 | 3.71 | 4.86 |
| | 1.00 | 0.00 | 9.81 | 13.69 |
| | 0.33 | −0.48 | 41.56 | 38.57 |
| | 0.11 | −0.95 | 55.97 | 64.17 |
| | 0.03 | −1.43 | 63.81 | 87.95 |
| | 0.01 | −1.91 | 74.61 | 80.01 |
| | 0.00 | −2.39 | 90.25 | 96.01 |
| | 0.00 | −2.86 | 114.07 | 107.04 |
| WV-34295 | 2.99 | 0.48 | 2.61 | 2.64 |
| | 1.00 | 0.00 | 7.80 | 9.35 |
| | 0.33 | −0.48 | 29.42 | 27.89 |
| | 0.11 | −0.95 | 55.63 | 67.07 |
| | 0.03 | −1.43 | 73.79 | 68.05 |
| | 0.01 | −1.91 | 70.26 | 104.87 |
| | 0.00 | −2.39 | 86.17 | 87.30 |
| | 0.00 | −2.86 | 113.69 | 109.19 |
| WV-24004-P1 | 2.99 | 0.48 | 5.89 | 6.11 |
| | 1.00 | 0.00 | 10.61 | 11.15 |
| | 0.33 | −0.48 | 20.74 | 22.34 |
| | 0.11 | −0.95 | 38.54 | 49.66 |
| | 0.03 | −1.43 | 54.14 | 70.84 |
| | 0.01 | −1.91 | 82.81 | 89.42 |
| | 0.00 | −2.39 | 65.60 | 85.22 |
| | 0.00 | −2.86 | 122.73 | 126.51 |
| WV-24004-P2 | 2.99 | 0.48 | 7.71 | 6.11 |
| | 1.00 | 0.00 | 9.94 | 16.95 |
| | 0.33 | −0.48 | 19.84 | 27.99 |
| | 0.11 | −0.95 | 41.17 | 47.66 |
| | 0.03 | −1.43 | 61.73 | 76.78 |
| | 0.01 | −1.91 | 87.26 | 83.73 |
| | 0.00 | −2.39 | 108.90 | 110.55 |
| | 0.00 | −2.86 | 91.06 | 112.93 |

TABLE 27

Activities of certain oligonucleotide compositions. Certain oligonucleotide compositions were tested in a luciferase reporting assay (procedures as shown in Example 3). Oligonucleotide were tested at multiple concentrations (shown as nM and Log dose nM).

| | Conc. nM | Conc. [Log (dose nM)] | Rho-Wt | | RhoP23H | |
|---|---|---|---|---|---|---|
| WV-24658 | 2.99 | 0.48 | 93.07 | 87.17 | 9.85 | 7.53 |
| | 1.00 | 0.00 | 82.99 | 92.94 | 14.35 | 19.35 |
| | 0.33 | −0.48 | 84.01 | 105.83 | 42.08 | 35.60 |
| | 0.11 | −0.95 | 85.76 | 82.60 | 58.29 | 69.84 |
| | 0.03 | −1.43 | 76.29 | 78.60 | 76.81 | 76.82 |
| | 0.01 | −1.91 | 98.01 | 116.05 | 78.18 | 93.07 |
| | 0.00 | −2.39 | 112.01 | 83.41 | 76.82 | 120.79 |
| | 0.00 | −2.86 | 104.23 | 102.52 | 119.65 | 116.45 |
| WV-34283 | 2.99 | 0.48 | 91.72 | 90.04 | 8.70 | 9.65 |
| | 1.00 | 0.00 | 81.84 | 102.52 | 15.41 | 20.82 |
| | 0.33 | −0.48 | 75.32 | 83.74 | 35.45 | 41.65 |
| | 0.11 | −0.95 | 75.71 | 79.51 | 52.23 | 75.51 |
| | 0.03 | −1.43 | 80.59 | 81.27 | 87.18 | 63.34 |
| | 0.01 | −1.91 | 72.46 | 88.93 | 60.96 | 84.40 |
| | 0.00 | −2.39 | 82.06 | 77.78 | 76.97 | 98.83 |
| | 0.00 | −2.86 | 95.64 | 94.99 | 113.89 | 100.54 |
| WV-34284 | 2.99 | 0.48 | 94.53 | 91.94 | 6.64 | 6.09 |
| | 1.00 | 0.00 | 74.34 | 81.99 | 17.90 | 17.98 |
| | 0.33 | −0.48 | 72.71 | 82.76 | 33.64 | 34.78 |
| | 0.11 | −0.95 | 72.01 | 99.63 | 52.80 | 52.79 |
| | 0.03 | −1.43 | 82.67 | 65.31 | 68.64 | 91.45 |
| | 0.01 | −1.91 | 96.69 | 93.75 | 71.78 | 97.17 |
| | 0.00 | −2.39 | 81.35 | 81.22 | 83.03 | 85.22 |
| | 0.00 | −2.86 | 121.61 | 97.40 | 126.18 | 126.89 |
| WV-34287 | 2.99 | 0.48 | 80.37 | 78.28 | 5.72 | 5.74 |
| | 1.00 | 0.00 | 76.94 | 103.77 | 15.01 | 19.22 |
| | 0.33 | −0.48 | 77.35 | 78.39 | 35.69 | 42.25 |
| | 0.11 | −0.95 | 66.01 | 71.66 | 42.52 | 50.54 |
| | 0.03 | −1.43 | 61.80 | 87.21 | 65.45 | 67.48 |
| | 0.01 | −1.91 | 74.04 | 82.64 | 82.37 | 86.34 |
| | 0.00 | −2.39 | 84.70 | 78.23 | 75.36 | 109.99 |
| | 0.00 | −2.86 | 106.77 | 90.25 | 113.27 | 107.37 |
| WV-34290 | 2.99 | 0.48 | 73.67 | 97.57 | 5.69 | 6.41 |
| | 1.00 | 0.00 | 71.26 | 90.79 | 12.45 | 17.71 |
| | 0.33 | −0.48 | 65.92 | 87.68 | 31.63 | 37.12 |
| | 0.11 | −0.95 | 62.45 | 62.99 | 51.56 | 61.34 |
| | 0.03 | −1.43 | 71.95 | 76.41 | 73.67 | 71.58 |
| | 0.01 | −1.91 | 89.60 | 83.14 | 88.56 | 82.83 |
| | 0.00 | −2.39 | 90.22 | 93.04 | 87.84 | 82.90 |
| | 0.00 | −2.86 | 108.57 | 93.71 | 116.53 | 105.06 |
| WV-34294 | 2.99 | 0.48 | 89.34 | 90.92 | 12.09 | 8.75 |
| | 1.00 | 0.00 | 82.13 | 77.32 | 22.18 | 21.55 |
| | 0.33 | −0.48 | 72.00 | 72.35 | 34.57 | 47.02 |
| | 0.11 | −0.95 | 81.59 | 76.18 | 54.15 | 56.14 |
| | 0.03 | −1.43 | 65.71 | 83.38 | 65.64 | 77.07 |
| | 0.01 | −1.91 | 84.10 | 74.48 | 66.73 | 93.21 |
| | 0.00 | −2.39 | 81.31 | 69.62 | 82.96 | 106.40 |
| | 0.00 | −2.86 | 99.12 | 98.19 | 124.03 | 98.25 |
| WV-34296 | 2.99 | 0.48 | 71.24 | 75.10 | 11.82 | 8.61 |
| | 1.00 | 0.00 | 71.25 | 90.72 | 13.48 | 15.68 |
| | 0.33 | −0.48 | 78.00 | 94.18 | 41.01 | 47.01 |
| | 0.11 | −0.95 | 72.84 | 67.66 | 53.16 | 74.65 |
| | 0.03 | −1.43 | 55.36 | 96.32 | 69.21 | 62.00 |
| | 0.01 | −1.91 | 59.62 | 69.13 | 74.68 | 75.11 |
| | 0.00 | −2.39 | 81.38 | 84.57 | 101.21 | 90.16 |
| | 0.00 | −2.86 | 117.43 | 98.10 | 121.25 | 116.13 |
| WV-34297 | 2.99 | 0.48 | 63.23 | 81.91 | 7.98 | 4.74 |
| | 1.00 | 0.00 | 76.39 | 91.65 | 14.18 | 18.12 |
| | 0.33 | −0.48 | 63.15 | 96.33 | 46.19 | 45.01 |
| | 0.11 | −0.95 | 87.44 | 67.58 | 53.92 | 57.84 |
| | 0.03 | −1.43 | 93.42 | 92.85 | 67.39 | 82.97 |
| | 0.01 | −1.91 | 70.56 | 81.61 | 73.68 | 95.35 |
| | 0.00 | −2.39 | 100.08 | 94.45 | 89.88 | 92.82 |
| | 0.00 | −2.86 | 95.46 | 97.60 | 112.59 | 112.70 |
| WV-34300 | 2.99 | 0.48 | 78.74 | 90.09 | 5.51 | 7.15 |
| | 1.00 | 0.00 | 97.50 | 90.97 | 18.46 | 23.05 |
| | 0.33 | −0.48 | 91.32 | 82.17 | 42.33 | 34.19 |
| | 0.11 | −0.95 | 91.05 | 107.59 | 63.45 | 73.90 |
| | 0.03 | −1.43 | 85.43 | 90.45 | 85.27 | 75.26 |
| | 0.01 | −1.91 | 92.83 | 107.39 | 108.61 | 90.19 |

TABLE 27-continued

Activities of certain oligonucleotide compositions. Certain oligonucleotide compositions were tested in a luciferase reporting assay (procedures as shown in Example 3). Oligonucleotide were tested at multiple concentrations (shown as nM and Log dose nM).

| | Conc. nM | Conc. [Log (dose nM)] | Rho-Wt | | RhoP23H | |
|---|---|---|---|---|---|---|
| | 0.00 | −2.39 | 102.43 | 81.18 | 77.41 | 108.61 |
| | 0.00 | −2.86 | 99.40 | 110.33 | 118.21 | 124.94 |
| WV-23658 | 2.99 | 0.48 | 60.99 | 84.33 | 3.71 | 4.86 |
| | 1.00 | 0.00 | 84.38 | 101.29 | 9.81 | 13.69 |
| | 0.33 | −0.48 | 73.99 | 79.68 | 41.56 | 38.57 |
| | 0.11 | −0.95 | 88.15 | 96.46 | 55.97 | 64.17 |
| | 0.03 | −1.43 | 81.19 | 102.47 | 63.81 | 87.95 |
| | 0.01 | −1.91 | 92.22 | 88.68 | 74.61 | 80.01 |
| | 0.00 | −2.39 | 86.34 | 91.32 | 90.25 | 96.01 |
| | 0.00 | −2.86 | 103.95 | 99.60 | 114.07 | 107.04 |

TABLE 28

Activities of certain oligonucleotide compositions. Certain oligonucleotide compositions were tested in a luciferase reporting assay (procedures as shown in Example 3). Oligonucleotide were tested at multiple concentrations

| | Conc. nM | Conc. [Log (dose nM)] | WT Rho | |
|---|---|---|---|---|
| WV-24668 | 10.00 | 1.00 | 91.96 | 86.23 |
| | 3.30 | 0.52 | 100.95 | 103.14 |
| | 1.12 | 0.05 | 78.64 | 82.08 |
| | 0.37 | −0.43 | 95.81 | 122.54 |
| | 0.12 | −0.91 | 86.01 | 86.57 |
| | 0.04 | −1.39 | 74.89 | 85.11 |
| | 0.01 | −1.86 | 101.47 | 76.34 |
| | 0.00 | −2.34 | 105.00 | 97.54 |
| WV-34301 | 10.00 | 1.00 | 74.48 | 74.19 |
| | 3.30 | 0.52 | 96.64 | 94.04 |
| | 1.12 | 0.05 | 70.99 | 98.08 |
| | 0.37 | −0.43 | 85.02 | 75.27 |
| | 0.12 | −0.91 | 93.55 | 97.22 |
| | 0.04 | −1.39 | 85.84 | 96.92 |
| | 0.01 | −1.86 | 86.29 | 95.50 |
| | 0.00 | −2.34 | 109.49 | 100.20 |
| WV-34302 | 10.00 | 1.00 | 59.94 | 93.97 |
| | 3.30 | 0.52 | 80.41 | 83.71 |
| | 1.12 | 0.05 | 65.65 | 75.92 |
| | 0.37 | −0.43 | 77.89 | 93.23 |
| | 0.12 | −0.91 | 74.28 | 89.98 |
| | 0.04 | −1.39 | 79.83 | 75.92 |
| | 0.01 | −1.86 | 88.39 | 101.46 |
| | 0.00 | −2.34 | 97.94 | 98.81 |
| WV-34311 | 10.00 | 1.00 | 62.29 | 75.77 |
| | 3.30 | 0.52 | 78.74 | 79.20 |
| | 1.12 | 0.05 | 60.20 | 86.45 |
| | 0.37 | −0.43 | 78.43 | 75.70 |
| | 0.12 | −0.91 | 73.28 | 85.42 |
| | 0.04 | −1.39 | 85.86 | 84.02 |
| | 0.01 | −1.86 | 83.86 | 97.07 |
| | 0.00 | −2.34 | 101.10 | 107.83 |
| WV-34316 | 10.00 | 1.00 | 80.56 | 82.57 |
| | 3.30 | 0.52 | 93.70 | 87.42 |
| | 1.12 | 0.05 | 82.33 | 81.23 |
| | 0.37 | −0.43 | 82.22 | 87.81 |
| | 0.12 | −0.91 | 78.55 | 86.00 |
| | 0.04 | −1.39 | 87.88 | 78.13 |
| | 0.01 | −1.86 | 82.08 | 85.62 |
| | 0.00 | −2.34 | 99.32 | 89.74 |
| WV-34319 | 10.00 | 1.00 | 62.36 | 64.72 |
| | 3.30 | 0.52 | 88.53 | 80.13 |
| | 1.12 | 0.05 | 79.60 | 94.19 |
| | 0.37 | −0.43 | 75.06 | 76.00 |
| | 0.12 | −0.91 | 81.20 | 83.96 |
| | 0.04 | −1.39 | 83.70 | 97.55 |

TABLE 28-continued

Activities of certain oligonucleotide compositions. Certain oligonucleotide compositions were tested in a luciferase reporting assay (procedures as shown in Example 3). Oligonucleotide were tested at multiple concentrations

| | | | | |
|---|---|---|---|---|
| | 0.01 | −1.86 | 89.53 | 90.40 |
| | 0.00 | −2.34 | 83.29 | 109.02 |
| WV-34327 | 10.00 | 1.00 | 67.92 | 80.94 |
| | 3.30 | 0.52 | 82.88 | 84.38 |
| | 1.12 | 0.05 | 71.43 | 86.40 |
| | 0.37 | −0.43 | 85.47 | 102.77 |
| | 0.12 | −0.91 | 73.45 | 83.77 |
| | 0.04 | −1.39 | 95.13 | 88.68 |
| | 0.01 | −1.86 | 79.74 | 90.67 |
| | 0.00 | −2.34 | 90.06 | 90.69 |
| WV-24004 | 10.00 | 1.00 | 10.00 | 14.94 |
| | 3.30 | 0.52 | 37.61 | 29.56 |
| | 1.12 | 0.05 | 53.94 | 55.88 |
| | 0.37 | −0.43 | 58.96 | 80.82 |
| | 0.12 | −0.91 | 85.98 | 82.75 |
| | 0.04 | −1.39 | 88.42 | 108.25 |
| | 0.01 | −1.86 | 87.14 | 115.72 |
| | 0.00 | −2.34 | 111.84 | 119.25 |

| | Conc. nM | Conc. [Log (dose nM)] | Rho-Wt | | RhoP23H | |
|---|---|---|---|---|---|---|
| WV-24668 | 2.99 | 0.48 | 91.96 | 86.23 | 4.65 | 6.67 |
| | 1.00 | 0.00 | 100.95 | 103.14 | 15.37 | 18.35 |
| | 0.33 | −0.48 | 78.64 | 82.08 | 33.64 | 33.17 |
| | 0.11 | −0.95 | 95.81 | 122.54 | 76.89 | 54.78 |
| | 0.03 | −1.43 | 86.01 | 86.57 | 77.40 | 81.02 |
| | 0.01 | −1.91 | 74.89 | 85.11 | 82.10 | 66.75 |
| | 0.00 | −2.39 | 101.47 | 76.34 | 88.65 | 79.84 |
| | 0.00 | −2.86 | 105.00 | 97.54 | 103.27 | 97.24 |
| WV-34301 | 2.99 | 0.48 | 74.48 | 74.19 | 4.91 | 4.72 |
| | 1.00 | 0.00 | 96.64 | 94.04 | 17.43 | 18.62 |
| | 0.33 | −0.48 | 70.99 | 98.08 | 40.18 | 46.30 |
| | 0.11 | −0.95 | 85.02 | 75.27 | 73.67 | 69.00 |
| | 0.03 | −1.43 | 93.55 | 97.22 | 74.60 | 86.43 |
| | 0.01 | −1.91 | 85.84 | 96.92 | 74.46 | 69.88 |
| | 0.00 | −2.39 | 86.29 | 95.50 | 76.59 | 98.09 |
| | 0.00 | −2.86 | 109.49 | 100.20 | 108.40 | 120.83 |
| WV-34302 | 2.99 | 0.48 | 59.94 | 93.97 | 6.47 | 4.46 |
| | 1.00 | 0.00 | 80.41 | 83.71 | 12.48 | 19.15 |
| | 0.33 | −0.48 | 65.65 | 75.92 | 39.24 | 38.89 |
| | 0.11 | −0.95 | 77.89 | 93.23 | 58.99 | 65.92 |
| | 0.03 | −1.43 | 74.28 | 89.98 | 71.98 | 69.14 |
| | 0.01 | −1.91 | 79.83 | 75.92 | 75.20 | 74.81 |
| | 0.00 | −2.39 | 88.39 | 101.46 | 80.13 | 108.06 |
| | 0.00 | −2.86 | 97.94 | 98.81 | 85.27 | 101.68 |
| WV-34311 | 2.99 | 0.48 | 62.29 | 75.77 | 7.07 | 6.78 |
| | 1.00 | 0.00 | 78.74 | 79.20 | 18.20 | 22.23 |
| | 0.33 | −0.48 | 60.20 | 86.45 | 43.26 | 45.74 |
| | 0.11 | −0.95 | 78.43 | 75.70 | 67.84 | 70.07 |
| | 0.03 | −1.43 | 73.28 | 85.42 | 72.64 | 87.16 |
| | 0.01 | −1.91 | 85.86 | 84.02 | 77.65 | 72.31 |
| | 0.00 | −2.39 | 83.86 | 97.07 | 105.07 | 99.82 |
| | 0.00 | −2.86 | 101.10 | 107.83 | 114.23 | 120.32 |
| WV-34316 | 2.99 | 0.48 | 80.56 | 82.57 | 7.66 | 5.41 |
| | 1.00 | 0.00 | 93.70 | 87.42 | 23.39 | 20.40 |
| | 0.33 | −0.48 | 82.33 | 81.23 | 42.52 | 40.89 |
| | 0.11 | −0.95 | 82.22 | 87.81 | 53.62 | 66.35 |
| | 0.03 | −1.43 | 78.55 | 86.00 | 74.56 | 83.08 |
| | 0.01 | −1.91 | 87.88 | 78.13 | 67.23 | 75.53 |
| | 0.00 | −2.39 | 82.08 | 85.62 | 68.98 | 90.39 |
| | 0.00 | −2.86 | 99.32 | 89.74 | 102.10 | 127.21 |
| WV-34319 | 2.99 | 0.48 | 62.36 | 64.72 | 5.58 | 7.00 |
| | 1.00 | 0.00 | 88.53 | 80.13 | 19.66 | 27.74 |
| | 0.33 | −0.48 | 79.60 | 94.19 | 44.50 | 52.57 |
| | 0.11 | −0.95 | 75.06 | 76.00 | 67.61 | 69.55 |
| | 0.03 | −1.43 | 81.20 | 83.96 | 67.62 | 85.42 |
| | 0.01 | −1.91 | 83.70 | 97.55 | 68.43 | 68.53 |
| | 0.00 | −2.39 | 89.53 | 90.40 | 98.89 | 87.48 |
| | 0.00 | −2.86 | 83.29 | 109.02 | 100.03 | 107.19 |
| WV-34327 | 2.99 | 0.48 | 67.92 | 80.94 | 7.67 | 6.11 |
| | 1.00 | 0.00 | 82.88 | 84.38 | 14.55 | 23.36 |
| | 0.33 | −0.48 | 71.43 | 86.40 | 51.29 | 54.22 |
| | 0.11 | −0.95 | 85.47 | 102.77 | 67.22 | 62.91 |
| | 0.03 | −1.43 | 73.45 | 83.77 | 71.86 | 79.94 |

TABLE 28-continued

Activities of certain oligonucleotide compositions. Certain oligonucleotide compositions were tested in a luciferase reporting assay (procedures as shown in Example 3). Oligonucleotide were tested at multiple concentrations

| | | | | | | |
|---|---|---|---|---|---|---|
| | 0.01 | −1.91 | 95.13 | 88.68 | 75.78 | 80.81 |
| | 0.00 | −2.39 | 79.74 | 90.67 | 113.70 | 97.08 |
| | 0.00 | −2.86 | 90.06 | 90.69 | 92.86 | 111.90 |
| WV-34295 | 2.99 | 0.48 | 46.43 | 68.59 | 2.61 | 2.64 |
| | 1.00 | 0.00 | 72.94 | 80.65 | 7.80 | 9.35 |
| | 0.33 | −0.48 | 79.08 | 83.63 | 29.42 | 27.89 |
| | 0.11 | −0.95 | 80.25 | 82.59 | 55.63 | 67.07 |
| | 0.03 | −1.43 | 89.96 | 100.79 | 73.79 | 68.05 |
| | 0.01 | −1.91 | 96.16 | 80.38 | 70.26 | 104.87 |
| | 0.00 | −2.39 | 86.83 | 70.78 | 86.17 | 87.30 |
| | 0.00 | −2.86 | 108.51 | 72.79 | 113.69 | 109.19 |
| WV-24004 | 2.99 | 0.48 | 10.00 | 14.94 | 7.71 | 6.11 |
| | 1.00 | 0.00 | 37.61 | 29.56 | 9.94 | 16.95 |
| | 0.33 | −0.48 | 53.94 | 55.88 | 19.84 | 27.99 |
| | 0.11 | −0.95 | 58.96 | 80.82 | 41.17 | 47.66 |
| | 0.03 | −1.43 | 85.98 | 82.75 | 61.73 | 76.78 |
| | 0.01 | −1.91 | 88.42 | 108.25 | 87.26 | 83.73 |
| | 0.00 | −2.39 | 87.14 | 115.72 | 108.90 | 110.55 |
| | 0.00 | −2.86 | 111.84 | 119.25 | 91.06 | 112.93 |

TABLE 29A

Activities of certain oligonucleotide compositions. Certain oligonucleotide compositions were tested in a 293T stable cells with transfection (procedures as shown in example 4). Oligonucleotide were tested at multiple concentrations (shown as nM and Log dose nM).

| | Conc. nM | Conc. [Log (dose nM)] | WT Rho | |
|---|---|---|---|---|
| WV-24658 | 10.00 | 1.00 | 92.78 | 136.64 |
| | 3.30 | 0.52 | 94.01 | 101.00 |
| | 1.12 | 0.05 | 77.24 | 68.90 |
| | 0.37 | −0.43 | 84.30 | 99.13 |
| | 0.12 | −0.91 | 106.00 | 86.89 |
| | 0.04 | −1.39 | 106.92 | 89.03 |
| | 0.01 | −1.86 | 92.79 | 109.91 |
| | 0.00 | −2.34 | 110.92 | 102.10 |
| WV-34283 | 10.00 | 1.00 | 64.99 | 56.32 |
| | 3.30 | 0.52 | 73.22 | 70.47 |
| | 1.12 | 0.05 | 93.29 | 69.78 |
| | 0.37 | −0.43 | 80.61 | 95.91 |
| | 0.12 | −0.91 | 112.62 | 100.70 |
| | 0.04 | −1.39 | 95.02 | 92.99 |
| | 0.01 | −1.86 | 109.37 | 152.86 |
| | 0.00 | −2.34 | 97.91 | 96.05 |
| WV-34284 | 10.00 | 1.00 | 58.62 | 62.30 |
| | 3.30 | 0.52 | 60.07 | 74.32 |
| | 1.12 | 0.05 | 72.23 | 95.43 |
| | 0.37 | −0.43 | 93.09 | 99.26 |
| | 0.12 | −0.91 | 96.27 | 105.96 |
| | 0.04 | −1.39 | 98.91 | 100.02 |
| | 0.01 | −1.86 | 97.80 | 142.26 |
| | 0.00 | −2.34 | 107.94 | 84.55 |
| WV-34287 | 10.00 | 1.00 | 76.37 | 81.46 |
| | 3.30 | 0.52 | 60.30 | 103.46 |
| | 1.12 | 0.05 | 73.93 | 90.88 |
| | 0.37 | −0.43 | 103.29 | 94.87 |
| | 0.12 | −0.91 | 111.85 | 95.44 |
| | 0.04 | −1.39 | 107.01 | 100.89 |
| | 0.01 | −1.86 | 91.29 | 115.09 |
| | 0.00 | −2.34 | 109.10 | 109.16 |
| WV-34290 | 10.00 | 1.00 | 82.63 | 80.98 |
| | 3.30 | 0.52 | 54.13 | 87.74 |
| | 1.12 | 0.05 | 84.02 | 76.61 |
| | 0.37 | −0.43 | 70.31 | 92.96 |
| | 0.12 | −0.91 | 113.35 | 84.72 |
| | 0.04 | −1.39 | 80.15 | 118.56 |
| | 0.01 | −1.86 | 77.78 | 127.74 |
| | 0.00 | −2.34 | 112.95 | 81.95 |

TABLE 29A-continued

Activities of certain oligonucleotide compositions. Certain oligonucleotide compositions were tested in a 293T stable cells with transfection (procedures as shown in example 4). Oligonucleotide were tested at multiple concentrations (shown as nM and Log dose nM).

| | Conc. nM | Conc. [Log (dose nM)] | WT Rho | |
|---|---|---|---|---|
| WV-34294 | 10.00 | 1.00 | 61.03 | 58.92 |
| | 3.30 | 0.52 | 67.14 | 81.36 |
| | 1.12 | 0.05 | 82.44 | 65.20 |
| | 0.37 | −0.43 | 93.31 | 96.50 |
| | 0.12 | −0.91 | 123.57 | 88.39 |
| | 0.04 | −1.39 | 100.98 | 97.61 |
| | 0.01 | −1.86 | 94.53 | 110.34 |
| | 0.00 | −2.34 | 118.36 | 93.75 |
| WV-34296 | 10.00 | 1.00 | 76.64 | 106.47 |
| | 3.30 | 0.52 | 69.48 | 74.54 |
| | 1.12 | 0.05 | 100.73 | 58.50 |
| | 0.37 | −0.43 | 109.69 | 69.68 |
| | 0.12 | −0.91 | 85.37 | 102.84 |
| | 0.04 | −1.39 | 111.84 | 111.38 |
| | 0.01 | −1.86 | 74.74 | 121.86 |
| | 0.00 | −2.34 | 93.20 | 90.95 |
| WV-34297 | 10.00 | 1.00 | 83.48 | 94.07 |
| | 3.30 | 0.52 | 72.70 | 70.49 |
| | 1.12 | 0.05 | 72.80 | 56.16 |
| | 0.37 | −0.43 | 108.83 | 119.50 |
| | 0.12 | −0.91 | 106.98 | 87.70 |
| | 0.04 | −1.39 | 78.16 | 90.14 |
| | 0.01 | −1.86 | 72.81 | 109.92 |
| | 0.00 | −2.34 | 102.94 | 64.69 |
| WV-34300 | 10.00 | 1.00 | 97.61 | 136.18 |
| | 3.30 | 0.52 | 88.20 | 83.07 |
| | 1.12 | 0.05 | 87.78 | 76.99 |
| | 0.37 | −0.43 | 113.93 | 119.57 |
| | 0.12 | −0.91 | 129.76 | 108.09 |
| | 0.04 | −1.39 | 120.01 | 139.41 |
| | 0.01 | −1.86 | 128.14 | 96.85 |
| | 0.00 | −2.34 | 120.34 | 131.68 |
| WV-24004 | 10.00 | 1.00 | 14.64 | 20.45 |
| | 3.30 | 0.52 | 32.73 | 35.46 |
| | 1.12 | 0.05 | 57.58 | 57.73 |
| | 0.37 | −0.43 | 60.90 | 68.60 |
| | 0.12 | −0.91 | 69.38 | 88.46 |
| | 0.04 | −1.39 | 101.13 | 88.69 |
| | 0.01 | −1.86 | 80.33 | 99.42 |
| | 0.00 | −2.34 | 105.84 | 110.56 |

TABLE 29B

Activities of certain oligonucleotide compositions. Certain oligonucleotide compositions were tested in a 293T stable cells with transfection (procedures as shown in example 4). Oligonucleotide were tested at multiple concentrations (shown as nM and Log dose nM).

| | Conc. nM | Conc. [Log (dose nM)] | WT Rho | |
|---|---|---|---|---|
| WV-24668 | 10.00 | 1.00 | 91.96 | 86.23 |
| | 3.30 | 0.52 | 100.95 | 103.14 |
| | 1.12 | 0.05 | 78.64 | 82.08 |
| | 0.37 | −0.43 | 95.81 | 122.54 |
| | 0.12 | −0.91 | 86.01 | 86.57 |
| | 0.04 | −1.39 | 74.89 | 85.11 |
| | 0.01 | −1.86 | 101.47 | 76.34 |
| | 0.00 | −2.34 | 105.00 | 97.54 |
| WV-34301 | 10.00 | 1.00 | 74.48 | 74.19 |
| | 3.30 | 0.52 | 96.64 | 94.04 |
| | 1.12 | 0.05 | 70.99 | 98.08 |
| | 0.37 | −0.43 | 85.02 | 75.27 |
| | 0.12 | −0.91 | 93.55 | 97.22 |
| | 0.04 | −1.39 | 85.84 | 96.92 |
| | 0.01 | −1.86 | 86.29 | 95.50 |
| | 0.00 | −2.34 | 109.49 | 100.20 |
| WV-34302 | 10.00 | 1.00 | 59.94 | 93.97 |
| | 3.30 | 0.52 | 80.41 | 83.71 |
| | 1.12 | 0.05 | 65.65 | 75.92 |
| | 0.37 | −0.43 | 77.89 | 93.23 |
| | 0.12 | −0.91 | 74.28 | 89.98 |
| | 0.04 | −1.39 | 79.83 | 75.92 |
| | 0.01 | −1.86 | 88.39 | 101.46 |
| | 0.00 | −2.34 | 97.94 | 98.81 |
| WV-34311 | 10.00 | 1.00 | 62.29 | 75.77 |
| | 3.30 | 0.52 | 78.74 | 79.20 |
| | 1.12 | 0.05 | 60.20 | 86.45 |
| | 0.37 | −0.43 | 78.43 | 75.70 |
| | 0.12 | −0.91 | 73.28 | 85.42 |
| | 0.04 | −1.39 | 85.86 | 84.02 |
| | 0.01 | −1.86 | 83.86 | 97.07 |
| | 0.00 | −2.34 | 101.10 | 107.83 |

TABLE 29B-continued

Activities of certain oligonucleotide compositions. Certain oligonucleotide compositions were tested in a 293T stable cells with transfection (procedures as shown in example 4). Oligonucleotide were tested at multiple concentrations (shown as nM and Log dose nM).

| | Conc. nM | Conc. [Log (dose nM)] | WT Rho | |
|---|---|---|---|---|
| WV-34316 | 10.00 | 1.00 | 80.56 | 82.57 |
| | 3.30 | 0.52 | 93.70 | 87.42 |
| | 1.12 | 0.05 | 82.33 | 81.23 |
| | 0.37 | −0.43 | 82.22 | 87.81 |
| | 0.12 | −0.91 | 78.55 | 86.00 |
| | 0.04 | −1.39 | 87.88 | 78.13 |
| | 0.01 | −1.86 | 82.08 | 85.62 |
| | 0.00 | −2.34 | 99.32 | 89.74 |
| WV-34319 | 10.00 | 1.00 | 62.36 | 64.72 |
| | 3.30 | 0.52 | 88.53 | 80.13 |
| | 1.12 | 0.05 | 79.60 | 94.19 |
| | 0.37 | −0.43 | 75.06 | 76.00 |
| | 0.12 | −0.91 | 81.20 | 83.96 |
| | 0.04 | −1.39 | 83.70 | 97.55 |
| | 0.01 | −1.86 | 89.53 | 90.40 |
| | 0.00 | −2.34 | 83.29 | 109.02 |
| WV-34327 | 10.00 | 1.00 | 67.92 | 80.94 |
| | 3.30 | 0.52 | 82.88 | 84.38 |
| | 1.12 | 0.05 | 71.43 | 86.40 |
| | 0.37 | −0.43 | 85.47 | 102.77 |
| | 0.12 | −0.91 | 73.45 | 83.77 |
| | 0.04 | −1.39 | 95.13 | 88.68 |
| | 0.01 | −1.86 | 79.74 | 90.67 |
| | 0.00 | −2.34 | 90.06 | 90.69 |
| WV-24004 | 10.00 | 1.00 | 10.00 | 14.94 |
| | 3.30 | 0.52 | 37.61 | 29.56 |
| | 1.12 | 0.05 | 53.94 | 55.88 |
| | 0.37 | −0.43 | 58.96 | 80.82 |
| | 0.12 | −0.91 | 85.98 | 82.75 |
| | 0.04 | −1.39 | 88.42 | 108.25 |
| | 0.01 | −1.86 | 87.14 | 115.72 |
| | 0.00 | −2.34 | 111.84 | 119.25 |

TABLE 30

Activities of certain oligonucleotide compositions. Certain oligonucleotide compositions were tested in a 293T stable cells with transfection (procedures as shown in example 4). Oligonucleotide were tested at multiple concentrations (shown as nM and Log dose nM).

| | Conc. nM | Conc. [Log (dose nM)] | Rho-Wt | | RhoP23H | |
|---|---|---|---|---|---|---|
| WV-24658 | 10 | 1.00 | 92.78 | 136.64 | 19.95 | 21.87 |
| | 3.3 | 0.52 | 94.01 | 101 | 20.91 | 18.27 |
| | 1.12 | 0.05 | 77.24 | 68.9 | 47.26 | 43.12 |
| | 0.37 | −0.43 | 84.3 | 99.13 | 64.89 | 69.32 |
| | 0.12 | −0.91 | 106 | 86.89 | 94.65 | 96.03 |
| | 0.04 | −1.39 | 106.92 | 89.03 | 109.19 | 105.46 |
| | 0.01 | −1.86 | 92.79 | 109.91 | 102.96 | 111.26 |
| | 0.004 | −2.34 | 110.92 | 102.1 | 119.86 | 106.26 |
| WV-34283 | 10 | 1.00 | 64.99 | 56.32 | 13.27 | 16.16 |
| | 3.3 | 0.52 | 73.22 | 70.47 | 19.92 | 20.36 |
| | 1.12 | 0.05 | 93.29 | 69.78 | 41.91 | 43.58 |
| | 0.37 | −0.43 | 80.61 | 95.91 | 63.58 | 78.46 |
| | 0.12 | −0.91 | 112.62 | 100.7 | 83.53 | 91.75 |
| | 0.04 | −1.39 | 95.02 | 92.99 | 128.98 | 118.61 |
| | 0.01 | −1.86 | 109.37 | 152.86* | 103.12 | 96.57 |
| | 0.004 | −2.34 | 97.91 | 96.05 | 115.32 | 120.55 |
| WV-34284 | 10 | 1.00 | 58.62 | 62.3 | 16.49 | 15.99 |
| | 3.3 | 0.52 | 60.07 | 74.32 | 17.49 | 19.86 |
| | 1.12 | 0.05 | 72.23 | 95.43 | 45.88 | 38.51 |
| | 0.37 | −0.43 | 93.09 | 99.26 | 69.86 | 67.31 |
| | 0.12 | −0.91 | 96.27 | 105.96 | 90 | 98.25 |
| | 0.04 | −1.39 | 98.91 | 100.02 | 101.63 | 102.59 |
| | 0.01 | −1.86 | 97.8 | 142.26 | 95.4 | 103.03 |
| | 0.004 | −2.34 | 107.94 | 84.55 | 95.55 | 108.95 |

TABLE 30-continued

Activities of certain oligonucleotide compositions. Certain oligonucleotide compositions were tested in a 293T stable cells with transfection (procedures as shown in example 4). Oligonucleotide were tested at multiple concentrations (shown as nM and Log dose nM).

| | Conc. nM | Conc. [Log (dose nM)] | Rho-Wt | | RhoP23H | |
|---|---|---|---|---|---|---|
| WV-34287 | 10 | 1.00 | 76.37 | 81.46 | 19.13 | 12.96 |
| | 3.3 | 0.52 | 60.3 | 103.46 | 24.76 | 26.72 |
| | 1.12 | 0.05 | 73.93 | 90.88 | 49.56 | 50.5 |
| | 0.37 | −0.43 | 103.29 | 94.87 | 73.18 | 81.91 |
| | 0.12 | −0.91 | 111.85 | 95.44 | 80.48 | 103.56 |
| | 0.04 | −1.39 | 107.01 | 100.89 | 100.14 | 108.52 |
| | 0.01 | −1.86 | 91.29 | 115.09 | 106.37 | 95.95 |
| | 0.004 | −2.34 | 109.1 | 109.16 | 122.5 | 100.15 |
| WV-34290 | 10 | 1.00 | 82.63 | 80.98 | 18.59 | 13.92 |
| | 3.3 | 0.52 | 54.13 | 87.74 | 20.52 | 17.55 |
| | 1.12 | 0.05 | 84.02 | 76.61 | 44.55 | 47.03 |
| | 0.37 | −0.43 | 70.31 | 92.96 | 73.58 | 72.27 |
| | 0.12 | −0.91 | 113.35 | 84.72 | 75.98 | 88.25 |
| | 0.04 | −1.39 | 80.15 | 118.56 | 114.78 | 110.29 |
| | 0.01 | −1.86 | 77.78 | 127.74 | 88.66 | 96.73 |
| | 0.004 | −2.34 | 112.95 | 81.95 | 111.54 | 107.41 |
| WV-34294 | 10 | 1.00 | 61.03 | 58.92 | 15.44 | 20.93 |
| | 3.3 | 0.52 | 67.14 | 81.36 | 29.7 | 32.01 |
| | 1.12 | 0.05 | 82.44 | 65.2 | 55.16 | 51.93 |
| | 0.37 | −0.43 | 93.31 | 96.5 | 82.86 | 75.83 |
| | 0.12 | −0.91 | 123.57 | 88.39 | 88.58 | 91.82 |
| | 0.04 | −1.39 | 100.98 | 97.61 | 112.37 | 106.08 |
| | 0.01 | −1.86 | 94.53 | 110.34 | 117.73 | 96.08 |
| | 0.004 | −2.34 | 118.36 | 93.75 | 111.91 | 106.58 |
| WV-34296 | 10 | 1.00 | 76.64 | 106.47 | 19.29 | 17.37 |
| | 3.3 | 0.52 | 69.48 | 74.54 | 24.56 | 26.93 |
| | 1.12 | 0.05 | 100.73 | 58.5 | 43.1 | 43.18 |
| | 0.37 | −0.43 | 109.69 | 69.68 | 65.91 | 57.14 |
| | 0.12 | −0.91 | 85.37 | 102.84 | 71.96 | 93.28 |
| | 0.04 | −1.39 | 111.84 | 111.38 | 90.45 | 92.78 |
| | 0.01 | −1.86 | 74.74 | 121.86 | 112.49 | 95.1 |
| | 0.004 | −2.34 | 93.2 | 90.95 | 106.83 | 116.28 |
| WV-34297 | 10 | 1.00 | 83.48 | 94.07 | 25.89 | 17.4 |
| | 3.3 | 0.52 | 72.7 | 70.49 | 18.61 | 20.36 |
| | 1.12 | 0.05 | 72.8 | 56.16 | 40.44 | 41.94 |
| | 0.37 | −0.43 | 108.83 | 119.5 | 70.19 | 67.3 |
| | 0.12 | −0.91 | 106.98 | 87.7 | 95.69 | 74.21 |
| | 0.04 | −1.39 | 78.16 | 90.14 | 108.49 | 100.6 |
| | 0.01 | −1.86 | 72.81 | 109.92 | 103.84 | 83.16 |
| | 0.004 | −2.34 | 102.94 | 64.69 | 115.99 | 106.98 |
| WV-34300 | 10 | 1.00 | 97.61 | 136.18 | 26.54 | 32.58 |
| | 3.3 | 0.52 | 88.2 | 83.07 | 32.49 | 36.36 |
| | 1.12 | 0.05 | 87.78 | 76.99 | 68.12 | 56.32 |
| | 0.37 | −0.43 | 113.93 | 119.57 | 80.18 | 82.91 |
| | 0.12 | −0.91 | 129.76 | 108.09 | 109.22 | 73.9 |
| | 0.04 | −1.39 | 120.01 | 139.41 | 104.01 | 113.83 |
| | 0.01 | −1.86 | 128.14 | 96.85 | 125.9 | 96.51 |
| | 0.004 | −2.34 | 120.34 | 131.68 | 124.13 | 161.37* |
| WV-23658 | 10 | 1.00 | 159.25 | 193.47* | 29.78 | 27.38 |
| | 3.3 | 0.52 | 72.87 | 79.4 | 20.44 | 26.82 |
| | 1.12 | 0.05 | 72.23 | 67.25 | 37.89 | 33.54 |
| | 0.37 | −0.43 | 82.09 | 105.94 | 63.75 | 58.6 |
| | 0.12 | −0.91 | 100.44 | 98.89 | 93.91 | 96.67 |
| | 0.04 | −1.39 | 111.19 | 87.91 | 130.86 | 107.39 |
| | 0.01 | −1.86 | 97.22 | 116.54 | 111.08 | 94.4 |
| | 0.004 | −2.34 | 86.45 | 93.07 | 121.09 | 142* |

TABLE 31A

Activities of certain oligonucleotide compositions. Certain oligonucleotide compositions were tested in a 293T stable cells with transfection (procedures as shown in example 4). Oligonucleotide were tested at multiple concentrations (shown as nM and Log dose nM).

| | Conc. nM | Conc. [Log (dose nM)] | Rho-Wt | | RhoP23H | |
|---|---|---|---|---|---|---|
| WV-24668 | 10 | 1.00 | 64.71 | 86.26 | 11.15 | 8.82 |
| | 3.3 | 0.52 | 80.17 | 81.74 | 17.81 | 16.03 |
| | 1.12 | 0.05 | 86.47 | 83.39 | 36.12 | 38.75 |
| | 0.37 | −0.43 | 92.85 | 97.56 | 63.36 | 74.26 |
| | 0.12 | −0.91 | 108.82 | 143.94 | 89.43 | 86.97 |
| | 0.04 | −1.39 | 118.91 | 113.31 | 146.41 | 120.83 |
| | 0.01 | −1.86 | 103.77 | 89.39 | 130.79 | 103.05 |
| | 0.004 | −2.34 | 114.32 | 107.01 | 122.35 | 145.46 |
| WV-34301 | 10 | 1.00 | 83.27 | 126.39 | 21.22 | 19.28 |
| | 3.3 | 0.52 | 93.44 | 103.98 | 33.13 | 34.45 |
| | 1.12 | 0.05 | 87.15 | 93.27 | 52.54 | 58.72 |
| | 0.37 | −0.43 | 96.8 | 137.46 | 72.34 | 87.45 |
| | 0.12 | −0.91 | 121.57 | 134.78 | 96.78 | 116.67 |
| | 0.04 | −1.39 | 105.89 | 131.27 | 113.68 | 96.26 |
| | 0.01 | −1.86 | 98.68 | 120.49 | 107.63 | 97.68 |
| | 0.004 | −2.34 | 99.82 | 115.44 | 123.52 | 145.41* |
| WV-34302 | 10 | 1.00 | 55.09 | 75.57 | 9.36 | 10.63 |
| | 3.3 | 0.52 | 87.65 | 79.22 | 17.64 | 17.18 |
| | 1.12 | 0.05 | 71.15 | 87.89 | 44.92 | 35.08 |
| | 0.37 | −0.43 | 95.23 | 114.95 | 69.85 | 78.04 |
| | 0.12 | −0.91 | 107 | 117.65 | 90.13 | 90.22 |
| | 0.04 | −1.39 | 118.13 | 116.28 | 137.36 | 113.04 |
| | 0.01 | −1.86 | 161.83* | 90.9 | 130.66 | 110.33 |
| | 0.004 | −2.34 | 109.74 | 109.14 | 122.33 | 173.07* |
| WV-34311 | 10 | 1.00 | 56.23 | 72.26 | 9 | 9.36 |
| | 3.3 | 0.52 | 86.6 | 86.35 | 19.99 | 22.82 |
| | 1.12 | 0.05 | 81.56 | 79.26 | 53.86 | 43.76 |
| | 0.37 | −0.43 | 107.34 | 114.72 | 79.47 | 78.47 |
| | 0.12 | −0.91 | 114.19 | 110.13 | 112.45 | 106.34 |
| | 0.04 | −1.39 | 98.82 | 96.52 | 116.06 | 111 |
| | 0.01 | −1.86 | 130.25 | 136.72 | 108.62 | 97.46 |
| | 0.004 | −2.34 | 103.36 | 107.22 | 115.08 | 148.96* |
| WV-34316 | 10 | 1.00 | 68.54 | 75.09 | 11.26 | 10.67 |
| | 3.3 | 0.52 | 73.67 | 85.36 | 24.94 | 28.1 |
| | 1.12 | 0.05 | 106.31 | 96.1 | 58.16 | 52.36 |
| | 0.37 | −0.43 | 104 | 109.22 | 77.07 | 85.3 |
| | 0.12 | −0.91 | 133.87 | 101.93 | 99.14 | 105.98 |
| | 0.04 | −1.39 | 113.99 | 103.52 | 124.56 | 126.07 |
| | 0.01 | −1.86 | 130.65 | 114.24 | 101.1 | 102.12 |
| | 0.004 | −2.34 | 89.49 | 104.45 | 124.09 | 148.01* |
| WV-34319 | 10 | 1.00 | 55.58 | 71.19 | 9.6 | 9.6 |
| | 3.3 | 0.52 | 89.44 | 75.24 | 27.67 | 24.49 |
| | 1.12 | 0.05 | 99.67 | 89.96 | 66.32 | 47.44 |
| | 0.37 | −0.43 | 97.77 | 137.71 | 86.97 | 80.06 |
| | 0.12 | −0.91 | 118.86 | 102.57 | 98.67 | 127 |
| | 0.04 | −1.39 | 110.72 | 108.33 | 132.67 | 107.17 |
| | 0.01 | −1.86 | 111.24 | 74.38 | 134.49 | 99.55 |
| | 0.004 | −2.34 | 96.23 | 118.54 | 125.41 | 155.37* |
| WV-34327 | 10 | 1.00 | 40.1 | 81.53 | 7.26 | 8.36 |
| | 3.3 | 0.52 | 75.64 | 92.95 | 25.64 | 26.47 |
| | 1.12 | 0.05 | 101.34 | 89.84 | 58.43 | 47.59 |
| | 0.37 | −0.43 | 92.19 | 108.42 | 78.1 | 67.92 |
| | 0.12 | −0.91 | 126.55 | 109.56 | 93.53 | 103.45 |
| | 0.04 | −1.39 | 100.49 | 102.79 | 125.06 | 105.65 |
| | 0.01 | −1.86 | 100.89 | 127.87 | 108.96 | 101.94 |
| | 0.004 | −2.34 | 76.54 | 101.57 | 115.92 | 124.82 |
| WV-34295 | 10 | 1.00 | 142.41 | 204.35* | 22.22 | 20.76 |
| | 3.3 | 0.52 | 56.06 | 90.29 | 16.71 | 11.92 |
| | 1.12 | 0.05 | 62.84 | 106.16 | 24.99 | 24.86 |
| | 0.37 | −0.43 | 82.04 | 77.88 | 55.7 | 56.35 |
| | 0.12 | −0.91 | 89 | 121.45 | 73.94 | 73.01 |
| | 0.04 | −1.39 | 73.57 | 110.71 | 84.89 | 113.66 |
| | 0.01 | −1.86 | 74.76 | 86.55 | 100.12 | 107.92 |
| | 0.004 | −2.34 | 96.83 | 85.77 | 113.13 | 116.06 |

TABLE 31B

Activities of certain oligonucleotide compositions. WV-24004 was tested in a 293T stable cells with transfection ((four bioreps, procedures as shown in example 4) at multiple concentrations (shown as nM and Log dose nM).

| | | | Rho-Wt | | | | RhoP23H | | | |
|---|---|---|---|---|---|---|---|---|---|---|
| WV-24004 | 10 | 1.00 | 18.85 | 19.80 | 15.45 | 18.21 | 11.73 | 12.20 | 14.01 | 13.02 |
| | 3.3 | 0.52 | 27.65 | 27.99 | 26.57 | 31.28 | 11.58 | 14.31 | 17.37 | 16.22 |
| | 1.12 | 0.05 | 41.62 | 33.73 | 33.43 | 39.05 | 24.56 | 25.9 | 22.3 | 24.5 |
| | 0.37 | −0.43 | 49.35 | 49.39 | 40.39 | 49.69 | 27.13 | 37.94 | 37.59 | 36.13 |
| | 0.12 | −0.91 | 84.94 | 91.34 | 77.35 | 66.36 | 65.57 | 55.67 | 52.21 | 57.59 |
| | 0.04 | −1.39 | 70.96 | 60.54 | 69.06 | 71.5 | 84.02 | 93.96 | 89.05 | 66.91 |
| | 0.01 | −1.86 | 78.27 | 96.85 | 88.56 | 91.09 | 96.58 | 106.75 | 100.5 | 93.27 |
| | 0.004 | −2.34 | 87.49 | 98.93 | 83.4 | 98.67 | 85.42 | 117.74 | 106.21 | 140.95 |

TABLE 32

Activities of certain oligonucleotide compositions. Certain oligonucleotide compositions were tested in a 293T stable cells with gymnotic delivery (procedures as shown in example 5). Oligonucleotide were tested at a concentrations of 5 uM.

| 5 uM treatment | Wt Rho (5 uM) | | P23H (5 uM) | |
|---|---|---|---|---|
| WV-15309 | 100.43 | 92.28 | 105.31 | 78.40 |
| WV-24004 | 70.41 | 76.12 | 81.27 | 66.45 |
| WV-23658 | 86.50 | 87.95 | 67.72 | 69.98 |
| WV-23668 | 84.57 | 99.38 | 68.80 | 69.67 |
| WV-34326 | 98.39 | 89.40 | 49.28 | 53.61 |
| WV-34319 | 95.94 | 77.87 | 59.79 | 54.02 |
| WV-34327 | 80.65 | 86.22 | 61.54 | 61.59 |
| WV-34301 | 87.91 | 90.89 | 61.19 | 63.16 |
| WV-34292 | 93.62 | 101.06 | 63.38 | 61.87 |
| WV-24668 | 72.73 | 87.66 | 67.16 | 58.86 |
| WV-34309 | 94.50 | 88.65 | 63.21 | 63.76 |
| WV-34305 | 81.10 | 80.21 | 65.67 | 61.68 |
| WV-34312 | 87.06 | 83.50 | 67.15 | 60.25 |
| WV-34318 | 104.70 | 100.73 | 64.67 | 62.90 |
| WV-34284 | 86.20 | 101.99 | 63.60 | 65.79 |
| WV-34286 | 85.20 | 86.93 | 63.05 | 67.68 |
| WV-34311 | 98.08 | 94.56 | 67.62 | 63.55 |
| WV-34303 | 101.86 | 104.69 | 62.50 | 69.15 |
| WV-34287 | 88.49 | 88.77 | 67.20 | 65.06 |
| WV-34297 | 98.69 | 85.73 | 67.74 | 64.85 |
| WV-34316 | 99.78 | 112.53 | 66.70 | 66.28 |
| WV-34313 | 97.14 | 103.07 | 70.27 | 65.03 |
| WV-24654 | 90.61 | 101.95 | 69.28 | 66.50 |
| WV-34293 | 84.40 | 88.59 | 70.56 | 67.09 |
| WV-34296 | 93.66 | 91.67 | 74.66 | 63.29 |
| WV-34310 | 110.20 | 93.42 | 71.26 | 66.74 |
| WV-34306 | 100.23 | 89.07 | 73.74 | 64.80 |
| WV-34322 | 93.29 | 101.78 | 74.45 | 65.05 |
| WV-34323 | 87.34 | 95.69 | 72.53 | 67.73 |
| WV-34308 | 97.59 | 84.74 | 73.76 | 66.60 |
| WV-34289 | 89.33 | 90.29 | 70.94 | 69.86 |
| WV-34300 | 92.53 | 91.33 | 78.39 | 62.46 |
| WV-34324 | 101.34 | 85.81 | 74.71 | 66.52 |
| WV-34302 | 94.12 | 102.62 | 70.17 | 71.79 |
| WV-34285 | 104.33 | 93.72 | 69.62 | 73.73 |
| WV-24653 | 101.04 | 102.82 | 74.40 | 72.89 |
| WV-24004 | 70.41 | 76.12 | 81.27 | 66.45 |
| WV-34294 | 99.51 | 81.20 | 82.05 | 65.95 |
| WV-34325 | 96.04 | 104.18 | 81.63 | 66.44 |
| WV-34317 | 92.23 | 89.37 | 70.27 | 78.00 |
| WV-34307 | 84.33 | 97.03 | 80.34 | 68.06 |
| WV-34304 | 106.36 | 84.73 | 78.51 | 70.42 |
| WV-34315 | 96.63 | 88.04 | 77.05 | 71.99 |
| WV-24657 | 67.73 | 92.99 | 76.86 | 73.24 |
| WV-24658 | 83.45 | 97.85 | 78.88 | 73.74 |
| WV-34291 | 85.69 | 90.84 | 84.62 | 71.31 |
| WV-34283 | 84.52 | 94.01 | 84.49 | 73.11 |
| WV-34288 | 97.55 | 78.62 | 90.38 | 67.82 |
| WV-34290 | 94.87 | 100.67 | 86.95 | 72.18 |

TABLE 32-continued

Activities of certain oligonucleotide compositions. Certain oligonucleotide compositions were tested in a 293T stable cells with gymnotic delivery (procedures as shown in example 5). Oligonucleotide were tested at a concentrations of 5 uM.

| 5 uM treatment | Wt Rho (5 uM) | | P23H (5 uM) | |
|---|---|---|---|---|
| WV-24656 | 85.07 | 99.33 | 85.32 | 74.83 |
| WV-34298 | 94.42 | 94.26 | 88.32 | 76.21 |
| WV-24655 | 101.68 | 83.34 | 90.23 | 81.36 |
| WV-34299 | 95.03 | 85.15 | 88.21 | 85.23 |

TABLE 33

Activities of certain oligonucleotide compositions. Certain oligonucleotide compositions were tested in a 293T stable cells with gymnotic delivery (procedures as shown in Example 4). Oligonucleotide were tested at a concentrations of 5uM.

| 5 uM treatment | Wt Rho (5 uM) | | P23H (5 uM) | |
|---|---|---|---|---|
| WV-15309 | 100.43 | 92.28 | 105.31 | 78.40 |
| WV-24004 | 70.41 | 76.12 | 81.27 | 66.45 |
| WV-23658 | 86.50 | 87.95 | 67.72 | 69.98 |
| WV-23668 | 84.57 | 99.38 | 68.80 | 69.67 |
| WV-34326 | 98.39 | 89.40 | 49.28 | 53.61 |
| WV-34319 | 95.94 | 77.87 | 59.79 | 54.02 |
| WV-34327 | 80.65 | 86.22 | 61.54 | 61.59 |
| WV-34301 | 87.91 | 90.89 | 61.19 | 63.16 |
| WV-34292 | 93.62 | 101.06 | 63.38 | 61.87 |
| WV-24668 | 72.73 | 87.66 | 67.16 | 58.86 |
| WV-34309 | 94.50 | 88.65 | 63.21 | 63.76 |
| WV-34305 | 81.10 | 80.21 | 65.67 | 61.68 |
| WV-34312 | 87.06 | 83.50 | 67.15 | 60.25 |
| WV-34318 | 104.70 | 100.73 | 64.67 | 62.90 |
| WV-34284 | 86.20 | 101.99 | 63.60 | 65.79 |
| WV-34286 | 85.20 | 86.93 | 63.05 | 67.68 |
| WV-34311 | 98.08 | 94.56 | 67.62 | 63.55 |
| WV-34303 | 101.86 | 104.69 | 62.50 | 69.15 |
| WV-34287 | 88.49 | 88.77 | 67.20 | 65.06 |
| WV-34297 | 98.69 | 85.73 | 67.74 | 64.85 |
| WV-34316 | 99.78 | 112.53 | 66.70 | 66.28 |
| WV-34313 | 97.14 | 103.07 | 70.27 | 65.03 |
| WV-24654 | 90.61 | 101.95 | 69.28 | 66.50 |
| WV-34293 | 84.40 | 88.59 | 70.56 | 67.09 |

TABLE 34A

Activities of certain oligonucleotide compositions. Certain oligonucleotide compositions were tested in a 293T stable cells with gymnotic delivery (procedures as shown in Example 4). Oligonucleotide were tested at multiple concentrations (shown as nM and Log dose nM).

| | Conc. uM | Conc. [Log (dose uM)] | RhoP23H | |
|---|---|---|---|---|
| WV-23658 | 25.00 | 1.40 | 40.39 | 42.44 |
| | 10.00 | 1.00 | 54.00 | |
| | 3.98 | 0.60 | 57.99 | 58.90 |
| | 1.58 | 0.20 | 63.58 | 67.24 |
| | 0.65 | −0.19 | 65.40 | 76.30 |
| | 0.26 | −0.59 | 89.41 | 80.72 |
| | 0.10 | −0.99 | 88.21 | 97.31 |
| | 0.04 | −1.39 | 99.62 | 81.94 |
| WV-24004 | 25.00 | 1.40 | 31.60 | 35.81 |
| | 10.00 | 1.00 | 44.29 | 35.84 |
| | 3.98 | 0.60 | 39.51 | 46.72 |
| | 1.58 | 0.20 | 53.09 | 57.37 |
| | 0.65 | −0.19 | 50.83 | 51.45 |
| | 0.26 | −0.59 | 65.44 | 69.59 |
| | 0.10 | −0.99 | 76.38 | 68.45 |
| | 0.04 | −1.39 | 84.78 | 81.72 |
| WV-24668 | 25.00 | 1.40 | 27.16 | 27.30 |
| | 10.00 | 1.00 | 33.99 | 30.34 |
| | 3.98 | 0.60 | 42.79 | 36.03 |
| | 1.58 | 0.20 | 55.06 | 46.21 |
| | 0.65 | −0.19 | 56.57 | 52.35 |
| | 0.26 | −0.59 | 68.79 | 69.78 |
| | 0.10 | −0.99 | 73.10 | 67.22 |
| | 0.04 | −1.39 | 86.77 | 74.50 |
| WV-34284 | 25.00 | 1.40 | 44.62 | 47.28 |
| | 10.00 | 1.00 | 60.73 | 53.56 |
| | 3.98 | 0.60 | 60.79 | 50.10 |
| | 1.58 | 0.20 | 78.16 | 71.35 |
| | 0.65 | −0.19 | 79.22 | 72.86 |
| | 0.26 | −0.59 | 87.43 | 72.83 |
| | 0.10 | −0.99 | 96.72 | 100.33 |
| | 0.04 | −1.39 | 92.64 | 99.77 |
| WV-34301 | 25.00 | 1.40 | 40.58 | 41.45 |
| | 10.00 | 1.00 | 63.03 | 52.92 |
| | 3.98 | 0.60 | 66.00 | 54.15 |
| | 1.58 | 0.20 | 85.76 | 64.49 |
| | 0.65 | −0.19 | 69.62 | 82.84 |
| | 0.26 | −0.59 | 92.29 | 90.02 |
| | 0.10 | −0.99 | 86.11 | 96.17 |
| | 0.04 | −1.39 | 98.46 | 103.25 |
| WV-34305 | 25.00 | 1.40 | 33.39 | 36.30 |
| | 10.00 | 1.00 | 48.86 | 47.11 |
| | 3.98 | 0.60 | 52.57 | 52.21 |
| | 1.58 | 0.20 | 67.52 | 65.02 |
| | 0.65 | −0.19 | 71.00 | 67.16 |
| | 0.26 | −0.59 | 82.00 | 70.17 |
| | 0.10 | −0.99 | 80.69 | 91.33 |
| | 0.04 | −1.39 | 85.39 | 86.67 |
| WV-34309 | 25.00 | 1.40 | 27.65 | 24.52 |
| | 10.00 | 1.00 | 37.35 | 42.17 |
| | 3.98 | 0.60 | 42.85 | 43.80 |
| | 1.58 | 0.20 | 58.33 | 51.25 |
| | 0.65 | −0.19 | 63.69 | 62.02 |
| | 0.26 | −0.59 | 76.23 | 64.24 |
| | 0.10 | −0.99 | 78.57 | 87.01 |
| | 0.04 | −1.39 | 84.43 | 107.37 |
| WV-34318 | 25.00 | 1.40 | 37.91 | 39.94 |
| | 10.00 | 1.00 | 39.69 | 46.69 |
| | 3.98 | 0.60 | 52.65 | 44.85 |
| | 1.58 | 0.20 | 61.67 | 58.52 |
| | 0.65 | −0.19 | 72.43 | 43.29 |
| | 0.26 | −0.59 | 72.45 | 77.60 |
| | 0.10 | −0.99 | 72.22 | 85.62 |
| | 0.04 | −1.39 | 99.19 | 91.05 |
| WV-34319 | 25.00 | 1.40 | 36.87 | 32.51 |
| | 10.00 | 1.00 | 39.17 | 36.33 |
| | 3.98 | 0.60 | 39.92 | 45.59 |
| | 1.58 | 0.20 | 50.35 | 56.87 |
| | 0.65 | −0.19 | 60.26 | 55.02 |
| | 0.26 | −0.59 | 64.39 | 77.72 |
| | 0.10 | −0.99 | 72.04 | 81.76 |
| | 0.04 | −1.39 | 94.49 | 110.35 |
| WV-34327 | 25.00 | 1.40 | 31.05 | 32.43 |
| | 10.00 | 1.00 | 32.59 | 33.61 |
| | 3.98 | 0.60 | 38.93 | 41.42 |
| | 1.58 | 0.20 | 57.36 | 45.73 |
| | 0.65 | −0.19 | 59.16 | 58.93 |
| | 0.26 | −0.59 | 71.70 | 60.47 |
| | 0.10 | −0.99 | 85.81 | 66.87 |
| | 0.04 | −1.39 | 92.25 | 102.50 |

TABLE 34B

Activities of certain oligonucleotide compositions. Certain oligonucleotide compositions were tested in a 293T stable cells with gymnotic delivery (procedures as shown in Example 4). Oligonucleotide were tested at multiple concentrations (shown as nM and Log dose nM).

| | Conc. uM | Conc. [Log (dose uM)] | WT RhoH | |
|---|---|---|---|---|
| WV-23658 | 25.00 | 1.40 | 54.80 | 59.69 |
| | 10.00 | 1.00 | 75.13 | 68.14 |
| | 3.98 | 0.60 | 68.27 | 68.28 |
| | 1.58 | 0.20 | 78.03 | 77.46 |
| | 0.65 | −0.19 | 78.02 | 87.19 |
| | 0.26 | −0.59 | 79.28 | 83.81 |
| | 0.10 | −0.99 | 92.80 | 93.28 |
| | 0.04 | −1.39 | 96.79 | 77.50 |
| WV-24004 | 25.00 | 1.40 | 36.19 | 36.61 |
| | 10.00 | 1.00 | 48.78 | 45.90 |
| | 3.98 | 0.60 | 43.17 | 45.66 |
| | 1.58 | 0.20 | 53.81 | 50.70 |
| | 0.65 | −0.19 | 63.74 | 72.19 |
| | 0.26 | −0.59 | 59.16 | 68.78 |
| | 0.10 | −0.99 | 76.22 | 75.89 |
| | 0.04 | −1.39 | 78.04 | 85.41 |
| WV-24668 | 25.00 | 1.40 | 60.55 | 65.03 |
| | 10.00 | 1.00 | 63.18 | 78.86 |
| | 3.98 | 0.60 | 63.27 | 74.62 |
| | 1.58 | 0.20 | 82.47 | 78.47 |
| | 0.65 | −0.19 | 89.15 | 87.46 |
| | 0.26 | −0.59 | 98.48 | 90.30 |
| | 0.10 | −0.99 | 95.46 | 103.50 |
| | 0.04 | −1.39 | 91.23 | 85.79 |
| WV-34284 | 25.00 | 1.40 | 51.53 | 64.55 |
| | 10.00 | 1.00 | 73.37 | 77.24 |
| | 3.98 | 0.60 | 79.03 | 75.67 |
| | 1.58 | 0.20 | 93.83 | 88.29 |
| | 0.65 | −0.19 | 85.02 | 87.39 |
| | 0.26 | −0.59 | 100.68 | 96.06 |
| | 0.10 | −0.99 | 92.10 | 103.74 |
| | 0.04 | −1.39 | 85.60 | 86.97 |
| WV-34301 | 25.00 | 1.40 | 65.79 | 69.02 |
| | 10.00 | 1.00 | 88.95 | 75.89 |
| | 3.98 | 0.60 | 75.72 | 88.89 |
| | 1.58 | 0.20 | 97.70 | 84.28 |
| | 0.65 | −0.19 | 94.55 | 89.86 |
| | 0.26 | −0.59 | 90.81 | 93.57 |
| | 0.10 | −0.99 | 96.93 | 98.46 |
| | 0.04 | −1.39 | 87.61 | 80.03 |
| WV-34305 | 25.00 | 1.40 | 62.35 | 58.16 |
| | 10.00 | 1.00 | 79.41 | 80.34 |
| | 3.98 | 0.60 | 77.44 | 85.88 |
| | 1.58 | 0.20 | 91.52 | 91.83 |
| | 0.65 | −0.19 | 82.82 | 74.67 |
| | 0.26 | −0.59 | 88.89 | 90.06 |

TABLE 34B-continued

Activities of certain oligonucleotide compositions. Certain oligonucleotide compositions were tested in a 293T stable cells with gymnotic delivery (procedures as shown in Example 4). Oligonucleotide were tested at multiple concentrations (shown as nM and Log dose nM).

| | Conc. uM | Conc. [Log (dose uM)] | WT RhoH | |
|---|---|---|---|---|
| | 0.10 | −0.99 | 81.68 | 94.98 |
| | 0.04 | −1.39 | 86.74 | 79.63 |
| WV-34309 | 25.00 | 1.40 | 57.71 | 61.43 |
| | 10.00 | 1.00 | 75.74 | 79.16 |
| | 3.98 | 0.60 | 82.57 | 79.44 |
| | 1.58 | 0.20 | 83.96 | 82.97 |
| | 0.65 | −0.19 | 80.44 | 83.37 |
| | 0.26 | −0.59 | 91.03 | 87.60 |
| | 0.10 | −0.99 | 82.74 | 101.57 |
| | 0.04 | −1.39 | 74.78 | 81.76 |
| WV-34318 | 25.00 | 1.40 | 64.47 | 69.05 |
| | 10.00 | 1.00 | 82.93 | 77.61 |
| | 3.98 | 0.60 | 85.25 | 77.29 |
| | 1.58 | 0.20 | 100.80 | 81.91 |
| | 0.65 | −0.19 | 83.71 | 86.95 |
| | 0.26 | −0.59 | 90.98 | 93.54 |
| | 0.10 | −0.99 | 90.82 | 96.30 |
| | 0.04 | −1.39 | 90.87 | 85.78 |
| WV-34319 | 25.00 | 1.40 | | |
| | 10.00 | 1.00 | 84.12 | 98.16 |
| | 3.98 | 0.60 | 71.50 | 81.60 |
| | 1.58 | 0.20 | 84.53 | 87.52 |
| | 0.65 | −0.19 | 86.73 | 87.63 |
| | 0.26 | −0.59 | 88.91 | 89.98 |
| | 0.10 | −0.99 | 91.14 | 102.43 |
| | 0.04 | −1.39 | 87.71 | 87.73 |
| WV-34327 | 25.00 | 1.40 | | 82.61 |
| | 10.00 | 1.00 | 74.22 | 67.79 |
| | 3.98 | 0.60 | 75.15 | 75.23 |
| | 1.58 | 0.20 | 82.21 | 82.49 |
| | 0.65 | −0.19 | 85.22 | 88.18 |
| | 0.26 | −0.59 | 84.67 | 88.31 |
| | 0.10 | −0.99 | 102.20 | 86.67 |
| | 0.04 | −1.39 | 79.88 | 82.60 |

Example 3. Example Procedures

Various technologies are available for assessing provided oligonucleotides and compositions, for example, various experimental protocols can be used to test the activity of RHO oligonucleotides in vitro. Non-limiting examples of procedures which have been or which can be used to test the activity of RHO oligonucleotides and compositions are described herein.

Cells which can be used include human and mouse cells. In some experiments, Cos7 cells were used.

In some embodiments, for certain in vitro assay methods:

RHO-WT and RHO-P23H gene-containing luciferase plasmids were constructed, by inserting the RHO gene into the psiCHECK™-2 Vector, which comprises a luciferase gene. To construct a transfection control, the firefly luciferase gene was inserted into the multi-cloning site of the psiCHECK™-2 Vector.

All the assays unless otherwise specified were performed in vitro using Cos-7 cells as a transfection host. Plasmids and modified oligonucleotides (e.g., RHO oligonucleotides) were co-transfected using Lipofectamine™ 2000 Transfection Reagent (Cat. No. 11668019) as suggested by the vendors protocol. A non-targeting control was used in every experiment as a negative control. All the co-transfection experiments were carried out in 96 WP formats and the cells were further incubated for 48 hours in a cell culture hood at 37 degree C. All the experiments were carried out in biological duplicates.

Dual-Glo® Luciferase Assay System (Promega, Parts E2920, E2940 and E2980) was typically used to measure the luminescence intensity as per vendor protocols. Briefly, the following steps are used: Warm up all reagents and buffers to room temperature, transfer the contents of one bottle of Dual-Glo® Luciferase Buffer to one bottle of Dual-Glo® Luciferase Substrate to create the Dual-Glo®Luciferase Reagent. Mix by inversion until the substrate is thoroughly dissolved. Calculate the amount of Dual-Glo® Stop & Glo® Reagent needed to perform the desired experiments. Dilute the Dual-Glo® Stop & Glo® Substrate 1:100 into an appropriate volume of Dual-Glo® Stop & Glo® Buffer in a new container Measuring firefly luciferase activity: After 48 hours of incubation, take out all plates from the cell culture hood and let it cool down to room temperature. Then add a volume of Dual-Glo® Luciferase Reagent equal to the culture medium volume to each well and mix. Wait at least 10 minutes, then measure the firefly luminescence.

Measuring Renilla luciferase activity: Add a volume of Dual-Glo® Stop & Glo® Reagent equal to the original culture medium volume to each well and mix. Wait at least 10 minutes, and then measure luminescence.

Renilla Luciferase luminance intensity was providing measurements for target (RHO-WT or RhoP23H) expressions. Firefly Luciferase luminance was used as a normalization control for transfection of plasmids. All the measurements are reported as normalized values and expressed as percentage knock down compared to universal non-target sequence used.

Various RHO oligonucleotides and compositions can be tested for their ability to knockdown the activity, level and/or expression of wild-type and/or mutant RHO mRNA or protein.

Example 4. Example Procedures

In some embodiments, provided technologies are assessed utilizing cells expressing wild-type and/or mutant Rho. For example, in some embodiments, a useful protocol to establish 293T stable cell line with Wt and P23H Rhodopsin expression is described below.

293T cells with 50% confluence were infected with Rho-Wt and Rho-P23H lentivirus (Vigene Biosciences, Inc) with MOI: 0.5, 1, 2, 3, and 4. Next day, the infected cells were changed into 0.3 ug/ml puromycin selection medium. After two weeks, stable cells were evaluated by GFP expression in Florescent microscope and qPCR for rhodopsin mRNA expression.

Dose response assay with 293T stable cells by transfection

Oligonucleotides were diluted with $H_2O$ into 60 nM, and further 3-fold serial dilution for 7 times. Dilute the lipofectamine 2000 (ThermoFisher, cat #:11668019) 100× with opti-MEM, incubate for 5 minutes at RT. Mix 25 uL of oligonucleotide with 25 uL of lipofectamine 2000 transfection reagent, and incubate at RT for 15 min. Then Mix 50 uL oligonucleotide-lipofectamine 2000 complex with 100 uL 293T stable cells (10,000 per well) in 96-well plate with final oligonucleotide concentration at 10 nM, 3.33 nM, 1.11 nm, 0.37 nM, 0.12 nM, 41 pM, 13.7 pM, and 4.6 pM. Incubate cells at 37 C, 5% CO2 incubator for 2 days.

Dose response assay with 293T stable cells by gymnotic treatment.

In some embodiments, oligonucleotides are delivered gymnotically. For screening with 5 uM oligonucleotide, mix 15 uL of 50 uM oligonucleotide with 135 uL 293T stable cells (10.8k cells) for each well in 96 well plate, incubate for 2 days before mRNA analysis.

For dose response assay, oligonucleotides with 250 uM were diluted with 2.5×serial dilution for seven times. Mix 12 uL oligonucleotide with 108 uL 293T cells in serum reduced medium (1% FBS), and the final oligonucleotide concentrations are 25 uM, 10 uM, 4 uM, 1.6 uM, 0.64 uM, 0.26 uM, 0.10 uM, and 0.041 uM. Incubate cells for three days before mRNA analysis.

mRNA analysis with Tagman qPCR.

mRNA was extracted with Turbocapture 384 mRNA kit (Qiagen, cat #: 72271) and cDNA synthesis were performed with Transcriptor First Strand cDNA synthesis kit (Roche, cat #: 0489703001) following the manufacture instruction.

Rhodopsin mRNA expression was tested with Tagman qPCR with LightCycler® 480 Probes Master (Roche, cat #: 04887301001). qPCR probes were rhodopsin (Hs00892431_ml, FAM, 60×) and GAPDH (Hs02786624_g1, VIC PL, 60×) from ThermoFisher.

In some embodiments, the present disclosure provides the following example embodiments:

Example Embodiments

1. An oligonucleotide, wherein the base sequence of the oligonucleotide comprises at least 15, 16, 17, 18, 19, 20, 21, 22, 23, 24, or 25 contiguous nucleobases of a base sequence that is at least 75% identical or complementary to a base sequence of a RHO gene or a transcript thereof, wherein the oligonucleotide comprises at least one chiral internucleotidic linkage comprising a stereodefined linkage phosphorus.

2. An oligonucleotide, wherein the base sequence of the oligonucleotide comprises at least 15, 16, 17, 18, 19, 20, 21, 22, 23, 24, or 25 contiguous nucleobases of a base sequence that is identical or complementary to a base sequence of a RHO gene or a transcript thereof, wherein the oligonucleotide comprises at least one chiral internucleotidic linkage comprising a stereodefined linkage phosphorus.

3. An oligonucleotide, wherein the base sequence of the oligonucleotide comprises at least 15, 16, 17, 18, 19, 20, 21, 22, 23, 24, or 25 contiguous nucleobases of a base sequence that is at least 75% identical or complementary to a base sequence of a RHO gene or a transcript thereof, wherein the oligonucleotide comprises at least one chiral internucleotidic linkage comprising a stereodefined linkage phosphorus, and wherein the oligonucleotide is capable of decreasing the level, expression and/or activity of a RHO target gene or a gene product thereof.

4. An oligonucleotide, wherein the base sequence of the oligonucleotide comprises at least 15, 16, 17, 18, 19, 20, 21, 22, 23, 24, or 25 contiguous nucleobases of a base sequence that is identical or complementary to a base sequence of a RHO gene or a transcript thereof, wherein the oligonucleotide comprises at least one chiral internucleotidic linkage comprising a stereodefined linkage phosphorus, and wherein the oligonucleotide is capable of decreasing the level, expression and/or activity of a RHO target gene or a gene product thereof.

5. An oligonucleotide, whose base sequence is, comprises, or comprises a span of 10, 11, 12, 13, 14, 15, 16, 17, 18, 19 or 20 contiguous nucleobases of any base sequences in Table A1 or A2.

6. The oligonucleotide of Embodiment 5, wherein the oligonucleotide comprises at least one chiral internucleotidic linkage comprising a stereodefined linkage phosphorus.

7. An oligonucleotide, wherein the oligonucleotide comprises a plurality of chiral internucleotidic linkages each of which independently comprises a stereodefined linkage phosphorus, wherein the pattern of backbone chiral centers of the oligonucleotide comprises [(Rp/Op)n(Sp)m]y, wherein:

n is 1-10;

m is 1-50;

y is 2-10;

Op indicates a linkage phosphorus being achiral;

Rp indicates a linkage phosphorus having R configuration;

Sp indicates a linkage phosphorus having S configuration; and at least one [(Rp/Op)n(Sp)m] comprises RpSpSp.

8. The oligonucleotide of Embodiment 7, wherein the base sequence of the oligonucleotide is or comprises a sequence that is complementary to a target sequence in a RHO gene or a transcript thereof.

9. The oligonucleotide of any one of Embodiments 7-8, wherein the base sequence of the oligonucleotide comprises 10, 11, 12, 13, 14, 15, 16, 17, 18, 19, 20, 21, 22, 23, 24, or 25 or more contiguous nucleobases of a base sequence that is identical to or complementary to a base sequence of a RHO gene or a transcript thereof.

10. The oligonucleotide of any one of the preceding Embodiments, wherein the oligonucleotide is capable of decreasing the level, expression and/or activity of a RHO target gene or a gene product thereof.

11. The oligonucleotide of any one of the preceding Embodiments, wherein the RHO target gene is a mutant RHO target gene associated with a RHO-related condition, disorder or disease.

12. The oligonucleotide of any one of the preceding Embodiments, wherein the RHO target gene is a mutant RHO target gene comprising P23H and associated with a RHO-related condition, disorder or disease.

13. The oligonucleotide of any one of the preceding Embodiments, wherein the RHO target gene is a wild-type RHO target gene.

14. The oligonucleotide of any one of the preceding Embodiments, wherein the oligonucleotide selectively reduces levels and/or activities of nucleic acids associated with a condition, disorder or disease, and/or products encoded thereby, compared to those of nucleic acids less or not associated with a condition, disorder or disease.

15. The oligonucleotide of any one of the preceding Embodiments, wherein the oligonucleotide selectively reduces levels and/or activities of RHO transcripts comprising P23H mutation and/or products encoded thereby, compared to those of RHO transcripts comprising no P23H mutation and/or products encoded thereby.

16. The oligonucleotide of Embodiment 14 or 15, wherein the selectivity is at least 10, 50, 100, 500, 1000, 5000 fold or more.

17. The oligonucleotide of Embodiment 14 or 15, wherein the selectivity is at least 50 fold or more.

18. The oligonucleotide of any one of the preceding Embodiments, wherein one or more internucleotidic linkages each independently comprise a stereodefined linkage phosphorus in the Rp configuration.

19. The oligonucleotide of any one of the preceding Embodiments, wherein one or more internucleotidic linkages each independently comprise a stereodefined linkage phosphorus in the Sp configuration.

20. The oligonucleotide of any one of the preceding Embodiments, wherein a transcript is a RHO mRNA.

21. The oligonucleotide of any one of the preceding Embodiments, wherein the target base sequence in a RHO gene or a transcript thereof is a characteristic sequence of the RHO gene or a transcript thereof.

22. The oligonucleotide of any one of the preceding Embodiments, wherein the sequence of the contiguous nucleobases is characteristic of the RHO gene or a transcript thereof in that it is not identical or complementary to any other non-RHO sequences or transcripts thereof.

23. The oligonucleotide of any one of the preceding Embodiments, wherein the oligonucleotide is capable of selectively decreasing the level, expression and/or activity of a RHO gene or a product thereof that is associated with a condition, disorder or disease, compared to another RHO gene or a product thereof that is not associated or less associated with the condition, disorder or disease.

24. The oligonucleotide of any one of the preceding Embodiments, wherein the condition, disorder or disease is retinopathy.

25. The oligonucleotide of any one of the preceding Embodiments, wherein the condition, disorder or disease is retinitis pigmentosa.

26. The oligonucleotide of any one of the preceding Embodiments, wherein the RHO gene associated with retinopathy comprises disease-associated mutation(s).

27. The oligonucleotide of any one of the preceding Embodiments, wherein the selectivity is at least 2, 3, 4, 5, 6, 7, 8, 9, 10, 15, 20, 25, 30, 35, 40, 50, 60, 70, 80, 90 or 100 fold.

28. The oligonucleotide of any one of the preceding Embodiments, wherein the selectivity is at least 10 fold.

29. The oligonucleotide of any one of the preceding Embodiments, wherein the oligonucleotide has the structure of formula O—I or a salt thereof.

30. The oligonucleotide of any one of the preceding Embodiments, wherein the base sequence of the oligonucleotide is, comprises, or comprises a span of 10, 11, 12, 13, 14, 15, 16, 17, 18, 19 or 20 contiguous nucleobases of GGTACTCGAAGTGGCT (SEQ ID NO: 1), GGTACTCGAAGTGGCTG (SEQ ID NO: 2), GGTACTCGAAGTGGCTGC (SEQ ID NO: 3), GGTACTCGAAGTGGCTGCG (SEQ ID NO: 4), GGTACTCGAAGTGGCTGCGT (SEQ ID NO: 5), GTACTCGAAGTGGCTGCGT (SEQ ID NO: 6), TACTCGAAGTGGCTGCGT (SEQ ID NO: 7), ACTCGAAGTGGCTGCGT (SEQ ID NO: 8), or CTCGAAGTGGCTGCGT (SEQ ID NO: 11), wherein each T can be independently replaced by U and each U can be independently replaced with T.

31. The oligonucleotide of any one of the preceding Embodiments, wherein the base sequence of the oligonucleotide is, comprises, or comprises a span of 10, 11, 12, 13, 14, or 15 contiguous nucleobases of GGTACTCGAAGTGGCT (SEQ ID NO: 1), GGTACTCGAAGTGGCTG (SEQ ID NO: 2), GGTACTCGAAGTGGCTGC (SEQ ID NO: 3), GGTACTCGAAGTGGCTGCG (SEQ ID NO: 4), GGTACTCGAAGTGGCTGCGT (SEQ ID NO: 5), GTACTCGAAGTGGCTGCGT (SEQ ID NO: 6), TACTCGAAGTGGCTGCGT (SEQ ID NO: 7), ACTCGAAGTGGCTGCGT (SEQ ID NO: 8), or CTCGAAGTGGCTGCGT (SEQ ID NO: 11), wherein each T can be independently replaced by U.

32. The oligonucleotide of any one of the preceding Embodiments, wherein the base sequence of the oligonucleotide is, comprises, or comprises a span of 10, 11, 12, 13, 14, 15, or 16 contiguous nucleobases of GGTACTCGAAGTGGCT (SEQ ID NO: 1), GGTACTCGAAGTGGCTG (SEQ ID NO: 2), GGTACTCGAAGTGGCTGC (SEQ ID NO: 3), GGTACTCGAAGTGGCTGCG (SEQ ID NO: 4), GGTACTCGAAGTGGCTGCGT (SEQ ID NO: 5), GTACTCGAAGTGGCTGCGT (SEQ ID NO: 6), TACTCGAAGTGGCTGCGT (SEQ ID NO: 7), ACTCGAAGTGGCTGCGT (SEQ ID NO: 8), or CTCGAAGTGGCTGCGT (SEQ ID NO: 11), wherein each T can be independently replaced by U.

33. The oligonucleotide of any one of the preceding Embodiments, wherein the base sequence of the oligonucleotide is, comprises, or comprises a span of 10, 11, 12, 13, 14, 15, 16, 17, 18, 19, 20 or 21 contiguous nucleobases of GGTACTCGAAGTGGCT (SEQ ID NO: 1), GGTACTCGAAGTGGCTG (SEQ ID NO: 2), GGTACTCGAAGTGGCTGC (SEQ ID NO: 3), GGTACTCGAAGTGGCTGCG (SEQ ID NO: 4), GGTACTCGAAGTGGCTGCGT (SEQ ID NO: 5), GTACTCGAAGTGGCTGCGT (SEQ ID NO: 6), TACTCGAAGTGGCTGCGT (SEQ ID NO: 7), ACTCGAAGTGGCTGCGT (SEQ ID NO: 8), or CTCGAAGTGGCTGCGT (SEQ ID NO: 11), wherein each T can be independently replaced by U.

34. The oligonucleotide of any one of the preceding Embodiments, wherein the base sequence of the oligonucleotide is, comprises, or comprises a span of 10, 11, 12, 13, 14, 15, 16, 17, 18, 19, or 20 contiguous nucleobases of GGTACTCGAAGTGGCT (SEQ ID NO: 1), GGTACTCGAAGTGGCTG (SEQ ID NO: 2), GGTACTCGAAGTGGCTGC (SEQ ID NO: 3), GGTACTCGAAGTGGCTGCG (SEQ ID NO: 4), GGTACTCGAAGTGGCTGCGT (SEQ ID NO: 5), GTACTCGAAGTGGCTGCGT (SEQ ID NO: 6), TACTCGAAGTGGCTGCGT (SEQ ID NO: 7), ACTCGAAGTGGCTGCGT (SEQ ID NO: 8), or CTCGAAGTGGCTGCGT (SEQ ID NO: 11), wherein each T can be independently replaced by U or vice versa.

35. The oligonucleotide of any one of the preceding Embodiments, wherein the base sequence of the oligonucleotide is, comprises, or comprises a span of 10, 11, 12, 13, 14, 15, 16, 17, 18, 19, 20 or 21 contiguous nucleobases of GGTACTCGAAGTGGCT (SEQ ID NO: 1), GGTACTCGAAGTGGCTG (SEQ ID NO: 2), GGTACTCGAAGTGGCTGC (SEQ ID NO: 3), GGTACTCGAAGTGGCTGCG (SEQ ID NO: 4), GGTACTCGAAGTGGCTGCGT (SEQ ID NO: 5), GTACTCGAAGTGGCTGCGT (SEQ ID NO: 6), TACTCGAAGTGGCTGCGT (SEQ ID NO: 7), ACTCGAAGTGGCTGCGT (SEQ ID NO: 8), or CTCGAAGTGGCTGCGT (SEQ ID NO: 11), wherein each T can be independently replaced by U or vice versa.

36. The oligonucleotide of any one of the preceding Embodiments, wherein the base sequence of the oligonucleotide is, comprises, or comprises a span of 10, 11, 12, 13, 14, 15, 16, 17, 18, 19, or 20 contiguous nucleobases of GGTACTCGAAGTGGCT (SEQ ID NO: 1), GGTACTCGAAGTGGCTG (SEQ ID NO: 2), GGTACTCGAAGTGGCTGC (SEQ ID NO: 3), GGTACTCGAAGTGGCTGCG (SEQ ID NO: 4), GGTACTCGAAGTGGCTGCGT (SEQ ID NO: 5), GTACTCGAAGTGGCTGCGT (SEQ ID NO: 6), TACTCGAAGTGGCTGCGT (SEQ ID NO: 7), ACTCGAAGTGGCTGCGT (SEQ ID NO: 8), or CTCGAAGTGGCTGCGT (SEQ ID NO: 11), wherein each T can be independently replaced by U or vice versa.

37. The oligonucleotide of any one of the preceding Embodiments, wherein the base sequence of the oligonucleotide is, comprises, or comprises a span of 10, 11, 12, 13, 14, 15, 16, 17, 18, 19 or 20 contiguous nucleobases of GGTACTCGAAGTGGCT (SEQ ID NO: 1), GGTACTCGAAGTGGCTG (SEQ ID NO: 2), GGTACTCGAAGTGGCTGC (SEQ ID NO: 3), GGTACTCGAAGTGGCTGCG (SEQ ID NO: 4), GGTACTCGAAGTGGCTGCGT (SEQ ID NO: 5), GTACTCGAAGTGGCTGCGT (SEQ ID NO: 6), TACTCGAAGTGGCTGCGT (SEQ ID NO: 7), ACTCGAAGTGGCTGCGT (SEQ ID NO: 8), or CTCGAAGTGGCTGCGT (SEQ ID NO: 11), wherein each T can be independently replaced by U or vice versa.

38. The oligonucleotide of any one of the preceding Embodiments, wherein the base sequence of the oligonucleotide is, comprises, or comprises a span of 10, 11, 12, 13, 14, 15, 16, 17, 18, 19 or 20 contiguous nucleobases of GGTACTCGAAGTGGCT (SEQ ID NO: 1), GGTACTCGAAGTGGCTG (SEQ ID NO: 2), GGTACTCGAAGTGGCTGC (SEQ ID NO: 3), GGTACTCGAAGTGGCTGCG (SEQ ID NO: 4), GGTACTCGAAGTGGCTGCGT (SEQ ID NO: 5), GTACTCGAAGTGGCTGCGT (SEQ ID NO: 6), TACTCGAAGTGGCTGCGT (SEQ ID NO: 7), ACTCGAAGTGGCTGCGT (SEQ ID NO: 8), or CTCGAAGTGGCTGCGT (SEQ ID NO: 11), wherein each T can be independently replaced by U or vice versa.

39. The oligonucleotide of any one of the preceding Embodiments, wherein the base sequence of the oligonucleotide is, comprises, or comprises a span of 10, 11, 12, 13, 14, 15, 16, 17, 18, 19 or 20 contiguous nucleobases of a sequence selected from: GGTACTCGAAGTGGCT (SEQ ID NO: 1), GGTACTCGAAGTGGCTG (SEQ ID NO: 2), GGTACTCGAAGTGGCTGC (SEQ ID NO: 3), GGTACTCGAAGTGGCTGCG (SEQ ID NO: 4), GGTACTCGAAGTGGCTGCGT (SEQ ID NO: 5), GTACTCGAAGTGGCTGCGT (SEQ ID NO: 6), TACTCGAAGTGGCTGCGT (SEQ ID NO: 7), ACTCGAAGTGGCTGCGT (SEQ ID NO: 8), or CTCGAAGTGGCTGCGT (SEQ ID NO: 11);

wherein each T can be independently and optionally replaced by U.

40. The oligonucleotide of any one of the preceding Embodiments, wherein the sequence is GGTACTCGAAGTGGCT (SEQ ID NO: 1), GGTACTCGAAGTGGCTG (SEQ ID NO: 2), GGTACTCGAAGTGGCTGC (SEQ ID NO: 3), GGTACTCGAAGTGGCTGCG (SEQ ID NO: 4), GGTACTCGAAGTGGCTGCGT (SEQ ID NO: 5), GTACTCGAAGTGGCTGCGT (SEQ ID NO: 6), TACTCGAAGTGGCTGCGT (SEQ ID NO: 7), ACTCGAAGTGGCTGCGT (SEQ ID NO: 8), or CTCGAAGTGGCTGCGT (SEQ ID NO: 11).

41. The oligonucleotide any one of the preceding Embodiments, wherein the sequence is GGTACTCGAAGTGGCT (SEQ ID NO: 1), GGTACTCGAAGTGGCTG (SEQ ID NO: 2), GGTACTCGAAGTGGCTGC (SEQ ID NO: 3), GGTACTCGAAGTGGCTGCG (SEQ ID NO: 4), GGTACTCGAAGTGGCTGCGT (SEQ ID NO: 5), GTACTCGAAGTGGCTGCGT (SEQ ID NO: 6), TACTCGAAGTGGCTGCGT (SEQ ID NO: 7), ACTCGAAGTGGCTGCGT (SEQ ID NO: 8), or CTCGAAGTGGCTGCGT (SEQ ID NO: 11).

42. The oligonucleotide of any one of the preceding Embodiments, wherein the sequence is GGTACTCGAAGTGGCT (SEQ ID NO: 1), GGTACTCGAAGTGGCTG (SEQ ID NO: 2), GGTACTCGAAGTGGCTGC (SEQ ID NO: 3), GGTACTCGAAGTGGCTGCG (SEQ ID NO: 4), GGTACTCGAAGTGGCTGCGT (SEQ ID NO: 5), GTACTCGAAGTGGCTGCGT (SEQ ID NO: 6), TACTCGAAGTGGCTGCGT (SEQ ID NO: 7), ACTCGAAGTGGCTGCGT (SEQ ID NO: 8), or CTCGAAGTGGCTGCGT (SEQ ID NO: 11).

43. The oligonucleotide of any one of the preceding Embodiments, wherein the sequence is GGTACTCGAAGTGGCT (SEQ ID NO: 1), GGTACTCGAAGTGGCTG (SEQ ID NO: 2), GGTACTCGAAGTGGCTGC (SEQ ID NO: 3), GGTACTCGAAGTGGCTGCG (SEQ ID NO: 4), GGTACTCGAAGTGGCTGCGT (SEQ ID NO: 5), GTACTCGAAGTGGCTGCGT (SEQ ID NO: 6), TACTCGAAGTGGCTGCGT (SEQ ID NO: 7), ACTCGAAGTGGCTGCGT (SEQ ID NO: 8), or CTCGAAGTGGCTGCGT (SEQ ID NO: 11).

44. The oligonucleotide of any one of the preceding Embodiments, wherein the sequence is GGTACTCGAAGTGGCT (SEQ ID NO: 1), GGTACTCGAAGTGGCTG (SEQ ID NO: 2), GGTACTCGAAGTGGCTGC (SEQ ID NO: 3), GGTACTCGAAGTGGCTGCG (SEQ ID NO: 4), GGTACTCGAAGTGGCTGCGT (SEQ ID NO: 5), GTACTCGAAGTGGCTGCGT (SEQ ID NO: 6), TACTCGAAGTGGCTGCGT (SEQ ID NO: 7), ACTCGAAGTGGCTGCGT (SEQ ID NO: 8), or CTCGAAGTGGCTGCGT (SEQ ID NO: 11).

45. The oligonucleotide of any one of the preceding Embodiments, wherein the sequence is GGTACTCGAAGTGGCT (SEQ ID NO: 1), GGTACTCGAAGTGGCTG (SEQ ID NO: 2), GGTACTCGAAGTGGCTGC (SEQ ID NO: 3), GGTACTCGAAGTGGCTGCG (SEQ ID NO: 4), GGTACTCGAAGTGGCTGCGT (SEQ ID NO: 5), GTACTCGAAGTGGCTGCGT (SEQ ID NO: 6), TACTCGAAGTGGCTGCGT (SEQ ID NO: 7), ACTCGAAGTGGCTGCGT (SEQ ID NO: 8), or CTCGAAGTGGCTGCGT (SEQ ID NO: 11).

46. The oligonucleotide of any one of the preceding Embodiments, wherein the sequence is GGTACTCGAAGTGGCT (SEQ ID NO: 1), GGTACTCGAAGTGGCTG (SEQ ID NO: 2), GGTACTCGAAGTGGCTGC (SEQ ID NO: 3), GGTACTCGAAGTGGCTGCG (SEQ ID NO: 4), GGTACTCGAAGTGGCTGCGT (SEQ ID NO: 5), GTACTCGAAGTGGCTGCGT (SEQ ID NO: 6), TACTCGAAGTGGCTGCGT (SEQ ID NO: 7), ACTCGAAGTGGCTGCGT (SEQ ID NO: 8), or CTCGAAGTGGCTGCGT (SEQ ID NO: 11).

47. The oligonucleotide of any one of the preceding Embodiments, wherein the sequence is GGTACTCGAAGTGGCT (SEQ ID NO: 1), GGTACTCGAAGTGGCTG (SEQ ID NO: 2), GGTACTCGAAGTGGCTGC (SEQ ID NO: 3), GGTACTCGAAGTGGCTGCG (SEQ ID NO: 4), GGTACTCGAAGTGGCTGCGT (SEQ ID NO: 5), GTACTCGAAGTGGCTGCGT (SEQ ID NO: 6), TACTCGAAGTGGCTGCGT (SEQ ID NO: 7), ACTCGAAGTGGCTGCGT (SEQ ID NO: 8), or CTCGAAGTGGCTGCGT (SEQ ID NO: 11).

48. The oligonucleotide of any one of the preceding Embodiments, wherein the sequence is GGTACTCGAAGTGGCT (SEQ ID NO: 1), GGTACTCGAAGTGGCTG (SEQ ID NO: 2), GGTACTCGAAGTGGCTGC (SEQ ID NO: 3), GGTACTCGAAGTGGCTGCG (SEQ ID NO: 4), GGTACTCGAAGTGGCTGCGT (SEQ ID NO: 5), GTACTCGAAGTGGCTGCGT (SEQ ID NO: 6), TACTCGAAGTGGCTGCGT (SEQ ID NO: 7), ACTCGAAGTGGCTGCGT (SEQ ID NO: 8), or CTCGAAGTGGCTGCGT (SEQ ID NO: 11).

49. The oligonucleotide of any one of the preceding Embodiments, wherein the sequence is GGTACTCGAAGTGGCT (SEQ ID NO: 1), GGTACTCGAAGTGGCTG (SEQ ID NO: 2), GGTACTCGAAGTGGCTGC (SEQ ID NO: 3), GGTACTCGAAGTGGCTGCG (SEQ ID NO: 4), GGTACTCGAAGTGGCTGCGT (SEQ ID NO: 5), GTACTCGAAGTGGCTGCGT (SEQ ID NO: 6), TACTCGAAGTGGCTGCGT (SEQ ID NO: 7), ACTCGAAGTGGCTGCGT (SEQ ID NO: 8), or CTCGAAGTGGCTGCGT (SEQ ID NO: 11).

50. The oligonucleotide of any one of the preceding Embodiments, wherein the sequence is GGTACTCGAAGTGGCT (SEQ ID NO: 1), GGTACTCGAAGTGGCTG (SEQ ID NO: 2), GGTACTCGAAGTGGCTGC (SEQ ID NO: 3), GGTACTCGAAGTGGCTGCG (SEQ ID NO: 4), GGTACTCGAAGTGGCTGCGT (SEQ ID NO: 5), GTACTCGAAGTGGCTGCGT (SEQ ID NO: 6), TACTCGAAGTGGCTGCGT (SEQ ID NO: 7), ACTCGAAGTGGCTGCGT (SEQ ID NO: 8), or CTCGAAGTGGCTGCGT (SEQ ID NO: 11).

51. The oligonucleotide of any one of the preceding Embodiments, wherein at least one T is independently replaced by U.

52. The oligonucleotide of any one of Embodiments 1-50, wherein no T is replaced by U.

53. The oligonucleotide of any one of Embodiments 1-52, wherein the oligonucleotide comprises a plurality of chiral internucleotidic linkages each of which independently comprises a stereodefined linkage phosphorus, wherein the pattern of backbone chiral centers of the oligonucleotide comprises [(Rp/Op)n(Sp)m]y, wherein:

n is 1-10;

m is 1-50;

y is 1-10;

Op indicates a linkage phosphorus being achiral;

Rp indicates a linkage phosphorus having R configuration;

Sp indicates a linkage phosphorus having S configuration; and at least one [(Rp/Op)n(Sp)m] comprises RpSpSp.

54. The oligonucleotide of any one of the preceding Embodiments, wherein the pattern of backbone chiral centers comprises (Sp)t[(Rp/Op)n(Sp)m]y, wherein t is 1-50.

55. The oligonucleotide of any one of the preceding Embodiments, wherein the pattern of backbone chiral centers comprises (Sp)t[(Rp/Op)n(Sp)m]yRp, wherein t is 1-50.

56. The oligonucleotide of any one of the preceding Embodiments, wherein the pattern of backbone chiral centers comprises Rp(Sp)t[(Rp/Op)n(Sp)m]y, wherein t is 1-50.

57. The oligonucleotide of any one of the preceding Embodiments, wherein the pattern of backbone chiral centers comprises Rp(Sp)t[(Rp/Op)n(Sp)m]yRp, wherein t is 1-50.

58. The oligonucleotide of any one of the preceding Embodiments, wherein at least one [(Rp/Op)n(Sp)m] is independently [Rp(Sp)m].

59. The oligonucleotide of any one of the preceding Embodiments, wherein each [(Rp/Op)n(Sp)m] is independently [Rp(Sp)m].

60. The oligonucleotide of any one of the preceding Embodiments, wherein t is 2-50.

61. The oligonucleotide of any one of the preceding Embodiments, wherein each m is independently 2-50.

62. The oligonucleotide of any one of the preceding Embodiments, wherein y is 1.

63. The oligonucleotide of any one of the preceding Embodiments, wherein each Op indicates a linkage phosphorus being achiral in a natural phosphate linkage.

64. The oligonucleotide of any one of the preceding Embodiments, wherein at least one chiral internucleotidic linkage comprising a stereodefined linkage phosphorus is a phosphorothioate internucleotidic linkage.

65. The oligonucleotide of any one of the preceding Embodiments, wherein the oligonucleotide comprises a modified sugar.

66. The oligonucleotide of any one of the preceding Embodiments, wherein each sugar independently has the structure of

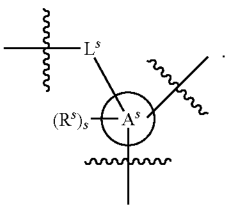

67. The oligonucleotide of any one of the preceding Embodiments, wherein each

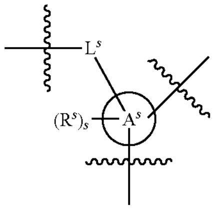

is independently

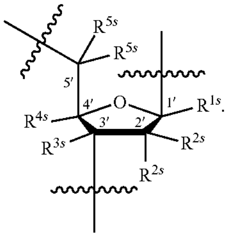

68. The oligonucleotide of Embodiment 67, wherein an occurrence of $R^{5s}$ is —H.

69. The oligonucleotide of any one of Embodiments 67-68, wherein an occurrence of $R^{4s}$ is —H.

70. The oligonucleotide of any one of Embodiments 67-69, wherein each occurrence of $R^{4s}$ is independently —H, or is taken together with a $R^{2s}$ to form.

71. The oligonucleotide of any one of Embodiments 67-70, wherein an occurrence of $R^{3s}$ is —H.

72. The oligonucleotide of any one of Embodiments 67-71, wherein each occurrence of $R^{3s}$ is —H.

73. The oligonucleotide of any one of Embodiments 67-72, wherein an occurrence of $R^{2s}$ is —H.

74. The oligonucleotide of any one of Embodiments 67-73, wherein an occurrence of $R^{1s}$ is —H.

75. The oligonucleotide of any one of Embodiments 67-74, wherein each occurrence of $R^{1s}$ is —H.

76. The oligonucleotide of Embodiment 67, wherein each

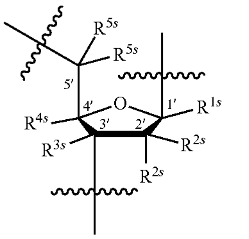

is independently

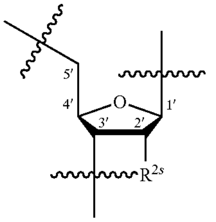

or

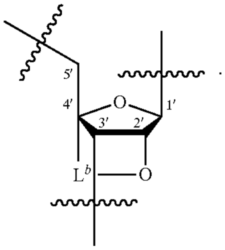

.

77. The oligonucleotide of any one of Embodiments 67-76, wherein an occurrence of $R^{2s}$ is —H.

78. The oligonucleotide of any one of Embodiments 67-77, wherein an occurrence of $R^{2s}$ is —F.

79. The oligonucleotide of any one of Embodiments 67-78, wherein an occurrence of $R^{2s}$ is —OR, wherein R is optionally substituted $C_{1-6}$ alkyl.

80. The oligonucleotide of any one of Embodiments 67-79, wherein an occurrence of $R^{2s}$ is —OMe.

81. The oligonucleotide of any one of Embodiments 67-80, wherein an occurrence of $R^{2s}$ is —$OCH_2CH_2OCH_3$.

82. The oligonucleotide of any one of Embodiments 67-81, wherein an occurrence of $R^{2s}$ is taken together with $R^{4s}$—$OCH_2CH_2OCH_3$.

83. The oligonucleotide of any one of Embodiments 67-82, wherein an occurrence of $L^b$ is optionally substituted —$CH_2$—.

84. The oligonucleotide of any one of Embodiments 67-83, wherein each occurrence of $L^b$ is independently optionally substituted —$CH_2$—.

85. The oligonucleotide of any one of Embodiments 67-84, wherein an occurrence of $L^b$ is —$CH_2$—.

86. The oligonucleotide of any one of Embodiments 67-85, wherein each occurrence of $L^b$ is —$CH_2$—.

87. The oligonucleotide of any one of the preceding Embodiments, wherein the oligonucleotide comprises 10, 11, 12, 13, 14, 15, 16, 17, 18, 19, 20 or more nucleobases.

88. The oligonucleotide of Embodiment 87, wherein each nucleobase independently comprises an optionally substituted aromatic ring.

89. The oligonucleotide of Embodiment 87, wherein each nucleobase independently optionally substituted A, T, C, G, or U, or an optionally substituted tautomer of A, T, C, G, or U.

90. The oligonucleotide of any one of the preceding Embodiments, wherein the oligonucleotide comprises a wing and a core, wherein each wing and core independently comprises 1, 2, 3, 4, 5, 6, 7, 8, 9, 10, 11, 12, 13, 14, 15, 16, 17, 18, 19 or 20 nucleobases.

91. The oligonucleotide of any one of the preceding Embodiments, wherein the oligonucleotide comprises two wings.

92. The oligonucleotide of any one of the preceding Embodiments, wherein the oligonucleotide comprises a wing-core-wing structure.

93. The oligonucleotide of any one of the preceding Embodiments, wherein the oligonucleotide consists of a wing-core-wing structure.

94. The oligonucleotide of any one of the preceding Embodiments, wherein each wing independently comprises a sugar modification that is not in the core.

95. The oligonucleotide of any one of the preceding Embodiments, wherein the core comprises no sugar modification that is 2'-OR, wherein R is optionally substituted $C_{1-6}$ alkyl.

96. The oligonucleotide of any one of the preceding Embodiments, wherein each sugar in a core is an unmodified DNA sugar.

97. The oligonucleotide of any one of the preceding Embodiments, wherein the first wing and the second wing comprise a common sugar modification.

98. The oligonucleotide of any one of the preceding Embodiments, wherein the pattern of sugar modifications of the first wing is the same as the pattern of sugar modifications of the second wing.

99. The oligonucleotide of any one of the preceding Embodiments, wherein all wing sugars have the same modification.

100. The oligonucleotide of any one of the preceding Embodiments, wherein a sugar comprises a 2'-modification.

101. The oligonucleotide of Embodiment 100, wherein the 2'-modification is 2'-OR, wherein R is optionally substituted $C_{1-6}$ alkyl.

102. The oligonucleotide of Embodiment 101, wherein R is —$CH_3$.

103. The oligonucleotide of Embodiment 102, wherein R is —$CH_2CH_2OCH_3$.

104. The oligonucleotide of any one of Embodiments 1-97, wherein the pattern of sugar modifications of the first wing differs from the pattern of sugar modifications of the second wing.

105. The oligonucleotide of Embodiment 104, wherein the first wing comprises a 2'-OMe modification and the second wing does not.

106. The oligonucleotide of Embodiment 104, wherein the second wing comprises a 2'-MOE modification and the first wing does not.

107. The oligonucleotide of Embodiment 104, wherein the first wing comprises a 2'-OMe modification and the second wing does not and wherein the second wing comprises a 2'-MOE modification and the first wing does not.

108. The oligonucleotide of any one of the preceding Embodiments, wherein each sugar in the same wing has the same modification.

109. The oligonucleotide of any one of the preceding Embodiments, wherein the second wing comprises one or more high-affinity sugars.

110. The oligonucleotide of Embodiment 101, wherein a high-affinity sugar is bonded to a neutral internucleotidic linkage.

111. The oligonucleotide of any one of Embodiments 1-96, wherein a first wing comprises one or more 2'-MOE modified sugars.

112. The oligonucleotide of any one of Embodiments 1-96, wherein each sugar in a first wing comprises 2'-MOE.

113. The oligonucleotide of any one of Embodiments 1-96 and 111-112, wherein a second wing comprises one or more 2'-MOE modified sugars.

114. The oligonucleotide of any one of Embodiments 1-96 and 111-113, wherein a second wing comprises one or more 2'-OMe modified sugars.

115. The oligonucleotide of any one of Embodiments 1-96 and 111-114, wherein each sugar in a second wing comprises a 2'-OR modification, wherein R is optionally substituted $C_{1-6}$ alkyl.

116. The oligonucleotide of any one of Embodiments 1-96 and 111-115, wherein each sugar in a second wing comprises the same sugar modification.

117. The oligonucleotide of any one of the preceding Embodiments, wherein the first wing is a wing to the 5'-end of a core (a 5'-wing), and the second wing is a wing to the 3'-end of a core (a 3'-wing).

118. The oligonucleotide of any one of the preceding Embodiments, wherein each wing independently comprises 2, 3, 4, 5, 6, 7, 8, 9 or 10 nucleobases.

119. The oligonucleotide of any one of the preceding Embodiments, wherein each wing comprises 5 and no more than 5 nucleobases.

120. The oligonucleotide of any one of the preceding Embodiments, wherein a core comprises 5, 6, 7, 8, 9, 10, 11, 12, 13, 14, 15, 16, 17, 18, 19 or 20 nucleobases.

121. The oligonucleotide of any one of the preceding Embodiments, wherein a core comprises 10 and no more than 10 nucleobases.

122. The oligonucleotide of any one of the preceding Embodiments, wherein a wing comprises one or more modified internucleotidic linkages.

123. The oligonucleotide of any one of the preceding Embodiments, wherein a wing comprises one or more modified internucleotidic linkages and one or more natural phosphate linkages.

124. The oligonucleotide of Embodiment 108, wherein a wing comprises 2, 3, 4, 5, or more consecutive natural phosphate linkages.

125. The oligonucleotide of any one of the preceding Embodiments, wherein each wing internucleotidic linkage is independently bonded to two wing nucleosides, and each core internucleotidic linkage is independently bonded to two core nucleosides or a wing nucleoside and a core nucleoside.

126. The oligonucleotide of any one of the preceding Embodiments, wherein a 5'-wing comprises one or more modified internucleotidic linkages.

127. The oligonucleotide of any one of the preceding Embodiments, wherein a 5'-wing comprises one or more phosphorothioate internucleotidic linkages.

128. The oligonucleotide of any one of the preceding Embodiments, wherein a 5'-wing comprises one or more phosphorothioate internucleotidic linkages, wherein each of the phosphorothioate internucleotidic linkage is Sp.

129. The oligonucleotide of any one of the preceding Embodiments, wherein a 5'-wing comprises one or more non-negatively charged internucleotidic linkages.

130. The oligonucleotide of any one of the preceding Embodiments, wherein a 5'-wing comprises 2, 3, 4, 5, or 6 non-negatively charged internucleotidic linkages.

131. The oligonucleotide of any one of the preceding Embodiments, wherein a 5'-wing comprises one or more natural phosphate linkages.

132. The oligonucleotide of any one of the preceding Embodiments, wherein a 3'-wing comprises one or more modified internucleotidic linkages.

133. The oligonucleotide of any one of the preceding Embodiments, wherein a 3'-wing comprises one or more phosphorothioate internucleotidic linkages.

134. The oligonucleotide of any one of the preceding Embodiments, wherein a 3'-wing comprises one or more phosphorothioate internucleotidic linkages, wherein each of the phosphorothioate internucleotidic linkage is Sp.

135. The oligonucleotide of any one of the preceding Embodiments, wherein a 3'-wing comprises one or more non-negatively charged internucleotidic linkages.

136. The oligonucleotide of any one of the preceding Embodiments, wherein a 3'-wing comprises 2, 3, 4, 5, or 6 non-negatively charged internucleotidic linkages.

137. The oligonucleotide of any one of the preceding Embodiments, wherein a 3'-wing comprises one or more natural phosphate linkages.

138. The oligonucleotide of any one of the preceding Embodiments, wherein the first internucleotidic linkage from the 5' end of a 5'-wing is a chiral internucleotidic linkage.

139. The oligonucleotide of any one of the preceding Embodiments, wherein the first internucleotidic linkage from the 5' end of a 5'-wing is a chiral internucleotidic linkage, and each other internucleotidic linkage that bonds to two 5'-wing nucleosides is independently a natural phosphate linkage or a non-negatively charged internucleotidic linkage.

140. The oligonucleotide of any one of the preceding Embodiments, wherein the first internucleotidic linkage from the 5' end of a 5'-wing is a chiral internucleotidic linkage, and each other internucleotidic linkage that bonds to two 5'-wing nucleosides is independently a natural phosphate linkage.

141. The oligonucleotide of any one of the preceding Embodiments, wherein the first internucleotidic linkage from the 5' end of a 5'-wing is a chiral internucleotidic linkage wherein the linkage phosphorus is in the Sp configuration.

142. The oligonucleotide of any one of Embodiments 1-140, wherein the first internucleotidic linkage from the 5' end of a 5'-wing is a chiral internucleotidic linkage wherein the linkage phosphorus is in the Rp configuration.

143. The oligonucleotide of any one of the preceding Embodiments, wherein the last wing internucleotidic linkage from the 5' end of a 5'-wing is a natural phosphate linkage.

144. The oligonucleotide of any one of the preceding Embodiments, wherein the first internucleotidic linkage from the 3' end of a 3'-wing is a chiral internucleotidic linkage.

145. The oligonucleotide of any one of the preceding Embodiments, wherein the first internucleotidic linkage from the 3' end of a 3'-wing is a chiral internucleotidic linkage, and each other internucleotidic linkage that bonds to two 3'-wing nucleosides is independently a natural phosphate linkage or a non-negatively charged internucleotidic linkage.

146. The oligonucleotide of any one of the preceding Embodiments, wherein the first internucleotidic linkage from the 3' end of a 3'-wing is a chiral internucleotidic linkage, and each other internucleotidic linkage that bonds to two 3'-wing nucleosides is independently a natural phosphate linkage.

147. The oligonucleotide of any one of the preceding Embodiments, wherein the first internucleotidic linkage from the 3' end of a 3'-wing is a chiral internucleotidic linkage wherein the linkage phosphorus is in the Sp configuration.

148. The oligonucleotide of any one of Embodiments 1-146, wherein the first internucleotidic linkage from the 3' end of a 3'-wing is a chiral internucleotidic linkage wherein the linkage phosphorus is in the Rp configuration.

149. The oligonucleotide of any one of the preceding Embodiments, wherein the last wing internucleotidic linkage from the 3' end of a 3'-wing is a natural phosphate linkage.

150. The oligonucleotide of any one of the preceding Embodiments, wherein one or more nucleosides comprising a 2'-OMe modification are independently bonded to one or two Sp chiral internucleotidic linkages.

151. The oligonucleotide of any one of the preceding Embodiments, wherein one or more nucleosides comprising a high affinity sugar are independently bonded to one or two natural phosphate linkages.

152. The oligonucleotide of any one of the preceding Embodiments, wherein one or more nucleosides comprising a high affinity sugar are independently bonded to one or two neutral internucleotidic linkages.

153. The oligonucleotide of any one of the preceding Embodiments, wherein one or more nucleosides comprising a 2'-MOE modification are independently bonded to one or two natural phosphate linkages.

154. The oligonucleotide of any one of the preceding Embodiments, wherein one or more nucleosides comprising a 2'-MOE modification are independently bonded to one or two neutral internucleotidic linkages.

155. The oligonucleotide of any one of the preceding Embodiments, wherein each core internucleotidic linkage is independently a phosphorothioate internucleotidic linkage.

156. The oligonucleotide of any one of the preceding Embodiments, wherein the pattern of backbone chiral centers of the core comprises or consists of (Np)t[(Op/Rp)n(Sp)m]y, wherein:

t is 1-50;

n is 1-10;

m is 1-50;

y is 1-10;

each Np is independently Rp or Sp;

Op indicates a linkage phosphorus being achiral;

Rp indicates a linkage phosphorus having R configuration; and

Sp indicates a linkage phosphorus having S configuration.

157. The oligonucleotide of any one of the preceding Embodiments, wherein the pattern of backbone chiral centers of the core comprises or consists of (Np)t[(Op/Rp)n(Sp)m]yRp, wherein:

t is 1-50;

n is 1-10;

m is 1-50;

y is 1-10;

each Np is independently Rp or Sp;

Op indicates a linkage phosphorus being achiral;

Rp indicates a linkage phosphorus having R configuration; and

Sp indicates a linkage phosphorus having S configuration.

158. The oligonucleotide of Embodiment 156 or 157, wherein at least one Np is Sp.

159. The oligonucleotide of Embodiment 156 or 157, wherein (Np)t is Rp(Np)t-1.

160. The oligonucleotide of Embodiment 156 or 157, wherein (Np)t is Rp(Sp)t-1.

161. The oligonucleotide of Embodiment 156 or 157, wherein each Np is Sp.

162. The oligonucleotide of any one of Embodiments 156-161, wherein at least one (Op/Rp) is Rp.

163. The oligonucleotide of any one of Embodiments 156-161, wherein each (Op/Rp) is Rp.

164. The oligonucleotide of any one of Embodiments 156-163, wherein at least one n is 1.

165. The oligonucleotide of any one of Embodiments 156-163, wherein each n is 1.

166. The oligonucleotide of any one of Embodiments 156-165, wherein t is 2, 3, 4, 5, 6, 7, 8, 9 or 10.

167. The oligonucleotide of any one of Embodiments 156-166, wherein at least one m is 2-50.

168. The oligonucleotide of any one of Embodiments 156-166, wherein each m is independently 2-50.

169. The oligonucleotide of any one of Embodiments 156-166, wherein each m is independently 2, 3, 4, 5, 6, 7, 8, 9 or 10.

170. The oligonucleotide of any one of Embodiments 156-166, wherein at least one m is 1.

171. The oligonucleotide of any one of Embodiments 156-166, wherein one m is 1, and each other m is independently 2-50.

172. The oligonucleotide of any one of Embodiments 156-171, wherein y is 1.

173. The oligonucleotide of any one of Embodiments 156-171, wherein y is 2, 3, 4 or 5.

174. The oligonucleotide of any one of Embodiments 156-173, wherein the pattern of backbone chiral centers of the core comprises RpSpRp.

175. The oligonucleotide of any one of Embodiments 156-173, wherein the pattern of backbone chiral centers of the core comprises (Sp)tRpSpRp.

176. The oligonucleotide of any one of Embodiments 156-173, wherein the pattern of backbone chiral centers of the core comprises RpSpRpSpSp.

177. The oligonucleotide of any one of Embodiments 156-173, wherein the pattern of backbone chiral centers of the core comprises (Sp)tRpSpRpSpSp.

178. The oligonucleotide of any one of Embodiments 156-177, wherein the first Np of (Np)t in (Np)t[(Op/Rp)n(Sp)m]y or (Np)t[(Op/Rp)n(Sp)m]yRp represents linkage phosphorus stereochemistry of the first internucleotidic linkage of a core from 5' to 3'.

179. The oligonucleotide of any one of Embodiments 156-177, wherein the last Sp of (Np)t[(Op/Rp)n(Sp)m]y or the last Rp of (Np)t[(Op/Rp)n(Sp)m]yRp represents linkage phosphorus stereochemistry of the last internucleotidic linkage of a core from 5' to 3'.

180. The oligonucleotide of any one of the preceding Embodiments, wherein the base sequence of the oligonucleotide comprises a nucleobase which is or is complementary to a characteristic nucleobase in a characteristic sequence element that can differentiate a target nucleic acid from other nucleic acids.

181. The oligonucleotide of any one of the preceding Embodiments, wherein the base sequence of the oligonucleotide comprises a nucleobase which is or is complementary to a nucleobase that can differentiate one allele from the other allele(s).

182. The oligonucleotide of Embodiment 180 or 181, wherein the nucleobase which is or is complementary to a point mutation.

183. The oligonucleotide of any one of the preceding Embodiments, wherein the base sequence of the oligonucleotide comprises a nucleobase which is or is complementary to an allele of a SNP or a point mutation.

184. The oligonucleotide of any one of the preceding Embodiments, wherein the base sequence of the oligonucleotide comprises a nucleobase which is complementary to an allele of a SNP that is on the same strand of a mutation associated with a condition, disorder or disease.

185. The oligonucleotide of any one of the preceding Embodiments, wherein the mutation associated with a condition, disorder or disease is disease-associated mutation(s) in RHO.

186. The oligonucleotide of any one of the preceding Embodiments, wherein the mutation is Rho P23H.

187. The oligonucleotide of any one of the preceding Embodiments, wherein the condition, disorder or disease is retinopathy (e.g, retinal degeneration, retinal degenerative disease, retinal degenerative disorder, inherited retinal degenerative disorder, retinitis pigmentosa, autosomal dominant retinitis pigmentosa, etc.).

188. The oligonucleotide of any one of Embodiments 180-187, wherein an Rp internucleotidic linkage is at −3, −2, −1, +1, +2, or +3 position relative to the nucleobase, wherein "−" is counting toward the 5'-end, "+" is counting toward the 3'-end, and an internucleotidic linkage is at −1 position if it bonds to the 5' of the nucleoside comprising the nucleobase, at +1 position if it bonds to the 3' of the nucleoside comprising the nucleobase.

189. The oligonucleotide of Embodiment 188, wherein an Rp internucleotidic linkage is −3 position relative to the nucleobase.

190. The oligonucleotide of Embodiment 188, wherein an Rp internucleotidic linkage is −2 position relative to the nucleobase.

191. The oligonucleotide of Embodiment 188, wherein an Rp internucleotidic linkage is −1 position relative to the nucleobase.

192. The oligonucleotide of Embodiment 188, wherein an Rp internucleotidic linkage is +1 position relative to the nucleobase.

193. The oligonucleotide of Embodiment 188, wherein an Rp internucleotidic linkage is +2 position relative to the nucleobase.

194. The oligonucleotide of Embodiment 188, wherein an Rp internucleotidic linkage is +3 position relative to the nucleobase.

195. The oligonucleotide of any one of Embodiments 188-194, wherein the Rp is the Rp of an RpSpSp pattern.

196. The oligonucleotide of any one of Embodiments 188-194, wherein the Rp is the Rp of an SpRpSpSp pattern.

197. The oligonucleotide of any one of Embodiments 180-194, wherein the nucleobase is within a core.

198. The oligonucleotide of Embodiment 197, wherein the nucleobase is the $3^{rd}$, $4^{th}$, $5^{th}$, $6^{th}$, $7^{th}$, $8^{th}$, $9^{th}$, $10^{th}$, $11^{th}$, $12^{th}$, $13^{th}$, $14^{th}$ or $15^{th}$ nucleobase of the core from 5' to 3'.

199. The oligonucleotide of Embodiment 197, wherein the nucleobase is the $3^{rd}$, $4^{th}$, $5^{th}$, $6^{th}$, $7^{th}$, or $8^{th}$ nucleobase of the core from 5' to 3'. 200. The oligonucleotide of Embodiment 197, wherein the nucleobase is the $5^{th}$, $6^{th}$, or $7^{th}$ nucleobase of the core.

201. The oligonucleotide of Embodiment 197, wherein the nucleobase is the $5^{th}$ nucleobase of the core.

202. The oligonucleotide of Embodiment 197, wherein the nucleobase is the $6^{th}$ nucleobase of the core.

203. The oligonucleotide of Embodiment 197, wherein the nucleobase is the $7^{th}$ nucleobase of the core.

204. The oligonucleotide of any one of Embodiments 180-203, wherein the nucleobase is the $5^{th}$, $6^{th}$, $7^{th}$, $8^{th}$, $9^{th}$, $10^{th}$, $11^{th}$, $12^{th}$, $13^{th}$, $14^{th}$, $15^{th}$, $16^{th}$, $17^{th}$, $18^{th}$, $19^{th}$, $20^{th}$, $21^{st}$, $22^{nd}$, $23^{rd}$, $24^{th}$ or $25^{th}$ nucleobase of the oligonucleotide from 5' to 3'.

205. The oligonucleotide of any one of Embodiments 180-203, wherein the nucleobase is the $5^{th}$, $6^{th}$, $7^{th}$, $8^{th}$, $9^{th}$, $10^{th}$, $11^{th}$, $12^{th}$ or $13^{th}$ nucleobase of the oligonucleotide from 5' to 3'.

206. The oligonucleotide of Embodiment 205, wherein the nucleobase is the $10^{th}$, $11^{th}$, or $12^{th}$ nucleobase of the oligonucleotide.

207. The oligonucleotide of Embodiment 205, wherein the nucleobase is the $10^{th}$ nucleobase of the core.

208. The oligonucleotide of Embodiment 205, wherein the nucleobase is the $11t^{h}$ nucleobase of the core.

209. The oligonucleotide of Embodiment 205, wherein the nucleobase is the $12^{th}$ nucleobase of the core.

210. The oligonucleotide of any one of Embodiments 188-209, wherein the Rp is an Rp in the pattern of backbone chiral centers of any one of Embodiments 156-179.

211. The oligonucleotide of any one of the preceding Embodiments, wherein the oligonucleotide comprises one or more non-negatively charged internucleotidic linkages.

212. The oligonucleotide of any one of the preceding Embodiments, wherein the oligonucleotide comprises one or more non-negatively charged internucleotidic linkages having the structure of formula I, I-a-1, I-a-2, I-b, I-c, I-d, I-e, I-n-1, I-n-2, I-n-3, I-n-4, II, II-a-1, II-a-2, II-b-1, II-b-2, II-c-1, II-c-2, II-d-1, or II-d-2.

213. The oligonucleotide of any one of the preceding Embodiments, wherein the oligonucleotide comprises one or more neutral internucleotidic linkages.

214. The oligonucleotide of any one of the preceding Embodiments, wherein the oligonucleotide comprises one or more neutral internucleotidic linkages having the structure of formula I, I-a-1, I-a-2, I-b, I-c, I-d, I-e, I-n-1, I-n-2, I-n-3, I-n-4, II, II-a-1, II-a-2, II-b-1, II-b-2, II-c-1, II-c-2, II-d-1, or II-d-2.

215. The oligonucleotide of any one of the preceding Embodiments, wherein the non-negatively charged internucleotidic linkage or neutral internucleotidic linkage is n001.

216. The oligonucleotide of any one of Embodiments any one of the preceding Embodiments, wherein the non-negatively charged internucleotidic linkage or neutral internucleotidic linkage is chirally controlled.

217. The oligonucleotide of any one of Embodiments any one of the preceding Embodiments, wherein the non-negatively charged internucleotidic linkage or neutral internucleotidic linkage is in a wing.

218. The oligonucleotide of any one of the preceding Embodiments, wherein each internucleotidic linkage independently has the structure of formula I, I-a-1, I-a-2, I-b, I-c, I-d, I-e, I-n-1, I-n-2, I-n-3, I-n-4, II, II-a-1, II-a-2, II-b-1, II-b-2, II-c-1, II-c-2, II-d-1, or II-d-2, or a salt form thereof.

219. The oligonucleotide of any one of the preceding Embodiments, wherein each internucleotidic linkage is independently selected from natural phosphate linkages, phosphorothioate internucleotidic linkages and non-negatively charged internucleotidic linkages.

220. The oligonucleotide of any one of the preceding Embodiments, wherein each internucleotidic linkage is independently selected from natural phosphate linkages, phosphorothioate internucleotidic linkages and n001.

221. The oligonucleotide of any one of Embodiments 1-210, wherein each internucleotidic linkage is independently selected from a natural phosphate linkage and a phosphorothioate internucleotidic linkage.

222. The oligonucleotide of any one of the preceding Embodiments, wherein at least 60%, 70%, 75%, 80%, 85%, 90% or 95% of all chirally controlled phosphorothioate internucleotidic linkages are Sp.

223. The oligonucleotide of any one of the preceding Embodiments, wherein at least 60%, 70%, 75%, 80%, 85%, 90% or 95% of all chirally controlled non-negatively charged internucleotidic linkages are Rp.

224. The oligonucleotide of any one of the preceding Embodiments, wherein at least 60%, 70%, 75%, 80%, 85%, 90% or 95% of all chirally controlled internucleotidic linkages are Sp.

225. The oligonucleotide of any one of the preceding Embodiments, wherein at least 60%, 70%, 75%, 80%, 85%, 90% or 95% of all modified internucleotidic linkages are phosphorothioate internucleotidic linkages.

226. The oligonucleotide of any one of the preceding Embodiments, wherein at least 60%, 70%, 75%, 80%, 85%, 90% or 95% of all modified internucleotidic linkages are phosphorothioate internucleotidic linkages having a Sp configuration.

227. The oligonucleotide of any one of the preceding Embodiments, wherein at least 60%, 70%, 75%, 80%, 85%, 90% or 95% of all internucleotidic linkages are phosphorothioate internucleotidic linkages.

228. The oligonucleotide of any one of the preceding Embodiments, wherein at least 60%, 70%, 75%, 80%, 85%, 90% or 95% of all internucleotidic linkages are phosphorothioate internucleotidic linkages having a Sp configuration.

229. The oligonucleotide of any one of the preceding Embodiments, wherein each chiral internucleotidic linkage of the oligonucleotide independently comprises a stereodefined linkage phosphorus.

230. The oligonucleotide of any one of the preceding Embodiments, wherein each nucleobase of the oligonucleotide is independently optionally substituted A, 2AP, DAP, T, C, G or U, or an optionally substituted tautomer of A, T, C, G or U.

231. The oligonucleotide of any one of the preceding Embodiments, wherein each nucleobase of the oligonucleotide is independently optionally substituted A, T, C, G or U, or an optionally substituted tautomer of A, T, C, G or U.

232. The oligonucleotide of any one of the preceding Embodiments, wherein each nucleobase of the oligonucleotide is independently A, T, C, 5mC, G or U.

233. The oligonucleotide of any one of the preceding Embodiments, wherein the oligonucleotide chain is conjugated with a lipid moiety, a carbohydrate moiety, or a targeting moiety.

234. The oligonucleotide of any one of the preceding Embodiments, wherein the oligonucleotide comprises an additional chemical moiety which is capable of binding to ASPGR.

235. The oligonucleotide of any one of the preceding Embodiments, wherein the oligonucleotide comprises an additional chemical moiety which comprises GalNAc or derivative thereof capable of binding to ASPGR.

236. The oligonucleotide of any one of the preceding Embodiments, wherein the oligonucleotide comprises an additional chemical moiety which comprises

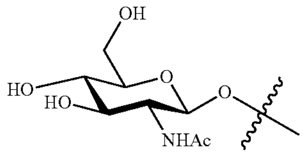

or

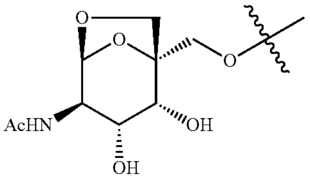

237. The oligonucleotide of any one of the preceding Embodiments, wherein the oligonucleotide comprises

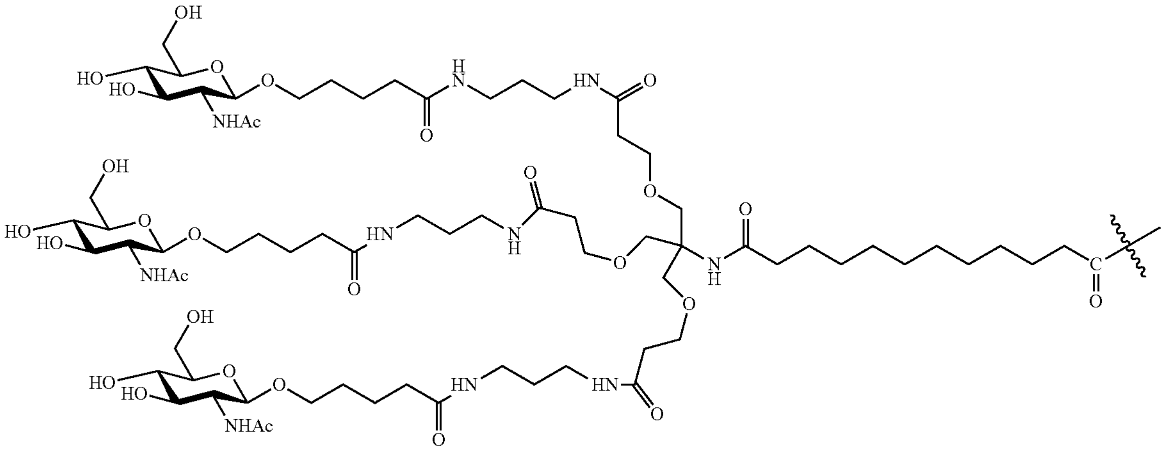

.

238. The oligonucleotide of any one of the preceding Embodiments, wherein the oligonucleotide comprises Mod012.

239. The oligonucleotide of any one of the preceding Embodiments, wherein the oligonucleotide comprises Mod039.

240. The oligonucleotide of any one of the preceding Embodiments, wherein the oligonucleotide comprises Mod062.

241. The oligonucleotide of any one of the preceding Embodiments, wherein the oligonucleotide comprises Mod085.

242. The oligonucleotide of any one of the preceding Embodiments, wherein the oligonucleotide comprises Mod086.

243. The oligonucleotide of any one of the preceding Embodiments, wherein the oligonucleotide comprises Mod094.

244. The oligonucleotide of any one of the preceding Embodiments, wherein the oligonucleotide comprises tgalmc6T.

245. An oligonucleotide selected from Table A1 or A2 or a salt form thereof.

246. An oligonucleotide, wherein the oligonucleotide is WV-20847, WV-20846, WV-20865, WV-20828, WV-21503, WV-21505, WV-23658, or WV-23668, or a salt form thereof.

247. An oligonucleotide, wherein the oligonucleotide is WV-34284, WV-34301, WV-34305, WV-34309, WV-34318, WV-34319, or WV-34327, or a salt form thereof.

248. An oligonucleotide, wherein the oligonucleotide is WV-34284 or a salt form thereof.

249. An oligonucleotide, wherein the oligonucleotide is WV-34301 or a salt form thereof.

250. An oligonucleotide, wherein the oligonucleotide is WV-34305 or a salt form thereof.

251. An oligonucleotide, wherein the oligonucleotide is WV-34309 or a salt form thereof.

252. An oligonucleotide, wherein the oligonucleotide is WV-34318 or a salt form thereof.

253. An oligonucleotide, wherein the oligonucleotide is WV-34319 or a salt form thereof.

254. An oligonucleotide, wherein the oligonucleotide is WV-34327 or a salt form thereof.

255. An oligonucleotide, wherein the oligonucleotide is WV-20846 or a salt form thereof.

256. An oligonucleotide, wherein the oligonucleotide is WV-WV-20847, WV-20846, WV-20865, WV-20828, WV-21503, or a salt form thereof.

257. An oligonucleotide, wherein the oligonucleotide is WV-21505, WV-23658, or WV-23668, or a salt form thereof.

258. An oligonucleotide, wherein the oligonucleotide is WV-23658, or WV-23668, or a salt form thereof.

259. An oligonucleotide, wherein the oligonucleotide is WV-20847, or a salt form thereof.

260. An oligonucleotide, wherein the oligonucleotide is WV-20846, or a salt form thereof.

261. An oligonucleotide, wherein the oligonucleotide is WV-20865, or a salt form thereof.

262. An oligonucleotide, wherein the oligonucleotide is WV-20828, or a salt form thereof.

263. An oligonucleotide, wherein the oligonucleotide is WV-21503, or a salt form thereof.

264. An oligonucleotide, wherein the oligonucleotide is WV-21505, or a salt form thereof.

265. An oligonucleotide, wherein the oligonucleotide is WV-23658, or a salt form thereof.

266. An oligonucleotide, wherein the oligonucleotide is WV-23668, or a salt form thereof.

267. The oligonucleotide of any one of the preceding Embodiments, wherein the oligonucleotide is in a form of a pharmaceutically acceptable salt.

268. The oligonucleotide of any one of the preceding Embodiments, wherein the oligonucleotide is a sodium salt form.

269. The oligonucleotide of any one of the preceding Embodiments, wherein each phosphorothioate internucleotidic linkage in the oligonucleotide independently has a diastereomeric purity of at least 90%, 95%, 96%, 97%, 98%, or 99%.

270. The oligonucleotide of any one of the preceding Embodiments, wherein the oligonucleotide has a diastereomeric purity of at least 50%, 60%, 70%, 80%, 85%, 90%, 95%, 96%, 97%, 98%, or 99%.

271. A chirally controlled oligonucleotide composition comprising a plurality of oligonucleotides, wherein the oligonucleotides share:

1) a common base sequence,
2) a common pattern of backbone linkages, and
3) a common pattern of backbone chiral center, wherein the composition is enriched, relative to a substantially racemic preparation of oligonucleotides sharing the common base sequence and pattern of backbone linkages, for oligonucleotides of the plurality, and each oligonucleotide of the plurality is independently an oligonucleotide of any one of Embodiments 1-268.

272. A chirally controlled oligonucleotide composition comprising a plurality of oligonucleotides, wherein the oligonucleotides share:

1) a common base sequence,
2) a common pattern of backbone linkages, and
3) the same linkage phosphorus stereochemistry at one or more chiral internucleotidic linkages (chirally controlled internucleotidic linkages), wherein about 1-100% of all oligonucleotides within the composition that share the common base sequence and common pattern of backbone linkages are the oligonucleotides of the plurality, and each oligonucleotide of the plurality is independently an oligonucleotide of any one of Embodiments 1-268.

273. A chirally controlled oligonucleotide composition comprising a plurality of oligonucleotides, wherein the oligonucleotides share:

1) a common constitution, and
2) the same linkage phosphorus stereochemistry at one or more chiral internucleotidic linkages (chirally controlled internucleotidic linkages), wherein about 1-100% of all oligonucleotides within the composition that share the common constitution are the oligonucleotides of the plurality, and each oligonucleotide of the plurality is independently an oligonucleotide of any one of Embodiments 1-268.

274. The composition of any one of Embodiments 271-273, wherein 5%, 10%, 15%, 20%, 25%, 30%, 35%, 40%, 45%, 50%, 60%, 70%, 75%, 80%, 85%, 90%, 95%, 96%, 97%, 98%, 99% or more of all oligonucleotides within the composition that share the common base sequence are the oligonucleotides of the plurality.

275. The composition of any one of Embodiments 271-273, wherein 5%, 10%, 15%, 20%, 25%, 30%, 35%, 40%, 45%, 50%, 60%, 70%, 75%, 80%, 85%, 90%, 95%, 96%, 97%, 98%, 99% or more of all oligonucleotides within the composition that share the common base sequence and common pattern of backbone linkages, or share the common constitution, are the oligonucleotides of the plurality.

276. The composition of any one of Embodiments 272-275, wherein the percentage is at least 50%.

277. The composition of any one of Embodiments 272-276, wherein each phosphorothioate internucleotidic linkage is independently chirally controlled.

278. The composition of any one of Embodiments 271-277, wherein substantially all oligonucleotides within the composition that share the common base sequence and common pattern of backbone linkages are the oligonucleotides of the plurality.

279. The composition of any one of Embodiments 271-272 and 274-278, wherein oligonucleotides of the plurality share the same constitution.

280. The composition of any one of Embodiments 271-279, wherein oligonucleotides of the plurality are identical.

281. The composition of Embodiment 280, wherein the composition is substantially free of other stereoisomeric forms of the oligonucleotides.

282. The composition of any one of Embodiments 271-279, wherein oligonucleotides of the plurality comprise one or more non-negatively charged internucleotidic linkages, one or more of which are not chirally controlled.

283. The composition of any one of Embodiments 271-282, wherein oligonucleotides of the plurality are each independently in a pharmaceutically acceptable salt form.

284. The composition of any one of Embodiments 271-282, wherein oligonucleotides of the plurality are each a sodium salt.

285. A pharmaceutical composition comprising a composition of any one of Embodiments 271-284 and a pharmaceutically acceptable carrier.

286. A pharmaceutical composition comprising or delivering an oligonucleotide of any one of the preceding Embodiments and a pharmaceutically acceptable carrier.

287. The composition of Embodiment 285 or 286, wherein the oligonucleotide is a pharmaceutically acceptable salt form.

288. The composition of Embodiment 287, wherein the oligonucleotide is a sodium salt form.

289. A method for preventing, treating or ameliorating a RHO-related condition, disorder or disease in a subject susceptible thereto or suffering therefrom, comprising administering to the subject a therapeutically effective amount of an oligonucleotide of any one of Embodiments 1-270 or a composition of any one of Embodiments 271-288.

290. The method of Embodiment 289, wherein the condition, disorder or disease is retinopathy.

291. The method of Embodiment 289, wherein the condition, disorder or disease is retinitis pigmentosa.

292. A method for decreasing the activity, expression and/or level of a RHO target gene or its gene product in a cell, comprising contacting the cell with an oligonucleotide of any one of Embodiments 11-270 or a composition of any one of Embodiments 271-288.

293. A method for preventing or treating retinitis pigmentosa, comprising administering to the subject a therapeutically effective amount of an oligonucleotide of 1-270 or a composition of any one of Embodiments 271-288.

294. A method for decreasing the activity, expression and/or level of a RHO target gene or its gene product in a cell, comprising contacting the cell with an oligonucleotide of 1-270 or a composition of any one of Embodiments 271-288.

295. A method for suppression of a transcript from a target RHO sequence for which one or more similar nucleic acid sequences exist within a population, each of the target and similar sequences contains a specific characteristic sequence element that defines the target sequence relative to the similar sequences, the method comprising steps of:

contacting a sample comprising transcripts of the target nucleic acid sequence with an oligonucleotide, or an oligonucleotide composition comprising a plurality of oligonucleotides sharing a common base sequence, wherein the base sequence of the oligonucleotide, or the common base sequence of the plurality of oligonucleotide, is or comprises a sequence that is complementary to the characteristic sequence element that defines the target nucleic acid sequence.

296. The method of Embodiment 295, wherein when the oligonucleotide, or the oligonucleotide composition, is contacted with a system comprising transcripts of both the target nucleic acid sequence and a similar nucleic acid sequences, transcripts of the target nucleic acid sequence are suppressed at a greater level than a level of suppression observed for a similar nucleic acid sequence.

297. The method of Embodiment 296, wherein suppression of the transcripts of the target nucleic acid sequence is 1.5, 2, 2.5, 3, 4, 5, 6, 7, 8, 9, 10, 20, 50, 100, 200, 500 fold or more of suppression observed for a similar nucleic acid sequence.

298. The method of any one of Embodiments 295-298, wherein the transcripts of the target nucleic acid sequence are associated with a condition, disorder or disease.

299. The method of any one of Embodiments 295-298, wherein the condition, disorder or disease is retinopathy.

300. The method of any one of Embodiments 295-298, wherein the condition, disorder or disease is retinitis pigmentosa.

301. The method of any one of Embodiments 295-300, wherein the transcripts of the target nucleic acid sequence comprises or encodes Rho P23H.

302. The method of any one of Embodiments 295-301, wherein transcripts of a similar nucleic acid sequence is not, or is less, associated with the condition, disorder or disease.

303. A method for allele-specific suppression of a transcript from a target RHO sequence for which a plurality of alleles exist within a population, each of which contains a specific characteristic sequence element that defines the allele relative to other alleles of the same target sequence, the method comprising steps of:

contacting a sample comprising transcripts of the target nucleic acid sequence with an oligonucleotide or an oligonucleotide composition comprising a plurality of oligonucleotides sharing a common base sequence, wherein the base sequence of the oligonucleotide, or the common base sequence of the plurality of oligonucleotide, is or comprises a sequence that is complementary to the characteristic sequence element that defines a particular allele.

304. The method of Embodiment 303, wherein when the oligonucleotide, or the oligonucleotide composition, is contacted with a system comprising transcripts of both the target allele and another allele of the same nucleic acid sequence, transcripts of the particular allele are suppressed at a greater level than a level of suppression observed for another allele of the same nucleic acid sequence.

305. The method of Embodiment 304, wherein suppression of the transcripts of the particularly allele is 1.5, 2, 2.5, 3, 4, 5, 6, 7, 8, 9, 10, 20, 50, 100, 200, 500 fold or more of suppression observed for another allele.

306. The method of any one of Embodiments 303-305, wherein the transcripts of the particular allele are associated with a condition, disorder or disease.

307. The method of any one of Embodiments 303-306, wherein the condition, disorder or disease is retinopathy.

308. The method of any one of Embodiments 303-306, wherein the condition, disorder or disease is retinitis pigmentosa.

309. The method of any one of Embodiments 303-308, wherein the transcripts of the target nucleic acid sequence comprises or encodes Rho P23H.

310. The method of any one of Embodiments 303-309, wherein transcripts of another allele is not, or is less, associated with the condition, disorder or disease.

311. The method of any one of Embodiments 295-310, wherein the characteristic sequence element comprises a SNP.

312. The method of any one of Embodiments 295-310, wherein the characteristic sequence element comprises SNP rs104893768.

313. The method of any one of Embodiments 295-312, wherein the characteristic sequence element comprises SNP rs104893768, and the transcript of an allele of SNP rs104893768 which comprises Rho P23H is selectively suppressed.

314. The method of any one of Embodiments 295-313, wherein the characteristic sequence element comprises SNP rs104893768, and the transcript of the A allele of SNP rs104893768 is selectively suppressed.

315. The method of any one of Embodiments 295-310, wherein the characteristic sequence element comprises a mutation.

316. The method of any one of Embodiments 295-310, wherein the characteristic sequence element comprises or encodes RhoP23H.

317. The method of any one of Embodiments 295-310, wherein the oligonucleotide or the oligonucleotide composition is of any one of Embodiments 1-288.

318. A compound, oligonucleotide, composition, or method described in the specification.

While various embodiments have been described and illustrated herein, those of ordinary skill in the art will readily envision a variety of other means and/or structures for performing the functions and/or obtaining the results and/or one or more of the advantages described in the present disclosure, and each of such variations and/or modifications is deemed to be included. More generally, those skilled in the art will readily appreciate that all parameters, dimensions, materials, and configurations described herein are meant to be example and that the actual parameters, dimensions, materials, and/or configurations may depend upon the specific application or applications for which the teachings of the present disclosure is/are used. Those skilled in the art will recognize, or be able to ascertain using no more than routine experimentation, many equivalents to the embodiments of the present disclosure. It is, therefore, to be understood that the foregoing embodiments are presented by way of example only and that, within the scope of the appended claims and equivalents thereto, claimed technologies may be practiced otherwise than as specifically described and claimed. In addition, any combination of two or more features, systems, articles, materials, kits, and/or methods, if such features, systems, articles, materials, kits, and/or methods are not mutually inconsistent, is included within the scope of the present disclosure.

The invention claimed is:

1. An oligonucleotide, wherein the oligonucleotide comprises a plurality of chiral internucleotidic linkages each of which independently comprises a stereodefined linkage phosphorus, wherein the pattern of backbone chiral centers of the oligonucleotide comprises [(Rp/Op)n(Sp)m]y, wherein:

n is 1-10;

m is 1-50;

y is 2-10;

Op indicates a linkage phosphorus being achiral;

Rp indicates a linkage phosphorus having R configuration;

Sp indicates a linkage phosphorus having S configuration;

at least one [(Rp/Op)n(Sp)m] comprises RpSpSp; and wherein:

the oligonucleotide comprises a natural phosphate linkage;

the oligonucleotide comprises one or more modified internucleotidic linkages and each modified internucleotidic linkage is independently a phosphorothioate internucleotidic linkage; and the base sequence of the oligonucleotide is or comprises a sequence that is at least 75% identical or complementary to a target sequence in a RHO gene or a transcript thereof and the base sequence of the oligonucleotide is complementary to a RHO sequence at a SNP, wherein the SNP is rs104893768.

2. The oligonucleotide of claim 1, wherein the base sequence of the oligonucleotide comprises 10, 11, 12, 13, 14, 15, 16, 17, 18, 19, 20, 21, 22, 23, 24, or 25 or more contiguous nucleobases of a base sequence that is identical to or complementary to a base sequence of a RHO gene or a transcript thereof.

3. The oligonucleotide of claim 1, wherein the pattern of backbone chiral centers comprises (Sp)t[(Rp(Sp)m]y, wherein t is 1-50 and each m is independently 2-50.

4. The oligonucleotide of claim 3, wherein the oligonucleotide comprises or consists of a wing-core-wing structure, wherein each sugar in a wing independently comprises 2'-OR, wherein R is substituted or unsubstituted $C_{1-6}$ alkyl.

5. The oligonucleotide of claim 4, wherein the core comprises no sugar modification that is 2'-OR, wherein R is substituted or unsubstituted $C_{1-6}$ alkyl.

6. The oligonucleotide of claim 5, wherein each wing independently comprises 2 nucleobases.

7. The oligonucleotide of claim 6, wherein the core comprises 10 nucleobases.

8. The oligonucleotide of claim 7, wherein each wing independently comprises one or more phosphorothioate internucleotidic linkages and optionally one or more natural phosphate linkages.

9. The oligonucleotide of claim 8, wherein the pattern of backbone chiral centers of the core comprises (Sp)t[(Rp)n(Sp)m]y, wherein:

t is 1-50;

n is 1;

m is 2-50;

y is 1-10;

Rp indicates a linkage phosphorus having R configuration; and

Sp indicates a linkage phosphorus having S configuration.

10. The oligonucleotide of claim 9, wherein the base sequence of the core comprises a nucleobase which is or is complementary to a nucleobase that can differentiate one Rho allele from the other allele(s), wherein an Rp internucleotidic linkage of RpSpSp or SpRpSpSp is at −3, −2,−1, +1, +2, or +3 position relative to the nucleobase, wherein "−" is counting toward the 5'-end, "+" is counting toward the 3'-end, and an internucleotidic linkage is at −1 position if it bonds to the 5' of the nucleoside comprising the nucleobase, at +1 position if it bonds to the 3' of the nucleoside comprising the nucleobase.

11. The oligonucleotide of claim 1, wherein the oligonucleotide is conjugated with a lipid moiety, a carbohydrate moiety, or a targeting moiety.

12. The oligonucleotide of claim 1, wherein the oligonucleotide is in a form of a pharmaceutically acceptable salt.

13. The oligonucleotide of claim 1, wherein each phosphorothioate internucleotidic linkage in the oligonucleotide independently has a diastereomeric purity of at least 90%.

14. A chirally controlled oligonucleotide composition comprising a plurality of oligonucleotides, wherein the oligonucleotides share:

1) a common constitution, and 2) the same linkage phosphorus stereochemistry at one or more chiral internucleotidic linkages (chirally controlled internucleotidic linkages), wherein about 1-100% of all oligonucleotides within the composition that share the common constitution are the oligonucleotides of the plurality, and each oligonucleotide of the plurality is independently an oligonucleotide of claim 1.

15. The composition of claim 14, wherein each phosphorothioate internucleotidic linkage is independently chirally controlled.

16. A pharmaceutical composition comprising an oligonucleotide of claim 1 and a pharmaceutically acceptable carrier.

17. A method for preventing, treating or ameliorating a RHO-related condition, disorder or disease in a subject susceptible thereto or suffering therefrom, comprising administering to the subject a therapeutically effective amount of an oligonucleotide of claim 1.

18. The method of claim 17, wherein the RHO-related condition, disorder or disease is retinopathy or retinitis pigmentosa.

19. A method for decreasing the activity, expression and/or level of a RHO target gene or its gene product in a cell, comprising contacting the cell with an oligonucleotide of claim 1.

20. The oligonucleotide of claim 1, wherein the oligonucleotide is:

Geo*SGeoTeoAeom5Ceo*RT*Sm5C*SG*SA*SA*SG*ST*SG*RG Sm5C*STeoGeom5CeoGeo*STeo (SEQ ID NO: 311), or Geo*SGeoTeoAeom5Ceo*RT*Sm5C*SG*SA*SA*SG*ST*SG*RG*Sm5C*SmU*SmG*Sm5mC*SmG*SmU (SEQ ID NO: 148), or a pharmaceutically acceptable salt form thereof, wherein:

f represents a 2'-F modified nucleoside;

m represents a 2'-OMe modified nucleoside;

eo represents a 2'-$OCH_2CH_2OCH_3$ modified nucleoside;

m5 represents a nucleobase of 5-methylcytosine;

m5Ceo represents 5-methyl 2'-O-methoxyethyl C;

*S represents a phosphorothioate internucleotidic linkage in the Sp configuration; and

*R represents a phosphorothioate internucleotidic linkage in the Rp configuration.

* * * * *

SEQUENCE LISTING

```
<160> NUMBER OF SEQ ID NOS: 368

<210> SEQ ID NO 1
<211> LENGTH: 16
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(16)
<223> OTHER INFORMATION: each T can be independently substituted with U

<400> SEQUENCE: 1

ggtactcgaa gtggct                                                      16


<210> SEQ ID NO 2
<211> LENGTH: 17
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(17)
<223> OTHER INFORMATION: each T can be independently substituted with U

<400> SEQUENCE: 2

ggtactcgaa gtggctg                                                     17


<210> SEQ ID NO 3
<211> LENGTH: 18
```

<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(18)
<223> OTHER INFORMATION: each T can be independently substituted with U

<400> SEQUENCE: 3
ggtactcgaa gtggctgc 18

<210> SEQ ID NO 4
<211> LENGTH: 19
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: each T can be independently substituted with U

<400> SEQUENCE: 4
ggtactcgaa gtggctgcg 19

<210> SEQ ID NO 5
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(20)
<223> OTHER INFORMATION: each T can be independently substituted with U

<400> SEQUENCE: 5
ggtactcgaa gtggctgcgt 20

<210> SEQ ID NO 6
<211> LENGTH: 19
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(19)
<223> OTHER INFORMATION: each T can be independently substituted with U

<400> SEQUENCE: 6
gtactcgaag tggctgcgt 19

<210> SEQ ID NO 7
<211> LENGTH: 18
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(18)
<223> OTHER INFORMATION: each T can be independently substituted with U

<400> SEQUENCE: 7
tactcgaagt ggctgcgt 18

<210> SEQ ID NO 8

<211> LENGTH: 17
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(17)
<223> OTHER INFORMATION: each T can be independently substituted with U

<400> SEQUENCE: 8
actcgaagtg gctgcgt 17

<210> SEQ ID NO 9
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(20)
<223> OTHER INFORMATION: each T can be independently substituted with U
and vice versa

<400> SEQUENCE: 9
ggtactcgaa gtggcugcgu 20

<210> SEQ ID NO 10
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(20)
<223> OTHER INFORMATION: each T can be independently substituted with U
and vice versa

<400> SEQUENCE: 10
ggtactcgaa gtggcugcgu 20

<210> SEQ ID NO 11
<211> LENGTH: 16
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(16)
<223> OTHER INFORMATION: each T can be independently substituted with U

<400> SEQUENCE: 11
ctcgaagtgg ctgcgt 16

<210> SEQ ID NO 12
<211> LENGTH: 20
<212> TYPE: DNA
<213> ORGANISM: Artificial Sequence
<220> FEATURE:
<223> OTHER INFORMATION: Synthetic

<400> SEQUENCE: 12
acgcagccac ttcgagtacc 20

<210> SEQ ID NO 13
<211> LENGTH: 20

<212> TYPE: DNA
<213> ORGANISM: Artificial Sequence
<220> FEATURE:
<223> OTHER INFORMATION: Synthetic

<400> SEQUENCE: 13
acgcagcccc ttcgagtacc 20

<210> SEQ ID NO 14
<211> LENGTH: 20
<212> TYPE: DNA
<213> ORGANISM: Artificial Sequence
<220> FEATURE:
<223> OTHER INFORMATION: Synthetic

<400> SEQUENCE: 14
gcgcagccgc ttcgagtacc 20

<210> SEQ ID NO 15
<211> LENGTH: 20
<212> TYPE: DNA
<213> ORGANISM: Artificial Sequence
<220> FEATURE:
<223> OTHER INFORMATION: Synthetic

<400> SEQUENCE: 15
ggtactcgaa gtggctgcgt 20

<210> SEQ ID NO 16
<211> LENGTH: 20
<212> TYPE: DNA
<213> ORGANISM: Artificial Sequence
<220> FEATURE:
<223> OTHER INFORMATION: Synthetic

<400> SEQUENCE: 16
ggtactcgaa gtggutgcgt 20

<210> SEQ ID NO 17
<211> LENGTH: 20
<212> TYPE: DNA
<213> ORGANISM: Artificial Sequence
<220> FEATURE:
<223> OTHER INFORMATION: Synthetic

<400> SEQUENCE: 17
ggtactugaa gtggctgugt 20

<210> SEQ ID NO 18
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(20)
<223> OTHER INFORMATION: each T can be independently substituted with U

<400> SEQUENCE: 18
tcgaagtggc tgcgtaccac 20

<210> SEQ ID NO 19
<211> LENGTH: 20
<212> TYPE: DNA
<213> ORGANISM: Artificial Sequence
<220> FEATURE:

```
<223> OTHER INFORMATION: Synthetic
<220> FEATURE:
<221> NAME/KEY: misc_feature
<222> LOCATION: (1)..(20)
<223> OTHER INFORMATION: each T can be independently substituted with U

<400> SEQUENCE: 19

actcgaagtg gctgcgtacc                                                20


<210> SEQ ID NO 20
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(20)
<223> OTHER INFORMATION: each T can be independently substituted with U
      and vice versa

<400> SEQUENCE: 20

actcgaagtg gctgcguacc                                                20


<210> SEQ ID NO 21
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(20)
<223> OTHER INFORMATION: each T can be independently substituted with U
      and vice versa

<400> SEQUENCE: 21

ccttccctga aggttccucc                                                20


<210> SEQ ID NO 22
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(20)
<223> OTHER INFORMATION: each T can be independently substituted with U

<400> SEQUENCE: 22

ctcgaagggg ctccgcacca                                                20


<210> SEQ ID NO 23
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(20)
<223> OTHER INFORMATION: each T can be independently substituted with U

<400> SEQUENCE: 23

ctcgaagtgg ctgcgtacca                                                20


<210> SEQ ID NO 24
<211> LENGTH: 20
```

<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(20)
<223> OTHER INFORMATION: each T can be independently substituted with U
and vice versa

<400> SEQUENCE: 24
ctcgaagtgg ctgcguacca 20

<210> SEQ ID NO 25
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(20)
<223> OTHER INFORMATION: each T can be independently substituted with U

<400> SEQUENCE: 25
ctgctcgaag gggctccgca 20

<210> SEQ ID NO 26
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(20)
<223> OTHER INFORMATION: each T can be independently substituted with U

<400> SEQUENCE: 26
ctgctcgaag tggctccgca 20

<210> SEQ ID NO 27
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(20)
<223> OTHER INFORMATION: each T can be independently substituted with U

<400> SEQUENCE: 27
gctcgaaggg gctccgcacc 20

<210> SEQ ID NO 28
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(20)
<223> OTHER INFORMATION: each T can be independently substituted with U

<400> SEQUENCE: 28
gctcgaagtg gctccgcacc 20

```
<210> SEQ ID NO 29
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(20)
<223> OTHER INFORMATION: each T can be independently substituted with U
      and vice versa

<400> SEQUENCE: 29

gctgctcgaa ggggcuccgc                                                20


<210> SEQ ID NO 30
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(20)
<223> OTHER INFORMATION: each T can be independently substituted with U
      and vice versa

<400> SEQUENCE: 30

gctgctcgaa ggtgcuccgc                                                20


<210> SEQ ID NO 31
<211> LENGTH: 16
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(16)
<223> OTHER INFORMATION: each T can be independently substituted with U

<400> SEQUENCE: 31

ggtactcgaa gtggct                                                    16


<210> SEQ ID NO 32
<211> LENGTH: 16
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(16)
<223> OTHER INFORMATION: each T can be independently substituted with U

<400> SEQUENCE: 32

ggtactcgaa gtggct                                                    16


<210> SEQ ID NO 33
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(20)
<223> OTHER INFORMATION: each T can be independently substituted with U

<400> SEQUENCE: 33
```

ggtactcgaa gtggctgcgt 20

<210> SEQ ID NO 34
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(20)
<223> OTHER INFORMATION: each T can be independently substituted with U and vice versa

<400> SEQUENCE: 34
ggtactcgaa gtggcugcgu 20

<210> SEQ ID NO 35
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(20)
<223> OTHER INFORMATION: each T can be independently substituted with U

<400> SEQUENCE: 35
gtactcgaag tggctgcgta 20

<210> SEQ ID NO 36
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(20)
<223> OTHER INFORMATION: each T can be independently substituted with U and vice versa

<400> SEQUENCE: 36
gtactcgaag tggctgcgua 20

<210> SEQ ID NO 37
<211> LENGTH: 25
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(25)
<223> OTHER INFORMATION: each U can be independently substituted with T

<400> SEQUENCE: 37
gugguacgca gccacuucga guacc 25

<210> SEQ ID NO 38
<211> LENGTH: 16
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(16)
<223> OTHER INFORMATION: each T can be independently substituted with U

<400> SEQUENCE: 38
tactcgaagt ggctgc 16

<210> SEQ ID NO 39
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(20)
<223> OTHER INFORMATION: each T can be independently substituted with U

<400> SEQUENCE: 39
tactcgaagt ggctgcgtac 20

<210> SEQ ID NO 40
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(20)
<223> OTHER INFORMATION: each T can be independently substituted with U and vice versa

<400> SEQUENCE: 40
tactcgaagt ggctgcguac 20

<210> SEQ ID NO 41
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(20)
<223> OTHER INFORMATION: each T can be independently substituted with U

<400> SEQUENCE: 41
tcgaagtggc tgcgtaccac 20

<210> SEQ ID NO 42
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(20)
<223> OTHER INFORMATION: each T can be independently substituted with U

<400> SEQUENCE: 42
tgctcgaagg ggctccgcac 20

<210> SEQ ID NO 43
<211> LENGTH: 19
<212> TYPE: DNA
<213> ORGANISM: Artificial Sequence
<220> FEATURE:
<223> OTHER INFORMATION: Synthetic

<400> SEQUENCE: 43
gugcuaguag ccaaccccc 19

<210> SEQ ID NO 44
<211> LENGTH: 19
<212> TYPE: DNA
<213> ORGANISM: Artificial Sequence
<220> FEATURE:
<223> OTHER INFORMATION: Synthetic

<400> SEQUENCE: 44
gggggttggc tactagcac 19

<210> SEQ ID NO 45
<211> LENGTH: 20
<212> TYPE: DNA
<213> ORGANISM: Artificial Sequence
<220> FEATURE:
<223> OTHER INFORMATION: Synthetic

<400> SEQUENCE: 45
tcgaagtggc tgcgtaccac 20

<210> SEQ ID NO 46
<211> LENGTH: 20
<212> TYPE: DNA
<213> ORGANISM: Artificial Sequence
<220> FEATURE:
<223> OTHER INFORMATION: Synthetic

<400> SEQUENCE: 46
tcgaagtggc tgcgtaccac 20

<210> SEQ ID NO 47
<211> LENGTH: 20
<212> TYPE: DNA
<213> ORGANISM: Artificial Sequence
<220> FEATURE:
<223> OTHER INFORMATION: Synthetic

<400> SEQUENCE: 47
tcgaagtggc tgcgtaccac 20

<210> SEQ ID NO 48
<211> LENGTH: 20
<212> TYPE: DNA
<213> ORGANISM: Artificial Sequence
<220> FEATURE:
<223> OTHER INFORMATION: Synthetic

<400> SEQUENCE: 48
ctcgaagtgg ctgcgtacca 20

<210> SEQ ID NO 49
<211> LENGTH: 20
<212> TYPE: DNA
<213> ORGANISM: Artificial Sequence
<220> FEATURE:
<223> OTHER INFORMATION: Synthetic

<400> SEQUENCE: 49
ctcgaagtgg ctgcgtacca 20

<210> SEQ ID NO 50
<211> LENGTH: 20
<212> TYPE: DNA

<213> ORGANISM: Artificial Sequence
<220> FEATURE:
<223> OTHER INFORMATION: Synthetic

<400> SEQUENCE: 50
ctcgaagtgg ctgcgtacca 20

<210> SEQ ID NO 51
<211> LENGTH: 20
<212> TYPE: DNA
<213> ORGANISM: Artificial Sequence
<220> FEATURE:
<223> OTHER INFORMATION: Synthetic

<400> SEQUENCE: 51
actcgaagtg gctgcgtacc 20

<210> SEQ ID NO 52
<211> LENGTH: 20
<212> TYPE: DNA
<213> ORGANISM: Artificial Sequence
<220> FEATURE:
<223> OTHER INFORMATION: Synthetic

<400> SEQUENCE: 52
actcgaagtg gctgcgtacc 20

<210> SEQ ID NO 53
<211> LENGTH: 20
<212> TYPE: DNA
<213> ORGANISM: Artificial Sequence
<220> FEATURE:
<223> OTHER INFORMATION: Synthetic

<400> SEQUENCE: 53
actcgaagtg gctgcgtacc 20

<210> SEQ ID NO 54
<211> LENGTH: 20
<212> TYPE: DNA
<213> ORGANISM: Artificial Sequence
<220> FEATURE:
<223> OTHER INFORMATION: Synthetic

<400> SEQUENCE: 54
tactcgaagt ggctgcgtac 20

<210> SEQ ID NO 55
<211> LENGTH: 20
<212> TYPE: DNA
<213> ORGANISM: Artificial Sequence
<220> FEATURE:
<223> OTHER INFORMATION: Synthetic

<400> SEQUENCE: 55
tactcgaagt ggctgcgtac 20

<210> SEQ ID NO 56
<211> LENGTH: 20
<212> TYPE: DNA
<213> ORGANISM: Artificial Sequence
<220> FEATURE:
<223> OTHER INFORMATION: Synthetic

<400> SEQUENCE: 56
tactcgaagt ggctgcgtac 20

<210> SEQ ID NO 57
<211> LENGTH: 20
<212> TYPE: DNA
<213> ORGANISM: Artificial Sequence
<220> FEATURE:
<223> OTHER INFORMATION: Synthetic

<400> SEQUENCE: 57
gtactcgaag tggctgcgta 20

<210> SEQ ID NO 58
<211> LENGTH: 20
<212> TYPE: DNA
<213> ORGANISM: Artificial Sequence
<220> FEATURE:
<223> OTHER INFORMATION: Synthetic

<400> SEQUENCE: 58
gtactcgaag tggctgcgta 20

<210> SEQ ID NO 59
<211> LENGTH: 20
<212> TYPE: DNA
<213> ORGANISM: Artificial Sequence
<220> FEATURE:
<223> OTHER INFORMATION: Synthetic

<400> SEQUENCE: 59
gtactcgaag tggctgcgta 20

<210> SEQ ID NO 60
<211> LENGTH: 20
<212> TYPE: DNA
<213> ORGANISM: Artificial Sequence
<220> FEATURE:
<223> OTHER INFORMATION: Synthetic

<400> SEQUENCE: 60
ggtactcgaa gtggctgcgt 20

<210> SEQ ID NO 61
<211> LENGTH: 20
<212> TYPE: DNA
<213> ORGANISM: Artificial Sequence
<220> FEATURE:
<223> OTHER INFORMATION: Synthetic

<400> SEQUENCE: 61
ggtactcgaa gtggctgcgt 20

<210> SEQ ID NO 62
<211> LENGTH: 20
<212> TYPE: DNA
<213> ORGANISM: Artificial Sequence
<220> FEATURE:
<223> OTHER INFORMATION: Synthetic

<400> SEQUENCE: 62
ggtactcgaa gtggctgcgt 20

<210> SEQ ID NO 63
<211> LENGTH: 20
<212> TYPE: DNA
<213> ORGANISM: Artificial Sequence
<220> FEATURE:

<223> OTHER INFORMATION: Synthetic

<400> SEQUENCE: 63
ggtactcgaa gtggctgcgt 20

<210> SEQ ID NO 64
<211> LENGTH: 20
<212> TYPE: DNA
<213> ORGANISM: Artificial Sequence
<220> FEATURE:
<223> OTHER INFORMATION: Synthetic

<400> SEQUENCE: 64
tcgaagtggc tgcgtaccac 20

<210> SEQ ID NO 65
<211> LENGTH: 20
<212> TYPE: DNA
<213> ORGANISM: Artificial Sequence
<220> FEATURE:
<223> OTHER INFORMATION: Synthetic

<400> SEQUENCE: 65
tcgaagtggc tgcgtaccac 20

<210> SEQ ID NO 66
<211> LENGTH: 20
<212> TYPE: DNA
<213> ORGANISM: Artificial Sequence
<220> FEATURE:
<223> OTHER INFORMATION: Synthetic

<400> SEQUENCE: 66
tcgaagtggc tgcgtaccac 20

<210> SEQ ID NO 67
<211> LENGTH: 20
<212> TYPE: DNA
<213> ORGANISM: Artificial Sequence
<220> FEATURE:
<223> OTHER INFORMATION: Synthetic

<400> SEQUENCE: 67
ctcgaagtgg ctgcgtacca 20

<210> SEQ ID NO 68
<211> LENGTH: 20
<212> TYPE: DNA
<213> ORGANISM: Artificial Sequence
<220> FEATURE:
<223> OTHER INFORMATION: Synthetic

<400> SEQUENCE: 68
ctcgaagtgg ctgcgtacca 20

<210> SEQ ID NO 69
<211> LENGTH: 20
<212> TYPE: DNA
<213> ORGANISM: Artificial Sequence
<220> FEATURE:
<223> OTHER INFORMATION: Synthetic

<400> SEQUENCE: 69
ctcgaagtgg ctgcgtacca 20

<210> SEQ ID NO 70
<211> LENGTH: 20
<212> TYPE: DNA
<213> ORGANISM: Artificial Sequence
<220> FEATURE:
<223> OTHER INFORMATION: Synthetic

<400> SEQUENCE: 70
actcgaagtg gctgcgtacc 20

<210> SEQ ID NO 71
<211> LENGTH: 20
<212> TYPE: DNA
<213> ORGANISM: Artificial Sequence
<220> FEATURE:
<223> OTHER INFORMATION: Synthetic

<400> SEQUENCE: 71
actcgaagtg gctgcgtacc 20

<210> SEQ ID NO 72
<211> LENGTH: 20
<212> TYPE: DNA
<213> ORGANISM: Artificial Sequence
<220> FEATURE:
<223> OTHER INFORMATION: Synthetic

<400> SEQUENCE: 72
actcgaagtg gctgcgtacc 20

<210> SEQ ID NO 73
<211> LENGTH: 20
<212> TYPE: DNA
<213> ORGANISM: Artificial Sequence
<220> FEATURE:
<223> OTHER INFORMATION: Synthetic

<400> SEQUENCE: 73
tactcgaagt ggctgcgtac 20

<210> SEQ ID NO 74
<211> LENGTH: 20
<212> TYPE: DNA
<213> ORGANISM: Artificial Sequence
<220> FEATURE:
<223> OTHER INFORMATION: Synthetic

<400> SEQUENCE: 74
tactcgaagt ggctgcgtac 20

<210> SEQ ID NO 75
<211> LENGTH: 20
<212> TYPE: DNA
<213> ORGANISM: Artificial Sequence
<220> FEATURE:
<223> OTHER INFORMATION: Synthetic

<400> SEQUENCE: 75
tactcgaagt ggctgcgtac 20

<210> SEQ ID NO 76
<211> LENGTH: 20
<212> TYPE: DNA
<213> ORGANISM: Artificial Sequence
<220> FEATURE:
<223> OTHER INFORMATION: Synthetic

<400> SEQUENCE: 76
gtactcgaag tggctgcgta 20

<210> SEQ ID NO 77
<211> LENGTH: 20
<212> TYPE: DNA
<213> ORGANISM: Artificial Sequence
<220> FEATURE:
<223> OTHER INFORMATION: Synthetic

<400> SEQUENCE: 77
gtactcgaag tggctgcgta 20

<210> SEQ ID NO 78
<211> LENGTH: 20
<212> TYPE: DNA
<213> ORGANISM: Artificial Sequence
<220> FEATURE:
<223> OTHER INFORMATION: Synthetic

<400> SEQUENCE: 78
gtactcgaag tggctgcgta 20

<210> SEQ ID NO 79
<211> LENGTH: 20
<212> TYPE: DNA
<213> ORGANISM: Artificial Sequence
<220> FEATURE:
<223> OTHER INFORMATION: Synthetic

<400> SEQUENCE: 79
ggtactcgaa gtggctgcgt 20

<210> SEQ ID NO 80
<211> LENGTH: 20
<212> TYPE: DNA
<213> ORGANISM: Artificial Sequence
<220> FEATURE:
<223> OTHER INFORMATION: Synthetic

<400> SEQUENCE: 80
ggtactcgaa gtggctgcgt 20

<210> SEQ ID NO 81
<211> LENGTH: 20
<212> TYPE: DNA
<213> ORGANISM: Artificial Sequence
<220> FEATURE:
<223> OTHER INFORMATION: Synthetic

<400> SEQUENCE: 81
ggtactcgaa gtggctgcgt 20

<210> SEQ ID NO 82
<211> LENGTH: 20
<212> TYPE: DNA
<213> ORGANISM: Artificial Sequence
<220> FEATURE:
<223> OTHER INFORMATION: Synthetic

<400> SEQUENCE: 82
ggtactcgaa gtggctgcgt 20

<210> SEQ ID NO 83
<211> LENGTH: 20

<212> TYPE: DNA
<213> ORGANISM: Artificial Sequence
<220> FEATURE:
<223> OTHER INFORMATION: Synthetic

<400> SEQUENCE: 83
tcgaagtggc tgcgtaccac 20

<210> SEQ ID NO 84
<211> LENGTH: 20
<212> TYPE: DNA
<213> ORGANISM: Artificial Sequence
<220> FEATURE:
<223> OTHER INFORMATION: Synthetic

<400> SEQUENCE: 84
tcgaagtggc tgcgtaccac 20

<210> SEQ ID NO 85
<211> LENGTH: 20
<212> TYPE: DNA
<213> ORGANISM: Artificial Sequence
<220> FEATURE:
<223> OTHER INFORMATION: Synthetic

<400> SEQUENCE: 85
tcgaagtggc tgcgtaccac 20

<210> SEQ ID NO 86
<211> LENGTH: 20
<212> TYPE: DNA
<213> ORGANISM: Artificial Sequence
<220> FEATURE:
<223> OTHER INFORMATION: Synthetic

<400> SEQUENCE: 86
ctcgaagtgg ctgcgtacca 20

<210> SEQ ID NO 87
<211> LENGTH: 20
<212> TYPE: DNA
<213> ORGANISM: Artificial Sequence
<220> FEATURE:
<223> OTHER INFORMATION: Synthetic

<400> SEQUENCE: 87
ctcgaagtgg ctgcgtacca 20

<210> SEQ ID NO 88
<211> LENGTH: 20
<212> TYPE: DNA
<213> ORGANISM: Artificial Sequence
<220> FEATURE:
<223> OTHER INFORMATION: Synthetic

<400> SEQUENCE: 88
ctcgaagtgg ctgcgtacca 20

<210> SEQ ID NO 89
<211> LENGTH: 20
<212> TYPE: DNA
<213> ORGANISM: Artificial Sequence
<220> FEATURE:
<223> OTHER INFORMATION: Synthetic

<400> SEQUENCE: 89
actcgaagtg gctgcgtacc 20

<210> SEQ ID NO 90
<211> LENGTH: 20
<212> TYPE: DNA
<213> ORGANISM: Artificial Sequence
<220> FEATURE:
<223> OTHER INFORMATION: Synthetic

<400> SEQUENCE: 90
actcgaagtg gctgcgtacc 20

<210> SEQ ID NO 91
<211> LENGTH: 20
<212> TYPE: DNA
<213> ORGANISM: Artificial Sequence
<220> FEATURE:
<223> OTHER INFORMATION: Synthetic

<400> SEQUENCE: 91
actcgaagtg gctgcgtacc 20

<210> SEQ ID NO 92
<211> LENGTH: 20
<212> TYPE: DNA
<213> ORGANISM: Artificial Sequence
<220> FEATURE:
<223> OTHER INFORMATION: Synthetic

<400> SEQUENCE: 92
tactcgaagt ggctgcgtac 20

<210> SEQ ID NO 93
<211> LENGTH: 20
<212> TYPE: DNA
<213> ORGANISM: Artificial Sequence
<220> FEATURE:
<223> OTHER INFORMATION: Synthetic

<400> SEQUENCE: 93
tactcgaagt ggctgcgtac 20

<210> SEQ ID NO 94
<211> LENGTH: 20
<212> TYPE: DNA
<213> ORGANISM: Artificial Sequence
<220> FEATURE:
<223> OTHER INFORMATION: Synthetic

<400> SEQUENCE: 94
tactcgaagt ggctgcgtac 20

<210> SEQ ID NO 95
<211> LENGTH: 20
<212> TYPE: DNA
<213> ORGANISM: Artificial Sequence
<220> FEATURE:
<223> OTHER INFORMATION: Synthetic

<400> SEQUENCE: 95
gtactcgaag tggctgcgta 20

<210> SEQ ID NO 96
<211> LENGTH: 20
<212> TYPE: DNA
<213> ORGANISM: Artificial Sequence
<220> FEATURE:
<223> OTHER INFORMATION: Synthetic

<400> SEQUENCE: 96
gtactcgaag tggctgcgta 20

<210> SEQ ID NO 97
<211> LENGTH: 20
<212> TYPE: DNA
<213> ORGANISM: Artificial Sequence
<220> FEATURE:
<223> OTHER INFORMATION: Synthetic

<400> SEQUENCE: 97
gtactcgaag tggctgcgta 20

<210> SEQ ID NO 98
<211> LENGTH: 20
<212> TYPE: DNA
<213> ORGANISM: Artificial Sequence
<220> FEATURE:
<223> OTHER INFORMATION: Synthetic

<400> SEQUENCE: 98
ggtactcgaa gtggctgcgt 20

<210> SEQ ID NO 99
<211> LENGTH: 20
<212> TYPE: DNA
<213> ORGANISM: Artificial Sequence
<220> FEATURE:
<223> OTHER INFORMATION: Synthetic

<400> SEQUENCE: 99
ggtactcgaa gtggctgcgt 20

<210> SEQ ID NO 100
<211> LENGTH: 20
<212> TYPE: DNA
<213> ORGANISM: Artificial Sequence
<220> FEATURE:
<223> OTHER INFORMATION: Synthetic

<400> SEQUENCE: 100
ggtactcgaa gtggctgcgt 20

<210> SEQ ID NO 101
<211> LENGTH: 20
<212> TYPE: DNA
<213> ORGANISM: Artificial Sequence
<220> FEATURE:
<223> OTHER INFORMATION: Synthetic

<400> SEQUENCE: 101
ggtactcgaa gtggctgcgt 20

<210> SEQ ID NO 102
<211> LENGTH: 20
<212> TYPE: DNA
<213> ORGANISM: Artificial Sequence
<220> FEATURE:
<223> OTHER INFORMATION: Synthetic

<400> SEQUENCE: 102
tcgaagtggc tgcgtaccac 20

<210> SEQ ID NO 103
<211> LENGTH: 20
<212> TYPE: DNA
<213> ORGANISM: Artificial Sequence
<220> FEATURE:
<223> OTHER INFORMATION: Synthetic

<400> SEQUENCE: 103
tcgaagtggc tgcgtaccac 20

<210> SEQ ID NO 104
<211> LENGTH: 20
<212> TYPE: DNA
<213> ORGANISM: Artificial Sequence
<220> FEATURE:
<223> OTHER INFORMATION: Synthetic

<400> SEQUENCE: 104
tcgaagtggc tgcgtaccac 20

<210> SEQ ID NO 105
<211> LENGTH: 20
<212> TYPE: DNA
<213> ORGANISM: Artificial Sequence
<220> FEATURE:
<223> OTHER INFORMATION: Synthetic

<400> SEQUENCE: 105
ctcgaagtgg ctgcguacca 20

<210> SEQ ID NO 106
<211> LENGTH: 20
<212> TYPE: DNA
<213> ORGANISM: Artificial Sequence
<220> FEATURE:
<223> OTHER INFORMATION: Synthetic

<400> SEQUENCE: 106
ctcgaagtgg ctgcguacca 20

<210> SEQ ID NO 107
<211> LENGTH: 20
<212> TYPE: DNA
<213> ORGANISM: Artificial Sequence
<220> FEATURE:
<223> OTHER INFORMATION: Synthetic

<400> SEQUENCE: 107
ctcgaagtgg ctgcguacca 20

<210> SEQ ID NO 108
<211> LENGTH: 20
<212> TYPE: DNA
<213> ORGANISM: Artificial Sequence
<220> FEATURE:
<223> OTHER INFORMATION: Synthetic

<400> SEQUENCE: 108
actcgaagtg gctgcguacc 20

<210> SEQ ID NO 109
<211> LENGTH: 20
<212> TYPE: DNA
<213> ORGANISM: Artificial Sequence
<220> FEATURE:
<223> OTHER INFORMATION: Synthetic

<400> SEQUENCE: 109
actcgaagtg gctgcguacc 20

<210> SEQ ID NO 110
<211> LENGTH: 20
<212> TYPE: DNA
<213> ORGANISM: Artificial Sequence
<220> FEATURE:
<223> OTHER INFORMATION: Synthetic

<400> SEQUENCE: 110
actcgaagtg gctgcguacc 20

<210> SEQ ID NO 111
<211> LENGTH: 20
<212> TYPE: DNA
<213> ORGANISM: Artificial Sequence
<220> FEATURE:
<223> OTHER INFORMATION: Synthetic

<400> SEQUENCE: 111
tactcgaagt ggctgcguac 20

<210> SEQ ID NO 112
<211> LENGTH: 20
<212> TYPE: DNA
<213> ORGANISM: Artificial Sequence
<220> FEATURE:
<223> OTHER INFORMATION: Synthetic

<400> SEQUENCE: 112
tactcgaagt ggctgcguac 20

<210> SEQ ID NO 113
<211> LENGTH: 20
<212> TYPE: DNA
<213> ORGANISM: Artificial Sequence
<220> FEATURE:
<223> OTHER INFORMATION: Synthetic

<400> SEQUENCE: 113
tactcgaagt ggctgcguac 20

<210> SEQ ID NO 114
<211> LENGTH: 20
<212> TYPE: DNA
<213> ORGANISM: Artificial Sequence
<220> FEATURE:
<223> OTHER INFORMATION: Synthetic

<400> SEQUENCE: 114
gtactcgaag tggctgcgua 20

<210> SEQ ID NO 115
<211> LENGTH: 20
<212> TYPE: DNA
<213> ORGANISM: Artificial Sequence
<220> FEATURE:
<223> OTHER INFORMATION: Synthetic

<400> SEQUENCE: 115
gtactcgaag tggctgcgua 20

<210> SEQ ID NO 116

<211> LENGTH: 20
<212> TYPE: DNA
<213> ORGANISM: Artificial Sequence
<220> FEATURE:
<223> OTHER INFORMATION: Synthetic

<400> SEQUENCE: 116
gtactcgaag tggctgcgua 20

<210> SEQ ID NO 117
<211> LENGTH: 20
<212> TYPE: DNA
<213> ORGANISM: Artificial Sequence
<220> FEATURE:
<223> OTHER INFORMATION: Synthetic

<400> SEQUENCE: 117
ggtactcgaa gtggcugcgu 20

<210> SEQ ID NO 118
<211> LENGTH: 20
<212> TYPE: DNA
<213> ORGANISM: Artificial Sequence
<220> FEATURE:
<223> OTHER INFORMATION: Synthetic

<400> SEQUENCE: 118
ggtactcgaa gtggcugcgu 20

<210> SEQ ID NO 119
<211> LENGTH: 20
<212> TYPE: DNA
<213> ORGANISM: Artificial Sequence
<220> FEATURE:
<223> OTHER INFORMATION: Synthetic

<400> SEQUENCE: 119
ggtactcgaa gtggcugcgu 20

<210> SEQ ID NO 120
<211> LENGTH: 20
<212> TYPE: DNA
<213> ORGANISM: Artificial Sequence
<220> FEATURE:
<223> OTHER INFORMATION: Synthetic

<400> SEQUENCE: 120
ggtactcgaa gtggctgcgt 20

<210> SEQ ID NO 121
<211> LENGTH: 20
<212> TYPE: DNA
<213> ORGANISM: Artificial Sequence
<220> FEATURE:
<223> OTHER INFORMATION: Synthetic

<400> SEQUENCE: 121
ggtactcgaa gtggctgcgt 20

<210> SEQ ID NO 122
<211> LENGTH: 20
<212> TYPE: DNA
<213> ORGANISM: Artificial Sequence
<220> FEATURE:
<223> OTHER INFORMATION: Synthetic

<400> SEQUENCE: 122
ggtactcgaa gtggctgcgt 20

<210> SEQ ID NO 123
<211> LENGTH: 20
<212> TYPE: DNA
<213> ORGANISM: Artificial Sequence
<220> FEATURE:
<223> OTHER INFORMATION: Synthetic

<400> SEQUENCE: 123
ggtactcgaa gtggcugcgu 20

<210> SEQ ID NO 124
<211> LENGTH: 16
<212> TYPE: DNA
<213> ORGANISM: Artificial Sequence
<220> FEATURE:
<223> OTHER INFORMATION: Synthetic

<400> SEQUENCE: 124
tactcgaagt ggctgc 16

<210> SEQ ID NO 125
<211> LENGTH: 25
<212> TYPE: DNA
<213> ORGANISM: Artificial Sequence
<220> FEATURE:
<223> OTHER INFORMATION: Synthetic

<400> SEQUENCE: 125
gugguacgca gccacuucga guacc 25

<210> SEQ ID NO 126
<211> LENGTH: 25
<212> TYPE: DNA
<213> ORGANISM: Artificial Sequence
<220> FEATURE:
<223> OTHER INFORMATION: Synthetic

<400> SEQUENCE: 126
gugguacgca gccccuucga guacc 25

<210> SEQ ID NO 127
<211> LENGTH: 20
<212> TYPE: DNA
<213> ORGANISM: Artificial Sequence
<220> FEATURE:
<223> OTHER INFORMATION: Synthetic

<400> SEQUENCE: 127
ggtactcgaa gtggctgcgt 20

<210> SEQ ID NO 128
<211> LENGTH: 20
<212> TYPE: DNA
<213> ORGANISM: Artificial Sequence
<220> FEATURE:
<223> OTHER INFORMATION: Synthetic

<400> SEQUENCE: 128
ggtactcgaa gtggcugcgu 20

<210> SEQ ID NO 129
<211> LENGTH: 20
<212> TYPE: DNA

<213> ORGANISM: Artificial Sequence
<220> FEATURE:
<223> OTHER INFORMATION: Synthetic

<400> SEQUENCE: 129
ggtactcgaa gtggcugcgu 20

<210> SEQ ID NO 130
<211> LENGTH: 16
<212> TYPE: DNA
<213> ORGANISM: Artificial Sequence
<220> FEATURE:
<223> OTHER INFORMATION: Synthetic

<400> SEQUENCE: 130
tactcgaagt ggctgc 16

<210> SEQ ID NO 131
<211> LENGTH: 20
<212> TYPE: DNA
<213> ORGANISM: Artificial Sequence
<220> FEATURE:
<223> OTHER INFORMATION: Synthetic

<400> SEQUENCE: 131
ggtactcgaa gtggctgcgt 20

<210> SEQ ID NO 132
<211> LENGTH: 20
<212> TYPE: DNA
<213> ORGANISM: Artificial Sequence
<220> FEATURE:
<223> OTHER INFORMATION: Synthetic

<400> SEQUENCE: 132
ggtactcgaa gtggctgcgt 20

<210> SEQ ID NO 133
<211> LENGTH: 20
<212> TYPE: DNA
<213> ORGANISM: Artificial Sequence
<220> FEATURE:
<223> OTHER INFORMATION: Synthetic

<400> SEQUENCE: 133
ggtactcgaa gtggctgcgt 20

<210> SEQ ID NO 134
<211> LENGTH: 20
<212> TYPE: DNA
<213> ORGANISM: Artificial Sequence
<220> FEATURE:
<223> OTHER INFORMATION: Synthetic

<400> SEQUENCE: 134
ggtactcgaa gtggctgcgt 20

<210> SEQ ID NO 135
<211> LENGTH: 20
<212> TYPE: DNA
<213> ORGANISM: Artificial Sequence
<220> FEATURE:
<223> OTHER INFORMATION: Synthetic

<400> SEQUENCE: 135
ggtactcgaa gtggctgcgt 20

<210> SEQ ID NO 136
<211> LENGTH: 20
<212> TYPE: DNA
<213> ORGANISM: Artificial Sequence
<220> FEATURE:
<223> OTHER INFORMATION: Synthetic

<400> SEQUENCE: 136
ggtactcgaa gtggctgcgt 20

<210> SEQ ID NO 137
<211> LENGTH: 20
<212> TYPE: DNA
<213> ORGANISM: Artificial Sequence
<220> FEATURE:
<223> OTHER INFORMATION: Synthetic

<400> SEQUENCE: 137
ggtactcgaa gtggctgcgt 20

<210> SEQ ID NO 138
<211> LENGTH: 20
<212> TYPE: DNA
<213> ORGANISM: Artificial Sequence
<220> FEATURE:
<223> OTHER INFORMATION: Synthetic

<400> SEQUENCE: 138
ggtactcgaa gtggctgcgt 20

<210> SEQ ID NO 139
<211> LENGTH: 20
<212> TYPE: DNA
<213> ORGANISM: Artificial Sequence
<220> FEATURE:
<223> OTHER INFORMATION: Synthetic

<400> SEQUENCE: 139
ggtactcgaa gtggctgcgt 20

<210> SEQ ID NO 140
<211> LENGTH: 20
<212> TYPE: DNA
<213> ORGANISM: Artificial Sequence
<220> FEATURE:
<223> OTHER INFORMATION: Synthetic

<400> SEQUENCE: 140
ggtactcgaa gtggctgcgt 20

<210> SEQ ID NO 141
<211> LENGTH: 20
<212> TYPE: DNA
<213> ORGANISM: Artificial Sequence
<220> FEATURE:
<223> OTHER INFORMATION: Synthetic

<400> SEQUENCE: 141
ggtactcgaa gtggcugcgu 20

<210> SEQ ID NO 142
<211> LENGTH: 20
<212> TYPE: DNA
<213> ORGANISM: Artificial Sequence
<220> FEATURE:

<223> OTHER INFORMATION: Synthetic

<400> SEQUENCE: 142
ggtactcgaa gtggcugcgu 20

<210> SEQ ID NO 143
<211> LENGTH: 20
<212> TYPE: DNA
<213> ORGANISM: Artificial Sequence
<220> FEATURE:
<223> OTHER INFORMATION: Synthetic

<400> SEQUENCE: 143
ggtactcgaa gtggcugcgu 20

<210> SEQ ID NO 144
<211> LENGTH: 20
<212> TYPE: DNA
<213> ORGANISM: Artificial Sequence
<220> FEATURE:
<223> OTHER INFORMATION: Synthetic

<400> SEQUENCE: 144
ggtactcgaa gtggcugcgu 20

<210> SEQ ID NO 145
<211> LENGTH: 20
<212> TYPE: DNA
<213> ORGANISM: Artificial Sequence
<220> FEATURE:
<223> OTHER INFORMATION: Synthetic

<400> SEQUENCE: 145
ggtactcgaa gtggcugcgu 20

<210> SEQ ID NO 146
<211> LENGTH: 20
<212> TYPE: DNA
<213> ORGANISM: Artificial Sequence
<220> FEATURE:
<223> OTHER INFORMATION: Synthetic

<400> SEQUENCE: 146
ggtactcgaa gtggcugcgu 20

<210> SEQ ID NO 147
<211> LENGTH: 20
<212> TYPE: DNA
<213> ORGANISM: Artificial Sequence
<220> FEATURE:
<223> OTHER INFORMATION: Synthetic

<400> SEQUENCE: 147
ggtactcgaa gtggcugcgu 20

<210> SEQ ID NO 148
<211> LENGTH: 20
<212> TYPE: DNA
<213> ORGANISM: Artificial Sequence
<220> FEATURE:
<223> OTHER INFORMATION: Synthetic

<400> SEQUENCE: 148
ggtactcgaa gtggcugcgu 20

<210> SEQ ID NO 149
<211> LENGTH: 20
<212> TYPE: DNA
<213> ORGANISM: Artificial Sequence
<220> FEATURE:
<223> OTHER INFORMATION: Synthetic

<400> SEQUENCE: 149
ggtactcgaa gtggcugcgu 20

<210> SEQ ID NO 150
<211> LENGTH: 20
<212> TYPE: DNA
<213> ORGANISM: Artificial Sequence
<220> FEATURE:
<223> OTHER INFORMATION: Synthetic

<400> SEQUENCE: 150
ggtactcgaa gtggcugcgu 20

<210> SEQ ID NO 151
<211> LENGTH: 20
<212> TYPE: DNA
<213> ORGANISM: Artificial Sequence
<220> FEATURE:
<223> OTHER INFORMATION: Synthetic

<400> SEQUENCE: 151
ggtactcgaa gtggctgcgt 20

<210> SEQ ID NO 152
<211> LENGTH: 20
<212> TYPE: DNA
<213> ORGANISM: Artificial Sequence
<220> FEATURE:
<223> OTHER INFORMATION: Synthetic

<400> SEQUENCE: 152
ggtactcgaa gtggctgcgt 20

<210> SEQ ID NO 153
<211> LENGTH: 20
<212> TYPE: DNA
<213> ORGANISM: Artificial Sequence
<220> FEATURE:
<223> OTHER INFORMATION: Synthetic

<400> SEQUENCE: 153
ggtactcgaa gtggctgcgt 20

<210> SEQ ID NO 154
<211> LENGTH: 20
<212> TYPE: DNA
<213> ORGANISM: Artificial Sequence
<220> FEATURE:
<223> OTHER INFORMATION: Synthetic

<400> SEQUENCE: 154
ggtactcgaa gtggctgcgt 20

<210> SEQ ID NO 155
<211> LENGTH: 20
<212> TYPE: DNA
<213> ORGANISM: Artificial Sequence
<220> FEATURE:
<223> OTHER INFORMATION: Synthetic

<400> SEQUENCE: 155
ggtactcgaa gtggctgcgt 20

<210> SEQ ID NO 156
<211> LENGTH: 20
<212> TYPE: DNA
<213> ORGANISM: Artificial Sequence
<220> FEATURE:
<223> OTHER INFORMATION: Synthetic

<400> SEQUENCE: 156
ggtactcgaa gtggctgcgt 20

<210> SEQ ID NO 157
<211> LENGTH: 20
<212> TYPE: DNA
<213> ORGANISM: Artificial Sequence
<220> FEATURE:
<223> OTHER INFORMATION: Synthetic

<400> SEQUENCE: 157
ggtactcgaa gtggctgcgt 20

<210> SEQ ID NO 158
<211> LENGTH: 20
<212> TYPE: DNA
<213> ORGANISM: Artificial Sequence
<220> FEATURE:
<223> OTHER INFORMATION: Synthetic

<400> SEQUENCE: 158
ggtactcgaa gtggctgcgt 20

<210> SEQ ID NO 159
<211> LENGTH: 20
<212> TYPE: DNA
<213> ORGANISM: Artificial Sequence
<220> FEATURE:
<223> OTHER INFORMATION: Synthetic

<400> SEQUENCE: 159
ggtactcgaa gtggctgcgt 20

<210> SEQ ID NO 160
<211> LENGTH: 20
<212> TYPE: DNA
<213> ORGANISM: Artificial Sequence
<220> FEATURE:
<223> OTHER INFORMATION: Synthetic

<400> SEQUENCE: 160
ggtactcgaa gtggcugcgu 20

<210> SEQ ID NO 161
<211> LENGTH: 20
<212> TYPE: DNA
<213> ORGANISM: Artificial Sequence
<220> FEATURE:
<223> OTHER INFORMATION: Synthetic

<400> SEQUENCE: 161
ggtactcgaa gtggcugcgu 20

<210> SEQ ID NO 162
<211> LENGTH: 20

<212> TYPE: DNA
<213> ORGANISM: Artificial Sequence
<220> FEATURE:
<223> OTHER INFORMATION: Synthetic

<400> SEQUENCE: 162
ggtactcgaa gtggcugcgu 20

<210> SEQ ID NO 163
<211> LENGTH: 20
<212> TYPE: DNA
<213> ORGANISM: Artificial Sequence
<220> FEATURE:
<223> OTHER INFORMATION: Synthetic

<400> SEQUENCE: 163
ggtactcgaa gtggcugcgu 20

<210> SEQ ID NO 164
<211> LENGTH: 20
<212> TYPE: DNA
<213> ORGANISM: Artificial Sequence
<220> FEATURE:
<223> OTHER INFORMATION: Synthetic

<400> SEQUENCE: 164
ggtactcgaa gtggcugcgu 20

<210> SEQ ID NO 165
<211> LENGTH: 20
<212> TYPE: DNA
<213> ORGANISM: Artificial Sequence
<220> FEATURE:
<223> OTHER INFORMATION: Synthetic

<400> SEQUENCE: 165
ggtactcgaa gtggcugcgu 20

<210> SEQ ID NO 166
<211> LENGTH: 20
<212> TYPE: DNA
<213> ORGANISM: Artificial Sequence
<220> FEATURE:
<223> OTHER INFORMATION: Synthetic

<400> SEQUENCE: 166
ggtactcgaa gtggcugcgu 20

<210> SEQ ID NO 167
<211> LENGTH: 20
<212> TYPE: DNA
<213> ORGANISM: Artificial Sequence
<220> FEATURE:
<223> OTHER INFORMATION: Synthetic

<400> SEQUENCE: 167
ggtactcgaa gtggcugcgu 20

<210> SEQ ID NO 168
<211> LENGTH: 20
<212> TYPE: DNA
<213> ORGANISM: Artificial Sequence
<220> FEATURE:
<223> OTHER INFORMATION: Synthetic

<400> SEQUENCE: 168
ggtactcgaa gtggcugcgu 20

<210> SEQ ID NO 169
<211> LENGTH: 16
<212> TYPE: DNA
<213> ORGANISM: Artificial Sequence
<220> FEATURE:
<223> OTHER INFORMATION: Synthetic

<400> SEQUENCE: 169
ggtactcgaa gtggct 16

<210> SEQ ID NO 170
<211> LENGTH: 20
<212> TYPE: DNA
<213> ORGANISM: Artificial Sequence
<220> FEATURE:
<223> OTHER INFORMATION: Synthetic

<400> SEQUENCE: 170
tcgaaggggc tccgcaccac 20

<210> SEQ ID NO 171
<211> LENGTH: 20
<212> TYPE: DNA
<213> ORGANISM: Artificial Sequence
<220> FEATURE:
<223> OTHER INFORMATION: Synthetic

<400> SEQUENCE: 171
tcgaaggggc tccgcaccac 20

<210> SEQ ID NO 172
<211> LENGTH: 20
<212> TYPE: DNA
<213> ORGANISM: Artificial Sequence
<220> FEATURE:
<223> OTHER INFORMATION: Synthetic

<400> SEQUENCE: 172
tcgaaggggc tccgcaccac 20

<210> SEQ ID NO 173
<211> LENGTH: 20
<212> TYPE: DNA
<213> ORGANISM: Artificial Sequence
<220> FEATURE:
<223> OTHER INFORMATION: Synthetic

<400> SEQUENCE: 173
tcgaaggggc tccgcaccac 20

<210> SEQ ID NO 174
<211> LENGTH: 20
<212> TYPE: DNA
<213> ORGANISM: Artificial Sequence
<220> FEATURE:
<223> OTHER INFORMATION: Synthetic

<400> SEQUENCE: 174
tcgaaggggc tccgcaccac 20

<210> SEQ ID NO 175
<211> LENGTH: 20
<212> TYPE: DNA
<213> ORGANISM: Artificial Sequence
<220> FEATURE:
<223> OTHER INFORMATION: Synthetic

<400> SEQUENCE: 175
tcgaaggggc tccgcaccac 20

<210> SEQ ID NO 176
<211> LENGTH: 20
<212> TYPE: DNA
<213> ORGANISM: Artificial Sequence
<220> FEATURE:
<223> OTHER INFORMATION: Synthetic

<400> SEQUENCE: 176
tcgaaggggc tccgcaccac 20

<210> SEQ ID NO 177
<211> LENGTH: 20
<212> TYPE: DNA
<213> ORGANISM: Artificial Sequence
<220> FEATURE:
<223> OTHER INFORMATION: Synthetic

<400> SEQUENCE: 177
tcgaaggggc tccgcaccac 20

<210> SEQ ID NO 178
<211> LENGTH: 20
<212> TYPE: DNA
<213> ORGANISM: Artificial Sequence
<220> FEATURE:
<223> OTHER INFORMATION: Synthetic

<400> SEQUENCE: 178
tcgaaggggc tccgcaccac 20

<210> SEQ ID NO 179
<211> LENGTH: 20
<212> TYPE: DNA
<213> ORGANISM: Artificial Sequence
<220> FEATURE:
<223> OTHER INFORMATION: Synthetic

<400> SEQUENCE: 179
tcgaaggggc tccgcaccac 20

<210> SEQ ID NO 180
<211> LENGTH: 20
<212> TYPE: DNA
<213> ORGANISM: Artificial Sequence
<220> FEATURE:
<223> OTHER INFORMATION: Synthetic

<400> SEQUENCE: 180
ctcgaagggg ctccgcacca 20

<210> SEQ ID NO 181
<211> LENGTH: 20
<212> TYPE: DNA
<213> ORGANISM: Artificial Sequence
<220> FEATURE:
<223> OTHER INFORMATION: Synthetic

<400> SEQUENCE: 181
ctcgaagggg ctccgcacca 20

<210> SEQ ID NO 182
<211> LENGTH: 20
<212> TYPE: DNA
<213> ORGANISM: Artificial Sequence
<220> FEATURE:
<223> OTHER INFORMATION: Synthetic

<400> SEQUENCE: 182
ctcgaagggg ctccgcacca 20

<210> SEQ ID NO 183
<211> LENGTH: 20
<212> TYPE: DNA
<213> ORGANISM: Artificial Sequence
<220> FEATURE:
<223> OTHER INFORMATION: Synthetic

<400> SEQUENCE: 183
ctcgaagggg ctccgcacca 20

<210> SEQ ID NO 184
<211> LENGTH: 20
<212> TYPE: DNA
<213> ORGANISM: Artificial Sequence
<220> FEATURE:
<223> OTHER INFORMATION: Synthetic

<400> SEQUENCE: 184
ctcgaagggg ctccgcacca 20

<210> SEQ ID NO 185
<211> LENGTH: 20
<212> TYPE: DNA
<213> ORGANISM: Artificial Sequence
<220> FEATURE:
<223> OTHER INFORMATION: Synthetic

<400> SEQUENCE: 185
ctcgaagggg ctccgcacca 20

<210> SEQ ID NO 186
<211> LENGTH: 20
<212> TYPE: DNA
<213> ORGANISM: Artificial Sequence
<220> FEATURE:
<223> OTHER INFORMATION: Synthetic

<400> SEQUENCE: 186
ctcgaagggg ctccgcacca 20

<210> SEQ ID NO 187
<211> LENGTH: 20
<212> TYPE: DNA
<213> ORGANISM: Artificial Sequence
<220> FEATURE:
<223> OTHER INFORMATION: Synthetic

<400> SEQUENCE: 187
ctcgaagggg ctccgcacca 20

<210> SEQ ID NO 188
<211> LENGTH: 20
<212> TYPE: DNA
<213> ORGANISM: Artificial Sequence
<220> FEATURE:
<223> OTHER INFORMATION: Synthetic

<400> SEQUENCE: 188
ctcgaagggg ctccgcacca 20

<210> SEQ ID NO 189
<211> LENGTH: 20
<212> TYPE: DNA
<213> ORGANISM: Artificial Sequence
<220> FEATURE:
<223> OTHER INFORMATION: Synthetic

<400> SEQUENCE: 189
ctcgaagggg ctccgcacca 20

<210> SEQ ID NO 190
<211> LENGTH: 20
<212> TYPE: DNA
<213> ORGANISM: Artificial Sequence
<220> FEATURE:
<223> OTHER INFORMATION: Synthetic

<400> SEQUENCE: 190
gctcgaaggg gctccgcacc 20

<210> SEQ ID NO 191
<211> LENGTH: 20
<212> TYPE: DNA
<213> ORGANISM: Artificial Sequence
<220> FEATURE:
<223> OTHER INFORMATION: Synthetic

<400> SEQUENCE: 191
gctcgaaggg gctccgcacc 20

<210> SEQ ID NO 192
<211> LENGTH: 20
<212> TYPE: DNA
<213> ORGANISM: Artificial Sequence
<220> FEATURE:
<223> OTHER INFORMATION: Synthetic

<400> SEQUENCE: 192
gctcgaaggg gctccgcacc 20

<210> SEQ ID NO 193
<211> LENGTH: 20
<212> TYPE: DNA
<213> ORGANISM: Artificial Sequence
<220> FEATURE:
<223> OTHER INFORMATION: Synthetic

<400> SEQUENCE: 193
gctcgaaggg gctccgcacc 20

<210> SEQ ID NO 194
<211> LENGTH: 20
<212> TYPE: DNA
<213> ORGANISM: Artificial Sequence
<220> FEATURE:
<223> OTHER INFORMATION: Synthetic

<400> SEQUENCE: 194
gctcgaaggg gctccgcacc 20

<210> SEQ ID NO 195

<211> LENGTH: 20
<212> TYPE: DNA
<213> ORGANISM: Artificial Sequence
<220> FEATURE:
<223> OTHER INFORMATION: Synthetic

<400> SEQUENCE: 195
gctcgaaggg gctccgcacc 20

<210> SEQ ID NO 196
<211> LENGTH: 20
<212> TYPE: DNA
<213> ORGANISM: Artificial Sequence
<220> FEATURE:
<223> OTHER INFORMATION: Synthetic

<400> SEQUENCE: 196
gctcgaaggg gctccgcacc 20

<210> SEQ ID NO 197
<211> LENGTH: 20
<212> TYPE: DNA
<213> ORGANISM: Artificial Sequence
<220> FEATURE:
<223> OTHER INFORMATION: Synthetic

<400> SEQUENCE: 197
gctcgaaggg gctccgcacc 20

<210> SEQ ID NO 198
<211> LENGTH: 20
<212> TYPE: DNA
<213> ORGANISM: Artificial Sequence
<220> FEATURE:
<223> OTHER INFORMATION: Synthetic

<400> SEQUENCE: 198
gctcgaaggg gctccgcacc 20

<210> SEQ ID NO 199
<211> LENGTH: 20
<212> TYPE: DNA
<213> ORGANISM: Artificial Sequence
<220> FEATURE:
<223> OTHER INFORMATION: Synthetic

<400> SEQUENCE: 199
gctcgaaggg gctccgcacc 20

<210> SEQ ID NO 200
<211> LENGTH: 20
<212> TYPE: DNA
<213> ORGANISM: Artificial Sequence
<220> FEATURE:
<223> OTHER INFORMATION: Synthetic

<400> SEQUENCE: 200
tgctcgaagg ggctccgcac 20

<210> SEQ ID NO 201
<211> LENGTH: 20
<212> TYPE: DNA
<213> ORGANISM: Artificial Sequence
<220> FEATURE:
<223> OTHER INFORMATION: Synthetic

<400> SEQUENCE: 201
tgctcgaagg ggctccgcac 20

<210> SEQ ID NO 202
<211> LENGTH: 20
<212> TYPE: DNA
<213> ORGANISM: Artificial Sequence
<220> FEATURE:
<223> OTHER INFORMATION: Synthetic

<400> SEQUENCE: 202
tgctcgaagg ggctccgcac 20

<210> SEQ ID NO 203
<211> LENGTH: 20
<212> TYPE: DNA
<213> ORGANISM: Artificial Sequence
<220> FEATURE:
<223> OTHER INFORMATION: Synthetic

<400> SEQUENCE: 203
tgctcgaagg ggctccgcac 20

<210> SEQ ID NO 204
<211> LENGTH: 20
<212> TYPE: DNA
<213> ORGANISM: Artificial Sequence
<220> FEATURE:
<223> OTHER INFORMATION: Synthetic

<400> SEQUENCE: 204
tgctcgaagg ggctccgcac 20

<210> SEQ ID NO 205
<211> LENGTH: 20
<212> TYPE: DNA
<213> ORGANISM: Artificial Sequence
<220> FEATURE:
<223> OTHER INFORMATION: Synthetic

<400> SEQUENCE: 205
tgctcgaagg ggctccgcac 20

<210> SEQ ID NO 206
<211> LENGTH: 20
<212> TYPE: DNA
<213> ORGANISM: Artificial Sequence
<220> FEATURE:
<223> OTHER INFORMATION: Synthetic

<400> SEQUENCE: 206
tgctcgaagg ggctccgcac 20

<210> SEQ ID NO 207
<211> LENGTH: 20
<212> TYPE: DNA
<213> ORGANISM: Artificial Sequence
<220> FEATURE:
<223> OTHER INFORMATION: Synthetic

<400> SEQUENCE: 207
tgctcgaagg ggctccgcac 20

<210> SEQ ID NO 208
<211> LENGTH: 20
<212> TYPE: DNA

<213> ORGANISM: Artificial Sequence
<220> FEATURE:
<223> OTHER INFORMATION: Synthetic

<400> SEQUENCE: 208
tgctcgaagg ggctccgcac 20

<210> SEQ ID NO 209
<211> LENGTH: 20
<212> TYPE: DNA
<213> ORGANISM: Artificial Sequence
<220> FEATURE:
<223> OTHER INFORMATION: Synthetic

<400> SEQUENCE: 209
tgctcgaagg ggctccgcac 20

<210> SEQ ID NO 210
<211> LENGTH: 20
<212> TYPE: DNA
<213> ORGANISM: Artificial Sequence
<220> FEATURE:
<223> OTHER INFORMATION: Synthetic

<400> SEQUENCE: 210
ctgctcgaag gggctccgca 20

<210> SEQ ID NO 211
<211> LENGTH: 20
<212> TYPE: DNA
<213> ORGANISM: Artificial Sequence
<220> FEATURE:
<223> OTHER INFORMATION: Synthetic

<400> SEQUENCE: 211
ctgctcgaag gggctccgca 20

<210> SEQ ID NO 212
<211> LENGTH: 20
<212> TYPE: DNA
<213> ORGANISM: Artificial Sequence
<220> FEATURE:
<223> OTHER INFORMATION: Synthetic

<400> SEQUENCE: 212
ctgctcgaag gggctccgca 20

<210> SEQ ID NO 213
<211> LENGTH: 20
<212> TYPE: DNA
<213> ORGANISM: Artificial Sequence
<220> FEATURE:
<223> OTHER INFORMATION: Synthetic

<400> SEQUENCE: 213
ctgctcgaag gggctccgca 20

<210> SEQ ID NO 214
<211> LENGTH: 20
<212> TYPE: DNA
<213> ORGANISM: Artificial Sequence
<220> FEATURE:
<223> OTHER INFORMATION: Synthetic

<400> SEQUENCE: 214
ctgctcgaag gggctccgca 20

<210> SEQ ID NO 215
<211> LENGTH: 20
<212> TYPE: DNA
<213> ORGANISM: Artificial Sequence
<220> FEATURE:
<223> OTHER INFORMATION: Synthetic

<400> SEQUENCE: 215
ctgctcgaag gggctccgca 20

<210> SEQ ID NO 216
<211> LENGTH: 20
<212> TYPE: DNA
<213> ORGANISM: Artificial Sequence
<220> FEATURE:
<223> OTHER INFORMATION: Synthetic

<400> SEQUENCE: 216
ctgctcgaag gggctccgca 20

<210> SEQ ID NO 217
<211> LENGTH: 20
<212> TYPE: DNA
<213> ORGANISM: Artificial Sequence
<220> FEATURE:
<223> OTHER INFORMATION: Synthetic

<400> SEQUENCE: 217
ctgctcgaag gggctccgca 20

<210> SEQ ID NO 218
<211> LENGTH: 20
<212> TYPE: DNA
<213> ORGANISM: Artificial Sequence
<220> FEATURE:
<223> OTHER INFORMATION: Synthetic

<400> SEQUENCE: 218
ctgctcgaag gggctccgca 20

<210> SEQ ID NO 219
<211> LENGTH: 20
<212> TYPE: DNA
<213> ORGANISM: Artificial Sequence
<220> FEATURE:
<223> OTHER INFORMATION: Synthetic

<400> SEQUENCE: 219
ctgctcgaag gggctccgca 20

<210> SEQ ID NO 220
<211> LENGTH: 20
<212> TYPE: DNA
<213> ORGANISM: Artificial Sequence
<220> FEATURE:
<223> OTHER INFORMATION: Synthetic

<400> SEQUENCE: 220
gctgctcgaa ggggcuccgc 20

<210> SEQ ID NO 221
<211> LENGTH: 20
<212> TYPE: DNA
<213> ORGANISM: Artificial Sequence
<220> FEATURE:

<223> OTHER INFORMATION: Synthetic

<400> SEQUENCE: 221
gctgctcgaa ggggcuccgc 20

<210> SEQ ID NO 222
<211> LENGTH: 20
<212> TYPE: DNA
<213> ORGANISM: Artificial Sequence
<220> FEATURE:
<223> OTHER INFORMATION: Synthetic

<400> SEQUENCE: 222
gctgctcgaa ggggcuccgc 20

<210> SEQ ID NO 223
<211> LENGTH: 20
<212> TYPE: DNA
<213> ORGANISM: Artificial Sequence
<220> FEATURE:
<223> OTHER INFORMATION: Synthetic

<400> SEQUENCE: 223
gctgctcgaa ggggcuccgc 20

<210> SEQ ID NO 224
<211> LENGTH: 20
<212> TYPE: DNA
<213> ORGANISM: Artificial Sequence
<220> FEATURE:
<223> OTHER INFORMATION: Synthetic

<400> SEQUENCE: 224
gctgctcgaa ggggcuccgc 20

<210> SEQ ID NO 225
<211> LENGTH: 20
<212> TYPE: DNA
<213> ORGANISM: Artificial Sequence
<220> FEATURE:
<223> OTHER INFORMATION: Synthetic

<400> SEQUENCE: 225
gctgctcgaa ggggcuccgc 20

<210> SEQ ID NO 226
<211> LENGTH: 20
<212> TYPE: DNA
<213> ORGANISM: Artificial Sequence
<220> FEATURE:
<223> OTHER INFORMATION: Synthetic

<400> SEQUENCE: 226
gctgctcgaa ggggcuccgc 20

<210> SEQ ID NO 227
<211> LENGTH: 20
<212> TYPE: DNA
<213> ORGANISM: Artificial Sequence
<220> FEATURE:
<223> OTHER INFORMATION: Synthetic

<400> SEQUENCE: 227
gctgctcgaa ggggcuccgc 20

-continued

<210> SEQ ID NO 228
<211> LENGTH: 20
<212> TYPE: DNA
<213> ORGANISM: Artificial Sequence
<220> FEATURE:
<223> OTHER INFORMATION: Synthetic

<400> SEQUENCE: 228
gctgctcgaa ggggcuccgc 20

<210> SEQ ID NO 229
<211> LENGTH: 20
<212> TYPE: DNA
<213> ORGANISM: Artificial Sequence
<220> FEATURE:
<223> OTHER INFORMATION: Synthetic

<400> SEQUENCE: 229
gctgctcgaa ggggcuccgc 20

<210> SEQ ID NO 230
<211> LENGTH: 20
<212> TYPE: DNA
<213> ORGANISM: Artificial Sequence
<220> FEATURE:
<223> OTHER INFORMATION: Synthetic

<400> SEQUENCE: 230
tcgaagtggc tccgcaccac 20

<210> SEQ ID NO 231
<211> LENGTH: 20
<212> TYPE: DNA
<213> ORGANISM: Artificial Sequence
<220> FEATURE:
<223> OTHER INFORMATION: Synthetic

<400> SEQUENCE: 231
tcgaagtggc tccgcaccac 20

<210> SEQ ID NO 232
<211> LENGTH: 20
<212> TYPE: DNA
<213> ORGANISM: Artificial Sequence
<220> FEATURE:
<223> OTHER INFORMATION: Synthetic

<400> SEQUENCE: 232
tcgaagtggc tccgcaccac 20

<210> SEQ ID NO 233
<211> LENGTH: 20
<212> TYPE: DNA
<213> ORGANISM: Artificial Sequence
<220> FEATURE:
<223> OTHER INFORMATION: Synthetic

<400> SEQUENCE: 233
tcgaagtggc tccgcaccac 20

<210> SEQ ID NO 234
<211> LENGTH: 20
<212> TYPE: DNA
<213> ORGANISM: Artificial Sequence
<220> FEATURE:
<223> OTHER INFORMATION: Synthetic

<400> SEQUENCE: 234
tcgaagtggc tccgcaccac 20

<210> SEQ ID NO 235
<211> LENGTH: 20
<212> TYPE: DNA
<213> ORGANISM: Artificial Sequence
<220> FEATURE:
<223> OTHER INFORMATION: Synthetic

<400> SEQUENCE: 235
tcgaagtggc tccgcaccac 20

<210> SEQ ID NO 236
<211> LENGTH: 20
<212> TYPE: DNA
<213> ORGANISM: Artificial Sequence
<220> FEATURE:
<223> OTHER INFORMATION: Synthetic

<400> SEQUENCE: 236
tcgaagtggc tccgcaccac 20

<210> SEQ ID NO 237
<211> LENGTH: 20
<212> TYPE: DNA
<213> ORGANISM: Artificial Sequence
<220> FEATURE:
<223> OTHER INFORMATION: Synthetic

<400> SEQUENCE: 237
tcgaagtggc tccgcaccac 20

<210> SEQ ID NO 238
<211> LENGTH: 20
<212> TYPE: DNA
<213> ORGANISM: Artificial Sequence
<220> FEATURE:
<223> OTHER INFORMATION: Synthetic

<400> SEQUENCE: 238
tcgaagtggc tccgcaccac 20

<210> SEQ ID NO 239
<211> LENGTH: 20
<212> TYPE: DNA
<213> ORGANISM: Artificial Sequence
<220> FEATURE:
<223> OTHER INFORMATION: Synthetic

<400> SEQUENCE: 239
tcgaagtggc tccgcaccac 20

<210> SEQ ID NO 240
<211> LENGTH: 20
<212> TYPE: DNA
<213> ORGANISM: Artificial Sequence
<220> FEATURE:
<223> OTHER INFORMATION: Synthetic

<400> SEQUENCE: 240
ctcgaagtgg ctccgcacca 20

<210> SEQ ID NO 241
<211> LENGTH: 20

<212> TYPE: DNA
<213> ORGANISM: Artificial Sequence
<220> FEATURE:
<223> OTHER INFORMATION: Synthetic

<400> SEQUENCE: 241
ctcgaagtgg ctccgcacca 20

<210> SEQ ID NO 242
<211> LENGTH: 20
<212> TYPE: DNA
<213> ORGANISM: Artificial Sequence
<220> FEATURE:
<223> OTHER INFORMATION: Synthetic

<400> SEQUENCE: 242
ctcgaagtgg ctccgcacca 20

<210> SEQ ID NO 243
<211> LENGTH: 20
<212> TYPE: DNA
<213> ORGANISM: Artificial Sequence
<220> FEATURE:
<223> OTHER INFORMATION: Synthetic

<400> SEQUENCE: 243
ctcgaagtgg ctccgcacca 20

<210> SEQ ID NO 244
<211> LENGTH: 20
<212> TYPE: DNA
<213> ORGANISM: Artificial Sequence
<220> FEATURE:
<223> OTHER INFORMATION: Synthetic

<400> SEQUENCE: 244
ctcgaagtgg ctccgcacca 20

<210> SEQ ID NO 245
<211> LENGTH: 20
<212> TYPE: DNA
<213> ORGANISM: Artificial Sequence
<220> FEATURE:
<223> OTHER INFORMATION: Synthetic

<400> SEQUENCE: 245
ctcgaagtgg ctccgcacca 20

<210> SEQ ID NO 246
<211> LENGTH: 20
<212> TYPE: DNA
<213> ORGANISM: Artificial Sequence
<220> FEATURE:
<223> OTHER INFORMATION: Synthetic

<400> SEQUENCE: 246
ctcgaagtgg ctccgcacca 20

<210> SEQ ID NO 247
<211> LENGTH: 20
<212> TYPE: DNA
<213> ORGANISM: Artificial Sequence
<220> FEATURE:
<223> OTHER INFORMATION: Synthetic

<400> SEQUENCE: 247
ctcgaagtgg ctccgcacca 20

<210> SEQ ID NO 248
<211> LENGTH: 20
<212> TYPE: DNA
<213> ORGANISM: Artificial Sequence
<220> FEATURE:
<223> OTHER INFORMATION: Synthetic

<400> SEQUENCE: 248
ctcgaagtgg ctccgcacca 20

<210> SEQ ID NO 249
<211> LENGTH: 20
<212> TYPE: DNA
<213> ORGANISM: Artificial Sequence
<220> FEATURE:
<223> OTHER INFORMATION: Synthetic

<400> SEQUENCE: 249
ctcgaagtgg ctccgcacca 20

<210> SEQ ID NO 250
<211> LENGTH: 20
<212> TYPE: DNA
<213> ORGANISM: Artificial Sequence
<220> FEATURE:
<223> OTHER INFORMATION: Synthetic

<400> SEQUENCE: 250
gctcgaagtg gctccgcacc 20

<210> SEQ ID NO 251
<211> LENGTH: 20
<212> TYPE: DNA
<213> ORGANISM: Artificial Sequence
<220> FEATURE:
<223> OTHER INFORMATION: Synthetic

<400> SEQUENCE: 251
gctcgaagtg gctccgcacc 20

<210> SEQ ID NO 252
<211> LENGTH: 20
<212> TYPE: DNA
<213> ORGANISM: Artificial Sequence
<220> FEATURE:
<223> OTHER INFORMATION: Synthetic

<400> SEQUENCE: 252
gctcgaagtg gctccgcacc 20

<210> SEQ ID NO 253
<211> LENGTH: 20
<212> TYPE: DNA
<213> ORGANISM: Artificial Sequence
<220> FEATURE:
<223> OTHER INFORMATION: Synthetic

<400> SEQUENCE: 253
gctcgaagtg gctccgcacc 20

<210> SEQ ID NO 254
<211> LENGTH: 20
<212> TYPE: DNA
<213> ORGANISM: Artificial Sequence
<220> FEATURE:
<223> OTHER INFORMATION: Synthetic

<400> SEQUENCE: 254
gctcgaagtg gctccgcacc 20

<210> SEQ ID NO 255
<211> LENGTH: 20
<212> TYPE: DNA
<213> ORGANISM: Artificial Sequence
<220> FEATURE:
<223> OTHER INFORMATION: Synthetic

<400> SEQUENCE: 255
gctcgaagtg gctccgcacc 20

<210> SEQ ID NO 256
<211> LENGTH: 20
<212> TYPE: DNA
<213> ORGANISM: Artificial Sequence
<220> FEATURE:
<223> OTHER INFORMATION: Synthetic

<400> SEQUENCE: 256
gctcgaagtg gctccgcacc 20

<210> SEQ ID NO 257
<211> LENGTH: 20
<212> TYPE: DNA
<213> ORGANISM: Artificial Sequence
<220> FEATURE:
<223> OTHER INFORMATION: Synthetic

<400> SEQUENCE: 257
gctcgaagtg gctccgcacc 20

<210> SEQ ID NO 258
<211> LENGTH: 20
<212> TYPE: DNA
<213> ORGANISM: Artificial Sequence
<220> FEATURE:
<223> OTHER INFORMATION: Synthetic

<400> SEQUENCE: 258
gctcgaagtg gctccgcacc 20

<210> SEQ ID NO 259
<211> LENGTH: 20
<212> TYPE: DNA
<213> ORGANISM: Artificial Sequence
<220> FEATURE:
<223> OTHER INFORMATION: Synthetic

<400> SEQUENCE: 259
gctcgaagtg gctccgcacc 20

<210> SEQ ID NO 260
<211> LENGTH: 20
<212> TYPE: DNA
<213> ORGANISM: Artificial Sequence
<220> FEATURE:
<223> OTHER INFORMATION: Synthetic

<400> SEQUENCE: 260
tgctcgaagt ggctccgcac 20

<210> SEQ ID NO 261
<211> LENGTH: 20
<212> TYPE: DNA
<213> ORGANISM: Artificial Sequence
<220> FEATURE:
<223> OTHER INFORMATION: Synthetic

<400> SEQUENCE: 261
tgctcgaagt ggctccgcac 20

<210> SEQ ID NO 262
<211> LENGTH: 20
<212> TYPE: DNA
<213> ORGANISM: Artificial Sequence
<220> FEATURE:
<223> OTHER INFORMATION: Synthetic

<400> SEQUENCE: 262
tgctcgaagt ggctccgcac 20

<210> SEQ ID NO 263
<211> LENGTH: 20
<212> TYPE: DNA
<213> ORGANISM: Artificial Sequence
<220> FEATURE:
<223> OTHER INFORMATION: Synthetic

<400> SEQUENCE: 263
tgctcgaagt ggctccgcac 20

<210> SEQ ID NO 264
<211> LENGTH: 20
<212> TYPE: DNA
<213> ORGANISM: Artificial Sequence
<220> FEATURE:
<223> OTHER INFORMATION: Synthetic

<400> SEQUENCE: 264
tgctcgaagt ggctccgcac 20

<210> SEQ ID NO 265
<211> LENGTH: 20
<212> TYPE: DNA
<213> ORGANISM: Artificial Sequence
<220> FEATURE:
<223> OTHER INFORMATION: Synthetic

<400> SEQUENCE: 265
tgctcgaagt ggctccgcac 20

<210> SEQ ID NO 266
<211> LENGTH: 20
<212> TYPE: DNA
<213> ORGANISM: Artificial Sequence
<220> FEATURE:
<223> OTHER INFORMATION: Synthetic

<400> SEQUENCE: 266
tgctcgaagt ggctccgcac 20

<210> SEQ ID NO 267
<211> LENGTH: 20
<212> TYPE: DNA
<213> ORGANISM: Artificial Sequence
<220> FEATURE:
<223> OTHER INFORMATION: Synthetic

<400> SEQUENCE: 267
tgctcgaagt ggctccgcac 20

<210> SEQ ID NO 268
<211> LENGTH: 20
<212> TYPE: DNA
<213> ORGANISM: Artificial Sequence
<220> FEATURE:
<223> OTHER INFORMATION: Synthetic

<400> SEQUENCE: 268
tgctcgaagt ggctccgcac 20

<210> SEQ ID NO 269
<211> LENGTH: 20
<212> TYPE: DNA
<213> ORGANISM: Artificial Sequence
<220> FEATURE:
<223> OTHER INFORMATION: Synthetic

<400> SEQUENCE: 269
tgctcgaagt ggctccgcac 20

<210> SEQ ID NO 270
<211> LENGTH: 20
<212> TYPE: DNA
<213> ORGANISM: Artificial Sequence
<220> FEATURE:
<223> OTHER INFORMATION: Synthetic

<400> SEQUENCE: 270
ctgctcgaag tggctccgca 20

<210> SEQ ID NO 271
<211> LENGTH: 20
<212> TYPE: DNA
<213> ORGANISM: Artificial Sequence
<220> FEATURE:
<223> OTHER INFORMATION: Synthetic

<400> SEQUENCE: 271
ctgctcgaag tggctccgca 20

<210> SEQ ID NO 272
<211> LENGTH: 20
<212> TYPE: DNA
<213> ORGANISM: Artificial Sequence
<220> FEATURE:
<223> OTHER INFORMATION: Synthetic

<400> SEQUENCE: 272
ctgctcgaag tggctccgca 20

<210> SEQ ID NO 273
<211> LENGTH: 20
<212> TYPE: DNA
<213> ORGANISM: Artificial Sequence
<220> FEATURE:
<223> OTHER INFORMATION: Synthetic

<400> SEQUENCE: 273
ctgctcgaag tggctccgca 20

<210> SEQ ID NO 274

<211> LENGTH: 20
<212> TYPE: DNA
<213> ORGANISM: Artificial Sequence
<220> FEATURE:
<223> OTHER INFORMATION: Synthetic

<400> SEQUENCE: 274
ctgctcgaag tggctccgca 20

<210> SEQ ID NO 275
<211> LENGTH: 20
<212> TYPE: DNA
<213> ORGANISM: Artificial Sequence
<220> FEATURE:
<223> OTHER INFORMATION: Synthetic

<400> SEQUENCE: 275
ctgctcgaag tggctccgca 20

<210> SEQ ID NO 276
<211> LENGTH: 20
<212> TYPE: DNA
<213> ORGANISM: Artificial Sequence
<220> FEATURE:
<223> OTHER INFORMATION: Synthetic

<400> SEQUENCE: 276
ctgctcgaag tggctccgca 20

<210> SEQ ID NO 277
<211> LENGTH: 20
<212> TYPE: DNA
<213> ORGANISM: Artificial Sequence
<220> FEATURE:
<223> OTHER INFORMATION: Synthetic

<400> SEQUENCE: 277
ctgctcgaag tggctccgca 20

<210> SEQ ID NO 278
<211> LENGTH: 20
<212> TYPE: DNA
<213> ORGANISM: Artificial Sequence
<220> FEATURE:
<223> OTHER INFORMATION: Synthetic

<400> SEQUENCE: 278
ctgctcgaag tggctccgca 20

<210> SEQ ID NO 279
<211> LENGTH: 20
<212> TYPE: DNA
<213> ORGANISM: Artificial Sequence
<220> FEATURE:
<223> OTHER INFORMATION: Synthetic

<400> SEQUENCE: 279
ctgctcgaag tggctccgca 20

<210> SEQ ID NO 280
<211> LENGTH: 20
<212> TYPE: DNA
<213> ORGANISM: Artificial Sequence
<220> FEATURE:
<223> OTHER INFORMATION: Synthetic

<400> SEQUENCE: 280
gctgctcgaa ggtgcuccgc 20

<210> SEQ ID NO 281
<211> LENGTH: 20
<212> TYPE: DNA
<213> ORGANISM: Artificial Sequence
<220> FEATURE:
<223> OTHER INFORMATION: Synthetic

<400> SEQUENCE: 281
gctgctcgaa ggtgcuccgc 20

<210> SEQ ID NO 282
<211> LENGTH: 20
<212> TYPE: DNA
<213> ORGANISM: Artificial Sequence
<220> FEATURE:
<223> OTHER INFORMATION: Synthetic

<400> SEQUENCE: 282
gctgctcgaa ggtgcuccgc 20

<210> SEQ ID NO 283
<211> LENGTH: 20
<212> TYPE: DNA
<213> ORGANISM: Artificial Sequence
<220> FEATURE:
<223> OTHER INFORMATION: Synthetic

<400> SEQUENCE: 283
gctgctcgaa ggtgcuccgc 20

<210> SEQ ID NO 284
<211> LENGTH: 20
<212> TYPE: DNA
<213> ORGANISM: Artificial Sequence
<220> FEATURE:
<223> OTHER INFORMATION: Synthetic

<400> SEQUENCE: 284
gctgctcgaa ggtgcuccgc 20

<210> SEQ ID NO 285
<211> LENGTH: 20
<212> TYPE: DNA
<213> ORGANISM: Artificial Sequence
<220> FEATURE:
<223> OTHER INFORMATION: Synthetic

<400> SEQUENCE: 285
gctgctcgaa ggtgcuccgc 20

<210> SEQ ID NO 286
<211> LENGTH: 20
<212> TYPE: DNA
<213> ORGANISM: Artificial Sequence
<220> FEATURE:
<223> OTHER INFORMATION: Synthetic

<400> SEQUENCE: 286
gctgctcgaa ggtgcuccgc 20

<210> SEQ ID NO 287
<211> LENGTH: 20
<212> TYPE: DNA

<213> ORGANISM: Artificial Sequence
<220> FEATURE:
<223> OTHER INFORMATION: Synthetic

<400> SEQUENCE: 287
gctgctcgaa ggtgcuccgc 20

<210> SEQ ID NO 288
<211> LENGTH: 20
<212> TYPE: DNA
<213> ORGANISM: Artificial Sequence
<220> FEATURE:
<223> OTHER INFORMATION: Synthetic

<400> SEQUENCE: 288
gctgctcgaa ggtgcuccgc 20

<210> SEQ ID NO 289
<211> LENGTH: 20
<212> TYPE: DNA
<213> ORGANISM: Artificial Sequence
<220> FEATURE:
<223> OTHER INFORMATION: Synthetic

<400> SEQUENCE: 289
gctgctcgaa ggtgcuccgc 20

<210> SEQ ID NO 290
<211> LENGTH: 20
<212> TYPE: DNA
<213> ORGANISM: Artificial Sequence
<220> FEATURE:
<223> OTHER INFORMATION: Synthetic

<400> SEQUENCE: 290
ggtactcgaa gtggctgcgt 20

<210> SEQ ID NO 291
<211> LENGTH: 20
<212> TYPE: DNA
<213> ORGANISM: Artificial Sequence
<220> FEATURE:
<223> OTHER INFORMATION: Synthetic

<400> SEQUENCE: 291
ggtactcgaa gtggctgcgt 20

<210> SEQ ID NO 292
<211> LENGTH: 20
<212> TYPE: DNA
<213> ORGANISM: Artificial Sequence
<220> FEATURE:
<223> OTHER INFORMATION: Synthetic

<400> SEQUENCE: 292
ggtactcgaa gtggctgcgt 20

<210> SEQ ID NO 293
<211> LENGTH: 20
<212> TYPE: DNA
<213> ORGANISM: Artificial Sequence
<220> FEATURE:
<223> OTHER INFORMATION: Synthetic

<400> SEQUENCE: 293
ggtactcgaa gtggctgcgt 20

<210> SEQ ID NO 294
<211> LENGTH: 20
<212> TYPE: DNA
<213> ORGANISM: Artificial Sequence
<220> FEATURE:
<223> OTHER INFORMATION: Synthetic

<400> SEQUENCE: 294
ggtactcgaa gtggctgcgt 20

<210> SEQ ID NO 295
<211> LENGTH: 20
<212> TYPE: DNA
<213> ORGANISM: Artificial Sequence
<220> FEATURE:
<223> OTHER INFORMATION: Synthetic

<400> SEQUENCE: 295
ggtactcgaa gtggctgcgt 20

<210> SEQ ID NO 296
<211> LENGTH: 20
<212> TYPE: DNA
<213> ORGANISM: Artificial Sequence
<220> FEATURE:
<223> OTHER INFORMATION: Synthetic

<400> SEQUENCE: 296
ggtactcgaa gtggcugcgu 20

<210> SEQ ID NO 297
<211> LENGTH: 20
<212> TYPE: DNA
<213> ORGANISM: Artificial Sequence
<220> FEATURE:
<223> OTHER INFORMATION: Synthetic

<400> SEQUENCE: 297
ggtactcgaa gtggcugcgu 20

<210> SEQ ID NO 298
<211> LENGTH: 20
<212> TYPE: DNA
<213> ORGANISM: Artificial Sequence
<220> FEATURE:
<223> OTHER INFORMATION: Synthetic

<400> SEQUENCE: 298
ggtactcgaa gtggcugcgu 20

<210> SEQ ID NO 299
<211> LENGTH: 20
<212> TYPE: DNA
<213> ORGANISM: Artificial Sequence
<220> FEATURE:
<223> OTHER INFORMATION: Synthetic

<400> SEQUENCE: 299
ggtactcgaa gtggcugcgu 20

<210> SEQ ID NO 300
<211> LENGTH: 20
<212> TYPE: DNA
<213> ORGANISM: Artificial Sequence
<220> FEATURE:

<223> OTHER INFORMATION: Synthetic

<400> SEQUENCE: 300
ggtactcgaa gtggcugcgu 20

<210> SEQ ID NO 301
<211> LENGTH: 20
<212> TYPE: DNA
<213> ORGANISM: Artificial Sequence
<220> FEATURE:
<223> OTHER INFORMATION: Synthetic

<400> SEQUENCE: 301
ggtactcgaa gtggcugcgu 20

<210> SEQ ID NO 302
<211> LENGTH: 20
<212> TYPE: DNA
<213> ORGANISM: Artificial Sequence
<220> FEATURE:
<223> OTHER INFORMATION: Synthetic

<400> SEQUENCE: 302
ggtactcgaa gtggcugcgu 20

<210> SEQ ID NO 303
<211> LENGTH: 20
<212> TYPE: DNA
<213> ORGANISM: Artificial Sequence
<220> FEATURE:
<223> OTHER INFORMATION: Synthetic

<400> SEQUENCE: 303
ggtactcgaa gtggcugcgu 20

<210> SEQ ID NO 304
<211> LENGTH: 20
<212> TYPE: DNA
<213> ORGANISM: Artificial Sequence
<220> FEATURE:
<223> OTHER INFORMATION: Synthetic

<400> SEQUENCE: 304
ggtactcgaa gtggcugcgu 20

<210> SEQ ID NO 305
<211> LENGTH: 20
<212> TYPE: DNA
<213> ORGANISM: Artificial Sequence
<220> FEATURE:
<223> OTHER INFORMATION: Synthetic

<400> SEQUENCE: 305
ggtactcgaa gtggcugcgu 20

<210> SEQ ID NO 306
<211> LENGTH: 20
<212> TYPE: DNA
<213> ORGANISM: Artificial Sequence
<220> FEATURE:
<223> OTHER INFORMATION: Synthetic

<400> SEQUENCE: 306
ggtactcgaa gtggcugcgu 20

-continued

<210> SEQ ID NO 307
<211> LENGTH: 20
<212> TYPE: DNA
<213> ORGANISM: Artificial Sequence
<220> FEATURE:
<223> OTHER INFORMATION: Synthetic

<400> SEQUENCE: 307
ggtactcgaa gtggcugcgu 20

<210> SEQ ID NO 308
<211> LENGTH: 20
<212> TYPE: DNA
<213> ORGANISM: Artificial Sequence
<220> FEATURE:
<223> OTHER INFORMATION: Synthetic

<400> SEQUENCE: 308
ccttccctga aggttccucc 20

<210> SEQ ID NO 309
<211> LENGTH: 20
<212> TYPE: DNA
<213> ORGANISM: Artificial Sequence
<220> FEATURE:
<223> OTHER INFORMATION: Synthetic

<400> SEQUENCE: 309
ggtactcgaa gtggctgcgt 20

<210> SEQ ID NO 310
<211> LENGTH: 20
<212> TYPE: DNA
<213> ORGANISM: Artificial Sequence
<220> FEATURE:
<223> OTHER INFORMATION: Synthetic

<400> SEQUENCE: 310
ggtactcgaa gtggcugcgu 20

<210> SEQ ID NO 311
<211> LENGTH: 20
<212> TYPE: DNA
<213> ORGANISM: Artificial Sequence
<220> FEATURE:
<223> OTHER INFORMATION: Synthetic

<400> SEQUENCE: 311
ggtactcgaa gtggctgcgt 20

<210> SEQ ID NO 312
<211> LENGTH: 16
<212> TYPE: DNA
<213> ORGANISM: Artificial Sequence
<220> FEATURE:
<223> OTHER INFORMATION: Synthetic

<400> SEQUENCE: 312
ggtactcgaa gtggct 16

<210> SEQ ID NO 313
<211> LENGTH: 20
<212> TYPE: DNA
<213> ORGANISM: Artificial Sequence
<220> FEATURE:
<223> OTHER INFORMATION: Synthetic

<400> SEQUENCE: 313
ggtactcgaa gtggctgcgt 20

<210> SEQ ID NO 314
<211> LENGTH: 20
<212> TYPE: DNA
<213> ORGANISM: Artificial Sequence
<220> FEATURE:
<223> OTHER INFORMATION: Synthetic

<400> SEQUENCE: 314
ggtactcgaa gtggctgcgt 20

<210> SEQ ID NO 315
<211> LENGTH: 20
<212> TYPE: DNA
<213> ORGANISM: Artificial Sequence
<220> FEATURE:
<223> OTHER INFORMATION: Synthetic

<400> SEQUENCE: 315
ggtactcgaa gtggctgcgt 20

<210> SEQ ID NO 316
<211> LENGTH: 20
<212> TYPE: DNA
<213> ORGANISM: Artificial Sequence
<220> FEATURE:
<223> OTHER INFORMATION: Synthetic

<400> SEQUENCE: 316
ggtactcgaa gtggctgcgt 20

<210> SEQ ID NO 317
<211> LENGTH: 20
<212> TYPE: DNA
<213> ORGANISM: Artificial Sequence
<220> FEATURE:
<223> OTHER INFORMATION: Synthetic

<400> SEQUENCE: 317
ggtactcgaa gtggctgcgt 20

<210> SEQ ID NO 318
<211> LENGTH: 20
<212> TYPE: DNA
<213> ORGANISM: Artificial Sequence
<220> FEATURE:
<223> OTHER INFORMATION: Synthetic

<400> SEQUENCE: 318
ggtactcgaa gtggctgcgt 20

<210> SEQ ID NO 319
<211> LENGTH: 20
<212> TYPE: DNA
<213> ORGANISM: Artificial Sequence
<220> FEATURE:
<223> OTHER INFORMATION: Synthetic

<400> SEQUENCE: 319
ggtactcgaa gtggcugcgu 20

<210> SEQ ID NO 320
<211> LENGTH: 20

<212> TYPE: DNA
<213> ORGANISM: Artificial Sequence
<220> FEATURE:
<223> OTHER INFORMATION: Synthetic

<400> SEQUENCE: 320
ggtactcgaa gtggcugcgu 20

<210> SEQ ID NO 321
<211> LENGTH: 20
<212> TYPE: DNA
<213> ORGANISM: Artificial Sequence
<220> FEATURE:
<223> OTHER INFORMATION: Synthetic

<400> SEQUENCE: 321
ggtactcgaa gtggctgcgt 20

<210> SEQ ID NO 322
<211> LENGTH: 20
<212> TYPE: DNA
<213> ORGANISM: Artificial Sequence
<220> FEATURE:
<223> OTHER INFORMATION: Synthetic

<400> SEQUENCE: 322
ggtactcgaa gtggcugcgu 20

<210> SEQ ID NO 323
<211> LENGTH: 20
<212> TYPE: DNA
<213> ORGANISM: Artificial Sequence
<220> FEATURE:
<223> OTHER INFORMATION: Synthetic

<400> SEQUENCE: 323
ggtactcgaa gtggcugcgu 20

<210> SEQ ID NO 324
<211> LENGTH: 20
<212> TYPE: DNA
<213> ORGANISM: Artificial Sequence
<220> FEATURE:
<223> OTHER INFORMATION: Synthetic

<400> SEQUENCE: 324
ggtactcgaa gtggctgcgt 20

<210> SEQ ID NO 325
<211> LENGTH: 20
<212> TYPE: DNA
<213> ORGANISM: Artificial Sequence
<220> FEATURE:
<223> OTHER INFORMATION: Synthetic

<400> SEQUENCE: 325
ggtactcgaa gtggctgcgt 20

<210> SEQ ID NO 326
<211> LENGTH: 20
<212> TYPE: DNA
<213> ORGANISM: Artificial Sequence
<220> FEATURE:
<223> OTHER INFORMATION: Synthetic

<400> SEQUENCE: 326
ggtactcgaa gtggctgcgt 20

<210> SEQ ID NO 327
<211> LENGTH: 20
<212> TYPE: DNA
<213> ORGANISM: Artificial Sequence
<220> FEATURE:
<223> OTHER INFORMATION: Synthetic

<400> SEQUENCE: 327
ggtactcgaa gtggctgcgt 20

<210> SEQ ID NO 328
<211> LENGTH: 20
<212> TYPE: DNA
<213> ORGANISM: Artificial Sequence
<220> FEATURE:
<223> OTHER INFORMATION: Synthetic

<400> SEQUENCE: 328
ggtactcgaa gtggctgcgt 20

<210> SEQ ID NO 329
<211> LENGTH: 20
<212> TYPE: DNA
<213> ORGANISM: Artificial Sequence
<220> FEATURE:
<223> OTHER INFORMATION: Synthetic

<400> SEQUENCE: 329
ggtactcgaa gtggctgcgt 20

<210> SEQ ID NO 330
<211> LENGTH: 20
<212> TYPE: DNA
<213> ORGANISM: Artificial Sequence
<220> FEATURE:
<223> OTHER INFORMATION: Synthetic

<400> SEQUENCE: 330
ggtactcgaa gtggctgcgt 20

<210> SEQ ID NO 331
<211> LENGTH: 20
<212> TYPE: DNA
<213> ORGANISM: Artificial Sequence
<220> FEATURE:
<223> OTHER INFORMATION: Synthetic

<400> SEQUENCE: 331
ggtactcgaa gtggctgcgt 20

<210> SEQ ID NO 332
<211> LENGTH: 20
<212> TYPE: DNA
<213> ORGANISM: Artificial Sequence
<220> FEATURE:
<223> OTHER INFORMATION: Synthetic

<400> SEQUENCE: 332
ggtactcgaa gtggctgcgt 20

<210> SEQ ID NO 333
<211> LENGTH: 20
<212> TYPE: DNA
<213> ORGANISM: Artificial Sequence
<220> FEATURE:
<223> OTHER INFORMATION: Synthetic

<400> SEQUENCE: 333
ggtactcgaa gtggctgcgt 20

<210> SEQ ID NO 334
<211> LENGTH: 20
<212> TYPE: DNA
<213> ORGANISM: Artificial Sequence
<220> FEATURE:
<223> OTHER INFORMATION: Synthetic

<400> SEQUENCE: 334
ggtactcgaa gtggctgcgt 20

<210> SEQ ID NO 335
<211> LENGTH: 20
<212> TYPE: DNA
<213> ORGANISM: Artificial Sequence
<220> FEATURE:
<223> OTHER INFORMATION: Synthetic

<400> SEQUENCE: 335
ggtactcgaa gtggctgcgt 20

<210> SEQ ID NO 336
<211> LENGTH: 20
<212> TYPE: DNA
<213> ORGANISM: Artificial Sequence
<220> FEATURE:
<223> OTHER INFORMATION: Synthetic

<400> SEQUENCE: 336
ggtactcgaa gtggctgcgt 20

<210> SEQ ID NO 337
<211> LENGTH: 20
<212> TYPE: DNA
<213> ORGANISM: Artificial Sequence
<220> FEATURE:
<223> OTHER INFORMATION: Synthetic

<400> SEQUENCE: 337
ggtactcgaa gtggctgcgt 20

<210> SEQ ID NO 338
<211> LENGTH: 20
<212> TYPE: DNA
<213> ORGANISM: Artificial Sequence
<220> FEATURE:
<223> OTHER INFORMATION: Synthetic

<400> SEQUENCE: 338
ggtactcgaa gtggctgcgt 20

<210> SEQ ID NO 339
<211> LENGTH: 20
<212> TYPE: DNA
<213> ORGANISM: Artificial Sequence
<220> FEATURE:
<223> OTHER INFORMATION: Synthetic

<400> SEQUENCE: 339
ggtactcgaa gtggctgcgt 20

<210> SEQ ID NO 340
<211> LENGTH: 20
<212> TYPE: DNA
<213> ORGANISM: Artificial Sequence
<220> FEATURE:
<223> OTHER INFORMATION: Synthetic

<400> SEQUENCE: 340
ggtactcgaa gtggctgcgt 20

<210> SEQ ID NO 341
<211> LENGTH: 20
<212> TYPE: DNA
<213> ORGANISM: Artificial Sequence
<220> FEATURE:
<223> OTHER INFORMATION: Synthetic

<400> SEQUENCE: 341
ggtactcgaa gtggctgcgt 20

<210> SEQ ID NO 342
<211> LENGTH: 20
<212> TYPE: DNA
<213> ORGANISM: Artificial Sequence
<220> FEATURE:
<223> OTHER INFORMATION: Synthetic

<400> SEQUENCE: 342
ggtactcgaa gtggctgcgt 20

<210> SEQ ID NO 343
<211> LENGTH: 20
<212> TYPE: DNA
<213> ORGANISM: Artificial Sequence
<220> FEATURE:
<223> OTHER INFORMATION: Synthetic

<400> SEQUENCE: 343
ggtactcgaa gtggcugcgu 20

<210> SEQ ID NO 344
<211> LENGTH: 20
<212> TYPE: DNA
<213> ORGANISM: Artificial Sequence
<220> FEATURE:
<223> OTHER INFORMATION: Synthetic

<400> SEQUENCE: 344
ggtactcgaa gtggcugcgu 20

<210> SEQ ID NO 345
<211> LENGTH: 20
<212> TYPE: DNA
<213> ORGANISM: Artificial Sequence
<220> FEATURE:
<223> OTHER INFORMATION: Synthetic

<400> SEQUENCE: 345
ggtactcgaa gtggcugcgu 20

<210> SEQ ID NO 346
<211> LENGTH: 20
<212> TYPE: DNA
<213> ORGANISM: Artificial Sequence
<220> FEATURE:
<223> OTHER INFORMATION: Synthetic

<400> SEQUENCE: 346
ggtactcgaa gtggcugcgu 20

<210> SEQ ID NO 347
<211> LENGTH: 20
<212> TYPE: DNA
<213> ORGANISM: Artificial Sequence
<220> FEATURE:
<223> OTHER INFORMATION: Synthetic

<400> SEQUENCE: 347
ggtactcgaa gtggcugcgu 20

<210> SEQ ID NO 348
<211> LENGTH: 20
<212> TYPE: DNA
<213> ORGANISM: Artificial Sequence
<220> FEATURE:
<223> OTHER INFORMATION: Synthetic

<400> SEQUENCE: 348
ggtactcgaa gtggcugcgu 20

<210> SEQ ID NO 349
<211> LENGTH: 20
<212> TYPE: DNA
<213> ORGANISM: Artificial Sequence
<220> FEATURE:
<223> OTHER INFORMATION: Synthetic

<400> SEQUENCE: 349
ggtactcgaa gtggcugcgu 20

<210> SEQ ID NO 350
<211> LENGTH: 20
<212> TYPE: DNA
<213> ORGANISM: Artificial Sequence
<220> FEATURE:
<223> OTHER INFORMATION: Synthetic

<400> SEQUENCE: 350
ggtactcgaa gtggcugcgu 20

<210> SEQ ID NO 351
<211> LENGTH: 20
<212> TYPE: DNA
<213> ORGANISM: Artificial Sequence
<220> FEATURE:
<223> OTHER INFORMATION: Synthetic

<400> SEQUENCE: 351
ggtactcgaa gtggcugcgu 20

<210> SEQ ID NO 352
<211> LENGTH: 20
<212> TYPE: DNA
<213> ORGANISM: Artificial Sequence
<220> FEATURE:
<223> OTHER INFORMATION: Synthetic

<400> SEQUENCE: 352
ggtactcgaa gtggcugcgu 20

<210> SEQ ID NO 353

<211> LENGTH: 20
<212> TYPE: DNA
<213> ORGANISM: Artificial Sequence
<220> FEATURE:
<223> OTHER INFORMATION: Synthetic

<400> SEQUENCE: 353
ggtactcgaa gtggcugcgu 20

<210> SEQ ID NO 354
<211> LENGTH: 20
<212> TYPE: DNA
<213> ORGANISM: Artificial Sequence
<220> FEATURE:
<223> OTHER INFORMATION: Synthetic

<400> SEQUENCE: 354
ggtactcgaa gtggcugcgu 20

<210> SEQ ID NO 355
<211> LENGTH: 20
<212> TYPE: DNA
<213> ORGANISM: Artificial Sequence
<220> FEATURE:
<223> OTHER INFORMATION: Synthetic

<400> SEQUENCE: 355
ggtactcgaa gtggcugcgu 20

<210> SEQ ID NO 356
<211> LENGTH: 20
<212> TYPE: DNA
<213> ORGANISM: Artificial Sequence
<220> FEATURE:
<223> OTHER INFORMATION: Synthetic

<400> SEQUENCE: 356
ggtactcgaa gtggcugcgu 20

<210> SEQ ID NO 357
<211> LENGTH: 20
<212> TYPE: DNA
<213> ORGANISM: Artificial Sequence
<220> FEATURE:
<223> OTHER INFORMATION: Synthetic

<400> SEQUENCE: 357
ggtactcgaa gtggcugcgu 20

<210> SEQ ID NO 358
<211> LENGTH: 20
<212> TYPE: DNA
<213> ORGANISM: Artificial Sequence
<220> FEATURE:
<223> OTHER INFORMATION: Synthetic

<400> SEQUENCE: 358
ggtactcgaa gtggcugcgu 20

<210> SEQ ID NO 359
<211> LENGTH: 20
<212> TYPE: DNA
<213> ORGANISM: Artificial Sequence
<220> FEATURE:
<223> OTHER INFORMATION: Synthetic

<400> SEQUENCE: 359
ggtactcgaa gtggcugcgu 20

<210> SEQ ID NO 360
<211> LENGTH: 20
<212> TYPE: DNA
<213> ORGANISM: Artificial Sequence
<220> FEATURE:
<223> OTHER INFORMATION: Synthetic

<400> SEQUENCE: 360
ggtactcgaa gtggcugcgu 20

<210> SEQ ID NO 361
<211> LENGTH: 20
<212> TYPE: DNA
<213> ORGANISM: Artificial Sequence
<220> FEATURE:
<223> OTHER INFORMATION: Synthetic

<400> SEQUENCE: 361
ggtactcgaa gtggcugcgu 20

<210> SEQ ID NO 362
<211> LENGTH: 20
<212> TYPE: DNA
<213> ORGANISM: Artificial Sequence
<220> FEATURE:
<223> OTHER INFORMATION: Synthetic

<400> SEQUENCE: 362
ggtactcgaa gtggcugcgu 20

<210> SEQ ID NO 363
<211> LENGTH: 20
<212> TYPE: DNA
<213> ORGANISM: Artificial Sequence
<220> FEATURE:
<223> OTHER INFORMATION: Synthetic

<400> SEQUENCE: 363
ggtactcgaa gtggcugcgu 20

<210> SEQ ID NO 364
<211> LENGTH: 20
<212> TYPE: DNA
<213> ORGANISM: Artificial Sequence
<220> FEATURE:
<223> OTHER INFORMATION: Synthetic

<400> SEQUENCE: 364
ggtactcgaa gtggcugcgu 20

<210> SEQ ID NO 365
<211> LENGTH: 20
<212> TYPE: DNA
<213> ORGANISM: Artificial Sequence
<220> FEATURE:
<223> OTHER INFORMATION: Synthetic

<400> SEQUENCE: 365
ggtactcgaa gtggcugcgu 20

<210> SEQ ID NO 366
<211> LENGTH: 20
<212> TYPE: DNA

-continued

```
<213> ORGANISM: Artificial Sequence
<220> FEATURE:
<223> OTHER INFORMATION: Synthetic

<400> SEQUENCE: 366

ggtactcgaa gtggcugcgu                                                20


<210> SEQ ID NO 367
<211> LENGTH: 20
<212> TYPE: DNA
<213> ORGANISM: Artificial Sequence
<220> FEATURE:
<223> OTHER INFORMATION: Synthetic

<400> SEQUENCE: 367

ggtactcgaa gtggcugcgu                                                20


<210> SEQ ID NO 368
<211> LENGTH: 20
<212> TYPE: DNA
<213> ORGANISM: Artificial Sequence
<220> FEATURE:
<223> OTHER INFORMATION: Synthetic

<400> SEQUENCE: 368

ggtactcgaa gtggcugcgu                                                20
```